(12) United States Patent
Beaulieu et al.

(10) Patent No.: US 8,129,398 B2
(45) Date of Patent: Mar. 6, 2012

(54) HIV INTEGRASE INHIBITORS

(75) Inventors: Francis Beaulieu, Quebec (CA); Carl Ouellet, Boucherville (CA); B. Narasimhulu Naidu, Durham, CT (US); Manoj Patel, Berlin, CT (US); Yasutsugu Ueda, Clinton, CT (US); Timothy P. Connolly, Portland, CT (US); Jonathan R. Weiss, Boston, MA (US); Michael A. Walker, Durham, CT (US); Nicholas A. Meanwell, East Hampton, CT (US); Kevin M. Peese, Haddam, CT (US); Margaret E. Sorenson, Meriden, CT (US); Chen Li, South Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 429 days.

(21) Appl. No.: 12/406,268

(22) Filed: Mar. 18, 2009

(65) Prior Publication Data

US 2009/0253677 A1    Oct. 8, 2009

Related U.S. Application Data

(60) Provisional application No. 61/037,729, filed on Mar. 19, 2008.

(51) Int. Cl.
*A61K 31/505* (2006.01)
*C07D 487/12* (2006.01)

(52) U.S. Cl. .................................. 514/267; 544/252
(58) Field of Classification Search .................. None
See application file for complete search history.

(56) References Cited

U.S. PATENT DOCUMENTS 7,157,447 B2    1/2007   Naidu et al.
(Continued)

FOREIGN PATENT DOCUMENTS

EP           1 698 628         9/2006
(Continued)

*Primary Examiner* — Noble Jarrell
(74) *Attorney, Agent, or Firm* — James Epperson

(57) ABSTRACT

The disclosure generally relates to the novel compounds of formula I, including their salts, which inhibit HIV integrase and prevent viral integration into human DNA. This action makes the compounds useful for treating HIV infection and AIDS. The invention also encompasses pharmaceutical compositions and methods for treating those infected with HIV.

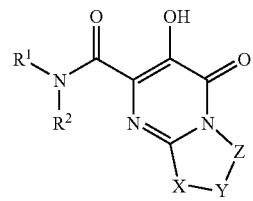

17 Claims, No Drawings

U.S. PATENT DOCUMENTS

| | | |
|---|---|---|
| 7,173,022 B2 | 2/2007 | Naidu et al. |
| 7,176,196 B2 | 2/2007 | Naidu et al. |
| 7,192,948 B2 | 3/2007 | Banville et al. |
| 7,273,859 B2 | 9/2007 | Naidu |
| 7,419,969 B2 | 9/2008 | Naidu et al. |
| 7,494,984 B2 | 2/2009 | Banville et al. |
| 2006/0046985 A1 | 3/2006 | Crescenzi et al. |
| 2007/0111984 A1 | 5/2007 | Naidu et al. |
| 2007/0112190 A1 | 5/2007 | Naidu |
| 2007/0281917 A1 | 12/2007 | Naidu et al. |
| 2008/0004265 A1 | 1/2008 | Walker et al. |
| 2008/0306051 A1 | 12/2008 | Naidu et al. |

FOREIGN PATENT DOCUMENTS

| | | | |
|---|---|---|---|
| WO | WO 2005/061490 | | 7/2005 |
| WO | WO 2005/061501 | | 7/2005 |
| WO | WO 2006/103399 | | 10/2006 |
| WO | WO 2006/121831 | | 11/2006 |
| WO | WO 2010088167 | * | 8/2010 |

* cited by examiner

HIV INTEGRASE INHIBITORS

CROSS-REFERENCE TO RELATED APPLICATIONS

This application claims the benefit of U.S. provisional application Ser. No. 61/037,729 filed Mar. 19, 2008.

BACKGROUND OF THE INVENTION

The disclosure generally relates to the novel compounds of formula I, including their salts, which inhibit HIV integrase and prevent viral integration into human DNA. This action makes the compounds useful for treating HIV infection and AIDS. The invention also encompasses pharmaceutical compositions and methods for treating those infected with HIV.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into four classes based on the viral protein they target and their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleoside reverse transcriptase inhibitors that behave as substrate mimics to halt viral cDNA synthesis. The non-nucleoside reverse transcriptase inhibitors, nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Further, J.; Satten, G. A.; Aschman, D. J.; Holmberg, S. D. *N. Engl. J. Med.* 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381-390). Clearly, there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase is a component of the pre-integration complex of the virus that is assembled in the cell shortly after infection (Chiu, T. K.; Davies, D. R. *Curr. Top. Med. Chem.* 2004, 4, 965-977). This enzyme catalyzes the integration of proviral DNA into the host genome and is absolutely required for viral infectivity. Early experiments showed that mutating the active site of integrase within a proviral clone produces virus unable to replicate due to its inability to insert into the host chromosome (Englund, G.; Theodore, T. S.; Freed, E. O.; Engleman, A.; Martin, M. A. *J. Virol.* 1995, 69, 3216-3219). Selective HIV integrase inhibitors have been shown to possess effective anti-HIV activity in cell culture (Hazuda, D. J.; Felock, P.; Witmer, M.; Wolfe, A; Stillmock, K.; Grobler, J. A.; Espeseth, A.; Gabryelski, L.; Schleif, W.; Blau, C.; Miller, M. D. *Science*, 2000, 287, 646-650), and it is clear that this class of inhibitors is very effective as part of a combination regimen containing HIV inhibitors of different classes. An HIV integrase inhibitor, raltegravir (ISENTRESS®), has been approved for use in treatment experienced patients based upon 48 week trial results (Cooper, D. A.; Gatell, J.; Rockstroh, J.; Katlama, C.; Yeni, P.; Lazzarin, A.; Xu, X.; Isaacs, R.; Teppler, H.; Nguyen, B. Y. 15*th Conference on Retroviruses and Opportunistic Infections*, Boston, Mass., Feb. 3-6, 2008 Abst. 105LB: Evering, T. H.; Markowitz, M. *Drugs Today*, 2007, 43, 865-877). In addition, a second integrase inhibitor, elvitegravir (GS-9137), completed a successful Phase II trial in combination with ritonavir boosting in naive and treatment experienced patients (Zolopa, A. 14*th Conference on Retroviruses and Opportunistic Infections*, Los Angeles, Calif. Feb. 25-28, 2007 Abst. 143LB). Thus, HIV-1 integrase is a promising target for novel anti-HIV-1 therapeutics.

The invention provides technical advantages, for example, the compounds are novel and inhibit HIV integrase. Additionally, the compounds provide advantages for pharmaceutical uses, for example, with regard to one or more of their mechanism of action, binding, inhibition efficacy, target selectivity, solubility, safety profiles, or bioavailability.

HIV integrase inhibitors have been disclosed in U.S. Pat. Nos. 7,176,196 and 7,173,022 and PCT publications WO 2004/58756 and WO 2004/58757.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention are compounds of Formula I

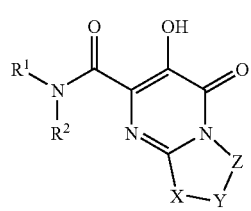

wherein:
$R^1$ is $(Ar^1)$alkyl, alkyl, (cycloalkyl)alkyl, diphenylalkyl, phenoxyalkyl, (PhNH)alkyl, (methylpyrrolidinyl)alkyl, (imidazolyl)alkyl(valerolactamyl)alkyl, (tetrahydrofuranyl) alkyl, ((fluoro)(methyl)pyridinyl)methyl, phenylcyclopropyl, or benzylpyrrolidinyl;

$R^2$ is hydrogen, alkyl, hydroxy or alkoxy;

$R^3$ is hydrogen, halo, hydroxy, alkoxy, cyano, alkyl, cycloalkyl, haloalkyl, hydroxyalkyl, alkoxyalkyl, alkoxy, haloalkoxy, $N(R^8)(R^9)$, $N(R^6)COR^7$, $N(R^6)SO_2R^7$, $N(R^6)CO_2R^7$, $N(R^6)SO_2N(R^8)(R^9)$, $CO_2R^6$, $CON(R^8)(R^9)$, $SOR^7$, $SO_2R^7$, $SO_2N(R^8)(R^9)$, $PO(OR^6)_2$, $R^{12}$, or $Ar^2$;

$R^4$ is hydrogen, halo, hydroxy, cyano, alkyl, alkoxy, haloalkyl, haloalkoxy, or $N(R^6)(R^6)$;

$R^5$ is hydrogen, halo, hydroxy, cyano, alkyl, alkoxy, haloalkyl, haloalkoxy, or $N(R^6)(R^6)$;

$R^6$ is hydrogen, alkyl, haloalkyl, or cycloalkyl;

$R^7$ is alkyl, haloalkyl, or cycloalkyl;

$R^8$ is hydrogen, alkyl, haloalkyl, hydroxyalkyl, alkoxyalkyl or dialkylaminoalkyl;

$R^9$ is hydrogen, alkyl, haloalkyl, hydroxyalkyl, alkoxyalkyl or dialkylaminoalkyl; or $N(R^8)(R^9)$ taken together is azetidinyl, pyrrolidinyl, $(R^{10})$-piperidinyl, $N-(R^{11})$-piperazinyl, morpholinyl, thiomorpholinyl, or dioxothiazinyl;

$R^{10}$ is hydrogen, alkyl, hydroxy, or hydroxyalkyl;

$R^{11}$ is hydrogen, alkyl, cyclolkyl, hydroxyalkyl, alkoxyalkyl, hydroxyalkoxyalkyl, phenyl, pyridinyl, (methylimidazolyl)methyl, $COR^6$, $CO_2R^6$, (hydroxyalkyl)CO, (alkoxyalkyl)CO, (tetrahydrofuranyl)CO, (methylisoxazolyl)CO, (thienyl)CO, (furanyl)CO, (pyridinyl)CO, $CON(R^8)(R^9)$, $SO_2R^7$, $SO_2N(R^8)(R^9)$, (dimethylisoxazolyl)$SO_2$, ((carboethoxy)thienyl)$SO_2$, (methylimidazolyl)$SO_2$, $R^{12}$ is azetidinonyl, pyrrolidinonyl, valerolactamyl, caprolactamyl, maleimido, oxazolidinonyl, imidazolidinonyl, triazolonyl, $N-(R^6)$-dioxothiazolidinyl or dioxothiazinyl, and is substituted with 0-2 substituents selected from the group consisting of alkyl, hydroxyalkyl, haloalkyl, alkoxyalkyl, and aminoalkyl;

$R^{13}$ is hydrogen, alkyl, alkylcarbonyl, alkoxycarbonyl, benzyloxycarbonyl, or alkylsulfonyl;

$R^{14}$ is $N(R^{15})(R^{15})$, $N(R^{15})$(benzyloxycarbonyl), $N(R^{15})$(alkyloxycarbonyl), $N(R^{15})$((hydroxyalkyl)oxycarbonyl), $N(R^{15})$((alkyloxy)alkyloxycarbonyl), $N(R^{15})CO(R^{16})$, $N(R^{15})((CO(N(R^{15})_2)alkyl)$, $N(R^{15})((CO_2CO(N(R^{15})_2)$ alkyl), $N(R^{15})CO((N(R^{15})_2)alkyl)$, $N(R^{15})CO((CON(R^{15})(R^{15})alkyl)$, $N(R^{15})COCO_2(R^{15})$, $N(R^{15})CO((CO_2(R^{15})$ alkyl), $N(R^{15})COCON(R^X)(R^{15})$, $N(R^{15})COCO((N(R^{15})(R^{15}))alkyl)$, $N(R^{15})CO(N(R^{15})_2)$, $N(R^{15})SO_2R^{16}$, $N(R^{15})SO_2(N(R^{15})_2)$, or $N(R^{15})COAr^3$;

or $R^{14}$ is hydroxy, alkoxy, (hydroxy)alkoxy, (alkoxy)alkoxy, $(R^{16}CO_2)$alkoxy, or $(PhCO_2)$alkoxy;

or $R^{14}$ is $N(R^{15})COCON(R^{15})$(alkoxyalkyl), $N(R^{15})COCON(R^{15})$(hydroxyalkyl), $N(R^{15})COCON(R^{15})$((tetrahydrofuranyl)methyl), $N(R^{15})COCON(R^{15})$((N,N-dimethylpyrazolyl)methyl), or $N(R^{15})CO((Ar^4)alkyl)$;

or $R^{14}$ is

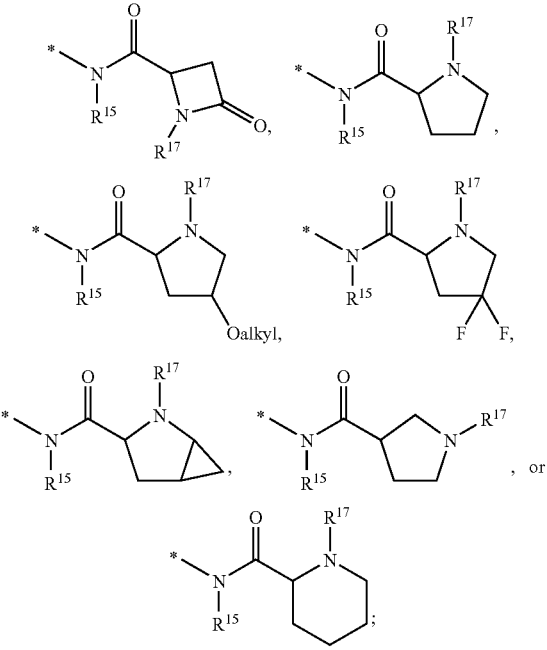

or $R^{14}$ is

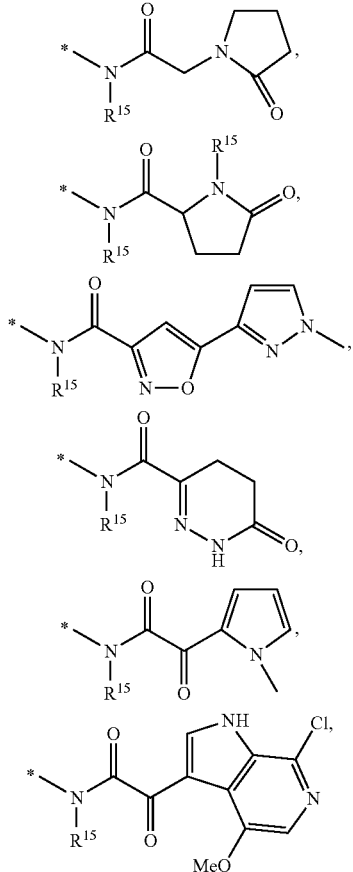

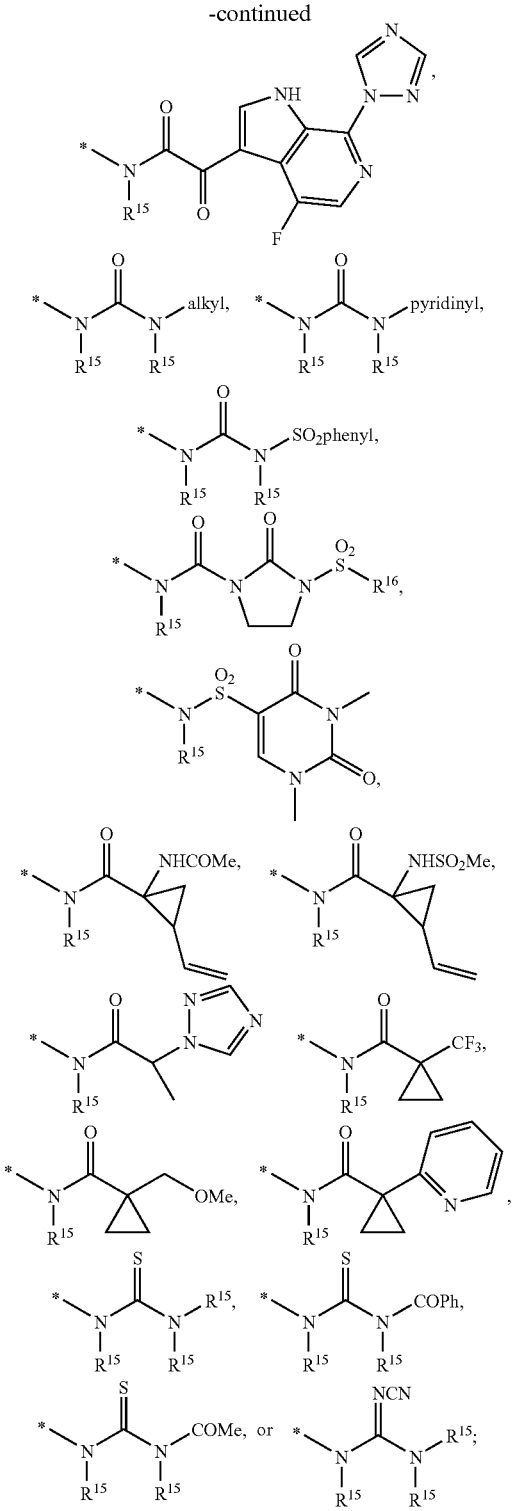

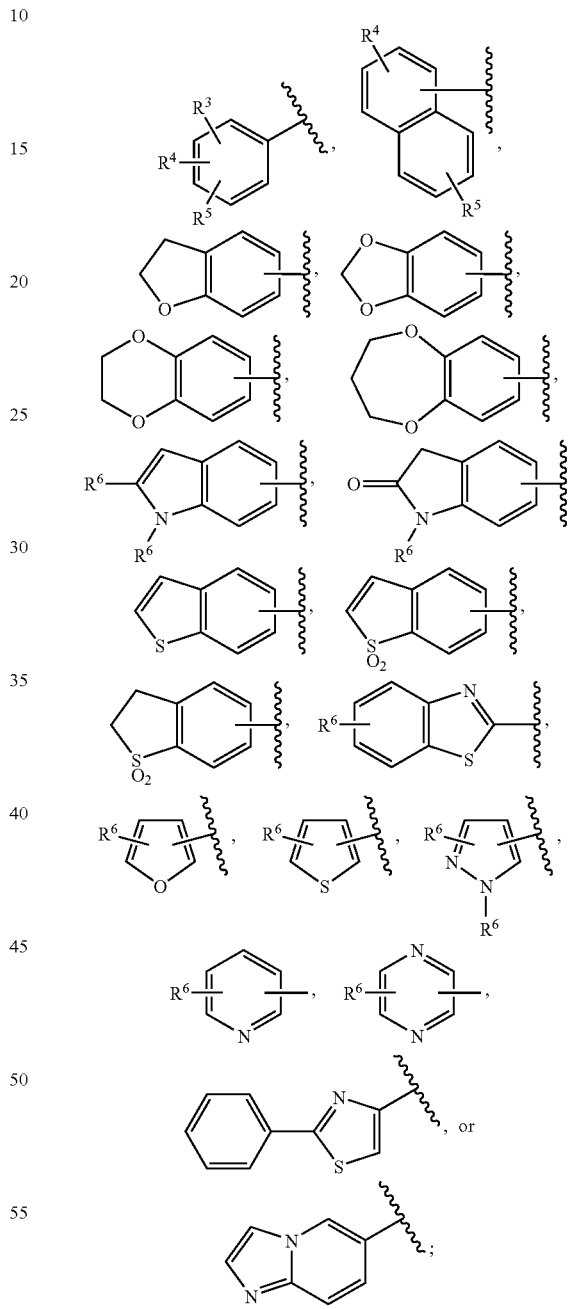

$R^{15}$ is hydrogen, alkyl, hydroxyalkyl, alkoxyalkyl, haloalkyl, or cycloalkyl;

or $N(R^{15})(R^{15})$ taken together is azetidinyl, pyrrolidinyl, $(R^{10})$-piperidinyl, $N-(R^{11})$-piperazinyl, morpholinyl, or thiomorpholinyl, and is substituted with 0-2 substituents selected from halo, hydroxy, alkoxy, alkyl, hydroxyalkyl, alkoxyalkyl, hydroxyalkyloxyalkyl, acetamido, $CO_2R^6$, and $CON(R^8)(R^9)$;

$R^{16}$ is alkyl, haloalkyl, cycloalkyl, (cycloalkyl)alkyl, hydroxyalkyl, alkoxyalkyl, tetrahydropyranyl, or $Ar^3$;

$R^{17}$ is hydrogen, alkyl, alkylCO, cycloalkylCO, alkyloxyCO, $CON(R^{15})(R^{15})$, $COCON(R^{15})(R^{15})$, $COAr_3$, alkylSO$_2$, cycloalkylSO$_2$, furanylSO$_2$, triazolylSO$_2$, or N-methylpyrrolylSO$_2$;

$Ar^1$ is $Ar^2$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, or hydroxypyridinyl, and is substituted with 0-3 substituents selected from the group consisting of oxo, halo, cyano, benzyl, alkyl, alkoxy, $N(R^8)(R^9)$, $CO_2R^6$, and $CON(R^8)(R^9)$;

Ar³ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyridinyl, pyrimidinyl, pyrazinyl, imidazopyridinyl, quinolinyl, isoquinolinyl, or phenyl, and is substituted with 0-3 substituents selected from the group consisting of oxo, halo, alkoxy, haloalkoxy, cyano, benzyl, alkyl, haloalkyl, N(R⁸)(R⁹), and N(R¹⁵)CO(R¹⁶);

Ar⁴ is pyrazolyl or triazolyl, and is substituted with 0-1 substituents selected from CO₂R⁶ and CON(R⁸)(R⁹);

X—Y—Z is

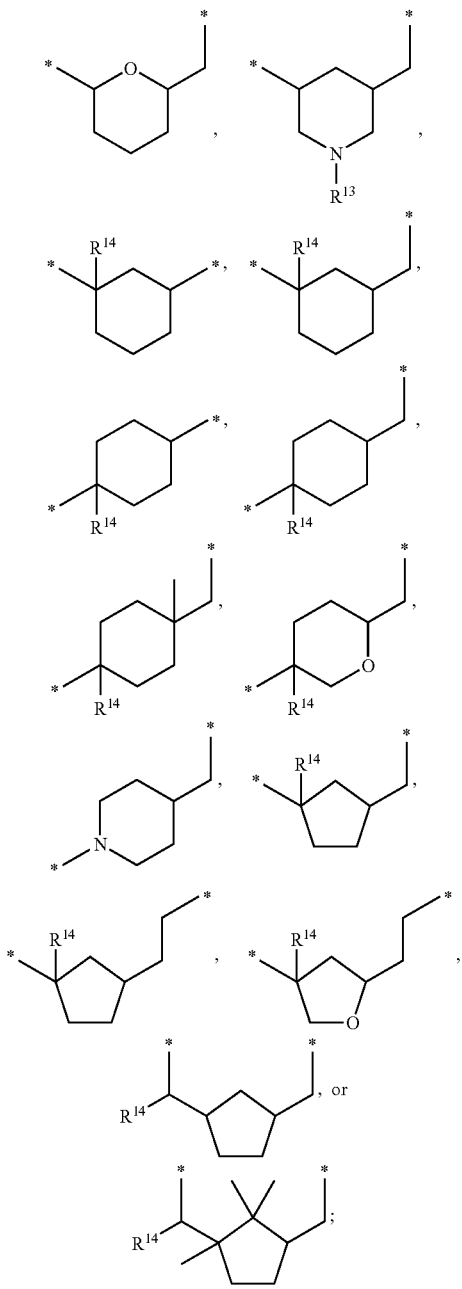

or a pharmaceutically acceptable salt thereof.

Another aspect of the invention is a compound of formula I wherein:

R¹ is (Ar¹)alkyl;
R² is hydrogen, alkyl, hydroxy or alkoxy;
R³ is hydrogen, halo, hydroxy, cyano, alkyl, haloalkyl, alkoxy, haloalkoxy, N(R⁸)(R⁹), N(R⁶)COR⁷, N(R⁶)SO₂R⁷, N(R⁶)CO₂R⁷, N(R⁶)SO₂N(R⁸)(R⁹), CO₂R⁶, CON(R⁸)(R⁹), SOR⁷, SO₂R⁷, SO₂N(R⁸)(R⁹), PO(OR⁶)₂, R¹², or Ar²;

R⁴ is hydrogen, halo, hydroxy, cyano, alkyl, alkoxy, haloalkyl, haloalkoxy, or N(R⁶)(R⁶);

R⁵ is hydrogen, halo, hydroxy, cyano, alkyl, alkoxy, haloalkyl, haloalkoxy, or N(R⁶)(R⁶);

R⁶ is hydrogen, alkyl, haloalkyl, or cycloalkyl;

R⁷ is alkyl, haloalkyl, or cycloalkyl;

R⁸ is hydrogen, alkyl, haloalkyl, hydroxyalkyl, alkoxyalkyl or dialkylaminoalkyl;

R⁹ is hydrogen, alkyl, haloalkyl, hydroxyalkyl, alkoxyalkyl or dialkylaminoalkyl; or N(R⁸)(R⁹) taken together is azetidinyl, pyrrolidinyl, (R¹⁰)-piperidinyl, N—(R¹¹)-piperazinyl, morpholinyl, thiomorpholinyl, or dioxothiazinyl;

R¹⁰ is hydrogen, alkyl, hydroxy, or hydroxyalkyl;

R¹¹ is hydrogen, alkyl, cyclolkyl, COR⁶, or CO₂R⁶;

R¹² is azetidinonyl, pyrrolidinonyl, valerolactamyl, caprolactamyl, maleimido, oxazolidinonyl, imidazolidinonyl, triazolonyl, N—(R⁶)-dioxothiazolidinyl or dioxothiazinyl, and is substituted with 0-2 substituents selected from the group consisting of alkyl, hydroxyalkyl, haloalkyl, alkoxyalkyl, and aminoalkyl;

R¹³ is hydrogen, alkyl, alkylcarbonyl, alkoxycarbonyl, benzyloxycarbonyl, or alkylsulfonyl;

R¹⁴ is N(R¹⁵)(R¹⁵), N(R¹⁵)(benzyloxycarbonyl), N(R¹⁵)(alkyloxycarbonyl), N(R¹⁵)CO(R¹⁶), N(R¹⁵)CO(alkyl(N(R¹⁵)₂)), N(R¹⁵)COCO₂(R¹⁵), N(R¹⁵)COCON(R¹⁵)(R¹⁵), N(R¹⁵)CO(N(R¹⁵)₂), N(R¹⁵)SO₂R¹⁶, N(R¹⁵)SO₂(N(R¹⁵)₂), or N(R¹⁵)COAr³;

or R¹⁴ is hydroxy, alkoxy, (hydroxy)alkoxy, (alkoxy)alkoxy, (R¹⁶CO₂)alkoxy, or (PhCO₂)alkoxy;

or R¹⁴ is

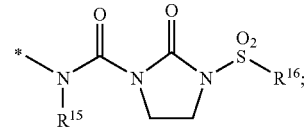

R¹⁵ is hydrogen, alkyl, haloalkyl, or cycloalkyl;

or N(R¹⁵)(R¹⁵) taken together is azetidinyl, pyrrolidinyl, (R¹⁰)-piperidinyl, N—(R¹¹)-piperazinyl, morpholinyl, or thiomorpholinyl;

R¹⁶ is alkyl, haloalkyl, or cycloalkyl;

Ar¹ is

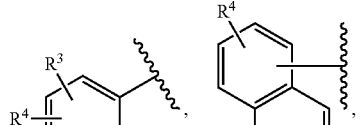

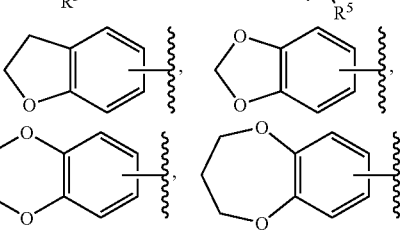

-continued

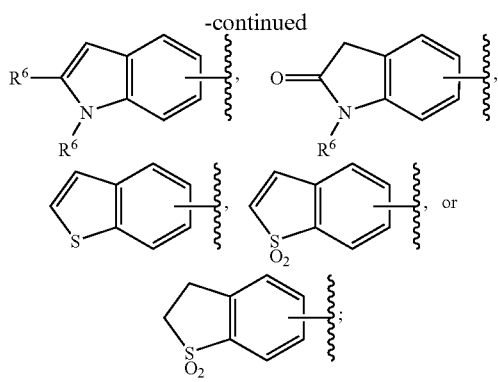

Ar² is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, or hydroxypyridinyl, and is substituted with 0-3 substituents selected from the group consisting of oxo, halo, cyano, benzyl, alkyl, alkoxy, $N(R^8)(R^9)$, $CO_2R^6$, and $CON(R^8)(R^9)$;

Ar³ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, or pyridinyl, and is substituted with 0-3 substituents selected from the group consisting of oxo, halo, alkoxy, cyano, benzyl, and alkyl; and X—Y—Z is

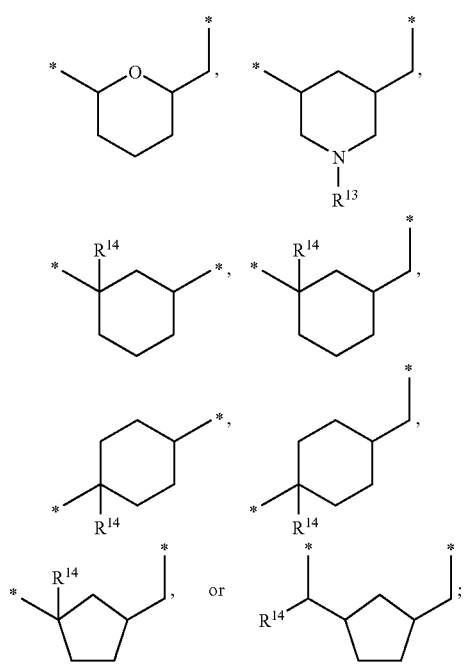

or a pharmaceutically acceptable salt thereof.

Another aspect of the invention is a compound of formula I where $R^1$ is (Ar¹)alkyl, alkyl, (cycloalkyl)alkyl, diphenylalkyl, phenoxyalkyl, (PhNH)alkyl, (methylpyrrolidinyl)alkyl, (imidazolyl)alkyl(valerolactamyl)alkyl, (tetrahydrofuranyl)alkyl, ((fluoro)(methyl)pyridinyl)methyl, phenylcyclopropyl, or benzylpyrrolidinyl;

$R^2$ is hydrogen;

$R^3$ is hydrogen, halo, hydroxy, alkoxy, cyano, alkyl, cycloalkyl, haloalkyl, hydroxyalkyl, alkoxyalkyl, alkoxy, haloalkoxy, $N(R^8)(R^9)$, $N(R^6)COR^7$, $N(R^6)SO_2R^7$, $N(R^6)CO_2R^7$, $N(R^6)SO_2N(R^8)(R^9)$, $CO_2R^6$, $CON(R^8)(R^9)$, $SO_2R^7$, $SO_2N(R^8)(R^9)$, or Ar²;

$R^4$ is hydrogen, halo, or alkyl;

$R^5$ is hydrogen, halo, or alkyl;

$R^6$ is hydrogen, alkyl, haloalkyl, or cycloalkyl;

$R^7$ is alkyl, haloalkyl, or cycloalkyl;

$R^8$ is hydrogen, alkyl, haloalkyl, hydroxyalkyl, alkoxyalkyl or dialkylaminoalkyl;

$R^9$ is hydrogen, alkyl, haloalkyl, hydroxyalkyl, alkoxyalkyl or dialkylaminoalkyl; or $N(R^8)(R^9)$ taken together is azetidinyl, pyrrolidinyl, $(R^{10})$-piperidinyl, $N—(R^{11})$-piperazinyl, morpholinyl, thiomorpholinyl, or dioxothiazinyl;

$R^{10}$ is hydrogen, alkyl, hydroxy, or hydroxyalkyl;

$R^{11}$ is hydrogen, alkyl, cyclolkyl, hydroxyalkyl, alkoxyalkyl, hydroxyalkoxyalkyl, phenyl, pyridinyl, (methylimidazolyl)methyl, $COR^6$, $CO_2R^6$, (hydroxyalkyl)CO, (alkoxyalkyl)CO, (tetrahydrofuranyl)CO, (methylisoxazolyl)CO, (thienyl)CO, (furanyl)CO, (pyridinyl)CO, $CON(R^8)(R^9)$, $SO_2R^7$, $SO_2N(R^8)(R^9)$, (dimethylisoxazolyl)$SO_2$, ((carboethoxy)thienyl)$SO_2$, (methylimidazolyl)$SO_2$,

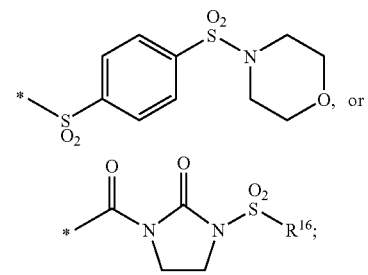

$R^{13}$ is hydrogen, alkyl, alkylcarbonyl, alkoxycarbonyl, benzyloxycarbonyl, or alkylsulfonyl;

$R^{14}$ is $N(R^{15})(R^{15})$, $N(R^{15})$(benzyloxycarbonyl), $N(R^{15})$(alkyloxycarbonyl), $N(R^{15})$((hydroxyalkyl)oxycarbonyl), $N(R^{15})$((alkyloxy)alkyloxycarbonyl), $N(R^{15})CO(R^{16})$, $N(R^{15})((CO(N(R^{15})_2)alkyl)$, $N(R^{15})((CO_2CO(N(R^{15})_2)alkyl)$, $N(R^{15})CO((N(R^{15})_2)alkyl)$, $N(R^{15})CO((CON(R^{15})(R^{15})alkyl)$, $N(R^{15})COCO_2(R^{15})$, $N(R^{15})CO((CO_2(R^{15})alkyl)$, $N(R^{15})COCON(R^{15})(R^{15})$, $N(R^{15})COCO((N(R^{15})(R^{15}))alkyl)$, $N(R^{15})CO(N(R^{15})_2)$, $N(R^{15})SO_2R^{16}$, $N(R^{15})SO_2(N(R^{15})_2)$, or $N(R^{15})COAr^3$;

or $R^{14}$ is hydroxy, alkoxy, (hydroxy)alkoxy, (alkoxy)alkoxy, $(R^{16}CO_2)$alkoxy, or $(PhCO_2)$alkoxy;

or $R^{14}$ is $N(R^{15})COCON(R^{15})$(alkoxyalkyl), $N(R^{15})COCON(R^{15})$(hydroxyalkyl), $N(R^{15})COCON(R^{15})$((tetrahydrofuranyl)methyl), $N(R^{15})COCON(R^{15})$((N,N-dimethylpyrazolyl)methyl), or $N(R^{15})CO((Ar^4)alkyl)$;

or $R^{14}$ is

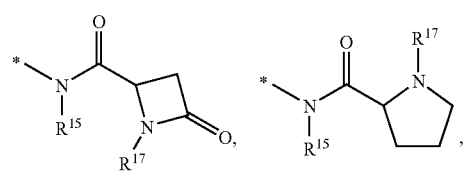

-continued

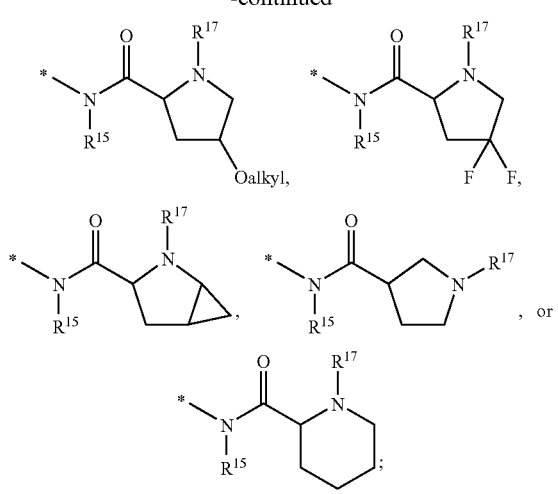

or $R^{14}$ is

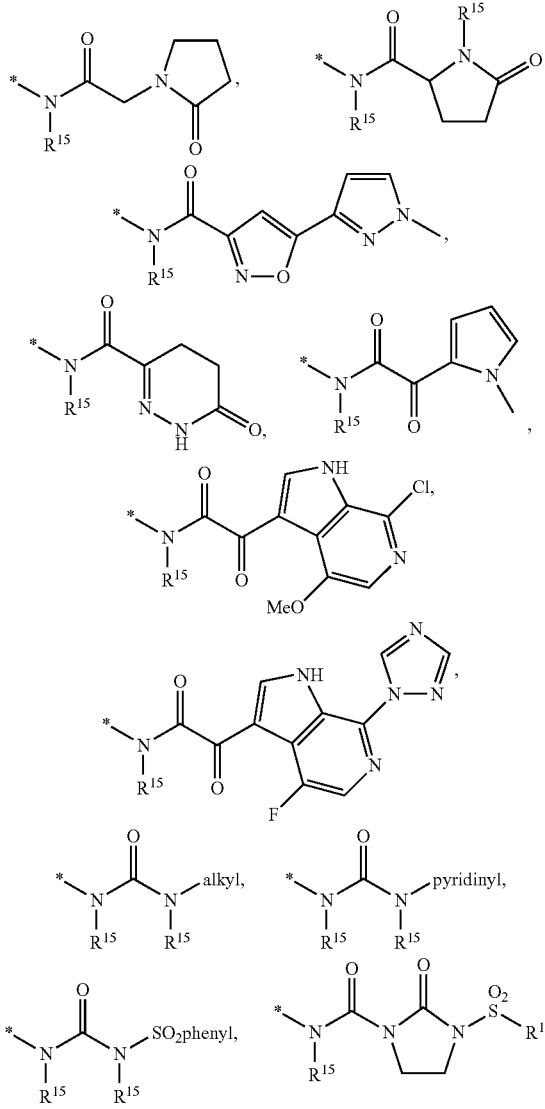

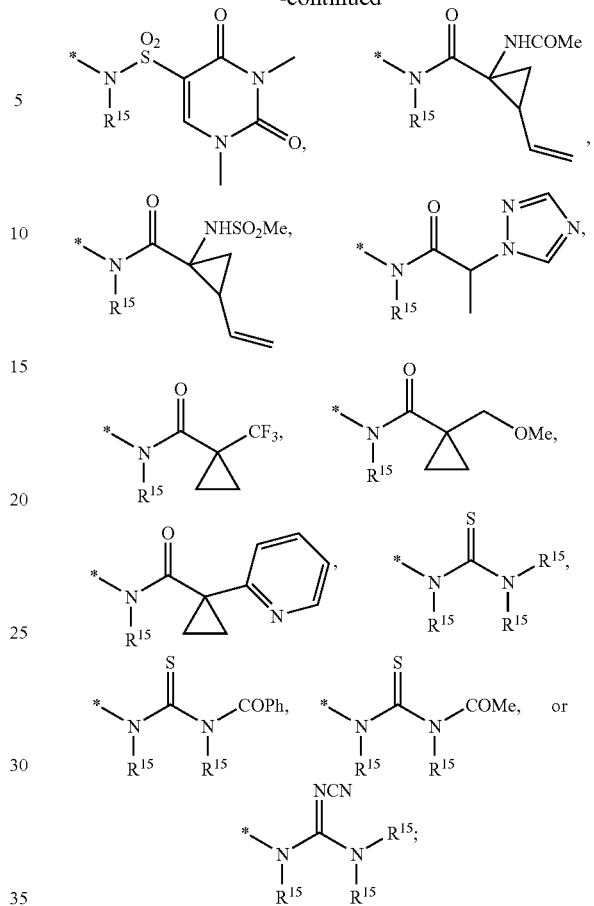

$R^{15}$ is hydrogen, alkyl, hydroxyalkyl, alkoxyalkyl, haloalkyl, or cycloalkyl;

or $N(R^{15})(R^{15})$ taken together is azetidinyl, pyrrolidinyl, $(R^{10})$-piperidinyl, $N-(R^{11})$-piperazinyl, morpholinyl, or thiomorpholinyl, and is substituted with 0-2 substituents selected from halo, hydroxy, alkoxy, alkyl, hydroxyalkyl, alkoxyalkyl, hydroxyalkyloxyalkyl, acetamido, $CO_2R^6$, and $CON(R^8)(R^9)$;

$R^{16}$ is alkyl, haloalkyl, cycloalkyl, (cycloalkyl)alkyl, hydroxyalkyl, alkoxyalkyl, tetrahydropyranyl, or $Ar^3$;

$R^{17}$ is hydrogen, alkyl, alkylCO, cycloalkylCO, alkyloxyCO, $CON(R^{15})(R^{15})$, $COCON(R^{15})(R^{15})$, $COAr_3$, alkylSO$_2$, cycloalkylSO$_2$, furanylSO$_2$, triazolylSO$_2$, or N-methylpyrrolylSO$_2$;

$Ar^1$ is

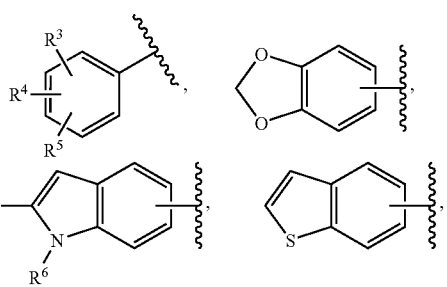

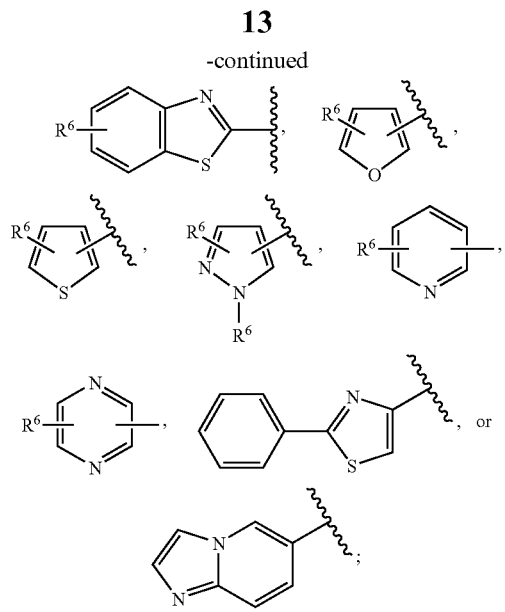

Ar² is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, or hydroxypyridinyl, and is substituted with 0-3 substituents selected from the group consisting of oxo, halo, cyano, benzyl, alkyl, alkoxy, $N(R^8)(R^9)$, $CO_2R^6$, and $CON(R^8)(R^9)$;

Ar³ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyridinyl, pyrimidinyl, pyrazinyl, imidazopyridinyl, quinolinyl, isoquinolinyl, or phenyl, and is substituted with 0-3 substituents selected from the group consisting of oxo, halo, alkoxy, haloalkoxy, cyano, benzyl, alkyl, haloalkyl, $N(R^8)(R^9)$, and $N(R^{15})CO(R^{16})$;

Ar⁴ is pyrazolyl or triazolyl, and is substituted with 0-1 substituents selected from $CO_2R^6$ and $CON(R^8)(R^9)$; and X—Y—Z is

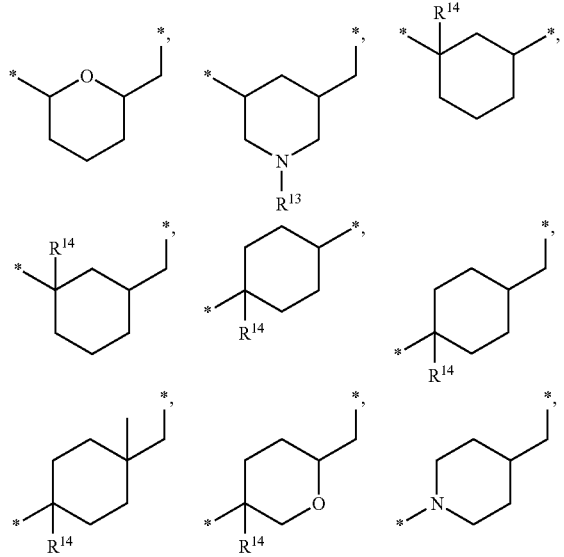

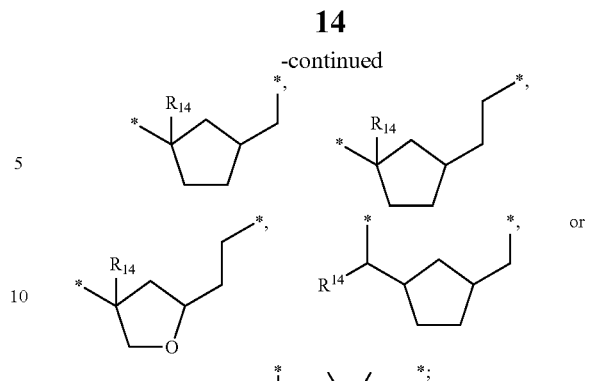

or a pharmaceutically acceptable salt thereof.

Another aspect of the invention is a compound of Formula I where $R^X$ is (Ar¹)alkyl.

Another aspect of the invention is a compound of Formula I where $R^1$ is (Ar¹)alkyl and $R_2$ is hydrogen.

Another aspect of the invention is a compound of Formula I where $R^1$ is

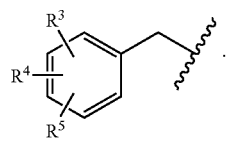

Another aspect of the invention is a compound of Formula I where $R^1$ is

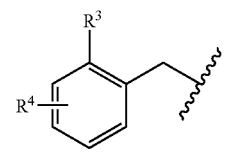

and $R^3$ is other than hydrogen or halo.

Another aspect of the invention is a compound of Formula I where $R^2$ is hydrogen.

Another aspect of the invention is a compound of Formula I where $R^3$ is $R^{12}$.

Another aspect of the invention is a compound of Formula I where $R^3$ is Ar².

Another aspect of the invention is a compound of Formula I where $R^3$ is $CON(R^8)(R^9)$, $SO_2N(R^8)(R^9)$, azetidinonyl, pyrrolidinonyl, valerolactamyl, caprolactamyl, oxazolidinonyl, imidazolidinonyl, dioxothiazinyl, N—(R⁶)-dioxothiazolidinyl, or triazolyl where triazolyl is substituted with 0-2 alkyl or oxo substituents.

Another aspect of the invention is a compound of Formula I where $R^3$ is halo, $CON(R^8)(R^9)$, oxazolidinonyl, or triazolyl where triazolyl is substituted with 0-2 alkyl or oxo substituents.

Another aspect of the invention is a compound of Formula I where $R^{14}$ is $N(R^{15})(R^{15})$, $N(R^{15})$(benzyloxycarbonyl), $N(R^{15})$(alkyloxycarbonyl), $N(R^{15})$((hydroxyalkyl)oxycarbonyl), $N(R^{15})$((alkyloxy)alkyloxycarbonyl), $N(R^{15})CO(R^{16})$, $N(R^{15})((CO(N(R^{15})_2)alkyl)$, $N(R^{15})((CO_2CO$ $(N(R^{15})_2)$alkyl), $N(R^{15})CO((N(R^{15})_2)$alkyl), $N(R^{15})CO$ $((CON(R^{15})(R^{15})$alkyl), $N(R^{15})COCO_2(R^{15})$, $N(R^{15})CO$ $((CO_2(R^{15})$alkyl), $N(R^{15})COCON(R^{15})(R^{15})$, $N(R^{15})$ $COCO((R^{15})(R^{15}))$alkyl), $N(R^{15})CO(N(R^{15})_2)$, $N(R^{15})$ $SO_2R^{16}$, $N(R^{15})SO_2(N(R^{15})_2)$, or $N(R^{15})COAr^3$.

Another aspect of the invention is a compound of Formula I where $R^{14}$ is $N(R^{15})COCON(R^{15})(R^{15})$.

Another aspect of the invention is a compound of Formula I where $Ar^2$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, or pyrrolyl, and is substituted with 0-2 substituents selected from the group consisting of halo and alkyl.

Another aspect of the invention is a compound of Formula I where $Ar^3$ is oxadiazolyl, pyrazolyl, or isoxazolyl.

Another aspect of the invention is a compound of Formula I where X—Y—Z is

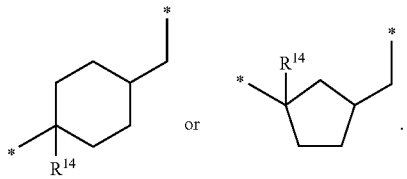

For a compound of Formula I, the scope of any instance of a variable substituent, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $Ar^1$, $Ar^2$, $Ar^3$, $Ar^4$, and X-Y-Z, can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. Parenthetic and multiparenthetic terms are intended to clarify bonding relationships to those skilled in the art. For example, a term such as ((R)alkyl) means an alkyl substituent further substituted with the substituent R.

"Dioxolanyphenyl" means

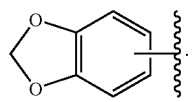

"Dioxothiazolidinyl" means

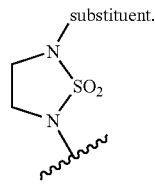

"Dioxothiazinyl" means

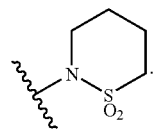

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. One example of a stereoisomeric form is shown below.

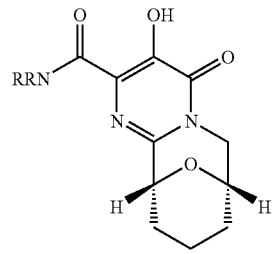

The invention includes all tautomeric forms of the compounds. An example of a tautomeric pair is shown below.

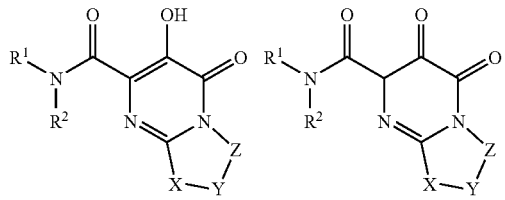

Synthetic Methods

The compounds may be made by methods known in the art including those described below and including variations within the skill of the art. Some reagents and intermediates are known in the art. Other reagents and intermediates can be made by methods known in the art using readily available materials. The following methods are for illustrative purposes and are not intended to limit the scope of the invention. It will be appreciated by those skilled in the art that there are a number of methods available for the synthesis of an appropriately substituted pyrimidinone heterocycles useful for making the compounds of the current invention and that their synthesis is not limited to the methods provided in the following examples. For example, one such method is shown in Scheme I and is similar to that reported in Journal of Heterocyclic Chemistry (1979), 16(7), 1423-4. In this scheme an alkyl- or arylnitrile 1-1 is combined with hydroxylamine to form intermediate 1-2 which in turn is reacted with dialkylbutynoate 1-3 to form intermediate 1-4. At high temperatures, such as that of refluxing xylenes, intermediate 1-4 undergoes a rearrangement reaction to yield the 5-hydroxy-6-oxo-1,6-dihydropyrimidine-4-carboxylate heterocycle 1-5 which can serve as an advanced intermediate for synthesizing some of the compounds of this invention. The variables (e.g. numbered "R" substituents) used to describe the synthesis of the compounds are intended only to illustrate how to make the compounds and are not to be confused with variables used in the claims or in other sections of the specification.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

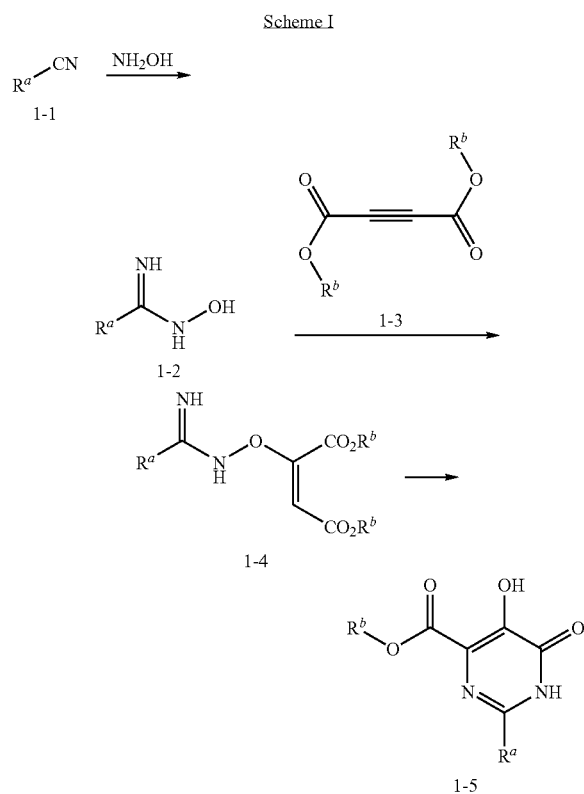

Scheme II demonstrates an alternative method for providing the 5-hydroxy-6-oxo-1,6-dihydropyrimidine-4-carboxylate heterocyclic system which is adapted from the procedure in Inorganic Chemistry (2001), 40(26), 6746-6756. In this scheme, a substituted derivative of glycolic acid, 2-1 is reacted with a diester of oxalic acid under Claisen condensation conditions (Org. React. 1, 266-322 (1942); Modern Synthetic Reactions (W. A. Benjamin, Menlo Park, Calif., 2nd ed., 1972) pp 734-746, J. Chem. Educ. 56, 721 (1979); J. Am. Chem. Soc. 103, 1338 (1981); Comp. Org. Syn. 2, 795-805 (1991)) to provide intermediate 2-2. This intermediate can be combined with an amidine, 2-3, under heating to yield the 5-hydroxy-6-oxo-1,6-dihydropyrimidine-4-carboxylate heterocycle, 2-4.

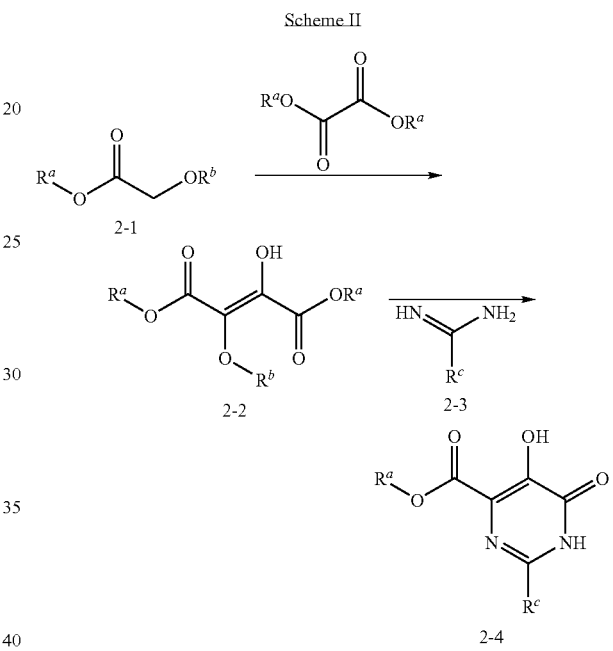

In Scheme III, peracylated glycoside 3-1 can be converted to intermediate 3-2 using synthetic procedures known to those skilled in the art, for example the method described in Carbohydrate Research (1982), 108(2), 229-35. Following this, a method similar to that described in Journal of Organic Chemistry (1988), 53(16), 3723-31 can be used to eliminate the acetoxy group at C-4 yielding a mixture of compounds, 3-3 and 3-4, which upon hydrogenation produce intermediate 3-5. The acetyl group of 3-5 can be removed using common conditions familiar to those skilled in the art. The synthesis of the 5-hydroxy-6-oxo-1,6-dihydropyrimidine-4-carboxylate ring of 3-7 can be assembled as described in Scheme I. Intermediate 3-7 is then treated with >3 equivalents of methanesulfonyl chloride and diisopropylethylamine to yield 3-8 which when treated with a base such as $K_2CO_3$ produces the bridged tricyclic-fused, 5-hydroxy-6-oxo-1,6-dihydropyrimidine-4-carboxylate template, 3-8. This intermediate can be converted to the corresponding amide, 3-10, using standard amide bond forming procedures familiar to those skilled in the art. For example, in one method intermediate 3-9 can be combined with the amine, 3-11 and a base such as triethylamine and the mixture heated to effect aminolysis of the ester bond. In another method the hydroxyl group of 3-9 is modified with a protecting group such as benzyl, or a group such as those mentioned in Greene's Protective Groups in Organic Synthesis, 4th Edition, Peter G. M. Wuts, Theodora W. Greene, John Wiley & Sons, Inc. 2007, Hoboken N.J. Following this the ester is hydrolyzed to the corresponding carboxylic acid and this is coupled with the amine 3-11 using an amide bond forming reagent such as N,N'-dicyclohexylcarbodiimide, O-benzotriazol-1-yl-N,N,N',N'-bis(pentamethylene)uronium hexafluorophosphate, 1-[3-(dimethylamino)propyl]-3-ethylcarbodiimide methiodide, bromotripyrrolidinophosphonium hexafluorophosphate or other amide bond forming reagents familiar to those skilled in the art. Following this the protecting is removed to produce 3-10.

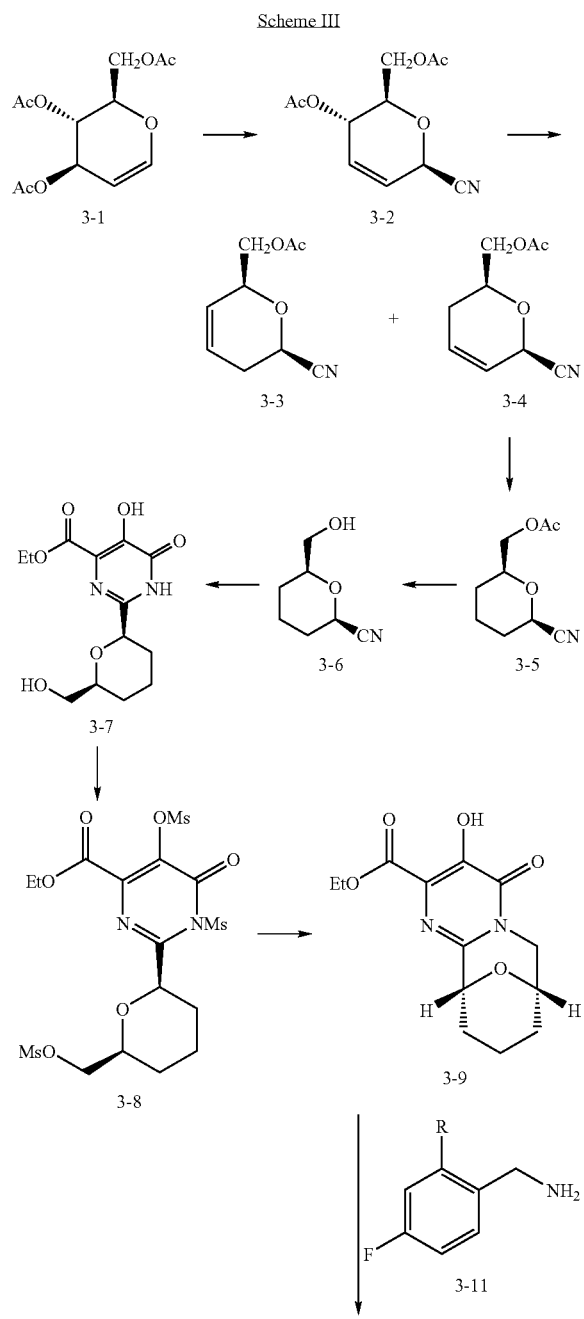

Scheme III

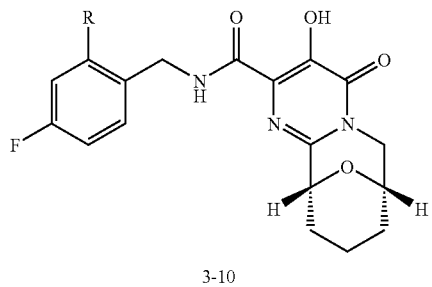

3-10

In Scheme IV, intermediate 4-1 (Tetrahedron Letters (1994), 35(26), 4515-18 and references cited therein) is reacted with benzyl bromide, in the presence of a base such as $K_2CO_3$, to form the N-benzyl derivative 4-2 (Synth. Commun. 1997, 27 (1), 69-71). It will be appreciated by those skilled in the art that the benzyl group attached to 4-2 serves as a protecting group and that other nitrogen protecting groups could be used in its place. The diester, 4-2 can be treated with lithium aluminum hydride to form the bis-alcohol 4-3. Upon treatment of this intermediate with 1 molar equivalent of tert-butyldiphenylsilyl chloride and sodium hydride the protected intermediate 4-3 is formed. Treatment of this intermediate using Swern reaction conditions (Tetrahedron 34, 1651 (1978)), affords intermediate 4-5. It will be appreciated by those skilled in the art that a number of procedures are available for the conversion of an alcohol to an aldehyde, such as those described in Comprehensive Organic Transformations: A Guide to Functional Group Preparations, Second Edition, Richard C. Larock, John Wiley and Sons, 1999, New York, N.Y. The aldehyde 4-5 can be is condensed with hydroxylamide to form intermediate 4-6, which is then transformed to the nitrile 4-7. One skilled in the art will appreciate that there are a number of methods available for transforming intermediates such as 4-6 into 4-7. For example Comprehensive Organic Functional Group Transformations II, Alan R. Katritzky, Otho Meth-Cohn, and Charles W. Rees, Elsevier, 1995. Upon treatment of this intermediate with hydroxylamine followed by dialkyl-butynoate, intermediate 4-9 is produced. Formation of the 5-hydroxy-6-oxo-1,6-dihydropyrimidine-4-carboxylate heterocycle and cyclization to form the bridged tricyclic fused ring system can be carried out as described in the previous schemes to afford intermediate 4-11. The ethylene-dicarboxylate group attached to the nitrogen atom of 4-11 can be removed under acidic conditions. The nitrogen is next protected as the corresponding benzylcarbamate (Cbz) using benzylchloroformate and diisopropyldiethylamine to yield 4-13. Amidation to form 4-14 can be accomplished as described previously and following this, removal of the Cbz-protecting group produces 4-15.

Scheme IV
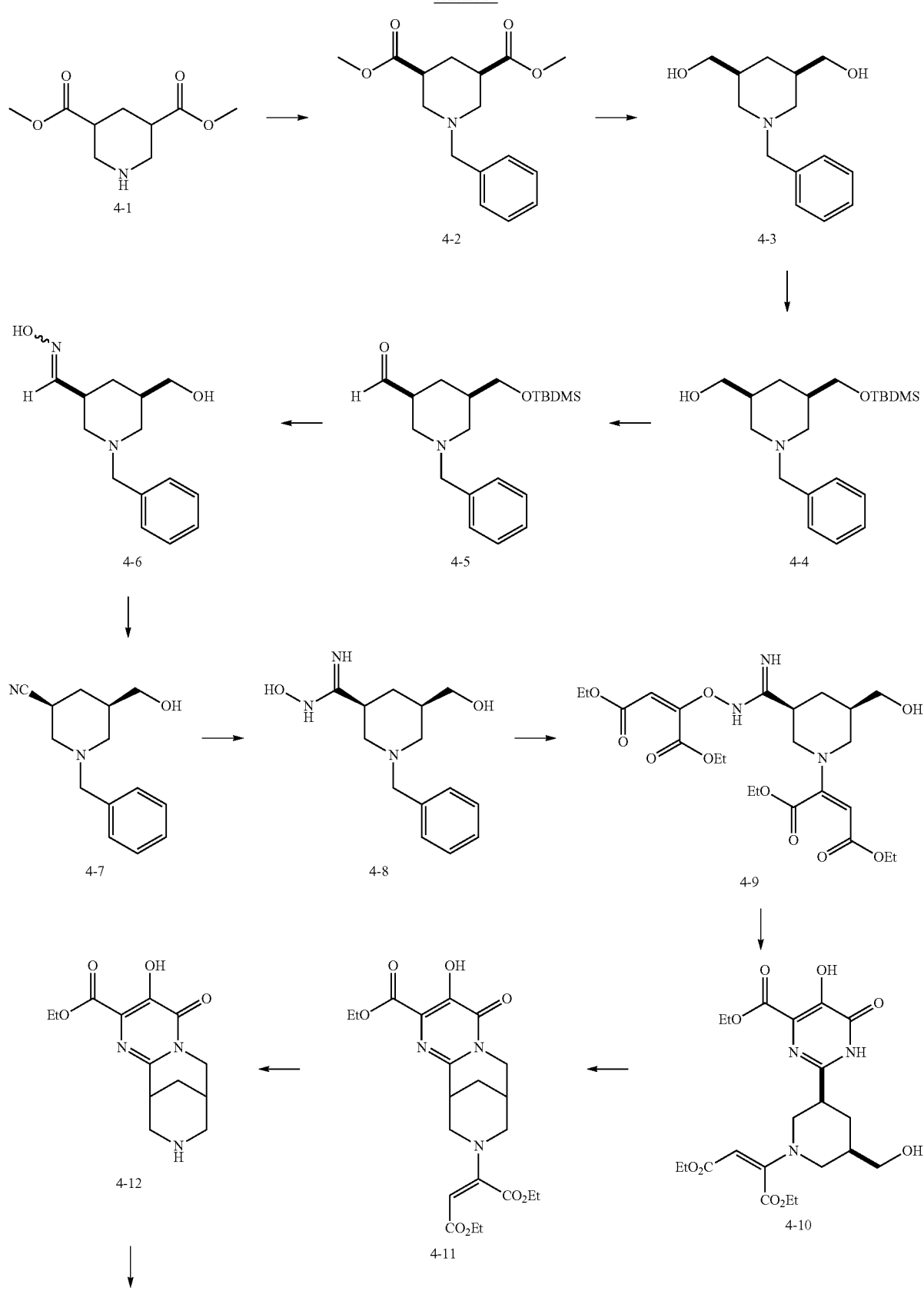

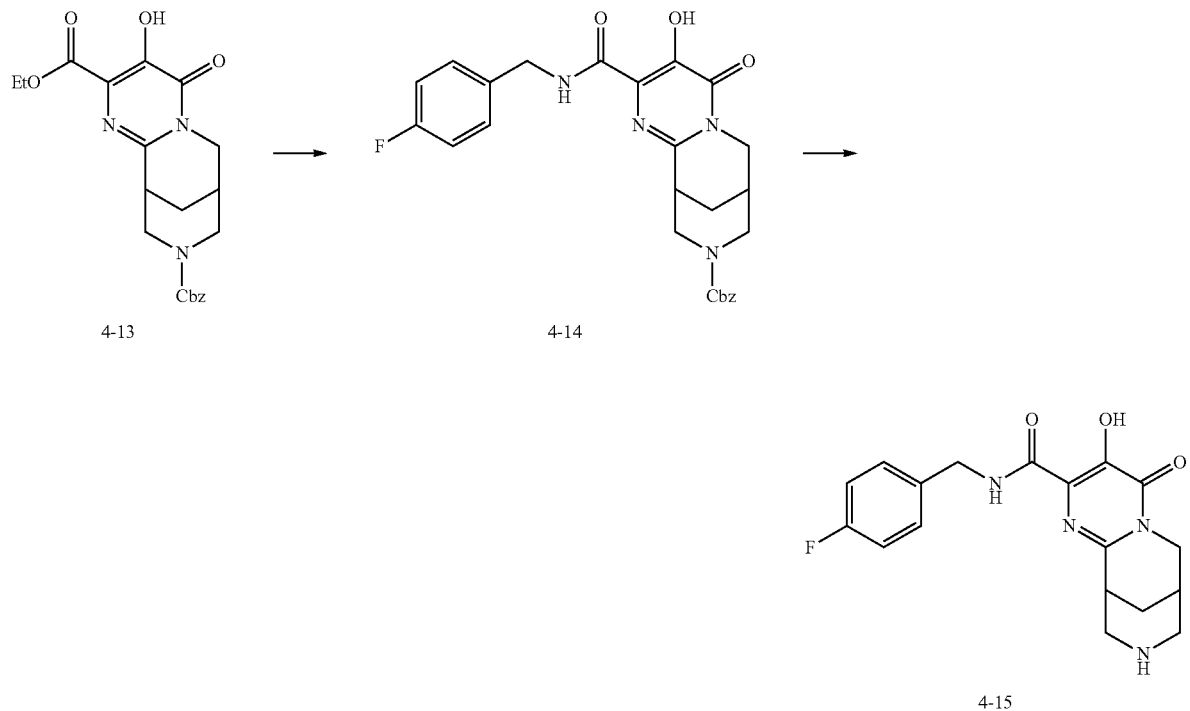

In Scheme V, diol 5-1 (Tetrahedron Letters (1971), (39), 3587-9; Journal of Organic Chemistry (1975), 40(17), 2488-95) is treated with tert-butyl dimethylsilylchloride in the presence of sodium hydride to deliver intermediate 5-2. Oxidation of this compound under Swern conditions, similar to that described above, yields aldehyde 5-3. Intermediate 5-4 can be synthesized by reacting 5-3 with methylamine and potassium cyanide in methanol. Following protection of the nitrogen group as the corresponding Cbz-derivative, the tert-butylsilyl protecting group can be removed to provide intermediate 5-6. Formation of the 5-hydroxy-6-oxo-1,6-dihydropyrimidine-4-carboxylate heterocycle and cyclization to form the bridged tricyclic fused ring system, as described in the previous schemes, affords intermediate 5-9.

Scheme V

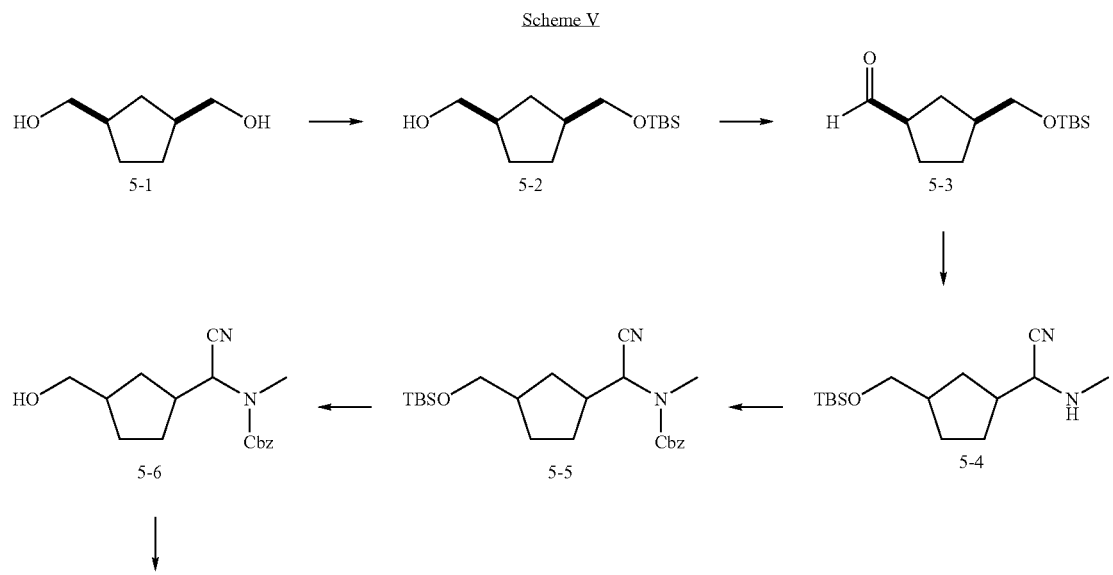

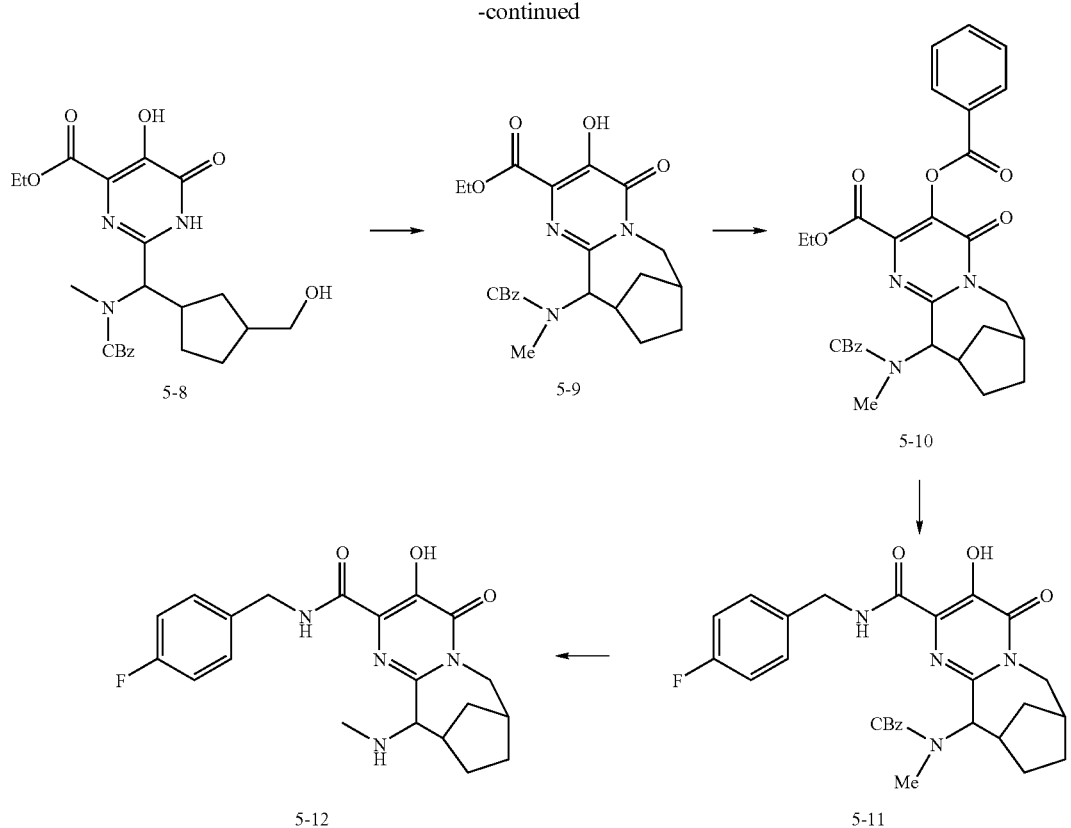

Scheme VI describes yet another method for the synthesis of compounds of this invention. In this method, intermediate 6-1 is converted to the corresponding diester, 6-3, via the anhydride 6-2. Reduction of the ester groups to provide intermediate 6-4, can be accomplished using procedures familiar to those skilled in the art. The subsequent synthetic steps from intermediate 6-4 to the final compound 6-10 can be accomplished using methods similar to those described in the schemes above.

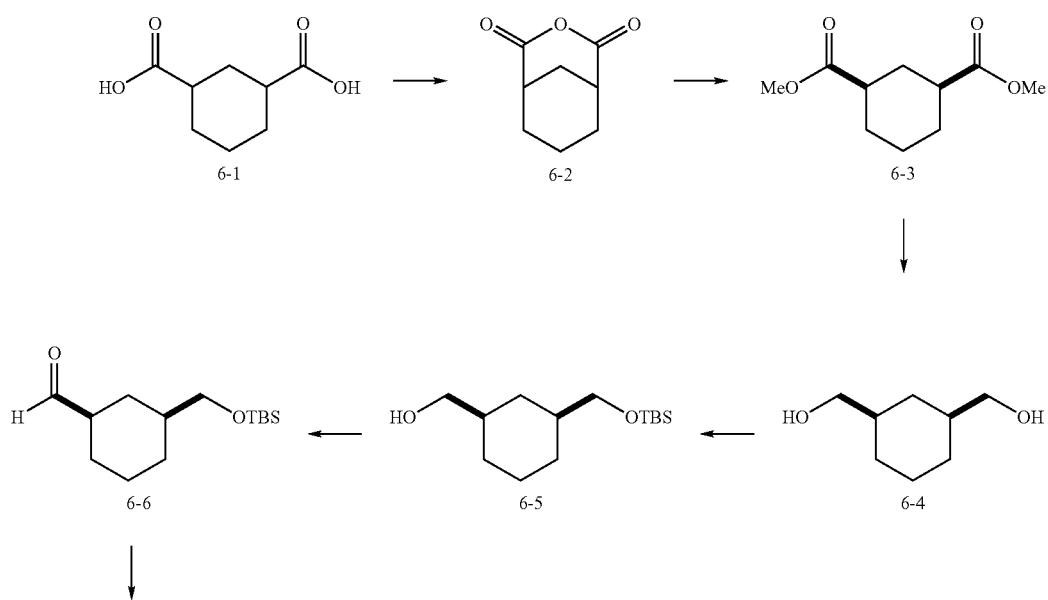

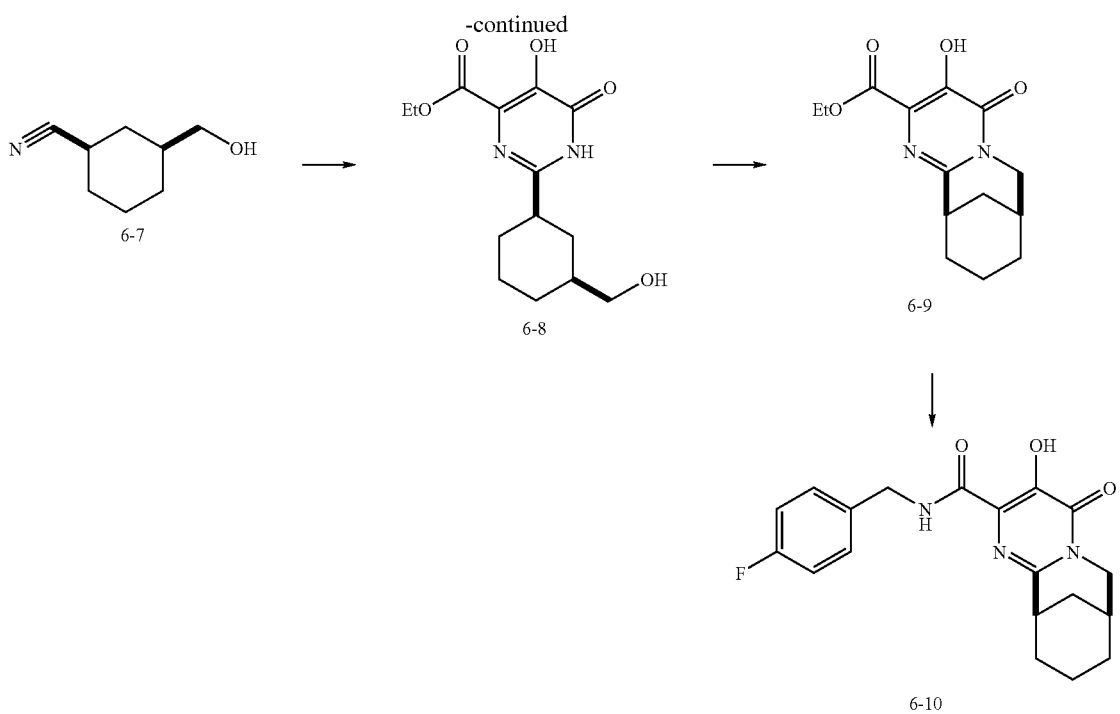
In Scheme VII, intermediate 5-3 is reacted with hydroxylamine to form, 7-1 and converted into the corresponding nitrile 7-2, as described above in Scheme IV for the synthesis of intermediate 4-7. The synthesis of compound 7-8 can be accomplished using methods similar to hose described in the schemes above.
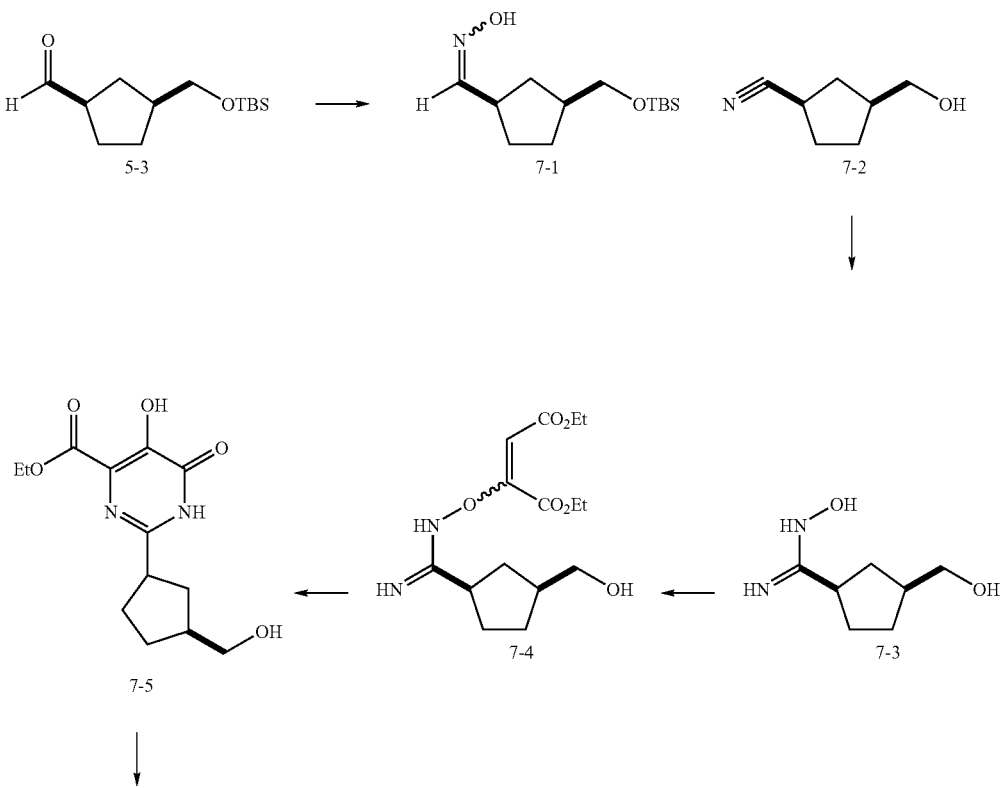

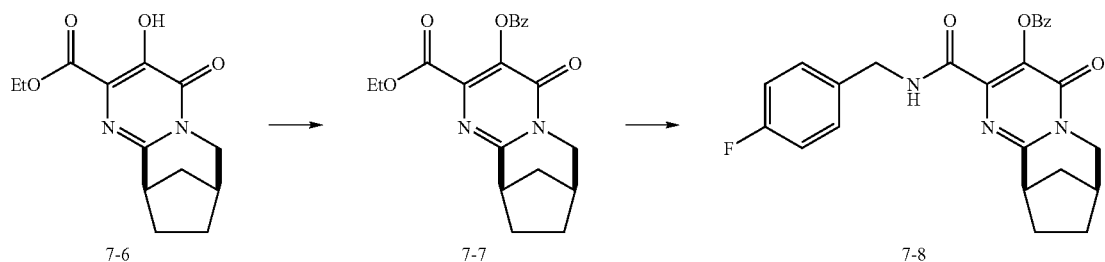

Treatment of intermediate 8-1, in Scheme VIII, under Strecker reaction conditions (Greenstein, M. Winitz, Chemistry of the Amino Acids vol. 3 (New York, 1961) pp 698-700, G. C. Barrett, Chemistry and Biochemistry of the Amino Acids (Chapman and Hall, New York, 1985) pp 251, 261) provides the amino nitrile 8-2. After protection of the amino-group as the corresponding Cbz-derivative, the 5-hydroxy-6-oxo-1,6-dihydropyrimidine-4-carboxylate heterocycle is formed by sequentially treating the nitrile with, hydroxylamine and diethyl but-2-ynedioate, then heating in xylenes. The cyclic ketal protecting group can be hydrolyzed under acidic conditions to furnish the ketone 8-5 which is then reduced with $NaBH_4$ to provide intermediate 8-6. Cyclization to form intermediate 8-7, can be achieved by first treating this intermediate with methane sulfonyl chloride/triethylamine, to effect mesylation of the hydroxyl group followed by treatment with cesium carbonate. The Cbz-group is hydrolytically removed under standard conditions resulting in intermediate 8-8. Formation of the corresponding 4-fluorobenzylamide can be accomplished using the methods described above. Intermediate 8-9 is then treated with an activated carboxylic acid, for example and acid chloride, or a carboxylic acid in the presence of an amide bond forming reagent to yield compound 8-10.

Scheme VIII

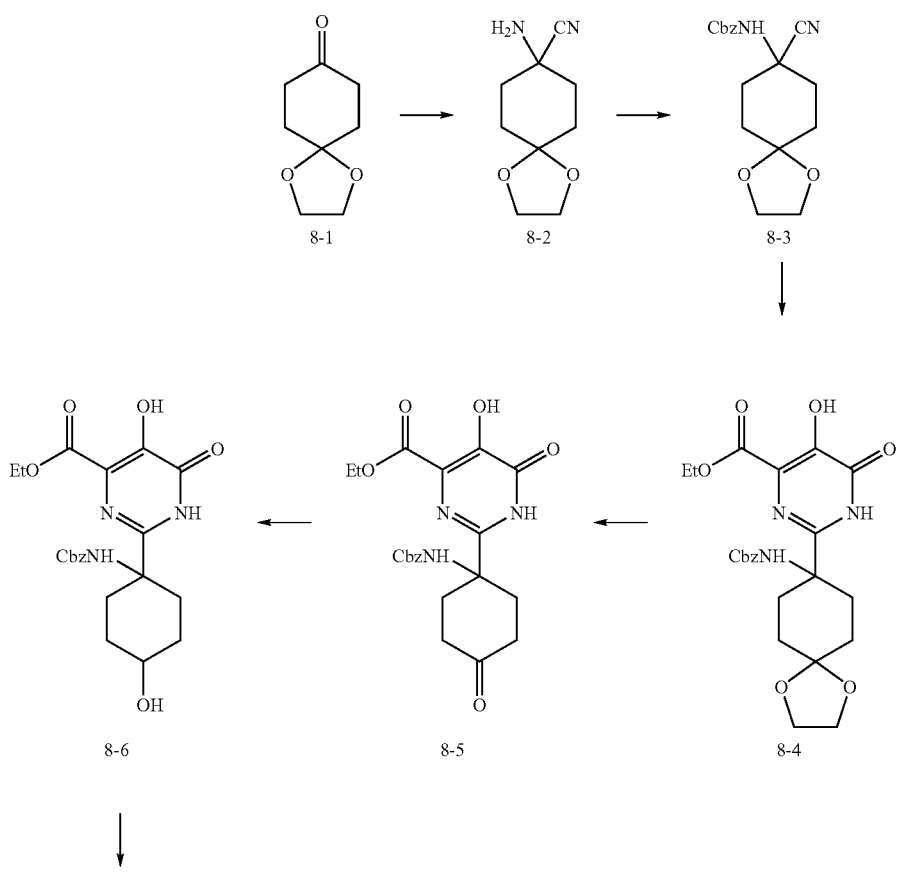

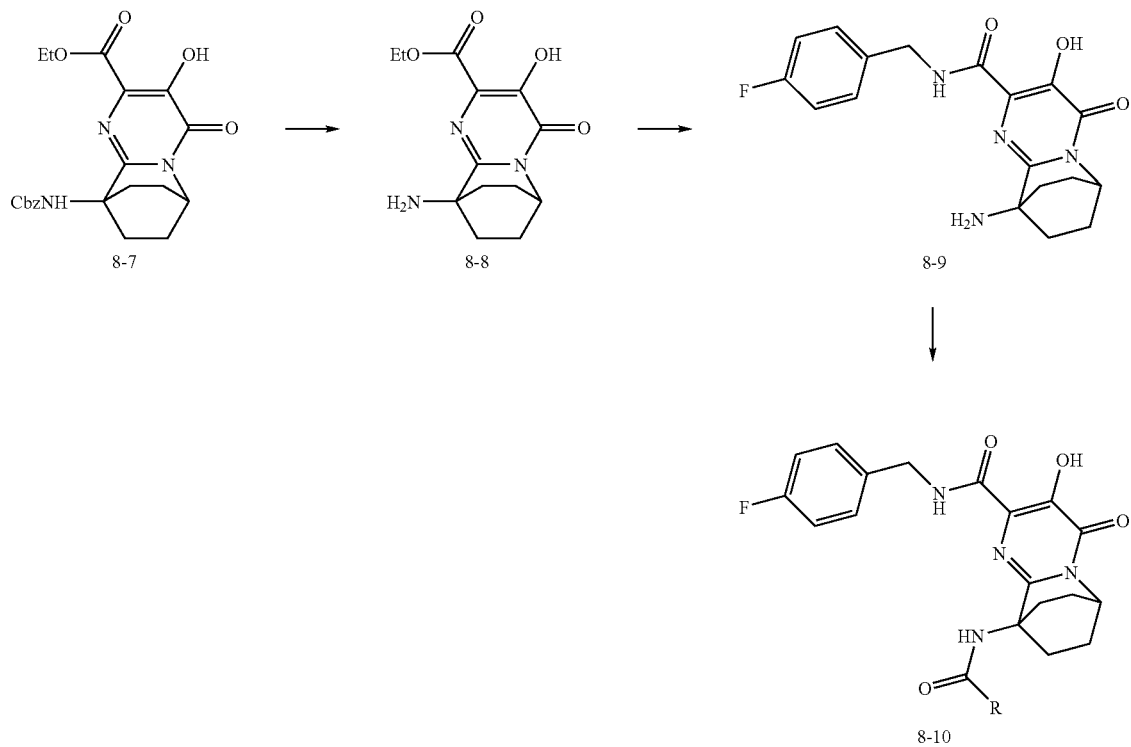

Scheme IX illustrates a method for the synthesis of intermediate 9-10. In the first step of the sequence compound 9-1 is treated with ethane 1,2-diol and toluene sulfonic acid which yields intermediate 9-2. The carboxylic ester group of 9-2 is reduced using lithium aluminum hydride affording 9-3. Treatment of this intermediate with SOCl$_2$ produces the chloride derivative 9-4. It will be appreciated by those skilled in the art that numerous methods exist for the substitution of an alcohol group with chloride some of which can be found in Comprehensive Organic Transformations: A Guide to Functional Group Preparations, Second Edition, Richard C. Larock, John Wiley and Sons, 1999, New York, N.Y. Hydrolysis of the cyclic ketal group of intermediate 9-4 provides a ketone, 9-5, which can be taken on as described in the previous schemes, to the 5-hydroxy-6-oxo-1,6-dihydropyrimidine-4-carboxylate derivative 9-9. Under basic conditions the tricyclic ring system is formed via nucleophilic displacement of the chloride group. Compound 9-10 can serve as an advanced intermediate in the synthesis of compounds of this invention.

Scheme IX

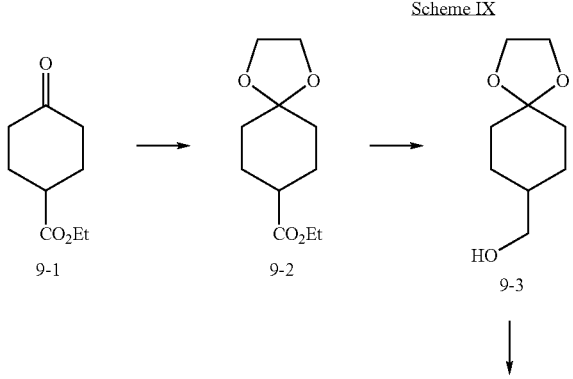

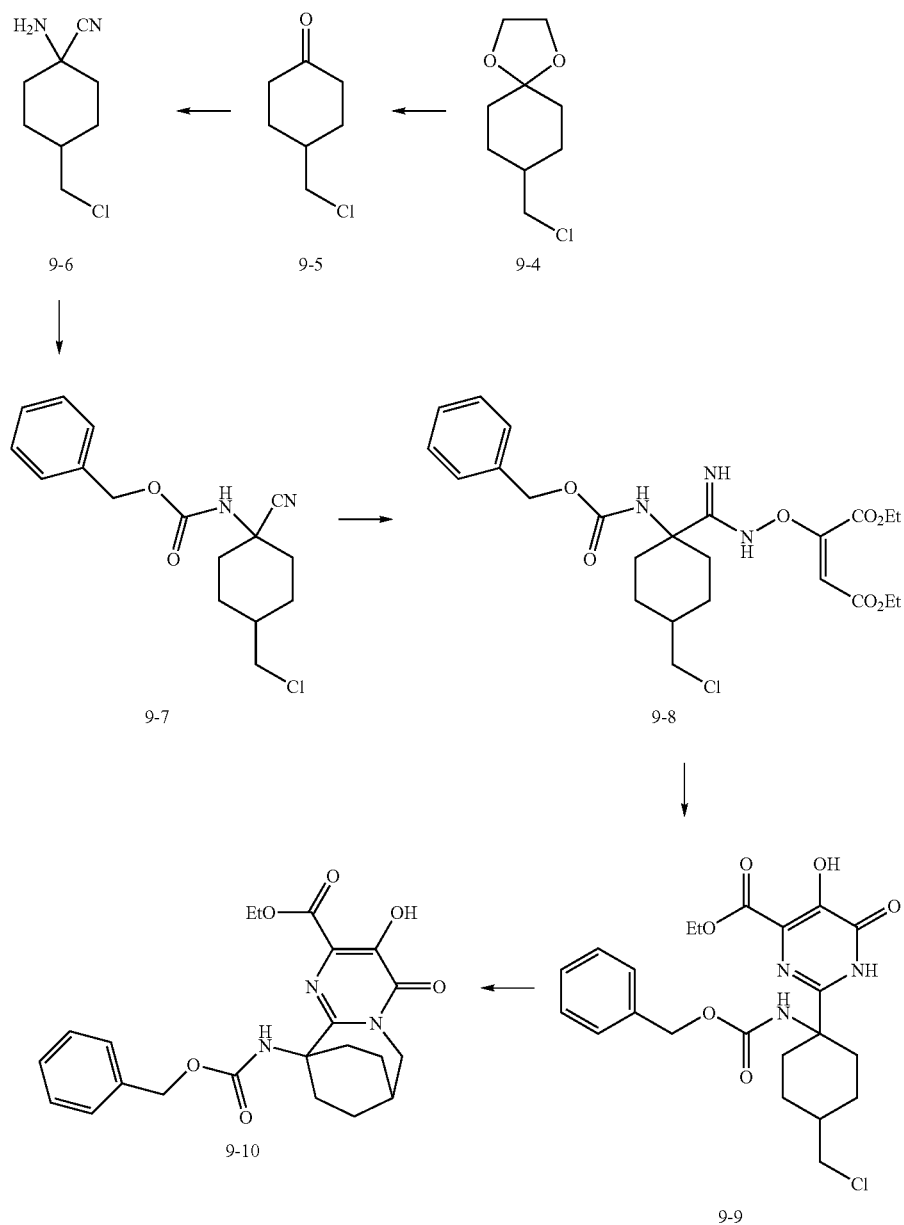

Another method for the synthesis of intermediate 9-10 is shown in Scheme X. In Scheme X, compound 10-1 can be prepared according to general procedure described in Journal of Organic Chemistry 1997, 62, 5284-5292 from commercially available ethyl 4-oxocyclohexanecarboxylate. A Strecker reaction, like that described in the schemes above produces the amino-nitrile intermediate 10-2 which is carried on to the N-protected intermediate 10-3. Treatment of this compound with hydroxylamine, followed by diethyl but-2-ynedioate and heating in xylenes affords 10-4. The final cyclization reaction can be carried out as before, via activation of the alcohol with methane sulfonyl chloride followed by ring closing nucleophilic attack by the pyrimidinone nitrogen-group.

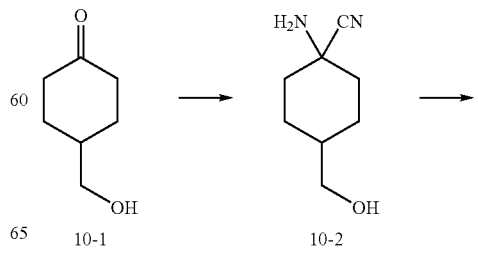

-continued

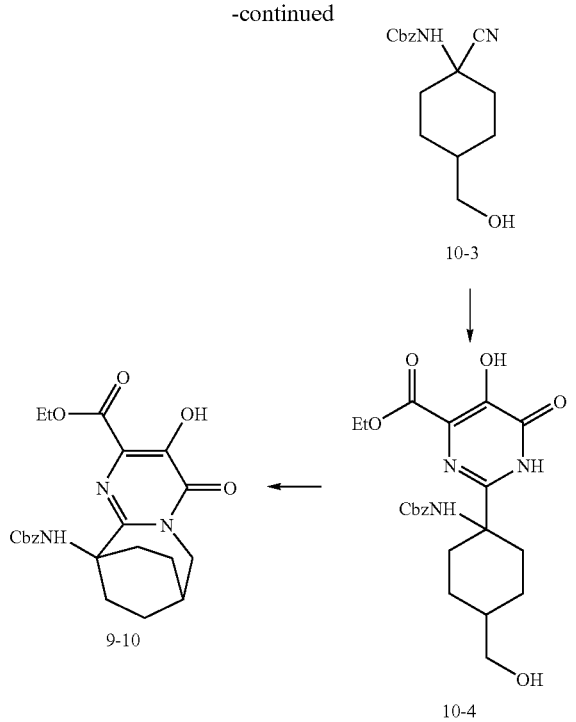

In Scheme XI intermediate 9-10 is treated with a substituted benzylic amine in the presence of triethylamine, with heating, to form the corresponding benzylamide 11-1. The Cbz protecting of 11-1 can be removed using standard hydrogenation conditions (e.g. $H_2$ and Pd/C) or other methods commonly known to one skilled in the art. In the final step amide, urea, carbamate, sulfonamide and related analogues can be synthesized directly form 11-3 under appropriate conditions. For example amides can be synthesized by treating 11-3 with a carboxylic acid chloride or by reacting it with a carboxylic acid in the presence of an amide bond forming reagent such as HATU. Other analogues are available by treating 11-3 with isocyantes, chlorosulfonates or chloroformates, to name a few. The analogues are treated with $MeNH_2$ in the event that the C3-hydroxyl group of the pyrimidinone ring has been modified.

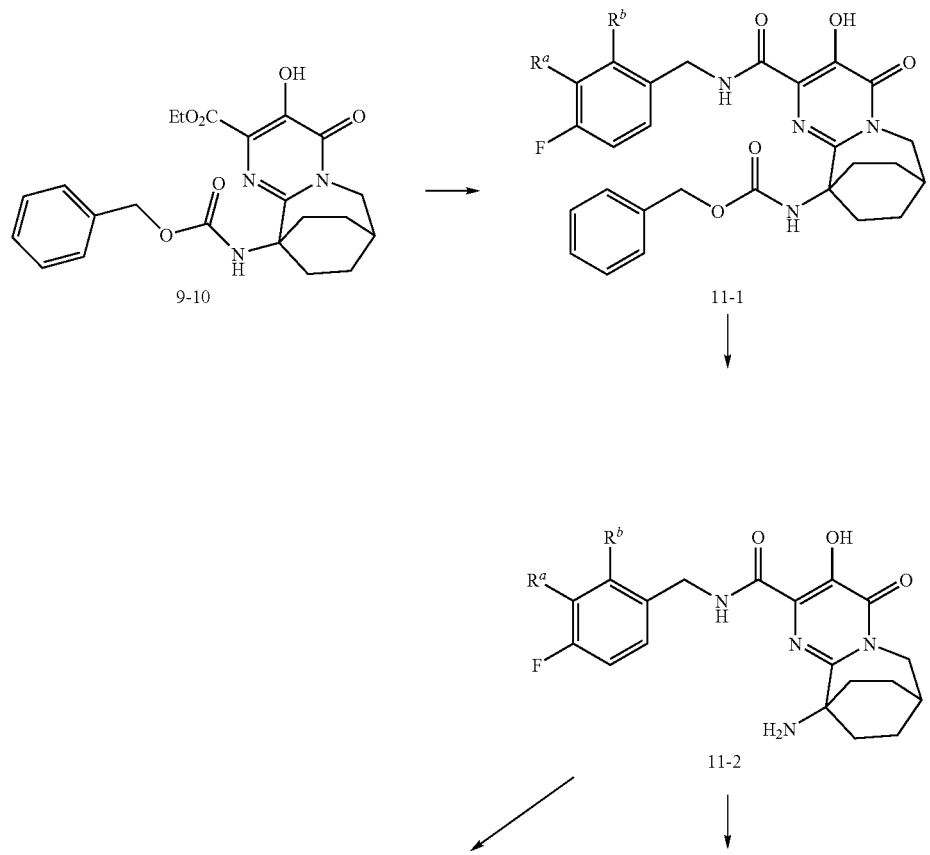

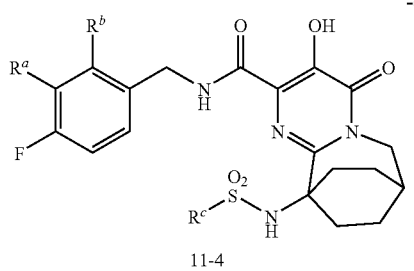
11-4

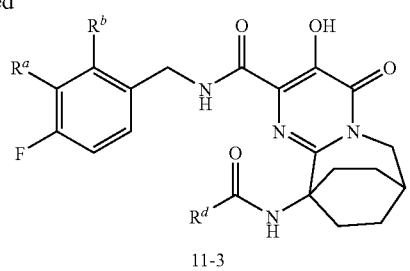
11-3

Compounds of this invention can also be synthesized according to the method illustrated in Scheme XII. In this Scheme 11-2 can be synthesized as before. This intermediate is then reacted with 2-chloro-2-oxoacetate in the presence of triethylamine to deliver 12-1. Following this 12-1 is heated with an amine to affect the formation of 12-2. In certain cases intermediate 12-1 need not be isolated but can be carried on to the 12-2 forming step immediately after work-up.

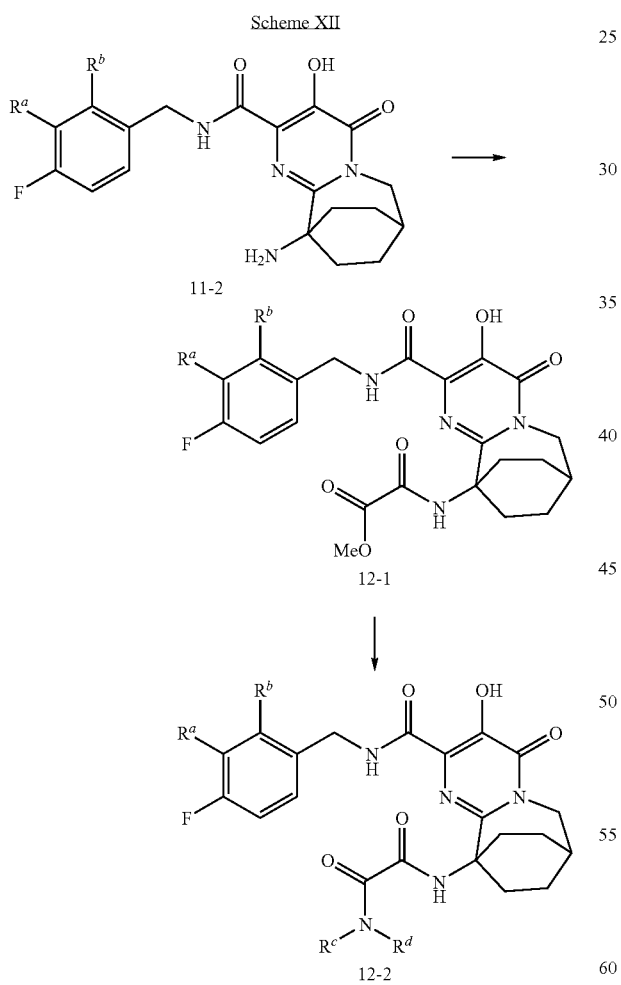

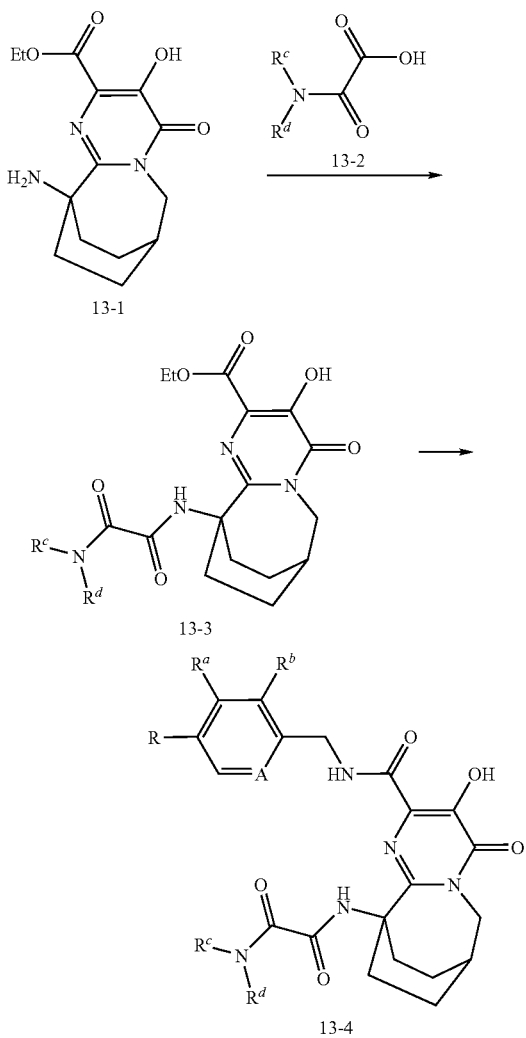

In Scheme XIII, intermediate 13-1 can be coupled with intermediate 13-2 under standard amide-bond forming conditions, for example using the HATU as the coupling reagent in the presence of diisopropyl ethylamine and DMAP. Intermediate 13-3 is then treated with a benzylamine, with heating, as described in the above schemes to produce 13-4.

In the method shown in Scheme XIV, intermediate 9-10 is benzoylated by treating it with benzoic acid anhydride and pyridine to form intermediate 14-1. The Cbz protecting group can then be removed by hydrogenolysis to yield intermediate 14-2. Intermediate 14-2 can be coupled with acid 14-3 and the resulting product, 14-4 reacted with a substituted benzyl or substituted phenylpropylamine to provide 14-5.

Scheme XIV
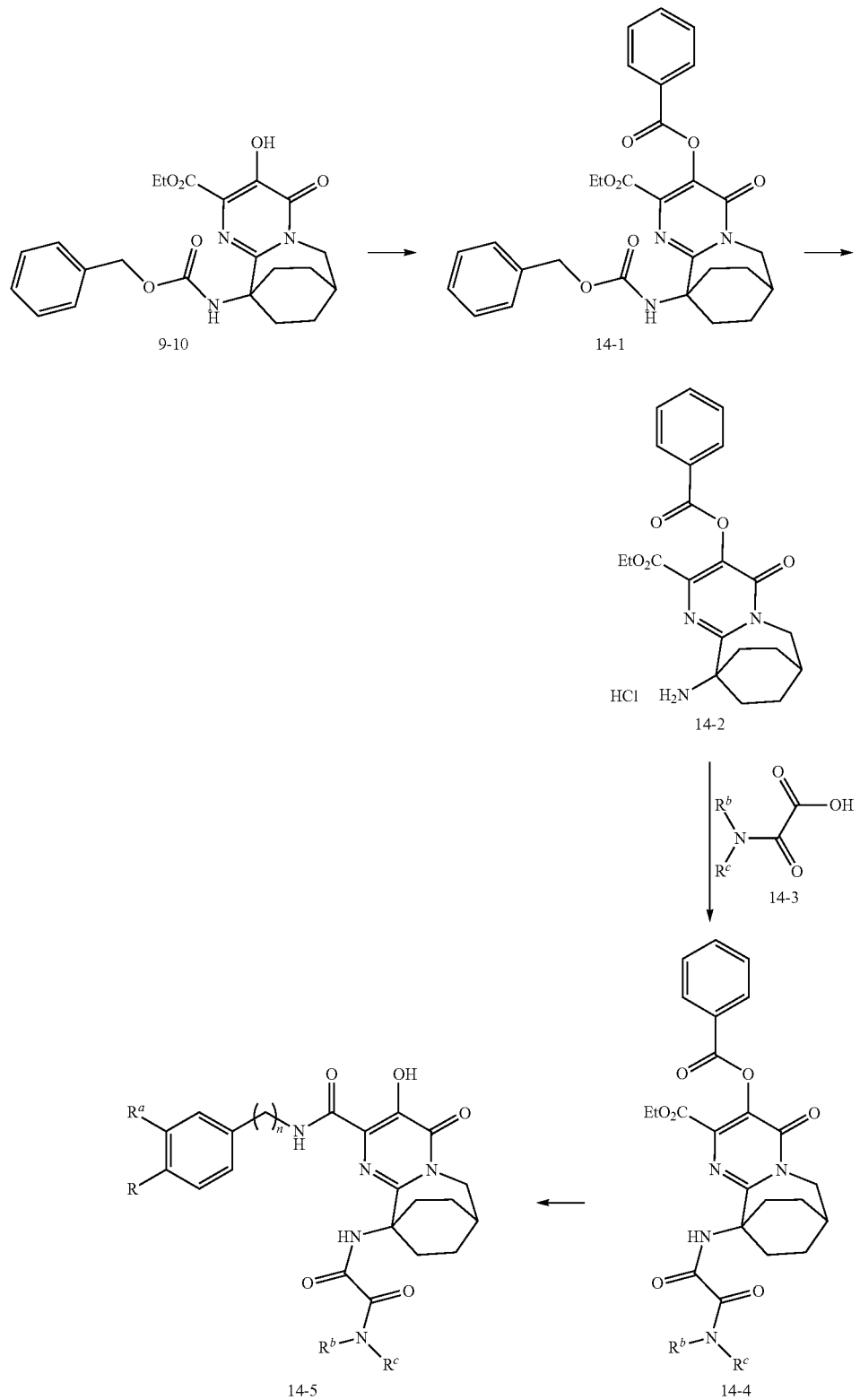
Scheme XV illustrates another method for the synthesis of compounds of this invention. Intermediate 15-1, prepared using methods similar to those described previously, is heated with a substituted piperazine to provide 15-2.

Scheme XV

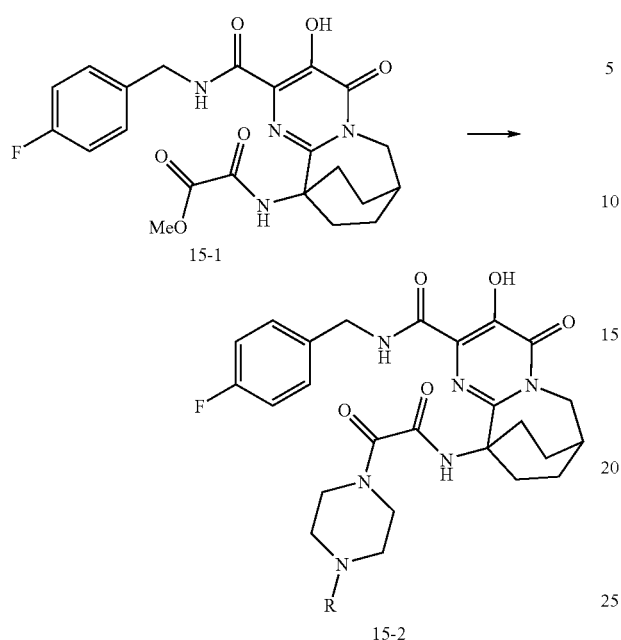

As shown in Scheme XVI, when 15-1 is reacted with piperazine as described in the previous scheme, intermediate 16-1 is produced. The unsubstituted nitrogen of the piperazine ring can be modified by the addition of $R^X$ to form 16-2. $R^X$ can be a substituted alkyl group, an acyl group, a sulfonyl group, a urea or related functionality.

Scheme XVI

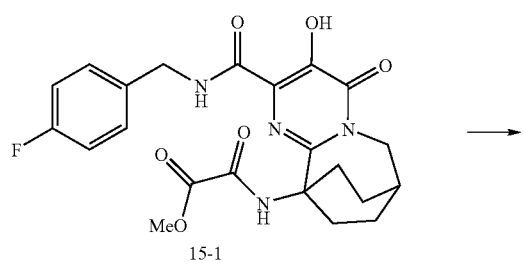

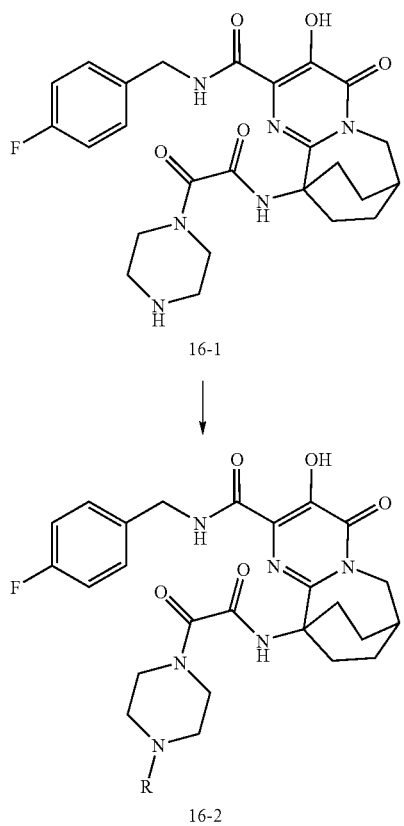

As shown in Scheme XVII, the bridgehead nitrogen of intermediate 17-1 can be transformed into the corresponding dimethylated analogue, 17-2 via reductive amination, using for example formaldehyde and sodium triacetoxy borohydride. In a similar fashion intermediate 17-3 can be synthesized by sequential introduction of the benzyl group via reductive amination (benzaldehyde, NaCNBH₃) followed by introducing of the methyl group in the same way. The benzyl group is then cleaved under reductive conditions, H₂ and Pd/C, to provide 17-4. The nitrogen atom 17-4 can be modified using methods similar to those described above.

Scheme XVII

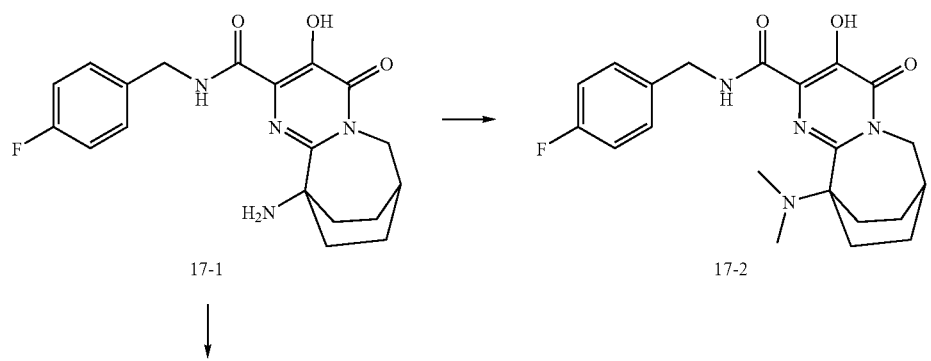

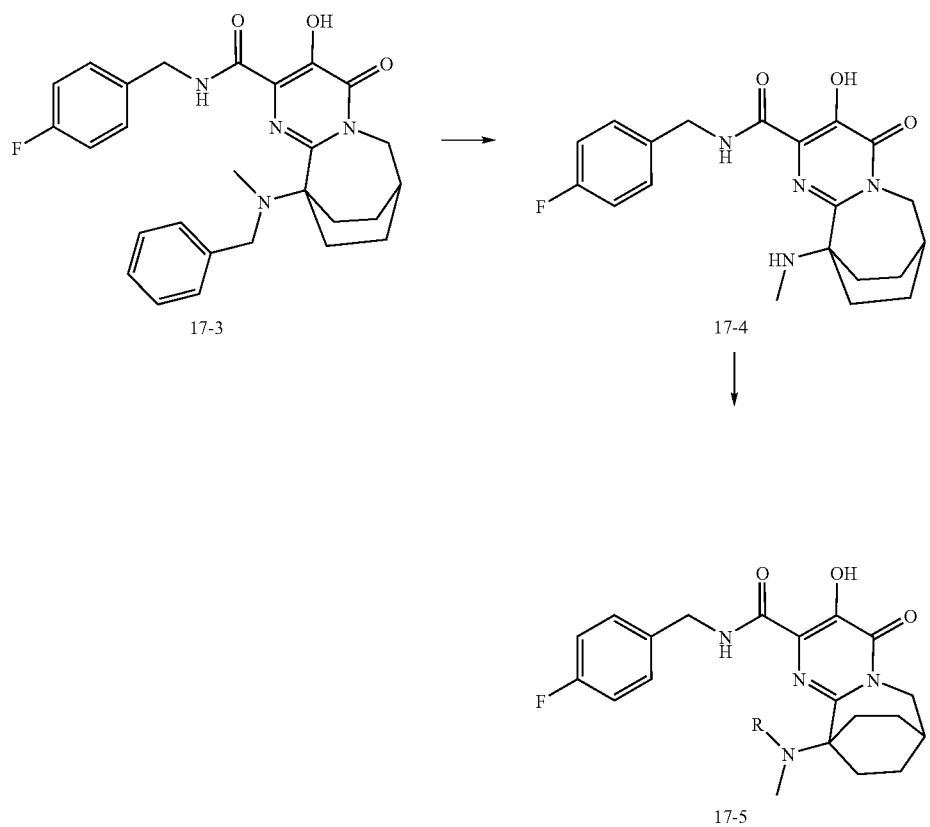
Additional methods for the synthesis of compounds of this invention are illustrated in Schemes XVIII and XIX.
Scheme XVIII
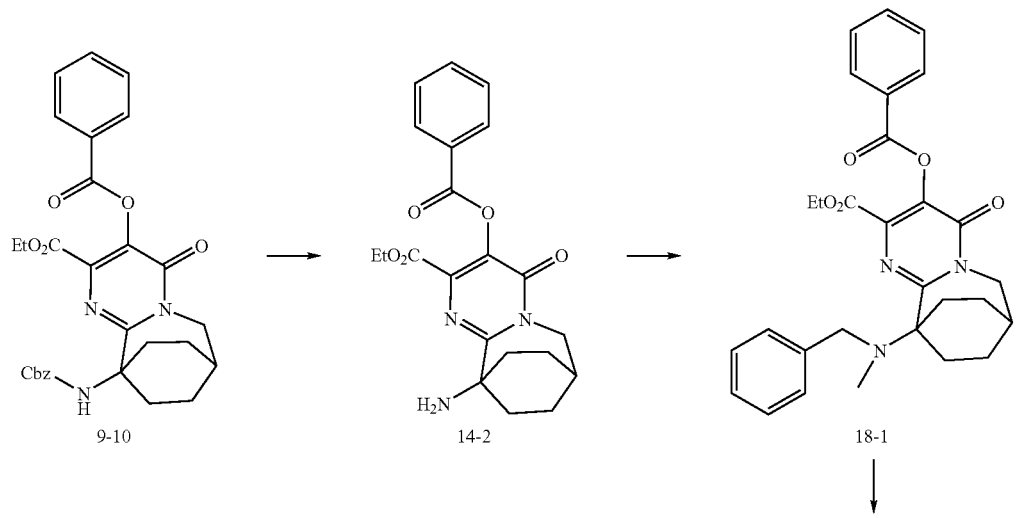

-continued
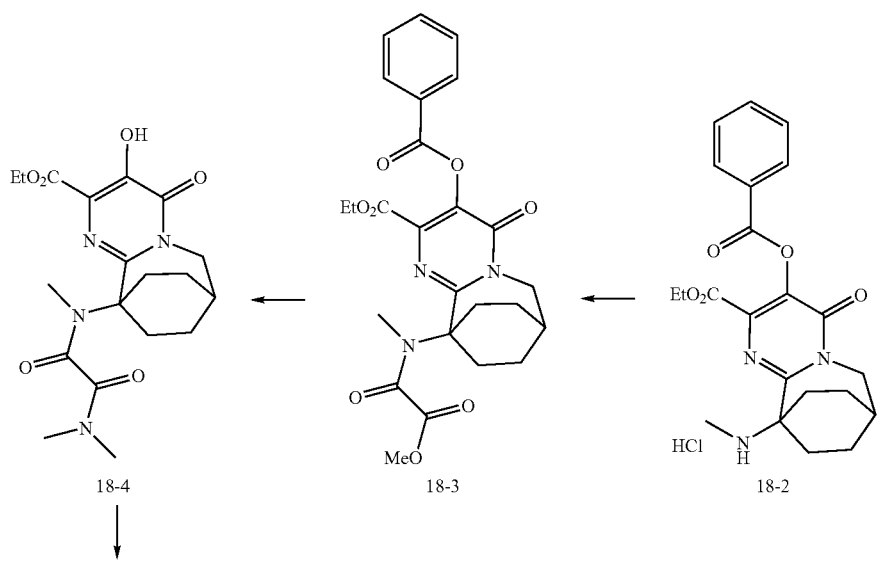
Scheme XIX
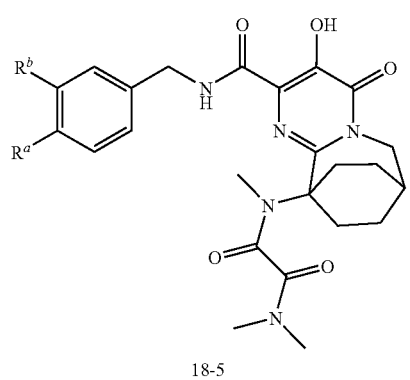
-continued
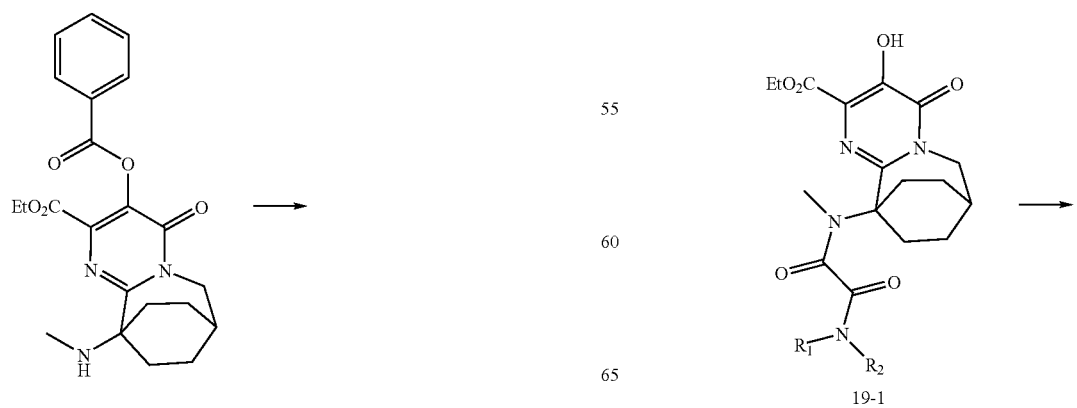

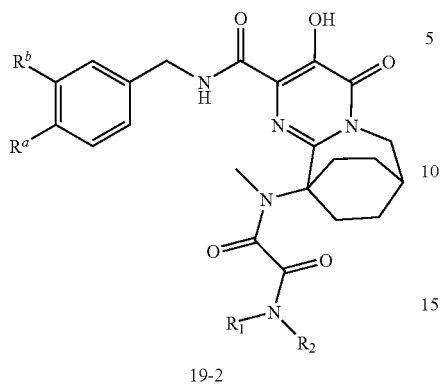

19-2

The method described in Scheme XX for the synthesis of intermediate 20-2 is similar to that described for intermediate 18-1 in Scheme XVIII except acetaldehyde is used in place of formaldehyde. The subsequent transformations rely on methods described above.

Scheme XX

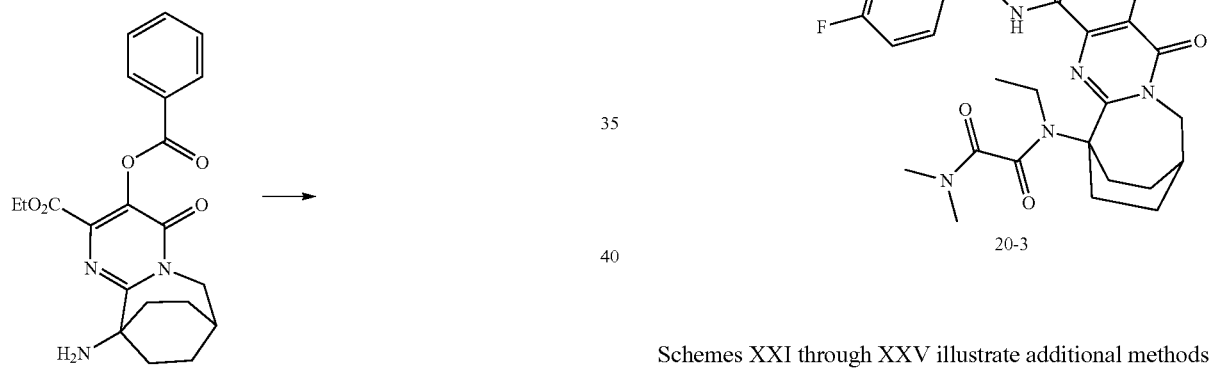

20-1    20-2

20-3

Schemes XXI through XXV illustrate additional methods for synthesizing compounds of this invention.

Scheme XXI

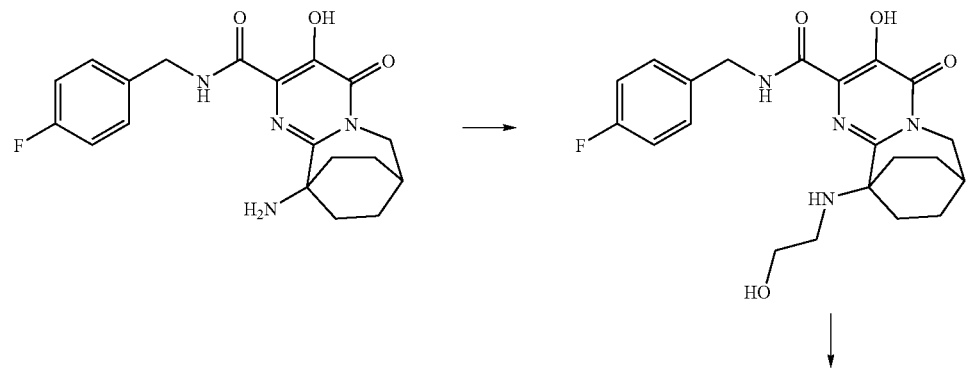

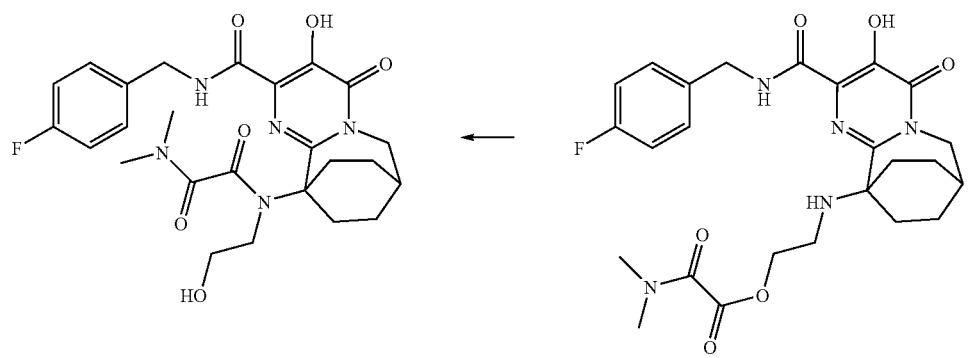
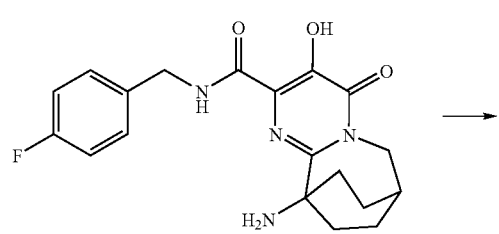
Scheme XXII
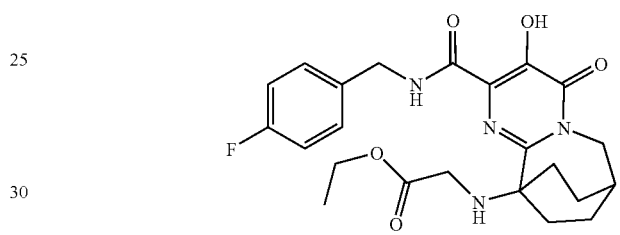
-continued
Scheme XXIII
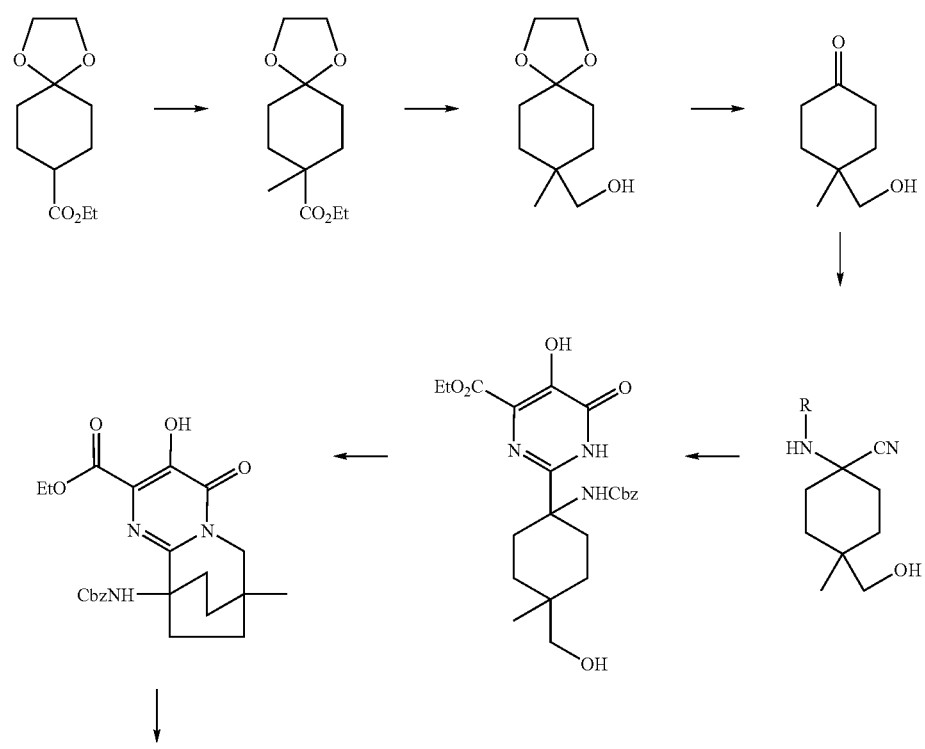

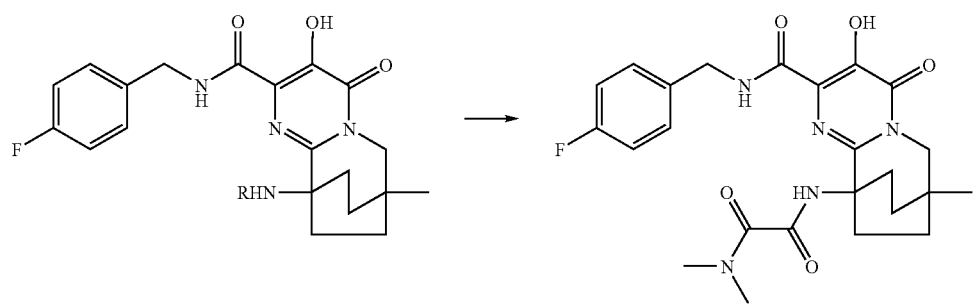
Scheme XXIV
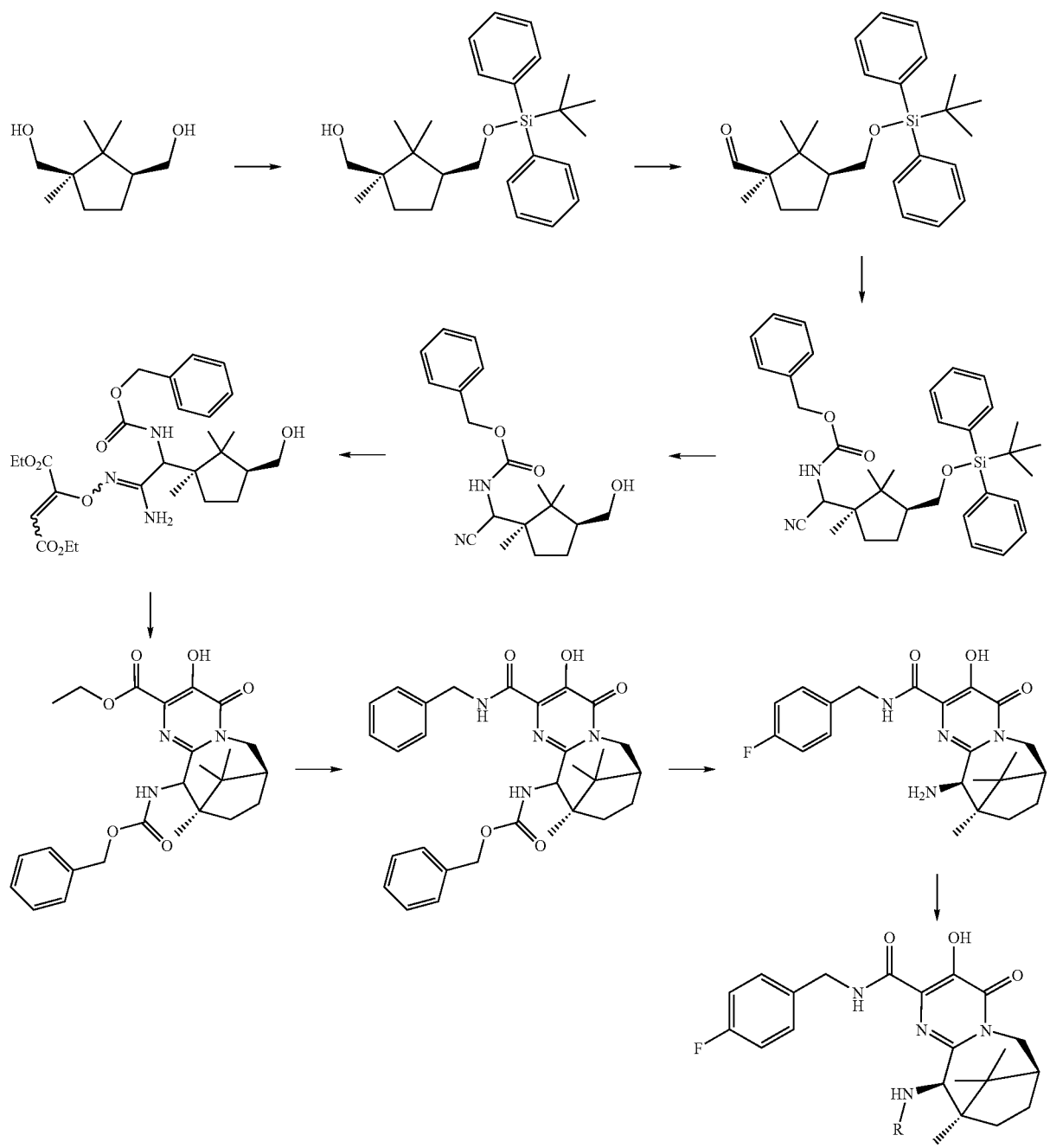

Scheme XXV

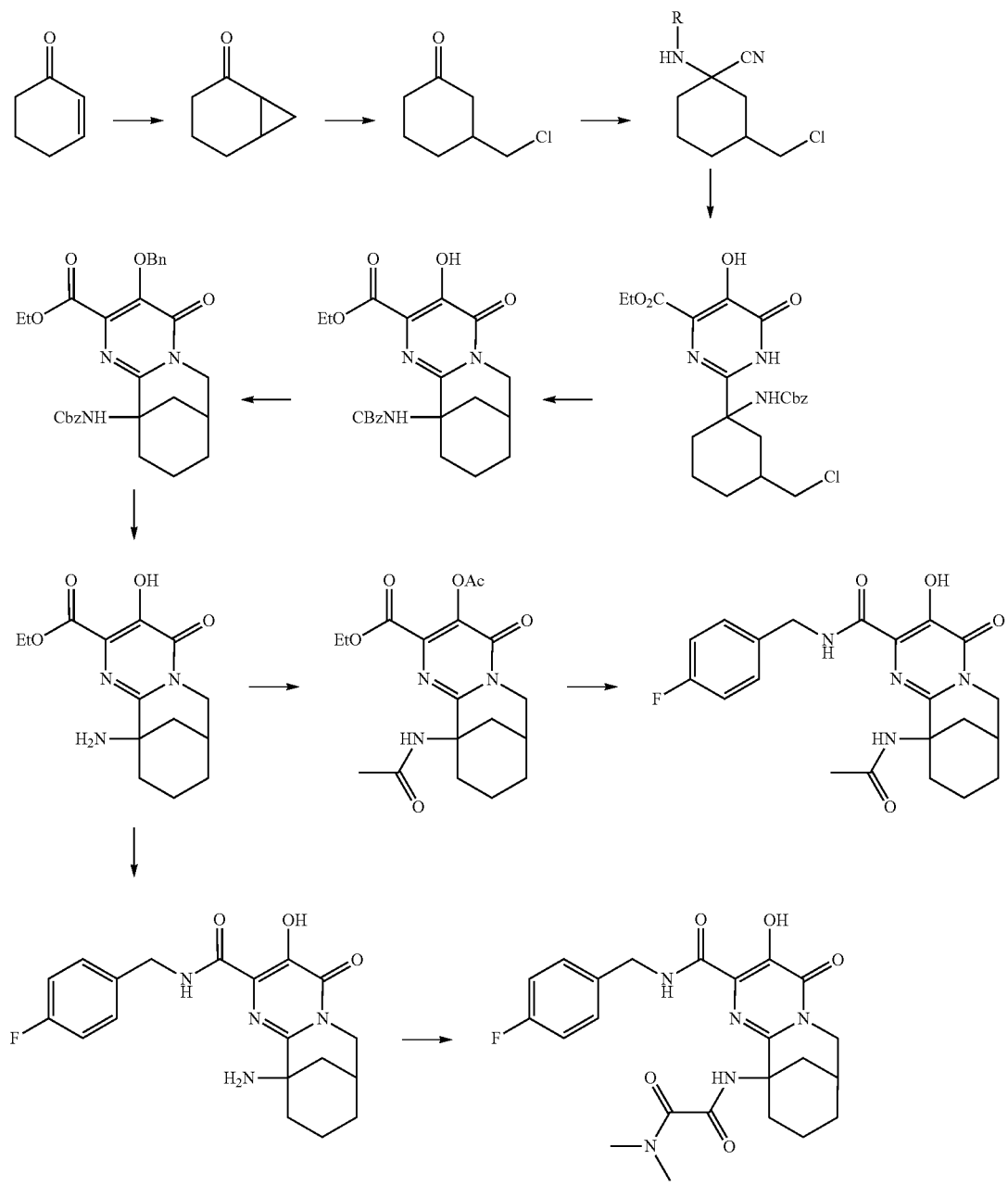

Scheme XXVI illustrates another method for the synthesis of compounds of this invention. In this method 3-oxocyclopentane carboxylic acid (26-1) is converted into the ketal-ester derived intermediate 26-2 (Tetrahedron (1977), 33, 1113) by stirring in methanol and acetyl chloride. Following this the ester group can be reduced, using LAH, to the corresponding alcohol, 26-3. The ketal group of intermediate 36-3 is removed under acidic conditions (p-toluene sulfonic acid) and the 5-hydroxy-6-oxo-1,6-dihydropyrimidine-4-carboxylate derivative 26-9 synthesized using the same reaction sequence used in the previous schemes. Formation of the final ring can be carried out by first treating 26-9 with methane sulfonyl chloride and triethylamine followed by a second step involving treatment with potassium carbonate. The product of this sequence, 26-10 can be esterified to form 26-11 using benzoic acid anhydride. Further transformation of this intermediate using the methods described previously provides, 26-12, 26-13 and 26-14.

Scheme XXVI
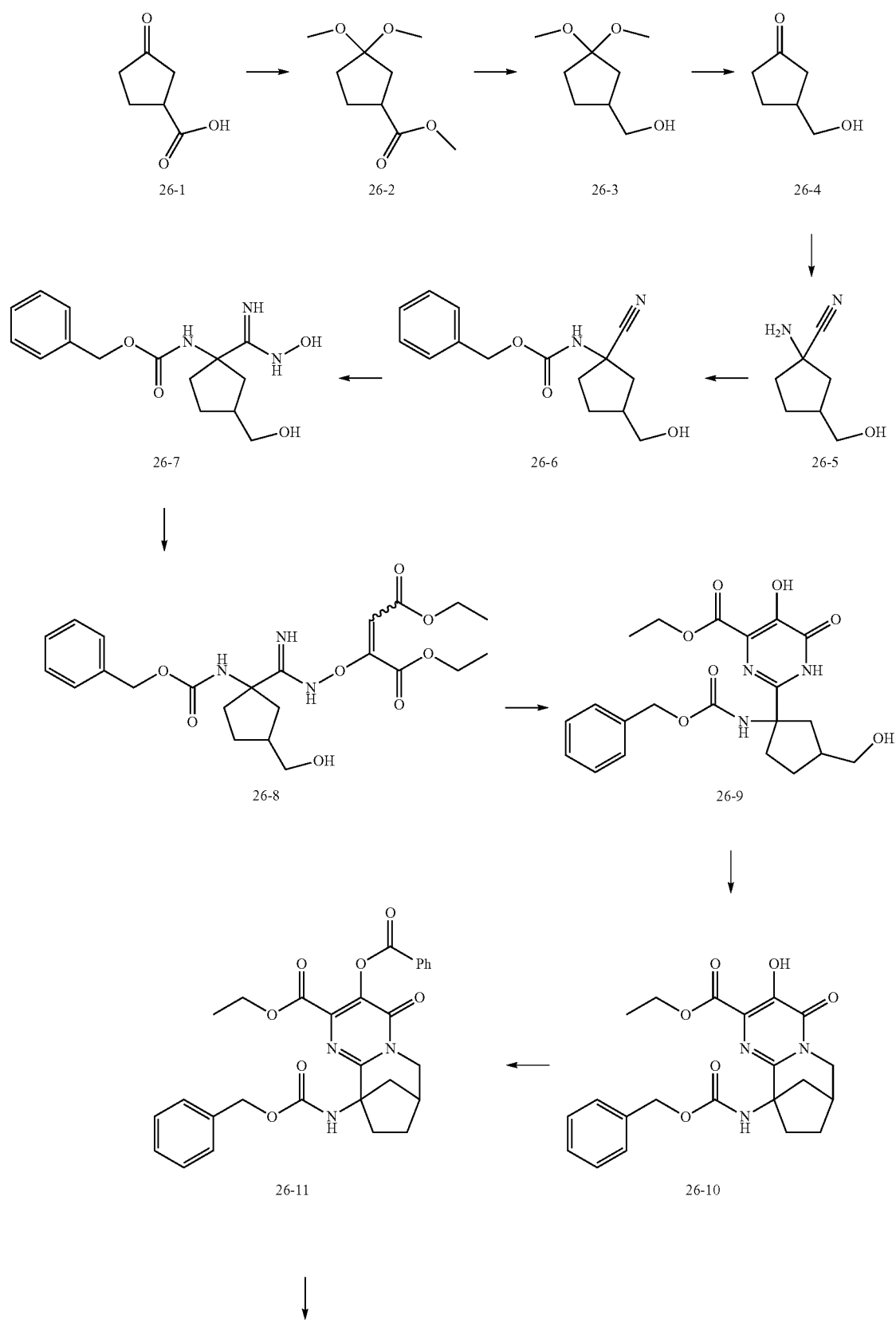

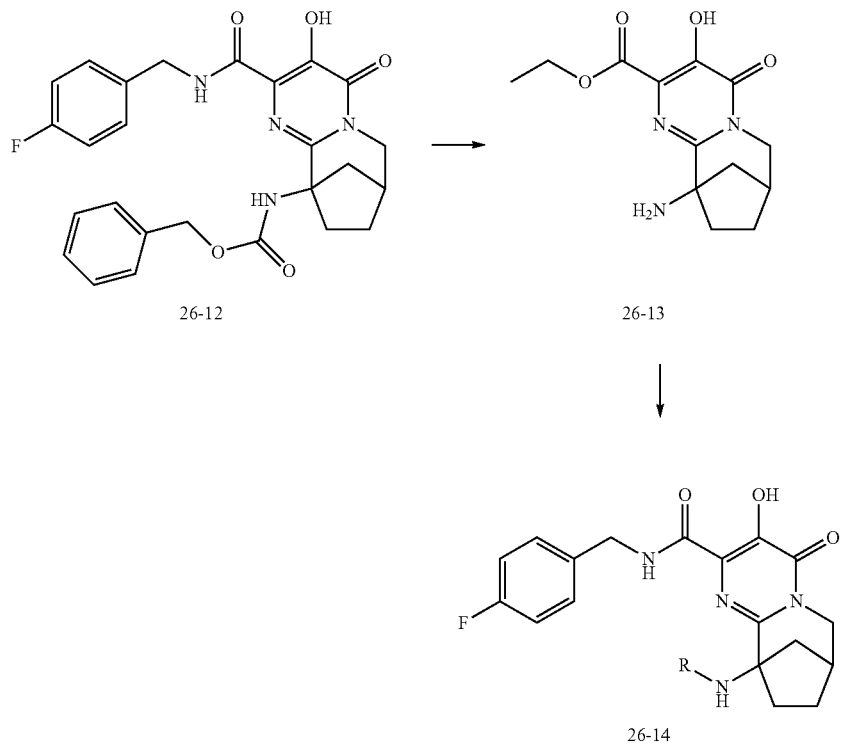

26-12 → 26-13

↓

26-14

A method for the synthesis of advanced intermediate 27-11 is shown in Scheme XXVII. Cyclopentenone, 27-1 can be converted to 27-2 (Tetrahedron Lett. 2005, 46, 6875-6878) by the nucleophilic addition of dimethylmalonate using 2,3,4,6,7,8-hexahydro-1H-pyrimido[1,2-a]pyrimidine as a base. Those skilled in the art will recognize this synthetic transformation as a Michael reaction which can be carried out under a number of different conditions in addition to those shown here as illustrated in; E. D. Bergmann et al., Org. React. 10, 179-555 (1959); H. O. House, Modern Synthetic Reactions (W. A. Benjamin, Menlo Park, Calif., 2nd ed., 1972) pp 595-623; M. E. Jung, Comp. Org. Syn. 4, 1-67 (1991). In the next step, a methylcarboxylate group of 27-2 is removed at elevated temperature in the presence of dimethyl 2-(3-oxocyclopentyl)malonate to yield intermediate 27-3. This intermediate is then converted to the corresponding dimethyl ketal and the methylcarboxylate group reduced to the corresponding alcohol using LiBH$_4$ to provide 27-5 (J. Org. Chem., 1986, 51 (21), 4000-4005). The ketal group is then hydrolyzed, yielding 27-6, then the pyrimidinone derivative, 27-10, synthesized in the same manner as that described in the above schemes wherein after formation of the amino nitrile, under Strecker reaction conditions, the amino group is protected with Cbz and the nitrile treated with hydroxylamine then diethyl but-2-ynedioate. The bridged bicyclic portion of 27-11 can be formed by treating intermediate 27-10 with methane sulfonyl chloride/triethylamine followed by treatment with a base such as K$_2$CO$_3$. Compound 27-11 can serve as an advanced intermediate for the synthesis of compounds of this invention as illustrated in Scheme XVIII.

Scheme XXVII

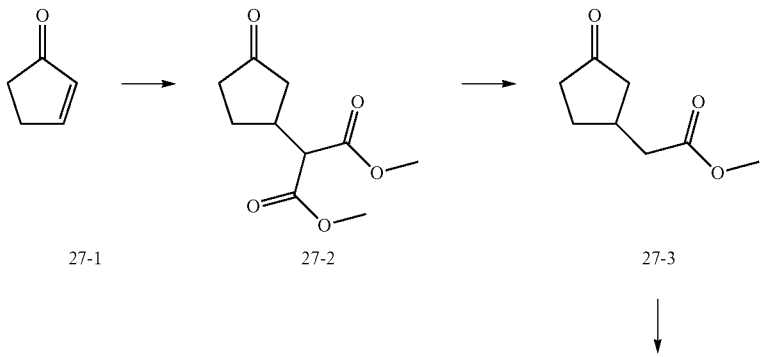

27-1    27-2    27-3

↓

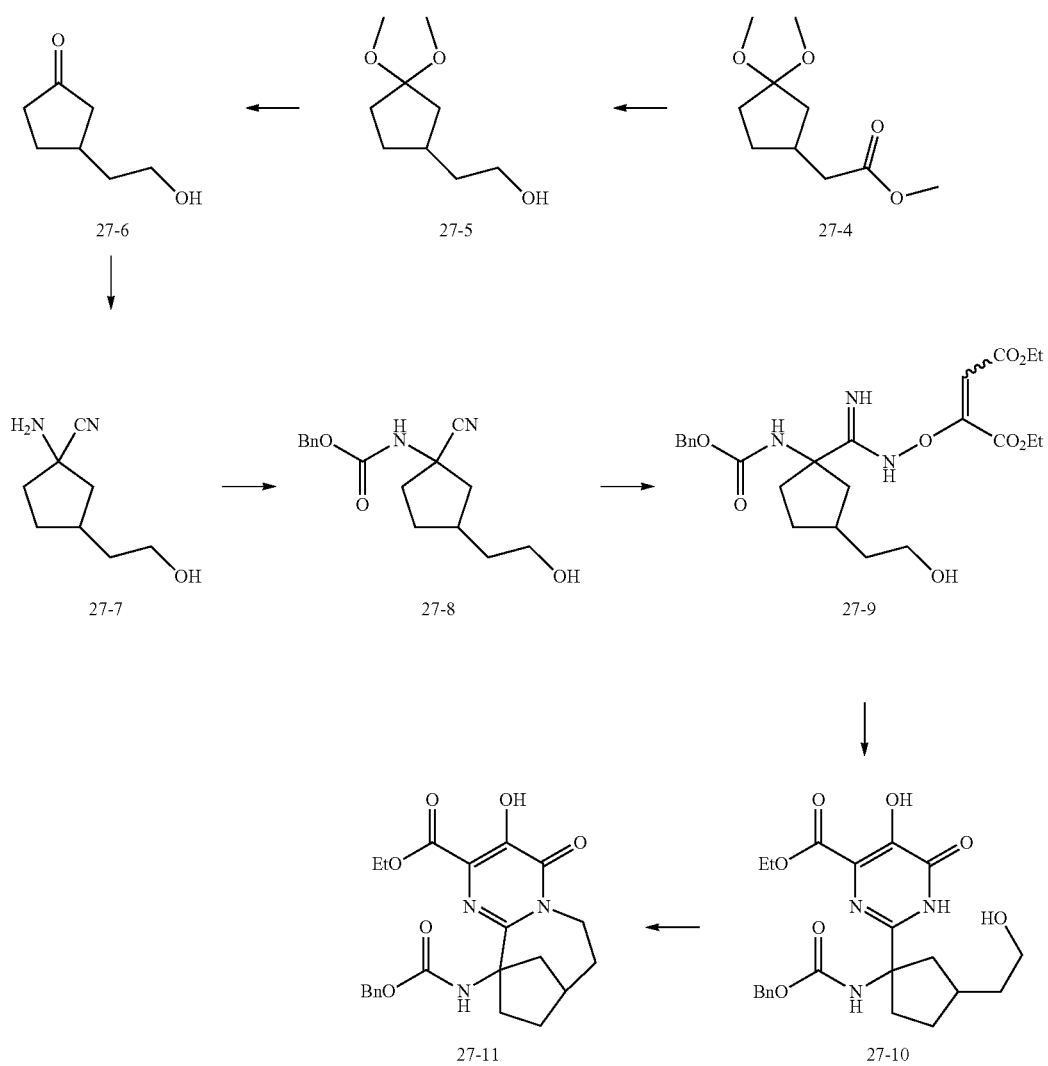
Compounds of this invention can also be synthesized according to Scheme XVIII through XXXIV.
Scheme XXVIII
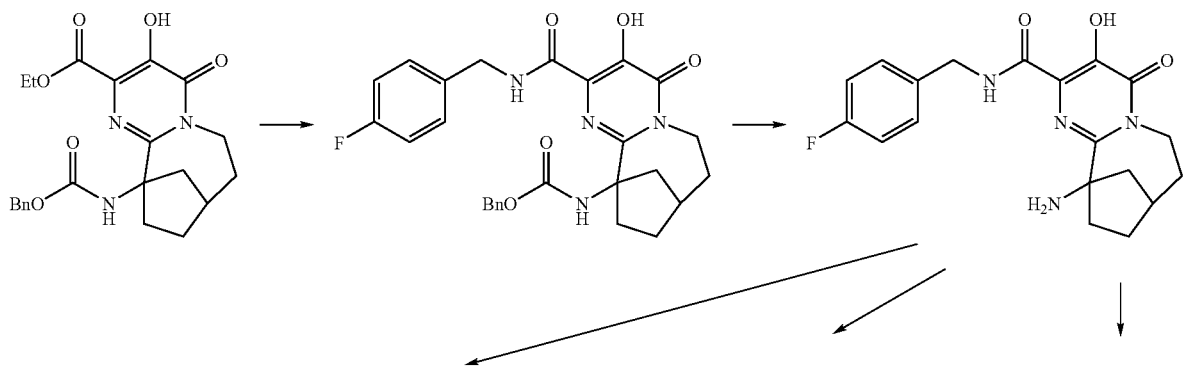

61
62
-continued
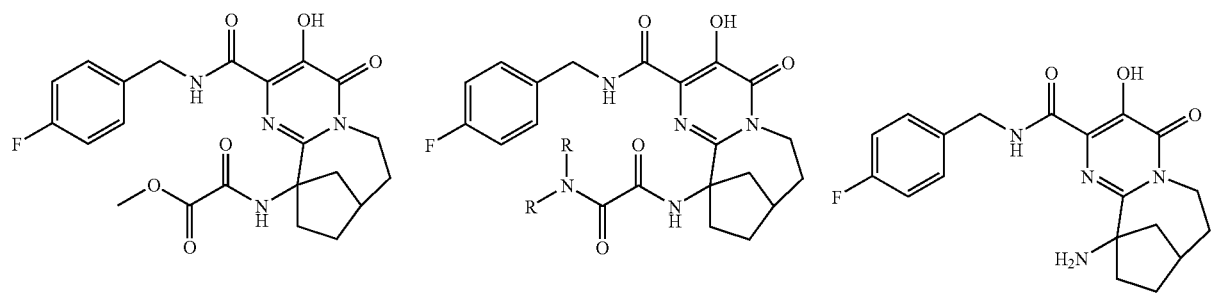
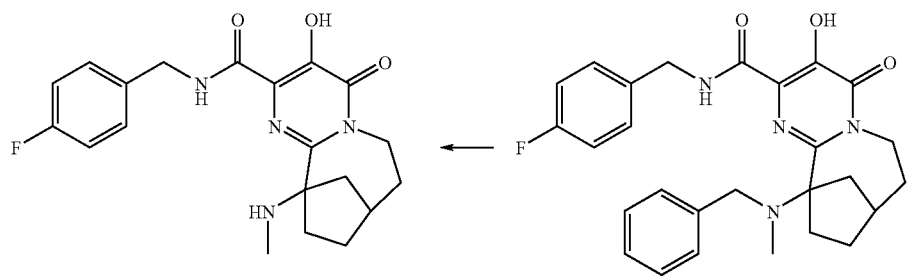
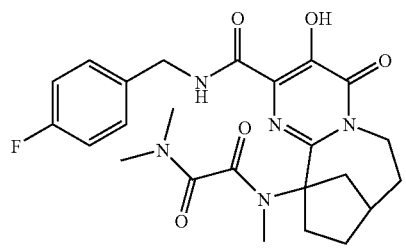
Scheme XXIX
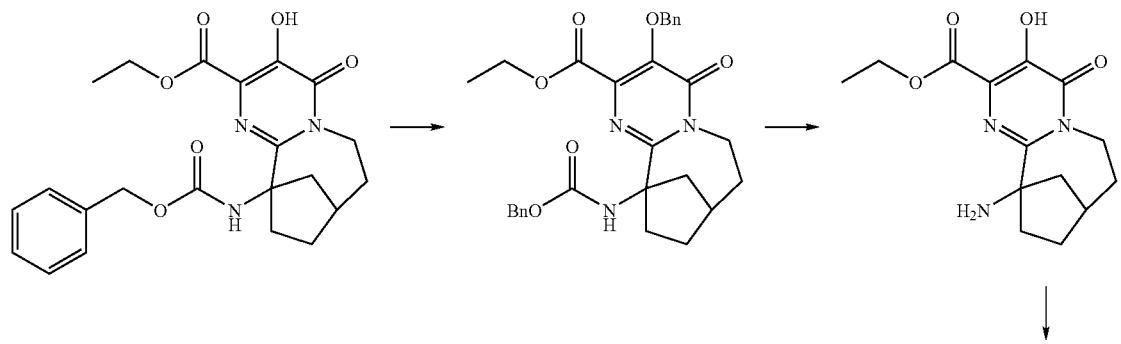

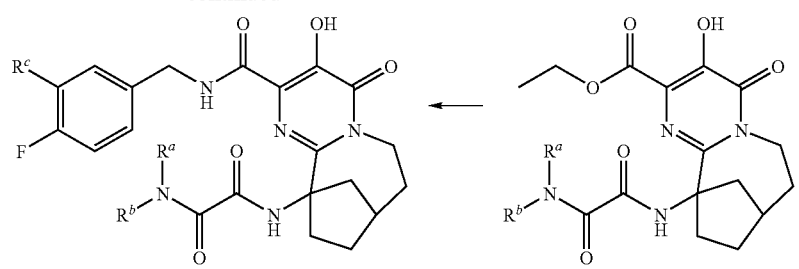
Scheme XXX
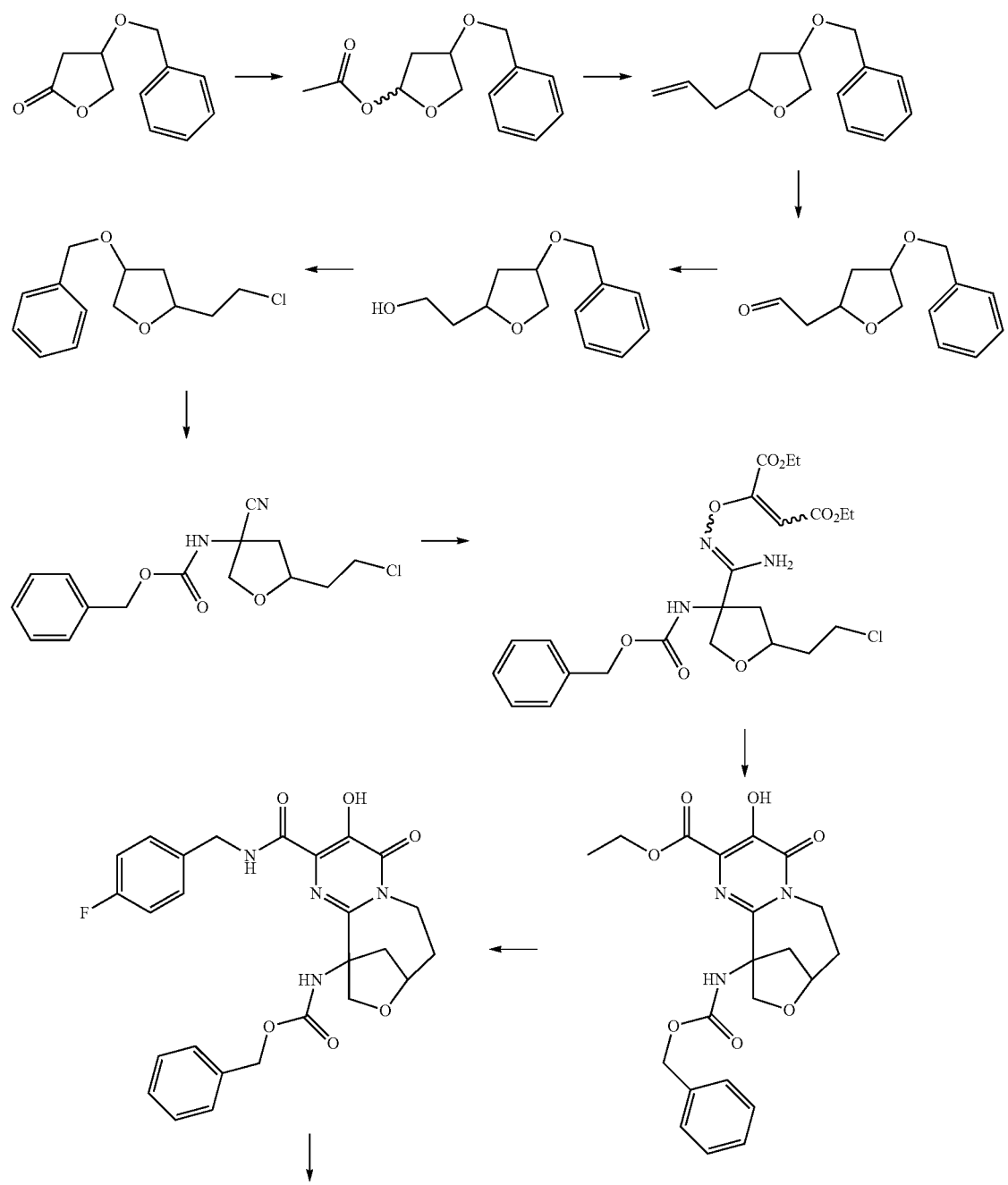

65
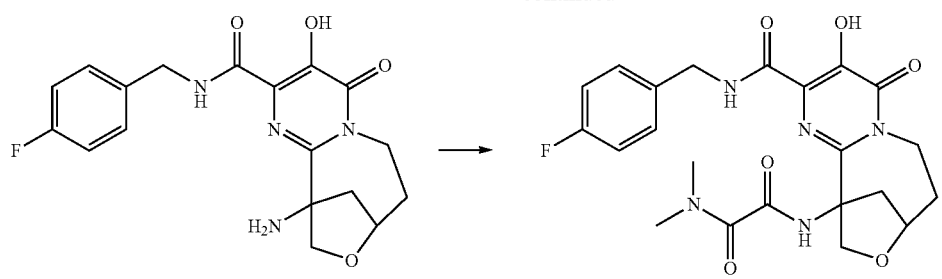
66
-continued
Scheme XXXI
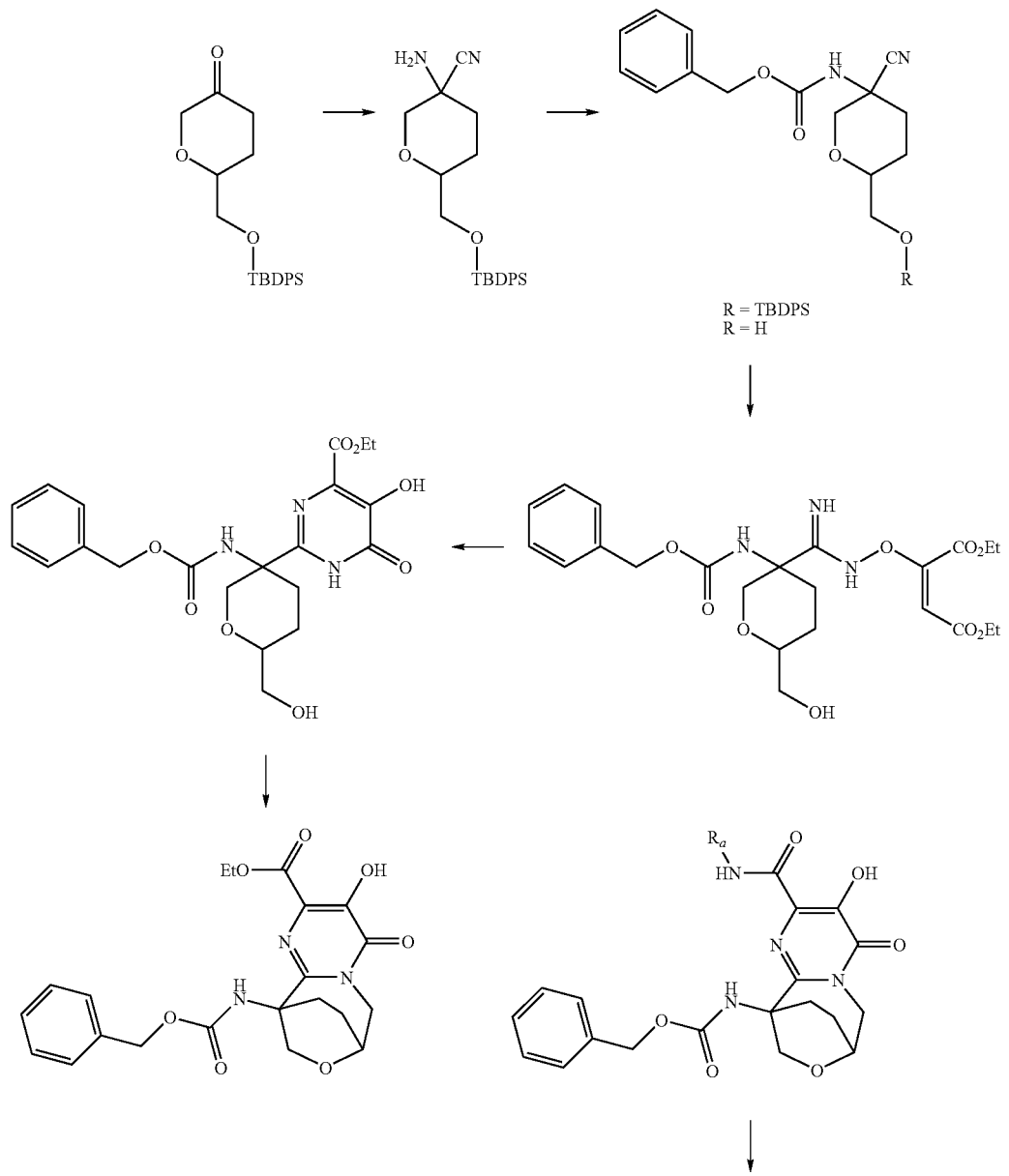

-continued
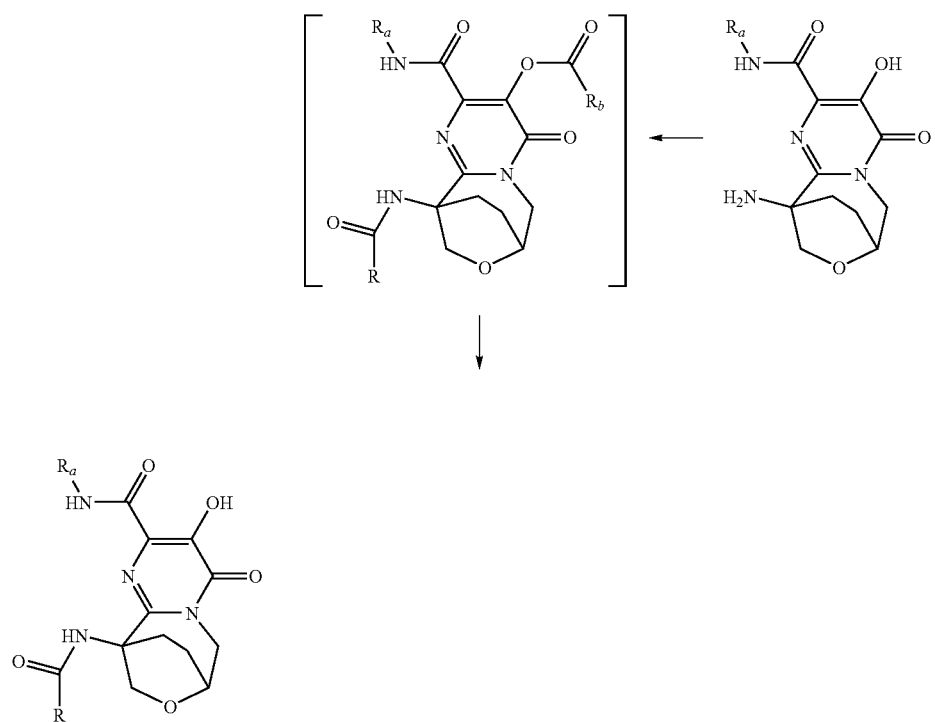
Scheme XXXII
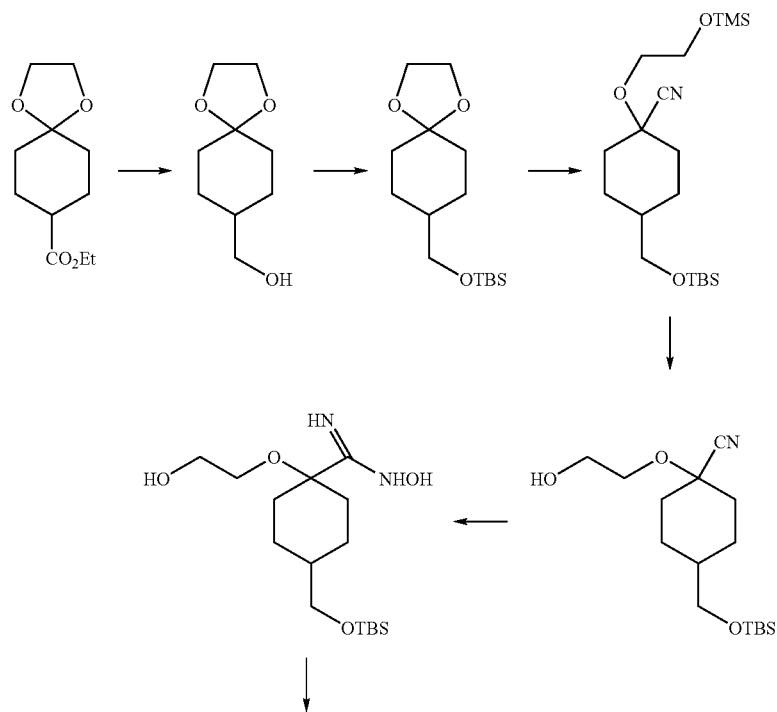

-continued
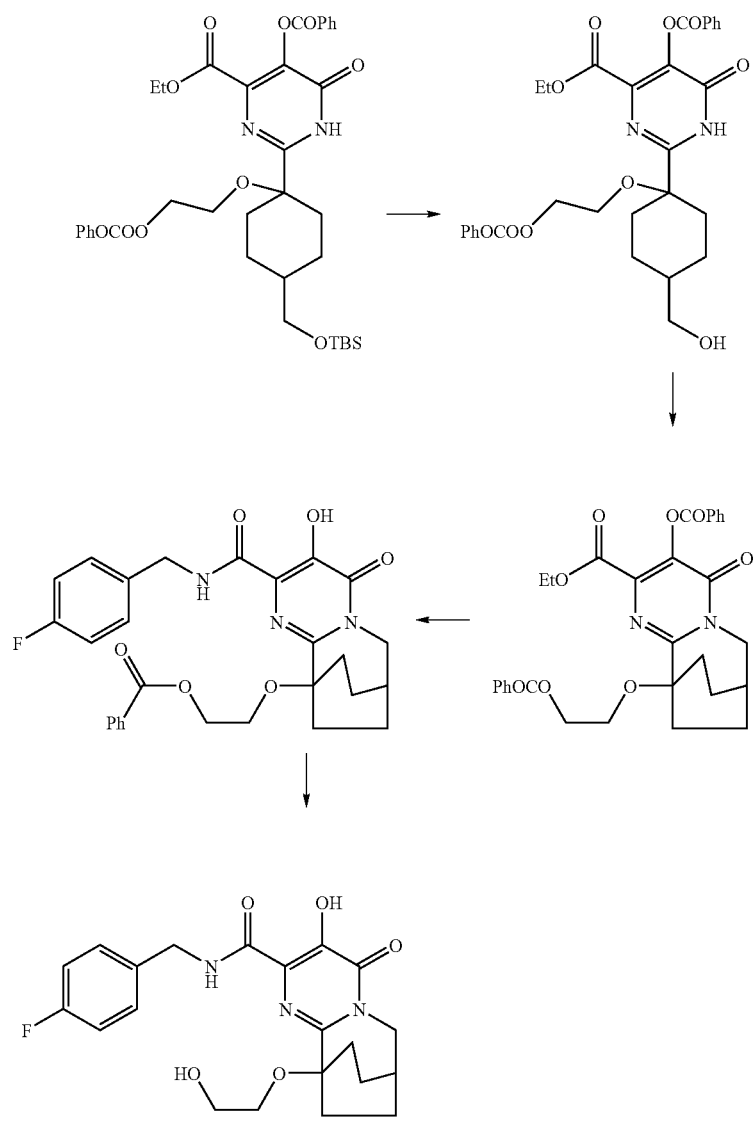
Scheme XXXIII
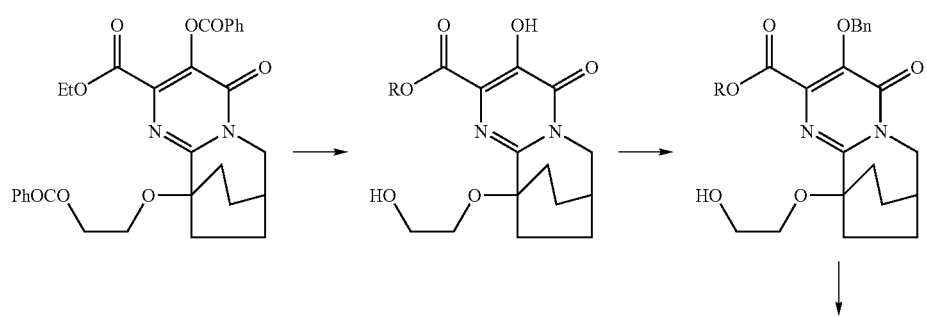

71 72
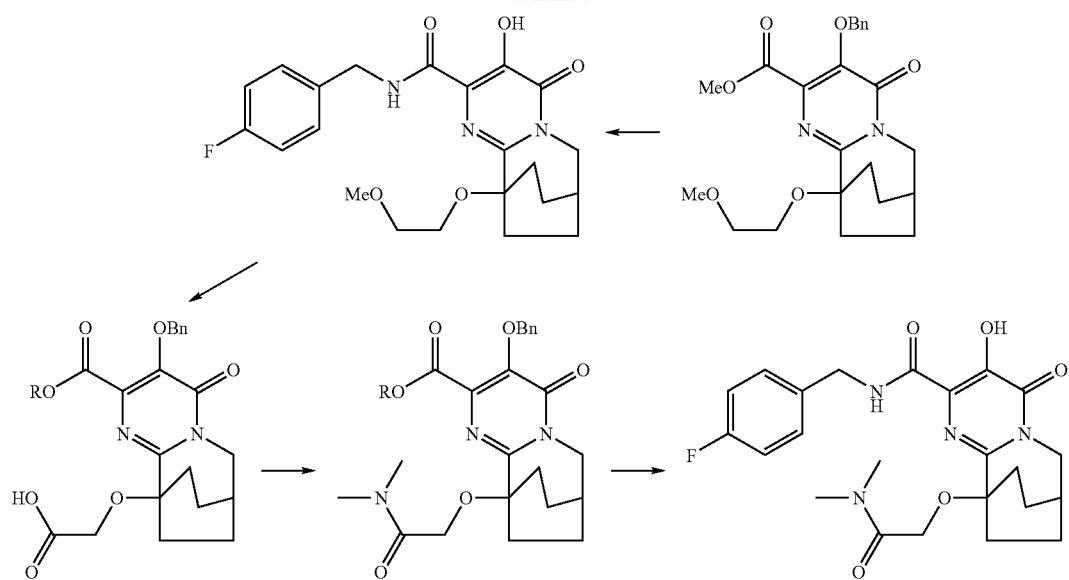
Scheme XXXIV
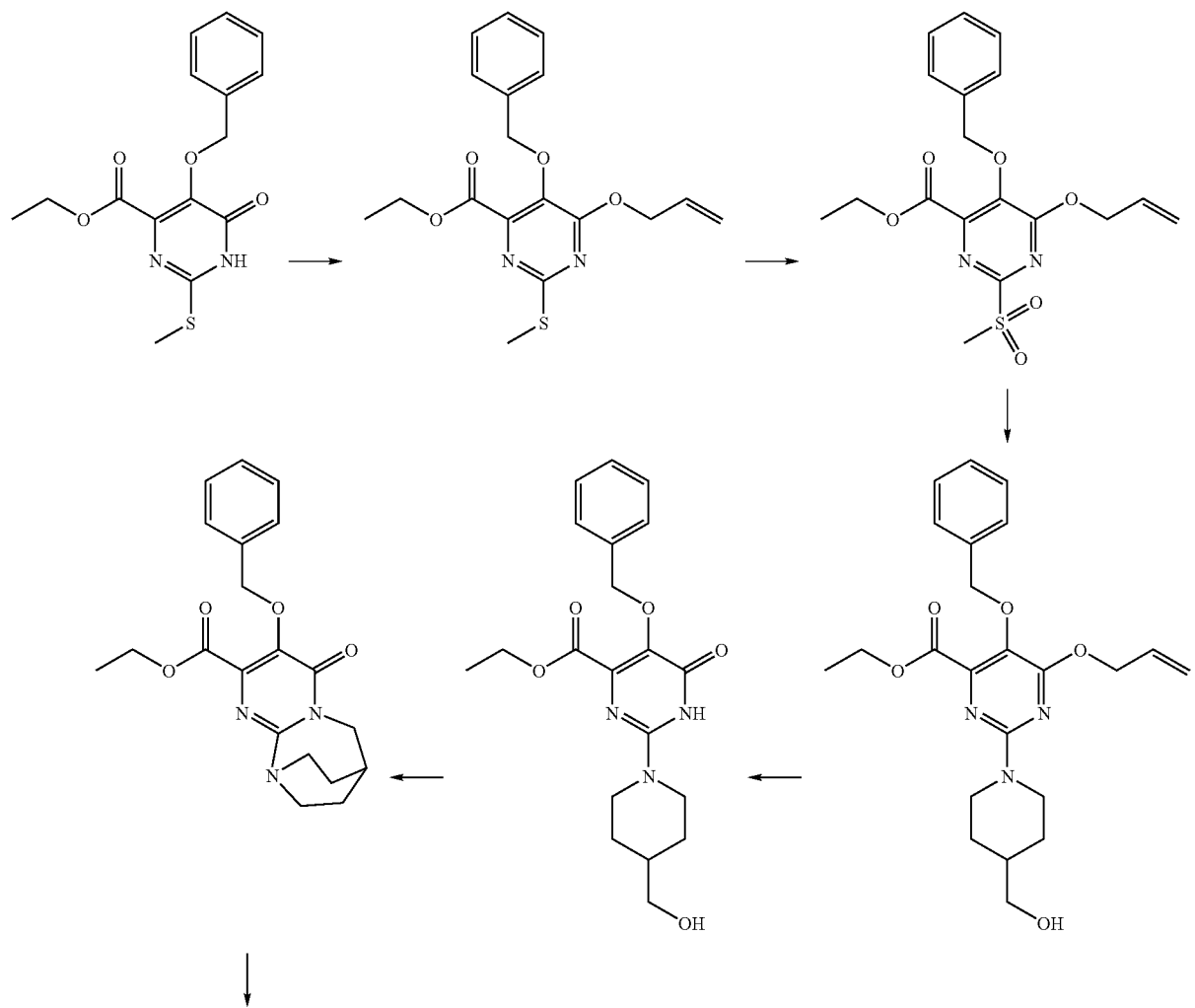

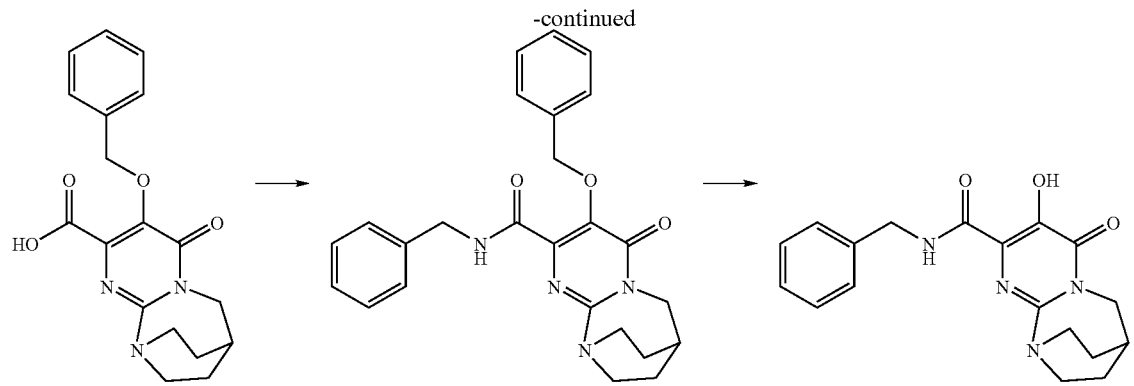

Biological Methods

HIV-Integrase Inhibition Activity. To evaluate in-vitro activity against HIV-integrase, 5 pmole of biotin labeled substrate DNA was bound to 100 μg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, *J. Virol.* 69, 5908-5911 (1995). The sequences of substrate and target DNA were described in *Nucleic Acid Research* 22, 1121-1122 (1994). Results are shown in the Table 1. Activity equal to A refers to a compound having $IC_{50}$=<10 nM while B and C denote compounds having $IC_{50}$=<10 nM and $IC_{50}$<100 nM and $IC_{50}$>100 nM respectively.

TABLE 2

| Compound | in vitro activity |
|---|---|
| Example 6 | B |
| Example 7 | B |
| Example 8 | A |
| Example 9 | C |
| Example 11 | B |
| Example 12 | A |
| Example 13 | A |
| Example 14 | B |
| Example 15 | A |
| Example 16 | A |
| Example 17 | A |
| Example 18 | A |
| Example 19 | C |
| Example 20 | A |
| Example 21 | A |
| Example 22 | B |
| Example 23 | A |
| Example 24 | A |
| Example 25 | A |
| Example 26 | A |
| Example 27 | B |
| Example 28 | A |
| Example 29 | B |
| Example 30 | B |
| Example 32 | A |
| Example 33 | A |
| Example 34 | A |
| Example 35 | A |
| Example 36 | A |

TABLE 2-continued

| Compound | in vitro activity |
|---|---|
| Example 37 | B |
| Example 38 | A |
| Example 39 | A |
| Example 40 | A |
| Example 41 | A |
| Example 42 | A |
| Example 43 | A |
| Example 45 | A |
| Example 46 | A |
| Example 47 | A |
| Example 48 | A |
| Example 49 | A |
| Example 50 | A |
| Example 51 | A |
| Example 52 | A |
| Example 53 | A |
| Example 54 | A |
| Example 56 | A |
| Example 57 | A |
| Example 58 | A |
| Example 59 | A |
| Example 60 | A |
| Example 61 | A |
| Example 62 | A |
| Example 63 | A |
| Example 64 | A |
| Example 65 | A |
| Example 66 | A |
| Example 67 | A |
| Example 68 | A |
| Example 69 | A |
| Example 70 | A |
| Example 71 | A |
| Example 72 | A |
| Example 73 | A |
| Example 74 | A |
| Example 75 | A |
| Example 76 | A |
| Example 77 | A |
| Example 78 | A |
| Example 79 | A |
| Example 80 | A |
| Example 81 | A |
| Example 82 | A |
| Example 83 | A |
| Example 84 | A |
| Example 85 | A |
| Example 86 | A |
| Example 87 | A |
| Example 88 | A |
| Example 89 | A |
| Example 90 | A |
| Example 91 | A |
| Example 92 | A |
| Example 93 | A |
| Example 94 | A |

TABLE 2-continued

| Compound | in vitro activity |
|---|---|
| Example 95 | A |
| Example 96 | A |
| Example 97 | A |
| Example 98 | A |
| Example 99 | A |
| Example 100 | A |
| Example 101 | A |
| Example 102 | A |
| Example 103 | A |
| Example 104 | A |
| Example 105 | A |
| Example 106 | B |
| Example 107 | B |
| Example 108 | B |
| Example 109 | B |
| Example 111 | A |
| Example 112 | A |
| Example 113 | A |
| Example 114 | A |
| Example 115 | A |
| Example 116 | A |
| Example 117 | B |
| Example 118 | A |
| Example 119 | A |
| Example 120 | A |
| Example 121 | A |
| Example 122 | A |
| Example 123 | B |
| Example 124 | A |
| Example 125 | A |
| Example 126 | A |
| Example 127 | B |
| Example 128 | A |
| Example 129 | A |
| Example 130 | A |
| Example 131 | B |
| Example 132 | A |
| Example 133 | A |
| Example 134 | A |
| Example 135 | A |
| Example 136 | A |
| Example 137 | A |
| Example 139 | A |
| Example 140 | A |
| Example 141 | A |
| Example 142 | A |
| Example 143 | A |
| Example 144 | A |
| Example 145 | A |
| Example 146 | A |
| Example 147 | A |
| Example 148 | A |
| Example 149 | A |
| Example 150 | C |
| Example 153 | A |
| Example 154 | A |
| Example 155 | A |
| Example 156 | A |
| Example 157 | A |
| Example 158 | A |
| Example 159 | A |
| Example 160 | A |
| Example 161 | A |
| Example 162 | A |
| Example 163 | A |
| Example 164 | A |
| Example 165 | A |
| Example 166 | A |
| Example 167 | A |
| Example 168 | A |
| Example 169 | A |
| Example 170 | A |
| Example 171 | A |
| Example 172 | A |
| Example 173 | A |
| Example 175 | A |
| Example 176 | B |

TABLE 2-continued

| Compound | in vitro activity |
|---|---|
| Example 180 | A |
| Example 181 | B |
| Example 182 | C |
| Example 183 | B |
| Example 184 | B |
| Example 185 | C |
| Example 186 | A |
| Example 187 | A |
| Example 188 | A |
| Example 189 | A |
| Example 190 | B |
| Example 191 | A |
| Example 192 | A |
| Example 193 | A |
| Example 194 | A |
| Example 195 | B |
| Example 196 | A |
| Example 199 | A |
| Example 200 | A |
| Example 201 | A |
| Example 202 | A |
| Example 203 | A |
| Example 204 | A |
| Example 205 | A |
| Example 206 | A |
| Example 207 | A |
| Example 208 | A |
| Example 209 | A |
| Example 210 | A |
| Example 211 | A |
| Example 212 | A |
| Example 213 | A |
| Example 214 | A |
| Example 215 | A |
| Example 216 | A |
| Example 217 | A |
| Example 218 | A |
| Example 219 | B |
| Example 220 | B |
| Example 221 | A |
| Example 222 | A |
| Example 225 | A |
| Example 226 | B |
| Example 234 | A |
| Example 235 | A |
| Example 236 | B |
| Example 237 | A |
| Example 238 | A |
| Example 239 | A |
| Example 240 | A |
| Example 241 | A |
| Example 242 | A |
| Example 243 | B |
| Example 244 | B |
| Example 245 | A |
| Example 246 | A |
| Example 247 | A |
| Example 248 | A |
| Example 249 | A |
| Example 250 | A |
| Example 251 | A |
| Example 252 | B |
| Example 253 | B |
| Example 254 | A |
| Example 255 | A |
| Example 256 | A |
| Example 257 | B |
| Example 258 | B |
| Example 259 | A |
| Example 260 | A |
| Example 261 | A |
| Example 262 | A |
| Example 263 | A |
| Example 264 | A |
| Example 265 | A |
| Example 266 | A |
| Example 267 | A |

TABLE 2-continued

| Compound | in vitro activity |
|---|---|
| Example 268 | A |
| Example 269 | A |
| Example 270 | A |
| Example 271 | A |
| Example 272 | A |
| Example 273 | A |
| Example 274 | A |
| Example 275 | A |
| Example 276 | A |
| Example 277 | B |
| Example 278 | A |
| Example 279 | A |
| Example 280 | A |
| Example 281 | A |
| Example 282 | A |
| Example 283 | A |
| Example 284 | A |
| Example 285 | A |
| Example 286 | A |
| Example 287 | A |
| Example 288 | A |
| Example 289 | A |
| Example 290 | A |
| Example 291 | A |
| Example 292 | A |
| Example 293 | A |
| Example 294 | A |
| Example 295 | A |
| Example 296 | A |
| Example 297 | A |
| Example 298 | A |
| Example 299 | A |
| Example 300 | A |
| Example 301 | B |
| Example 302 | A |
| Example 303 | C |
| Example 304 | A |
| Example 305 | A |
| Example 306 | C |
| Example 307 | A |
| Example 308 | C |
| Example 309 | A |
| Example 310 | A |
| Example 311 | A |
| Example 312 | A |
| Example 313 | A |
| Example 314 | A |
| Example 315 | A |
| Example 316 | A |
| Example 317 | A |
| Example 318 | A |
| Example 319 | A |
| Example 320 | A |
| Example 321 | A |
| Example 322 | A |
| Example 323 | A |
| Example 324 | A |
| Example 325 | A |
| Example 326 | A |
| Example 327 | A |
| Example 328 | B |
| Example 329 | A |
| Example 330 | A |
| Example 331 | A |
| Example 332 | B |
| Example 333 | A |
| Example 334 | A |
| Example 335 | A |
| Example 336 | C |
| Example 337 | C |
| Example 338 | C |
| Example 339 | B |
| Example 340 | C |
| Example 341 | C |
| Example 342 | B |
| Example 343 | B |
| Example 344 | B |
| Example 345 | B |
| Example 346 | C |
| Example 347 | C |
| Example 348 | C |
| Example 349 | A |
| Example 350 | C |
| Example 351 | C |
| Example 352 | C |
| Example 353 | A |
| Example 354 | B |
| Example 355 | A |
| Example 356 | C |
| Example 357 | A |
| Example 358 | B |
| Example 359 | A |
| Example 360 | A |
| Example 361 | A |
| Example 362 | A |
| Example 363 | B |
| Example 364 | B |
| Example 365 | C |
| Example 366 | A |
| Example 367 | A |
| Example 368 | A |
| Example 369 | A |
| Example 370 | A |
| Example 371 | A |
| Example 372 | A |
| Example 373 | A |
| Example 374 | A |
| Example 375 | A |
| Example 376 | A |
| Example 377 | B |
| Example 378 | B |
| Example 379 | A |
| Example 380 | A |
| Example 381 | A |
| Example 382 | B |
| Example 383 | A |
| Example 384 | A |
| Example 385 | B |
| Example 386 | A |
| Example 387 | A |
| Example 388 | A |
| Example 389 | B |
| Example 390 | B |
| Example 391 | A |
| Example 392 | C |
| Example 393 | A |
| Example 395 | A |
| Example 396 | C |
| Example 397 | A |
| Example 398 | A |
| Example 399 | A |
| Example 400 | A |
| Example 401 | A |
| Example 402 | A |
| Example 403 | A |
| Example 404 | A |
| Example 405 | A |
| Example 406 | A |
| Example 407 | A |
| Example 408 | A |
| Example 409 | A |
| Example 410 | A |
| Example 411 | A |
| Example 412 | A |
| Example 413 | A |
| Example 414 | A |
| Example 415 | A |
| Example 416 | A |
| Example 417 | A |
| Example 418 | A |

Inhibition of HIV replication. A recombinant NL-Rluc virus was constructed in which a section of the nef gene from NL4-3 was replaced with the Renilla Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/\text{drug conc.})^m]$ (Johnson V A, Byington R T. Infectivity Assay. In Techniques in HIV Research. ed. Aldovini A, Walker BD. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in the Table 2. Activity equal to A refers to a compound having $IC_{50}=<10$ nM while B and C denote compounds having $IC_{50}=<10$ nM and $IC_{50}<100$ nM and $IC_{50}>100$ nM respectively.

TABLE 2

| Example | Antiviral activity |
|---|---|
| Example 1 | B |
| Example 2 | B |
| Example 3 | B |
| Example 4 | C |
| Example 5 | B |
| Example 6 | C |
| Example 7 | C |
| Example 8 | B |
| Example 9 | C |
| Example 11 | C |
| Example 12 | B |
| Example 13 | B |
| Example 14 | B |
| Example 15 | B |
| Example 16 | A |
| Example 17 | A |
| Example 18 | A |
| Example 19 | C |
| Example 20 | A |
| Example 21 | A |
| Example 22 | A |
| Example 23 | A |
| Example 24 | A |
| Example 25 | A |
| Example 26 | A |
| Example 27 | B |
| Example 28 | A |
| Example 29 | B |
| Example 30 | A |
| Example 31 | A |
| Example 32 | A |
| Example 33 | A |
| Example 34 | A |
| Example 35 | A |
| Example 36 | A |
| Example 38 | B |
| Example 39 | B |
| Example 40 | A |
| Example 41 | A |
| Example 42 | A |
| Example 43 | A |
| Example 44 | A |
| Example 45 | A |
| Example 47 | B |
| Example 48 | A |
| Example 50 | A |
| Example 51 | A |
| Example 52 | A |
| Example 53 | A |
| Example 54 | A |
| Example 55 | A |
| Example 56 | A |
| Example 57 | A |
| Example 58 | A |
| Example 59 | A |
| Example 60 | A |
| Example 61 | A |
| Example 62 | A |
| Example 63 | A |
| Example 64 | A |
| Example 65 | A |
| Example 66 | A |
| Example 67 | A |
| Example 68 | B |
| Example 69 | A |
| Example 70 | A |
| Example 71 | A |
| Example 72 | A |
| Example 73 | A |
| Example 74 | A |
| Example 75 | A |
| Example 76 | A |
| Example 77 | A |
| Example 78 | A |
| Example 79 | A |
| Example 80 | A |
| Example 81 | A |
| Example 82 | A |
| Example 83 | B |
| Example 84 | C |
| Example 85 | A |
| Example 86 | A |
| Example 87 | A |
| Example 88 | A |
| Example 89 | A |
| Example 90 | A |
| Example 91 | A |
| Example 92 | A |
| Example 93 | A |
| Example 94 | A |
| Example 95 | A |
| Example 96 | A |
| Example 97 | A |
| Example 98 | A |
| Example 99 | A |
| Example 100 | A |
| Example 101 | A |
| Example 102 | A |
| Example 103 | A |
| Example 104 | A |
| Example 105 | A |
| Example 106 | B |
| Example 107 | B |
| Example 108 | C |
| Example 109 | C |
| Example 110 | B |
| Example 111 | A |
| Example 112 | A |
| Example 113 | A |
| Example 114 | A |
| Example 115 | A |
| Example 116 | A |
| Example 117 | B |
| Example 118 | A |
| Example 119 | A |
| Example 120 | A |
| Example 121 | A |
| Example 122 | A |
| Example 123 | B |
| Example 124 | A |
| Example 125 | B |
| Example 126 | A |
| Example 127 | B |

TABLE 2-continued

| Example | Antiviral activity |
|---|---|
| Example 128 | A |
| Example 129 | A |
| Example 130 | A |
| Example 131 | B |
| Example 132 | A |
| Example 133 | A |
| Example 134 | A |
| Example 135 | A |
| Example 136 | B |
| Example 137 | A |
| Example 138 | A |
| Example 139 | A |
| Example 140 | A |
| Example 141 | A |
| Example 142 | A |
| Example 143 | A |
| Example 144 | B |
| Example 145 | A |
| Example 146 | A |
| Example 147 | A |
| Example 148 | A |
| Example 149 | B |
| Example 150 | C |
| Example 153 | A |
| Example 154 | A |
| Example 155 | A |
| Example 156 | A |
| Example 157 | A |
| Example 158 | A |
| Example 159 | A |
| Example 160 | A |
| Example 161 | A |
| Example 162 | A |
| Example 163 | A |
| Example 164 | A |
| Example 165 | A |
| Example 166 | A |
| Example 167 | A |
| Example 168 | A |
| Example 169 | A |
| Example 170 | A |
| Example 171 | A |
| Example 172 | A |
| Example 173 | A |
| Example 180 | A |
| Example 186 | A |
| Example 187 | A |
| Example 188 | A |
| Example 189 | A |
| Example 190 | C |
| Example 191 | A |
| Example 192 | A |
| Example 193 | A |
| Example 194 | B |
| Example 195 | B |
| Example 196 | A |
| Example 197 | B |
| Example 198 | C |
| Example 199 | A |
| Example 200 | A |
| Example 201 | A |
| Example 202 | A |
| Example 203 | A |
| Example 204 | A |
| Example 205 | A |
| Example 206 | A |
| Example 207 | A |
| Example 208 | A |
| Example 209 | A |
| Example 210 | C |
| Example 211 | A |
| Example 212 | A |
| Example 213 | A |
| Example 214 | A |
| Example 215 | A |
| Example 216 | A |
| Example 218 | A |
| Example 219 | A |
| Example 220 | C |
| Example 221 | A |
| Example 222 | A |
| Example 223 | B |
| Example 224 | A |
| Example 225 | A |
| Example 227 | C |
| Example 228 | C |
| Example 229 | C |
| Example 230 | C |
| Example 231 | C |
| Example 232 | C |
| Example 233 | C |
| Example 234 | A |
| Example 235 | A |
| Example 236 | B |
| Example 237 | A |
| Example 238 | A |
| Example 239 | B |
| Example 240 | B |
| Example 241 | A |
| Example 242 | A |
| Example 243 | B |
| Example 245 | A |
| Example 246 | A |
| Example 247 | A |
| Example 248 | A |
| Example 249 | A |
| Example 250 | A |
| Example 251 | A |
| Example 253 | A |
| Example 254 | A |
| Example 255 | A |
| Example 256 | A |
| Example 259 | A |
| Example 262 | A |
| Example 263 | A |
| Example 264 | A |
| Example 265 | A |
| Example 266 | A |
| Example 267 | A |
| Example 268 | A |
| Example 270 | A |
| Example 271 | A |
| Example 272 | A |
| Example 273 | A |
| Example 274 | A |
| Example 275 | A |
| Example 276 | A |
| Example 280 | A |
| Example 281 | A |
| Example 282 | B |
| Example 283 | B |
| Example 284 | A |
| Example 285 | C |
| Example 286 | A |
| Example 287 | A |
| Example 288 | A |
| Example 289 | A |
| Example 290 | A |
| Example 291 | A |
| Example 292 | A |
| Example 293 | A |
| Example 294 | A |
| Example 295 | A |
| Example 296 | A |
| Example 297 | B |
| Example 298 | A |
| Example 299 | B |
| Example 300 | A |
| Example 302 | A |
| Example 303 | C |
| Example 304 | B |
| Example 305 | A |
| Example 306 | C |
| Example 309 | A |

TABLE 2-continued

| Example | Antiviral activity |
| --- | --- |
| Example 310 | A |
| Example 312 | A |
| Example 313 | A |
| Example 314 | A |
| Example 315 | B |
| Example 316 | A |
| Example 317 | A |
| Example 318 | A |
| Example 319 | A |
| Example 320 | A |
| Example 321 | B |
| Example 323 | A |
| Example 324 | A |
| Example 325 | A |
| Example 326 | B |
| Example 327 | A |
| Example 328 | B |
| Example 329 | A |
| Example 330 | A |
| Example 334 | A |
| Example 339 | B |
| Example 342 | A |
| Example 343 | A |
| Example 344 | A |
| Example 345 | B |
| Example 349 | A |
| Example 353 | A |
| Example 354 | B |
| Example 355 | A |
| Example 357 | A |
| Example 358 | A |
| Example 359 | A |
| Example 360 | A |
| Example 362 | A |
| Example 371 | A |
| Example 372 | A |
| Example 373 | A |
| Example 374 | A |
| Example 375 | A |
| Example 380 | A |
| Example 382 | B |
| Example 383 | A |
| Example 384 | A |
| Example 386 | A |
| Example 387 | A |
| Example 388 | A |
| Example 391 | A |
| Example 392 | C |
| Example 393 | B |
| Example 395 | A |
| Example 396 | C |
| Example 397 | A |
| Example 398 | A |
| Example 399 | A |
| Example 400 | A |
| Example 401 | A |
| Example 402 | A |
| Example 403 | A |
| Example 404 | A |
| Example 406 | A |
| Example 407 | A |
| Example 408 | A |
| Example 409 | B |
| Example 410 | A |
| Example 411 | A |
| Example 412 | A |
| Example 413 | A |
| Example 414 | A |
| Example 415 | A |
| Example 416 | A |
| Example 417 | A |
| Example 418 | A |

Table 3 shows the activity of a set representative compounds.

TABLE 3

| Example | $K_i$ µM | $EC_{50}$ µM |
| --- | --- | --- |
| Example 6 | 0.012 | 0.141 |
| Example 19 | 0.126 | 0.302 |
| Example 33 | 0.001 | 0.002 |
| Example 38 | 0.009 | 0.037 |
| Example 41 | 0.001 | <0.001 |
| Example 42 | 0.001 | 0.001 |
| Example 48 | 0.001 | 0.004 |
| Example 219 | 0.012 | 0.037 |
| Example 303 | 0.180 | 0.192 |
| Example 306 | 0.860 | 0.385 |
| Example 314 | <0.001 | <0.001 |
| Example 357 | 0.009 | 0.006 |
| Example 382 | 0.011 | 0.016 |
| Example 392 | 0.467 | 0.618 |
| Example 396 | 0.294 | 0.455 |

Pharmaceutical Composition and Methods of Use

The compounds of this invention inhibit HIV integrase. HIV integrase inhibitors belonging to a class of diketo acid compounds prevented viral integration and inhibited HIV-1 replication in cells (Hazuda et al. *Science* 2000, 287, 646). Recently reltegravir, an HIV integrase inhibitor, has been approved by the FDA for treating AIDS and HIV infection.

Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Table 4 lists some agents useful in treating AIDS and HIV infection which are suitable for this invention.

TABLE 4

| DRUG NAME | MANUFACTURER | INDICATION |
|---|---|---|
| ANTIVIRALS | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection, ARC, |
| AL-721 | Ethigen (Los Angeles, CA) | PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/ Novartis | HIV infection, AIDS, ARC |
| CI-1012 | Warner-Lambert | HIV-1 infection |
| Cidofovir | Gilead Science | CMV retinitis, herpes, papillomavirus |

TABLE 4-continued

| DRUG NAME | MANUFACTURER | INDICATION |
|---|---|---|
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptase inhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HIV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |

TABLE 4-continued

| DRUG NAME | MANUFACTURER | INDICATION |
|---|---|---|
| Saquinavir (protease inhibitor) | Hoffmann-LaRoche | HIV infection, AIDS, ARC |
| Stavudine; d4T Didehydrodeoxythymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) (reverse transcriptase inhibitor) | Gilead | HIV infection, AIDS |
| COMBIVIR ® (reverse transcriptase inhibitor) | GSK | HIV infection, AIDS |
| abacavir succinate (or ZIAGEN ®) (reverse transcriptase inhibitor) | GSK | HIV infection, AIDS |
| REYATAZ ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| TRIZIVIR ® | | HIV infection, AIDS |
| KALETRA ® | Abbott | HIV infection, AIDS, ARC |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. Amgen | Kaposi's sarcoma AIDS, in combination w/AZT |
| Granulocyte Colony Stimulating Factor | | |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

Abbreviations used in the schemes generally follow conventions used in the art. Chemical abbreviations used in the specification and Examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Intermediate 1

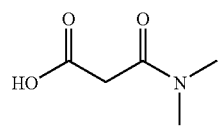

3-(Dimethylamino)-3-oxopropanoic acid. To a stirred solution of 3-tert-butoxy-3-oxopropanoic acid (680 mg, 4.25 mmol) and 2M dimethylamine in THF (3.18 mL, 6.37 mmol) in DMF (10 mL) was added diisopropyl-ethylamine (2.224 mL, 12.74 mmol), 4-(dimethylamino)pyridine (DMAP) (104 mg, 0.849 mmol) and O-(7-azabenzotriazol-1-yl)-N,N,N',N'-tetramethyluronium hexafluorophosphate (HATU) (2421 mg, 6.37 mmol) and the resulting mixture was stirred at room temperature for 16 h. Water was then added and the resulting mixture was extracted with ethyl acetate (2×50 mL), washed with 1N HCl (20 mL), dried (Na$_2$SO$_4$), filtered and concentrated to give crude product which was dissolved in CH$_2$Cl$_2$ (5.00 mL), treated with trifluoroacetic acid (4.91 mL, 63.7 mmol) and stirred at room temperature for 16 h. The solvent was then removed under reduced pressure to afford the title compound (230 mg, 41% yield) as a light-yellow solid, which was used in the next step without further purification. $^1$H NMR (500 MHz, DMSO-d$_6$) δ: 12.1 (1 H, br s), 3.4 (2 H, s), 2.9 (3 H, s), 2.8 (3 H, s). LCMS (M+H)=132.33.

Intermediate 2

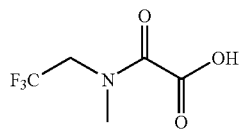

2-(Methyl(2,2,2-trifluoroethyl)amino)-2-oxoacetic acid. To a solution of methyl 2-(methyl(2,2,2-trifluoroethyl)amino)-2-oxoacetate (1.2 g, 6.03 mmol) in methanol (15 mL) and water (15.00 mL) was added LiOH (0.506 g, 12.05 mmol) and the mixture stirred for 2 h. The solution was then acidified with conc. HCl and concentrated. The solid was washed with CH$_2$Cl$_2$ (2×100 mL), filtered and the filtrate concentrated to afford the title compound (600 mg, 53.8% yield) (mixture of rotational isomers at room temperature) as an off-white solid. $^1$H NMR (500 MHz, DMSO-d$_6$) δ: 4.32 (1 H, q, J=9.36 Hz), 4.23 (1 H, q, J=9.46 Hz), 3.07 (2 H, s), 2.97 (1 H, s).

Intermediate 3

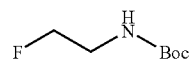

tert-Butyl 2-fluoroethylcarbamate. To a solution of 2-fluoroethanamine hydrochloride salt (2.5 g, 25.1 mmol) in THF (40 mL)/water (40 mL) at 0° C. was added sodium bicarbonate (8.44 g, 100 mmol), portion-wise. After 5 min, di-tert-butyl dicarbonate (7.00 mL, 30.1 mmol) was slowly added. The reaction was stirred under N$_2$ and allowed to warm to room temperature. The solution was concentrated, diluted with water (60 mL) and extracted with CH$_2$Cl$_2$ (3×75 mL). The organic layer was dried (MgSO$_4$) and concentrated to a give a crude oil which was purified by flash chromatography (Biotage flash chromatography system; 300 g SiO$_2$; 0-70% ethyl acetate:hexane over 2000 mL) to give the title compound as a clear oil (4.1 g, 100% yield). $^1$H NMR (400 MHz, CDCl$_3$) δ: 4.86 (1 H, brs), 4.47 (2 H, dt, J=47.43, 4.77 Hz), 3.43 (2 H, dq, J=27.92, 5.08 Hz), 1.45 (9 H, s).

Intermediate 4

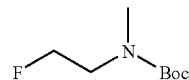

tert-Butyl 2-fluoroethyl(methyl)carbamate. To a solution of tert-butyl 2-fluoroethylcarbamate (4.1 g, 25.1 mmol) in THF (100 mL) at 0° C. was added sodium hydride, 60 wt % in mineral oil (1.507 g, 37.7 mmol) portion-wise. The reaction was stirred under N$_2$ for 15 minutes after which gas evolution ceased. Iodomethane (2.356 mL, 37.7 mmol) was added drop-wise and the reaction stirred under N$_2$. After 6 h, the reaction was quenched with water (100 mL) and concentrated. The aqueous solution was washed with CH$_2$Cl$_2$ (3×50 mL). The CH$_2$Cl$_2$ extracts were combined, washed with water (2×100 mL), dried (MgSO$_4$) and concentrated to afford the title compound (4.0 g, 90% yield) as a clear oil. $^1$H NMR (400 MHz, CDCl$_3$) δ: 4.58 (1H, brs), 4.47 (1 H, brs), 3.53 (1 H, brs), 3.47 (1 H, brs), 2.94 (3 H, s), 1.45 (9 H, s).

Intermediate 5

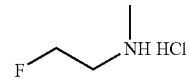

2-Fluoro-N-methylethanamine hydrochloride. To a solution of tert-butyl 2-fluoroethyl(methyl)carbamate (4.0 g, 22.57 mmol) in CH$_2$Cl$_2$ (10 mL) was added trifluoroacetic acid (10 mL, 130 mmol) and the reaction stirred under N$_2$ for 2 h. The solution was concentrated, dissolved in 1N HCl (30 mL), washed with Et$_2$O (2×30 mL) and the water removed to give the title compound HCl salt as a white solid. $^1$H NMR (500 MHz, CDCl$_3$) δ: 4.76 (2 H, dt, J=46.69, 4.27 Hz), 3.36 (2 H, dt, J=25.79, 3.97, 3.81 Hz), 2.84 (3 H, s).

Intermediate 6

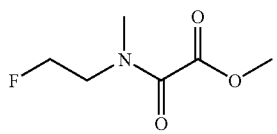

Methyl 2-((2-fluoroethyl)(methyl)amino)-2-oxoacetate. To a solution of 2-fluoro-N-methylethanamine hydrochloride salt (1 g, 8.81 mmol) in CH$_2$Cl$_2$ (40.0 mL) was added drop-wise diisopropyl-ethylamine (5.59 mL, 32.0 mmol) followed by the drop-wise addition of methyl 2-chloro-2-oxoacetate (0.981 g, 8.01 mmol) and the resulting mixture stirred for 3 h under N$_2$. The solution was concentrated and the residue was taken up in ethyl acetate (20 mL), washed with 1N HCl (2×15 mL) followed by saturated aqueous sodium bicarbonate (15 mL). The organic phase was dried (MgSO$_4$), filtered, and concentrated to give the title compound as a clear oil (1.2 g, 92% yield). $^1$H NMR (500 MHz, CDCl$_3$) δ: 4.46-4.73 (2 H, m) 3.82-3.93 (3 H, m) 3.60-3.77 (2 H, m) 3.01-3.20 (3 H, m). LCMS (M+H) calcd for C$_6$H$_{11}$FNO$_3$: 164.07; found: 164.11.

Intermediate 7

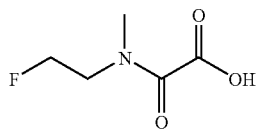

2-((2-Fluoroethyl)(methyl)amino)-2-oxoacetic acid. To a solution of ethyl 2-((2-fluoroethyl)(methyl)amino)-2-oxoacetate (1.2 g, 7.36 mmol) in methanol/water (30 mL, 1:1) was added LiOH (0.352 g, 14.71 mmol). The solution was stirred for 2 h. The methanol was removed by concentration and concentrated HCl (2 mL) was added. The solvent was removed and the residue dissolved in CH$_2$Cl$_2$ and filtered. The filtrate was concentrated to give the title compound as an off-white crystalline powder (0.615 g, 56% yield). $^1$H NMR (400 MHz, CDCl$_3$) δ: 4.47-4.89 (2 H, m) 3.67-4.39 (2 H, m) 3.07-3.60 (3 H, m).

Intermediate 8

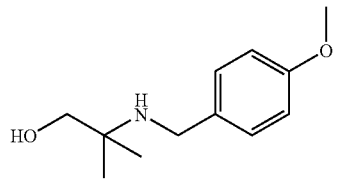

2-(4-Methoxybenzylamino)-2-methylpropan-1-ol. To a solution of 2-amino-2-methyl-1-propanol (8.4, 94 mmol) in 1,2-dichloroethane (150 mL) and acetic acid (4.3 mL, 77 mmol) was added 4-methoxy benzaldehyde (11.5 mL, 94 mmol). After stirring for 10 min, sodium triacetoxyborohydride (49.9 g, 235.5 mmol) was added portion-wise over 20 min. The resulting mixture was stirred at 60° C. for 2 h then cooled to room temperature and quenched with saturated NaHCO$_3$. The aqueous layer was washed with dichloromethane and made basic by the addition of 10N NaOH. The product was extracted with ethyl acetate, concentrated and crystallized from Et$_2$O/hexane to give the title compound as a white solid (11.95 g, 61% yield). $^1$H NMR (300 MHz, CDCl$_3$) δ: 7.32-7.20 (2H, m), 6.86-6.80 (2H, m), 3.76 (3H, s), 3.58 (2H, s), 3.30 (2H, s), 1.11 (6H, s). LCMS (M+H) calcd for C$_{12}$H$_{20}$NO$_2$: 210.14; found: 210.20.

Intermediate 9

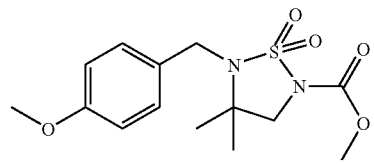

Methyl 5-(4-methoxybenzyl)-4,4-dimethyl-1,2,5-thiadiazolidine-2-carboxylate 1,1-dioxide. To a solution of 2-(4-methoxybenzylamino)-2-methylpropan-1-ol (12 g, 57.3 mmol) in THF (130 mL) was added (methoxycarbonylsulfamoyl)triethylammonium hydroxide(Burgess reagent) (44 g, 172 mmol) and the resulting mixture stirred at room temperature for 2 days. The mixture was diluted with ethyl acetate and washed with 1N HCl followed by brine. The organic phase was dried (Na$_2$SO$_4$), filtered and concentrated. The residue was purified by flash chromatography (Biotage flash chromatography system; 0%-70% ethyl acetate/hexane) to give a pale yellow oil that was further purified by flash chromatography eluting with 25% then 50% ethyl acetate/hexane to afford the title compound as a white solid (17.56 g, 93% yield). $^1$H NMR (500 MHz, CDCl$_3$) δ: 7.32-7.31 (2H, m), 6.86-6.84 (2H, m), 4.19 (2H, s), 3.89 (3H, s), 3.78 (3H, s), 3.64 (2H, s), 1.28 (6H, s).

Intermediate 10

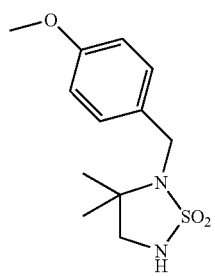

2-(4-Methoxybenzyl)-3,3-dimethyl-1,2,5-thiadiazolidine 1,1-dioxide. To a suspension of methyl 5-(4-methoxybenzyl)-4,4-dimethyl-1,2,5-thiadiazolidine-2-carboxylate 1,1-dioxide (17.56 g, 53.5 mmol) in methanol/water (300 mL, 2:1) was added 10 N NaOH (10.7 mL, 107 mmol) and the mixture stirred at room temperature for 4 h. The mixture was made acidic with 10 N HCl and washed with ethyl acetate. The combined organic layers were dried (Na$_2$SO$_4$), filtered and concentrated to give the title compound as a white solid (12.91 g, 89% yield). $^1$H NMR (500 MHz, CDCl$_3$) δ: 7.34-

7.32 (2H, m), 6.86-6.84 (2H, m), 4.74 (1H, brs), 4.18 (2H, s), 3.78 (3H, s), 3.24 (2H, s), 1.21 (9H, s).

Intermediate 11

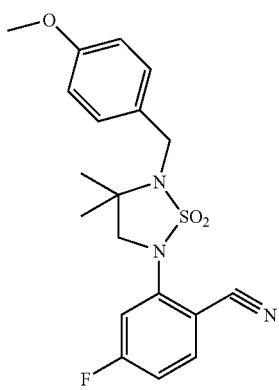

4-Fluoro-2-(5-(4-methoxybenzyl)-4,4-dimethyl-1,1-dioxido-1,2,5-thiadiazolidin-2-yl)benzonitrile. 2-Bromo-4-fluorobenzonitrile, tris(dibenzylideneacetone)dipalladium (0) (0.238 g, 0.26 mmol), 9,9-dimethyl-4,5-bis (diphenylphosphino)xanthene (0.231 g, 0.4 mmol) and potassium carbonate (5.72 g, 41.4 mmol) were stirred together. Added to this was a solution of 2-(4-methoxybenzyl)-3,3-dimethyl-1,2,5-thiadiazolidine 11-dioxide (8.00 g, 29.6 mmol) in dioxane (50 mL) and the resulting mixture stirred at 100° C. for 18 h. The cooled mixture was diluted with CH$_2$Cl$_2$ and the solids were removed by filtration. The solvent was evaporated leaving a yellow oil that was purified by flash chromatography (Biotage flash chromatography system, 5%-100% ethyl acetate/hexane) to give a cream colored solid that was triturated with ethyl acetate/hexane (1:4) to give the title compound as a white powder (4.6048 g, 42% yield). $^1$H NMR (500 MHz, CDCl$_3$) δ: 7.71-7.65 (2H, m), 7.37 (2H, d, J=8.5 Hz), 7.12-7.08 (1H, m), 6.88 (2H, d, J=8.5 Hz), 4.28 (2H, s), 3.80 (3H, s), 3.78 (2H, s), 1.42 (6H, s).

Intermediate 12

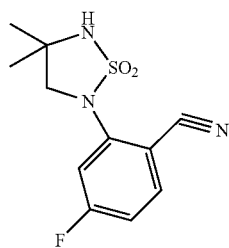

2-(4,4-Dimethyl-1,1-dioxido-1,2,5-thiadiazolidin-2-yl)-4-fluorobenzonitrile. To a solution of 4-fluoro-2-(5-(4-methoxybenzyl)-4,4-dimethyl-1,1'-dioxido-1,2,5-thiadiazolidin-2-yl)benzonitrile (4.6 g, 11.81 mmol) in dichloromethane (30 mL) was added trifluoroacetic acid (2.73 mL, 35.4 mmol) and the mixture stirred at room temperature for 18 h. The mixture was diluted with methanol and the white solid collected by filtration and discarded. The cloudy solution was concentrated and the resulting solid was triturated with methanol and then filtered to give the title compound as a white solid (3.18 g, 100% yield). LCMS (M+H) calcd for C$_{11}$H$_{13}$FN$_3$O$_2$S: 270.07; found: 270.00. $^1$H NMR (300 MHz, CDCl$_3$) δ: 7.66 (0.2H, dd, J=8.8, 5.8 Hz), 7.58 (1H, dd, J=9.5, 2.6 Hz), 7.10-7.04 (1H, m), 4.48 (1H, brs), 3.85 (2H, s), 1.55 (6H, s).

Intermediate 13

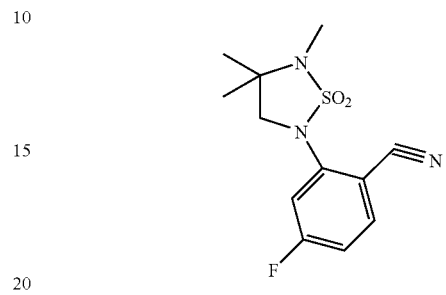

4-Fluoro-2-(4,4,5-trimethyl-1,1-dioxido-1,2,5-thiadiazolidin-2-yl)benzonitrile. To a solution of 2-(4,4-dimethyl-1,1-dioxido-1,2,5-thiadiazolidin-2-yl)-4-fluorobenzonitrile (3.18 g, 11.81 mmol) in DMF (40 mL) was added NaH (0.312 g, 12.99 mmol) and the mixture stirred for 5 min. Iodomethane (1.477 mL, 23.62 mmol) was added and the mixture stirred at 90° C. for 2 h then at room temperature for 16 h. The mixture was diluted with H$_2$O and extracted with ethyl acetate. The organic phase was washed two times with H$_2$O followed by brine, dried (Na$_2$SO$_4$), filtered and concentrated to give the title compound as a white solid (3.35 g, 100% yield). LCMS (M+H) calcd for C$_{12}$H$_{15}$FN$_3$O$_2$S: 284.08; found: 284.14. $^1$H NMR (300 MHz, CDCl$_3$) δ: 7.70-7.61 (2H, m), 7.11-7.05 (1H, m), 3.80 (2H, s), 2.73 (3H, s), 1.42 (6H, s).

Intermediate 14

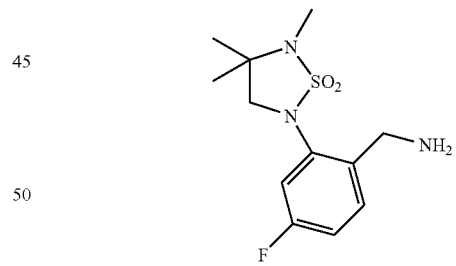

1-(4-Fluoro-2-(4,4,5-trimethyl-1,1-dioxido-1,2,5-thiadiazolidin-2-yl)phenyl)methanamine. To a solution of 4-fluoro-2-(4,4,5-trimethyl-1,1-dioxido-1,2,5-thiadiazolidin-2-yl) benzonitrile (3.34 g, 11.8 mmol) in CH$_2$Cl$_2$ (30 mL), ethyl acetate (30.0 mL) and ethanol (30.0 mL) was added 1N HCl (12 mL) followed by 10% palladium on carbon (0.377 g, 3.54 mmol). The mixture was shaken under H$_2$ at 50 psi for 22 h then filtered over CELITE® and concentrated. The solids were triturated with H$_2$O and removed by filtration. The aqueous solution was washed with ethyl acetate and lyophilized to give the title compound, as the HCl salt, as a white powder (3.44 g, 90% yield). LCMS (M+H) calcd for C$_{12}$H$_{19}$FN$_3$O$_2$S: 288.11; found: 288.19. $^1$H NMR (300 MHz, DMSO) δ: 8.35

(2H, brs), 7.71 (1H, dd, J=8.6, 6.4 Hz), 7.54 (1H, dd, J=9.9, 2.6 Hz), 7.43 (1H, td, J=8.4, 2.6 Hz), 4.19 (2H, s), 3.75 (2H, s), 2.63 (3H, s), 1.35 (6H, s).

Intermediate 15

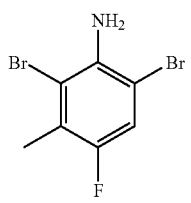

2,6-Dibromo-4-fluoro-3-methylaniline. To a stirred solution of 4-fluoro-3-methylaniline (12.76 g, 102 mmol) in 1:1 $CH_2Cl_2$/methanol (125 ml) was added, dropwise, a solution of bromine (13.14 ml, 255 mmol) in 1:1 $CH_2Cl_2$/methanol (125 ml) at room temperature over 1.5 h using an addition funnel. After 4 h, the reaction mixture was concentrated and the resulting residue was stirred with 1N $Na_2S_2O_3$ (100 mL) and ethyl acetate (150 mL) for 10 min then carefully basified with 1N $Na_2CO_3$ (150 mL). The organic layer was separated and the aqueous layer extracted with ethyl acetate (2×100 mL). The combined organic layers were washed with 1N $Na_2S_2O_3$ (100 mL) followed by brine (50 mL), then dried ($Na_2SO_4$/carbon), filtered and concentrated to give 2,6-dibromo-4-fluoro-3-methylaniline (28.6 g, 101 mmol, 99% yield) as a tan color solid. $^1$H NMR (400 MHz, $CDCl_3$) δ: 7.19 (1 H, d, J=8.5 Hz), 4.42 (2 H, brs), 2.31 (3 H, d, J=2.5 Hz). LCMS (M+H) calcd for $C_7H_7FN$: 283.89; found: 283.83.

Intermediate 16

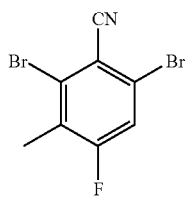

2,6-Dibromo-4-fluoro-3-methylbenzonitrile. To a mixture of 2,6-dibromo-4-fluoro-3-methylaniline (2.83 g, 10 mmol), acetic acid (7 mL) and water (4 mL) was added $H_2SO_4$ (1.492 mL, 28 mmol) and the resulting mixture stirred at 70° C. until it turned into a homogeneous solution. The reaction mixture was then cooled in ice-water bath and treated with 1N sodium nitrite (0.759 g, 11 mmol) over 15 min., to produce the corresponding diazonium salt.

In a separate flask, KCN (3.26 g, 50 mmol) was added in small portions over 15 min., to a solution of copper (II) sulfate (1.915 g, 12 mmol) in water (25 mL) at ice bath temperature. The ice bath was then removed after which sodium bicarbonate (6.72 g, 80 mmol) and benzene (20 mL) was added and the mixture warmed to 55° C. To this vigorously stirred mixture was added, dropwise over 15 min., the diazonium salt synthesized above. After 1 h, the mixture was carefully neutralized with saturated $Na_2CO_3$, then cooled to room temperature and extracted with $Et_2O$ (3×50 mL). The combined organic layers were washed with water (25 mL) followed by brine (25 mL), then dried ($Na_2SO_4$), filtered and concentrated to give the crude product which was purified by flash column chromatography on a silica gel column using 5% ethyl acetate/hexane as eluent to afford 2,6-dibromo-4-fluoro-3-methylbenzonitrile (1.1474 g, 3.92 mmol, 39% yield) as an off-white solid. $^1$H NMR (500 MHz, $CDCl_3$) δ: 7.41 (1 H, d, J=8.5 Hz), 2.38 (3 H, d, J=2.4 Hz).

Intermediate 17

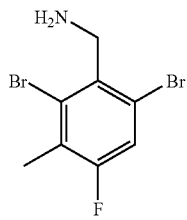

(2,6-Dibromo-4-fluoro-3-methylphenyl)methanamine. To a stirred solution of 2,6-dibromo-4-fluoro-3-methylbenzonitrile (1.145 g, 3.91 mmol) in THF (7 mL) was added 2M borane-methylsulfide complex (8 mL, 16.00 mmol) over 5 min at room temperature. After 30 min, the reaction mixture was warmed to 60° C. and stirred for an additional 1.6 h. The mixture was cooled then quenched by the careful addition of methanol (10 mL) and 4M HCl/dioxane (2 mL). After 30 min, the reaction mixture was heated to 50° C. for 45 min and concentrated. The residue was taken up in sat. $Na_2CO_3$ (20 mL) and extracted with $CH_2Cl_2$ (3×25 mL). The combined $CH_2Cl_2$ extracts were washed with water (20 mL) followed by brine (20 mL), then dried ($Na_2SO_4$), filtered and concentrated to afford (2,6-dibromo-4-fluoro-3-methylphenyl)methanamine (1.16 g, 3.91 mmol, 100% yield) as a white solid. $^1$H NMR (500 MHz, $CDCl_3$) δ: 7.31 (1 H, d, J=8.9 Hz), 4.19 (2 H, s), 2.34 (3 H, d, J=2.4 Hz), 1.59 (2 H, brs). LCMS (M+H) calcd for $C_{15}H_{21}N_2O_3$: 297.91; found: 297.85.

Intermediate 18

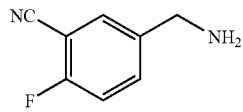

5-(Aminomethyl)-2-fluorobenzonitrile. A solution of 5-(bromomethyl)-2-fluorobenzonitrile (300 mg, 1.402 mmol) in 7M $NH_3$/methanol (5 mL, 35.0 mmol) was stirred at room temp for 18 h. After the removing the solvent the resulting residue was stirred with $Et_2O$/sat. $Na_2CO_3$. The aqueous layer was then separated and the organic layer dried ($Na_2SO_4$), filtered and concentrated to give a 3:1 mixture of the title compound, amine 5-(aminomethyl)-2-fluorobenzonitrile contaminated and 5,5'-azanediylbis(methylene)bis(2-fluorobenzonitrile). The mixture was used without further purification. $^1$H NMR (500 MHz, $CDCl_3$) δ: 7.48-7.66 (2 H, m), 7.07-7.21 (1 H, m), 3.89 (2 H, s).

Intermediate 19

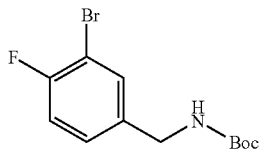

tert-Butyl 3-bromo-4-fluorobenzylcarbamate. To a solution of (3-bromo-4-fluorophenyl)methanamine, HCl (1 g, 4.16 mmol) in THF (10 mL)/water (10 mL) at 0° C. was added, portion-wise, sodium bicarbonate (1.397 g, 16.63 mmol). After 5 min, di-tert-butyl dicarbonate (1.062 mL, 4.57 mmol) was slowly added and the reaction stirred while gradually warming to room temperature. The solution was diluted with Et$_2$O (20 mL) and washed with 1N HCl (2×30 mL). The organic layer was dried (MgSO$_4$) and concentrated. The residue was purified by flash chromatography (Biotage flash chromatography system; 40 g SiO$_2$; 0-20% ethyl acetate:hexane) to give the title compound as a clear oil (1.26 g, 100% yield). $^1$H NMR (500 MHz, CDCl$_3$) δ: 7.49 (1 H, dd, J=6.53, 2.01 Hz), 7.17-7.25 (1 H, m), 7.08 (1 H, t, J=8.28 Hz), 4.87 (1 H, brs), 4.27 (2 H, d, J=5.77 Hz), 1.48 (9 H, s).

Intermediate 20

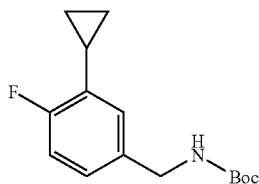

tert-Butyl 3-cyclopropyl-4-fluorobenzylcarbamate. Under N$_2$, a toluene (4.70 mL)/water (0.235 mL) solution of tert-butyl 3-bromo-4-fluorobenzylcarbamate (0.300 g, 0.986 mmol) was treated with potassium phosphate tribasic (0.733 g, 3.45 mmol), cyclopropylboronic acid (0.110 g, 1.282 mmol), and tricyclohexenylphosphene (0.028 g, 0.099 mmol) in was added palladium(II) acetate (0.011 g, 0.049 mmol). The reaction was stirred at 100° C. for 3 h. The solution was diluted with water (15 mL) then extracted with ethyl acetate (2×15 mL). The organic extracts were combined, washed with brine (20 mL), then dried (MgSO$_4$), filtered and concentrated. The residue was purified by flash chromatography (Biotage flash chromatography system; 60 g SiO$_2$; 0-20% ethyl acetate:hexane over 900 mL) to give the title compound as a white crystalline solid (0.230 g, 88% yield). $^1$H NMR (500 MHz, CDCl$_3$) δ: 6.98-7.05 (1 H, m), 6.90-6.97 (1 H, m), 6.79 (1 H, dd, J=7.02, 1.53 Hz), 4.75 (1 H, brs), 4.21 (2 H, d, J=5.49 Hz), 2.02-2.09 (1 H, m), 1.45 (9 H, s), 0.93-1.01 (2 H, m), 0.66-0.75 (2 H, m).

Intermediate 21

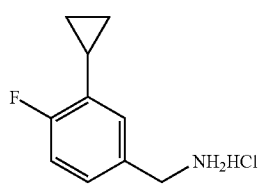

(3-Cyclopropyl-4-fluorophenyl)methanamine hydrochloride salt. To a solution of tert-butyl 3-cyclopropyl-4-fluorobenzylcarbamate (0.220 g, 0.829 mmol) in CH$_2$Cl$_2$ (5 mL) was added trifluoroacetic acid (5 mL, 64.9 mmol). The solution was stirred at room temperature for 1 h. To the solution was added 2M HCl in Et$_2$O (5 mL). The solids were collected via filtration to give the title compound as a white solid (0.154 g, 92% yield). $^1$H NMR (400 MHz, MeOD) δ: 7.21-7.33 (1 H, m), 7.03-7.16 (2 H, m), 4.06 (2 H, s), 2.06-2.18 (1 H, m), 0.99-1.09 (2 H, m), 0.74-0.86 (2 H, m). $^{13}$C NMR (500 MHz, MeOD) δ: 162.09 (1C, d, J=245.84 Hz), 131.64 (1C, d, J=14.64 Hz), 128.98 (1C, d, J=3.08 Hz), 127.33 (1C, d, J=8.48 Hz), 126.78 (1C, d, J=4.62 Hz), 115.15 (1C, d, J=23.12 Hz), 42.43 (1C, s), 8.03 (1C, d, J=5.39 Hz), 7.04 (1C, s).

Intermediate 22

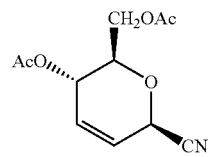

((2R,3S,6R)-3-Acetoxy-6-cyano-3,6-dihydro-2H-pyran-2-yl)methyl acetate. To (2R,3S,4R)-2-(acetoxymethyl)-3,4-dihydro-2H-pyran-3,4-diyl-diacetate (1.0 g, 3.67 mmol) in anhydrous CH$_2$Cl$_2$ (15 mL) was added dropwise, TMSCN (0.744 g, 7.51 mmol). The reaction mixture was stirred at 23° C. for 15 min. then BF$_3$-etherate (4 drops) added. The reaction mixture was stirred at 23° C. for 30 min. The solvent and excess TMSCN were removed in vacuo and the crude material purified by silica gel column chromatography (Biotage flash chromatography system) using ethyl acetate:hexane (20:80) to (1:1) resulting a complete separation of the C6-epimeric diastereomers. The first eluting compound (400 mg, 46% yield) was confirmed by NMR to be ((2R,3S,6S)-3-acetoxy-6-cyano-3,6-dihydro-2H-pyran-2-yl)methyl acetate while the slower eluting compound (260 mg, 30% yield) confirmed by NMR to be ((2R,3S,6R)-3-acetoxy-6-cyano-3,6-dihydro-2H-pyran-2-yl)methyl acetate. $^1$H NMR (400 MHz, CDCl$_3$) δ ppm 6.07 (1H, dt, J=10.1, 2.5 Hz), 5.95 (1 H, ddd, J=10.2, 2.0, 1.9 Hz), 5.28-5.35 (1 H, m, J=8.1, 2.4, 2.2, 2.2 Hz), 5.14 (1 H, q, J=2.5 Hz), 4.27-4.33 (1 H, m), 4.19-4.25 (1 H, m), 3.84 (1 H, ddd, J=8.4, 5.9, 2.9 Hz), 2.11 (3 H, s), 2.08 (3H, s).

Intermediate 23

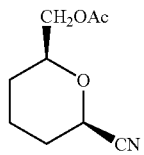

((2S,6R)-6-Cyanotetrahydro-2H-pyran-2-yl)methyl acetate. To a dry THF (200 mL) solution containing ((2R,3S,6R)-3-acetoxy-6-cyano-3,6-dihydro-2H-pyran-2-yl)methyl acetate (5.5 g, 23 mmol), diphenylsilane (8.47, 46 mmol) and zinc chloride (7.52 g, 55.2 mmol) was added after N$_2$ bubbling, Pd(PPh$_3$)$_4$ (2.66 g, 2.30 mmol). The reaction mixture was stirred at 23° C. for 4 h. (monitored by TLC). The reaction mixture was filtered through a short silica gel column using $CH_2Cl_2$ as solvent. The solvent was removed under reduced pressure and the crude material was purified by a silica gel column (Biotage flash chromatography system) using ethyl acetate:hexane (1:5) to (1:2) to afford 2.8 g (67% yield) mixture of ((2S,6R)-6-cyano-5,6-dihydro-2H-pyran-2-yl)methyl acetate and((2S,6R)-6-cyano-3,6-dihydro-2H-pyran-2-yl)methyl acetate. $^1$H NMR (400 MHz, $CDCl_3$) δ ppm 6.06-6.15 (0.5 H, m, J=7.6, 5.3, 2.8, 2.8 Hz), 5.93-6.02 (0.5 H, m, J=10.4, 5.2, 2.6, 2.6 Hz), 5.69-5.79 (1 H, m), 4.54 (0.5 H, dd, J=9.9, 3.8 Hz), 4.48 (0.5 H, m), 4.11-4.23 (2 H, m), 3.89 (1 H, m), 2.59-2.69 (1 H, m), 2.33-2.42 (1 H, m,), 2.16-2.22 (1 H, m), 2.14 (3 H, s), 2.12 (3H, s). To the mixture of ((2S,6R)-6-cyano-5,6-dihydro-2H-pyran-2-yl)methyl acetate and ((2S,6R)-6-cyano-3,6-dihydro-2H-pyran-2-yl) methyl acetate. (2.6 g, 14.4 mmol) in ethyl acetate (200 mL) was added Pd/C (5%) (0.200 g). The reaction mixture was stirred at 23° C. for 6 h. under a hydrogen atmosphere (balloon). The Pd/C was then removed by filtration and the solvent evaporated in vacuo to afford 2.20 g (84% yield) of the target compound. $^1$H NMR (400 MHz, $CDCl_3$) δ ppm 4.28 (1 H, dd, J=11.7, 2.7 Hz), 4.03-4.14 (2 H, m), 3.59-3.67 (1 H, m), 2.11 (3 H, s), 1.94-2.04 (2 H, m), 1.80-1.91 (1 H, m), 1.54-1.65 (2 H, m), 1.33-1.45 (1 H, m).

Intermediate 24

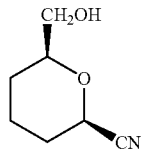

(2R,6S)-6-(Hydroxymethyl)tetrahydro-2H-pyran-2-carbonitrile. To ((2S,6R)-6-cyanotetrahydro-2H-pyran-2-yl)methyl acetate (3.90 g, 21.29 mmol) in methanol (300 mL) was added $Et_3N$ (30 mL). The reaction mixture was stirred at 23° C. for 18 h. The solvents were evaporated in vacuo. The residue was redissolved in methanol the solvent removed in vacuo (2×20 mL). The crude material was then purified on a silica gel column (Biotage flash chromatography system) eluting with a gradient mixture ethyl acetate (100%) to ethyl acetate:methanol (8:2) to afford 2.20 g (73% yield) of the title compound. $^1$H NMR (400 MHz, $CDCl_3$) δ ppm 4.31 (1 H, dd, J=11.6, 2.5 Hz), 3.58-3.63 (2 H, m), 3.51-3.57 (1 H, m), 2.06 (1 H, s), 1.94-2.03 (2 H, m), 1.79-1.90 (1 H, m), 1.53-1.65 (2 H, m), 1.36-1.47 (1 H, m).

Intermediate 25

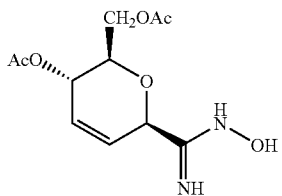

((2R,3S,6R)-3-Acetoxy-6-(N-hydroxycarbamimidoyl)-3,6-dihydro-2H-pyran-2-yl)methyl acetate. To (2R,6S)-6-(hydroxymethyl)tetrahydro-2H-pyran-2-carbonitrile (1.90 g, 13.46 mmol) in EtOH (11.0 mL) and $H_2O$ (11.0 mL) was added hydroxylamine (1.24 mL, 20.19 mmol). The reaction mixture was stirred at 80° C. for 3 h. The solvent was evaporated in vacuo and residual volatile impurities removed by azeotropic distillation with EtOH (2×20 mL) to afford 2.10 g (90% yield) of the title compound. LCMS ($^+$ESI, M+H$^+$) m/z 175.

Intermediate 26

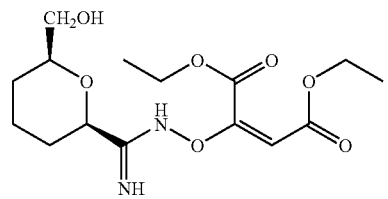

Diethyl 2-((2R,6S)-6-(hydroxymethyl) tetrahydro-2H-pyran-2-carboximidamidooxy)maleate. To ((2R,3S,6R)-3-acetoxy-6-(N-hydroxycarbamimidoyl)-3,6-dihydro-2H-pyran-2-yl)methyl acetate (2.33 g, 13.4 mmol) in EtOH (15 mL) was added diethylacetylenedicarboxylate (3.20 mL, 20.1 mmol) and the reaction mixture was stirred at 60° C. for 3 h. The solvent was removed in vacuo to afford 2.40 g (52% yield) of the title compound as an amber oil. LCMS ($^+$ESI, M+H$^+$) m/z 345.

Intermediate 27

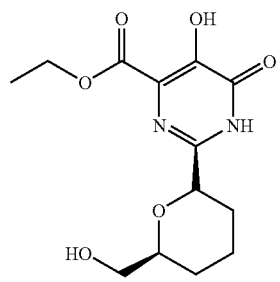

Ethyl 5-hydroxy-2-((2S,6S)-6-(hydroxymethyl)tetrahydro-2H-pyran-2-yl)-6-oxo-1,6-dihydropyrimidine-4-carboxylate. Diethyl 2-((2R,6S)-6-(hydroxymethyl)tetrahydro-2H-pyran-2-carboximidamidooxy) maleate (2.20 g, 6.39 mmol) in trimethylbenzene (25 mL) was heated in a sealed tube at 180° C. for 18 h. The solvent was removed in vacuo and the crude material was purified by preparative HPLC using a C18 column and trifluoroacetic acid in the mobile phase to afford 1.90 g (99% yield) of the title compound. $^1$H NMR (400 MHz, $CDCl_3$) δ ppm 12.52 (1 H, brs), 10.5-11.0 (1 H, brs), 4.46-4.57 (3 H, m), 3.70-3.82 (3 H, m), 3.56-3.64 (1 H, m), 2.24-2.33 (1 H, m), 1.96-2.07 (1 H, m), 1.58-1.76 (4H, m), 1.46-1.64 (3 H, J=7.4 Hz).

Intermediate 28

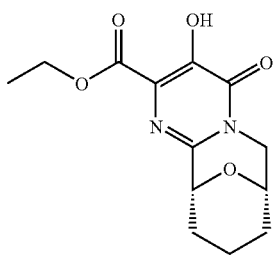

Ethyl (7S,11R)-3-hydroxy-4-oxo-6,7,8,9,10,11-hexahydro-4H-7,11-epoxypyrimido[1,2-a]azocine-2-carboxylate.
To ethyl 5-hydroxy-2-((2S,6S)-6-(hydroxymethyl)tetrahydro-2H-pyran-2-yl)-6-oxo-1,6-dihydropyrimidine-4-carboxylate (1.90 g, 6.37 mmol)in dry THF (60 mL) was added methanesulfonyl chloride (1.49 mL, 19.1 mmol) and di-isopropyl-ethylamine (3.56 mL, 20.0 mmol) at 0° C. The reaction mixture was stirred at 23° C. for 3 h. The THF was removed in vacuo, the crude material was dissolved in ethyl acetate (50 mL) and washed with 1N NaHCO$_3$ (50 mL). The aqueous solution was then washed with ethyl acetate (3×20 mL) and the combined organic fractions were dried (MgSO$_4$) filtered and concentrated in vacuo to give a brown oil. The crude oil was dissolved in EtOH:THF (20 mL:20 mL) and to this was added K$_2$CO$_3$ (0.881 g, 6.37 mmol) and H$_2$O (1.0 mL). The reaction mixture was stirred at 65° C. for 17 h. The solvent was removed in vacuo, the crude material was dissolved in ethyl acetate (50 mL) and washed with H$_2$0 (50 mL) and HCl aq. 1N (50 mL). The acidic aqueous phase was extracted with ethyl acetate (2×50 mL). The combined organic fractions were dried (MgSO$_4$) and concentrated in vacuo. The crude material was purified by preparative HPLC using a C18 column and trifluoroacetic acid in the mobile phase to afford the compound 1.16 g (65% yield) of the title compound. $^1$H NMR (400 MHz, CDCl$_3$) δ ppm 10.75 (1 H, s), 4.94 (1 H, d, J=2.3 Hz), 4.49-4.58 (3 H, m), 4.01-4.13 (2 H, m), 2.05-2.17 (2 H, m,), 1.96 (1 H, dd, J=13.6, 2.0 Hz), 1.76 (2 H, m), 1.39-1.49 (4 H, m). LCMS ($^+$ESI, M+H$^+$) m/z 281. HRMS (ESI$^+$) calculated for C$_{13}$H$_{16}$N$_2$O$_5$ [M+H$^+$]: 281.1137; found: 281.1147.

Intermediate 29

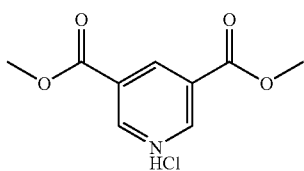

Dimethylpyridine-3,5-dicarboxylate hydrochloride. To pyridine-3,5-dicarboxylic acid (19.9 g, 119.1 mmol) in methanol (400 mL) was added of 2,2-dimethoxypropane (160 mL, 1.3 mol) and concentrated HCl (15 mL). The reaction mixture was refluxed for 18 h under an atmosphere of Ar. The solvent was evaporated then ether (100 mL) was added to the crude material and the resulting mixture heated to reflux. The mixture was allowed to remain at reflux for 2 hours then s allowed to cool to 23° C. and the precipitate filtered. The precipitate was dried to afford 27.5 g (86% yield) of the title compound as described in J. Org. Chem. Vol. 16, No 10, 1996. LCMS ($^+$ESI, M+H$^+$) m/z: 196.

Intermediate 30

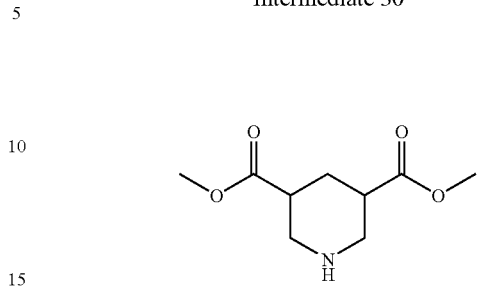

Dimethylpiperidine-3,5-dicarboxylate. To dimethylpyridine-3,5-dicarboxylate (15.0 g, 76.87 mmol) in acetic acid (150 mL) was added platinum oxide (0,250 mg, 1.1 mmol). The reaction mixture was stirred at 23° C. for 36 h under 45 psi of H$_2$. PtO$_2$ was removed by filtration on CELITE®, washed with acetic acid (20 mL) and the solvent removed in vacuo. A solution of NaHCO$_3$ (1M, 100 mL)) was then added and the organic material was extracted with CH$_2$Cl$_2$ (3×100 mL). The combined extracts were dried (MgSO$_4$) and concentrated to afford 13.7 g (88.6% yield) of the title compound. LCMS ($^+$ESI, M+H$^+$) m/z: 202.

Intermediate 31

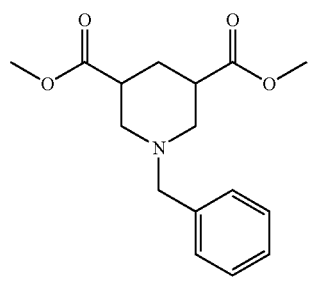

Dimethyl 1-benzylpiperidine-3,5-dicarboxylate. To dimethyl piperidine-3,5-dicarboxylate (7.5 g, 37.3 mmol) in acetonitrile (100 mL) was added K$_2$CO$_3$ (20.6 g, 149.1) and benzylbromide (4.43 mL, 37.3 mmol). The reaction mixture was stirred at 23° C. for 4 hours. The K$_2$CO$_3$ was removed by filtration and the solvent evaporated in vacuo. A solution of NaHCO$_3$ (1M, 150 mL) was added and the organic material extracted with ethyl acetate (3×50 mL), then dried (MgSO$_4$) and concentrated in vacuo. The crude material was purified on a Silica gel column (Biotage flash chromatography system), eluting with a gradient of ethyl acetate/hexane (10:90) to (35:65) to afford the title compound as the cis diastereomer 1.6 g which eluted after the corresponding trans diastereomer. (based on the NMR reported in Synthetic Communications 1997, 27 (1), 69-71.). $^1$H NMR (400 MHz, CDCl$_3$) δ ppm 7.26-7.36 (5 H, m), 3.68 (6 H, s), 3.59 (2 H, s), 3.15 (2 H, m), 2.66 (2 H, t, J=12.0 Hz), 2.36 (1 H, d, J=13.1 Hz), 2.05 (2 H, t, J=11.4 Hz), 1.56 (1 H, q, J=12.9 Hz). LCMS ($^+$ESI, M+H$^+$) m/z: 292.

Intermediate 32

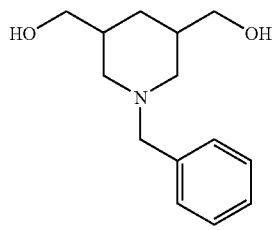

(1-Benzylpiperidine-3,5-diyl)dimethanol. To dimethyl 1-benzylpiperidine-3,5-dicarboxylate (1.5 g, 5.15 mmol) in dry THF (30 mL) was added a solution of lithium aluminum hydride in THF (2M, 3.87 mL, 7.73 mmol) at 0° C. The reaction mixture was stirred at 0° C. for 30 min. then warmed to 23° C. and stirred for 1.5 hour. A solution of methanol (0.5 mL) and (0.25 mL) was added followed by a 15% solution of NaOH (0.250 mL). The mixture was stirred for 1 hour at 23° C. then filtered. The organic material was extracted with ethyl acetate (3×20 mL) and the combined extracts were dried (MgSO$_4$) and concentrated in vacuo to afford 0.91 g (75% yield) of the title compound. $^1$H NMR (400 MHz, CDCl$_3$) δ ppm 7.26-7.35 (5H, m), 3.59 (2H, s), 3.44-3.55 (4 H, m), 3.06 (2 H, dt, J=10.6, 1.8 Hz), 1.88-1.98 (2 H, m), 1.79-1.86 (1 H, m), 1.68 (3 H, m). LCMS ($^+$ESI, M+H$^+$) m/z: 236.

Intermediate 33

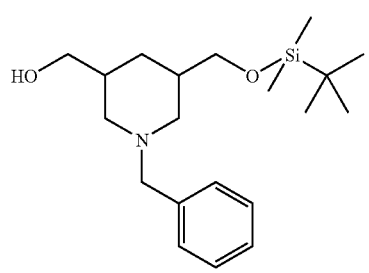

(1-Benzyl-5-((tert-butyldimethylsilyloxy)methyl)piperidin-3-yl)methanol. To 1-benzylpiperidine-3,5-diyl)dimethanol (0.5 g, 2.125 mmol) in dry THF (20 mL) was added NaH (60% in mineral oil)(90 mg, 2.23 mmol). The reaction mixture was stirred at 23° C. for 45 min. then, t-butyldimethylchlorosilane (0.352 g, 2.37 mmol) added and the reaction mixture stirred at 23° C. for 2 hours. The mixture was poured into ether (75 mL), washed with 10% aqueous K$_2$CO$_3$ (30 mL) then dried (MgSO$_4$) and concentrated in vacuo. The crude material was purified on a Silica gel column (Biotage flash chromatography system), eluting with a gradient of ethyl acetate:hexane (9:1) to ethyl acetate 100% to afford 0.340 g (43% yield) of the title compound. $^1$H NMR (400 MHz, CDCl$_3$) δ ppm 7.25-7.36 (5 H, m), 3.59 (2 H, s), 3.45-3.55 (4 H, m), 2.99-3.09 (2 H, m), 1.93-1.55 (5 H, m), 1.24-1.34 (1 H, m), 0.87 (9 H, s), 0.62-0.74 (1 H, m), 0.02 (6 H, s). LCMS ($^+$ESI, M+H$^+$) m/z: 350.

Intermediate 34

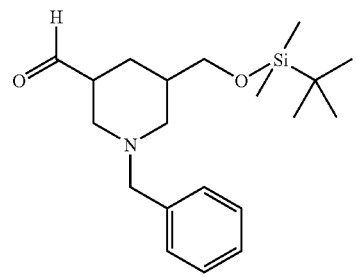

1-Benzyl-5-((tert-butyldimethylsilyloxy)methyl)piperidine-3-carbaldehyde. To a solution of oxalyl chloride (1.40 mL, 16.02 mmol) in dichloromethane (100 mL) at −78° C. was added, dropwise, dry DMSO (1.78 mL, 25.03 mmol). After 10 min at −78° C., a solution of 1-benzyl-5-((tert-butyldimethylsilyloxy)methyl)piperidin-3-yl)methanol (3.50 g, 19.01 mmol) in CH$_2$Cl$_2$ (100 mL) was slowly added and the reaction stirred at −78° C. After 1 h, triethylamine (6.98 mL, 50.1 mmol) was added and stirring continued at −78° C. for 10 min after which the reaction was allowed to warm to 23° C. The resulting solution was neutralized with 1N HCl (pH~6)and the phases separated. The aqueous solution was washed with CH$_2$Cl$_2$ (3×50 mL) and the combined organic fractions dried over MgSO$_4$, filtered and concentrated in vacuo to afford the title compound 3.39 g (76% yield) as a light yellow oil. $^1$H NMR (400 MHz, CDCl$_3$) δ ppm 9.61 (1 H, s), 7.59-7.67 (2 H, m), 7.42-7.49 (3 H, m), 4.22-4.30 (1 H, m), 4.10-4.18 (1 H, m), 3.70-3.81 (1 H, m), 3.52 (1 H, dt, J=10.4, 5.2 Hz), 3.35 (1 H, dd, J=11.9, 1.8 Hz), 3.14 (1H, m), 2.76 (1 H, tt, J=12.1, 3.9 Hz), 2.52-2.58 (1 H, m), 2.39-2.48 (1 H, m), 2.17-2.28 (1 H, m), 1.43 (1 H, t, J=7.3 Hz), 1.18-1.27 (1 H, m), 0.83 (9 H, m), 0.01 (6 H, m).

Intermediate 35

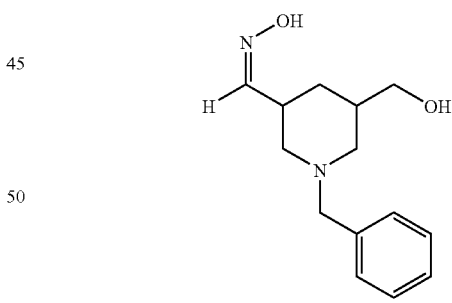

(Z)-1-Benzyl-5-(hydroxymethyl)piperidine-3-carbaldehyde oxime. To a mixture of 1-benzyl-5-((tert-butyldimethylsilyloxy)methyl)piperidine-3-carbaldehyde (3.39 g, 9.75 mmol) in EtOH (50 mL) was added an aqueous solution of NH$_2$OH—HCl (3.75M, 3.12 mL, 11.7 mmol) followed by an aqueous solution of NaOAc (1.5M, 5.2 mL, 7.8 mmol). The reaction mixture was stirred at room temperature for 18 h. H$_2$O (30 mL) was then added and the EtOH was partially removed in vacuo (~40 mL). The reaction mixture was diluted with ethyl acetate and washed with saturated NaHCO$_3$. The combined aqueous fractions were extracted with ethyl acetate (3×50 mL) and the combined organic fractions were washed with brine and dried (MgSO$_4$) and concentrated in vacuo to afford 3.31 g (94% yield) of the title compound. $^1$H NMR (400 MHz, CDCl$_3$) δ ppm 7.25-7.35 (6 H, m), 3.58 (2 H, d, J=4.5 Hz), 3.43-3.54 (2 H, m), 3.03 (2 H, d, J=4.5 Hz), 2.57-2.68 (1 H, m) 1.90-2.01 (2 H, m), 1.80-1.89 (1 H, m), 1.65-1.77 (2 H, m), 0.93-1.01 (1 H, m). LCMS ($^+$ESI, M+H$^+$) m/z 249.

Intermediate 36

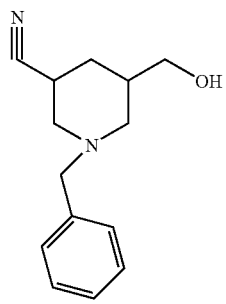

1-Benzyl-5-(hydroxymethyl)piperidine-3-carbonitrile. To 1-benzyl-5-(hydroxymethyl)piperidine-3-carbaldehyde oxime (3.3 g, 13.30 mmol) in CH$_2$Cl$_2$ (15 mL) at 23° C. was added 2-chloro-1-methylpyridine iodide (3.73 g, 14.62 mmol) in one portion and the resulting mixture stirred at 23° C. for 10 min. Et$_3$N was then added and the reaction mixture stirred for 3 hours (color changed from light yellow to light brown). The solution was neutralized with HCl (5%), to approximately pH 6 and the organic material was extracted with CH$_2$Cl$_2$ (3×25 mL). The combined organic fractions were dried (MgSO$_4$) and concentrated in vacuo to afford 3.06 g (95% yield) of the title compound. $^1$H NMR (400 MHz, CDCl$_3$) δ ppm 7.28-7.37 (5 H, m), 3.51-3.60 (4 H, m), 3.11 (1 H, ddd, J=11.0, 1.9, 1.8 Hz), 2.98 (1 H, d, J=7.6 Hz), 2.73-2.82 (1 H, m), 2.12-2.22 (2 H, m), 1.80-1.92 (2 H, m), 1.45 (1 H, br s), 1.27-1.38 (1 H, m). LCMS ($^+$ESI, M+H$^+$) m/z: 231.

Intermediate 37

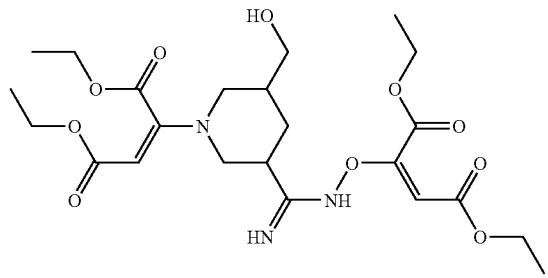

Diethyl 2-(1-((E)-1,4-diethoxy-1,4-dioxobut-2-en-2-yl)-5-(hydroxymethyl)piperidine-3-carboximidamidooxy)maleate. To a solution of 1-benzyl-5-(hydroxymethyl)piperidine-3-carbonitrile (2.93 g, 11.14 mmol) in EtOH (45.0 mL) was added diethyl acetylenedicarboxylate (2.67 mL, 16.71 mmol). The mixture was allowed to stir at 60° C. for 2 h. The solvent was removed in vacuo. The crude product was purified using a silica gel column (Biotage flash chromatography system) using ethyl acetate and hexane as eluent in a ratio 60:40 to followed by ethyl acetate:methanol (8:2) to afford 1.21 g (21% yield) of the title compound. $^1$H NMR (400 MHz, CDCl$_3$) δ ppm 5.77 (1 H, d, J=15.4 Hz), 5.26 (1 H, s), 4.98 (1 H, s), 4.82 (1 H, d, J=7.3 Hz), 4.31-4.44 (4 H, m), 4.08-4.21 (4 H, m), 3.42-3.66 (2 H, m), 2.92-3.03 (1 H, m), 2.62-2.73 (1 H, m), 2.44-2.55 (1 H, m), 2.04-2.14 (2 H, m), 1.86-1.96 (2 H, m), 1.23-1.41 (12 H, m). LCMS ($^+$ESI, M+H$^+$) m/z: 514.

Intermediate 38

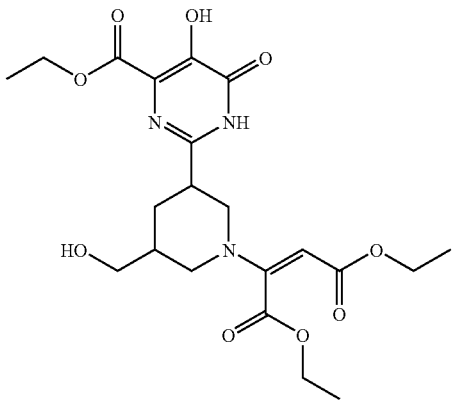

Diethyl 2-(3-(4-(ethoxycarbonyl)-5-hydroxy-6-oxo-1,6-dihydropyrimidin-2-yl)-5-(hydroxymethyl)piperidin-1-yl) maleate. To diethyl 2-(1-((E)-1,4-diethoxy-1,4-dioxobut-2-en-2-yl)-5-(hydroxymethyl)piperidine-3-carboximidamidooxy)maleate (1.20 g, 2.34 mmol) was added xylene (15 mL) and the reaction mixture was stirred at 160° C. for 6 hours in a sealed tube. The solvent was removed in vacuo to afford 1.05 g (99% yield) of the title compound. LCMS ($^+$ESI, M+H$^+$) m/z: 468.

Intermediate 39

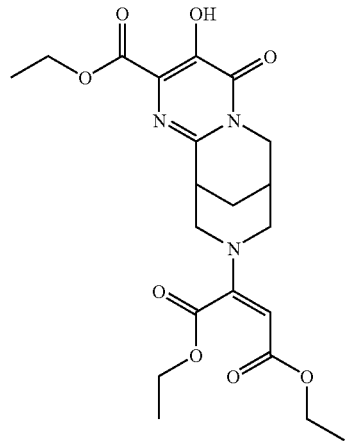

Diethyl-2-(2-(ethoxycarbonyl)-3-hydroxy-4-oxo-7,8,10,11-tetrahydro-4H-7,11-methanopyrimido[1,2-a][1,5]diazocin-9(6H)-yl)-2-butenedioate. To diethyl 2-(3-(4-(ethoxycarbonyl)-5-hydroxy-6-oxo-1,6-dihydropyrimidin-2-yl)-5-(hydroxymethyl)piperidin-1-yl)maleate (1.05 g, 2.32 mmol)

in THF at 0° C. was added triethylamine (0.975 mL, 6.99 mmol) and methanesulfonyl chloride (0.541 mL, 6.99 mmol). The reaction mixture was stirred at 23° C. for 3 hours. H$_2$O (50 mL) was then added and the mixture was extracted with ethyl acetate (3×50 mL). The combined organic fractions were dried (MgSO$_4$) and concentrated in vacuo. To the crude material dissolved in EtOH (40 mL) were added K$_2$CO$_3$ (0.643 g, 4.66 mmol) and H$_2$O (1.7 mL). The reaction mixture was stirred at 23° C. for 36 hours. The solvent was removed in vacuo and the crude material was purified by silica gel column chromatography (Biotage flash chromatography system) using a gradient of ethyl acetate:methanol:AcOH (95:4:1) to (40:40:10) to afford 1.05 g (33% yield) of the title compound. $^1$H NMR (400 MHz, DMSO-D6) δ ppm 3.83-4.26 (7 H, m), 2.68-3.40 (6H, m), 2.02 (1 H, m), 1.79-1.89 (2 H, m), 1.07-1.31 (10 H, m). LCMS ($^+$ESI, M+H$^+$) m/z: 450.

Intermediate 40

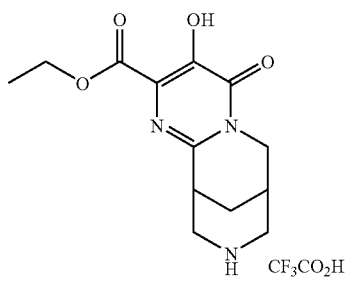

Ethyl 3-hydroxy-4-oxo-6,7,8,9,10,11-hexahydro-4H-7,11-methanopyrimido[1,2-a][1,5]diazocine-2-carboxylate. To diethyl-2-(2-(ethoxycarbonyl)-3-hydroxy-4-oxo-7,8,10,11-tetrahydro-4H-7,11-methanopyrimido[1,2-a][1,5]diazocin-9(6H)-yl)-2-butenedioate (0.300 g, 0.673 mmol) in acetonitrile (15 mL) was added trifluoroacetic acid (1 mL) at 23° C. The reaction mixture was stirred at 23° C. for 6 hours. CH$_3$CN and trifluoroacetic acid were then removed in vacuo and the crude material was redissolved in toluene and dried again (2×30 mL) to afford 234 mg (90% yield) of the title trifluoroacetic salt. LCMS ($^+$ESI, M+H$^+$) m/z: 280.

Intermediate 41

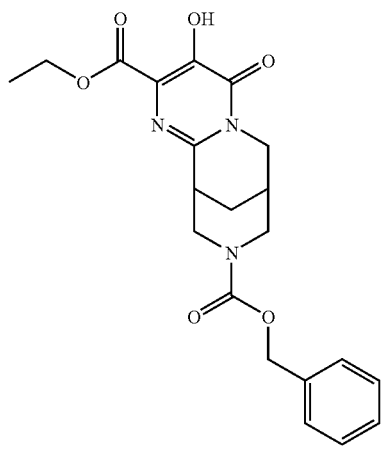

9-Benzyl 2-ethyl 3-hydroxy-4-oxo-7,8,10,11-tetrahydro-4H-7,11-methanopyrimido[1,2-a][1,5]diazocine-2,9(6H)-dicarboxylate. To ethyl 3-hydroxy-4-oxo-6,7,8,9,10,11-hexahydro-4H-7,11-methanopyrimido[1,2-a][1,5]diazocine-2-carboxylate (0.26 g, 0.661 mmol) in CH$_2$Cl$_2$ (5 mL) was added diisopropylethylamine (0.576 mL, 3.31 mmol) and benzylchloroformate (0.102 mL, 0.727 mmol). The reaction mixture was stirred at 23° C. for 16 hours. HCl (1N, 15 mL) was then added to the reaction mixture and the organic material extracted with CH$_2$Cl$_2$ (3×15 mL) and ethyl acetate (3×15 mL). The combined organic fractions were dried (MgSO$_4$) and concentrated in vacuo. The organic material was purified by Silica gel column chromatography (Biotage flash chromatography system) eluting with gradient of ethyl acetate 100% to ethyl acetate methanol (1:9) to afford 0.036 g (13% yield) of the title compound. $^1$H NMR (400 MHz, MeOD) δ ppm 7.36 (5 H, s), 4.95-5.10 (2 H, m) 3.95-4.40 (2 H, br m), 2.75-3.30 (5 H, br m), 1.75-2.50 (4 H, m), 0.95-1.45 (4 H, m). LCMS ($^+$ESI, M+H$^+$) m/z: 414.

Intermediate 42

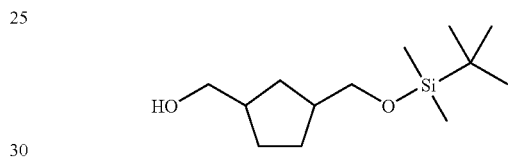

(3-((Tert-butyldimethylsilyloxy)methyl)cyclopentyl)methanol. To a solution of NaH (60% in oil) (3.53 g, 88.3 mmol) in dry THF (400 mL) was added cyclopentane-1,3-diyldimethanol (10.0 g, 76.8 mmol) in dry THF (100 mL). The reaction mixture was stirred at 23° C. for 45 min. A solution of t-butyldimethyllchlorosilane (13.89 g, 92.2 mmol) in dry THF (30 mL) was then added and the reaction mixture stirred at 23° C. for 4 hours. The reaction mixture was poured into ether (150 mL), washed with 10% aqueous K$_2$CO$_3$ (30 mL), dried (MgSO$_4$) and concentrated in vacuo. The crude material was purified on a Silica gel column (Biotage flash chromatography system), eluted with ethyl acetate:hexane (1:9) to ethyl acetate (4:6) to afford 12.3 g (66% yield) of the title compound. $^1$H NMR (400 MHz, CDCl$_3$) δ ppm 3.49-3.58 (4 H, m), 2.09-2.19 (2 H, m), 1.94 (1 H, dt, J=12.6, 7.5 Hz), 1.69-1.79 (2 H, m), 1.56 (1 H, br s), 1.32-1.44 (2 H, m), 0.91 (9 H, m), 0.06 (6 H, m).

Intermediate 43

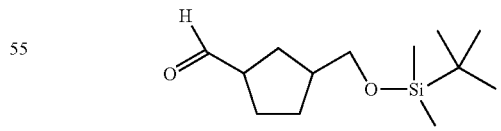

3-((Tert-butyldimethylsilyloxy)methyl)cyclopentanecarbaldehyde. To a solution of oxalyl chloride (3.44 mL, 39.3 mmol) in dichloromethane (200 mL) at −78° C. was added, dropwise, dry DMSO (4.36 mL, 61.4 mmol). After 10 min at −78° C., a solution of (3-((tert-butyldimethylsilyloxy)methyl)cyclopentyl)methanol (6.0 g, 24.56 mmol) in CH$_2$Cl$_2$ (180 mL) was slowly added and the mixture stirred at −78° C. After 1 h, triethylamine (17.11 mL, 122.8 mmol) was added and stirring continued at −78° C. for 10 min after which the mixture was allowed to warm to 23° C. The reaction mixture was diluted with HCl 1N (pH~6) and the phases separated. The organic fraction was dried (MgSO₄), filtered and concentrated in vacuo to give 5.81 g (97% yield) of the title compound as a light yellow oil. ¹H NMR (400 MHz, CDCl₃) δ ppm 9.62 (1 H, d, J=2.5 Hz), 3.54 (2 H, ddd, J=12.0, 10.0, 6.3 Hz), 2.73-2.82 (1 H, m), 2.14-2.24 (1 H, m), 1.89-2.00 (2 H, m), 1.74-1.85 (2 H, m), 1.57 (1 H, dt, J=13.1, 8.6 Hz), 1.33-1.44 (1 H, m), 0.91 (9 H, s), 0.06 (6 H, s).

Intermediate 44

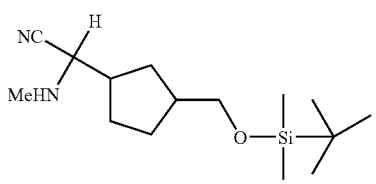

2-(3-((Tert-butyldimethylsilyloxy)methyl)cyclopentyl)-2-(methylamino)acetonitrile. To 3-((tert-butyldimethylsilyloxy)methyl)-cyclopentanecarbaldehyde (5.8 g, 23.94 mmol) in H₂O (8 mL) and methanol (10 mL) was added methylamine (0.0755 g, 23.94 mmol) at 0° C. This mixture was then added at 0° C. to KCN (1.56 g, 23.94 mmol) in H₂O (3 mL). The resulting reaction mixture was stirred at 23° C. for 18 hours. The organic material was extracted with ethyl acetate (3×100 mL) and the combined organic fractions were dried (MgSO₄) and concentrated in vacuo. ¹H NMR (400 MHz, CDCl₃) δ ppm 4.27-4.38 (2 H, m), 3.49-3.60 (1 H, m), 2.55 (3 H, s), 2.00-2.35 (4 H, m), 1.65-1.96 (2 H, m), 1.42-1.54 (2 H, m), 1.22 (1 H, ddd, J=13.4, 9.3, 3.8 Hz), 0.89 (9 H, s), 0.05 (6 H, m). LCMS (⁺ESI, M+H⁺) m/z 283.

Intermediate 45

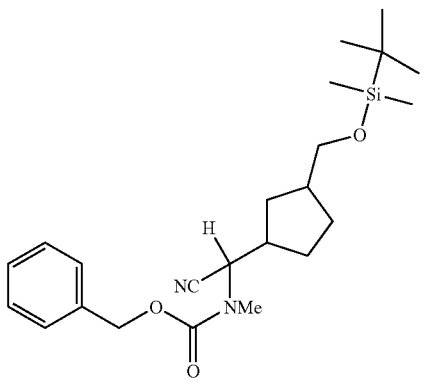

Benzyl (3-((tert-butyldimethylsilyloxy)methyl)cyclopentyl)(cyano)methyl(methyl)-carbamate. To 2-(3-((tert-butyldimethylsilyloxy)methyl)cyclopentyl)-2-(methylamino)acetonitrile (6.0 g, 21.24 mmol) in THF (33 mL), H₂O (15 mL) was added, at 0, ° C. Na₂CO₃ (4.50 g, 42.48 mmol) followed by the dropwise addition of benzyl chloroformate (3.89 mL, 27.6 mmol) over 10 min. The reaction mixture was stirred at 0° C. for 30 min. then at 23° C. for 18 hours. H₂O (150 mL) was then added and the organic material was extracted with ethyl acetate (3×100 mL). The combined organic fractions were dried (MgSO₄) and concentrated in vacuo. The crude material was purified on a Silica gel column (Biotage flash chromatography system), eluted with a gradient of ethyl acetate:hexane (1:4) to (1:1) to afford 3.90 g (44% yield) of the title compound. ¹H NMR (400 MHz, CDCl₃) δ ppm 7.34-7.45 (5 H, m), 5.33 (2 H, s), 5.18-5.25 (1H, m), 3.48-3.59 (2 H, m), 3.00 (3 H, s), 2.35-2.47 (2 H, m), 1.55-2.25 (6 H, m), 0.94 (9 H, s), 0.05 (6 H, s). LCMS (⁺ESI, M+H⁺) m/z 417.

Intermediate 46

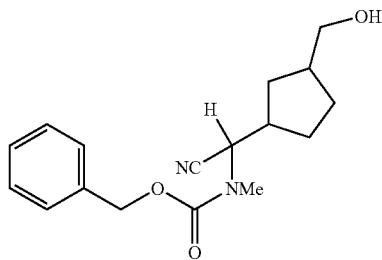

Benzyl cyano(3-(hydroxymethyl)cyclopentyl)methyl(methyl)carbamate. To benzyl (3-((tert-butyldimethylsilyloxy)methyl)cyclopentyl)(cyano)methyl(methyl)-carbamate (2.0 g, 4.80 mmol) in dry THF (40 mL) cooled to 0° C. was added tetrabutyl-ammoniumfluoride (1M in THF 17.28 mL). The reaction mixture was stirred at 23° C. for 5 hours. H₂O (20 mL) was added to the reaction mixture and the organic material extracted with ethyl acetate (3×30 mL). The combined organic fractions were dried (MgSO₄) and concentrated in vacuo. The crude material was purified on a Silica gel column (Biotage flash chromatography system), eluted with a gradient of ethyl acetate:hexane (3:7) to ethyl acetate 100% to afford 0.550 g (38% yield) of the title compound. ¹H NMR (400 MHz, CDCl₃) δ ppm 7.39 (5 H, m), 5.13-5.25 (2 H, m), 5.07 (1 H, br s), 3.50-3.60 (2 H, m), 3.01 (3 H, s), 1.30-2.52 (8 H, m). LCMS (⁺ESI, M+H⁺) m/z 303.

Intermediate 47

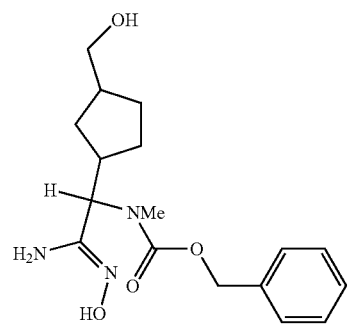

Benzyl 2-amino-2-(hydroxyimino)-1-(3-(hydroxymethyl)cyclopentyl)ethyl(methyl)carbamate. To a solution of benzyl cyano(3-(hydroxymethyl)cyclopentyl)methyl(methyl)carbamate (0.540 g, 1.79 mmol) in ethanol (20 mL) was added 50% aqueous solution of hydroxylamine (0.07 mL, 2.15 mmol). The reaction mixture was stirred at 60° C. for 18 hours. The solvent was removed in vacuo to afford 0.610 g (76% yield) of title compound ¹H NMR (400 MHz, CDCl₃) δ ppm 7.33-7.43 (5 H, m), 7.14-7.23 (2 H, m), 5.18 (2 H, br s), 4.87-4.93 (1 H, m), 4.24 (1 H, m), 3.49-3.60 (2 H, m), 2.83-

2.94 (3 H, br s), 2.60-2.71 (1 H, m), 2.11-2.49 (2 H, m), 1.60-2.11 (3 H, m), 1.25-1.55 (2 H, m). (⁺ESI, M+H⁺) 2 peaks m/z 336.

Intermediate 48

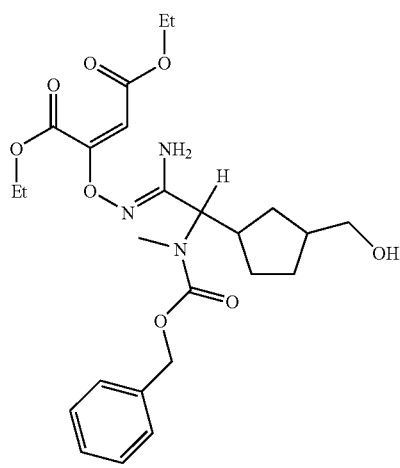

Diethyl 2-(1-amino-2-((benzyloxycarbonyl)(methyl)amino)-2-(3-(hydroxymethyl)cyclopentyl)ethylideneaminooxy)maleate. To benzyl 2-amino-2-(hydroxyimino)-1-(3-(hydroxymethyl)cyclopentyl)ethyl(methyl)carbamate (0.800 g, 1.78 mmol) in EtOH (40 mL) was added diethylacetylenedicarboxylate (0.428 ml, 2.67 mmol). The reaction mixture was stirred at 23° C. for 2 days. The solvent was removed in vacuo and the crude material purified on a Silica gel column (Biotage flash chromatography system), eluted with a gradient of ethyl acetate:hexane (1:5) to (1:1) to afford 0.570 g (52% yield) of the title compound. ¹H NMR (400 MHz, CDCl₃) δ ppm 7.33-7.42 (5 H, m), 5.17-5.25 (3 H, m), 4.12-4.40 (4 H, m), 3.55 (2 H, m), 2.83-2.94 (4 H, m), 2.70-2.75 (1 H, m), 2.17-2.09 (2 H, m), 1.82-2.00 (3 H, m), 1.21-1.342 (7 H, m). LCMS (⁺ESI, M+H⁺) m/z 506.

Intermediate 49

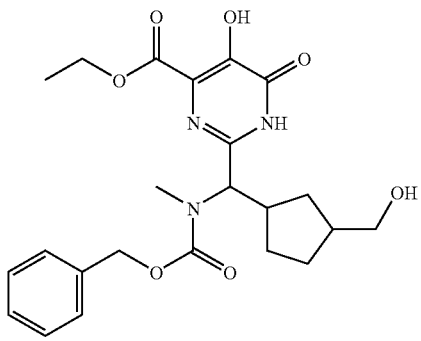

Ethyl 2-(((benzyloxycarbonyl) (methyl)amino) (3-(hydroxymethyl)cyclopentyl)methyl)-5-hydroxy-6-oxo-1,6-dihydropyrimidine-4-carboxylate. To the diethyl 2-(1-amino-2-((benzyloxycarbonyl)(methyl)amino)-2-(3-(hydroxymethyl)cyclopentyl)ethylideneaminooxy)maleate (0.710 g, 1.40 mmol) was added xylene (30 mL) and the reaction mixture was stirred at 120° C. for 36 hours. Xylene was removed in vacuo to afford 0.53 g (82% yield) of the title compound. LCMS (⁺ESI, M+H⁺) m/z 460.

Intermediate 50

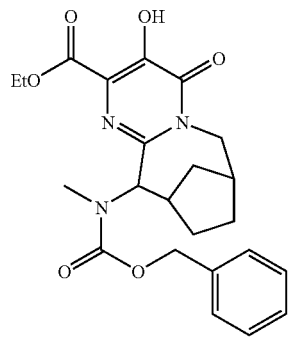

Ethyl 11-(((benzyloxy)carbonyl) (methyl)amino)-3-hydroxy-4-oxo-6,7,8,9,10,11-hexahydro-4H-7,11-methanopyrimido[1,2-a]azocine-2-carboxylate. To ethyl 2-(((benzyloxycarbonyl)(methyl)amino)(3-(hydroxymethyl)cyclopentyl)methyl)-5-hydroxy-6-oxo-1,6-dihydropyrimidine-4-carboxylate (0.235 g, 0.511 mmol)in THF (30 mL) at 0° C. was added triethylamine (0.214 mL, 1.53 mmol) and methanesulfonyl chloride (0.119 mL, 1.53 mmol). The reaction mixture was stirrer at 23° C. for 3 hours. H₂O (50 mL) was then added and the reaction mixture extracted with ethyl acetate (3×50 mL). The combined organic fractions were dried (MgSO₄) and concentrated in vacuo. LCMS (⁺ESI, M+H⁺) m/z 694. To the crude ethyl 2-(((benzyloxycarbonyl)(methyl)amino)(3-((methylsulfonyloxy)methyl)cyclopentyl)methyl)-1-(methylsulfonyl)-5-(methylsulfonyloxy)-6-oxo-1,6-dihydropyrimidine-4-carboxylate (0.252 g, 0.363 mmol) dissolved in DMF (40 mL) was added Cs₂CO₃ (0.590 g, 1.816 mmol). The reaction mixture was stirred at 80° C. for 12 hours. HCl (1N, 40 ml) was added and the organic material was extracted with ethyl acetate (3×30 mL). The combined organic fractions were dried (MgSO₄) and concentrated in vacuo to afford the title compound. LCMS (⁺ESI, M+H⁺) m/z 442.

Intermediate 51

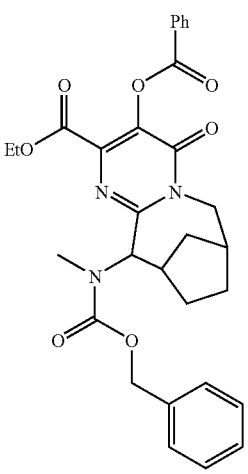

Ethyl 3-(benzoyloxy)-11-(((benzyloxy)carbonyl)(methyl) amino)-4-oxo-6,7,8,9,10,11-hexahydro-4H-7,10-methanopyrimido[1,2-a]azocine-2-carboxylate. To Ethyl 11-(((benzyloxy)carbonyl)(methyl)amino)-3-hydroxy-4-oxo-6,7,8,9,10,11-hexahydro-4H-7,10-methanopyrimido[1,2-a]azocine-2-carboxylate in pyridine (5 mL) was added benzoic anhydride (0.136 g, 0.600 mmol) and the reaction mixture was stirred at 23° C. for 2 days. Pyridine was then removed under vacuum. H$_2$O (25 mL) was added and the organic material was extracted with ethyl acetate (3×25 mL). The combined organic fractions were dried (MgSO$_4$) and concentrated in vacuo. The crude material was purified using preparative HPLC on a LUNA C18 column to afford 0.033 g (12% yield) of the title compound. $^1$H NMR (400 MHz, CDCl$_3$) δ ppm 8.20 (2 H, d, J=7.8 Hz), 7.67 (1 H, t, J=6.9 Hz), 7.52 (2 H, t, J=7.7 Hz), 7.28-7.41 (4H, m), 5.15-5.27 (2 H, m), 4.22-4.33 (2 H, m), 3.47 (1H, m), 3.15 (3 H, m), 2.65 (2 H, s), 2.11 (1 H, m), 2.03 (1 H, d, J=4.8 Hz), 1.60-1.89 (3 H, m), 1.25-1.55 (3 H, m), 1.16 (3 H, m). LCMS ($^+$ESI, M+H$^+$) m/z 546. HRMS (ESI$^+$) calculated for C$_{30}$H$_{31}$N$_3$O$_7$ [M+H$^+$]: 546.2240 found: 546.2240.

Intermediate 52

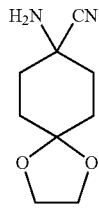

8-Amino-1,4-dioxaspiro[4.5]decane-8-carbonitrile. To a stirred solution of NH$_4$OH (250 mL) and methanol (250 mL) was added 1,4-cycloxexanedione monoethylene ketal (29.25 g, 186.64 mmol), NH$_4$Cl (19.97 g, 373 mmol) and NaCN (18.28 g, 373 mmol). After 16 h at room temperature, the reaction mixture was extracted with CH$_2$Cl$_2$ (250 mL×2), and the combined organic fractions were washed with water (500 mL), dried (Na$_2$SO$_4$), filtered and concentrated to afforded the title compound as a colorless liquid (29 g, 85% yield). $^1$H NMR (500 MHz, CDCl$_3$) δ: 3.90-3.96 (m, 4H), 2.01-2.04 (m, 2H), 1.80-1.97 (m, 6H), 1.75 (s, 2H). LCMS (M+H)=183.23.

Intermediate 53

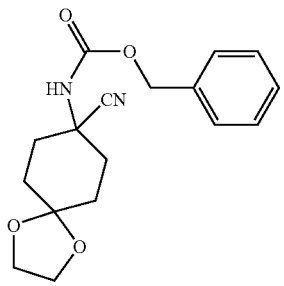

Benzyl 8-cyano-1,4-dioxaspiro[4.5]decan-8-ylcarbamate. Benzyl chloroformate (24.18 mL, 169.4 mmol) was added dropwise to a biphasic system of water (300 mL) and CH$_2$Cl$_2$ (150 mL) containing 8-amino-1,4-dioxaspiro[4.5]decane-8-carbonitrile (28 g, 154 mmol) and Na$_2$CO$_3$.H$_2$O (22.9 g, 185 mmol) at 0° C. and stirred for 2 h. The mixture was then allowed to warm to room temperature and stirred for 18 h. The mixture was then diluted with CH$_2$Cl$_2$ (250 mL), washed with sat. NaHCO$_3$ (200 mL), water (200 mL), followed by brine (100 mL) then dried (Na$_2$SO$_4$), filtered and concentrated to give a brown oil. Flash chromatography on silica gel (using a 5% to 40% ethyl acetate-hexane gradient) afforded the title compound as a white solid (45 g, 92% yield). $^1$H NMR (500 MHz, CDCl$_3$) δ: 7.30-7.35 (m, 5H), 5.11 (s, 2H), 4.90 (brs, 1H), 3.86-3.96 (m, 4H), 2.36-2.41 (m, 2H), 1.84-2.01 (m, 4H), 1.73-1.76 (m, 2H). LCMS (M+H)=317.30.

Intermediate 54

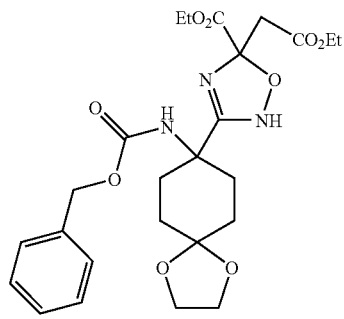

Ethyl 3-(8-(benzyloxycarbonylamino)-1,4-dioxaspiro[4.5]decan-8-yl)-5-(2-ethoxy-2-oxoethyl)-2,5-dihydro-1,2,4-oxadiazole-5-carboxylate. A mixture of benzyl 8-cyano-1,4-dioxaspiro[4.5]decan-8-ylcarbamate (37.4 g, 118.33 mmol), hydroxylamine (7.98 mL, 130 mmol, 50 wt % in water) in EtOH (750 mL) was heated at 70° C. for 48 h. The mixture was then cooled to room temperature and treated with diethyl acetylenedicarboxylate (22.73 mL, 142 mmol). After 48 h at room temperature, the reaction mixture was concentrated and the resulting yellow residue was taken up in ethyl acetate (500 mL), washed with water (2×100 mL) followed by brine (100 mL), then dried (Na$_2$SO$_4$), filtered and concentrated to give a yellow oil. Flash chromatography on silica gel (using 5% to 50% ethyl acetate-hexane gradient) afforded the title compound as a yellow oil (50 g, 82% yield). $^1$H NMR (500 MHz, CDCl$_3$) δ: 7.33-7.37 (m, 5H), 5.80 (s, 1H), 5.07 (s, 2H), 4.84 (d, 1H, J=23.8 Hz), 4.33 (q, 1H, J=7.02 Hz), 4.27 (q, 1H, J=7.22 Hz), 4.09-4.20 (m, 3H), 3.93 (s, 2H), 3.90-3.92 (m, 2H), 2.16-2.23 (m, 4H), 2.03 (s, 1H), 1.62-1.74 (m, 4H), 1.24-1.37 (m, 6H). LCMS (M+H)=336.14.

Intermediate 55

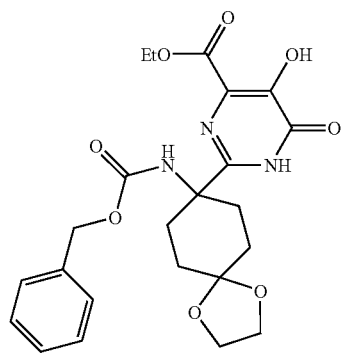

Ethyl 2-(8-(benzyloxycarbonylamino)-1,4-dioxaspiro[4.5]decan-8-yl)-5-hydroxy-6-oxo-1,6-dihydropyrimidine-4-carboxylate. A solution of ethyl 3-(8-(benzyloxycarbonylamino)-1,4-dioxaspiro[4.5]decan-8-yl)-5-(2-ethoxy-2-oxoethyl)-2,5-dihydro-1,2,4-oxadiazole-5-carboxylate (6.2 g, 11.9 mmol) in xylenes (300 mL) was placed in a pre-heated oil bath and stirred for 16 h at 140° C. The reaction mixture was then cooled and extracted with 0.2 M aq. NaOH (3×100 mL) and the combined aqueous fractions were extracted with ethyl acetate (250 mL). The aqueous layer was then acidified with conc. HCl and extracted with CH$_2$Cl$_2$ (3×100 mL). The CH$_2$Cl$_2$ fractions were dried (Na$_2$SO$_4$), filtered and concentrated to afford the title compound as a light yellow solid (4.1 g, 70% yield). $^1$H NMR (500 MHz, DMSO-D6) δ: 12.55 (s, 1H), 10.25 (s, 1H), 7.28-7.36 (m, 6H), 4.99 (s, 2H), 4.29 (q, 2H, J=7.5 Hz), 3.85 (brs, 4H), 2.03-2.08 (m, 4H), 1.71-1.76 (m, 2H), 1.29 (t, 3H, J=7.5 Hz). LCMS (M+H)=474.48.

Intermediate 56

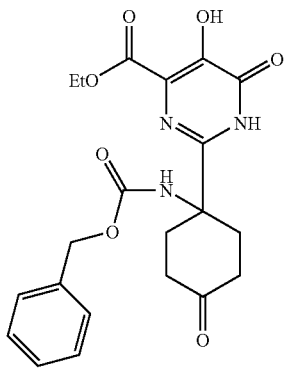

Ethyl 2-(1-(benzyloxycarbonylamino)-4-oxocyclohexyl)-5-hydroxy-6-oxo-1,6-dihydropyrimidine-4-carboxylate. A solution of ethyl 2-(8-(benzyloxycarbonylamino)-1,4-dioxaspiro[4.5]decan-8-yl)-5-hydroxy-6-oxo-1,6-dihydropyrimidine-4-carboxylate (1.8 g, 3.8 mmol) in THF (200 mL) was added 2N HCl (12 ml, 24 mmol) and the resulting mixture was heated for 2 h at 60° C. The reaction mixture was then cooled and extracted with CH$_2$Cl$_2$ (3×100 mL). The CH$_2$Cl$_2$ fractions were dried (Na$_2$SO$_4$), filtered and concentrated to afford the title compound as a light yellow solid (1.5 g, 92% yield). $^1$H NMR (500 MHz, CDCl$_3$) δ: 12.11 (s, 1H), 11.09 (s, 1H), 7.17-7.29 (m, 5H), 6.36 (s, 1H), 5.00 (s, 2H), 4.44 (q, 2H, J=7.02 Hz), 2.49-2.57 (m, 8H), 1.42 (q, 3H, J=7.05 Hz). LCMS (M+H)=430.38.

Intermediate 57

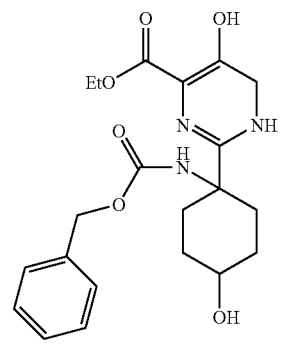

Ethyl 2-(1-(benzyloxycarbonylamino)-4-hydroxycyclohexyl)-5-hydroxy-1,6-dihydropyrimidine-4-carboxylate. To a solution of ethyl 2-(1-(benzyloxycarbonylamino)-4-oxocyclohexyl)-5-hydroxy-6-oxo-1,6-dihydropyrimidine-4-carboxylate (1.5 g, 3.5 mmol) in methanol (35 mL) at room temperature was added NaBH$_4$ (138 mg, 3.66 mol) and the resulting mixture was stirred for 1 h. Methanol was then removed under reduced pressure and the mixture was diluted with CH$_2$Cl$_2$ (200 mL), washed with 1N HCl (100 mL) followed by brine (100 mL). The organic fraction was dried (Na$_2$SO$_4$), filtered and concentrated to afford the title compound as a light yellow solid (1.3 g, 86% yield). $^1$H NMR (500 MHz, DMSO-D6) δ: 12.46 (s, 1H), 10.24 (s, 1H), 7.31-7.35 (m, 5H), 7.11 (brs, 1H), 4.28-4.32 (m, 2H), 4.29 (q, 2H, J=7.22 Hz), 3.43-3.46 (m, 1H), 2.31-2.33 (m, 1H), 2.15-2.22 (m, 2H), 1.77-1.83 (m, 2H), 1.65-1.67 (m, 2H), 1.44-1.49 (m, 2H), 1.28 (t, 3H, J=7.22 Hz). LCMS (M+H)=432.37.

Intermediate 58

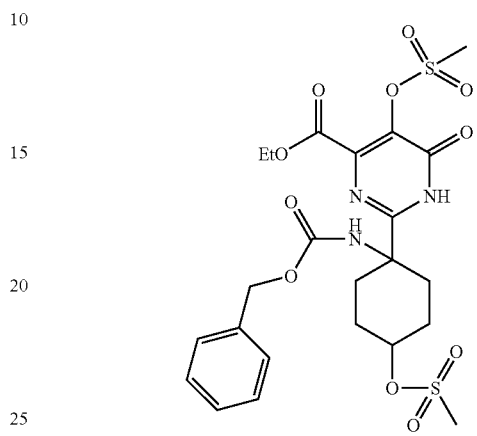

Ethyl 2-(1-(benzyloxycarbonylamino)-4-(methylsulfonyloxy)cyclohexyl)-5-(methylsulfonyloxy)-1,6-dihydropyrimidine-4-carboxylate. To a stirred solution of ethyl 2-(1-(benzyloxycarbonylamino)-4-hydroxycyclohexyl)-5-hydroxy-1,6-dihydropyrimidine-4-carboxylate (1.75 g, 4.05 mmol) in THF (25 mL) was added methanesulfonyl chloride (0.94 mmol, 12.17 mmol) and triethylamine (1.7 mL, 12.75 mmol) at 5° C. and the mixture stirred at room temperature for 18 h. The resulting white precipitate was filtered off and washed with THF. The filtrate and washings were concentrated to afford an amber oil. A solution of this oil in methanol (20 mL) was treated with K$_2$CO$_3$ (560 mg, 4.05 mmol) at room temperature for 3 h. The mixture was then concentrated and the residue dissolved in ethyl acetate (200 mL), washed with 1N HCl (100 mL) followed by brine (100 mL) and then dried (Na$_2$SO$_4$), filtered and concentrated to give 2.3 g of the title compound as an amber oil, which was used in the next step without further purification. LCMS (M+H)=588.41.

Intermediate 59

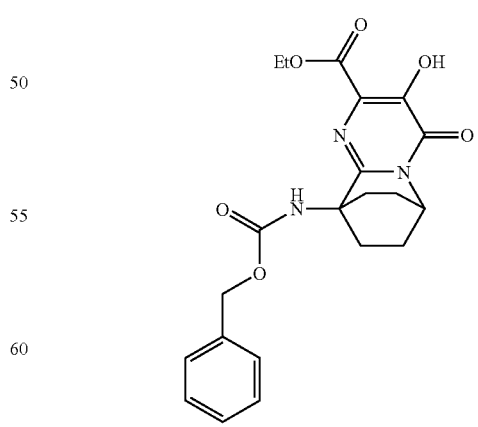

6,9-Ethano-4H-pyrido[1,2-a]pyrimidine-2-carboxylic acid, 6,7,8,9-tetrahydro-3-hydroxy-4-oxo-9-[[(phenylmethoxy)carbonyl]amino]-, ethyl ester. A mixture of ethyl 2-(1-(benzyloxycarbonylamino)-4-(methylsulfonyloxy)cyclohexyl)-5-(methylsulfonyloxy)-1,6-dihydropyrimidine-4-carboxylate (2.35 g, 4 mmol) and cesium carbonate (1.3 g, 4 mmol) in DMF (25 mL) was heated at 60° C. for 18 h. The reaction mixture was then cooled and concentrated under vacuum. The residue was taken up in to ethyl acetate (200 mL) and extracted with 0.2 M aq. NaOH (3×100 mL). The combined aqueous fractions were extracted with ethyl acetate. The aqueous layer was then acidified with conc. HCl and extracted with CH₂Cl₂ (3×100 mL). The CH₂Cl₂ fractions were dried (Na₂SO₄), filtered and concentrated to afford the title compound as a brown solid (800 mg). ¹H NMR (500 MHz, CDCl₃) δ: 10.81 (s, 1H), 7.30-7.40 (m, 6H), 6.74 (s, 1H), 5.30 (s, 1H), 5.13 (s, 2H), 4.46 (q, 2H, J=7.17 Hz), 3.05-3.10 (m, 2H), 2.15-2.22 (m, 2H), 1.99-2.04 (m, 2H), 1.52-1.55 9 m, 2H), 1.43 (t, 3H, J=7.17). LCMS (M+H)= 414.07.

Intermediate 60

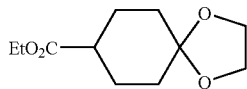

Ethyl 1,4-dioxaspiro[4.5]decane-8-carboxylate. A mixture of ethyl 4-oxocyclohexanecarboxylate (500 g, 2.94 mol), ethane-1,2-diol (656 mL, 11.76 mol) and p-toluene sulfonic acid (10.06 g, 0.053 mol) was stirred at room temperature under nitrogen atmosphere for 3 days. After pouring in to diethyl ether (1 L), the mixture was washed with water (500 ml), dilute NaHCO₃ solution (300 mL) followed by brine (500 mL). The organic layer was then dried (Na₂SO₄) filtered and concentrated to afford (590 g, 94% yield) the title compound as a colorless oil. Ref. *J. Org. Chem.* 1997, 62, 5284-5292.

Intermediate 61

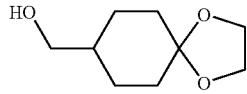

1,4-Dioxaspiro[4.5]decan-8-ylmethanol. A 12-L, four-necked flask equipped with a mechanical stirrer, dropping funnel, thermometer and a nitrogen-inlet tube was flushed with nitrogen and then charged with a 1.0 M LAH (2754 mL, 2754 mmol). The mixture was cooled (0-4° C. internal temperature, 2-propanol/dry ice bath) and a solution of ethyl 1,4-dioxaspiro[4.5]decane-8-carboxylate (590 g, 2754 mmol) was added over 3.5 h via dropping funnel. The reaction mixture was then stirred for 3 h while allowing it to warm to room temperature then stirred for an additional 16 h at room temp. The reaction mixture was then cooled (0° C.) bath and diluted with ethyl ether (3 L). The reaction mixture was then carefully quenched by adding water (100 mL, over 1 h), followed by 15% aqueous NaOH (100 mL, over 40 min) and water (300 ml, over 30 min). After the mixture was stirred for 1 h, sodium sulfate was added and stirring continued for 10 min. The white precipitate was the filtered off and the cake was washed with ether and the filtrate concentrated to afford the title compound (440 g, 92% yield) as a light yellow liquid. Ref. *J. Org. Chem.* 1997, 62, 5284-5292.

Intermediate 62

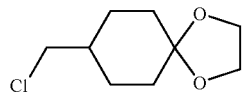

8-(Chloromethyl)-1,4-dioxaspiro[4.5]decane. SOCl₂ (37.1 mL, 509 mmol, 1.3 equiv) was slowly added to a stirred solution of 1,4-dioxaspiro[4.5]decan-8-ylmethanol (67.3 g, 391 mmol) and pyridine (94.8 mL, 1175 mmol, 3 equiv.) in CHCl₃ (400 mL) Caution: The reaction is exothermic. The resulting yellow mixture was heated at reflux for 1.5 h and concentrated. The residue was partitioned between water (500 ml) and ether (500 ml). The layers were separated and the aqueous layer was re-extracted with ether (200 ml). The combined ether layers were washed with 1N HCl (2×100 ml), water (200 ml) followed by brine (200 ml), then dried (MgSO₄), filtered and concentrated to give the title compound as a dark amber oil (65.7 g, 88% yield). ¹H NMR (500 MHz, CDCl₃) δ: 3.94 (4 H, t, J=2.9 Hz), 3.41 (2 H, d, J=6.4 Hz), 1.83-1.88 (2 H, m), 1.75-1.79 (2 H, m), 1.63-1.73 (1 H, m), 1.55 (2 H, td, J=4.3, 13.2 Hz), 1.29-1.39 (2 H, m).

Intermediate 63

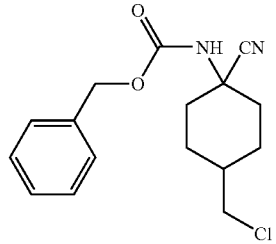

Benzyl 4-(chloromethyl)-1-cyanocyclohexylcarbamate. To a stirred solution of 8-(chloromethyl)-1,4-dioxaspiro[4.5]decane (78 g, 409 mmol) in THF (200 mL) was added 1N aq. HCl (500 mL, 500 mmol) at room temperature. After 24 h, 30% NH₄OH (106 mL, 818 mmol) followed by NaCN (22.05 g, 450 mmol) were added and stirring continued for an additional 72 h at rt. The reaction mixture was then extracted with CH₂Cl₂ (5×100 mL). The combined CH₂Cl₂ extracts were treated with Na₂CO₃ (50.7 g, 409 mmol) in water (200 mL) followed by benzylchloroformate (58.4 mL, 409 mmol) at 0° C. and the resulting mixture allowed to warm to room temp and stirred overnight (16 h). After this, the reaction mixture was washed with sat. NaHCO₃ (200 mL), then dried (Na₂SO₄), filtered and concentrated to afford a yellow residue. To this residue was added 20% ethyl acetate/hexane (150 mL) and the precipitated product was triturated with hexane (500 mL) and filtered. The filter cake was washed with hexane to afford benzyl 4-(chloromethyl)-1-cyanocyclohexylcarbamate (77 g, 251 mmol, 61% yield) as a pale yellow solid. ¹H NMR (500 MHz, CDCl₃) δ: 7.31-7.40 (5 H, m), 5.14 (2 H, s), 4.92 (0.8 H, br.s.), 4.78 (0.2 H, br.s), 3.42 (2 H, dd, J=6.6, 2.3

Hz), 2.55-2.61 (2 H, m), 2.21-2.28 (1 H, m), 2.04 (2 H, s), 1.30-1.83 (4 H, m). LCMS (M+H) calcd for $C_{16}H_{20}ClN_2O_2$: 307.12; found: 307.07.

Intermediate 64

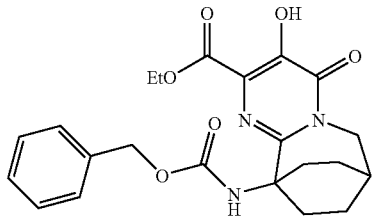

Ethyl 10-(((benzyloxy)carbonyl)amino)-3-hydroxy-4-oxo-4,6,7,8,9,10-hexahydro-7,10-ethanopyrimido[1,2-a]azepine-2-carboxylate. A solution of benzyl 4-(chloromethyl)-1-cyanocyclohexylcarbamate (10 g, 32.6 mmol) and 50% aq. hydroxylamine (19.97 mL, 326 mmol) in THF (120 mL) was heated at reflux for 5 h. It was then cooled, diluted with ethyl acetate (300 mL), washed with water (2×50 mL) followed by brine (100 mL). The organic layer was then concentrated to half its original volume. Water (2 mL) and diethyl but-2-ynedioate (5.22 mL, 32.6 mmol) were then added and the mixture stirred at room temperature 24 h. The reaction mixture was diluted with $Et_2O$ (150 mL), washed with water (2×50 mL) followed by brine (75 mL), then dried ($Na_2SO_4$), filtered and concentrated to give a yellow oil (17.2 g). A solution of the oil in xylene (250 mL) was heated at 125° C. (internal temperature) until reaction was complete (5-12 h). It was then cooled, concentrated and the resulting yellow residue stirred with $K_2CO_3$ (9.21 g, 66.7 mmol) in DMF (300 mL) at 90° C. for 3 h. After cooling it was diluted with $Et_2O$ (300 mL), extracted with water (100 mL) and 0.1 N NaOH (100 mL). The organic layer was discarded and the aqueous layer carefully acidified with conc. HCl and extracted with $Et_2O$ (3×300 mL). The combined ether layers were dried ($Na_2SO_4$), filtered and concentrated. The crude material was then crystallized or precipitated with ethyl acetate to give the title compound as a light yellow solid (3.4 g, 24% yield). $^1$H NMR (500 MHz, $CDCl_3$) δ: 10.81 (s, 1H), 7.29-7.36 (m, 6H), 5.29 (s, 1H), 5.10 (s, 2H), 4.41 (q, 2H, J=7.27 Hz), 4.13 (d, 2H, J=3.66 Hz), 2.43-2.47 (m, 2H), 1.94-2.02 9 m, 2H), 1.79-1.85 (m, 2H), 1.65-1.72 (m, 2H), 1.40 (t, 3H, J=7.17). LCMS (M+H)=428.26.

Intermediate 65

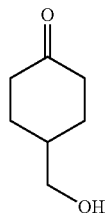

4-(Hydroxymethyl)cyclohexanone. Prepared according to general procedure described in Journal of Organic Chemistry 1997, 62, 5284-5292 from commercially available ethyl 4-oxocyclohexanecarboxylate.

Intermediate 66

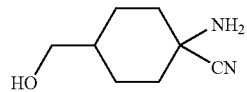

1-Amino-4-(hydroxymethyl)cyclohexanecarbonitrile. To a stirred solution of $NH_4OH$ (125 mL) and methanol (50 mL) was added 4-(hydroxymethyl)cyclohexanone (10 g, 78 mmol), $NH_4Cl$ (8.35 g, 156 mmol) and NaCN (7.65 g, 156 mmol). After 16 h at room temperature, the reaction mixture was extracted with $CH_2Cl_2$ (250 mL×2), and 4:1 chloroform:2-propanol, and the combined organic fractions washed with water (500 mL), dried ($Na_2SO_4$), filtered and concentrated to afforded the title compound as a colorless liquid (8 g, 67% yield). $^1$H NMR (500 MHz, $CDCl_3$) δ: 3.51 (d, 2H, J=4.58 Hz), 2.07-2.09 (m, 2H), 1.86-1.91 (m, 4H), 1.68 (s, 2H), 1.47-1.53 (m, 3H), 1.41 9 brs, 1H), 1.30-1.36 9 m, 2H). LCMS (M+H)=155.18.

Intermediate 67

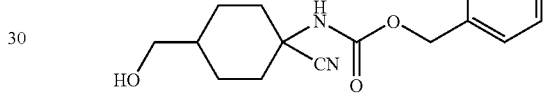

1-Cyano-4-(hydroxymethyl)cyclohexylcarbamate. Benzyl chloroformate (8.15 mL, 57.1 mmol) was added dropwise to a biphasic mixture of water (110 mL) and $CH_2Cl_2$ (55 mL) containing 1-amino-4-(hydroxymethyl)cyclohexanecarbonitrile (7 g, 45.4 mmol) and $Na_2CO_3 \cdot H_2O$ (5.63 g, 45.4 mmol) at 0° C. then stirred for 2 h. The mixture was then allowed to warm to room temperature and stirred for 18 h. The mixture was diluted with $CH_2Cl_2$ (200 mL), washed with sat. $NaHCO_3$ (100 mL), water (100 mL) followed by brine (100 mL), then dried ($Na_2SO_4$), filtered and concentrated to give brown oil. Flash chromatography on silica gel (using 5% to 40% ethyl acetate/hexane gradient) afforded the title compound as a light yellow viscous oil (8 g, 61% yield). $^1$H NMR (500 MHz, $CDCl_3$) δ: 7.33-7.36 (m, 5H), 5.13 (s, 2H), 5.08 (brs, 1H), 3.50 (t, 2H, J=5.8 Hz), 2.52-2.56 (m, 2H), 1.88-1.91 (m, 2H), 1.61-1.63 (m, 1H), 1.36-1.48 (m, 4H). LCMS (M+H)=289.19.

Intermediate 68

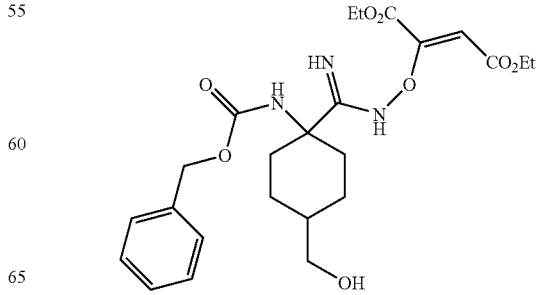

Diethyl (2Z)-2-((((1-(((benzyloxy)carbonyl)amino)-4-(hydroxymethyl)cyclohexyl)(imino)methyl)amino)oxy)-2-butenedioate. A mixture of 1-cyano-4-(hydroxymethyl)cyclohexylcarbamate (6.5 g, 22.54 mmol), 50% aq. hydroxylamine (1.66 mL, 27.05 mmol) in EtOH (150 mL) was heated at 70° C. for 18 h. The mixture was then cooled to room temperature and treated with diethyl acetylenedicarboxylate (4.33 mL, 27.1 mmol). After 18 h at room temperature, the reaction mixture was concentrated and the resulting yellow residue was taken up in ethyl acetate (250 mL), washed with water (2×100 mL) followed by brine (100 mL), then dried (Na$_2$SO$_4$), filtered and concentrated to give yellow oil. Flash column chromatography on silica gel (using 5% to 50% ethyl acetate-hexane gradient) afforded the title compound as a mixture of isomers and as a yellow oil (8 g, 72% yield). $^1$H NMR (500 MHz, CDCl$_3$) δ: 7.30-7.36 (m, 6H), 5.59 (s, 0.5 H), 5.75 (s, 0.5 H), 5.13 (s, 1H), 5.04 (s, 2H), 4.32-4.36 (m, 1H), 4.24-4.29 (m, 1H), 4.09-4.17 (m, 4H), 3.46-3.51 (m, 2H), 2.54-2.58 (m, 2H), 1.45-1.57 (m, 5H), 1.23-1.26 (m, 6H). LCMS (M+H)=492.36.

Intermediate 69

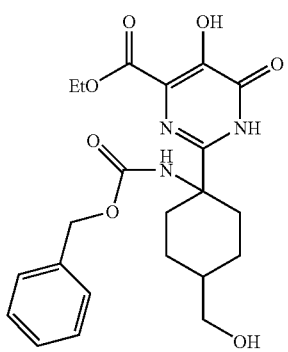

Ethyl 2-(1-(benzyloxycarbonylamino)-4-(hydroxymethyl)cyclohexyl)-5-hydroxy-6-oxo-1,6-dihydropyrimidine-4-carboxylate. A solution of diethyl (2Z)-2-((((1-(((benzyloxy)carbonyl)amino)-4-(hydroxymethyl)cyclohexyl)(imino)methyl)amino)oxy)-2-butenedioate (7 g, 14.24 mmol) in xylenes (400 mL) was placed in a pre-heated oil bath and stirred for 16 h at 140° C. The reaction mixture was then cooled, extracted with 0.2 M aq. NaOH (3×100 mL) and the combined aqueous layers washed with ethyl acetate (250 mL). The aqueous layer was acidified with conc. HCl and extracted with CH$_2$Cl$_2$ (3×100 mL). The CH$_2$Cl$_2$ extracts were dried (Na$_2$SO$_4$), filtered and concentrated to afford the title compound as a light yellow solid (3.1 g, 49% yield). $^1$H NMR (500 MHz, DMSO-D6) δ: 12.00 (s, 1H), 10.77 (s, 1H), 7.24-7.36 (m, 6H), 5.45 (brs, 1H), 5.01 (s, 2H), 4.39-4.45 (m, 2H), 3.50 (d, 2H, J=6.41 Hz), 2.51-2.62 (m, 2H), 1.64-1.75 (m, 5H), 1.44-1.51 9 m, 2H), 1.40-1.44 (m, 3H). LCMS (M+H)=446.27.

Intermediate 70

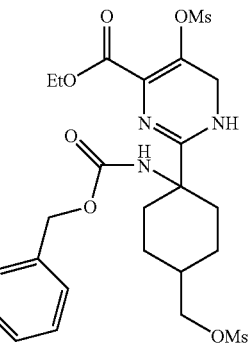

Ethyl 2-(1-(benzyloxycarbonylamino)-4-((methylsulfonyloxy)methyl)cyclohexyl)-5-(methylsulfonyloxy)-1,6-dihydropyrimidine-4-carboxylate. To a stirred solution of ethyl 2-(1-(benzyloxycarbonylamino)-4-(hydroxymethyl)cyclohexyl)-5-hydroxy-6-oxo-1,6-dihydropyrimidine-4-carboxylate (1.85 g, 4.15 mmol) in THF (40 mL) cooled to 0° C. was added methanesulfonyl chloride (0.96 mmol, 12.45 mmol) and triethylamine (1.79 mL, 12.87 mmol). The mixture was allowed to warm to room temperature and stirred for 18 h. The resulting precipitate was filtered off and washed with THF. The filtrate and washings were concentrated to afford an amber oil. A solution of this oil in methanol (10 mL) was treated with K$_2$CO$_3$ (574 mg, 4.15 mmol) at room temperature for 3 h. The mixture was then concentrated and the residue was dissolved in ethyl acetate (200 mL), washed with 1N HCl (100 mL) followed by brine (100 mL), then dried (Na$_2$SO$_4$), filtered and concentrated to give 2.3 g of title compound as a yellow oil. LCMS (M+H)=602.45.

Intermediate 64

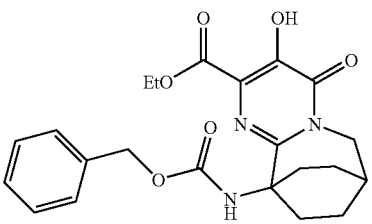

Ethyl 10-(((benzyloxy)carbonyl)amino)-3-hydroxy-4-oxo-4,6,7,8,9,10-hexahydro-7,10-ethanopyrimido[1,2-a]azepine-2-carboxylate. A mixture of ethyl 2-(1-(benzyloxycarbonylamino)-4-((methylsulfonyloxy)methyl)cyclohexyl)-5-(methylsulfonyloxy)-1,6-dihydropyrimidine-4-carboxylate (2.25 g, 3.74 mmol) and cesium carbonate (1.22 g, 3.74 mmol) in DMF (40 mL) was heated at 60° C. for 18 h. The reaction mixture was then cooled and concentrated in vacuo. The residue was taken up in ethyl acetate (200 mL) and extracted with 0.2 M aq. NaOH (3×50 mL). The combined aqueous phase was washed with ethyl acetate (250 mL). The aqueous layer was then acidified with conc. HCl and extracted with CH$_2$Cl$_2$ (3×100 mL). The CH$_2$Cl$_2$ extracts were dried (Na$_2$SO$_4$), filtered and concentrated to afford the title compound as a brown solid (400 mg). $^1$H NMR (500 MHz, CDCl$_3$) δ: 10.81 (s, 1H), 7.29-7.36 (m, 6H), 5.29 (s, 1H), 5.10 (s, 2H), 4.41 (q, 2H, J=7.27 Hz), 4.13 (d, 2H, J=3.66 Hz), 2.43-2.47 (m, 2H), 1.94-2.02 9 m, 2H), 1.79-1.85 (m, 2H), 1.65-1.72 (m, 2H), 1.40 (t, 3H, J=7.17). LCMS (M+H)= 428.26.

Intermediate 71

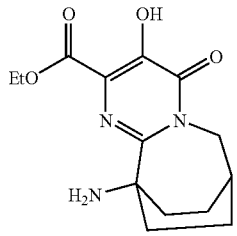

Ethyl 10-amino-3-hydroxy-4-oxo-4,6,7,8,9,10-hexahydro-7,10-ethanopyrimido[1,2-a]azepine-2-carboxylate. To a mixture of ethyl 10-(((benzyloxy)carbonyl)amino)-3-hydroxy-4-oxo-4,6,7,8,9,10-hexahydro-7,10-ethanopyrimido[1,2-a]azepine-2-carboxylate (2 g, 4.68 mmol) in ethanol (75 mL) was added 1N HCl (5.15 mL, 5.15 mmol) followed by Pd/C (0.498 g, 0.468 mmol) and the mixture stirred under 1 atm of hydrogen for 18 h. The mixture was then filtered through a pad of CELITE® and the pad washed with dichloromethane. The filtrate was then concentrated to afford the title compound (1.4 g, 91% yield) as an off-white solid. $^1$H NMR (500 MHz, DMSO-$d_6$) δ: 10.5 (1 H, brs), 4.3 (2 H, q, J=7.02 Hz), 4.0 (2 H, d, J=3.66 Hz), 2.4 (1 H, brs), 2.0-2.1 (4 H, m), 1.8-1.9 (2 H, m), 1.7-1.8 (2 H, m), 1.3 (3 H, t, J=7.02 Hz). LCMS (M+H)=294.32.

Intermediate 72

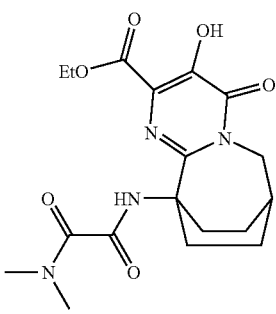

Ethyl 10-(((dimethylamino)(oxo)acetyl)amino)-3-hydroxy-4-oxo-4,6,7,8,9,10-hexahydro-7,10-ethanopyrimido[1,2-a]azepine-2-carboxylate. To a stirred solution of ethyl 10-amino-3-hydroxy-4-oxo-4,6,7,8,9,10-hexahydro-7,10-ethanopyrimido[1,2-a]azepine-2-carboxylate (250 mg, 0.895 mmol) and 2-(dimethylamino)-2-oxoacetic acid (157 mg, 1.343 mmol) in DMF (6 mL) was added diisopropyl-ethylamine (0.498 mL, 2.86 mmol), 4-(dimethylamino)pyridine (DMAP) (21.87 mg, 0.179 mmol) and O-(7-azabenzotriazol-1-yl)-N,N,N',N'-tetramethyluronium hexafluorophosphate (HATU) (511 mg, 1.343 mmol) and the resulting mixture stirred at room temperature for 5 hr. Solvent was removed under reduced pressure. The crude material was diluted with ethyl acetate (50 mL) and washed with 1N HCl (20 mL), dried (Na$_2$SO$_4$) and concentrated to yield the title compound.

Intermediate 73

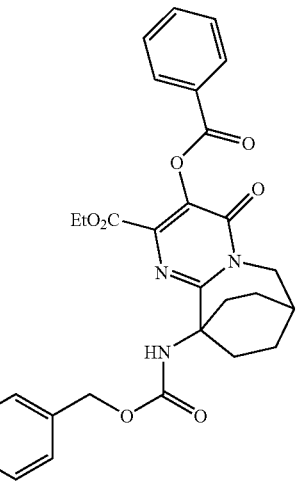

Ethyl 10-(((benzyloxy)carbonyl)amino)-4-oxo-3-((phenylcarbonyl)oxy)-4,6,7,8,9,10-hexahydro-7,11-ethanopyrimido[1,2-a]azepine-2-carboxylate. To a solution of ethyl 10-(((benzyloxy)carbonyl)amino)-3-hydroxy-4-oxo-4,6,7,8,9,10-hexahydro-7,10-ethanopyrimido[1,2-a]azepine-2-carboxylate (13.9 g, 32.5 mmol) in pyridine (150 mL) was added benzoic anhydride (11.03 g, 48.8 mmol) and the resulting mixture was stirred at room temp for 16 h. Solvent was removed under reduced pressure and the residue was diluted with ethyl acetate (500 mL), washed with 1N HCl (100 mL), sat. NaHCO$_3$ followed by brine, then dried (Na$_2$SO$_4$), filtered and concentrated. The crude material was then triturated with ethyl acetate/hexane and dried to afford the title compound (16 g, 30.1 mmol, 93% yield) as a light yellow solid. $^1$H NMR (500 MHz, CDCl$_3$) δ: 8.16 (2 H, dd, J=8.28, 1.25 Hz), 7.59-7.64 (1 H, m), 7.48 (2 H, t, J=7.78 Hz), 7.26-7.38 (5 H, m), 5.27 (1 H, s), 5.08 (2 H, s), 4.24 (2 H, q, J=7.03 Hz), 4.13 (2 H, d, J=3.76 Hz), 2.84-2.99 (2 H, m), 2.45 (1 H, brs), 1.85-2.05 (4 H, m), 1.67-1.77 (2 H, m), 1.11 (3 H, t, J=7.15 Hz). LCMS (M+H)=532.24.

Intermediate 74

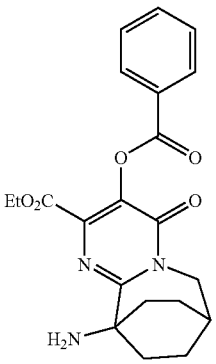

Ethyl 10-amino-4-oxo-3-((phenylcarbonyl)oxy)-4,6,7,8,9,10-hexahydro-7,10-ethanopyrimido[1,2-a]azepine-2-carboxylate hydrochloride. To a mixture of ethyl 10-(((benzyloxy)carbonyl)amino)-4-oxo-3-((phenylcarbonyl)oxy)-4,6,7,8,9,10-hexahydro-7,10-ethanopyrimido[1,2-a]azepine-2-carboxylate (16 g, 30.1 mmol) in ethyl acetate (300 mL) and methanol (150 mL) was added 1N HCl (31.6 mL, 31.6 mmol) followed by Pd/C (3.20 g, 3.01 mmol) and the mixture was stirred under balloon hydrogen atmosphere for 2 h. The mixture was then filtered through a pad of CELITE® and the pad was thoroughly washed with ethyl acetate. The filtrate was concentrated under reduced pressure and dried under high vacuum overnight to afford the title compound (12.75 g, 98% yield),as an off-white solid. $^1$H NMR (500 MHz, CDCl$_3$) δ: 8.11-8.16 (2 H, m), 7.62 (1 H, t, J=7.40 Hz), 7.48 (2 H, t, J=7.78 Hz), 4.19 (2 H, q, J=7.11 Hz), 4.13 (2 H, d, J=3.51 Hz), 2.71-2.83 (2 H, m), 2.53 (1 H, brs), 2.32-2.46 (2 H, m), 2.01-2.13 (2 H, m), 1.74-1.85 (2 H, m), 1.03 (3 H, t, J=7.03 Hz). LCMS (M+H)=398.10.

Intermediate 75

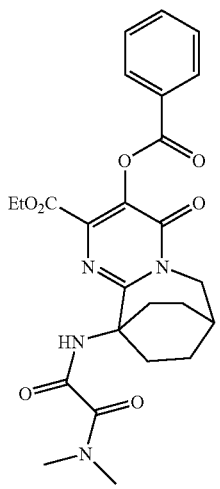

Ethyl 10-(((dimethylamino) (oxo)acetyl)amino)-4-oxo-3-((phenylcarbonyl)oxy)-4,6,7,8,9,10-hexahydro-7,10-ethanopyrimido[1,2-a]azepine-2-carboxylate. To a stirred solution of ethyl 10-amino-4-oxo-3-((phenylcarbonyl)oxy)-4,6,7,8,9,10-hexahydro-7,10-ethanopyrimido[1,2-a]azepine-2-carboxylate hydrochloride (2.4 g, 5.53 mmol) in DMF (50 mL) as added 2-(dimethylamino)-2-oxoacetic acid (1.295 g, 11.06 mmol), diisopropyl-ethylamine (5.80 mL, 33.2 mmol) and the resulting mixture was stirred at room temperature for 3 h. Water was then added and the mixture extracted with ethyl acetate (2×200 mL). The organic solution was washed with 1N HCl (50 mL), dried (Na$_2$SO$_4$), filtered and concentrated. The crude material was triturated with ethyl acetate/hexane to afford the title compound (2.5 g, 5.04 mmol, 91% yield) as a light yellow solid. $^1$H NMR (500 MHz, CDCl$_3$) δ: 9.33 (1 H, brs), 8.18 (2 H, d, J=7.02 Hz), 7.64 (1 H, t, J=7.48 Hz), 7.50 (2 H, t, J=7.93 Hz), 4.29 (2 H, q, J=7.02 Hz), 4.17 (2 H, d, J=3.66 Hz), 3.34 (3 H, s), 3.03 (3 H, s), 2.88-3.00 (2 H, m), 2.50 (1 H, brs), 1.93-2.10 (4 H, m), 1.73-1.82 (2 H, m), 1.18 (3 H, t, J=7.17 Hz). LCMS (M+H)=497.79.

Intermediate 76

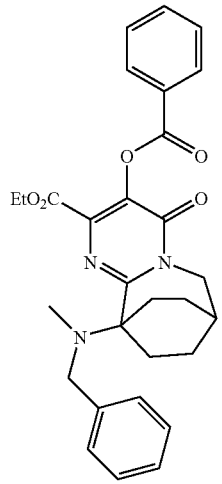

Ethyl 10-(benzyl(methyl)amino)-4-oxo-3-((phenylcarbonyl)oxy)-4,6,7,8,9,10-hexahydro-7,10-ethanopyrimido[1,2-a]azepine-2-carboxylate. To a stirred solution of ethyl 10-amino-4-oxo-3-((phenylcarbonyl)oxy)-4,6,7,8,9,10-hexahydro-7,10-ethanopyrimido[1,2-a]azepine-2-carboxylate hydrochloride (12.75 g, 29.4 mmol) in 1,2-dichloroethane (500 mL) was added triethylamine (4.10 mL, 29.4 mmol) and the resulting mixture was stirred for 5 min. Benzaldehyde (5.94 mL, 58.8 mmol), AcOH (1.682 mL, 29.4 mmol) and NaCNBH$_3$ (5.54 g, 88 mmol) were then added and the mixture stirred at room temp for 6 h. Formaldehyde (4.38 mL, 58.8 mmol) was then added to the reaction and the mixture was stirred at room temperature for 16 h. The reaction was quenched with sat. NaHCO$_3$ and extracted with dichloromethane, dried (Na$_2$SO$_4$), filtered and concentrated. The crude product was the recrystallized from ethyl acetate to afford the title compound (11.6 g, 23.13 mmol, 79% yield)as an off-white solid. $^1$H NMR (500 MHz, CDCl$_3$) δ: 8.20 (2 H, d, J=7.32 Hz), 7.63 (1 H, t, J=7.32 Hz), 7.50 (2 H, t, J=7.78 Hz), 7.39 (2 H, d, J=7.63 Hz), 7.31 (2 H, t, J=7.48 Hz), 7.20-7.23 (1 H, m), 4.28-4.34 (2 H, m), 4.09 (4 H, brs), 2.53 (3 H, s), 2.47 (1 H, brs), 2.32-2.42 (2 H, m), 2.02-2.10 (2 H, m), 1.89-1.99 (2 H, m), 1.66-1.74 (2 H, m), 1.22 (3 H, t, J=7.17 Hz). LCMS (M+H)=502.37.

Intermediate 77

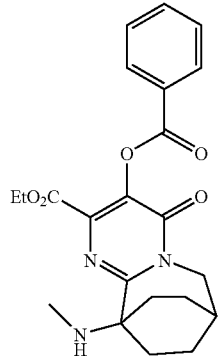

Ethyl 10-(methylamino)-4-oxo-3-((phenylcarbonyl)oxy)-4,6,7,8,9,10-hexahydro-7,10-ethanopyrimido[1,2-a]azepine-2-carboxylate hydrochloride. To a mixture of ethyl 10-amino-4-oxo-3-((phenylcarbonyl)oxy)-4,6,7,8,9,10-hexahydro-7,10-ethanopyrimido[1,2-a]azepine-2-carboxylate hydrochloride (6 g, 11.96 mmol) in ethyl acetate (100 mL) and ethanol (100 mL) was added 1N HCl (12.56 mL, 12.56 mmol) followed by Pd/C (1.273 g, 1.196 mmol) and the mixture stirred under 1 atm of hydrogen for 2 h. The mixture was then filtered (filter paper) and the solid thoroughly washed with ethyl acetate. The filtrate was concentrated under reduced pressure and dried under high vacuum overnight to afford the title compound (4.8 g, 90% yield)as an off-white solid. $^1$H NMR (500 MHz, CDCl$_3$) δ: 8.15 (2 H, d, J=7.28 Hz), 7.62-7.67 (1 H, m), 7.47-7.52 (2 H, m), 4.26 (2 H, q, J=7.03 Hz), 4.11 (2 H, d, J=3.76 Hz), 2.76 (3 H, s), 2.56 (1 H, brs), 2.16-2.25 (2 H, m), 2.00-2.13 (4 H, m), 1.68-1.82 (3 H, m), 1.12 (3 H, t, J=7.03 Hz). LCMS (M+H)=412.78.

Intermediate 78

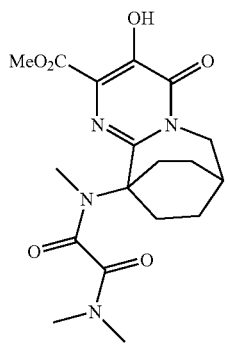

Methyl 10-(((dimethylamino)(oxo)acetyl)(methyl)amino)-3-hydroxy-4-oxo-4,6,7,8,9,10-hexahydro-7,11-ethanopyrimido[1,2-a]azepine-2-carboxylate. To a solution of ethyl 10-(methylamino)-4-oxo-3-((phenylcarbonyl)oxy)-4,6,7,8,9,10-hexahydro-7,10-ethanopyrimido[1,2-a]azepine-2-carboxylate hydrochloride salt (4.7 g, 10.49 mmol) in dichloromethane (100 mL) at 0° C. was added diisopropyl-ethylamine (5.50 mL, 31.5 mmol) followed by methyl 2-chloro-2-oxoacetate (0.967 mL, 10.49 mmol) and the resulting mixture stirred at room temp for 2 h. The reaction mixture was then washed with 1N HCl (50 mL) followed by brine (100 mL), then dried (Na$_2$SO$_4$), filtered, concentrated and dried under high vacuum for 2 hr. The crude material was treated with 2M Me$_2$NH in methanol (52.5 mL, 105 mmol) and stirred at 50° C. for 16 h. The mixture was allowed to cool to room temperature and concentrated, diluted with ethyl acetate, washed with 0.2N NaOH (2×75 mL). The NaOH layer was acidified with conc. HCl and extracted with dichloromethane, then dried (Na$_2$SO$_4$), filtered and concentrated to provide the title compound (3.5 g, 85% yield). $^1$H NMR (500 MHz, CDCl$_3$) δ: 10.09 (1 H, s), 3.93 (3 H, s), 3.16 (3 H, s), 3.11 (3 H, s), 3.02 (3 H, s), 2.52 (1 H, brs), 2.05-2.15 (2 H, m), 1.81-2.00 (2 H, m), 1.50-1.80 (6 H, m). LCMS (M+H)=393.15.

Intermediate 79

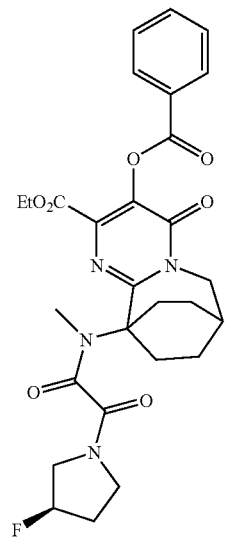

Ethyl 10-((((3R)-3-fluoro-1-pyrrolidinyl)(oxo)acetyl)(methyl)amino)-4-oxo-3-((phenylcarbonyl)oxy)-4,6,7,8,9,10-hexahydro-7,10-ethanopyrimido[1,2-a]azepine-2-carboxylate. To a stirred solution of ethyl 10-(methylamino)-4-oxo-3-((phenylcarbonyl)oxy)-4,6,7,8,9,10-hexahydro-7,10-ethanopyrimido[1,2-a]azepine-2-carboxylate hydrochloride (120 mg, 0.268 mmol) in DMF (4 mL) was added (R)-2-(3-fluoropyrrolidin-1-yl)-2-oxoacetic acid (130 mg, 0.804 mmol), diisopropylethylamine (0.281 mL, 1.607 mmol), O-(7-azabenzotriazol-1-yl)-N,N,N',N'-tetramethyluronium hexafluorophosphate (HATU) (306 mg, 0.804 mmol), 4-(dimethylamino)pyridine (DMAP) (9.82 mg, 0.080 mmol) and the resulting mixture stirred at room temperature for 16 h. The mixture was quenched with water and diluted with ethyl acetate, washed with 1N HCl, followed by sat.NaHCO$_3$, dried (Na$_2$SO$_4$) filtered and concentrated. The crude product was purified on Biotage flash chromatography system using 30-100% ethyl acetate/hexane gradient to afford the title compound (80 mg, 0.144 mmol, 54% yield) as a white solid. $^1$H NMR (500 MHz, CDCl$_3$) δ: 8.12-8.23 (2 H, m), 7.64 (1 H, t, J=7.48 Hz), 7.44-7.56 (2 H, m), 5.11-5.42 (1 H, m), 4.08-4.27 (2 H, m), 3.28-4.01 (9 H, m), 3.18 (3 H, d, J=3.05 Hz), 2.50 (1 H, brs), 1.72-2.37 (6 H, m), 0.99-1.11 (3 H, m). LCMS (M+H)=555.76.

Intermediate 80

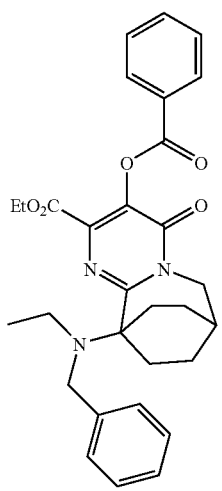

Ethyl 10-(benzyl(ethyl)amino)-4-oxo-3-((phenylcarbonyl)oxy)-4,6,7,8,9,10-hexahydro-7,10-ethanopyrimido[1,2-a]azepine-2-carboxylate. To a stirred solution of Ethyl 10-amino-4-oxo-3-((phenylcarbonyl)oxy)-4,6,7,8,9,10-hexahydro-7,10-ethanopyrimido[1,2-a]azepine-2-carboxylate hydrochloride (200 mg, 0.461 mmol) in 1,2-dichloroethane (10 mL) was added triethylamine (0.064 mL, 0.461 mmol) and the resulting mixture stirred for 5 min. Benzaldehyde (0.186 mL, 1.844 mmol), AcOH (0.053 mL, 0.922 mmol) and NaCNBH$_3$ (87 mg, 1.383 mmol) were then added and the mixture stirred for 6 h. Acetaldehyde (0.182 mL, 3.23 mmol) was then added to the reaction and the this was stirred at room temperature for 16 h. The mixture was then quenched with sat. NaHCO$_3$ and extracted with dichloromethane, dried (Na$_2$SO$_4$), filtered and concentrated to afford title compound.

Intermediate 81

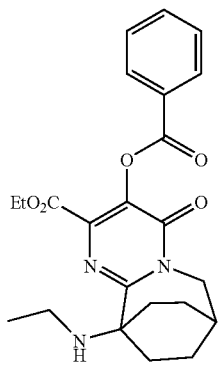

Ethyl 10-(ethylamino)-4-oxo-3-((phenylcarbonyl)oxy)-4,6,7,8,9,10-hexahydro-7,10-ethanopyrimido[1,2-a]azepine-2-carboxylate. To a mixture of ethyl 10-(benzyl(ethyl)amino)-4-oxo-3-((phenylcarbonyl)oxy)-4,6,7,8,9,10-hexahydro-7,10-ethanopyrimido[1,2-a]azepine-2-carboxylate (120 mg, 0.233 mmol) in methanol (5 mL) was added 1N HCl (0.256 mL, 0.256 mmol) followed by Pd/C (24.77 mg, 0.023 mmol) and the mixture stirred under 1 atm hydrogen for 18 h. The mixture was filtered and the solids thoroughly washed with dichloromethane. The filtrate was concentrated under reduced pressure and dried under high vacuum overnight to afford the title compound.

Intermediate 82

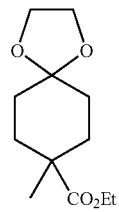

Ethyl 8-methyl-1,4-dioxaspiro[4.5]decane-8-carboxylate. Lithium diethylamide was prepared by adding (5 min) nBuLi in hexanes (94 mL, 150 mmol) to a solution of diisopropylamine (22.80 mL, 160 mmol) in THF (50 mL) at −30° C. (dry ice/acetone) under N$_2$. After 20 min, ethyl 1,4-dioxaspiro[4.5]decane-8-carboxylate (21.43 g, 100 mmol) in THF (25 mL) was added over 5 min. After 20 min, iodomethane (28.4 g, 200 mmol) in THF (25 mL) was added over 5 min. The resulting solution was stirred at −30° C. for 20 min and then allowed to slowly warm to room temperature overnight under N$_2$. The reaction was quenched with water (200 mL). The solution was concentrated to remove THF. The aqueous solution was extracted with CH$_2$Cl$_2$ (3×100 mL) and the organic layer dried (MgSO$_4$), filtered, and concentrated to yield ethyl 8-methyl-1,4-dioxaspiro[4.5]decane-8-carboxylate (22 g, 96 mmol, 96% yield) as a yellow oil. LCMS: m/z 229 (M+H). $^1$H NMR (500 MHz, CHLOROFORM-d) δ ppm 4.13 (2 H, q, J=7.22 Hz), 3.92 (4 H, s), 2.06-2.16 (2 H, m), 1.57-1.66 (4 H, m), 1.51 (2 H, dd, J=12.97, 4.12 Hz), 1.24 (3 H, t, J=7.17 Hz), 1.17 (3 H, s).

Intermediate 83

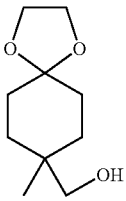

(8-Methyl-1,4-dioxaspiro[4.5]decan-8-yl)methanol. Yield: 100% (clear oil). $^1$H NMR (500 MHz, CHLOROFORM-d) δ ppm 3.87-3.97 (4 H, m), 3.38 (2 H, s), 1.66 (1 H, d, J=3.66 Hz), 1.59-1.65 (3 H, m), 1.53-1.59 (2 H, m), 1.52 (1 H, d, J=4.58 Hz), 1.45 (1 H, brs), 1.40 (2 H, t, J=5.80 Hz), 1.37 (1 H, s), 0.96 (3 H, s). LCMS: m/z 187 (M+H).

Intermediate 84

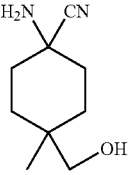

1-Amino-4-(hydroxymethyl)-4-methylcyclohexanecarbonitrile. Yield: 73.3% (crude oil). LCMS: m/z 169.21 (M+H).

Intermediate 85

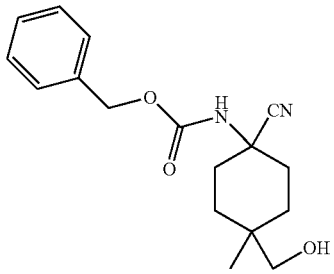

Benzyl 1-cyano-4-(hydroxymethyl)-4-methylcyclohexylcarbamate. Yield: 21% (yellow oil; column-purified). LCMS: m/z 303.98 (M+H). HPLC: retention time=1.90 min (area percent=: 100%). $^1$H NMR (500 MHz, CHLOROFORM-d) δ ppm 7.26-7.59 (5 H, m) 5.13 (2 H, brs) 4.99 (1 H, d, J=3.05 Hz) 3.32-3.47 (2 H, m) 2.11-2.50 (2 H, m) 1.85-2.11 (1 H, m) 1.28-1.85 (8 H, m) 0.91-1.06 (3 H, m).

Intermediate 86

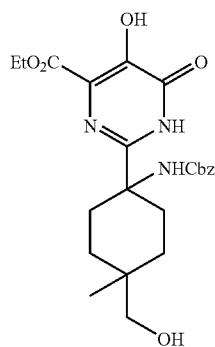

Ethyl 2-(1-(benzyloxycarbonylamino)-4-(hydroxymethyl)cyclohexyl)-5-hydroxy-6-oxo-1,6-dihydropyrimidine-4-carboxylate. Yield: 42% (crude glassy solid). HPLC: retention time=1.78 min (area percent=100%). LCMS: m/z 460.21 (M+H). $^1$H NMR (500 MHz, CHLOROFORM-d) δ ppm 0.97 (s, 3 H) 1.27-1.40 (m, 4 H) 1.42 (t, J=6.56 Hz, 3 H) 1.67 (d, J=9.16 Hz, 2 H) 1.97-2.03 (m, 2 H) 2.04 (s, 1 H) 2.06 (d, J=1.22 Hz, 1 H) 2.20 (br. s., 4 H) 3.35 (s, 1 H) 3.48 (s, 1 H) 4.41-4.47 (m, 2 H) 5.07 (br. s., 2 H) 7.33 (br. s., 6 H) 10.78 (br. s., 1 H).

Intermediate 87

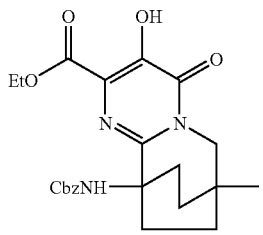

7,10-Ethanopyrimido[1,2-a]azepine-2-carboxylic acid, 4,6,7,8,9,10-hexahydro-3-hydroxy-7-methyl-4-oxo-10-[[(phenylmethoxy)carbonyl]amino]-, ethyl ester. Yield: 18% (crude oil), Used as is for next reaction. HPLC: retention time=2.43 min (area percent=:15%). LCMS: m/z 441.94 (M+H).

Intermediate 88

((1R,3S)-1,2,2-Trimethylcyclopentane-1,3-diyl)dimethanol. A solution of (1R,3S)-1,2,2-trimethylcyclopentane-1,3-dicarboxylic acid (26.25 g, 131 mmol) in THF (400 mL) was cooled in an ice bath (10° C.) and to this was added 1M LiAlH$_4$/THF (328 mL, 328 mmol), dropwise over 1 h. The ice bath was removed and the white slurry was stirred for 5 h at room temperature and 17 h at reflux. After cooling to room temperature, the mixture was diluted with Et$_2$O (500 mL), cooled in an ice bath and carefully quenched with water (12.2 mL), 15% NaOH (12.2 mL) and water (36.7 mL). After stirring for 30 min at room temperature, the white slurry was filtered through a pad of CELITE®, then dried (Na$_2$SO$_4$), filtered and concentrated to give ((1R,3S)-1,2,2-trimethylcyclopentane-1,3-diyl)dimethanol (21.665 g, 126 mmol, 96% yield) as a white solid. $^1$H NMR (500 MHz, CDCl$_3$) δ: 3.73 (1 H, dd, J=10.2, 5.3 Hz), 3.58 (1 H, d, J=10.7 Hz), 3.51 (1 H, dd, J=10.1, 8.5 Hz), 3.46 (1 H, d, J=10.7 Hz), 2.04-2.12 (1 H, m), 1.89-1.99 (1 H, m), 1.55-1.64 (1 H, m), 1.31-1.41 (2 H, m), 1.22 (2 H, brs), 1.02 (3 H, s), 1.01 (3 H, s), 0.78 (3 H, s).

Intermediate 89

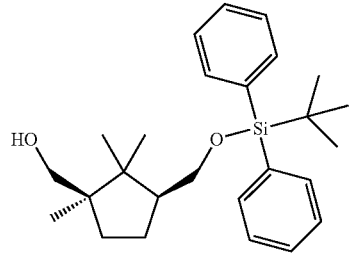

((1R,3S)-3-((tert-Butyldiphenylsilyloxy)methyl)-1,2,2-trimethylcyclopentyl)methanol. To a stirred solution of((1R,3S)-1,2,2-trimethylcyclopentane-1,3-diyl)dimethanol (18.19 g, 106 mmol) and imidazole (8.63 g, 127 mmol) in DMF (400 mL) at 0° C. (ice bath) was added tert-butylchlorodiphenylsilane (28.8 mL, 111 mmol) over 5 min. The reaction mixture was stirred overnight (16 h) while slowly warming to room temperature. The reaction mixture was then diluted with Et$_2$O (1000 mL), washed with water (5×100 mL) followed by brine (100 mL), then dried (Na$_2$SO$_4$), filtered and concentrated to give a color less liquid. Flash column chromatography on silica gel column using 9:1 and 4:1 hexane/ethyl acetate as eluent provided ((1R,3S)-3-((tert-butyldiphenylsilyloxy)methyl)-1,2,2-trimethylcyclopentyl)methanol (40.5 g, 99 mmol, 93% yield) as a colorless viscous oil. $^1$H NMR (500 MHz, CDCl$_3$) δ: 7.64-7.69 (4 H, m), 7.35-7.44 (6 H, m), 3.70 (1 H, dd, J=10.1, 6.4 Hz), 3.54 (2 H, dt, J=10.4, 6.7 Hz), 3.44 (1 H, dd, J=10.7, 5.5 Hz), 2.09-2.18 (1 H, m), 1.82-1.92 (1 H, m), 1.49-1.58 (1 H, m), 1.24-1.36 (3 H, m), 1.04 (9 H, s), 0.98 (3 H, s), 0.97 (3 H, s), 0.75 (3 H, s). LCMS (M+H) calcd for $C_{26}H_{39}O_2Si$: 411.27; found: 411.31.

Intermediate 90

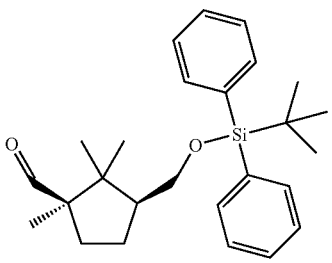

(1R,3S)-3-((tert-Butyldiphenylsilyloxy)methyl)-1,2,2-trimethylcyclopentanecarbaldehyde. A solution of 4-methylmorpholine (17.33 g, 148 mmol) in $CH_2Cl_2$ (400 mL) was dried over $Mg_2SO_4$ for 15 min and filtered into a round bottom flask containing ((1R,3S)-3-((tert-butyldiphenylsilyloxy)methyl)-1,2,2-trimethylcyclopentyl)methanol (40.5 g, 99 mmol). To the resulting clear solution was added 4 A° powdered molecular sieves (20 g), tetrapropylammonium perruthenate (TPAP) (0.693 g, 1.972 mmol) and stirred for 4 h at room temperature. The reaction was concentrated to ~100 mL, diluted with hexane/$Et_2O$ (9:1, 500 mL) and filtered through a plug of silica gel. The plug was washed with 500 mL of hexane/$Et_2O$ (9:1). The filtrate was concentrated to afford (1R,3S)-3-((tert-butyldiphenylsilyloxy)methyl)-1,2,2-trimethylcyclopentanecarbaldehyde (32.61 g, 80 mmol, 81% yield) as a viscous pale yellow oil. $^1$H NMR (500 MHz, $CDCl_3$) δ: 9.63 (1 H, s), 7.66 (4 H, dd, J=7.9, 1.5 Hz), 7.35-7.45 (6 H, m), 3.66-3.71 (1 H, dd, J=10.2, 6.9 Hz), 3.56 (1 H, dd, J=10.4, 7.0 Hz), 2.29 (1 H, ddd, J=13.7, 11.4, 6.0 Hz), 2.09-2.18 (1 H, m), 1.87-1.96 (1 H, m), 1.28-1.44 (2 H, m), 1.06 (3 H, s), 1.02-1.05 (12 H, s), 0.81 (3 H, s). LCMS (M+Na) calcd for $C_{26}H_{36}NaO_2Si$: 431.25; found: 431.52.

Intermediate 91

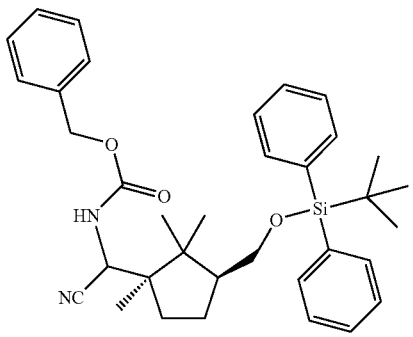

Benzyl((1R,3S)-3-((tert-butyldiphenylsilyloxy)methyl)-1,2,2-trimethyl-cyclopentyl)(cyano) ethylcarbamate. To a stirred mixture of(1R,3S)-3-((tert-butyldiphenylsilyloxy)methyl)-1,2,2-trimethylcyclopentanecarbaldehyde (8.2 g, 20.07 mmol) and zinc(II) iodide (0.641 g, 2.007 mmol) was added trimethylsilyl cyanide (2.94 mL, 22.07 mmol) at room temperature. Note: The reaction was warm to touch within 5 min after the addition of TMSCN. After 15 min, 7N ammonia/methanol (40 mL, 1848 mmol) was added and stirring continued overnight (17 h) at room temperature. The reaction mixture was concentrated and the resulting residue taken up in toluene and concentrated to remove traces of methanol/$NH_3$. The resulting white slurry was dissolved in $CH_2Cl_2$ (50 mL) and 1N aq. $Na_2CO_3$ (25 mL), and treated with benzylchloroformate (3.15 mL, 22.07 mmol) at room temperature. After 3 h, the organic layer was separated and the aqueous layer extracted with $CH_2Cl_2$ (25 mL). The combined $CH_2Cl_2$ layers were dried ($Na_2SO_4$), filtered and concentrated to give a color less oil. Flash column chromatography on silica gel column using 10, 15 and 20% ethyl acetate/hexane gave benzyl((1R,3S)-3-((tert-butyldiphenylsilyloxy)methyl)-1,2,2-trimethyl-cyclopentyl)(cyano) ethylcarbamate (9.4 g, 16.53 mmol, 82% yield) as a white foam. $^1$H NMR (500 MHz, $CDCl_3$) δ: 7.61-7.67 (4 H, m), 7.31-7.46 (11 H, m), 5.09-5.19 (2 H, m), 4.97 (1 H, d, J=10.1 Hz), 4.78 (1 H, d, J=10.1 Hz), 3.62-3.69 (1 H, m), 3.52 (1 H, dd, J=10.1, 7.0 Hz), 2.13 (1 H, tt, J=9.7, 6.7 Hz), 1.83-1.93 (1 H, m), 1.65-1.74 (1 H, m), 1.58-1.64 (1 H, m), 1.28-1.38 (1 H, m), 1.14 (3 H, s), 1.01-1.05 (9 H, m), 0.95 (3 H, s), 0.81 (3 H, s). LCMS (M+Na) calcd for $C_{35}H_{44}NaN_2O_3Si$:591.30; found: 591.63.

Intermediate 92

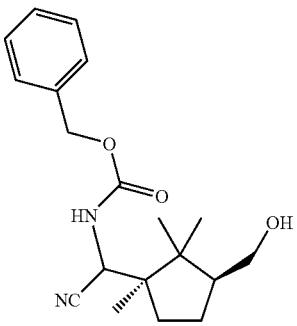

Benzyl cyano((1R,3S)-3-(hydroxymethyl)-1,2,2-trimethylcyclopentyl)methylcarbamate. To a stirred colorless solution of benzyl ((1R,3S)-3-((tert-butyldiphenylsilyloxy)methyl)-1,2,2-trimethylcyclopentyl)(cyano)methylcarbamate (9.4 g, 16.53 mmol) in THF (50 mL) was added IN tetrabutyl ammonium fluoride/THF (19.83 mL, 19.83 mmol) at room temperature. The resulting yellow mixture was stirred for 24 h and then concentrated. The residue was taken up in ethyl acetate (150 mL), washed with 1N aq. HCl (30 mL0, water (50 mL) followed by brine (2×25 mL), then dried ($Na_2SO_4$), filtered and concentrated to give a colorless oil. Flash column chromatography on silica gel column using 3:7 and 3:2 ethyl acetate/hexane (product came out with 3:2 ethyl acetate/hexane) provided benzyl cyano((1R,3S)-3-(hydroxymethyl)-1,2, 2-trimethylcyclopentyl)methylcarbamate (5.22 g, 15.80 mmol, 96% yield) as a white foam. $^1$H NMR (500 MHz, $CDCl_3$) δ: 7.31-7.41 (5 H, m), 5.09-5.20 (2 H, m), 5.01 (1 H, d, J=10.1 Hz), 4.82 (1 H, d, J=10.1 Hz), 3.66-3.75 (1 H, m), 3.48-3.56 (1 H, m), 2.06-2.15 (1 H, m), 1.93-2.04 (1 H, m), 1.72-1.81 (1 H, m), 1.64-1.71 (1 H, m), 1.37-1.48 (1 H, m), 1.18-1.22 (1 H, m), 1.17 (3 H, s), 1.00 (3 H, s), 0.84 (3 H, s). LCMS (M+H) calcd for $C_{19}H_{27}N_2O_3$: 331.20; found: 331.14.

Intermediate 93

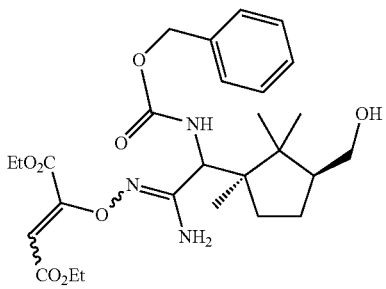

Diethyl 2-(1-amino-2-(benzyloxycarbonylamino)-2-((1R,3S)-3-(hydroxymethyl)-, 2,2-trimethylcyclopentyl)ethylideneaminooxy)but-2-enedioate. A clear homogeneous solution benzyl cyano((1R,3S)-3-(hydroxymethyl)-1,2,2-trimethylcyclopentyl)methylcarbamate (5.22 g, 15.80 mmol) and 50% aq. hydroxylamine (1.484 mL, 24.22 mmol) in EtOH (50 mL) was stirred for 40 h at 50° C. It was then concentrated and the resulting residue redissolved in EtOH (50 mL) and treated with diethyl acetylenedicarboxylate (3.03 mL, 18.96 mmol). After 4 h at 40° C., the reaction mixture was concentrated and the resulting yellow residue purified by flash column chromatography on silica gel column using 20, 40, 60 and 75% ethyl acetate/hexane (product came out with 75% ethyl acetate/hexane) to provide diethyl 2-(1-amino-2-(benzyloxycarbonylamino)-2-((1R,3S)-3-(hydroxymethyl)-1,2,2-trimethylcyclopentyl)ethylideneaminooxy)but-2-enedioate (6.051 g, 11.34 mmol, 72% yield) as a white foam. $^1$H NMR (500 MHz, CDCl$_3$) δ: 7.28-7.39 (5 H, m), 5.75 (0.5 H, s), 5.22 (0.5 H, brs), 5.06-5.16 (3 H, m), 4.91 (1 H, brs), 4.23-4.41 (3 H, m), 4.13-4.19 (2 H, m), 3.68-3.75 (1 H, m), 3.46-3.55 (1 H, m), 2.01-2.11 (1 H, m), 1.86-1.99 (1 H, m), 1.67-1.80 (1 H, m), 1.23-1.38 (7 H, m), 1.15-1.19 (1 H, m), 1.11 (2 H, s), 1.07 (1 H, s), 1.03 (2 H, s), 0.99 (1 H, s), 0.85 (3 H, s). LCMS (M+H) calcd for C$_{27}$H$_{40}$N$_3$O$_8$: 534.28; found: 534.26.

Intermediate 94

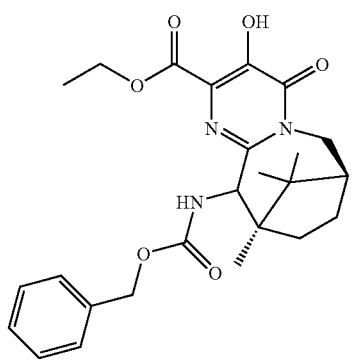

Ethyl (7S,10R)-11-(((benzyloxy)carbonyl)amino)-3-hydroxy-10,12,12-trimethyl-4-oxo-6,7,8,9,10,11-hexahydro-4H-7,10-methanopyrimido[1,2-a]azocine-2-carboxylate. A solution of diethyl 2-(1-amino-2-(benzyloxycarbonylamino)-2-((1R,3S)-3-(hydroxymethyl)-1,2,2-trimethylcyclopentyl)ethylideneaminooxy)but-2-enedioate (6.05 g, 11.34 mmol) in xylene (250 mL) was heated at 125-130° C. for 8 h. The dark reaction mixture was concentrated and the resulting residue was used in the next step without purification. The above crude product was dissolved in DMF (40 mL) and stirred with K$_2$CO$_3$ (3 g, 21.71 mmol) and methanesulfonyl chloride (0.779 mL, 10 mmol) for 2 h at room temperature and 28 h at 90° C. After cooling to room temperature it was diluted with ethyl acetate (200 mL), neutralized with 1N aq. HCl. The organic layer was separated and washed with water (2×50 mL) followed by brine (50 mL), then dried (Na$_2$SO$_4$), filtered and concentrated to give a brown paste. Purification by preparative HPLC on a C$_{18}$ column using methanol/water (0.1% trifluoroacetic acid, gradient elution starting with 30% methanol/water) provided the title compound (1.4595 g, 3.11 mmol, 27% yield) as a brown solid.

Intermediate 95

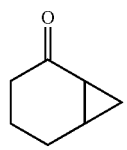

Bicycle[4.1.0]heptan-2-one. The title compound was prepared by following the procedure described in O. O. Grygorenko et al., *Tetrahedron: Asymmetry*, 2006, 17, 252. In a dry round bottom flask, 60% (in mineral oil) NaH (4.49 g, 112 mmol) was triturated with hexanes three times, and placed under high vacuum to further dry. To DMSO (100 mL) in an oven-dried three neck flask under nitrogen was added the concentrated NaH in small portions. The temperature was kept between 15-25° C. Once gas evolution had subsided, trimethylsulfoxonium iodide (24.73 g, 112 mmol) was added via a powder addition funnel in small portions keeping the temperature between 15-25° C. The suspension was allowed to stir for 2 h during which time it became a milky solution. Cyclohex-2-enone (10 g, 104 mmol) in DMSO (25 mL) was then slowly added drop-wise. The solution became red and was stirred for 0.5 h at room temperature and 2 h at 50° C. It was then poured into 100 mL of ice water. The water was extracted with Et$_2$O (4×100 mL). The ether extracts were combined, dried (MgSO$_4$) and concentrated under reduced pressure. The resulting red oil was purified by distillation. Fractions distilling ate 65 and 70° C. were collected. Yield: 72% (liquid). HPLC: retention time=1.05 min (area percent=: 70%). $^1$H NMR (500 MHz, CHLOROFORM-d) δ ppm 1.07 (ddd, J=9.84, 8.16, 5.19 Hz, 1 H) 1.19 (q, J=5.39 Hz, 1 H) 1.54-1.63 (m, 1 H) 1.63-1.77 (m, 3 H) 1.84-1.92 (m, 1 H) 1.92-1.99 (m, 1 H) 2.03 (ddd, J=18.31, 11.60, 6.71 Hz, 1 H) 2.27 (dt, J=18.31, 4.58 Hz, 1 H).

Intermediate 96

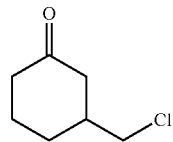

3-(Chloromethyl)cyclohexanone. The title compound was prepared following the procedure described in (N. Di Bello et al., *Synthesis*, 1978, 227. To a solution of bicycle[4.1.0]heptan-2-one (13.8 g, 125 mmol) in acetonitrile (300 mL) was added pyridine hydrochloride (43.3 g, 375 mmol) which had been triturated with Et$_2$O and dried under high vacuum. The solution was stirred under N$_2$ at 82° C., overnight. The reaction mixture was partially concentrated, poured into brine (200 mL) and extracted with Et$_2$O (4×100 mL). The ether extracts were combined, washed with brine (100 mL), dried and concentrated. The residual oil was purified on a Biotage flash chromatography system (15% ethyl acetate in hexanes) to yield the title compound (13.4 g, 91 mmol, 73.1% yield) as an oil. LCMS: 147.09 (M+H), 149.10 (M+3, 30% rel. intensity). $^1$H NMR (500 MHz, CHLOROFORM-d) δ ppm 1.51-1.60 (m, 1 H) 1.62-1.74 (m, 1 H) 1.95-2.02 (m, 1 H) 2.06-2.13 (m, J=13.47, 9.80, 3.62, 3.62 Hz, 1 H) 2.13-2.20 (m, 1 H) 2.20-2.31 (m, 2 H) 2.35-2.43 (m, 1 H) 2.45-2.51 (m, 1 H) 3.45-3.55 (m, 2 H). 13C NMR (126 MHz, CHLOROFORM-d) δ ppm 24.63, 28.75, 40.85, 41.15, 45.39, 210.25.

Intermediate 97

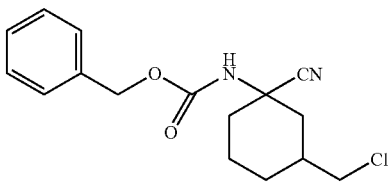

Benzyl 3-(chloromethyl)-1-cyanocyclohexylcarbamate. Yield: 46% (oil). HPLC: retention time=2.77 min. LCMS: m/z 307 (M+H).

Intermediate 98

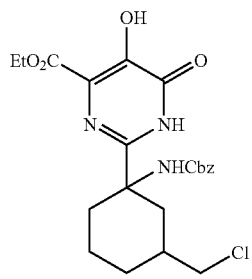

Ethyl 2-(1-(benzyloxycarbonylamino)-3-(chloromethyl) cyclohexyl)-5-hydroxy-6-oxo-1,6-dihydropyrimidine-4-carboxylate. LCMS: m/z 464 (M+H) observed.

Intermediate 99

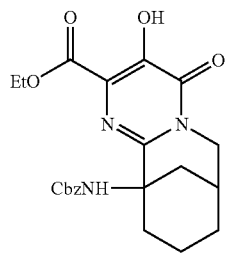

7,11-Methano-4H-pyrimido[1,2-a]azocine-2-carboxylic acid, 6,7,8,9,10,11-hexahydro-3-hydroxy-4-oxo-11-[[(phenylmethoxy)carbonyl]amino]-, ethyl ester. LCMS: m/z 428 (M+H) observed.

Intermediate 100

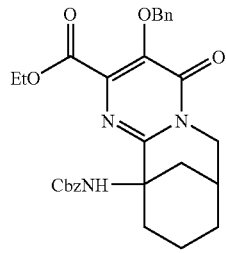

7,11-Methano-4H-pyrimido[1,2-a]azocine-2-carboxylic acid, 6,7,8,9,10,11-hexahydro-4-oxo-3-(phenylmethoxy)-11-[[(phenylmethoxy)carbonyl]amino]-, ethyl ester. Yield: 1% HPLC: retention time=3.03 min (area percent=: 75%). LCMS: m/z 518.16 (M+H). $^1$H NMR: In agreement with structure. Impurities present.

Intermediate 101

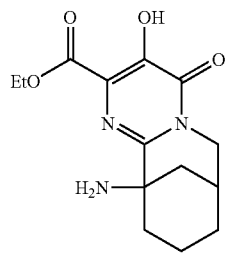

Ethyl 1-amino-5-hydroxy-6-oxo-3,7-diazatricyclo [7.3.1.0$^{2,7}$]trideca-2,4-diene-4-carboxylate. LCMS: m/z 294.46 (M+H).

Intermediate 102

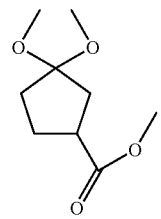

Methyl 3,3-dimethoxycyclopentanecarboxylate. (Tetrahedron, (1977), 33, 1113) A solution of 3-oxocyclopentanecarboxylic acid (10.013 g, 78 mmol) and trimethyl orthoformate (60.5 mL, 547 mmol) in MeOH (120 mL) was treated with acetyl chloride (7.78 mL, 109 mmol) and stirred under a nitrogen atmosphere for 5 days. The reaction solution was poured into a stirred suspension of anhydrous sodium carbonate (32 g) in pentane (250 mL) and stirred for 3 hrs. The solids were removed by filtration (2×) and concentrated under reduced pressure to give the target compound (15.4 g, 82 mmol, 105% yield) as a pale yellow oil. $^1$H NMR (500 MHz, CDCl$_3$) δ ppm 3.67 (3 H, s), 3.20 (3 H, s), 3.18 (3 H, s), 2.82-2.93 (1 H, m), 2.01-2.15 (2 H, m), 1.77-2.01 (4 H, m).

Intermediate 103

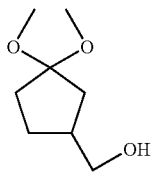

(3,3-Dimethoxycyclopentyl)methanol. A solution of methyl 3,3-dimethoxycyclopentanecarboxylate, methyl 3,3-dimethoxycyclopentanecarboxylate (14.68 g, 78 mmol), in THF (100 mL) was cooled (0° C. ice bath) and treated with 1.0N lithium aluminum hydride in THF (74.1 mL, 74.1 mmol) by dropwise addition. Upon completion of the addition, the reaction was warmed to room temperature and stirred for 6 hrs. The reaction was quenched by slow addition of Na$_2$SO$_4$-10H$_2$O (17 g). The suspension was stirred for 1 hr, treated with anhyd. Na$_2$SO$_4$, and filtered. The filtrate was concentrated to afford the target compound (12.01 g, 75.0 mmol, 96% yield) as a colourless oil. $^1$H NMR (500 MHz, CDCl$_3$) δ ppm 3.54 (2 H, s), 3.20 (3 H, s), 3.19 (3 H, s), 2.21-2.32 (1 H, m), 1.99 (1H, dd, J=13.28, 9.00 Hz), 1.85-1.91 (1 H, m), 1.78-1.85 (2 H, m), 1.73-1.78 (1 H, m), 1.56 (1 H, dd, J=13.12, 7.32 Hz), 1.40-1.48 (1 H, m).

Intermediate 104

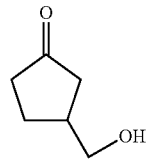

3-(Hydroxymethyl)cyclopentanone. A solution of (3,3-dimethoxycyclopentyl)methanol, (3,3-dimethoxycyclopentyl)methanol (12.01 g, 75.0 mmol), in Et$_2$O (80 mL), was treated with p-toluene sulfonic acid monohydrate (0.4 g, 2.103 mmol) and stirred for 2 hrs. The reaction was poured into water (50 mL) and the layers were separated. The aqueous layer was saturated with sodium chloride then extracted with CH$_2$Cl$_2$ (5×50 mL) and EtOAc (4×50 mL). The combined extracts were dried (MgSO$_4$), filtered and concentrated under reduced pressure to give the target compound (8.01 g, 70.2 mmol, 94% yield), as a brownish-yellow oil. $^1$H NMR (500 MHz, CDCl$_3$) δ ppm 1.66-1.77 (m, 1 H) 2.01 (dd, J=18.01, 8.85 Hz, 1 H) 2.08-2.24 (m, 2 H) 2.27-2.40 (m, 2 H) 2.40-2.50 (m, 1 H) 3.63-3.68 (m, 2 H).

Intermediate 105

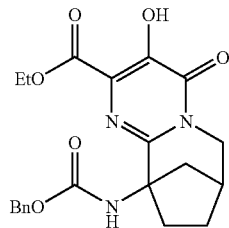

7,10-Methanopyrimido[1,2-a]azepine-2-carboxylic acid, 4,6,7,8,9,10-hexahydro-3-hydroxy-4-oxo-10-[[(phenylmethoxy)carbonyl]amino]-, ethyl ester. A solution of ethyl 2-(1-(benzyloxycarbonylamino)-3-((methylsulfonyloxy)methyl)cyclopentyl)-1-(methylsulfonyl)-5-(methylsulfonyloxy)-6-oxo-1,6-dihydropyrimidine-4-carboxylate (6.10 g, 9.16 mmol) in THF (50 mL) and EtOH (50 mL) was treated with potassium carbonate (2.56 g, 18.52 mmol). The reaction was stirred for 20 hrs at room temp., then warmed (45° C. oil bath) for 5 hrs. The solvent was removed by rotary evaporator. The residue was partitioned between ethyl acetate (100 mL) and water (100 mL), and after separation of the layers, the basic aqueous layer was further extracted with ethyl acetate (2×50 mL). The basic aqueous layer was made acidic with 6.0 N HCl and extracted with ethyl acetate (2×75 mL). The combined organic extracts were dried (MgSO$_4$), filtered and concentrated under reduced pressure to give the target compound and unreacted bis-mesylate intermediate (1:1 mixture, 1.887 g) as an amber oil/glassy foam. LC/MS (M+H)=414.24. This was used in the subsequent step without further purification or characterization.

Intermediate 106

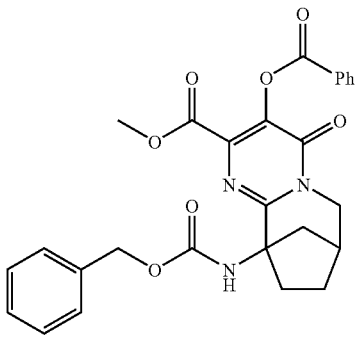

7,10-Methanopyrimido[1,2-a]azepine-2-carboxylic acid, 3-(benzoyloxy)-4,6,7,8,9,10-hexahydro-4-oxo-10-[[(phenylmethoxy)carbonyl]amino]-, ethyl ester. A solution of 7,10-methanopyrimido[1,2-a]azepine-2-carboxylic acid, 4,6,7,8,9,10-hexahydro-3-hydroxy-4-oxo-10-[[(phenylmethoxy)carbonyl]amino]-, ethyl ester (1.887 g, 4.56 mmol) in pyridine (50 mL) was treated with benzoic anhydride (1.53 g, 6.76 mmol) and stirred at room temperature for 16 hrs. The solvent was removed under reduced pressure and the residue was diluted with ethyl acetate (75 mL), and washed with 1.0N HCl (75 ml), saturated NaHCO$_3$ solution (75 mL) followed by brine, then dried (MgSO$_4$) filtered and concentrated under reduced pressure. The residue was purified by flash silica gel column chromatography, affording a yellow oil after concentration. This was dried once from Et$_2$O, then the resulting solid was triturated with Et$_2$O. The target compound (0.466 g, 0.900 mmol, 19.7% yield) was isolated as a white solid after filtration. $^1$H NMR (500 MHz, CDCl$_3$) δ ppm 8.17 (2H, d, J=7.02 Hz), 7.64 (1 H, t, J=7.48 Hz), 7.50 (2 H, t, J=7.78 Hz), 7.28-7.43 (5 H, m), 6.63 (1 H, br s), 5.12 (2 H, s), 4.26 (2 H, q, J=7.32 Hz), 3.84-4.01 (2 H, m), 2.93-3.05 (1 H, m), 2.76-2.85 (1 H, m), 2.54-2.68 (1 H, m), 2.23-2.37 (1 H, m), 1.98-2.10 (2 H, m), 1.65-1.77 (1 H, m), 1.11 (3 H, t, J=7.02 Hz). LC/MS (M+H)=518.28. HPLC purity>98%.

Intermediate 107

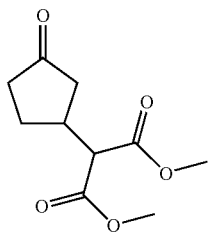

Dimethyl 2-(3-oxocyclopentyl)malonate. Tetrahedron Letters 2005, 46, 6875-6878. To a solution of cyclopent-2-enone (99.82 g, 1216 mmol) and dimethyl malonate (560 mL, 4887 mmol) in dry toluene (1000 mL) was added 2,3,4,6,7,8-hexahydro-1H-pyrimido[1,2-a]pyrimidine (5.10 g, 36.6 mmol). The reaction was stirred at room temperature under nitrogen for 16 hrs, then concentrated under reduced pressure to ~½ volume. The crude product was filtered through a short path of silica gel (3.5×4 cm), eluting with ethyl acetate. The filtrate was concentrated under vacuum pump rotary evaporation (70-75° C. water bath) for 2 hrs, affording the target compound (247.7 g, 1098 mmol, 90% yield). $^1$H NMR (500 MHz, CDCl$_3$) δ ppm 3.76 (3 H, s), 3.74 (3 H, s), 3.37 (1 H, d, J=9.46 Hz), 2.80-2.91 (1 H, m), 2.49 (1 H, dd, J=18.31, 7.63 Hz), 2.29-2.37 (1 H, m), 2.15-2.28 (2 H, m), 2.00 (1 H, ddd, J=18.46, 10.99, 1.37 Hz), 1.58-1.71 (1 H, m).

Intermediate 108

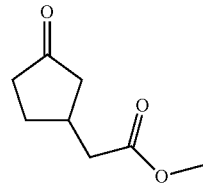

Methyl 2-(3-oxocyclopentyl)acetate. A 1000 mL flask was charged with dimethyl 2-(3-oxocyclopentyl)malonate (329.1 g, 1536 mmol), and dodecanedioic acid (283 g, 1229 mmol). The mixture was heated (210° C., oil bath) under a nitrogen atmosphere for 20 hrs, then distilled (~1 torr, 180° C. oil bath) to give the title compound (170.4 g, 1091 mmol, 71.0% yield) as a pale yellow oil. $^1$H NMR (500 MHz, CDCl$_3$) δ ppm 3.68 (3 H, s), 2.55-2.66 (1 H, m), 2.40-2.51 (3 H, m), 2.27-2.35 (1 H, m), 2.13-2.26 (2 H, m), 1.87 (1 H, ddd, J=18.23, 10.30, 1.37 Hz), 1.53-1.63 (1 H, m). $^{13}$C NMR (126 MHz, CDCl$_3$) δ ppm 218.36, 172.58, 51.78, 44.70, 39.53, 38.40, 33.52, 29.31.

Intermediate 109

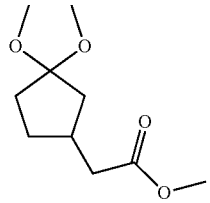

Methyl 2-(3,3-dimethoxycyclopentyl)acetate. Tetrahedron, 57 (2001), 5183. A mixture of Montmorillonite K$_{10}$ (188 g, 571 mmol) in trimethyl orthoformate (316 mL, 2856 mmol) was stirred for 2 hrs under nitrogen. To the mixture was slowly added methyl 2-(3-oxocyclopentyl)acetate (89.2 g, 571 mmol), as a suspension in pentane (500 mL). The mixture was stirred for 16 hrs, then filtered through a CELITE® pad rinsing with pentane. The filtrate was concentrated under reduced pressure to afford the title compound (104.9 g, 519 mmol, 91% yield) as an amber oil. $^1$H NMR (400 MHz, CDCl$_3$) δ ppm 3.67 (3 H, s) 3.20 (6 H, s) 2.35-2.46 (3 H, m) 2.11 (1 H, dd, J=13.18, 7.40 Hz) 1.86-1.96 (2 H, m) 1.74-1.83 (1 H, m) 1.44 (1 H, dd, J=13.05, 8.53 Hz) 1.34 (1 H, dd, J=12.55, 8.78 Hz). $^{13}$C NMR (101 MHz, CDCl$_3$) δ ppm 172.73, 110.91, 50.93, 48.80, 48.61, 40.27, 39.66, 33.51, 33.25, 29.37.

Intermediate 110

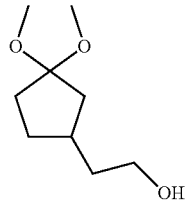

2-(3,3-Dimethoxycyclopentyl)ethanol. J. Org. Chem., 1986, 51 (21), 4000-4005. A 5000 mL large neck round bottom flask was charged with a solution of methyl 2-(3,3-dimethoxycyclopentyl)acetate (238 g, 1177 mmol) in THF (1100 mL). To the solution was added LiBH$_4$, 2.0 M in THF (706 mL, 1412 mmol) over approximately 1 min, followed by dropwise addition of methanol (57.1 mL, 1412 mmol). Note: vigorous exotherm. The reaction was stirred for 16 hrs, monitoring by $^1$H and $^{13}$C NMR. The reaction was quenched by the addition of sat'd ammonium chloride solution (600 mL), then diluted with Et$_2$O (~500 mL), and the layers were separated. The aqueous layer was extracted with CH$_2$Cl$_2$ (300 mL), and the combined organic extracts were concentrated. The resulting oil was diluted with CH$_2$Cl$_2$ (200 mL), dried (MgSO$_4$), filtered and concentrated to yield 2-(3,3-dimethoxycyclopentyl)ethanol (203.3 g, 1167 mmol, 99% yield).

Intermediate 111

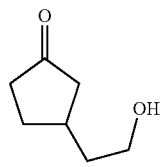

3-(2-Hydroxyethyl)cyclopentanone. A solution of 2-(3,3-dimethoxycyclopentyl)ethanol (203.3 g, 1167 mmol), in Et$_2$O (1000 mL) was treated with p-toluene sulfonic acid (6.66 g, 35.0 mmol) and stirred for 16 hrs. The solution was extracted with water (4×100 mL) and the combined extracts were concentrated under reduced pressure to give the title compound (142.33 g, 1110 mmol, 95% yield), as a dark brown oil. $^1$H NMR (500 MHz, CDCl$_3$) δ ppm 3.64-3.76 (2 H, m), 2.41 (1 H, dd, J=17.85, 7.17 Hz), 2.24-2.35 (2 H, m), 2.13-2.23 (2 H, m), 1.82 (1 H, dd, J=18.01, 10.38 Hz), 1.64-1.77 (2 H, m), 1.49-1.60 (1 H, m). $^{13}$C NMR (126 MHz, CDCl$_3$) δ ppm 219.75, 61.30, 45.21, 38.54, 38.41, 34.01, 29.67.

Intermediate 112

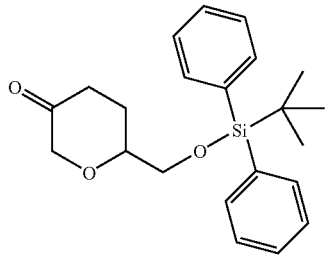

6-((tert-Butyldiphenylsilyloxy)methyl)dihydro-2H-pyran-3(4H)-one. Prepared according to the general procedure described in Bioorganic Med. Chem. 2006, 14, 3953-3966.

Intermediate 113

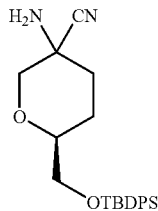

Cis-3-Amino-6-((tert-butyldiphenylsilyloxy)methyl)tetrahydro-2H-pyran-3-carbonitrile and trans-3-amino-6-(y(tert-butyldiphenylsilyloxy)methyl)tetrahydro-2H-pyran-3-carbonitrile. To a stirred solution of NH$_4$OH (188 mL) and methanol (75 mL) was added 6-((tert-butyldiphenylsilyloxy) methyl)dihydro-2H-pyran-3(4H)-one (35 g, 95 mmol), NH$_4$Cl (10.16 g, 190 mmol) followed by NaCN (9.31 g, 190 mmol). After 16 at room temperature, the reaction mixture was extracted with CH$_2$Cl$_2$ (250 mL×2), washed with water (500 mL), then dried (Na$_2$SO$_4$), filtered and concentrated. The crude product was purified by silica gel column chromatography (10% to 50% ethyl acetate/hexane) to afford a 1:1 mixture of C3-epimeric diastereomers, cis (14.9 g, 40% yield) and trans (15.1 g, 40% yield). Trans-isomer: $^1$H NMR (500 MHz, CDCl$_3$) δ: 7.62-7.71 (4 H, m), 7.32-7.47 (6 H, m), 4.03 (1 H, dd, J=11.14, 2.90 Hz), 3.77 (1 H, dd, J=10.53, 5.34 Hz), 3.62 (1 H, dd, J=10.53, 5.65 Hz), 3.36-3.43 (1 H, m), 3.20 (1 H, d, J=11.29 Hz), 2.18-2.25 (1 H, m), 1.82-1.87 (1 H, m), 1.72-1.78 (1 H, m), 1.71 (2 H, s), 1.62-1.67 (1 H, m), 1.06 (9 H, s). LCMS (M+H)=395.33. Cis-isomer: $^1$H NMR (500 MHz, CDCl$_3$) δ: 7.61-7.69 (4 H, m), 7.33-7.48 (6 H, m), 3.86 (1 H, dd, J=11.44, 1.98 Hz), 3.72 (1 H, dd, J=10.68, 5.19 Hz), 3.68 (1 H, d, J=11.60 Hz), 3.61 (1 H, dd, J=10.68, 5.19 Hz), 3.44-3.51 (1 H, m), 2.05-2.08 (1 H, m), 1.73 (2 H, brs), 1.61-1.71 (3 H, m), 1.05 (9 H, s). LCMS (M+H)=395.33.

Intermediate 114

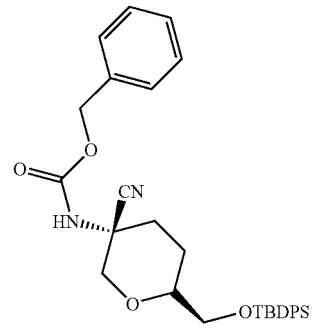

Benzyl cis-6-((tert-butyldiphenylsilyloxy)methyl)-3-cyanotetrahydro-2H-pyran-3-ylcarbamate. Benzyl chloroformate (5.42 mL, 38 mmol) was added to a biphasic mixture of water (110 mL) and CH$_2$Cl$_2$ (55 mL) containing cis-3-amino-6-((tert-butyldiphenylsilyloxy)methyl)tetrahydro-2H-pyran-3-carbonitrile (15 g, 38.0 mmol) and Na$_2$CO$_3$·H$_2$O (4.71 g, 38.0 mmol) at 0° C. and the mixture was stirred for 2 h. The mixture was then allowed to warm to room temperature and stirred for 18 h. The mixture was then diluted with CH$_2$Cl$_2$ (200 mL), washed with sat. NaHCO$_3$ (100 mL), water (100 mL) followed by brine (100 mL), then dried (Na$_2$SO$_4$), filtered and concentrated to give a brown oil. Flash column chromatography on silica gel, using a 5% to 40% ethyl acetate-hexane gradient, afforded the title compound as a light yellow liquid (18.4 g, 92% yield). $^1$H NMR (500 MHz, CDCl$_3$) δ: 7.60-7.72 (4 H, m), 7.30-7.48 (12 H, m), 5.14 (2 H, s), 4.93 (1 H, s), 3.77 (1 H, dd, J=10.53, 5.34 Hz), 3.62 (1 H, dd, J=10.53, 5.65 Hz), 3.37-3.46 (1 H, m), 3.21 (1 H, d, J=10.99 Hz), 2.45 (1 H, dd, J=12.51, 2.75 Hz), 1.79-1.92 (2 H, m), 1.63-1.74 (1 H, m), 1.05 (9 H, s). LCMS (M+H)=527.1.

Intermediate 115

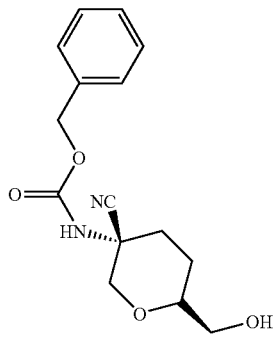

Benzyl cis-3-cyano-6-(hydroxymethyl)tetrahydro-2H-pyran-3-ylcarbamate. To a solution of benzyl cis-6-((tert-butyldiphenylsilyloxy)methyl)-3-cyanotetrahydro-2H-pyran-3-ylcarbamate (11.6 g, 21.94 mmol) in THF (200 mL) at 0° C. was added 1M tetrabutyl ammonium fluoride/THF (43.9 mL, 43.9 mmol) and the resulting mixture heated at 60° C. for 2 h. After cooling to room temperature, the solvent was removed under reduced pressure and the crude product was purified by Biotage flash chromatography using 30% to 100% ethyl acetate/hexane to afford the title compound (3.0 g, 47% yield)

as a yellow oil. $^1$H NMR (500 MHz, CDCl$_3$) δ: 7.32-7.38 (m, 6H), 5.13 (s, 1H), 4.99 (brs, 1H), 4.65-4.72 (m, 1H), 3.60-3.66 (m, 2H), 3.45-3.49 (m, 1H), 3.26 (d, 1H, J=11.29 Hz), 2.44-2.47 (m, 1H), 1.83-1.91 (m, 1H), 1.69-1.77 (m, 2H). LCMS (M+H)=291.4.

Intermediate 116

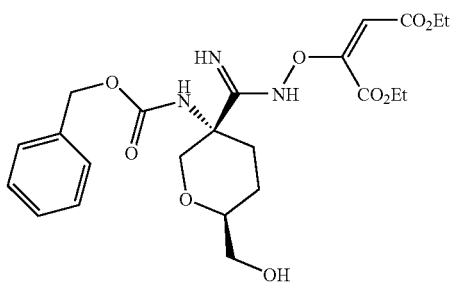

Ethyl 3-(cis-3-(benzyloxycarbonylamino)-6-(hydroxymethyl)tetrahydro-2H-pyran-3-yl)-5-(2-ethoxy-2-oxoethyl)-2,5-dihydro-1,2,4-oxadiazole-5-carboxylate: To a solution of benzyl cis-3-cyano-6-(hydroxymethyl)tetrahydro-2H-pyran-3-ylcarbamate (2.0 g, 6.89 mmol) in EtOH (60 mL) was added 50% hydroxylamine (1.267 mL, 20.67 mmol) and the reaction mixture was stirred 80° C. for 3 h. The reaction mixture was then cooled and concentrated and then dissolved in EtOH (100 mL) and treated with diethyl acetylenedicarboxylate (1.654 mL, 10.34 mmol). After stirring for 18 h at room temperature, the reaction mixture was diluted with ethyl acetate (250 mL), washed with H$_2$O (2×100 mL) followed by brine (50 mL), then dried over Na$_2$SO$_4$, filtered and concentrated. The crude was then purified by column chromatography using a Biotage flash chromatography system (10% to 50% ethyl acetate) to give a yellow oil (2.7 g, 79% yield) which was ~2:1 mixture of two diastereomers. $^1$H NMR (500 MHz, CDCl$_3$) δ: 7.31-7.37 (m, 6H), 6.04 (s, 0.5 H), 5.76 (s, 1H), 5.16 (s, 0.5 H), 5.07 (s, 2H), 4.80 (d, 1H, J=10.98 Hz), 4.09-4.16 (m, 4H), 3.57-3.68 (m, 5H), 2.27-2.30 (m, 1H), 1.94-2.00 (m, 2H), 1.72-1.78 (m, 6H). LCMS (M+H)= 494.27.

Intermediate 117

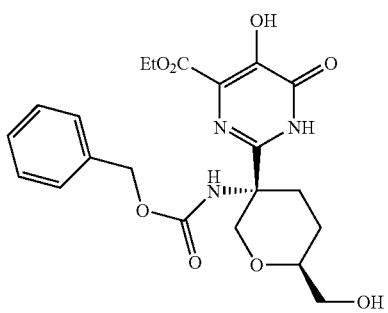

Ethyl 2-(cis-3-(benzyloxycarbonylamino)-6-(hydroxymethyl)tetrahydro-2H-pyran-3-yl)-5-hydroxy-6-oxo-1,6-dihydropyrimidine-4-carboxylate. A solution of ethyl 3-(cis-3-(benzyloxycarbonylamino)-6-(hydroxymethyl)tetrahydro-2H-pyran-3-yl)-5-(2-ethoxy-2-oxoethyl)-2,5-dihydro-1,2,4-oxadiazole-5-carboxylate (2.5 g, 5.07 mmol) in xylene (100 mL) was placed in a pre-heated oil bath and stirred for 16 h at 140° C. The reaction mixture was cooled and extracted with 0.2 M aq. NaOH (3×75 mL) and the combined aqueous phase was washed with ethyl acetate (100 mL). The aqueous layer was then acidified with conc. HCl and extracted with CH$_2$Cl$_2$ (3×100 mL). The CH$_2$Cl$_2$ solution was dried (Na$_2$SO$_4$), filtered and concentrated to afford the title compound as a light yellow solid (1.6 g, 71% yield). $^1$H NMR (500 MHz, CDCl$_3$) δ: 10.76 (s, 1H), 7.28-7.36 (m, 6H), 5.79 (s, 1H), 5.03 (s, 2H), 4.70 (d, 1H, J=11.9 Hz), 4.41 (q, 2H, J=7.02 Hz), 3.85-3.92 (m, 1H), 3.72 (d, 1H, J=9.46 Hz), 3.58-3.64 (m, 2H), 2.28-2.31 (m, 1H), 2.10-2.20 (m, 1H), 1.54-1.70 (m, 3H), 1.38 (t, 3H, J=7.17 Hz). LCMS (M+H)=448.28.

Intermediate 118

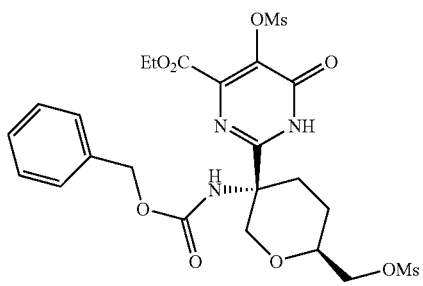

Ethyl 2-(3-(benzyloxycarbonylamino)-6-((methylsulfonyloxy)methyl)tetrahydro-2H-pyran-3-yl)-5-(methylsulfonyloxy)-6-oxo-1,6-dihydropyrimidine-4-carboxylate. To a stirred solution of ethyl 2-(cis-3-(benzyloxycarbonylamino)-6-(hydroxymethyl)tetrahydro-2H-pyran-3-yl)-5-hydroxy-6-oxo-1,6-dihydropyrimidine-4-carboxylate (1.7 g, 3.80 mmol) in THF (50 mL) at 0 C was added methanesulfonyl chloride (0.623 mL, 8.05 mmol) and triethylamine (2.65 mL, 19.00 mmol) in an ice bath and the mixture stirred at room temperature for 18 h. Water (50 mL) was then added and the mixture extracted with ethyl acetate (2×100 mL), washed with 1N HCl (50 mL) followed by brine (100 mL), then dried (Na$_2$SO$_4$), filtered and concentrated to give 1.9 g (83% yield) of the title compound as a light yellow solid along with tris-mesylate as a minor product by LC-MS. LCMS (M+H)= 604.25.

Intermediate 119

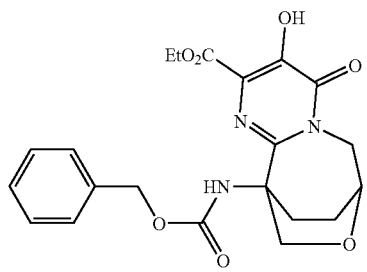

Ethyl 10-(((benzyloxy)carbonyl)amino)-3-hydroxy-4-oxo-4,6,7,8,9,10-hexahydro-7,10-(epoxymethano)pyrimido[1,2-a]azepine-2-carboxylate. A mixture of ethyl 2-(3-(benzyloxycarbonylamino)-6-((methylsulfonyloxy)methyl)

tetrahydro-2H-pyran-3-yl)-5-(methylsulfonyloxy)-6-oxo-1,6-dihydropyrimidine-4-carboxylate (360 mg, 0.596 mmol) and Cs$_2$CO$_3$ (194 mg, 0.596 mmol) in DMF (6 mL) was heated at 60° C. for 18 h. The reaction mixture was cooled to room temperature and concentrated under reduced pressure. The resulting residue was taken up in ethyl acetate (200 mL) and extracted with 0.2 M aq. NaOH (3×50 mL). The combined aqueous phase was washed with ethyl acetate (150 mL). The aqueous layer was then acidified with conc. HCl and extracted with CH$_2$Cl$_2$ (3×100 mL). The CH$_2$Cl$_2$ extracts were dried (Na$_2$SO$_4$), filtered and concentrated to afford the title compound as a light yellow solid (140 mg, 55% yield). $^1$H NMR (500 MHz, CDCl$_3$) δ: 10.62 (s, 1H), 7.31-7.36 (m, 5H), 6.76 (s, 1H), 5.10 (s, 2H), 4.60-4.64 (m, 1H), 4.41-4.48 (m, 1H), 4.40 (q, 2H, J=7.02 Hz), 4.10-4.16 (m, 2H), 2.91-2.95 (m, 1H), 2.35-2.40 (m, 1H), 1.82-1.97 (m, 1H), 1.58-1.64 (m, 1H), 1.37 (t, 3H, J=7.02 Hz). LCMS (M+H) 430.46.

Intermediate 120

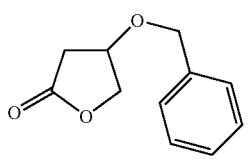

4-(Benzyloxy)dihydrofuran-2(3H)-one. To a stirred solution of 4-hydroxydihydrofuran-2(3H)-one (25 g, 245 mmol) and benzyl 2,2,2-trichloroacetimidate (68.6 mL, 367 mmol) in CH$_2$Cl$_2$ (500 mL) and cyclohexane (500 mL) at 0° C. was added, dropwise, trifluoromethanesulfonic acid (2.175 mL, 24.49 mmol) over 10 min. The reaction mixture was stirred for 2 h at 0° C. and 48 h at room temperature. After this, it was diluted with hexanes (0.75 L), filtered and the filtrate washed with sat. aq. NaHCO$_3$ (150 mL), dried (Na$_2$SO$_4$), filtered and concentrated. The resulting yellow oil was purified by flash column chromatography on silica gel column using 5-40% ethyl acetate/hexane (5% increment for every liter) to afford 4-(benzyloxy)dihydrofuran-2(3H)-one (35.52 g, 185 mmol, 75% yield) as a clear yellow oil. $^1$H NMR (500 MHz, CDCl$_3$) δ: 7.34-7.39 (2 H, m), 7.29-7.34 (3 H, m), 4.53 (1 H, d, J$_{AB}$=11.9 Hz), 4.52 (1 H, d, J$_{AB}$=11.90 Hz), 4.34-4.41 (3 H, m), 2.64-2.68 (2 H, m).

Intermediate 121

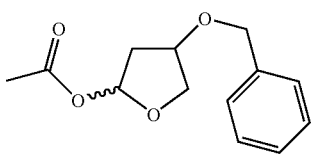

4-(Benzyloxy)tetrahydrofuran-2-yl acetate. To a stirred solution of 4-(benzyloxy)dihydrofuran-2(3H)-one (3.15 g, 16.39 mmol) in CH$_2$Cl$_2$ (100 mL) was added, dropwise, 1M DIBAL-H/toluene (2.56 g, 18.03 mmol) over 10 min at −78° C. After 2 h, pyridine (3.98 mL, 49.2 mmol), solid 4-(dimethylamino)pyridine (DMAP) (2.202 g, 18.03 mmol) and Ac$_2$O (6.19 mL, 65.6 mmol) were added and the solution was stirred for 6 h at −78° C. and slowly warmed to room temperature overnight (15 h). The resulting orange reaction mixture was stirred with sat. NH$_4$Cl (50 mL) for 30 min. The organic layer was separated and washed with 1N aq. NaHSO$_4$ (3×50 mL). The combined aq. layers were extracted with CH$_2$Cl$_2$ (2×50 mL) and the combined CH$_2$Cl$_2$ layers washed with 1N aq. NaHSO$_4$ (50 mL), sat. NaHCO$_3$ (50 mL) followed by brine (50 mL), then dried (Na$_2$SO$_4$), filtered and concentrated to afford a yellow oil. Flash column chromatography on a silica gel column using 15-30% ethyl acetate/hexane provided 4-(benzyloxy)tetrahydrofuran-2-yl acetate (3.5769 g, 15.14 mmol, 92% yield) as a clear oil. $^1$H NMR (500 MHz, CDCl$_3$) δ: 7.26-7.39 (5 H, m), 6.41 (0.3 H, dd, J=5.7, 2.0 Hz), 6.24-6.30 (0.7 H, dd, J=4.9, 1.8 Hz), 4.46-4.58 (2 H, m), 4.32-4.37 (0.3 H, m), 4.22-4.28 (0.7 H, m), 4.00-4.10 (2 H, m), 2.15-2.38 (2 H, m), 2.07 (3 H, s). LCMS (M-C$_2$H$_3$O) calcd for C$_{13}$H$_{16}$O$_4$: 177.09; found: 177.0.

Intermediate 122

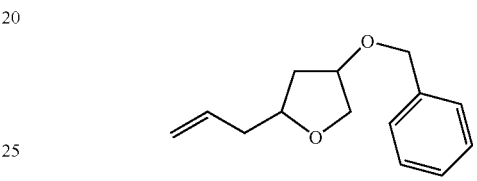

2-Allyl-4-(benzyloxy)tetrahydrofuran. To a stirred solution of 4-(benzyloxy)tetrahydrofuran-2-yl acetate (3.57 g, 15.11 mmol) and allyltrimethylsilane (9.65 mL, 60.4 mmol) in CH$_2$Cl$_2$ (200 mL) at −78° C. was added a solution of tin(IV) bromide (7.95 g, 18.13 mmol) in CH$_2$Cl$_2$ (20 mL) over 15 min. After 1 h, the ice bath was removed and stirring continued at room temperature for 3 h. The CH$_2$Cl$_2$ was removed using a rotoevaporator and the residue taken up in 1:1 Et$_2$O/hexane (200 mL), washed with sat. Na$_2$CO$_3$ (2×50 mL), water (2×50 mL) followed by brine (50 ml), then dried (Na$_2$SO$_4$), filtered and concentrated to give 2-allyl-4-(benzyloxy)tetrahydrofuran (3.15 g, 14.43 mmol, 95% yield). $^1$H NMR (400 MHz, CDCl$_3$) δ: 7.27-7.39 (5 H, m), 5.76-5.90 (1 H, m), 5.03-5.15 (2 H, m), 4.49 (1.6 H, d, J=2.3 Hz), 4.43 (0.4 H, d, J=2.3 Hz), 4.17-4.23 (1 H, m), 4.01 (0.45 H, d, J=1.8 Hz), 3.98 (0.55 H, d, J=1.8 Hz), 3.85-3.94 (1 H, m), 3.73 (1 H, dd, J=9.8, 5.3 Hz), 2.43-2.53 (1 H, m), 2.30-2.40 (1 H, m), 2.19-2.28 (1 H, m), 1.69-1.77 (1 H, m). LCMS (M+H) calcd for C$_{14}$H$_{19}$O$_2$: 219.14; found: 219.05.

Intermediate 123

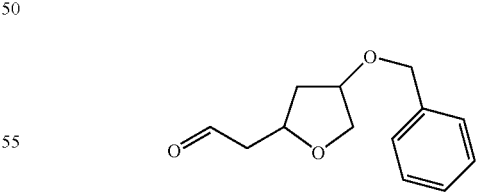

2-(4-(Benzyloxy)tetrahydrofuran-2-yl)acetaldehyde. To a stirred solution of 2-allyl-4-(benzyloxy)tetrahydrofuran (3.1 g, 14.20 mmol) in THF (100 mL) and water (100 mL) was added osmium tetroxide (2 mL, 0.327 mmol) at room temperature. After a few minutes, sodium periodate (7.59 g, 35.5 mmol) was added in small portions over 15 min. After 20 h, the reaction mixture was diluted with ether (200 mL), filtered and the filtrate washed with water (2×50 mL) followed by brine (50 mL), then dried (Na$_2$SO$_4$), filtered and concentrated to give a gray oil. Flash column chromatography on a silica gel column using 15-30% ethyl acetate/hexane (5% increment) gave 2-(4-(benzyloxy)tetrahydrofuran-2-yl)acetaldehyde (2.4624 g, 11.18 mmol, 79% yield) as a colorless liquid consisting of a ~4:1 mixture of diastereomers. $^1$H NMR (500 MHz, CDCl$_3$) δ: 9.81 (0.8 H, s), 9.77 (0.2 H, s), 7.23-7.37 (5 H, m), 4.48 (1.6 H, s), 4.41 (0.4 H, s), 4.29-4.31 (1 H, m), 4.23-4.20 (0.8 H, m), 4.12-4.09 (0.2 H, m), 4.04-4.06 (0.8 H, m), 3.90-3.94 (0.2 H, m), 3.73 (0.8 H, dd, J=9.9, 4.7 Hz), 3.64 (0.2 H, dd, J=9.9, 4.7 Hz), 2.82-2.94 (1 H, m), 2.60-2.73 (1 H, m), 2.25-2.39 (1 H, m), 1.77 (0.8 H, m), 1.59-1.69 (0.2 H, m). LCMS (M+H) calcd for C$_{13}$H$_{17}$O$_3$: 221.12; found: 221.05.

Intermediate 124

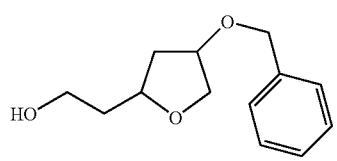

2-(4-(Benzyloxy)tetrahydrofuran-2-yl)ethanol. To a stirred solution of 2-(4-(benzyloxy)tetrahydrofuran-2-yl)acetaldehyde (2.46 g, 11.17 mmol) in methanol (50 mL) was added NaBH$_4$ (0.423 g, 11.17 mmol), in small portions, at room temperature. After 2 h, the reaction mixture was concentrated and the residue was taken up in sat. Na$_2$CO$_3$ (25 mL) and extracted with CH$_2$Cl$_2$ (3×25 mL). The combined CH$_2$Cl$_2$ layers were dried (Na$_2$SO$_4$), filtered and concentrated to give 2-(4-(benzyloxy)tetrahydrofuran-2-yl)ethanol (2.3847 g, 10.73 mmol, 96% yield) as a colorless oil consisting of a ~4:1 mixture of diastereomers. $^1$H NMR (500 MHz, CDCl$_3$) δ: 7.23-7.38 (5 H, m), 4.49 (1.6 H, s), 4.42 (0.4 H, d, J=1.5 Hz), 4.17-4.29 (1 H, m), 3.99-4.11 (2 H, m), 3.74-3.82 (2 H, m), 3.70 (0.8 H, dd, J=9.8, 4.9 Hz), 3.61 (0.2 H, dd, J=9.9, 5.0 Hz), 2.52 (0.8 H, t, J=5.6 Hz), 2.48 (0.2 H, t, J=5.6 Hz), 2.30 (0.8 H, dt, J=13.6, 7.2 Hz), 2.16-2.25 (0.2 H, m), 1.61-1.99 (3 H, m). LCMS (M+H) calcd for C$_{13}$H$_{19}$O$_3$: 223.13; found: 223.07.

Intermediate 125

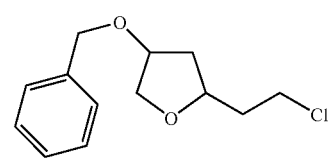

4-(Benzyloxy)-2-(2-chloroethyl)tetrahydrofuran. To an ice-cold stirred solution of oxalyl chloride (1.005 mL, 11.48 mmol) in CH$_2$Cl$_2$ (30 mL) was added DMF (0.914 mL, 11.80 mmol), dropwise, over 10 min. The ice bath was removed and the white slurry stirred for 30 min at room temperature. The reaction was cooled to 0° C. in an ice bath and a solution of 2-(4-(benzyloxy)tetrahydrofuran-2-yl)ethanol (2.3847 g, 10.73 mmol) in CH$_2$Cl$_2$ (30 mL) was rapidly added via cannula. The resulting clear yellow solution was stirred for 2 h at room temperature and 3 h at reflux. After cooling to room temperature the mixture was concentrated and the resulting yellow residue taken up in Et$_2$O (100 mL), washed with water (3×50 mL) followed by brine (25 mL), then dried (MgSO$_4$), filtered and concentrated to give a colorless liquid. Flash column chromatography on a silica gel column using 9:1 hexane/ethyl acetate provided 4-(benzyloxy)-2-(2-chloroethyl)tetrahydrofuran (2.47 g, 10.26 mmol, 96% yield) as a colorless oil. $^1$H NMR (500 MHz, CDCl$_3$) δ: 7.27-7.37 (5 H, m), 4.48 (1.6 H, s), 4.41 (0.4 H, s), 4.17-4.23 (1 H, m), 3.96-4.11 (2 H, m), 3.72 (0.8 H, dd, J=10.1, 4.9 Hz), 3.59-3.70 (2.2 H, m), 2.30 (0.8 H, dt, J=13.4, 7.0 Hz), 2.09-2.25 (1.2 H, m), 1.89-2.01 (1 H, m), 1.69-1.74 (0.8 H, m), 1.57-1.64 (0.2 H, m). LCMS (M+H) calcd for C$_{13}$H$_{18}$ClO$_3$: 241.1; found: 241.05.

Intermediate 126

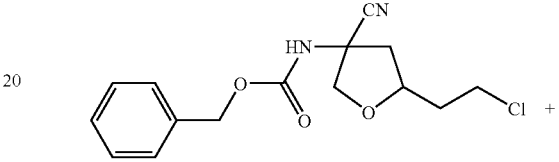

Benzyl 5-(2-chloroethyl)-3-cyanotetrahydrofuran-3-yl-carbamate. A solution of 4-(benzyloxy)-2-(2-chloroethyl)tetrahydrofuran (2.47 g, 10.26 mmol) in ethyl acetate (50 mL) was deoxygenated for 5 min by bubbling N$_2$ through. 10% Pd/C (0.145 g, 1.363 mmol) was added the flask evacuated then placed under 1 atm H$_2$ for 4 h. The reaction was filtered and concentrated to give a colorless oil (1.74 g) which was used in the next step without purification. A solution of 4-methylmorpholine N-oxide (1.803 g, 15.39 mmol) in CH$_2$Cl$_2$ (50 mL), intermediate 5-(2-chloroethyl)tetrahydrofuran-3-ol and 4 Å powdered molecular sieves (4 g) was stirred for 30 min. To this mixture was added tetrapropylammonium perruthenate (0.036 g, 0.103 mmol) and stirring continued for 24 h at room temperature. The reaction was concentrated, then diluted with Et$_2$O (100 mL) and filtered through a plug of CELITE®. The filtrate was concentrated to afford 5-(2-chloroethyl)dihydrofuran-3(2H)-one as viscous colorless oil. To a stirred mixture of 5-(2-chloroethyl)dihydrofuran-3(2H)-one, aqueous ammonia (5 mL) and 1N HCl (10 mL) in methanol 20 mL was added NaCN (0.43 g, 8.77 mmol) at room temperature. The yellow solution was stirred for 42 h and concentrated. The solution was made basic with sat. Na$_2$CO$_3$ (20 mL) and extracted with CH$_2$Cl$_2$ (3×25 mL). To the combined CH$_2$Cl$_2$ extracts was added sat. Na$_2$CO$_3$ (10 mL), and the mixture cooled to 0° C. with an ice bath and treated with benzyl chloroformate (1.465 mL, 10.26 mmol). After 1 h, the ice bath was removed and the reaction was stirred at room temperature for 4 h. The organic layer was separated, dried (Na$_2$SO$_4$), filtered, concentrated and purified by flash column chromatography on silica gel column using 10, 20, 30 and 40% ethyl acetate/hexane to afford the title compound benzyl 5-(2-chloroethyl)-3-cyanotetrahydrofuran-3-ylcarbamate (0.863 g, 2.80 mmol, 27% yield), viscous pale yellow oil. $^1$H NMR (500 MHz, CDCl$_3$) δ: 7.12-7.42 (5 H, m), 5.16 (2 H, s), 4.40 (0.2 H, d, J=9.8 Hz), 4.25-4.33 (0.8 H, m), 4.10-4.19 (1 H, m), 3.95 (0.2 H, d, J=9.8 Hz), 3.56-3.68 (1.8 H, m), 2.86 (1 H, dd, J=13.4, 7.0 Hz), 2.53-2.62 (1 H, m), 2.27 (1 H, dd, J=13.4, 8.9 Hz), 1.94-2.17 (2 H, m). LCMS (M+H) calcd for C$_{15}$H$_{18}$ClN$_2$O$_3$: 309.10; found: 309.10.

Intermediate 127

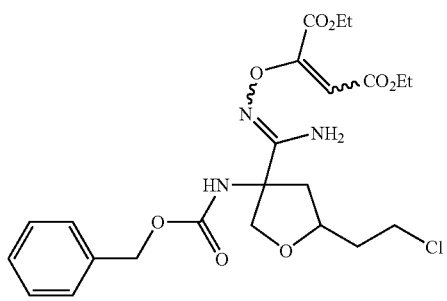

Diethyl 2-(amino(3-(benzyloxycarbonylamino)-5-(2-chloroethyl)tetrahydrofuran-3-yl)methyleneaminooxy)but-2-enedioate. A solution of benzyl 5-(2-chloroethyl)-3-cyanotetrahydrofuran-3-ylcarbamate (0.86 g, 2.79 mmol) and 50% aq. hydroxylamine (0.853 mL, 13.93 mmol) in THF (25 mL) was stirred at room temperature for 18 h. The mixture was concentrated and the residue was redissolved in EtOH (20 mL) and treated with diethyl acetylenedicarboxylate (0.490 mL, 3.06 mmol) at room temperature. After 24 h, the reaction mixture was concentrated and the resulting pale yellow residue was taken up in $Et_2O$ (75 mL), washed with 1% aq. $NH_4OH$ (20 mL), water (20 mL) followed by brine (20 mL), then dried ($Na_2SO_4$), filtered, concentrated and purified by flash column chromatography on silica gel column using 1:3, 2:3 and 1:1 ethyl acetate/hexane to afford diethyl 2-(amino(3-(benzyloxycarbonylamino)-5-(2-chloroethyl)tetrahydrofuran-3-yl)methyleneaminooxy)but-2-enedioate (1.1707 g, 2.287 mmol, 82% yield) as a pale yellow paste. $^1$H NMR (500 MHz, $CDCl_3$) δ: 7.30-7.39 (5 H, m), 5.75-5.88 (2 H, m), 5.26-5.62 (2 H, m), 5.05-5.12 (2 H, m), 4.21-4.37 (3 H, m), 4.12-4.20 (3 H, m), 4.02-4.10 (1 H, m), 3.57-3.67 (2 H, m), 2.60-2.85 (1 H, m), 1.87-2.20 (3 H, m), 1.29-1.38 (3 H, m), 1.22-1.28 (3 H, m). LCMS (M+H) calcd for $C_{23}H_{31}ClN_3O_8$: 512.18; found: 512.25.

Intermediate 128

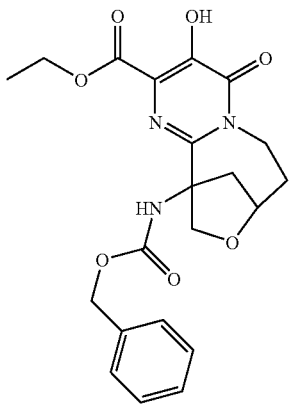

Ethyl 11-(((benzyloxy)carbonyl)amino)-3-hydroxy-4-oxo-7,8,10,11-tetrahydro-4H,6H-8,11-methanopyrimido[2,1-d][1,5]oxazocine-2-carboxylate. A solution of diethyl 2-(amino(3-(benzyloxycarbonylamino)-5-(2-chloroethyl)tetrahydrofuran-3-yl)methyleneaminooxy)but-2-enedioate (115 g, 2.246 mmol) in xylene (50 mL) was heated at 135-140° C. (oil bath temp.) for 4 h, then cooled, concentrated and the resulting residue dissolved in DMF (20 mL) and stirred with $K_2CO_3$ (0.621 g, 4.49 mmol) at 80-85° C. After 9 h, the reaction was cooled, concentrated and the residue was acidified with 1M aq. HCl (20 mL) and extracted with $CH_2Cl_2$ (2×25 mL). The combined organic layers were washed with water (25 mL) followed by brine (25 mL), then dried ($Na_2SO_4$), filtered and concentrated to give dark brown paste which was triturated with ethyl acetate to provide the a by-product, ethyl 3-hydroxy-4,6-dioxo-9,10-dihydro-4H,8H-10,12a-methanopyrimido[1',2':3,4]imidazo[5,1-c][1,4]oxazepine-2(12H)-carboxylate (0.1922 g, 0.598 mmol, 27% yield) as a gray powder. The mother liquor was purified by prep-HPLC to afford the title compound (0.071 g, 0.165 mmol, 7% yield) as an off-white solid. Ethyl 3-hydroxy-4,6-dioxo-9,10-dihydro-4H,8H-10,12a-methanopyrimido[1',2':3,4]imidazo[5,1-c][1,4]oxazepine-2(12H)-carboxylate: $^1$H NMR (500 MHz, $CDCl_3$) δ: 11.20 (1 H, brs), 4.85 (1 H, m), 4.49 (2 H, q, J=7.3 Hz), 4.28 (1 H, d, J=8.9 Hz), 4.14 (1 H, dd, J=13.4, 7.6 Hz), 4.08 (1 H, dd, J=8.9, 1.0 Hz), 3.42 (1 H, ddd, J=13.4, 11.3, 6.1 Hz), 2.69 (1 H, ddd, J=11.3, 6.3, 1.4 Hz), 2.00-2.07 (1 H, m), 1.89 (1 H, dd, J=11.3, 1.0 Hz), 1.71 (1 H, ddd, J=13.2, 11.5, 7.9 Hz), 1.44 (3 H, t, J=7.3 Hz). LCMS (M+H) calcd for $C_{14}H_{16}N_3O_6$: 322.10; found: 322.08. Ethyl 11-(((benzyloxy)carbonyl)amino)-3-hydroxy-4-oxo-7,8,10,11-tetrahydro-4H,6H-8,11-methanopyrimido[2,1-d][1,5]oxazocine-2-carboxylate. $^1$H NMR (500 MHz, $CDCl_3$) δ: 10.48 (1 H, brs), 7.29-7.42 (5 H, m), 6.70 (1 H, brs), 5.45 (1 H, dd, J=15.3, 3.4 Hz), 5.14 (2 H, d, $J_{AB}$=12.4 Hz), 4.78 (1 H, t, J=6.7 Hz), 4.57 (2 H, d, $J_{AB}$=10.4 Hz), 4.37 (2 H, q, J=7.2 Hz), 3.72 (1 H, t, J=13.6 Hz), 3.02 (1 H, dd, J=11.7, 8.4 Hz), 2.14-2.23 (1 H, m), 1.87 (1 H, d, J=12.5 Hz), 1.58-1.67 (1 H, m), 1.35 (3 H, t, J=7.2 Hz). LCMS (M+H) calcd for $C_{21}H_{24}N_3O_7$: 430.16; found: 430.12.

Intermediate 129

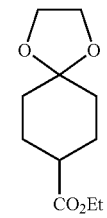

Ethyl 1,4-dioxaspiro[4.5]decane-8-carboxylate. This compound was prepared from ethyl cyclohexanone-4-carboxylate by following the procedure of Pearson et al. (*J. Org. Chem.*, 1997, 62, 5284). A mixture of ethylene glycol (131 mL, 2350 mmol), ethyl 4-oxocyclohexanecarboxylate (100 g, 588 mmol), and p-toluene sulfonic acid monohydrate (2.012 g, 10.58 mmol) in benzene (125 mL) was stirred overnight at room temperature, under $N_2$. The solution was poured into $Et_2O$ (1 L) and the mixture washed with water (3×300 mL), sat. $NaHCO_3$ (100 mL) followed by brine (100 mL). The organic layer was then dried ($MgSO_4$), filtered, and concentrated to yield the title compound (125.5 g, 586 mmol, 100% yield) as a clear oil: LCMS m/z 215.13 (M+H).

Intermediate 130

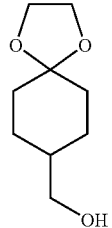

1,4-Dioxaspiro[4.5]decan-8-ylmethanol. The procedure of Pearson at al., *J. Org. Chem.*, 1997, 62, 5284 was followed. To a stirred 1M solution of lithium aluminum hydride (148 mL, 148 mmol) cooled to 0° C., in an ice-bath, was added a solution of ethyl 1,4-dioxaspiro[4.5]decane-8-carboxylate (31.8 g, 148 mmol) in THF (30 mL), dropwise, over a period of 50 min. The ice-bath was removed and the mixture stirred under $N_2$ overnight. It was then cooled and water (20 mL) slowly added under vigorous stirring [note: very vigorous reaction with heat and foam generation] followed by the addition of 15% NaOH (20 mL). The insoluble material was removed by filtration through CELITE®, washing with THF. The combined filtrate and washings were dried ($Na_2SO_4$), filtered and concentrated to provide the title compound, 1,4-dioxaspiro[4.5]decan-8-ylmethanol (26.3 g, 153 mmol, 103% yield) as a clear oil: LCMS: m/z 173 (M+H) at 0.67 min; $^1$H NMR (500 MHz, $CDCl_3$) δ ppm 1.11-1.25 (2H, m), 1.39-1.52 (3H, m), 1.70 (4H, d, J=9.5 Hz), 2.75 (1H, s), 3.39 (2H, d, J=6.4 Hz), 3.86-3.89 (4H, m); $^{13}$C NMR (126 MHz, $CDCl_3$) δ ppm 26.7, 34.2, 39.1, 64.3, 67.5, 109.2.

Intermediate 131

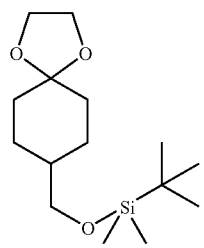

(1,4-Dioxaspiro[4.5]decan-8-ylmethoxy)(tert-butyl)dimethylsilane. To a solution of 1,4-dioxaspiro[4.5]decan-8-ylmethanol (8.60 g, 49.9 mmol) and imidazole (8.50 g, 125 mmol) in DMF (50 mL) was added tert-butyldimethylsilyl chloride (9.03 g, 59.9 mmol), and the mixture stirred at room temp. for 18 hours. The mixture was concentrated in vacuo and the residue redissolved in ethyl acetate (20 mL), washed with water followed by brine, then dried ($Na_2SO_4$), and concentrated in vacuo to provide the title compound (14.5 g, 50.6 mmol, 101% yield) as a clear oil: LCMS: m/z 287 (M+H); $^1$H NMR (500 MHz, $CDCl_3$) δ ppm 0.01 (6H, s), 0.86 (9H, s),1.14-1.26 (2H, m), 1.45-1.54 (3H, m), 1.67-1.82 (4H, m), 3.40 (2H, d, J=6.7 Hz), 3.91 (4H, s); $^{13}$C NMR (126 MHz, $CDCl_3$) δ ppm-5.25, 18.5, 26.1, 26.9, 34.3, 39.2, 64.3, 68.0, 109.3.

Intermediate 132

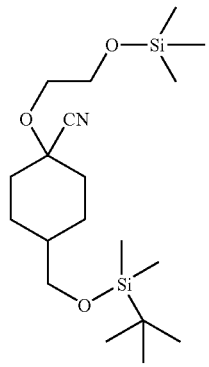

4-((tert-Butyldimethylsilyloxy)methyl)-1-(2-(trimethylsilyloxy)ethoxy)cyclohexanecarbonitrile. Reference: G. Olah et al., Synthesis, 498 (1983). Zinc iodide (0.034 g, 0.107 mmol) was added to a mixture of (1,4-dioxaspiro[4.5]decan-8-ylmethoxy)(tert-butyl)dimethylsilane (14.5 g, 50.6 mmol) and trimethylsilyl cyanide (6.79 mL, 50.6 mmol) at 10° C. under an atmosphere of $N_2$, and the mixture stirred at room temperature overnight. The reaction mixture was treated with additional aliquots of $ZnI_2$ and trimethylsilylcyanide and heated overnight until NMR ($CDCl_3$) and HPLC analysis indicated significant conversion to the title product. The mixture was then diluted with $CH_2Cl_2$ (25 mL) and washed with water followed by brine, then dried and concentrated to yield 15.7 g of a light red oil, which was purified by $SiO_2$ column chromatography (530 g, $SiO_2$, 3-5-10-20-40% ethyl acetate/$CH_2Cl_2$) to obtain the title compound (11.0 g, 28.5 mmol, 56% yield) as an amber oil: $SiO_2$-TLC: $R_f$=0.62 (5% ethyl acetate/$CH_2Cl_2$), molybdate stain; LCMS: m/z 386 (M+H, minor) and 359 (M-CN, major); $^1$H NMR (500 MHz, $CDCl_3$) δ ppm 0.03, 0.03 (6H, 2s), 0.11, 0.11 (9H, 2s), 0.88 (9H, s), 1.21-1.32 (2H, m), 1.46-1.56 (3H, m), 1.87 (2H, dd, J=14.2, 2.3 Hz), 2.26 (2H, d, J=11.9 Hz), 3.43 (2H, d, J=6.4 Hz), 3.69 (2H, t, J=4.9 Hz), 3.75 (2H, t, J=5.0 Hz), $^{13}$C NMR (126 MHz, $CDCl_3$) δ ppm-5.31, −0.23, 18.4, 26.0, 26.1, 35.1, 39.3, 61.9, 66.8, 67.5, 76.5, 119.8.

Intermediate 133

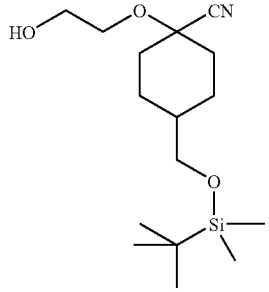

4-((tert-Butyldimethylsilyloxy)methyl)-1-(2-hydroxyethoxy)cyclohexanecarbonitrile. To a solution of 4-((tert-butyldimethylsilyloxy)methyl)-1-(2-(trimethylsilyloxy)ethoxy)cyclohexanecarbonitrile (9.70 g, 25.1 mmol) in methanol (25 mL) was added pyridine hydrochloride (2.91 g, 25.1 mmol) and the mixture stirred at room temperature for 30 min. The reaction was immediately quenched by careful addition of sat'd aqueous $NaHCO_3$ (30 mL), and extracted with ethyl acetate (25 mL×2). The combined organic extracts were washed with brine, dried ($Na_2SO_4$) and concentrated to provide 5.82 g of a cloudy light brown oil, which was purified by column chromatography (SiO$_2$, 300 g, 20% ethyl acetate/ CH$_2$Cl$_2$) to provide the title compound, 4-((tert-butyldimethylsilyloxy)methyl)-1-(2-hydroxyethoxy)cyclohexanecarbonitrile (3.45 g, 11.0 mmol, 44% yield) as an amber oil: TLC: R$_f$ 0.15 (5% ethyl acetate/CH$_2$Cl$_2$), 0.51 (20% ethyl acetate/CH$_2$Cl$_2$); molybdate stain; LC/MS: m/z 314 (M+H), 287 (M−CN), 331 (M+H$_2$O); $^1$H NMR (500 MHz, CDCl$_3$) δ ppm 0.03 (6H, s), 0.88 (9H, s),1.23 (1H, t, J=7.0 Hz), 1.25-1.33 (2H, m), 1.42-1.56 (3H, m), 1.88 (2H, d, J=11.9 Hz), 2.27 (2H, d, J=12.8 Hz), 3.43 (2H, d, J=6.4 Hz), 3.71-3.81 (4H, m); $^{13}$C NMR (126 MHz, CDCl$_3$) δ ppm-5.32, 18.4, 26.0, 26.1, 35.2, 39.3, 61.8, 66.6, 67.4, 76.6, 119.6.

Intermediate 134

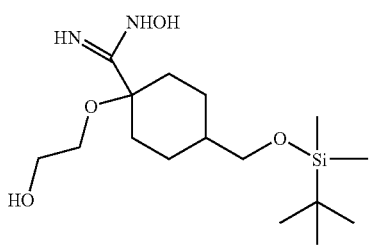

4-((tert-Butyldimethylsilyloxy)methyl)-N-hydroxy-1-(2-hydroxyethoxy)cyclohexane carboximidamide. A mixture of 4-((tert-butyldimethylsilyloxy)methyl)-1-(2-hydroxyethoxy)cyclohexane carbonitrile (3.44 g, 10.97 mmol) and 50% aq. hydroxylamine (0.725 g, 10.97 mmol) in ethanol (17 mL) was heated at 80° C. (oil bath temp) for 6 h. The mixture was concentrated to dryness in vacuo and the residual solid triturated with ethanol to obtain the title compound, 4-((tert-butyldimethylsilyloxy)methyl)-N-hydroxy-1-(2-hydroxyethoxy)cyclohexanecarboximidamide (3.30 g, 9.52 mmol, 87% yield) as a tan crystalline powder: HPLC: retention time=1.96 min (area percent=91%); LCMS: m/z 347 (M+H), 369 (M+Na); $^1$H NMR (500 MHz, CDCl$_3$) δ ppm 0.02 (6H, s), 0.87 (9H, s),1.23 (1H, t, J=7.0 Hz), 1.25-1.34 (2H, m), 1.49-1.58 (2H, m), 1.57-1.63 (1H, m), 1.67-1.77 (2H, m), 2.05-2.16 (2H, m), 3.41-3.46 (4H, m), 3.69-3.72 (2H, m), 4.78 (2H, s), 7.95 (1H, brs); $^{13}$C NMR (126 MHz, CDCl$_3$) δ ppm-5.22, 18.5, 25.0, 26.1, 32.0, 38.6, 62.1, 64.1, 66.9, 77.9, 154.7.

Intermediate 135

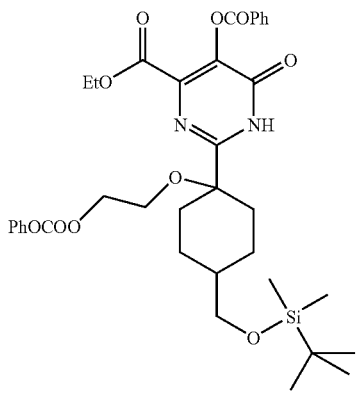

Ethyl 5-(benzoyloxy)-2-(1-(2-(benzoylperoxy)ethoxy)-4-((tert-butyldimethylsilyloxy)methyl)cyclohexyl)-6-oxo-1,6-dihydropyrimidine-4-carboxylate. To a cold solution of 4-((tert-butyldimethylsilyloxy)methyl)-N-hydroxy-1-(2-hydroxyethoxy)cyclohexanecarboximidamide (3.80 g, 10.97 mmol) in ethanol (40 mL) was added diethyl but-2-ynedioate (2.05 g, 12.05 mmol) and the mixture stirred at room temp. under N$_2$ for 6 h and then kept in a freezer overnight. The mixture was concentrated to dryness in vacuo to provide diethyl 2-(4-((tert-butyldimethylsilyloxy)methyl)-1-(2-hydroxyethoxy)cyclohexanecarboxy imidamidooxy)fumarate (6.03 g, 11.67 mmol, 106% yield) as a crude oil: HPLC: retention time=3.81 min (area percent=78%); LCMS: m/z 517 (M+). A solution of this crude oil (6.00 g, 11.61 mmol) in xylene (220 mL) was heated at 150° C. under N$_2$ for 4.5 h. The mixture was concentrated in vacuo to obtain 7.0 g of the crude pyrimidinone as a light brown oil. The crude oil (7.0 g) was dissolved in pyridine (50 mL) and added benzoic anhydride (5.52 g, 11 mmol) added after which the mixture stirred at room temp. overnight. Most of pyridine was removed in vacuo, and the residual oil dissolved in ethyl acetate (30 mL) and washed sequentially with 1N HCl, sat'd aq. NaHCO$_3$ followed by brine, then dried (Na$_2$SO$_4$) and concentrated to dryness to provide 8.4 g of a crude 1 oil, which was purified by column chromatography (SiO$_2$, 215 g, 5-10% ethyl acetate/CH$_2$Cl$_2$) to yield the title compound, ethyl 5-(benzoyloxy)-2-(1-(2-(benzoyloxy)ethoxy)-4-((tert-butyldimethylsilyloxy)methyl)cyclohexyl)-6-oxo-1,6-dihydropyrimidine-4-carboxylate (3.7 g, 5.45 mmol, 47% yield) as an amber oil: HPLC: retention time=4.48 min(area percent=95%); TLC: RF 0.55 (10% ethyl acetate/CH$_2$Cl$_2$); LCMS: m/z 679 (M+H); $^1$H NMR (500 MHz, CDCl$_3$) δ ppm 0.03 (6H, s), 0.87 (9H, s), 1.13 (3H, t, J=7.2 Hz), 1.50 (2H, m), 1.60-1.70 (1H, m), 1.71-1.84 (4H, m), 2.24 (2H, m), 3.49 (2H, d, J=7.0 Hz), 3.66 (2H, t, J=4.5 Hz), 4.26 (2H, q, J=7.3 Hz), 4.46 (2H, q, J=4.5 Hz), 7.41 (2H, t, J=7.8 Hz), 7.48 (2H, t, J=7.8 Hz), 7.50-7.55 (1H, m), 7.62 (1H, t, J=7.5 Hz), 8.03 (2H, d, J=7.3 Hz), 8.17 (2H, d, J=7.0 Hz), 11.20 (1H, br). $^{13}$C NMR (126 MHz, CDCl$_3$) δ ppm-5.22, 14.0, 18.4, 24.3, 26.1, 31.9, 37.5, 61.6, 62.2, 64.0, 66.4, 78.9, 128.4, 128.6, 128.7, 129.8, 129.9, 130.7, 133.2, 134.1, 138.4, 142.8, 158.8, 160.0, 162.9, 163.5, 166.7.

Intermediate 136

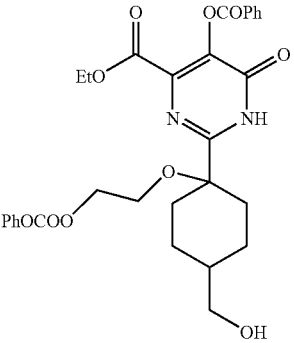

Ethyl 5-(benzoyloxy)-2-(1-(2-(benzoylperoxy)ethoxy)-4-(hydroxymethyl)cyclohexyl)-6-oxo-1,6-dihydropyrimidine-4-carboxylate. Journal of Organic Chemistry 45:4797 (1980). To a solution of ethyl 5-(benzoyloxy)-2-(1-(2-(benzoylperoxy)ethoxy)-4-((tert-butyldimethylsilyloxy)methyl)cyclohexyl)-6-oxo-1,6-dihydropyrimidine-4-carboxylate (4.28 g, 6.30 mmol) in EtOH (30 mL) was added a dilute HCl solution in EtOH (5 mL; prepared from 6N-HCl 0.3 mL and 95% EtOH 9.7 mL), and the mixture stirred at room temp for 2 h. The mixture was concentrated in vacuo and the residue taken up in ethyl acetate (20 mL), washed with water, sat'd NaHCO₃ followed by brine, then dried (Na₂SO₄) and concentrated. The residue was dissolved in CH₂Cl₂ and diluted with hexanes and concentrated to dryness to obtain 3.26 g of a tan foam which was triturated with hexanes to provide the title compound, ethyl 5-(benzoyloxy)-2-(1-(2-(benzoyloxy) ethoxy)-4-(hydroxymethyl)cyclohexyl)-6-oxo-1,6-dihydropyrimidine-4-carboxylate (3.21 g, 5.69 mmol, 90% yield) as a tan colored foam: HPLC: retention time=2.66 min (area percent=86%): TLC: RF 0.5 (50% ethyl acetate/CH₂Cl₂); LCMS: m/z 565 (M+H); ¹H NMR (500 MHz, CDCl₃) δ ppm 1.12 (3H, t, J=7.2 Hz), 1.58-1.68 (2H, m), 1.69-1.74 (1H, m), 1.74-1.86 (4H, m), 2.14-2.24 (2H, m), 3.58 (2H, d, J=6.4 Hz), 4.26 (2H, q, J=7.1 Hz), 4.48 (2H, t, J=5 Hz), 7.45 (2H, t, J=7.8 Hz), 7.50 (2H, t, J=7.6 Hz), 7.55 (1H, t, J=7.3 Hz), 7.64 (1H, t, J=7.5 Hz), 8.08 (2H, d, J=7.6 Hz), 8.18 (2H, d, J=7.9 Hz), 10.29 (1H, br); ¹³C NMR (126 MHz, CDCl₃) δ ppm 14.0, 24.0, 31.7, 37.2, 61.7, 62.3, 64.0, 65.9, 78.6, 128.3, 128.7, 128.7, 129.6, 129.9, 130.7, 133.4, 134.2, 138.6, 142.6, 157.8, 159.9, 162.9, 163.5, 166.8.

Intermediate 137

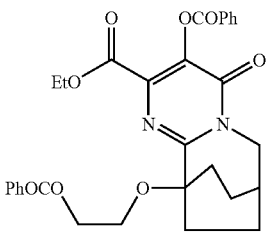

5-Benzoyloxy-1-(2-benzoyloxy-ethoxy)-6-oxo-3,7-diazatricyclo[7.2.2.0²,⁷]trideca-2,4-diene-4-carboxylic acid ethyl ester. Under N₂, to a cold (ice-bath), stirred solution of ethyl 5-(benzoyloxy)-2-(1-(2-(benzoylperoxy)ethoxy)-4-(hydroxymethyl)cyclohexyl)-6-oxo-1,6-dihydropyrimidine-4-carboxylate (1.13 g, 2.001 mmol) in THF (10 mL) was added, triethylamine (0.279 mL, 2.00 mmol), followed by methane sulfonylchloride (0.156 mL, 2.001 mmol), and the mixture stirred at room temperature overnight. Additional triethylamine (50 mg, 0.5 mmol) and methane sulfonylchloride (40 uL, 0.5 mmol) were added and the mixture stirred at room temperature 2 h. The mixture was diluted with ethyl acetate (15 mL) and washed with water followed by brine, then dried (Na₂SO₄) and concentrated to provide ethyl 5-(benzoyloxy)-2-(1-(2-(benzoyloxy)ethoxy)-4-((methylsulfonyloxy)methyl)cyclohexyl)-6-oxo-1,6-dihydropyrimidine-4-carboxylate (1.27 g, 1.976 mmol, 99%) as a tan foam: HPLC: retention time=3.00 min (area percent=71%); LCMS: m/z 643 (M+H). To a solution of this compound (1.27 g, 1.98 mmol) in DMF (10 mL) was added cesium carbonate (0.644 g, 1.98 mmol) and the mixture stirred for 6 h at 60° C. in an oil bath under N₂. The mixture was concentrated and the residue taken up in ethyl acetate (20 mL), washed with 1M-aq. K₂CO₃, water, followed by brine, then dried (Na₂SO₄), filtered and concentrated to provide 930 mg of a light brown crystalline powder. This was purified by silica gel column chromatography (60 g SiO₂, 5-10% ethyl acetate/CH₂Cl₂) to provide the title compound (382 mg, 0.699 mmol, 35% yield) as an off-white crystalline solid: HPLC: retention time=3.24 min (area percent=94%); TLC: RF 0.6 (10% ethyl acetate/ CH₂Cl₂): LCMS: m/z 547 (M+H); ¹H NMR (500 MHz, CDCl₃) δ ppm 1.19 (3H, t, J=7.0 Hz), 1.66-1.79 (2H, m), 1.89-2.01 (2H, m), 2.07-2.16 (2H, m), 2.17-2.27 (2H, m), 2.46 (1H, brs), 4.00 (2H, t, J=5.2 Hz), 4.09 (2H, d, J=3.7 Hz), 4.27 (2H, q, J=7.0 Hz), 4.62 (2H, t, J=5.3 Hz), 7.43 (2H, t, J=7.8 Hz), 7.49 (2H, t, J=7.8 Hz), 7.55 (1H, t, J=7.5 Hz), 7.63 (1H, t, J=7.5 Hz), 8.06 (2H, dd, J=8.4, 1.1 Hz), 8.19 (2H, dd, J=8.4, 1.1 Hz); ¹³C NMR (126 MHz, CDCl₃) δ ppm 14.0, 23.3, 27.7, 30.9, 54.2, 62.1, 62.2, 64.8, 78.0, 128.4, 128.6, 128.7, 129.8, 130.5, 130.7, 133.0, 134.0, 136.6, 140.7, 159.9, 161.2, 162.9, 163.8, 166.7.

Intermediate 138

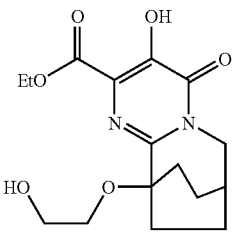

5-Hydroxy-1-(2-hydroxy-ethoxy)-6-oxo-3,7-diazatricyclo[7.2.2.0²,⁷]trideca-2,4-diene-4-carboxylic acid ethyl ester. At room temperature, to a cold (ice-cooling) and stirred solution of 5-benzoyloxy-1-(2-benzoyloxy-ethoxy)-6-oxo-3,7-diazatricyclo[7.2.2.0²,⁷]trideca-2,4-diene-4-carboxylic acid ethyl ester (330 mg, 0.604 mmol) in THF (6 mL) and EtOH (3.00 mL) was added 21% sodium ethanolate in EtOH (0.676 mL, 1.81 mmol) diluted with EtOH (3 mL) and the mixture stirred under N₂ for 1 h. The mixture was diluted with ethyl acetate (10 mL) and extracted with water (10 mL×2). The aqueous extracts were acidified with 1N-HCl (3 mL) and extracted with ethyl acetate (10 mL×5). The ethyl acetate extracts were washed with brine, dried (Na₂SO₄) and concentrated to provide the title compound (130 mg, 0.38 mmol; 64% yield) as an oil: HPLC: retention time=1.33 min (area percent=95%); LCMS: m/z 339 (M+H); ¹H NMR (500 MHz, CDCl₃) δ ppm 1.43 (3H, t, J=7.2 Hz), 1.65 (2H, dt, J=12.3, 6.2 Hz), 1.85-1.97 (2H, m), 1.99-2.17 (4H, m), 2.46 (1H, brs), 3.60 (2H, t, J=4 Hz), 3.75 (2H, d, J=4.1 Hz), 4.06-4.15 (2H, m), 4.45 (2H, q, J=7.0 Hz), 10.48 (1H, brs); ¹³C NMR (126 MHz, CDCl₃) δ ppm 14.0, 23.2, 27.6, 30.5, 53.9, 62.0, 63.2, 65.3, 76.7, 124.1, 148.2, 154.3, 159.7, 169.1.

Intermediate 139

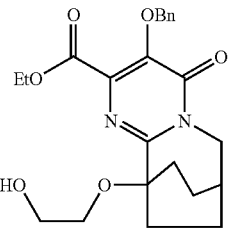

5-Benzyloxy-1-(2-hydroxy-ethoxy)-6-oxo-3,7-diazatricyclo[7.2.2.0²,⁷]trideca-2,4-diene-4-carboxylic acid ethyl ester. To a solution of 5-hydroxy-1-(2-hydroxyethoxy)-6- oxo-3,7-diazatricyclo[7.2.2.0$^{2,7}$]trideca-2,4-diene-4-carboxylic acid ethyl ester (203 mg, 0.600 mmol) in DMF (1 mL) was added K$_2$CO$_3$ (249 mg, 1.80 mmol) and (bromomethyl)benzene (103 mg, 0.600 mmol) and the mixture stirred at room temperature overnight under N$_2$. Additional (bromomethyl)benzene (206 mg, 1.2 mmol, 2 eq.) and K$_2$CO$_3$ (166 mg, 1.2 mmol, 2 eq.) were added and the mixture stirred overnight. The mixture was concentrated in vacuo to remove most of DMF, and the residue was diluted with ethyl acetate (15 mL), washed with water followed by brine, then dried (Na$_2$SO$_4$) and concentrated to provide an amber oil which was purified by silica gel column chromatography (18 g SiO$_2$, 45% ethyl acetate/CH$_2$Cl$_2$) to gave the title compound (141 mg, 0.329 mmol, 55% yield) as an amber oil; HPLC: retention time=2.18 min (area percent=92%); LCMS: m/z 429 (M+H); $^1$H NMR (500 MHz, CDCl$_3$) δ ppm 1.28 (3H, t, J=7.2 Hz), 1.63 (2H, ddd, J=14.3, 7.5, 7.2 Hz), 1.83-1.94 (2H, m), 2.06 (4H, t, J=7.6 Hz), 2.42 (1H, brs), 3.59 (2H, t, J=4 Hz), 3.70 (2H, d, J=4 Hz), 4.05 (2H, d, J=4.0 Hz), 4.31 (2H, q, J=7.2 Hz), 5.22 (2H, s), 7.27 (1H, t, J=7.4 Hz), 7.32 (2H, t, J=7.2 Hz), 7.46 (2H, d, J=6.7 Hz); $^{13}$C NMR (126 MHz, CDCl$_3$) δ ppm 14.1, 23.2, 27.6, 30.5, 53.6, 62.1, 62.2, 65.3, 74.5, 76.7, 128.3, 128.5, 128.6, 136.8, 140.0, 142.4, 159.2, 161.3, 163.9.

Intermediate 140

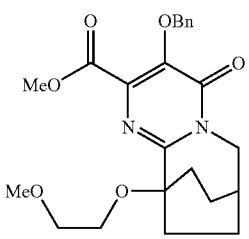

5-Benzyloxy-1-(2-methoxy-ethoxy)-6-oxo-3,7-diazatricyclo[7.2.2.0$^{2,7}$]trideca-2,4-diene-4-carboxylic acid methyl ester. To a solution of 5-benzyloxy-1-(2-hydroxy-ethoxy)-6-oxo-3,7-diazatricyclo[7.2.2.0$^{2,7}$]trideca-2,4-diene-4-carboxylic acid ethyl ester (105 mg, 0.245 mmol) in DMF (1 mL) was added 60% NaH (15 mg, 0.37 mmol) and the mixture stirred at room temp. for 15 min. under N$_2$. After H$_2$ gas evolution had ceased, MeI (0.031 mL, 0.490 mmol) was added and the mixture stirred at room temperature overnight. The mixture was concentrated and the residue was taken up in ethyl acetate (10 mL), washed with water followed by brine, then dried (Na$_2$SO$_4$) and concentrated to provide 85 mg of a crude oil which was purified by C-18 reverse phase column chromatography (YMC AQ, 18-22-26-30-34% CH$_3$CN/H$_2$O with 01% trifluoroacetic acid) to provide 8 mg (0.019 mmol, 8% yield) of the title compound as an amber film: HPLC: retention time=2.30 min (area percent=91%); LC/MS: m/z 429 (M+H); $^1$H NMR (500 MHz, CDCl$_3$) δ ppm 1.66-1.70 (2H, m), 1.87-2.02 (2H, m), 2.12 (4H, t, J=7.5 Hz), 2.46 (1H, brs), 3.39 (3H, s), 3.62 (2H, t, J=4.7 Hz), 3.73 (2H, d, J=4.7 Hz), 3.84 (3H, s), 4.07 (2H, d, J=3.7 Hz), 5.26 (2H, s), 7.31 (1H, t, J=7.0 Hz), 7.36 (2H, t, J=7.3 Hz), 7.48 (2H, d, J=7.6 Hz).

Intermediate 141

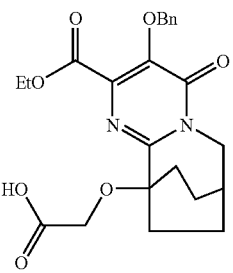

5-Benzyloxy-1-carboxymethoxy-6-oxo-3,7-diazatricyclo[7.2.2.0$^{2,7}$]trideca-2,4-diene-4-carboxylic acid ethyl ester. To a solution of 5-benzyloxy-1-(2-methoxy-ethoxy)-6-oxo-3,7-diazatricyclo[7.2.2.0$^{2,7}$]trideca-2,4-diene-4-carboxylic acid methyl ester (180 mg, 0.42 mmol) in DMF (3 mL) was added pyridinium dichromate (237 mg, 0.630 mmol) and the mixture vigorously stirred for 14 days at room temperature under N$_2$. The solvent was removed in vacuo and the residue was stirred in a mixture of ethyl acetate (10 mL) and water for 30 min. The insoluble materials were filtered off (CELITE®), and the organic filtrate was extracted with sat'd aq. NaHCO$_3$. The aqueous solution was acidified with 1N HCl, and extracted with ethyl acetate (10 mL). The ethyl acetate extract was washed with brine, dried (Na$_2$SO$_4$), and concentrated to provide the title compound (27 mg, 0.061 mmol, 15% yield) as a light yellow film. HPLC: retention time=2.38 min (area percent=80%); LCMS: m/z 443 (M+H); $^1$H NMR (400 MHz, CDCl$_3$) δ ppm 1.34 (3H, t, J=7.0 Hz), 1.71 (2H, m), 1.97 (2H, m), 2.05-2.21 (4H, m), 2.51 (1H, brs), 4.05 (2H, s), 4.12 (2H, d, J=2.7 Hz), 4.35 (2H, q, J=7.0 Hz), 5.28 (2H, s), 7.31-7.39 (3H, m), 7.48 (2H, d, J=7.0 Hz); $^{13}$C NMR (101 MHz, CDCl$_3$) δ ppm 13.5, 22.6, 27.0, 30.1, 53.3, 62.1, 63.3, 74.2, 78.5, 128.0, 128.2, 128.7, 135.9, 139.4, 141.7, 158.9, 160.3, 162.5, 170.4.

Intermediate 142

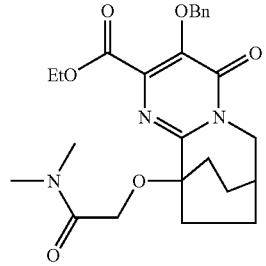

5-Benzyloxy-1-dimethylcarbamoylmethoxy-6-oxo-3,7-diazatricyclo[7.2.2.0$^{2,7}$]trideca-2,4-diene-4-carboxylic acid ethyl ester. To a solution of 5-benzyloxy-1-carboxymethoxy-6-oxo-3,7-diazatricyclo[7.2.2.02,7]trideca-2,4-diene-4-carboxylic acid ethyl ester (25 mg, 0.057 mmol) in DMF (1 mL) was added O-(7-azabenzotriazol-1-yl)-N,N,N',N'-tetramethyluronium hexafluorophosphate (HATU) (43 mg, 0.11 mmol) and 4-(dimethylamino)pyridine (DMAP) (14 mg, 0.11 mmol) and the mixture stirred at room temperature for 15 min under N$_2$. To this was added a 2M THF solution of dimethylamine (0.057 mL, 0.11 mmol) and the mixture stirred at room temperature for 90 min. The mixture was concentrated and the residue taken up in ethyl acetate (10 mL), washed with 1N HCl followed by brine, then dried (Na$_2$SO$_4$) and concentrated to provide the title compound (36 mg, 0.057 mmol, 100% yield) as a crude amber film: HPLC: retention time=2.15 min; LCMS: m/z 470 (M+H); $^1$H NMR (400 MHz, CDCl$_3$) δ ppm 1.23 (3H, t, J=6.6 Hz), 1.65-1.76 (2H, m), 1.88-2.01 (2H, m), 2.11-2.26 (4H, m), 2.46 (1H, brs), 2.90 (3H, s), 2.95 (3H, s), 4.10 (2H, t, J=7.0 Hz), 4.23-4.33 (4H, m), 5.24 (2H, s), 7.27-7.38 (3H, m), 7.46 (2H, d, J=7.0 Hz).

Intermediate 143

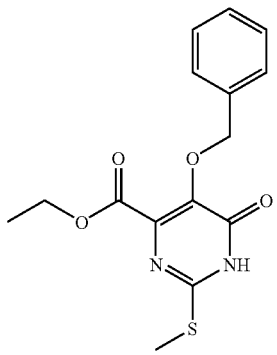

2-Methylsulfanyl-1,6-dihydro-6-oxo-5-(phenylmethoxy)-4-pyrimidinecarboxylic acid, ethyl ester. A solution of diethyl oxalate (21.06 g, 0.144 mol) and ethyl benzyloxyacetate (28.0 g, 0.144 mol) in dry THF (200 ml) was treated at 22° C. with sodium hydride (6.34 g of a 60% dispersion in mineral oil, 0.158 mol). Ethanol (0.05 mL) was added and the resulting mixture was stirred at 22° C. for 18 hours. The THF was removed under reduced pressure and the residue was dissolved in a solution of sodium ethoxide (0.072 mol, prepared from 1.65 g of sodium) in ethanol (200 ml). Then powdered 2-methyl-2-thiopseudourea sulfate (20.1 g, 0.072 mol) was added and the resulting mixture was heated at 60° C. for 6 hours. Acetic acid (5 ml) was added and the ethanol was removed under reduced pressure. The residual paste was partitioned between water and dichloromethane and the aqueous phase was extracted twice with dichloromethane. The combined organic phases were washed with saturated sodium bicarbonate followed by brine, dried over anhydrous magnesium sulfate, filtered, and concentrated under reduced pressure. Chromatography on silica gel (elution with a gradient of ethyl acetate 0-20% in toluene) followed by crystallization from ethyl acetate-hexane gave 8.34 g (18% yield) of the title compound; mp 109-110° C. $^1$H NMR 400 MHz (CDCl$_3$) δ: 1.35 (3H, t, J=7.1 Hz, CH$_3$), 2.62 (3H, s, SCH$_3$), 4.37 (2H, q, J=7.1 Hz, CH$_2$), 5.28 (2H, s, OCH$_2$), 7.35-7.52 (5H, m, aromatics), 12.2 (1H, broad s, NH). Anal. Calcd for C$_{15}$H$_{16}$N$_2$O$_4$S: C, 56.23; H, 5.03; N, 8.74. Found: C, 56.23; H, 4.86; N, 8.76.

Intermediate 144

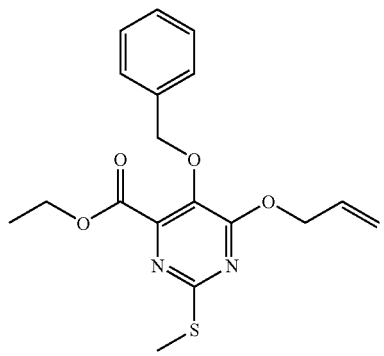

Ethyl 6-(allyloxy)-5-(benzyloxy)-2-(methylthio)pyrimidine-4-carboxylate. To a solution of 2-methylsulfanyl-1,6-dihydro-6-oxo-5-(phenylmethoxy)-4-pyrimidinecarboxylic acid, ethyl ester (4.28 g, 13.36 mmol) in DMF (70 mL) was added Cs$_2$CO$_3$ (4.35 g, 13.36 mmol) followed by 3-bromoprop-1-ene (1.156 mL, 13.36 mmol). The resulting mixture was stirred at 80° C. for 1 h, cooled to room temperature and partitioned between ethyl acetate and hexane. The organic phase was washed with water followed by brine, dried (Na$_2$SO$_4$) and filtered. Concentration gave an oil that was purified by flash column chromatography (Biotage flash chromatography system, 0%-40% ethyl acetate/hexane, 16 CV) to give the title compound as a yellow oil (1.8144 g, 38% yield). $^1$H NMR (300 MHz, CDCl$_3$) δ: 7.41-7.37 (2H, m), 7.36-7.28 (3H, m), 6.10-5.97 (1H, m), 5.40 (2H, dq, J=17.2, 1.5 Hz), 5.29 (2H, dq, J=10.5, 1.2 Hz), 5.03 (2H, s), 4.93 (2H, dt, J=5.6, 1.4 Hz), 4.32 (2H, q, J=7.1 Hz), 4.32 (2H, q, J=7.1 Hz), 2.50 (2H, q, J=7.1 Hz), 1.28 (3H, t, J=7.1 Hz). LCMS (M+H) calcd for C$_{18}$H$_{21}$N$_2$O$_4$S: 361.12; found: 361.21.

Intermediate 145

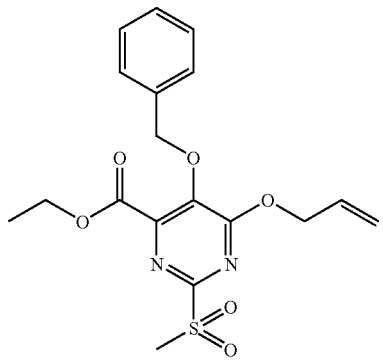

Ethyl 6-(allyloxy)-5-(benzyloxy)-2-(methylsulfonyl)pyrimidine-4-carboxylate. To a solution of ethyl 6-(allyloxy)-5-(benzyloxy)-2-(methylthio)pyrimidine-4-carboxylate (1.813 g, 5.03 mmol) in CH$_2$Cl$_2$ (100 mL) was added 3-chloroperbenzoic acid (MCPBA) (2.59 g, 11.57 mmol). The resulting mixture was stirred at room temperature for 3 h. The mixture was washed with aqueous sodium bisulfite followed by saturated, aqueous sodium bicarbonate. The organic phase was dried (Na$_2$SO$_4$), filtered and concentrated affording the title compound as a colorless oil. (1.9127 g, 97% yield). $^1$H NMR (300 MHz, CDCl$_3$) δ: 7.40-7.31 (5H, m), 6.13-6.00 (1H, m), 5.51-5.54 (1H, m), 5.39-5.34 (1H, m), 5.20 (2H, s), 5.08-5.05 (2H, m), 4.34 (2H, q, J=7.2 Hz), 3.30 (3H, s), 1.30 (3H, t, J=7.1 Hz). LCMS (M+H) calcd for C$_{18}$H$_{21}$N$_2$O$_6$S: 393.11; found: 393.19.

Intermediate 146

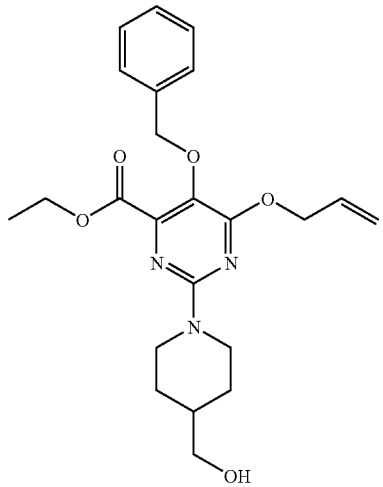

Ethyl 6-(allyloxy)-5-(benzyloxy)-2-(4-(hydroxymethyl) piperidin-1-yl)pyrimidine-4-carboxylate. A solution of ethyl 6-(allyloxy)-5-(benzyloxy)-2-(methylsulfonyl)pyrimidine-4-carboxylate (1.911 g, 4.87 mmol) in THF (40 mL) was stirred with molecular sieves for 30 min. To this mixture was added piperidin-4-ylmethanol (1.683 g, 14.61 mmol) and the resulting mixture was stirred overnight at 70° C. The mixture was cooled to room temperature and diluted with ethyl acetate and washed with water followed by brine then dried ($Na_2SO_4$). Filtration followed by concentration gave a yellow oil that was purified by flash column chromatography (Biotage flash chromatography system; 0%-100%, 10 CV) to afford the title compound as a yellow oil (1.2043 g, 58% yield). $^1$H NMR (300 MHz, $CDCl_3$) δ: 7.42-7.39 (2H, m), 7.35-7.27 (3H, m), 6.10-5.97 (1H, m), 5.42-5.34 (1H, m), 5.28-5.22 (1H, m), 4.91 (2H, s), 4.87-4.84 (2H, m), 4.72-4.63 (2H, m), 4.30 (2H, q, J=7.1 Hz), 3.50 (2H, t, J=5.8 Hz), 2.80 (2H, td, J=12.8, 1.8 Hz), 1.79-1.64 (3H, m), 1.28 (3H, t, J=7.1 Hz), 1.23-1.10 (2H, m).

Intermediate 147

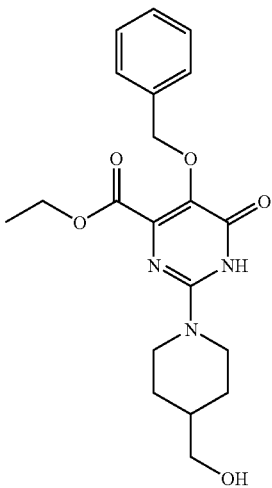

Ethyl 5-(benzyloxy)-2-(4-(hydroxymethyl)piperidin-1-yl)-6-oxo-1,6-dihydropyrimidine-4-carboxylate. A solution of ethyl 6-(allyloxy)-5-(benzyloxy)-2-(4-(hydroxymethyl) piperidin-1-yl)pyrimidine-4-carboxylate (1.206 g, 2.82 mmol) in n-propanol (10 mL) was sparged with $N_2$. Rhodium (III) chloride (0.030 g, 0.141 mmol) was added and the resulting mixture was stirred overnight at 100° C. The mixture was cooled to room temperature and partitioned between water and $CH_2Cl_2$. The organic phase was dried ($Na_2SO_4$), filtered and concentrated to give a yellow solid that was triturated with $Et_2O$. The product was collected by filtration to give the title compound as a white solid (0.8252 g, 76% yield). $^1$H NMR (300 MHz, $CDCl_3$) δ: 7.43 (2H, d, J=7.3 Hz), 7.37-7.29 (3H, m), 5.05 (2H, s), 4.46 (2H, d, J=13.1 Hz), 4.31 (2H, q, J=7.1 Hz), 3.44 (2H, d, J=5.8 Hz), 2.94-2.88 (2H, m), 1.74 (2H, d, J=13.1 Hz), 1.73-1.66 (1H, m), 1.29 (3H, t, J=7.2 Hz), 1.28-1.22 (2H, m). LCMS (M+H) calcd for $C_{20}H_{26}N_3O_5$: 388.18; found: 388.23.

Intermediate 148

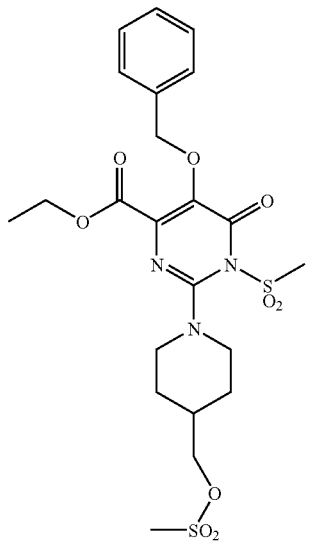

Ethyl 5-(benzyloxy)-1-(methylsulfonyl)-2-(4-((methylsulfonyloxy)methyl)piperidin-1-yl)-6-oxo-1,6-dihydropyrimidine-4-carboxylate. To a solution of ethyl 5-(benzyloxy)-2-(4-(hydroxymethyl)piperidin-1-yl)-6-oxo-1,6-dihydropyrimidine-4-carboxylate (0.814 g, 2.1 mmol) in THF (20 mL) was added methanesulfonyl chloride (0.327 mL, 4.20 mmol) followed by $Et_3N$ (0.732 mL, 5.25 mmol). The resulting mixture was stirred at room temperature for 2.5 h (white solids precipitated out over the reaction time). The mixture was diluted with ethyl acetate (50 mL) and washed with water followed by brine. The organic phase was dried ($Na_2SO_4$), filtered and concentrated to give the title compound as an amber oil (1.1320 g, 99% yield). $^1$H NMR (500 MHz, $CDCl_3$) δ: 7.44 (2H, d, J=7.32 Hz), 7.39-7.32 (3H, m), 4.98 (2H, s), 4.67-4.64 (2H, m), 4.35 (2H, q, J=7.1 Hz), 4.09 (2H, d, J=6.4 Hz), 3.46 (3H, s), 3.02 (3H, s), 2.91 (2H, td, J=12.9, 2.4 Hz), 2.08-2.00 (1H, m), 1.86-1.84 (2H, m), 1.35-1.28 (5H, m). LCMS (M+H) calcd for $C_{22}H_{30}N_3O_9S_2$: 544.14; found: 544.30.

Intermediate 149

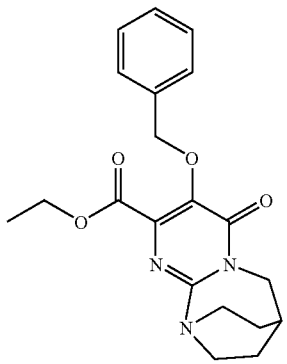

Ethyl 3-(benzyloxy)-4-oxo-6,7,8,9-tetrahydro-4H-7,10-ethanopyrimido[1,2-a][1,3]diazepine-2-carboxylate. A mixture of ethyl 5-(benzyloxy)-1-(methylsulfonyl)-2-(4-((methylsulfonyloxy)methyl)piperidin-1-yl)-6-oxo-1,6-dihydropyrimidine-4-carboxylate and $K_2CO_3$ (0.051 g, 0.368 mmol) in ethanol (10 mL) was stirred at 60° C. for 4 h and cooled to room temperature. Water was added and the product was extracted with ethyl acetate. The organic phase was washed with brine then dried (Na$_2$SO$_4$), filtered and concentrated. The residue was purified by flash column chromatography (Biotage flash chromatography system; 0%-10% methanol/CH$_2$Cl$_2$, 25 CV; 10% methanol/CH$_2$Cl$_2$, 5 CV) to give the title compound as a white glass (0.0248 g, 37% yield). $^1$H NMR (500 MHz, CDCl$_3$) δ: 7.44 (2H, dd, J=7.3 Hz), 7.30-7.22 (3H, m), 5.27 (2H, s), 4.22 (2H, q, J=7.1 Hz), 4.01-3.94 (2H, m), 3.77-3.70 (2H, m), 3.67 (2H, brs), 3.02 (1H, brs), 2.29-2.24 (2H, m), 1.93-1.88 (2H, m), 1.22 (3H, t, J=7.0 Hz). LCMS (M+H) calcd for C$_{20}$H$_{24}$N$_3$O$_4$: 370.17; found: 370.30.

Intermediate 150

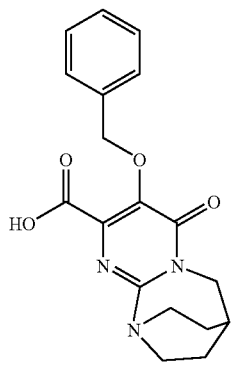

3-(Benzyloxy)-4-oxo-6,7,8,9-tetrahydro-4H-7,10-ethanopyrimido[1,2-a][1,3]diazepine-2-carboxylic acid. A mixture of ethyl 3-(benzyloxy)-4-oxo-6,7,8,9-tetrahydro-4H-7,10-ethanopyrimido[1,2-a][1,3]diazepine-2-carboxylate (0.5491 g, 1.486 mmol) and LiOH.H$_2$O (0.071 g, 2.97 mmol) in ethanol (12 mL) and water (3.00 mL) was stirred at room temperature for 6 h. The mixture was acidified with concentrated HCl and the product was extracted with ethyl acetate. The organic phase was washed with brine, then dried (Na$_2$SO$_4$), filtered and concentrated to give the title compound as a white solid (0.4521 g, 89% yield). $^1$H NMR (500 MHz, CD$_3$OD) δ: 7.53-7.49 (2H, m), 7.42-7.36 (3H, m), 5.27 (2H, d, J=15.3 Hz), 4.11-4.00 (4H, m), 3.96 (2H, d, J=14.0 Hz), 3.17-3.13 (1H, m), 2.45-2.39 (2H, m), 2.10-2.03 (2H, m). LCMS (M+H) calcd for C$_{18}$H$_{20}$N$_3$O$_4$: 342.14; found: 342.20.

Intermediate 151

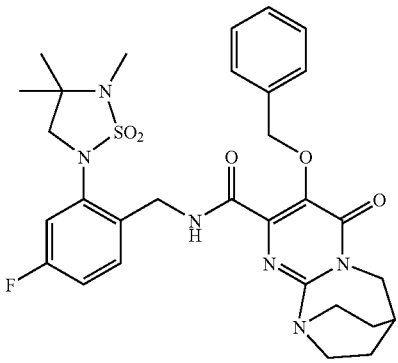

3-(Benzyloxy)-N-(4-fluoro-2-(4,4,5-trimethyl-1,1-dioxido-1,2,5-thiadiazolidin-2-yl)benzyl)-4-oxo-6,7,8,9-tetrahydro-4H-7,10-ethanopyrimido[1,2-a][1,3]diazepine-2-carboxamide. A mixture of 3-(benzyloxy)-4-oxo-6,7,8,9-tetrahydro-4H-7,10-ethanopyrimido[1,2-a][1,3]diazepine-2-carboxylic acid (0.03 g, 0.088 mmol), 1-(4-fluoro-2-(4,4,5-trimethyl-1,1-dioxido-1,2,5-thiadiazolidin-2-yl)phenyl)methanamine hydrochloride salt (0.043 g, 0.132 mmol), O-(7-azabenzotriazol-1-yl)-N,N,N',N'-tetramethyluronium hexafluorophosphate (HATU) (0.100 g, 0.264 mmol), 4-(dimethylamino)pyridine (DMAP) (1.074 mg, 8.79 µmol) and diisopropyl ethylamine (0.077 mL, 0.439 mmol) in DMF (2 mL) was stirred at room temperature for 1 h. The mixture was diluted with ethyl acetate and washed with 0.5 N HCl, water followed by brine. The organic phase was dried (Na$_2$SO$_4$), filtered and concentrated to give the title compound as a crude yellow oil. LCMS (M+H) calcd for C$_{30}$H$_{36}$FN$_6$O$_5$S: 611.24; found: 611.33.

Intermediate 152

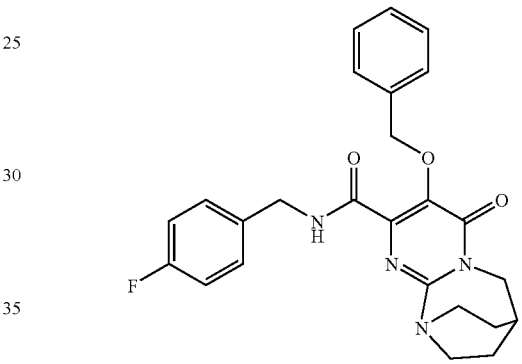

3-(Benzyloxy)-N-(4-fluorobenzyl)-4-oxo-6,7,8,9-tetrahydro-4H-7,10-ethanopyrimido[1,2-a][1,3]diazepine-2-carboxamide. Formed from 3-(benzyloxy)-4-oxo-6,7,8,9-tetrahydro-4H-7,10-ethanopyrimido[1,2-a][1,3]diazepine-2-carboxylic acid and 4-fluorobenzylamine to give the title compound as a yellow residue LCMS (M+H) calcd for C$_{25}$H$_{26}$FN$_4$O$_3$: 449.19; found: 449.25.

Intermediate 153

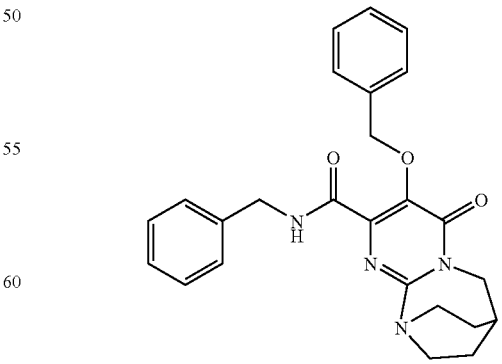

N-Benzyl-3-(benzyloxy)-4-oxo-6,7,8,9-tetrahydro-4H-7,10-ethanopyrimido[1,2-a][1,3]diazepine-2-carboxamide. Formed from 3-(benzyloxy)-4-oxo-6,7,8,9-tetrahydro-4H-7, 10-ethanopyrimido[1,2-a][1,3]diazepine-2-carboxylic acid and benzylamine to give the title compound as a yellow residue. LCMS (M+H) calcd for $C_{25}H_{27}N_4O_3$: 431.20; found: 431.30.

Intermediate 154

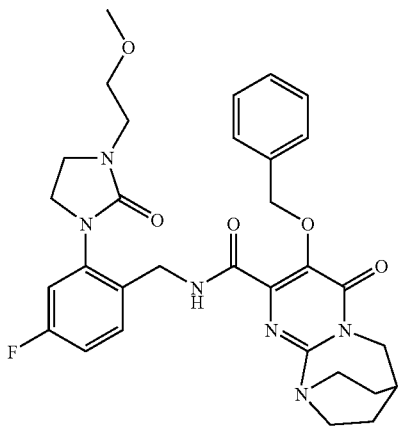

3-(Benzyloxy)-N-(4-fluoro-2-(3-(2-methoxyethyl)-2-oxo-1-imidazolidinyl)benzyl)-4-oxo-6,7,8,9-tetrahydro-4H-7,10-ethanopyrimido[1,2-a][1,3]diazepine-2-carboxamide. Formed from 3-(benzyloxy)-4-oxo-6,7,8,9-tetrahydro-4H-7,10-ethanopyrimido[1,2-a][1,3]diazepine-2-carboxylic acid and 1-(2-aminomethyl)-5-fluorophenyl)-3-(2-methoxyethyl)imidazolidin-2-one to give the title compound as a yellow residue. LCMS (M+H) calcd for $C_{31}H_{36}FN_6O_5$: 591.27; found: 591.34.

Intermediate 155

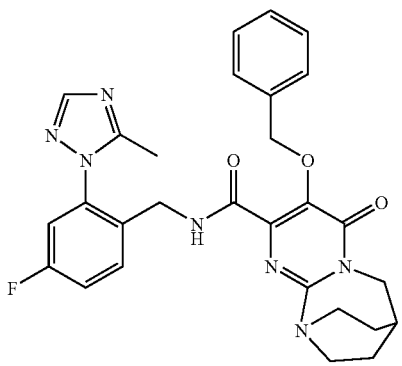

3-(Benzyloxy)-N-(4-fluoro-2-(5-methyl-1H-1,2,4-triazol-1-yl)benzyl)-4-oxo-6,7,8,9-tetrahydro-4H-7,10-ethanopyrimido[1,2-a][1,3]diazepine-2-carboxamide. Formed from 3-(benzyloxy)-4-oxo-6,7,8,9-tetrahydro-4H-7,10-ethanopyrimido[1,2-a][1,3]diazepine-2-carboxylic acid and (4-fluoro-2-(5-methyl-1H-1,2,4-triazol-1-yl)phenyl)methanamine to give the title compound as a white glass. LCMS (M+H) calcd for $C_{28}H_{29}FN_7O_3$: 530.23; found: 530.24.

Intermediate 156

3-(Benzyloxy)-N-(4-fluoro-2-(5-methyl-1H-1,2,3-triazol-1-yl)benzyl)-4-oxo-6,7,8,9-tetrahydro-4H-7,10-ethanopyrimido[1,2-a][1,3]diazepine-2-carboxamide. Formed from 3-(benzyloxy)-4-oxo-6,7,8,9-tetrahydro-4H-7,10-ethanopyrimido[1,2-a][1,3]diazepine-2-carboxylic acid and (4-fluoro-2-(5-methyl-1H-1,2,3-triazo-1-yl)phenyl-methanamine to give the title compound as a yellow residue (5.5 mg, 15% yield). LCMS (M+H) calcd for $C_{28}H_{29}FN_7O_3$: 530.23; found: 530.17.

Intermediate 157

3-(Benzyloxy)-N-(4-fluoro-2-(3-methyl-2-oxo-1-imidazolidinyl)benzyl)-4-oxo-6,7,8,9-tetrahydro-4H-7,10-ethanopyrimido[1,2-a][1,3]diazepine-2-carboxamide. Formed from 3-(benzyloxy)-4-oxo-6,7,8,9-tetrahydro-4H-7,10-ethanopyrimido[1,2-a][1,3]diazepine-2-carboxylic acid and 1-(2-(aminomethyl)-5-fluorophenyl)-3-methylimidazolidin-2-one to give the title compound as a yellow residue (4.7 mg, 13% yield). LCMS (M+H) calcd for $C_{29}H_{32}FN_6O_4$: 547.24; found: 547.20.

Example 1 through can be synthesized according to Scheme III

EXAMPLE 1

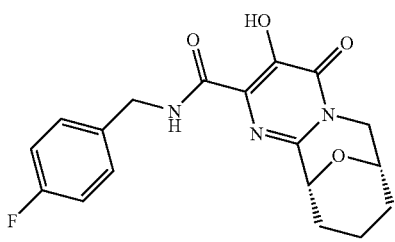

7,11-Epoxy-4H-pyrimido[1,2-a]azocine-2-carboxamide, N-[(4-fluorophenyl)methyl]-6,7,8,9,10,11-hexahydro-3-hydroxy-4-oxo-, (7S,11R)—. To ethyl (7S,11R)-3-hydroxy-4-oxo-6,7,8,9,10,11-hexahydro-4H-7,11-epoxypyrimido[1,2-a]azocine-2-carboxylate (0.050 mg, 0.18 mmol) in EtOH (10 mL) was added 4-fluorobenzylamine (0.081 g, 0.71 mmol). The reaction mixture was stirred at reflux for 4 hours in a sealed tube. The solvent was removed in vacuo and the product purified by preparative HPLC (C18 column) to afford 0.029 g (45% yield) of the title compound. $^1$H NMR (400 MHz, CDCl$_3$) δ ppm 12.05 (1 H, s), 7.86 (1 H, m), 7.31-7.38 (2 H, m), 7.04-7.16 (2 H, m), 4.77 (1 H, d, J=2.3 Hz), 4.53-4.65 (3 H, m), 4.01-4.10 (2 H, m), 2.03-2.14 (2 H, m), 1.85 (1 H, dd, J=13.6, 1.8 Hz), 1.76 (2 H, d, J=2.0 Hz), 1.31-1.43 (1 H, m).). LCMS ($^+$ESI, M+H$^+$) m/z 360. HRMS (ESI$^+$) calculated for C$_{13}$H$_{16}$N$_2$O$_5$ [M+H$^+$]:360.1360; found: 360.1351.

EXAMPLE 2

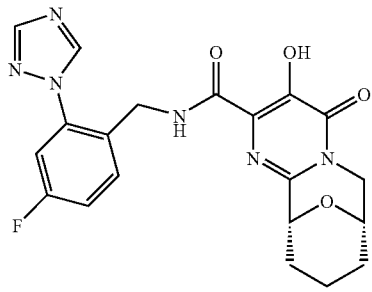

7,11-Epoxy-4H-pyrimido[1,2-a]azocine-2-carboxamide, N-[[4-fluoro-2-(1H-1,2,4-triazol-1-yl)phenyl]methyl]-6,7,8,9,10,11-hexahydro-3-hydroxy-4-oxo-, (7S,11R)—. To ethyl (7S,11R)-3-hydroxy-4-oxo-6,7,8,9,10,11-hexahydro-4H-7,11-epoxypyrimido[1,2-a]azocine-2-carboxylate (0.050, 0.18 mmol) in EtOH (5 mL) was added (4-fluoro-2-(1H-1,2,4-triazol-1-yl)phenyl)methanamine hydrochloride (0.081 mg, 0.36 mmol) and diisopropylethylamine (0.063 mL, 0.36 mmol). The reaction mixture was heated in a microwave oven at 160° C. for 3 h. LC-MS showed ~50% conversion to the target compound. The reaction mixture was stirred at 160° C. for an additional 3 h. EtOH was removed in vacuo and the crude material was purified by preparative HPLC using a C18 column and trifluoroacetic acid in the mobile phase. Solvent from the purification was removed and CH$_3$CN (5 mL) and H$_2$O (1 mL) were added and the resulting solution frozen and lyophilized overnight (16 h) to afford 21 mg (28% yield) of the title compound. $^1$H NMR (400 MHz, CDCl$_3$) δ ppm 11.95 (1H, br s), 8.56 (1 H, s), 8.47 (1 H, t, J=6.2 Hz), 8.28 (1 H, s), 7.62-7.74 (1 H, m), 7.21-7.29 (1 H, m), 7.12-7.19 (1 H, m), 4.80 (1H, d, J=2.3 Hz), 4.47-4.56 (3 H, m), 3.98-4.10 (2 H, m), 2.06-2.18 (2 H, m), 1.86 (1 H, dd, J=13.6, 1.8 Hz), 1.75 (2H, d, J=1.5 Hz), 1.29-1.41 (1 H, m).). LCMS ($^+$ESI, M+H$^+$) m/z 427. HRMS (ESI$^+$) calculated for C$_{20}$H$_{19}$FN$_6$O$_4$ [M+H$^+$]:427.1530; found: 427.1530.

EXAMPLE 3

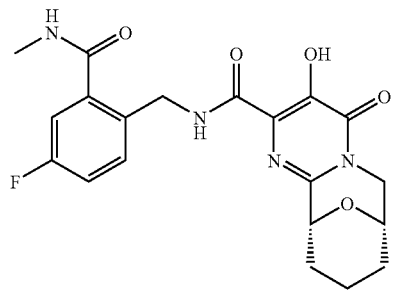

7,11-Epoxy-4H-pyrimido[1,2-a]azocine-2-carboxamide, N-[[4-fluoro-2-[(methylamino)carbonyl]phenyl]methyl]-6,7,8,9,10,11-hexahydro-3-hydroxy-4-oxo-, (7S,11R)—. $^1$H NMR (400 MHz, CDCl$_3$) δ ppm 8.55 (1 H, s), 7.38-7.45 (1 H, m), 7.24-7.31 (2 H, m), 4.72 (1H, d, J=2.3 Hz), 4.47-4.54 (3 H, m), 3.83-3.98 (2 H, m), 2.78 (2 H, d, J=4.6 Hz), 1.89-1.99 (2 H, m), 1.73 (2 H, m), 1.49-1.54 (1 H, m), 1.34-1.17 (1 H, m). LCMS ($^+$ESI, M+H$^+$) m/z 417. HRMS (ESI$^+$) calculated for C$_{20}$H$_{21}$FN$_4$O$_5$ [M+H$^+$]: 417.1574; found: 417.1575.

EXAMPLE 4

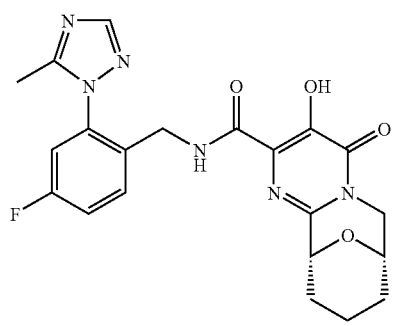

7,11-Epoxy-4H-pyrimido[1,2-a]azocine-2-carboxamide, N-[[4-fluoro-2-(5-methyl-1H-1,2,4-triazol-1-yl)phenyl]methyl]-6,7,8,9,10,11-hexahydro-3-hydroxy-4-oxo-, (7S,11R)—. $^1$H NMR (400 MHz, DMSO-D6) δ ppm 12.04 (1 H, s), 8.09 (1 H, s), 7.50-7.60 (2 H, m), 7.45 (1 H, td, J=8.5, 2.4 Hz), 4.70 (1 H, s), 4.47 (1 H, s), 4.11-4.22 (2 H, m), 3.81-3.92 (2 H, m), 2.33 (3 H, s), 1.85-1.96 (2 H, m), 1.68-1.80 (2H, m), 1.54 (1 H, br d), 1.27-1.39 (1 H, m).). LCMS ($^+$ESI, M+H$^+$) m/z 441. HRMS (ESI$^+$) calculated for C$_{28}$H$_{27}$FN$_4$O$_6$ [M+H$^+$]: 441.1687; found: 441.1688.

EXAMPLE 5

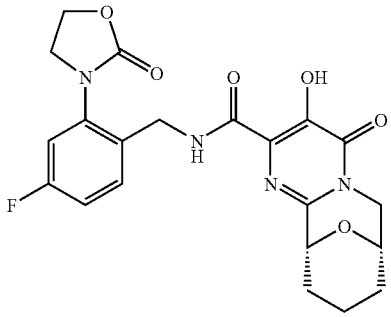

7,11-Epoxy-4H-pyrimido[1,2-a]azocine-2-carboxamide, N-[[4-fluoro-2-(2-oxo-3-oxazolidinyl)phenyl]methyl]-6,7,8,9,10,11-hexahydro-3-hydroxy-4-oxo-, (7S,11R)—. $^1$H NMR (400 MHz, CDCl$_3$) δ ppm 12.07 (1 H, s), 8.41 (1 H, s), 7.55 (1H, dd, J=8.5, 6.2 Hz), 7.09 (1 H, td, J=8.1, 2.4 Hz), 7.01 (1 H, dd, J=9.1, 2.5 Hz), 4.80 (1 H, s), 4.56-4.63 (3 H, m), 4.01-4.11 (4 H, m), 2.01-2.13 (2 H, m), 1.90 (1H, m), 1.59-1.75 (3 H, m), 1.25-1.37 (2 H, m). LCMS ($^+$ESI, M+H$^+$) m/z 445. HRMS (ESI$^+$) calculated for C$_{21}$H$_{21}$FN$_4$O$_6$ [M+H$^+$]: 445.1523; found: 445.1530.

Examples 6 and 7 can be synthesized according to Scheme IV

EXAMPLE 6

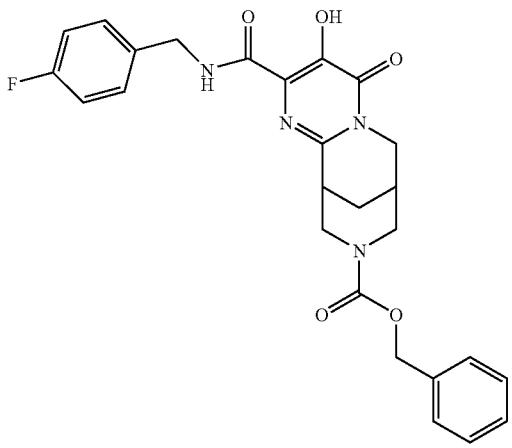

7,11-Methano-4H-pyrimido[1,2-a][1,5]diazocine-9(6H)-carboxylic acid, 2-[[[(4-fluorophenyl)methyl]amino]carbonyl]-7,8,10,11-tetrahydro-3-hydroxy-4-oxo-, phenylmethyl ester. To 9-benzyl 2-ethyl 3-hydroxy-4-oxo-7,8,10,11-tetrahydro-4H-7,11-methanopyrimido[1,2-a][1,5]diazocine-2,9(6H)-dicarboxylate (0.035 g, 0.085 mmol) in ethanol (2.0 mL) was added 4-fluorobenzylamine (0.030 mL, 0.254 mmol) and triethylamine (0.035 mL, 0.254 mmol). The reaction mixture was stirred at reflux for 65 hours. HCl (1M, 20 mL) was added and the organic material extracted with ethyl acetate (3×10 mL), and the combined organic fractions dried (MgSO$_4$) then concentrated in vacuo. The crude material was purified by preparative HPLC (C18 column) to afford 40 mg (76% yield) of the title compound. $^1$H NMR (400 MHz, CDCl$_3$) δ ppm 11.95 (1 H, br s), 7.83 (1 H, br s), 7.27-7.38 (5 H, m), 7.02-7.12 (4 H, m), 5.96-5.10 (2 H, m), 4.61-4.70 (1 H, m), 4.49 (2 H, d, J=6.3 Hz), 4.33 (1H, s), 4.17 (1 H, d, J=15.4 Hz), 3.88-3.98 (1 H, m), 3.11 (2 H, s), 2.48 (1 H, s), 1.62 (3 H, br s). LCMS ($^+$ESI, M+H$^+$) m/z 493. HRMS (ESI$^+$) calculated for C$_{26}$H$_{25}$FN$_4$O$_5$ [M+H$^+$]: 493.1887; found: 493.1870.

EXAMPLE 7

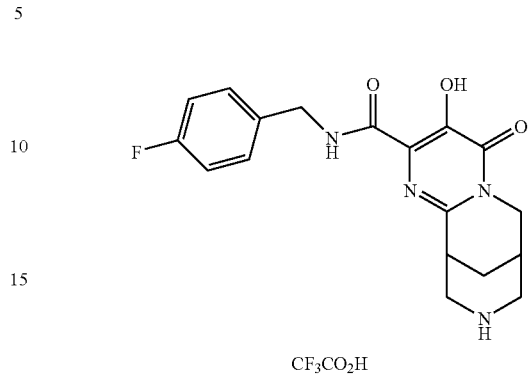

CF$_3$CO$_2$H 7,11-Methano-4H-pyrimido[1,2-a][1,5]diazocine-2-carboxamide, N-[(4-fluorophenyl)methyl]-6,7,8,9,10,11-hexahydro-3-hydroxy-4-oxo-. To 7,11-methano-4H-pyrimido[1,2-a][1,5]diazocine-9(6H)-carboxylic acid, 2-[[[(4-fluorophenyl)methyl]amino]carbonyl]-7,8,10,11-tetrahydro-3-hydroxy-4-oxo-, phenylmethyl ester (0.029 g, 0.059 mmol) dissolved in acetic acid (5 mL) was added Pd/C (10%, 0.025 g). The reaction mixture was shaken at 23° C. under 40 psi of hydrogen for 16 hours. Pd/C was removed by filtration on CELITE®. The acetic acid was removed in vacuo and remaining traces of acetic acid removed by azeotroping with toluene (2×25 mL). The crude material was purified by preparative HPLC (C18 column) to afford 0.0055 g (28% yield) of the title compound as a trifluoroacetic acid salt. $^1$H NMR (400 MHz, MeOD) δ ppm 9.17 (1H, br s), 7.40 (2 H, dd, J=8.6, 5.6 Hz), 7.06 (2 H, t, J=8.8 Hz), 4.53 (2 H, s), 4.33-4.44 (1 H, m), 4.05 (1 H, dd, J=15.4, 6.3 Hz), 3.54-3.66 (2 H, m), 3.41-3.52 (3 H, m), 2.81 (1 H, br s), 2.19-2.30 (2 H, m). LCMS ($^+$ESI, M+H$^+$) m/z 359. HRMS (ESI$^+$) calculated for C$_{18}$H$_{19}$FN$_4$O$_3$ [M+H$^+$]: 359.1519 found: 359.1520.

Examples 8 and 9 can be synthesized according to Scheme V

EXAMPLE 8

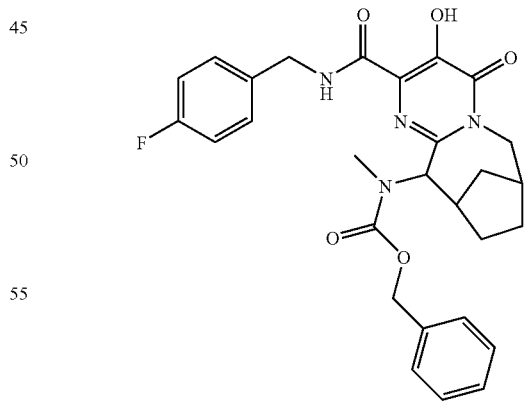

Carbamic acid, [2-[[[(4-fluorophenyl)methyl]amino]carbonyl]-6,7,8,9,10,11-hexahydro-3-hydroxy-4-oxo-7,10-methano-4H-pyrimido[1,2-a]azocin-11-yl]methyl-, phenylmethyl ester. To ethyl 3-(benzoyloxy)-11-(((benzyloxy)carbonyl)(methyl)amino)-4-oxo-6,7,8,9,10,11-hexahydro-4H-7,10-methanopyrimido[1,2-a]azocine-2-carboxylate (0.026 g, 0.048 mmol) in EtOH: DMF (3 mL: 1 mL) was added p-fluorobenzylamine (0.018 g, 0.143 mmol). The reaction mixture was stirred at 85° C. for 18 hours. HCl 1N (50 mL) was then added and the organic material extracted with ethyl acetate (3×50 mL). The combined organic fractions were dried (MgSO$_4$) and concentrated in vacuo. The crude compound was purified by preparative HPLC(C18 column) to afford 0.012 g (60% yield)of the target compound. $^1$H NMR (400 MHz, CDCl$_3$) δ ppm 7.50-7.65 (2 H, m), 7.16-7.37 (5 H, m), 6.98-7.09 (2 H, m), 5.40-5.00 (2 H, m), 4.31-4.62 (2 H, m), 2.92-2.98 (3 H, m), 2.62-2.69 (3 H, m), −1.92-2.45 (2 H, m), 1.55-1.86 (3 H, m), 1.21-1.48 (3 H, m). LCMS ($^+$ESI, M+H$^+$) m/z 521.

EXAMPLE 9

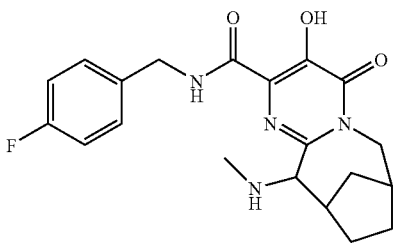

7,10-Methano-4H-pyrimido[1,2-a]azocine-2-carboxamide, N-[(4-fluorophenyl)methyl]-6,7,8,9,10,11-hexahydro-3-hydroxy-11-(methylamino)-4-oxo-. To carbamic acid, [2-[[[(4-fluorophenyl)methyl]amino]carbonyl]-6,7,8,9,10,11-hexahydro-3-hydroxy-4-oxo-7,10-methano-4H-pyrimido[1,2-a]azocin-11-yl]methyl-, phenylmethyl ester (0.068 g, 0.131 mmol) in ethyl acetate (2 mL) was added Pd/C (10%, 0.010 g) and the reaction mixture was stirred at 23° C. for 3 hours under H$_2$. The Pd/C was then removed by filtration and the solvent was evaporated in vacuo to afford, after crystallization in hot ethanol (2 mL), 0.004 g (8% yield) of the title compound. $^1$H NMR (400 MHz, MeOD) δ ppm 7.36 (2 H, m), 7.05 (2 H, t, J=8.2 Hz), 4.51-4.62 (2 H, m), 2.25-2.93 (6 H, m), 1.60-2.06 (5 H, m), 1.10-1.45 (3 H, m). LCMS ($^+$ESI, M+H$^+$) m/z 387.

Examples 10 through 17 can be synthesized according to Scheme VIII

EXAMPLE 10

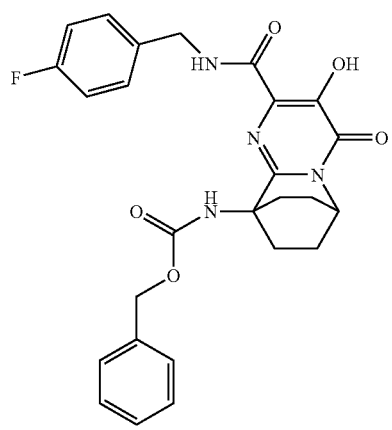

Benzyl (2-((4-fluorobenzyl)carbamoyl)-3-hydroxy-4-oxo-7,8-dihydro-4H-6,9-ethanopyrido[1,2-a]pyrimidin-9(6H)-yl)carbamate. A mixture of 6,9-ethano-4H-pyrido[1,2-a]pyrimidine-2-carboxylic acid, 6,7,8,9-tetrahydro-3-hydroxy-4-oxo-9-[[(phenylmethoxy)carbonyl]amino]-, ethyl ester (500 mg, 1.21 mmol) and 4-fluoro benzylamine (0.41 mL, 3.63 mmol) in EtOH (10 mL) was heated at 90° C. for 20 h. The reaction mixture was then cooled, concentrated and purified on a C-18 column using methanol/H$_2$O (containing 0.1% trifluoroacetic acid) as eluent to afford the title compound (295 mg, 45% yield) as a yellow solid. $^1$H NMR (500 MHz, DMSO-D$_6$) δ: 10.25 (s, 1H), 7.48 (s, 1H), 7.34-7.40 (m, 7H), 7.15-7.21 (m, 3H), 5.08 (s, 2H), 4.51 (s, 2H), 3.85 (s, 1H), 2.84-2.91 (m, 2H), 1.92-2.00 (m, 2H), 1.65-1.73 (m, 2H), 1.41-1.49 (m, 2H). LCMS (M+H)=493.24.

EXAMPLE 11

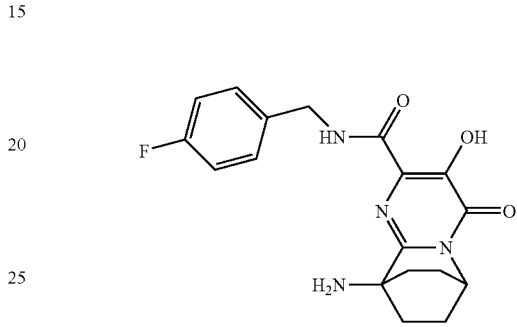

6,9-Ethano-4H-pyrido[1,2-a]pyrimidine-2-carboxamide, 9-amino-N-[(4-fluorophenyl)methyl]-6,7,8,9-tetrahydro-3-hydroxy-4-oxo-. To a mixture of benzyl (2-((4-fluorobenzyl)carbamoyl)-3-hydroxy-4-oxo-7,8-dihydro-4H-6,9-ethanopyrido[1,2-a]pyrimidin-9(6H)-yl)carbamate (135 mg, 0.27 mmol) in EtOH (5 mL) was added 10% Pd/C (50 mg) and the mixture was stirred under 1 atm of hydrogen for 18 h. The mixture was then filtered through a pad of CELITE® and the pad was washed with ethyl acetate. The filtrate was then concentrated to afford the title compound (80 mg, 82% yield) as a light yellow solid. $^1$H NMR (500 MHz, CDCl$_3$) δ: 10.15 (s, 1H), 7.99 (brs, 1H), 7.32 (dd, 2H, J=8.54, 5.19 Hz), 7.04 (t, 2H), J=8.7 Hz), 5.33 (s, 1H), 4.58 (d, 2H, J=6.41 Hz), 1.95-2.00 (m, 4H), 1.78-1.82 (m, 2H), 1.54-1.58 (m, 2H). LCMS (M+H)=359.18.

EXAMPLE 12

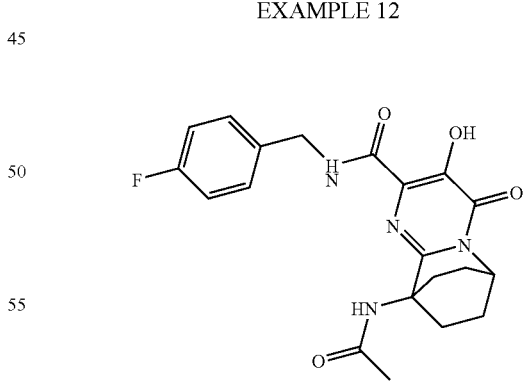

6,9-Ethano-4H-pyrido[1,2-a]pyrimidine-2-carboxamide, 9-(acetylamino)-N-[(4-fluorophenyl)methyl]-6,7,8,9-tetrahydro-3-hydroxy-4-oxo-. To a stirred solution of 6,9-ethano-4H-pyrido[1,2-a]pyrimidine-2-carboxamide, 9-amino-N-[(4-fluorophenyl)methyl]-6,7,8,9-tetrahydro-3-hydroxy-4-oxo- (20 mg, 0.056 mmol) in CH$_2$Cl$_2$ (2 mL) was added triethylamine (0.1 mL) followed by acetyl chloride (0.1 mL). After 16 at room temperature, the reaction mixture was concentrated to give a residue which was dissolved in methanol (2 mL) and treated with 2M dimethylamine/methanol (0.5 mL). The resulting reaction mixture was stirred at 60° C. for 2 h, cooled and purified by preparative HPLC to afford the title compound as a white solid (10 mg, 45% yield). $^1$H NMR (500 MHz, CDCl$_3$) δ: 12.30 (s, 1H), 7.61 (brs, 1H), 7.34 (dd, 2H, J=8.7 and 5.34 Hz), 7.07 (t, 2H, J=8.69 Hz), 6.79 (s, 1H), 5.34 (s, 1H), 4.62 (d, 2H, J=6.1 Hz), 3.08-3.14 (m, 2H), 2.03 (s, 3H), 1.98-2.02 (m, 2H), 1.71-1.82 (m, 2H), 1.49-1.55 (m, 2H). LCMS (M+H)=401.22. HPLC purity: >95%.

EXAMPLE 13

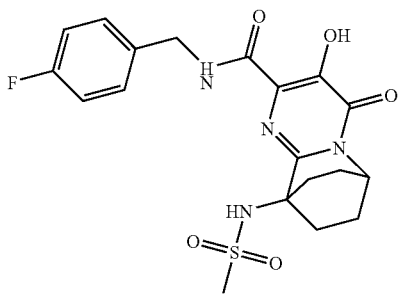

6,9-ethano-4H-pyrido[1,2-a]pyrimidine-2-carboxamide, N-[(4-fluorophenyl)methyl]-6,7,8,9-tetrahydro-3-hydroxy-9-[(methylsulfonyl)amino]-4-oxo-. White solid, $^1$H NMR (500 MHz, CDCl$_3$) δ: 12.41 (s, 1H), 8.17 (s, 1H), 7.35 (dd, 2H, J=8.7 and 5.34 Hz), 7.03 (t, 2H, J=8.54 Hz), 5.78 (s, 1H), 5.34 (s, 1H), 4.61 (d, 2H, J=6.41 Hz), 3.07 (s, 3H), 2.58-2.62 (m, 2H), 2.0-2.05 (m, 2H), 1.81-1.87 (m, 4H). LCMS (M+H)=436.97. HPLC purity: >95%.

EXAMPLE 14

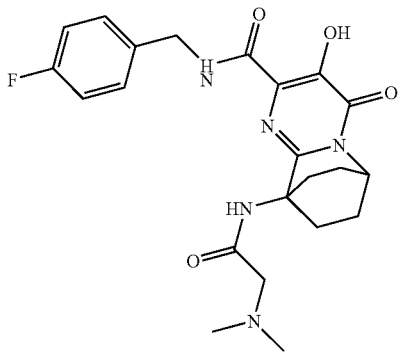

6,9-Ethano-4H-pyrido[1,2-a]pyrimidine-2-carboxamide, 9-[[(dimethylamino)acetyl]amino]-N-[(4-fluorophenyl)methyl]-6,7,8,9-tetrahydro-3-hydroxy-4-oxo-. Off-white solid (19% yield) $^1$H NMR (500 MHz, CDCl$_3$) δ: 12.31 (s, 1H), 8.65 (s, 1H), 7.35 (dd, 2H, J=8.55 and 5.49 Hz), 7.0 (, 2H, J=8.69 Hz), 5.30 (s, 1H), 4.58 (d, 2H, J=6.1 Hz), 3.80 (s, 1H), 2.93-3.10 (m, 2H), 2.89 (s, 6H), 1.96-2.01 (m, 2H), 1.80-1.86 (m, 2H), 1.52-1.57 (m, 2H). LCMS (M+H)=444.29. HPLC purity: >95%.

EXAMPLE 15

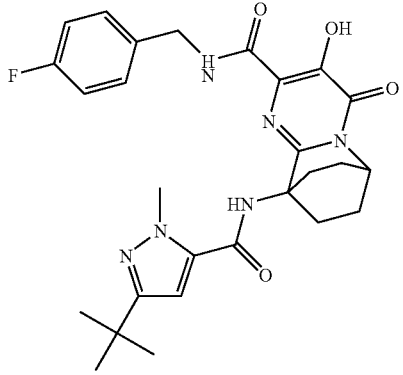

6,9-Ethano-4H-pyrido[1,2-a]pyrimidine-2-carboxamide, 9-[[[3-(1,1-dimethylethyl)-1-methyl-1H-pyrazol-5-yl]carbonyl]amino]-N-[(4-fluorophenyl)methyl]-6,7,8,9-tetrahydro-3-hydroxy-4-oxo-. Off-white solid (14% yield). $^1$H NMR (500 MHz, CDCl$_3$) δ: 12.35 (s, 1H), 7.55 (s, 1H), 7.41 (s, 1H), 7.28-7.31 (m, 2H), 7.03 (t, 2H, J=7.93 Hz), 6.23 (s, 1H), 5.38 (s, 1H), 4.61 (s, 2H), 4.09 (s, 3H), 3.11-3.16 (m, 2H), 2.04-2.09 (m, 2H), 1.84-1.90 (m, 2H), 1.64-1.69 (m, 2H), 1.22 (s, 9H). LCMS (M+H)=523.42. HPLC purity: >95%.

EXAMPLE 16

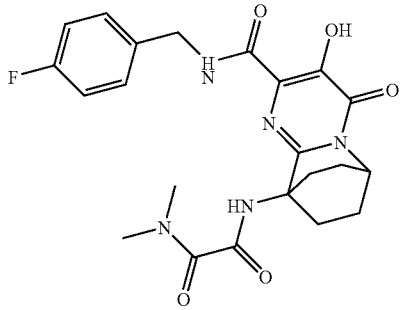

Ethanediamide, N'-[2-[[[(4-fluorophenyl)methyl]amino]carbonyl]-7,8-dihydro-3-hydroxy-4-oxo-6,9-ethano-4H-pyrido[1,2-a]pyrimidin-9(6H)-yl]-N,N-dimethyl-. To a stirred solution of N,N-dimethyloxamic acid (26 mg, 0.22 mmol) and N-methylmorpholine (0.05 mL) in CH$_2$Cl$_2$ (3 mL) was added isopropyl chloroformate (0.22 mL, 0.22 mmol, 1M in toluene). After 2 h at room temperature, 6,9-ethano-4H-pyrido[1,2-a]pyrimidine-2-carboxamide, 9-amino-N-[(4-fluorophenyl)methyl]-6,7,8,9-tetrahydro-3-hydroxy-4-oxo- (20 mg, 0.056 mmol) in CH$_2$Cl$_2$ (1 mL) was added in one portion and the mixture stirred at room temperature. After 16 h at room temperature, the reaction mixture was concentrated to give crude material which was dissolved in methanol (2 mL) and treated with 2M dimethylamine/methanol (0.5 mL). The resulting reaction mixture stirred at 60° C. for 2 h, cooled and purified by preparative HPLC to afford the title compound as a white solid (9 mg, 35% yield). $^1$H NMR (500 MHz, CDCl$_3$) δ: 12.31 (s, 1H), 8.73 (s, 1H), 8.02 (s, 1H), 7.36 (dd, 2H, J=8.39 and 5.34 Hz), 7.05 (t, 2H, J=8.55 Hz), 5.34 (s, 1H), 4.60 (d, 2H, J=6.1 Hz), 3.38 (s, 3H), 3.01 (s, 3H), 2.98-3.04

(m, 2H), 2.01-2.06 (m, 2H), 1.82-1.87 (m, 2H), 1.59-1.64 (m, 2H). LCMS (M+H)=458.15. HPLC purity: >95%.

EXAMPLE 17

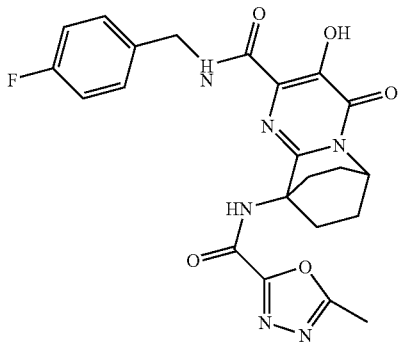

6,9-Ethano-4H-pyrido[1,2-a]pyrimidine-2-carboxamide, N-[(4-fluorophenyl)methyl]-6,7,8,9-tetrahydro-3-hydroxy-9-[[(5-methyl-1,3,4-oxadiazol-2-yl)carbonyl]amino]-4-oxo-. To a stirred solution of 6,9-ethano-4H-pyrido[1,2-a]pyrimidine-2-carboxamide, 9-amino-N-[(4-fluorophenyl)methyl]-6,7,8,9-tetrahydro-3-hydroxy-4-oxo- (20 mg, 0.056 mmol) and triethylamine (0.1 mL) in CH$_2$Cl$_2$ (3 mL) was added a freshly prepared solution of 5-methyl-1,3,4-oxadiazole-2-carbonyl chloride (0.56 mmol) in CH$_2$Cl$_2$ (2 mL) at room temperature. After 16 h at room temperature, the reaction mixture was concentrated to give crude material which was dissolved in methanol (2 mL) and treated with 2M dimethylamine/methanol (0.5 mL). The resulting reaction mixture was stirred at 60° C. for 2 h, then cooled and purified by preparative HPLC to afford the title compound as a white solid (6 mg, 23% yield). $^1$H NMR (500 MHz, CDCl$_3$) δ: 12.34 (s, 1H), 8.77 (s, 1H), 7.89 (s, 1H), 7.41 (dd, 2H. J=8.54 and 5.19 Hz), 7.11 (t, 2H, J=8.7 Hz), 5.36 (s, 1H), 4.64 (d, 2H), 3.12-3.18 (m, 2H), 2.65 (s, 3H), 2.04-2.08 (m, 2H), 1.85-1.91 (m, 2H), 1.61-1.68 (m, 2H). LCMS (M+H)=469.10. HPLC purity: >95%.
Examples 18 through 56 can be synthesized according to Schemes IX through XI

EXAMPLE 18

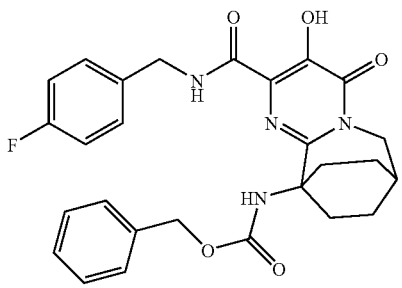

Benzyl (2-((4-fluorobenzyl)carbamoyl)-3-hydroxy-4-oxo-6,7,8,9-tetrahydro-7,10-ethanopyrimido[1,2-a]azepin-10(4H)-yl)carbamate. A mixture of ethyl 10-(((benzyloxy)carbonyl)amino)-3-hydroxy-4-oxo-4,6,7,8,9,10-hexahydro-7,10-ethanopyrimido[1,2-a]azepine-2-carboxylate (5.00 g, 11.70 mmol), (4-fluorophenyl)methanamine (2.67 mL, 23.39 mmol) and Et$_3$N (3.26 mL, 23.39 mmol) in ethanol (78 mL) was stirred at 90° C. for 16 h, cooled and concentrated. The resulting pale yellow foam was dissolved in ethyl acetate and washed with 1N HCl. The organic phase was washed with brine, dried (Na$_2$SO$_4$), filtered and concentrated. The residue was taken up in hot ethyl acetate and hexane was added until the solution became slightly cloudy. After cooling, the title compound was collected by filtration as a white solid (4.8203 g, 81% yield). $^1$H NMR (500 MHz, DMSO-D6) δ: 10.25 (s, 1H), 7.52 (s, 1H), 7.34-7.40 (m, 8H), 7.15-7.21 (m, 2H), 5.72 (s, 1H), 4.91 (s, 2H), 4.40 (d, 2H, J=6.4 Hz), 4.15 (s, 2H), 2.48-2.52 9 m, 2H), 2.02-2.08 (m, 2H), 1.94-1.98 (m, 2H), 1.63-1.70 (m, 2H). LCMS (M+H)=507.42.

EXAMPLE 19

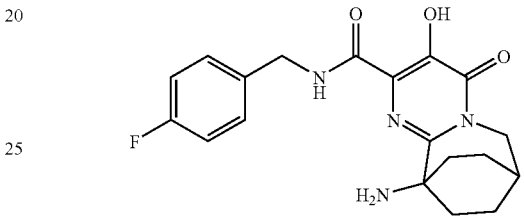

10-Amino-N-(4-fluorobenzyl)-3-hydroxy-4-oxo-4,6,7,8,9,10-hexahydro-7,10-ethanopyrimido[1,2-a]azepine-2-carboxamide. To a mixture of benzyl (2-((4-fluorobenzyl)carbamoyl)-3-hydroxy-4-oxo-6,7,8,9-tetrahydro-7,10-ethanopyrimido[1,2-a]azepin-10(4H)-yl)carbamate (300 mg, 0.59 mmol) in methanol (3 mL) was added 10% Pd/C (315 mg) and the mixture was stirred under balloon hydrogen atmosphere for 18 h. The mixture was then filtered through a pad of CELITE® and the pad washed with ethyl acetate. The filtrate was concentrated to afford the title compound (160 mg, 72% yield) as a light yellow solid. $^1$H NMR (500 MHz, DMSO-d$_6$) δ: 12.22 (s, 1H), 9.50 (brs, 1H), 7.35-7.41 (m, 2H), 7.19-7.22 (m, 2H), 4.54 (d, 2H, J=5.8 Hz), 4.01 (s, 2H), 2.42-2.48 (m, 3H), 2.08 (s, 2H), 1.98-2.03 (m, 2H), 1.84-1.90 (m, 2H), 1.70-1.78 (m, 2H). LCMS (M+H)=373.28.

EXAMPLE 20

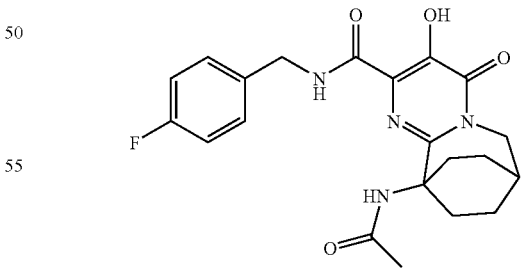

10-(Acetylamino)-N-(4-fluorobenzyl)-3-hydroxy-4-oxo-4,6,7,8,9,10-hexahydro-7,10-ethanopyrimido[1,2-a]azepine-2-carboxamide. To a stirred solution of 10-amino-N-(4-fluorobenzyl)-3-hydroxy-4-oxo-4,6,7,8,9,10-hexahydro-7,10-ethanopyrimido[1,2-a]azepine-2-carboxamide (25 mg, 0.067 mmol) in CH$_2$Cl$_2$ (2 mL) was added triethylamine (0.05 mL) followed by acetyl chloride (0.05 mL). After 16 h at room temperature the reaction mixture was concentrated to give crude product which was dissolved in methanol (2 mL) and treated with 2M dimethylamine/methanol (0.5 mL). The resulting reaction mixture stirred at 60° C. for 2 h, cooled and purified by preparative HPLC to afford the title compound as a white solid (3 mg, 11% yield). $^1$H NMR (500 MHz, CDCl$_3$) δ: 12.00 (s, 1H), 7.32-7.35 (m, 3H), 7.04-7.09 (m, 2H), 6.69 (s, 1H), 4.57 (d, 2H, J=5.8 Hz), 4.14 (d, 2H, J=3.66 Hz), 2.63-2.66 (m, 2H), 2.44-2.47 (m, 1H), 1.91-1.97 (m, 4H), 1.86 (s, 3H), 1.63-1.67 (m, 2H). LCMS (M+H)=415.29. HPLC purity: >95%.

EXAMPLE 21

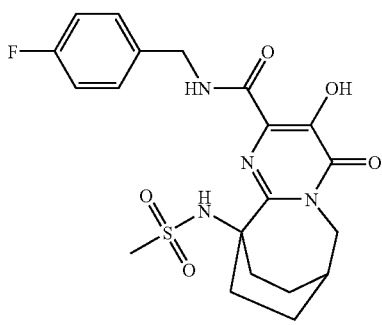

N-(4-Fluorobenzyl)-3-hydroxy-10-((methylsulfonyl)amino)-4-oxo-4,6,7,8,9,10-hexahydro-7,10-ethanopyrimido[1,2-a]azepine-2-carboxamide. White solid (11 mg, 36% yield). $^1$H NMR (500 MHz, CDCl$_3$) δ: 11.99 (s, 1H), 8.85 (s, 1H), 7.34 (dd, 2H, J=8.54 & 5.19 Hz), 6.98-7.04 (m, 2H), 4.84 (s, 1H), 4.53 (d, 2H, J=6.41 Hz), 4.15 (d, 2H, J=3.97 Hz), 3.04 (s, 3H), 2.51 (d, 1H, J=3.05 Hz), 2.07-2.24 (m, 4H), 1.87-1.98 (m, 2H), 1.65-1.75 (m, 2H). LCMS (M+H)=451.2. HPLC purity: >95%.

EXAMPLE 22

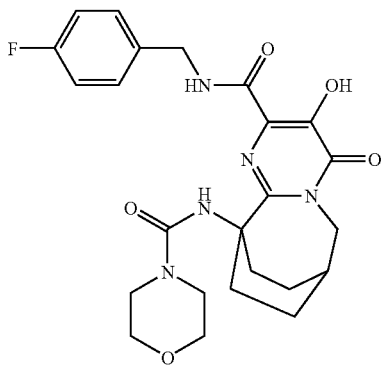

N-(4-Fluorobenzyl)-3-hydroxy-10-((4-morpholinylcarbonyl)amino)-4-oxo-4,6,7,8,9,10-hexahydro-7,10-ethanopyrimido[1,2-a]azepine-2-carboxamide. White solid (10 mg, 31% yield). $^1$H NMR (500 MHz, CDCl$_3$) δ: 12.00 (s, 1H), 8.70 (s, 1H), 7.37 (s, 1H), 7.31 (dd, 2H, J=8.39 Hz & 5.34 Hz), 7.08 (t, 2H, J=8.55 Hz), 4.58 (d, 2H, J=5.80 Hz), 4.18 (d, 2H, J=3.97 Hz), 3.46-3.48 (m, 4H), 3.11-3.16 (m, 4H), 2.46-2.57 (m, 3H), 1.89-2.05 (m, 4H), 1.62-1.71 (m, 2H). LCMS (M+H)=486.23. HPLC purity: >95%.

EXAMPLE 23

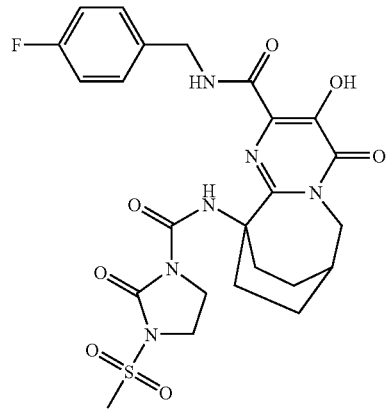

N-(4-Fluorobenzyl)-3-hydroxy-10-(((3-(methylsulfonyl)-2-oxo-1-imidazolidinyl)carbonyl)amino)-4-oxo-4,6,7,8,9,10-hexahydro-7,10-ethanopyrimido[1,2-a]azepine-2-carboxamide. White solid (9 mg, 24% yield). $^1$H NMR (500 MHz, CDCl$_3$) δ: 12.30 (s, 1H), 10.08 (s, 1H), 9.00 (s, 1H), 7.38 (dd, 2H, J=8.39 and 5.34 Hz), 7.00 (t, 2 Hz, J=8.70 Hz), 4.66 (d, 2H, J=6.71 Hz), 4.18 (d, 2H, J=3.66 Hz), 3.88-3.97 9 m, 4H), 2.97-3.05 (m, 2H), 2.92 (s, 3H), 2.48 (brs, 1H), 1.97-2.06 (m, 2H), 1.70-1.78 (m, 4H). LCMS (M+H)=563.19. HPLC purity: >95%.

EXAMPLE 24

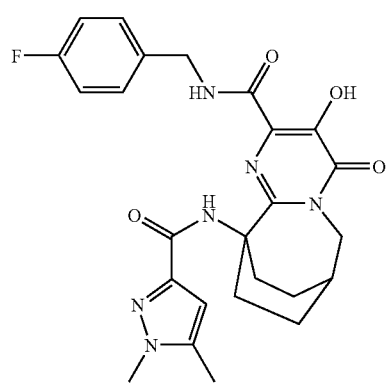

10-(((1,5-Dimethyl-1H-pyrazol-3-yl)carbonyl)amino)-N-(4-fluorobenzyl)-3-hydroxy-4-oxo-4,6,7,8,9,10-hexahydro-7,10-ethanopyrimido[1,2-a]azepine-2-carboxamide. White solid (12 mg, 36% yield). $^1$H NMR (500 MHz, CDCl$_3$) δ: 11.89 (s, 1H), 8.37 (s, 1H), 7.97 (s, 1H), 7.20 (dd, 2H, J=8.39 and 5.34 Hz), 7.00 (t, 2H, J=8.70 Hz), 6.46 (s, 1H), 4.60 (d, 2H, J=6.71 Hz), 4.19 (d, 2H, J=3.97 Hz), 3.41 (s, 3H), 2.84-2.93 (m, 2H), 2.50 (brs, 1H), 2.19 (s, 3H), 1.97-2.09 (m, 4H), 1.68-1.78 (m, 2H). (M+H)=495.2. HPLC purity: >95%.

EXAMPLE 25

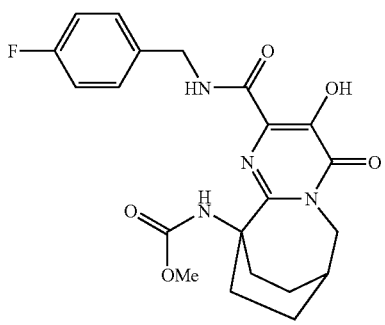

Methyl (2-((4-fluorobenzyl)carbamoyl)-3-hydroxy-4-oxo-6,7,8,9-tetrahydro-7,10-ethanopyrimido[1,2-a]azepin-10(4H)-yl)carbamate. White solid (4 mg, 14% yield). $^1$H NMR (500 MHz, CDCl$_3$) δ: 11.99 (s, 1H), 7.59 (s, 1H), 7.29-7.35 (m, 2H), 7.02-7.08 (m, 2H), 5.57 (s, 1H), 4.56 (d, 2H, J=5.80 Hz), 4.15 (d, 2H, J=3.66 Hz), 3.39 (s, 3H), 2.49 (s, 1H), 2.03-2.10 (m, 4H), 1.88-1.96 (m, 2H), 1.64-1.72 (m, 2H). LCMS (M+H)=451.2. HPLC purity: >95%.

EXAMPLE 26

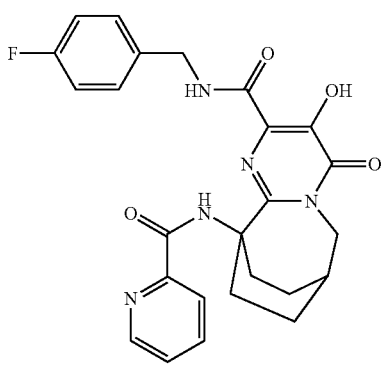

N-(4-Fluorobenzyl)-3-hydroxy-4-oxo-10-((2-pyridinylcarbonyl)amino)-4,6,7,8,9,10-hexahydro-7,10-ethanopyrimido[1,2-a]azepine-2-carboxamide. Off-white solid (6 mg, 19% yield). $^1$H NMR (500 MHz, CDCl$_3$) δ: 11.99 (s, 1H), 10.13 (s, 1H), 8.08-8.17 (m, 2H), 7.79-7.84 (m, 1H), 7.76 (d, 1H, J=4.58 Hz), 7.34 (dd, 2H, J=8.39 & 5.34 Hz), 7.26-7.30 (m, 1H), 7.04 (t, 2H, J=8.70 Hz), 4.67 (d, 2H, J=6.10 Hz), 4.21 (d, 2H, J=3.66 Hz), 3.04-3.14 (m, 2H), 2.48 (s, 1H), 2.02-2.14 (m, 2H), 1.89-1.98 (m, 2H), 1.72-1.82 (m, 2H). LCMS (M+H)=478.24. HPLC purity: >95%.

EXAMPLE 27

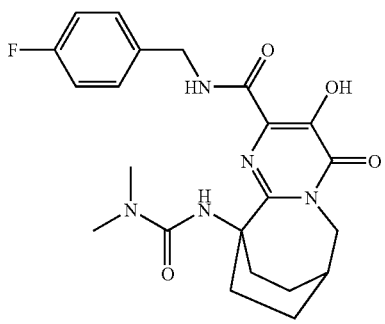

10-((Dimethylcarbamoyl)amino)-N-(4-fluorobenzyl)-3-hydroxy-4-oxo-4,6,7,8,9,10-hexahydro-7,10-ethanopyrimido[1,2-a]azepine-2-carboxamide. Off-white solid (7 mg, 24% yield). $^1$H NMR (500 MHz, CDCl$_3$) δ: 11.89 (s, 1H), 7.29-7.35 (m, 3H), 7.08 (t, 2H, J=8.55 Hz), 5.54 (s, 1H), 4.54 (d, 2H, J=5.80 Hz), 4.16 (d, 2H, J=3.66 Hz), 2.64 (s, 6H), 2.55-2.61 (m, 2H), 2.45 (s, 1H), 1.88-2.00 (m, 4H), 1.61-1.69 (m, 2H). LCMS (M+H)=444.21. HPLC purity: >95%.

EXAMPLE 28

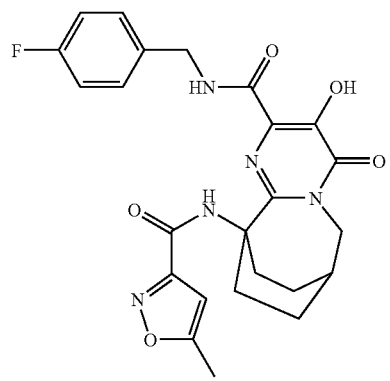

N-(4-Fluorobenzyl)-3-hydroxy-10-(((5-methyl-3-isoxazolyl)carbonyl)amino)-4-oxo-4,6,7,8,9,10-hexahydro-7,10-ethanopyrimido[1,2-a]azepine-2-carboxamide. White solid (12 mg, 37% yield). $^1$H NMR (500 MHz, CDCl$_3$) δ: 12.01 (s, 1H), 9.05 (s, 1H), 7.97-8.05 (m, 1H), 7.40 (dd, 2H, J=8.55 & 5.49 Hz), 7.03 (t, 2H, J=8.55 Hz), 6.38 (s, 1H), 4.60 (d, 2H, J=6.10 Hz), 4.17 (d, 2H, J=3.97 Hz), 2.91-3.01 (m, 2H), 2.48 (s, 1H), 2.46 (s, 3H), 2.00-2.11 (m, 2H), 1.87-1.96 (m, 2H), 1.71-1.79 (m, 2H). LCMS (M+H)=482.24. HPLC purity: >95%.

EXAMPLE 29

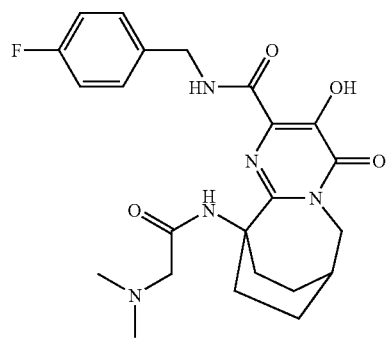

10-((N,N-Dimethylglycyl)amino)-N-(4-fluorobenzyl)-3-hydroxy-4-oxo-4,6,7,8,9,10-hexahydro-7,10-ethanopyrimido[1,2-a]azepine-2-carboxamide. Off-white solid (10 mg, 33% yield). $^1$H NMR (500 MHz, CDCl$_3$) δ: 12.1 (1 H, brs), 9.0 (1 H, brs), 8.8 (1 H, s), 7.4 (2 H, dd, J=8.55, 5.49 Hz), 7.0 (2 H, t, J=8.55 Hz), 4.6 (2 H, d, J=6.41 Hz), 4.1 (2 H, d, J=3.66 Hz), 3.6 (2 H, s), 2.7 (6 H, s), 2.4-2.5 (3 H, m), 2.0-2.1 (2 H, m), 1.9-2.0 (2 H, m), 1.6-1.7 (2 H, m). LCMS (M+H)=458.20. HPLC purity: >95%.

EXAMPLE 30

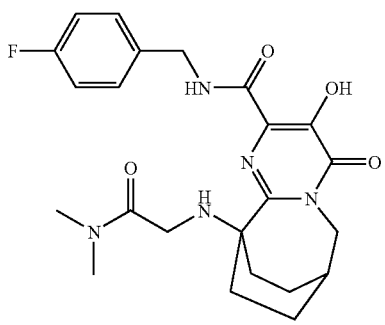

10-((2-(Dimethylamino)-2-oxoethyl)amino)-N-(4-fluorobenzyl)-3-hydroxy-4-oxo-4,6,7,8,9,0-hexahydro-7,10-ethanopyrimido[1,2-a]azepine-2-carboxamide. Off-white solid (10 mg, 33% yield). $^1$H NMR (500 MHz, CDCl$_3$) δ: 12.6 (1 H, brs), 8.8 (1 H, s), 7.4 (2 H, dd, J=8.55, 5.19 Hz), 7.0-7.0 (2 H, m), 4.5 (2 H, d, J=6.41 Hz), 4.1 (2 H, d, J=3.66 Hz), 4.0 (2 H, s), 3.0 (3 H, s), 2.8 (3 H, s), 2.5-2.6 (3 H, m), 2.2-2.2 (2 H, m), 2.0-2.1 (2 H, m), 1.7-1.8 (2 H, m). LCMS (M+H)= 458.17. HPLC purity: >95%.

EXAMPLE 31

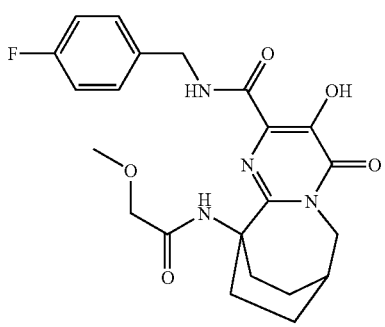

N-(4-Fluorobenzyl)-3-hydroxy-10-((methoxyacetyl)amino)-4-oxo-4,6,7,8,9,10-hexahydro-7,10-ethanopyrimido[1,2-a]azepine-2-carboxamide. Off-white solid (7 mg, 24% yield). $^1$H NMR (500 MHz, CDCl$_3$) δ: 12.0 (1 H, s), 8.4 (1H, s), 7.7 (1 H, brs), 7.3 (2 H, dd, J=8.39, 5.34 Hz), 7.1 (2 H, t, J=8.55 Hz), 4.6 (2 H, d, J=6.10 Hz), 4.2 (2 H, d, J=3.66 Hz), 3.8 (2 H, s), 3.1 (3 H, s), 2.9-3.0 (2 H, m), 2.5 (1 H, s), 2.0-2.1 (2 H, m), 1.8-1.9 (2 H, m), 1.6-1.7 (2 H, m). LCMS (M+H)= 445.4. HPLC purity: >95%.

EXAMPLE 32

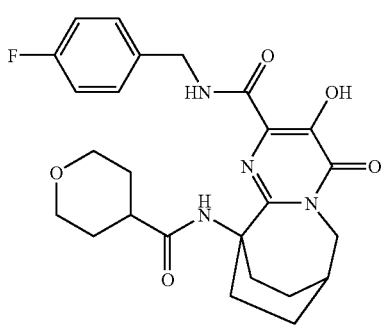

N-(4-Fluorobenzyl)-3-hydroxy-4-oxo-10-((tetrahydro-2H-pyran-4-ylcarbonyl)amino)-4,6,7,8,9,10-hexahydro-7,10-ethanopyrimido[1,2-a]azepine-2-carboxamide. Off-white solid (5 mg, 15% yield). $^1$H NMR (500 MHz, CDCl$_3$) δ: 12.1 (1 H, brs), 7.3-7.4 (4 H, m), 7.1 (2 H, t, J=8.55 Hz), 4.6 (2 H, d, J=6.10 Hz), 4.2 (2 H, d, J=3.66 Hz), 3.8-3.9 (2 H, m), 3.3 (2 H, td, J=11.44, 2.44 Hz), 2.7-2.8 (4 H, m), 2.5 (1 H, brs), 2.2-2.3 (1 H, m, J=11.37, 11.37, 4.12, 3.97 Hz), 1.9-2.0 (2 H, m), 1.8-1.9 (2 H, m), 1.5-1.6 (4 H, m). LCMS (M+H)=485.38. HPLC purity: >95%.

EXAMPLE 33

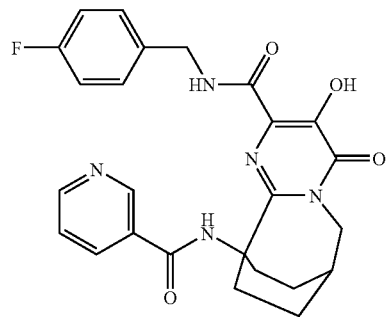

N-(4-Fluorobenzyl)-3-hydroxy-4-oxo-10-((3-pyridinylcarbonyl)amino)-4,6,7,8,9,10-hexahydro-7,10-ethanopyrimido[1,2-a]azepine-2-carboxamide. Off-white solid (8 mg, 20% yield). $^1$H NMR (500 MHz, CDCl$_3$) δ: 9.2 (1 H, s), 8.7 (1 H, d, J=5.19 Hz), 8.5 (1 H, d, J=7.93 Hz), 8.0 (1 H, s), 7.6 (1 H, dd, J=7.93, 5.49 Hz), 7.4 (1 H, brs), 7.1 (2 H, dd, J=8.24, 5.49 Hz), 6.9 (2 H, t, J=8.55 Hz), 4.5 (2 H, d, J=5.80 Hz), 4.2 (2 H, d, J=3.66 Hz), 2.7-2.8 (2 H, m), 2.5 (1 H, brs), 2.1-2.2 (2 H, m), 2.0-2.1 (2 H, m), 1.7-1.8 (2 H, m). LCMS (M+H)= 478.35. HPLC purity: >95%.

EXAMPLE 34

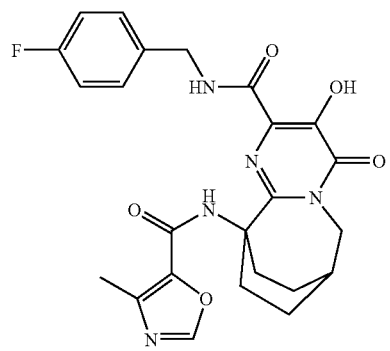

N-(4-Fluorobenzyl)-3-hydroxy-10-(((4-methyl-1,3-oxazol-5-yl)carbonyl)amino)-4-oxo-4,6,7,8,9,10-hexahydro-7,10-ethanopyrimido[1,2-a]azepine-2-carboxamide. Off-white solid (7 mg, 22% yield). $^1$H NMR (500 MHz, CDCl$_3$) δ: 12.0 (1 H, brs), 8.2 (1 H, s), 7.5 (1 H, brs), 7.3 (2 H, dd, J=8.39, 5.34 Hz), 7.1 (2 H, t, J=8.55 Hz), 6.9 (1 H, s), 4.6 (2 H, d, J=5.80 Hz), 4.2 (2 H, d, J=3.97 Hz), 2.9-3.0 (2 H, m), 2.5 (1 H, brs), 2.4 (3 H, s), 2.0-2.1 (2 H, m), 1.9-2.0 (2 H, m), 1.7-1.8 (2 H, m). LCMS (M+H)=482.33. HPLC purity: >95%.

EXAMPLE 35

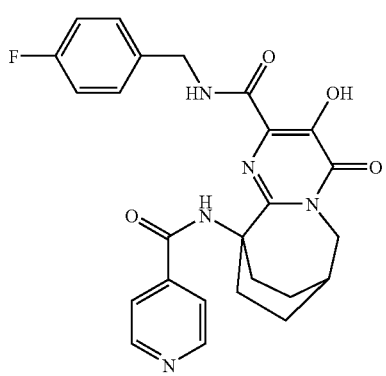

N-(4-Fluorobenzyl)-3-hydroxy-4-oxo-10-((4-pyridinylcarbonyl)amino)-4,6,7,8,9,10-hexahydro-7,10-ethanopyrimido[1,2-a]azepine-2-carboxamide. Off-white solid (8 mg, 20% yield). $^1$H NMR (500 MHz, CDCl$_3$) δ: 8.6 (2 H, d, J=5.80 Hz), 8.0 (1 H, s), 7.7 (2 H, d, J=5.49 Hz), 7.2-7.2 (3 H, m), 7.1 (2 H, t, J=8.55 Hz), 4.5 (2 H, d, J=6.10 Hz), 4.2 (2 H, d, J=3.97 Hz), 2.9-2.9 (2 H, m), 2.6 (1 H, brs), 2.0-2.1 (4 H, m), 1.7-1.8 (2 H, m). LCMS (M+H)=478.35. HPLC purity: >95%.

EXAMPLE 36

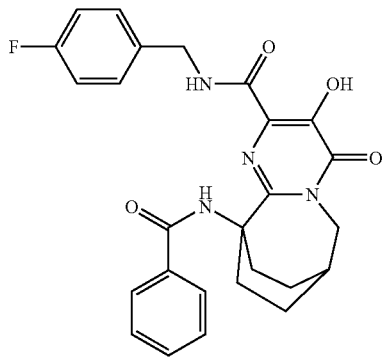

N-(4-Fluorobenzyl)-3-hydroxy-4-oxo-10-((phenylcarbonyl)amino)-4,6,7,8,9,10-hexahydro-7,10-ethanopyrimido[1,2-a]azepine-2-carboxamide. Off-white solid (11 mg, 35% yield). $^1$H NMR (500 MHz, CDCl$_3$) δ: 11.9 (1 H, brs), 7.7 (2 H, d, J=8.24 Hz), 7.5 (1 H, t, J=7.93 Hz), 7.4 (1 H, s), 7.3-7.3 (1 H, m), 7.2-7.3 (2 H, m), 7.1 (2 H, dd, J=8.55, 5.49 Hz), 7.0 (2 H, t, J=8.39 Hz), 4.4 (2 H, d, J=6.41 Hz), 4.2 (2 H, d, J=3.66 Hz), 2.8-2.9 (2 H, m), 2.5 (1 H, brs), 2.0-2.1 (4 H, m), 1.7-1.8 (2 H, m). LCMS (M+H)=477.37. HPLC purity: >95%.

EXAMPLE 37

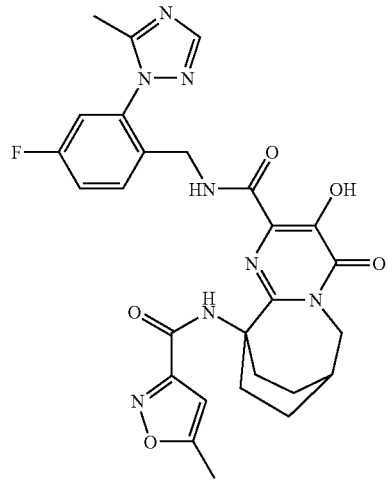

N-(4-Fluoro-2-(5-methyl-1H-1,2,4-triazol-1-yl)benzyl)-3-hydroxy-10-((((5-methyl-3-isoxazolyl)carbonyl)amino)-4-oxo-4,6,7,8,9,10-hexahydro-7,10-ethanopyrimido[1,2-a]azepine-2-carboxamide. Off-white solid (18 mg, 29% yield). $^1$H NMR (500 MHz, CDCl$_3$) δ: 11.74 (1 H, brs), 8.94 (1 H, s), 8.00 (1 H, brs), 7.95 (1H, s), 7.67 (1 H, dd, J=8.24, 5.80 Hz), 7.26-7.33 (1 H, m), 7.02 (1 H, dd, J=8.09, 2.29 Hz), 6.39 (1 H, s), 4.39 (2 H, d, J=6.10 Hz), 4.16 (2 H, d, J=3.36 Hz), 2.91-3.00 (2 H, m), 2.51 (1 H, brs), 2.45 (6 H, s), 2.00-2.09 (2 H, m), 1.89-1.98 (2 H, m), 1.69-1.79 (2 H, m). LCMS (M+H)= 563.72. HPLC purity: >95%.

EXAMPLE 38

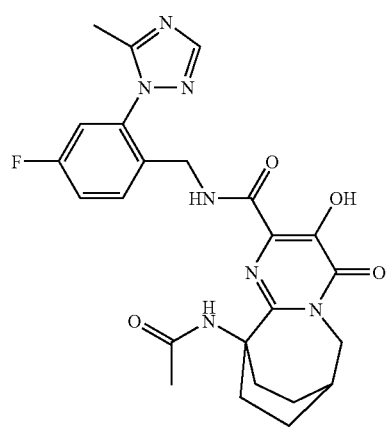

10-(Acetylamino)-N-(4-fluoro-2-(5-methyl-1H-1,2,4-triazol-1-yl)benzyl)-3-hydroxy-4-oxo-4,6,7,8,9,10-hexahydro-7,10-ethanopyrimido[1,2-a]azepine-2-carboxamide. Off-white solid (6 mg, 11% yield). $^1$H NMR (500 MHz, CDCl$_3$) δ: 11.86 (1 H, brs), 8.10 (1 H, brs), 8.08 (1 H, s), 7.71 (1 H, dd, J=8.70, 6.26 Hz), 7.57 (1 H, s), 7.28-7.35 (1 H, m), 7.00-7.08 (1 H, m), 4.30 (2 H, d, J=6.10 Hz), 4.15 (2H, d, J=3.66 Hz), 2.83-2.92 (2 H, m), 2.52 (3 H, s), 1.99 (3 H, s), 1.93-2.03 (3 H, m), 1.78-1.88 (2 H, m), 1.57-1.70 (2 H, m). LCMS (M+H)=496.66. HPLC purity: >95%.

EXAMPLE 39

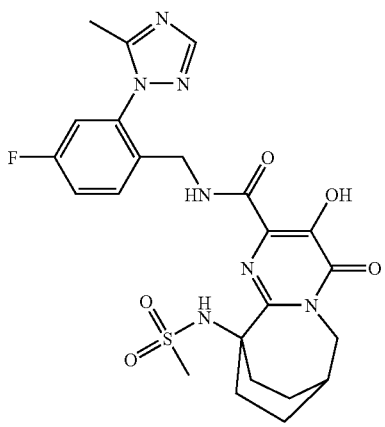

N-(4-Fluoro-2-(5-methyl-1H-1,2,4-triazol-1-yl)benzyl)-3-hydroxy-10-((methylsulfonyl)amino)-4-oxo-4,6,7,8,9,10-hexahydro-7,10-ethanopyrimido[1,2-a]azepine-2-carboxamide. Tan solid (12 mg, 21% yield). $^1$H NMR (500 MHz, CDCl$_3$) δ: 12.70 (1 H, brs), 8.69-8.76 (1 H, m), 8.36 (1 H, s), 7.80 (1 H, dd, J=8.55, 5.80 Hz), 7.30-7.37 (1 H, m), 7.01 (1 H, dd, J=7.63, 2.14 Hz), 5.30 (1 H, brs), 4.32 (2 H, d, J=6.10 Hz), 4.13 (2 H, d, J=3.36 Hz), 3.03 (3 H, s), 2.54 (3 H, s), 2.49 (1 H, brs), 2.09-2.25 (4 H, m), 1.88-1.98 (2 H, m), 1.63-1.75 (2 H, m). LCMS (M+H)=532.63. HPLC purity: >95%.

EXAMPLE 40

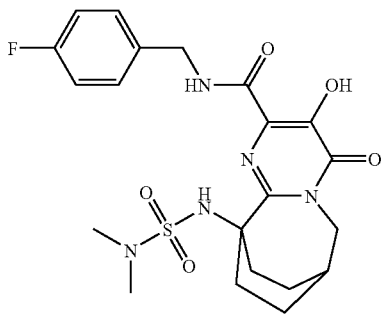

10-((Dimethylsulfamoyl)amino)-N-(4-fluorobenzyl)-3-hydroxy-4-oxo-4,6,7,8,9,10-hexahydro-7,10-ethanopyrimido[1,2-a]azepine-2-carboxamide. To a solution of 10-amino-N-(4-fluorobenzyl)-3-hydroxy-4-oxo-4,6,7,8,9,10-hexahydro-7,10-ethanopyrimido[1,2-a]azepine-2-carboxamide (25 mg, 0.067 mmol) in CH$_2$Cl$_2$ (2 mL) was added Et$_3$N (0.047 mL, 0.336 mmol) followed by dimethylsulfamoyl chloride (0.036 mL, 0.336 mmol) and the resulting mixture was stirred at room temperature overnight. The reaction mixture was concentrated to give crude product which was dissolved in methanol (2 mL) and treated with sodium ethoxide (0.2 ml, 21 wt % in ethanol) and the heated at 70° C. overnight. The mixture was then cooled, concentrated and purified by preparative HPLC to afford the title compound as a white solid (3.5 mg, 11% yield). $^1$H NMR (500 MHz, CDCl$_3$) δ: 12.00 (s, 1H), 8.90 (s, 1H), 7.34 (dd, 2H, J=8.39 & 5.34 Hz), 7.01 (t, 2H, J=8.55 Hz), 4.53 (d, 2H, J=6.41 Hz), 4.15 (d, 2H, J=3.97 Hz), 2.77 (s, 6H), 2.50 (s, 1H), 2.12 (t, 4H, J=7.63 Hz), 1.85-1.97 (m, 2H), 1.64-1.73 (m, 2H). LCMS (M+H)=480.21. HPLC purity: >95%.

EXAMPLE 41

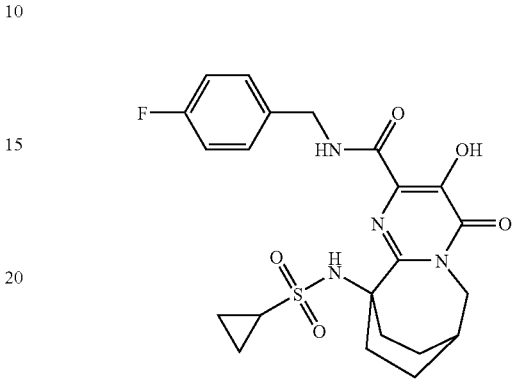

10-((Cyclopropylsulfonyl)amino)-N-(4-fluorobenzyl)-3-hydroxy-4-oxo-4,6,7,8,9,10-hexahydro-7,10-ethanopyrimido[1,2-a]azepine-2-carboxamide. Off-white solid. (7.5 mg, 25% yield). $^1$H NMR (500 MHz CDCl$_3$) δ: 11.9 (1 H, brs), 8.9-8.9 (1 H, m), 8.8-9.0 (1 H, m), 7.3 (2 H, dd, J=8.55, 5.49 Hz), 7.0 (2 H, t, J=8.70 Hz), 4.8 (1 H, brs), 4.5 (2 H, d, J=6.41 Hz), 4.1 (2 H, d, J=3.97 Hz), 2.5-2.5 (2 H, m), 2.2 (4 H, t, J=7.78 Hz), 1.9-2.0 (2 H, m), 1.6-1.7 (2 H, m), 1.1-1.2 (2 H, m), 1.0-1.0 (2 H, m). LCMS (M+H)=477.31. HPLC purity: >95%.

EXAMPLE 42

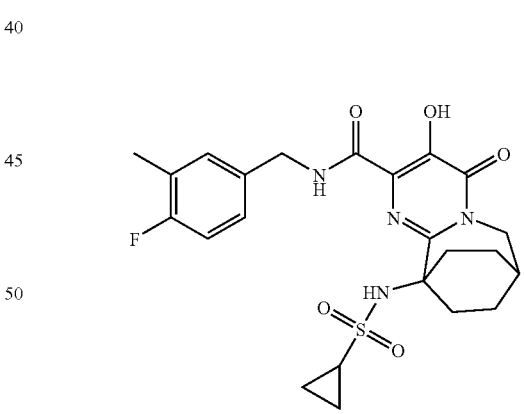

10-((Cyclopropylsulfonyl)amino)-N-(4-fluoro-3-methylbenzyl)-3-hydroxy-4-oxo-4,6,7,8,9,10-hexahydro-7,10-ethanopyrimido[1,2-a]azepine-2-carboxamide. Off-white solid (15 mg, 25% yield). $^1$H NMR (400 MHz, CDCl$_3$) δ: 11.94 (1 H, brs), 8.86 (1 H, brs), 7.20 (1 H, d, J=7.28 Hz), 7.12-7.18 (1 H, m), 4.83 (1 H, brs), 4.51 (2H, d, J=6.27 Hz), 4.17 (2 H, d, J=4.02 Hz), 2.46-2.56 (2 H, m), 2.27 (3 H, d, J=1.76 Hz), 2.25-2.26 (1 H, m), 2.16-2.20 (3 H, m), 1.91-1.98 (2 H, m), 1.65-1.75 (2 H, m), 1.13-1.18 (2 H, m), 0.98-1.07 (2 H, m). LCMS (M+H)=491.02. HPLC purity: >95%.

EXAMPLE 43

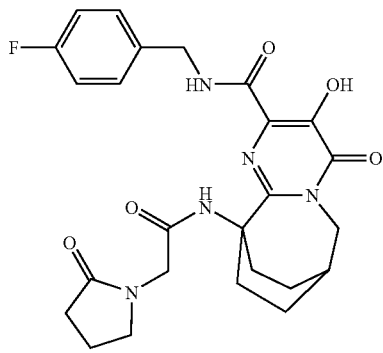

N-(4-Fluorobenzyl)-3-hydroxy-4-oxo-10-(((2-oxo-1-pyrrolidinyl)acetyl)amino)-4,6,7,8,9,10-hexahydro-7,10-ethanopyrimido[1,2-a]azepine-2-carboxamide. White crystalline solid (23 mg, 39% yield). $^1$H NMR (500 MHz, CDCl$_3$) δ: 12.8 (1 H, s), 9.6 (1 H, brs), 8.5 (1 H, s), 7.4 (2 H, dd, J=8.24, 5.49 Hz), 7.0 (2 H, t, J=8.70 Hz), 4.6 (2 H, d, J=6.41 Hz), 4.1 (2 H, d, J=3.66 Hz), 3.9 (2H, s), 3.5 (2 H, t, J=7.17 Hz), 2.9-3.1 (2 H, m), 2.4 (1 H, brs), 2.2 (2 H, t, J=7.93 Hz), 2.0-2.1 (2 H, m), 1.9-2.0 (2 H, m), 1.6-1.7 (4 H, m). LCMS (M+H)=498.24. HPLC purity: >95%.

EXAMPLE 44

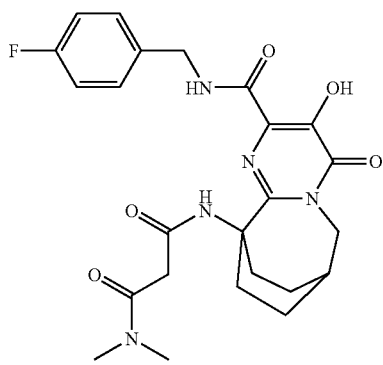

N'-(2-((4-Fluorobenzyl)carbamoyl)-3-hydroxy-4-oxo-6,7,8,9-tetrahydro-7,10-ethanopyrimido[1,2-a]azepin-10(4H)-yl)-N,N-dimethylpropanediamide. White solid (11 mg, 34% yield). $^1$H NMR (500 MHz, CDCl$_3$) δ: 12.3 (1 H, s), 10.3 (1 H, s), 9.6 (1 H, brs), 7.3-7.4 (2 H, m), 7.0-7.0 (2 H, m), 4.6 (2 H, d, J=6.71 Hz), 4.2 (2 H, d, J=3.66 Hz), 3.3 (2 H, s), 3.1-3.1 (2 H, m), 3.1 (3 H, s), 2.8 (3 H, s), 2.5 (1 H, brs), 2.0-2.0 (2 H, m), 1.7-1.8 (4 H, m). LCMS (M+H)=486.45. HPLC purity: >95%.

EXAMPLE 45

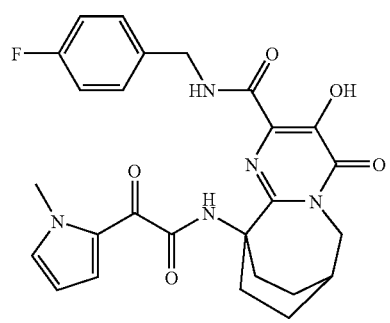

N-(4-Fluorobenzyl)-3-hydroxy-10-(((1-methyl-1H-pyrrol-2-yl)(oxo)acetyl)amino)-4-oxo-4,6,7,8,9,10-hexahydro-7,10-ethanopyrimido[1,2-a]azepine-2-carboxamide. Off-white solid (19 mg, 31% yield). $^1$H NMR (500 MHz, CDCl$_3$) δ: 11.91 (1 H, brs), 9.15 (1 H, s), 8.05 (1 H, brs), 7.91 (1 H, dd, J=4.39, 1.63 Hz), 7.31-7.37 (2 H, m), 6.93-7.00 (3 H, m), 6.19 (1 H, dd, J=4.39, 2.38 Hz), 4.60 (2 H, d, J=6.27 Hz), 4.16 (2 H, d, J=3.76 Hz), 3.77 (3 H, s), 2.79-2.90 (2 H, m), 2.44-2.53 (1 H, m), 1.86-2.07 (4 H, m), 1.68-1.79 (2 H, m). LCMS (M+H)=508.10. HPLC purity: >95%.

EXAMPLE 46

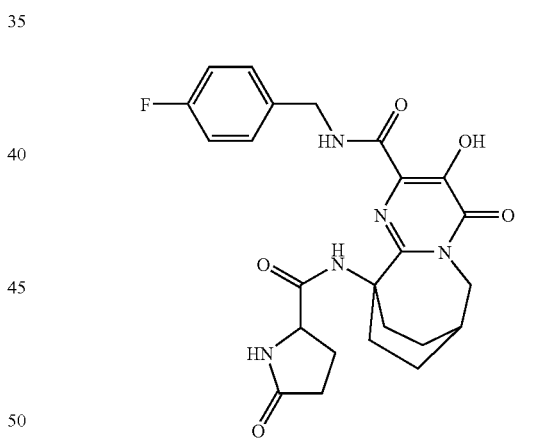

N-(4-Fluorobenzyl)-3-hydroxy-4-oxo-10-((5-oxoprolyl)amino)-4,6,7,8,9,10-hexahydro-7,10-ethanopyrimido[1,2-a]azepine-2-carboxamide. White solid (23 mg, 39% yield). $^1$H NMR (500 MHz, CDCl$_3$) δ: 12.71 (1 H, brs), 8.50 (1 H, s), 7.63 (1 H, brs), 7.44-7.49 (2 H, m), 7.01 (2 H, t, J=8.70 Hz), 5.93 (1 H, s), 4.75 (1 H, dd, J=14.19, 6.87 Hz), 4.60 (1 H, dd, J=14.19, 6.26 Hz), 4.24 (1 H, dd), 4.04-4.13 (2 H, m), 2.95-3.09 (2 H, m), 2.53-2.64 (1 H, m), 2.47 (1 H, brs), 2.34-2.40 (2 H, m), 2.19-2.28 (1 H, m), 1.95-2.07 (2 H, m), 1.69-1.76 (2 H, m), 1.59-1.67 (2 H, m). LCMS (M+H)=484.49. HPLC purity: >95%.

EXAMPLE 47

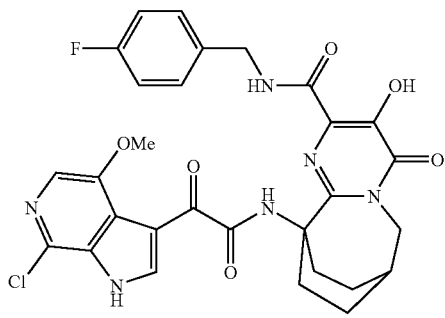

10-(((7-Chloro-4-methoxy-1H-pyrrolo[2,3-c]pyridin-3-yl)(oxo)acetyl)amino)-N-(4-fluorobenzyl)-3-hydroxy-4-oxo-4,6,7,8,9,10-hexahydro-7,10-ethanopyrimido[1,2-a]azepine-2-carboxamide. Off-white solid (23 mg, 29% yield). $^1$H NMR (500 MHz, CDCl$_3$) δ: 11.87 (1 H, brs), 9.24-9.34 (2 H, m), 8.97 (1 H, d, J=2.75 Hz), 8.09 (1 H, brs), 7.84 (1 H, s), 7.39 (2 H, dd, J=8.09, 5.65 Hz), 6.91 (2 H, t, J=8.39 Hz), 4.62 (2 H, d, J=6.10 Hz), 4.19 (2 H, d, J=3.36 Hz), 3.95 (3 H, s), 2.79-2.91 (2 H, m), 2.53 (1 H, brs), 1.95-2.10 (4 H, m), 1.73-1.80 (2 H, m). LCMS (M+H)=609.60. HPLC purity: >95%.

EXAMPLE 48

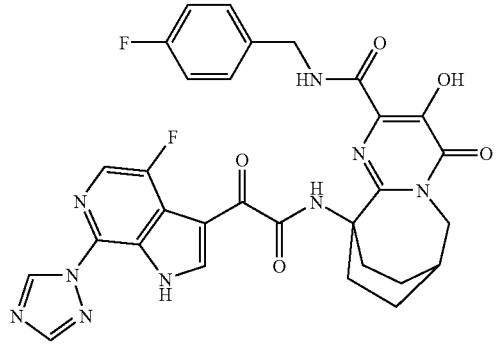

N-(4-Fluorobenzyl)-10-(((4-fluoro-7-(1H-1,2,4-triazol-1-yl)-1H-pyrrolo[2,3-c]pyridin-3-yl)(oxo)acetyl)amino)-3-hydroxy-4-oxo-4,6,7,8,9,10-hexahydro-7,10-ethanopyrimido[1,2-a]azepine-2-carboxamide. Yellow slid (15 mg, 18% yield). $^1$H NMR (500 MHz, CDCl$_3$) δ: 12.02 (1 H, brs), 11.16 (1 H, brs), 9.64 (1 H, s), 9.31 (1H, s), 8.78 (1 H, s), 8.20 (1 H, s), 8.09 (1 H, brs), 7.94 (1 H, s), 7.44-7.53 (2 H, m), 6.95-7.02 (2 H, m), 4.66 (2 H, d, J=6.41 Hz), 4.19 (2 H, d, J=3.36 Hz), 2.89-3.00 (2 H, m), 2.54 (1 H, brs), 2.02-2.13 (2 H, m), 1.89-1.99 (2 H, m), 1.72-1.83 (2 H, m). LCMS (M+H)=630.75. HPLC purity: >95%.

EXAMPLE 49

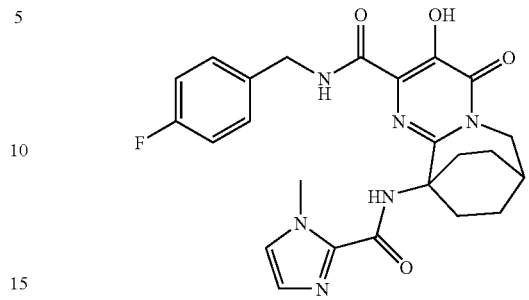

N-(4-Fluorobenzyl)-3-hydroxy-10-(((1-methyl-1H-imidazol-2-yl)carbonyl)amino)-4-oxo-4,6,7,8,9,10-hexahydro-7,11-ethanopyrimido[1,2-a]azepine-2-carboxamide. Off-white solid (10.5 mg, 18% yield). $^1$H NMR (500 MHz, CDCl$_3$) δ: 11.95 (1 H, brs), 9.66 (1 H, s), 8.44 (1 H, t, J=6.26 Hz), 7.32-7.35 (2 H, m), Y7.00-7.03 (2 H, m), 6.87 (1 H, s), 6.56 (1 H, d, J=1.22 Hz), 4.61 (2 H, d, J=6.41 Hz), 4.18 (2 H, d, J=3.97 Hz), 3.99 (3 H, s), 2.89-2.97 (2 H, m), 2.50 (1 H, brs), 1.92-2.08 (4 H, m), 1.70-1.79 (2 H, m). (M+H)=480.97. HPLC purity: >95%.

EXAMPLE 50

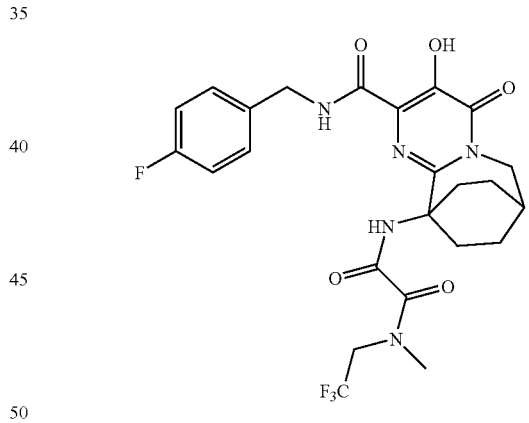

N'-(2-((4-Fluorobenzyl)carbamoyl)-3-hydroxy-4-oxo-6,7,8,9-tetrahydro-7,10-ethanopyrimido[1,2-a]azepin-10(4H)-yl)-N-methyl-N-(2,2,2-trifluoroethyl)ethanediamide. Crystalline white solid (22 mg, 33% yield). $^1$H NMR (500 MHz, CDCl$_3$) δ: 12.02 (0.4 H, s), 11.98 (0.6 H, s), 8.95 (0.6 H, s), 8.55 (0.4 H, s), 8.27 (0.4 H, brs), 8.17 (0.6 H, brs), 7.33-7.40 (2 H, m), 6.99-7.06 (2 H, m), 4.67 (1.3 H, q, J=8.85 Hz), 4.58 (1.3 H, d, J=6.41 Hz), 4.54 (0.7 H, d, J=6.41 Hz), 4.16 (2H, t, J=3.51 Hz), 3.89-3.95 (0.7 H, m), 3.44 (1.2 H, s), 3.02 (1.8 H, s), 2.59-2.70 (2H, m), 2.50 (1 H, brs), 1.90-2.06 (4 H, m), 1.66-1.76 (2 H, m). LCMS (M+H)=540.01. HPLC purity: >95%.

EXAMPLE 51

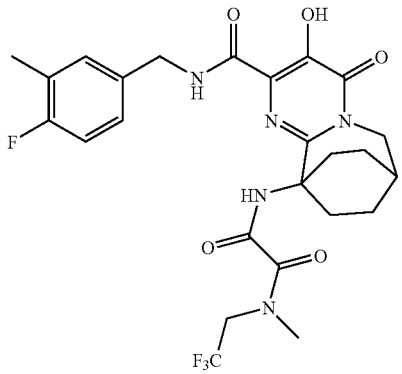

N'-(2-((4-Fluoro-3-methylbenzyl)carbamoyl)-3-hydroxy-4-oxo-6,7,8,9-tetrahydro-7,10-ethanopyrimido[1,2-a]azepin-10(4H)-yl)-N-methyl-N-(2,2,2-trifluoroethyl)ethanediamide. Crystalline off-white solid (26 mg, 40% yield). $^1$H NMR (500 MHz, CDCl$_3$) δ: 12.06 (0.4 H, s), 12.02 (0.6 H, s), 8.97 (0.6 H, s), 8.51 (0.4 H, s), 8.26 (0.4 H, brs), 8.17 (0.6 H, m), 7.14-7.23 (2 H, m), 6.92-6.99 (1 H, m), 4.65-4.70 (1.3 H, m), 4.70 (1.3 H, s), 4.54 (1.3 H, d, J=6.10 Hz), 4.50 (0.7 H, d, J=6.10 Hz), 4.16 (2 H, t, J=3.66 Hz), 3.91 (0.7 H, q, J=8.85 Hz), 3.43 (1.2 H, s), 3.03 (1.8 H, s), 2.57-2.71 (2 H, m), 2.50 (1 H, brs), 2.26 (3 H, s), 1.91-2.07 (4 H, m), 1.67-1.76 (2 H, m). LCMS (M+H)+=554.02. HPLC purity: >95%.

EXAMPLE 52

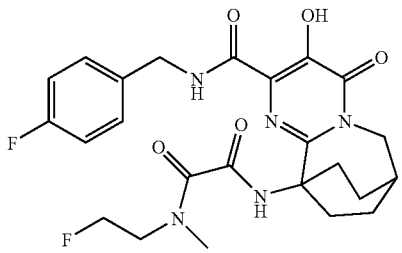

N'-(2-((4-Fluorobenzyl)carbamoyl)-3-hydroxy-4-oxo-6,7,8,9-tetrahydro-7,10-ethanopyrimido[1,2-a]azepin-10(4H)-yl)-N-(2-fluoroethyl)-N-methylethanediamide. A mixture of 10-amino-N-(4-fluorobenzyl)-3-hydroxy-4-oxo-4,6,7,8,9,10-hexahydro-7,10-ethanopyrimido[1,2-a]azepine-2-carboxamide (0.05 g, 0.122 mmol), 2-((2-fluoroethyl)(methyl)amino)-2-oxoacetic acid (0.036 g, 0.245 mmol), diisopropyl ethylamine (0.128 mL, 0.734 mmol), O-(7-azabenzotriazol-1-yl)-N,N,N',N'-tetramethyluronium hexafluorophosphate (HATU) (0.093 g, 0.245 mmol) and 4-(dimethylamino)pyridine (DMAP) (2.99 mg, 0.024 mmol) in DMF (1.2 mL) was stirred at room temperature for 16 h. The mixture was diluted with 1N HCl and extracted with ethyl acetate. Solids precipitated out of the biphasic mixture and were collected by filtration to give the title compound as white needles (0.0394 g, 60% yield). $^1$H NMR (500 MHz, CDCl$_3$) δ: 11.92-12.05 (1 H, m), 8.16-8.68 (2 H, m), 7.28-7.42 (2 H, m), 6.91-7.10 (2 H, m), 4.37-4.75 (4 H, m), 4.16 (2 H, t, J=4.58 Hz), 3.94-4.08 (1 H, m), 3.50-3.65 (1 H, m), 2.91-3.43 (3 H, m), 2.53-2.66 (2 H, m), 2.45-2.52 (1 H, m), 1.88-2.11 (4 H, m), 1.61-1.78 (2 H, m). LCMS (M+H) calcd for C$_{24}$H$_{28}$F$_2$N$_5$O$_5$: 504.20; found: 504.02.

EXAMPLE 53

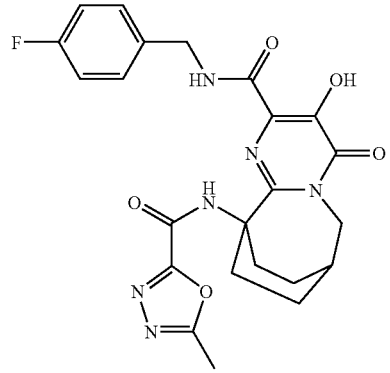

N-(4-Fluorobenzyl)-3-hydroxy-10-(((5-methyl-1,3,4-oxadiazol-2-yl)carbonyl)amino)-4-oxo-4,6,7,8,9,10-hexahydro-7,11-ethanopyrimido[1,2-a]azepine-2-carboxamide. To a suspension of potassium 5-methyl-1,3,4-oxadiazole-2-carboxylate (112 mg, 0.671 mmol) in CH$_2$Cl$_2$ (2 mL, contains cat. DMF) was added oxalyl chloride (0.369 mL, 0.738 mmol) and the mixture was stirred at room temp for 2 h. Solvent was then removed under reduced pressure. The crude acid chloride was then diluted with CH$_2$Cl$_2$ (1.000 mL) and was added to a pre-stirred solution of 10-amino-N-(4-fluorobenzyl)-3-hydroxy-4-oxo-4,6,7,8,9,10-hexahydro-7,10-ethanopyrimido[1,2-a]azepine-2-carboxamide (25 mg, 0.067 mmol) and triethylamine (0.103 mL, 0.738 mmol) in CH$_2$Cl$_2$ (2 mL) and the resulting solution stirred at room temperature. After 16 at room temperature, the reaction mixture was concentrated to give crude product which was dissolved in methanol (2 mL) and treated with 2M dimethylamine/methanol (0.5 mL). The resulting reaction mixture stirred at 60° C. for 2 h, cooled and purified by preparative HPLC to afford the title compound as a white solid (8 mg, 25% yield). $^1$H NMR (500 MHz, CDCl$_3$) δ: 12.09 (s, 1H), 8.08 (s, 1H), 7.47 (dd, 2H, J=8.55 & 5.49 Hz), 7.00-7.06 (m, 2H), 4.63 (d, 2H, J=6.41 Hz), 4.18 (d, 2H, J=3.66 Hz), 2.94-3.03 (m, 2H), 2.64 (s, 3H), 2.48-2.55 (m, 1H), 2.01-2.14 (m, 2H), 1.87-1.95 (m, 2H), 1.73-1.81 (m, 2H). LCMS (M+H)= 483.27. HPLC purity: >95%.

EXAMPLE 54

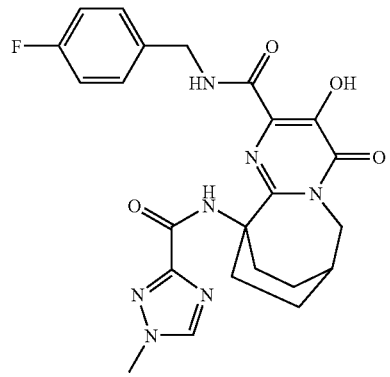

N-(4-Fluorobenzyl)-3-hydroxy-10-(((1-methyl-1H-1,2,4-triazol-3-yl)carbonyl)amino)-4-oxo-4,6,7,8,9,10-hexahydro-7,10-ethanopyrimido[1,2-a]azepine-2-carboxamide. Off-white solid (12 mg, 36% yield). $^1$H NMR (500 MHz, CDCl$_3$) δ: 12.05 (1 H, brs), 9.74 (1 H, s), 8.28 (1 H, brs), 7.42 (2 H, dd, J=8.24, 5.19 Hz), 7.04-7.18 (2 H, m), 4.76 (2 H, d, J=5.80 Hz), 4.21 (2 H, d, J=3.66 Hz), 3.97 (3H, s), 3.11-3.26 (2 H, m), 2.55 (1 H, brs), 2.04-2.18 (2 H, m), 1.81-1.96 (2 H, m), 1.72-1.87 (2 H, m). LCMS (M+H)=482.1. HPLC purity: >95%.

EXAMPLE 55

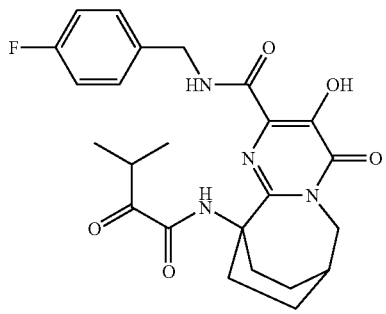

N-(4-Fluorobenzyl)-3-hydroxy-10-((3-methyl-2-oxobutanoyl)amino)-4-oxo-4,6,7,8,9,10-hexahydro-7,10-ethanopyrimido[1,2-a]azepine-2-carboxamide. Thick film (2.7 mg, 11% yield). $^1$H NMR (500 MHz, CDCl$_3$) δ: 12.18 (1 H, brs), 9.24 (1 H, s), 7.84 (1 H, brs), 7.43-7.56 (2 H, m), 7.06-7.14 (2 H, m), 4.64 (2 H, d, J=6.10 Hz), 4.27 (2 H, d, J=3.97 Hz), 3.64 (1 H, dt, J=13.96, 6.90 Hz), 2.88-2.98 (2 H, m), 2.54 (1 H, brs), 2.02-2.1 (2 H, m), 1.84-1.92 (2 H, m), 1.71-1.80 (2 H, m), 1.12 (6H, d, J=7.02 Hz). LCMS (M+H)= 471.00. HPLC purity: >95%.

EXAMPLE 56

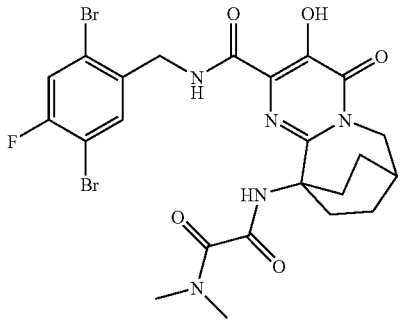

N'-(2-((2,5-Dibromo-4-fluorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide. A mixture of ethyl 10-(((benzyloxy)carbonyl)amino)-3-hydroxy-4-oxo-4,6,7,8,9,10-hexahydro-7,10-ethanopyrimido[1,2-a]azepine-2-carboxylate (0.08 g, 0.187 mmol), (2,5-dibromo-4-fluorophenyl)methanamine hydrochloride (0.080 g, 0.250 mmol) and Et$_3$N (0.139 mL, 1 mmol) in EtOH (3 mL) was heated at 90° C. for 22 h. Then, cooled, diluted with Ethyl acetate (50 mL), washed with 1N aq. HCl (2×5 mL), water (10 mL) followed by brine (10 mL), dried (Na$_2$SO$_4$), filtered and concentrated to give light purple foam which was used in the next without purification. To CH$_2$Cl$_2$ (5 mL) solution of this crude material was added HBr/AcOH (1.5 mL, 45% w/v) and the mixture stirred at room temperature for 4 h. The reaction mixture was concentrated and resulting light brown solid was used in the next step without purification. A 10 mL flask was charged with this intermediate and O-(7-azabenzotriazol-1-yl)-N,N,N',N'-tetramethyluronium hexafluorophosphate (HATU) (0.190 g, 0.5 mmol). To this was added diisopropylethylamine (0.3 mL, 1.718 mmol), N,N-dimethyloxamic acid (0.117 g, 1 mmol) and DMF (3 mL). After 4 h at room temperature, 2M Me$_2$NH/methanol (2 mL) was added and this was stirred at room temperature overnight (15 h). The solution was diluted with Et$_2$O (50 mL), washed with 1N HCl (10 ml), water (2×5 mL) followed by brine (5 mL), then dried (Na$_2$SO$_4$), filtered, concentrated and purified by preparative-HPLC to afford the title compound (0.0136 g, 0.020 mmol, 11% yield) as a white solid. $^1$H NMR (500 MHz, CDCl$_3$) δ: 11.84 (1H, s), 8.69 (1H, t, J=5.8 Hz), 7.98 (1H, s), 7.56 (1H, d, J=7.3 Hz), 7.35 (1H, d, J=7.9 Hz), 4.63 (2H, d, J=6.1 Hz), 4.17 (2H, d, J=3.7 Hz), 3.28 (3H, s), 2.89 (3H, s), 2.55-2.49 (3H, m), 2.16-2.10 (2H, m), 2.00-1.93 (2H, m), 1.76-1.69 (2H, m). LCMS (M+H) calcd for C$_{23}$H$_{25}$Br$_2$FN$_5$O$_5$: 628.02; found: 629.88.

Examples 57 through 105 can be synthesized according to Scheme XII

EXAMPLE 57

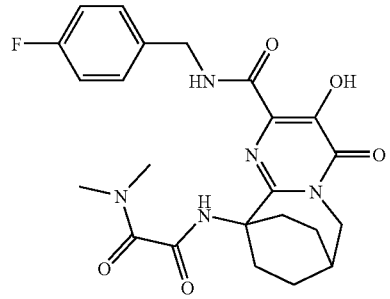

N'-(2-((4-Fluorobenzyl)carbamoyl)-3-hydroxy-4-oxo-6,7,8,9-tetrahydro-7,10-ethanopyrimido[1,2-a]azepin-10 (4H)-yl)-N,N-dimethylethanediamide. To a stirred solution of 10-amino-N-(4-fluorobenzyl)-3-hydroxy-4-oxo-4,6,7,8,9,10-hexahydro-7,10-ethanopyrimido[1,2-a]azepine-2-carboxamide (50 mg, 0.134 mmol) in CH$_2$Cl$_2$ (2 mL) at 0° C. was added Et$_3$N (0.094 mL, 0.671 mmol) followed by methyl 2-chloro-2-oxoacetate (0.1 mL, 0.671 mmol) and the resulting mixture was stirred at room temperature. After 16 h, the reaction mixture was concentrated to give crude product which was dissolved in EtOH (2 mL), treated with 2M dimethylamine/methanol (0.7 mL) and heated in a sealed tube at 85° C. for 2 h, cooled and purified by preparative HPLC to afford the title compound as a light yellow solid (9 mg, 13% yield). $^1$H NMR (500 MHz, CDCl$_3$) δ: 12.00 (s, 1H), 8.60 (s, 1H), 8.17 (s, 1H), 7.36 (dd, 2H, J=8.55 and 5.49 Hz), 7.00-7.04 (m, 2 Hz), 4.54 (d, 2H, J=6.1 Hz), 4.16 (d, 2H, J=3.66 Hz), 3.28 (s, 3H), 2.91 (s, 3H), 2.50-2.56 (m, 3H), 2.06-2.10 (m, 2H), 1.92-1.99 (m, 2H), 1.70-1.74 (m, 2H). LCMS (M+H)=472.37. HPLC purity: >95%.

EXAMPLE 58

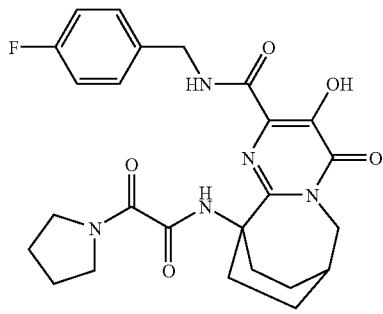

N-(4-Fluorobenzyl)-3-hydroxy-4-oxo-10-((oxo(1-pyrrolidinyl)acetyl)amino)-4,6,7,8,9,10-hexahydro-7,10-ethanopyrimido[1,2-a]azepine-2-carboxamide. Off-white solid (14 mg, 32% yield). $^1$H NMR (500 MHz, CDCl$_3$) δ: 12.00 (s, 1H), 9.25 (s, 1H), 8.22 (t, 1H, J=6.10 Hz), 7.38 (dd, 2H, J=8.55 & 6.19 Hz), 7.00-7.04 (m, 2H), 4.58 (d, 2H, J=2.75 Hz), 4.16 (d, 2H, J=3.66 Hz), 3.91 (t, 2H, J=6.87 Hz), 3.43 (t, 2H, J=7.02 Hz), 2.69-2.75 (m, 2H), 2.49 (brs, 1H), 1.91-2.03 (m, 6H), 1.82-1.88 (m, 2H), 1.67-1.76 (m, 2H), 1.67-1.76 (m, 2H). LCMS (M+H)=498.31. HPLC purity: >95%.

EXAMPLE 59

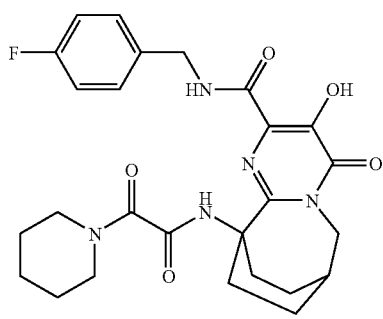

N-(4-Fluorobenzyl)-3-hydroxy-4-oxo-10-((oxo(1-piperidinyl)acetyl)amino)-4,6,7,8,9,10-hexahydro-7,10-ethanopyrimido[1,2-a]azepine-2-carboxamide. Off-white solid (11 mg, 25% yield). $^1$H NMR (500 MHz, CDCl$_3$) δ: 12.02 (s, 1H), 8.85 (s, 1H), 7.65 (s, 1H), 7.36 (dd, 2H, J=8.24 & 5.49 Hz), 7.00 (t, 2H, J=8.55 Hz), 4.53 (d, 2H, J=6.41 Hz), 4.16 (d, 2H, J=3.66 Hz), 3.69 (t, 2H, J=7.12 Hz), 3.47 (t, 2H, J=5.87 Hz), 2.39-2.53 (m, 3H), 2.10-2.20 (m, 2H), 1.89-1.98 (m, 2H), 1.53-1.74 (m, 8H). LCMS (M+H)=512.32. HPLC purity: >95%.

EXAMPLE 60

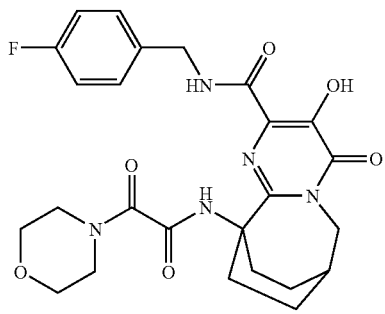

N-(4-Fluorobenzyl)-3-hydroxy-10-((4-morpholinyl(oxo)acetyl)amino)-4-oxo-4,6,7,8,9,10-hexahydro-7,10-ethanopyrimido[1,2-a]azepine-2-carboxamide. Off-white solid (8 mg, 24% yield). $^1$H NMR (500 MHz, CDCl$_3$) δ: 12.01 (s, 1H), 8.48 (t, 1H, J=5.80 Hz), 8.34 (s, 1H), 7.33-7.37 (m, 2H), 6.99-7.03 (m, 2H), 4.55 (d, 2H, J=6.41 Hz), 4.17 (d, 2H, J=3.97 Hz), 3.98-4.01 (m, 2H), 3.66-3.72 (m, 4H), 3.51-3.56 (m, 2H), 2.48-2.60 (m, 3H), 2.02-2.10 (m, 2H), 1.91-2.01 (m, 2H), 1.68-1.76 (m, 2H). LCMS (M+H)=514.30. HPLC purity: >95%.

EXAMPLE 61

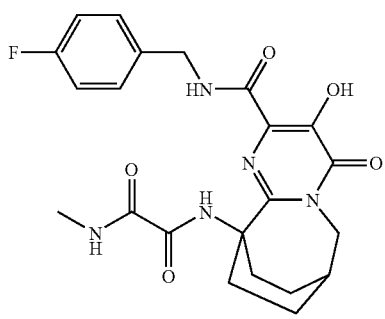

N-(2-((4-Fluorobenzyl)carbamoyl)-3-hydroxy-4-oxo-6,7,8,9-tetrahydro-7,10-ethanopyrimido[1,2-a]azepin-10(4H)-yl)-N'-methylethanediamide. Off-white solid (14 mg, 32% yield). $^1$H NMR (500 MHz, CDCl$_3$) δ: 12.01 (s, 1H), 9.79 (s, 1H), 7.98 (s, 1H), 7.43 (dd, 2H, J=8.39 & 5.34 Hz), 7.30-7.37 (m, 1H), 7.05 (t, 2H, J=8.70 Hz), 4.61 (d, 2H, J=6.41 hz), 4.15 (d, 2H, J=3.66 Hz), 2.88 (d, 3H, J=5.19 Hz), 2.79-2.87 (m, 2H), 2.49 (s, 1H), 1.98-2.07 (m, 2H), 1.80-1.87 (m, 2H), 1.70-1.78 (m, 2H). LCMS (M+H)=458.23. HPLC purity: >95%.

EXAMPLE 62

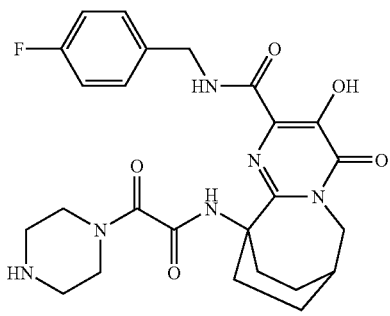

N-(4-Fluorobenzyl)-3-hydroxy-4-oxo-10-((oxo(1-piperazinyl)acetyl)amino)-4,6,7,8,9,10-hexahydro-7,10-ethanopyrimido[1,2-a]azepine-2-carboxamide. Off-white solid (40 mg, 19% yield). $^1$H NMR (500 MHz, MeOD) δ: 9.55 (1 H, brs), 8.93 (1 H, s), 7.48 (2 H, dd, J=8.24, 5.49 Hz), 7.06 (2 H, t, J=8.85 Hz), 4.65 (2 H, d, J=6.10 Hz), 4.23 (2 H, d, J=3.97 Hz), 3.83-3.94 (4 H, m), 3.21-3.34 (4 H, m), 2.55 (1 H, brs), 2.32-2.45 (2 H, m), 2.25-2.36 (2 H, m), 1.94-2.06 (2 H, m), 1.72-1.89 (2 H, m). LCMS (M+H)=513.44. HPLC purity: >95%.

EXAMPLE 63

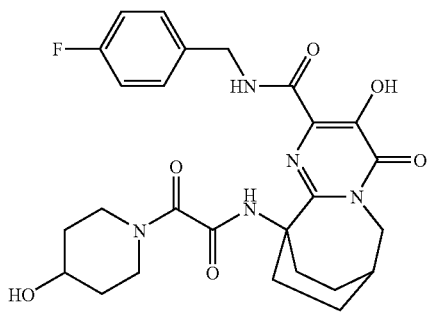

N-(4-Fluorobenzyl)-3-hydroxy-10-(((4-hydroxy-1-piperidinyl)(oxo)acetyl)amino)-4-oxo-4,6,7,8,9,10-hexahydro-7,10-ethanopyrimido[1,2-a]azepine-2-carboxamide. Light brown solid (3 mg, 10% yield). $^1$H NMR (500 MHz, CDCl$_3$) δ: 8.74 (1 H, brs), 7.92 (1 H, s), 7.34-7.43 (2 H, m), 7.01-7.09 (2 H, m), 4.54 (2 H, d, J=5.80 Hz), 4.13-4.24 (4 H, m), 4.01-4.08 (1 H, m), 3.85-3.94 (1 H, m), 3.62-3.69 (1 H, m), 3.33-3.38 (1 H, m), 2.45-2.53 (3 H, m), 1.92-2.06 (2 H, m), 1.84-1.92 (2 H, m), 1.73-1.86 (2 H, m). LCMS (M+H)=528.40. HPLC purity: >95%.

EXAMPLE 64

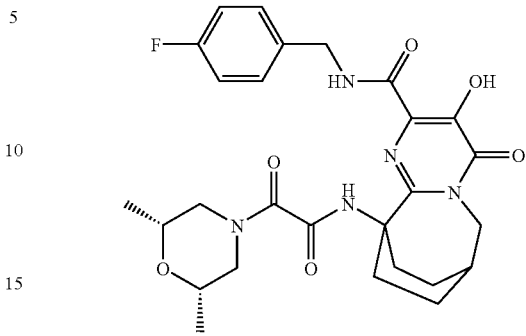

10-((((2R,6S)-2,6-Dimethyl-4-morpholinyl)(oxo)acetyl)amino)-N-(4-fluorobenzyl)-3-hydroxy-4-oxo-4,6,7,8,9,10-hexahydro-7,10-ethanopyrimido[1,2-a]azepine-2-carboxamide. Thick film (2.2 mg, 3% yield). $^1$H NMR (500 MHz, CDCl$_3$) δ: 12.25 (1 H, brs), 8.52 (1 H, brs), 8.48 (1 H, s), 7.46 (2 H, dd, J=8.55, 5.19 Hz), 7.12 (2 H, t, J=8.70 Hz), 4.78 (1 H, d, J=13.43 Hz), 4.63 (2 H, dd, J=5.95, 3.20 Hz), 4.28 (2 H, brs), 4.17 (1 H, s), 3.58-3.65 (1 H, m), 3.46-3.53 (1 H, m), 2.87 (1H, dd, J=13.43, 10.68 Hz), 2.54-2.66 (2 H, m), 2.59 (1 H, brs), 2.43 (2 H, dd, J=13.12, 10.68 Hz), 2.08-2.19 (2 H, m), 1.89-2.05 (2 H, m), 1.72-1.88 (2 H, m), 1.27 (3 H, d, J=6.10 Hz), 1.22 (3 H, d, J=6.41 Hz). LCMS (M+H)=542.44. HPLC purity: >95%.

EXAMPLE 65

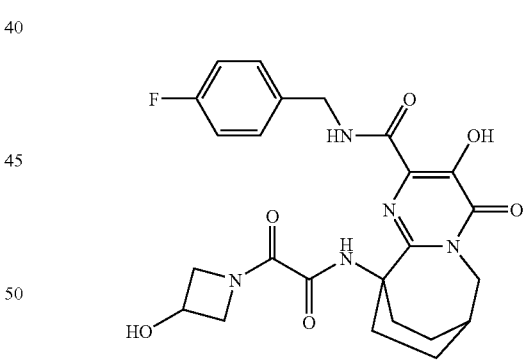

N-(4-Fluorobenzyl)-3-hydroxy-10-(((3-hydroxy-1-azetidinyl) (oxo)acetyl)amino)-4-oxo-4,6,7,8,9,10-hexahydro-7,10-ethanopyrimido[1,2-a]azepine-2-carboxamide. Off-white solid (3.5 mg, 7% yield). $^1$H NMR (500 MHz, CDCl$_3$) δ: 12.12 (1 H, brs), 9.64 (1 H, s), 8.14 (1 H, brs), 7.48 (2H, dd, J=8.55, 5.49 Hz), 7.03-7.19 (2 H, m), 4.84 (1 H, ddd, J=11.83, 6.49, 1.83 Hz), 4.64-4.72 (1 H, m), 4.56-4.67 (2 H, m), 4.47 (1 H, ddd, J=11.75, 4.12, 1.83 Hz), 4.33 (1 H, ddd, J=11.67, 6.79, 1.68 Hz), 4.14 (2 H, d, J=3.66 Hz), 3.90 (1 H, ddd, J=11.83, 4.20, 1.68 Hz), 2.82-2.98 (2 H, m), 2.58 (1 H, brs), 2.03-2.18 (2 H, m), 1.84-1.98 (2 H, m), 1.64-1.84 (2 H, m). LCMS (M+H)=500.39. HPLC purity: >95%.

EXAMPLE 66

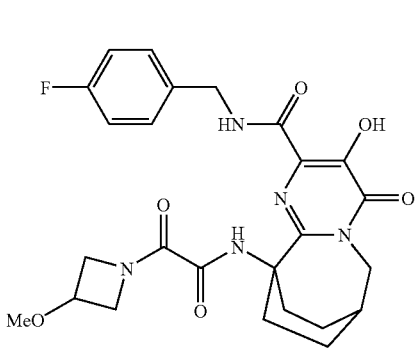

N-(4-Fluorobenzyl)-3-hydroxy-10-(((3-methoxy-1-azetidinyl) (oxo)acetyl)amino)-4-oxo-4,6,7,8,9,10-hexahydro-7,10-ethanopyrimido[1,2-a]azepine-2-carboxamide. Off-white solid (12 mg, 25% yield). $^1$H NMR (500 MHz, CDCl$_3$) δ: 12.12 (1 H, brs), 9.64 (1 H, s), 8.12 (1 H, brs), 7.46 (2H, dd, J=8.39, 5.34 Hz), 7.14 (2 H, t, J=8.70 Hz), 4.83 (1 H, dd, J=11.75, 6.26 Hz), 4.53-4.66 (2 H, m), 4.58 (1 H, dd, J=11.75, 2.29 Hz), 4.14-4.26 (2 H, m), 4.19 (2H, d, J=3.66 Hz), 3.92-4.08 (1 H, m), 2.82-2.96 (2 H, m), 2.54 (1 H, brs), 1.98-2.17 (2 H, m), 1.84-1.98 (2 H, m), 1.76-1.88 (2 H, m). LCMS (M+H)=514.23. HPLC purity: >95%.

EXAMPLE 67

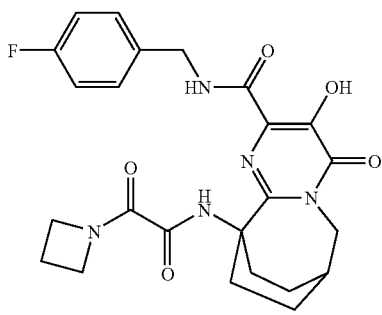

10-((1-Azetidinyl(oxo)acetyl)amino)-N-(4-fluorobenzyl)-3-hydroxy-4-oxo-4,6,7,8,9,10-hexahydro-7,10-ethanopyrimido[1,2-a]azepine-2-carboxamide. Off-white solid (20 mg, 45% yield). $^1$H NMR (500 MHz, CDCl$_3$) δ: 12.06 (1 H, brs), 9.67 (1 H, s), 8.12 (1 H, brs), 7.37-7.46 (2 H, m), 7.06 (2 H, t, J=8.55 Hz), 4.58-4.71 (4 H, m), 4.11 (2 H, d, J=3.66 Hz), 4.20 (2 H, t, J=7.78 Hz), 2.78-2.94 (2 H, m), 2.55 (1 H, brs), 2.33-2.47 (2 H, m), 1.89-2.02 (2 H, m), 1.76-1.94 (2 H, m), 1.71-1.88 (2 H, m). LCMS (M+H)=484.17. HPLC purity: >95%.

EXAMPLE 68

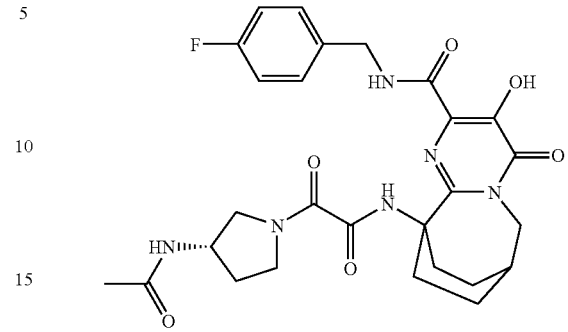

10-((((3S)-3-(Acetylamino)-1-pyrrolidinyl) (oxo)acetyl)amino)-N-(4-fluorobenzyl)-3-hydroxy-4-oxo-4,6,7,8,9,10-hexahydro-7,10-ethanopyrimido[1,2-a]azepine-2-carboxamide. White solid (12 mg, 25% yield). $^1$H NMR (500 MHz, CDCl$_3$) δ: 12.03 (1 H, brs), 9.46 (0.5 H, s), 9.35 (0.5 H, s), 8.13 (1 H, brs), 7.37-7.42 (2 H, m), 7.00-7.06 (2 H, m), 5.73 (1 H, brs), 4.45-4.64 (3 H, m), 4.00-4.24 (4 H, m), 3.85 (0.5 H, dd, J=13.43, 6.10 Hz), 3.71 (0.5 H, dd, J=13.43, 6.10 Hz), 3.49-3.58 (1 H, m), 2.70-2.81 (2 H, m), 2.49 (1 H, brs), 2.11-2.26 (2 H, m), 2.04 (1.6 H, s), 2.02 (1.4 H, s), 1.80-2.00 (4 H, m), 1.64-1.75 (2 H, m). LCMS (M+H)=555.56. HPLC purity: >95%.

EXAMPLE 69

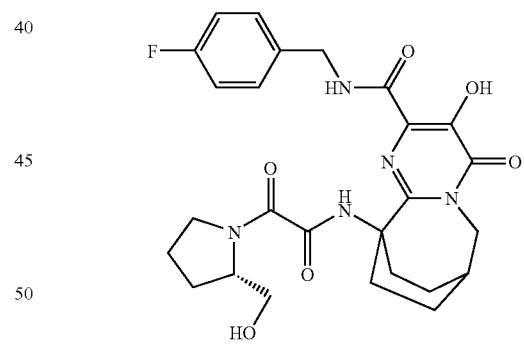

N-(4-Fluorobenzyl)-3-hydroxy-10-(((((2S)-2-(hydroxymethyl)-1-pyrrolidinyl)(oxo)acetyl)amino)-4-oxo-4,6,7,8,9,10-hexahydro-7,10-ethanopyrimido[1,2-a]azepine-2-carboxamide. Off-white solid (mixture of rotamers) (1.6 mg, 4% yield). $^1$H NMR (500 MHz, CDCl$_3$) δ: 9.47 (0.5 H, s), 9.25 (0.5 H, s), 8.04-8.17 (1 H, m), 7.32-7.42 (2 H, m), 6.97-7.08 (2 H, m), 4.41-4.69 (3 H, m), 4.09-4.24 (4 H, m), 3.77-4.08 (3 H, m), 3.43-3.70 (2 H, m), 2.68-2.87 (2 H, m), 2.50 (1 H, brs), 1.81-2.11 (4 H, m), 1.67-1.78 (2 H, m). LCMS (M+H)=528.49. HPLC purity: >95%.

EXAMPLE 70

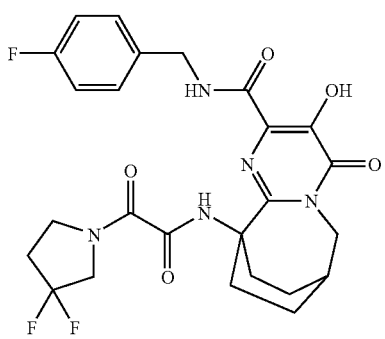

10-(((3,3-Difluoro-1-pyrrolidinyl)(oxo)acetyl)amino)-N-(4-fluorobenzyl)-3-hydroxy-4-oxo-4,6,7,8,9,10-hexahydro-7,10-ethanopyrimido[1,2-a]azepine-2-carboxamide. White solid (11 mg, 24% yield). $^1$H NMR (500 MHz, CDCl$_3$) δ: 11.99 (1 H, brs), 9.64 (0.6 H, s), 9.54 (0.4 H, s), 7.98-8.10 (1 H, m), 7.36-7.42 (2H, m), 6.99-7.07 (2 H, m), 4.59 (2 H, t, J=5.34 Hz), 4.23-4.34 (2 H, m), 4.16 (2 H, d, J=3.66 Hz), 3.76 & 3.68 (2 H, t, J=7.48 Hz), 2.73-2.87 (2 H, m), 2.49 (1 H, brs), 2.27-2.46 (2 H, m), 1.96-2.05 (2 H, m), 1.82-1.91 (2 H, m), 1.65-1.77 (2 H, m). LCMS (M+H)=534.35. HPLC purity: >95%.

EXAMPLE 71

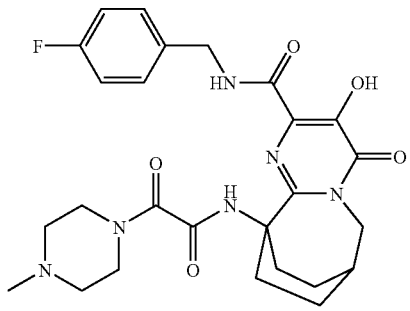

N-(4-Fluorobenzyl)-3-hydroxy-10-(((4-methyl-1-piperazinyl)(oxo)acetyl)amino)-4-oxo-4,6,7,8,9,10-hexahydro-7,10-ethanopyrimido[1,2-a]azepine-2-carboxamide. White solid (17 mg, 30% yield). $^1$H NMR (500 MHz, CDCl$_3$) δ: 12.03 (1 H, brs), 8.64 (1 H, s), 8.19 (1 H, t, J=5.95 Hz), 7.35 (2 H, dd, J=8.70, 5.34 Hz), 7.00-7.05 (2 H, m), 5.08-5.25 (1 H, m), 4.19-4.71 (4 H, m), 3.91-4.13 (1 H, m), 3.50-3.74 (3 H, m), 3.31 (1 H, brs), 2.88-3.01 (2 H, m), 2.85 (3 H, s), 2.55-2.69 (2 H, m), 2.51 (1 H, brs), 2.17 (1 H, brs), 1.66-2.05 (4 H, m). LCMS (M+H)=527.53. HPLC purity: >95%.

EXAMPLE 72

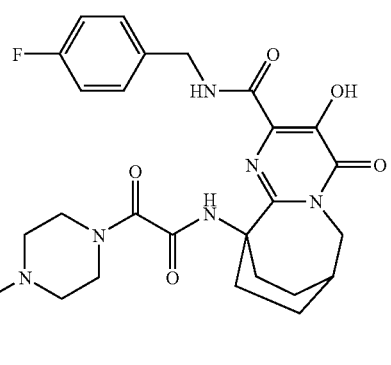

N-(4-Fluorobenzyl)-3-hydroxy-10-(((4-(2-hydroxyethyl)-1-piperazinyl)(oxo)acetyl)amino)-4-oxo-4,6,7,8,9,10-hexahydro-7,10-ethanopyrimido[1,2-a]azepine-2-carboxamide. White solid (6 mg, 10% yield). $^1$H NMR (500 MHz, CDCl$_3$) δ: 12.02 (1 H, brs), 8.67 (1 H, s), 8.17 (1 H, t, J=5.80 Hz), 7.33-7.37 (2 H, m), 7.01-7.05 (2 H, m), 4.52-4.62 (2 H, m), 4.11-4.24 (2 H, m), 4.00-4.06 (3 H, m), 3.15-3.20 (4 H, m), 2.56-2.66 (4 H, m), 2.47-2.54 (2 H, m), 1.92-2.04 (5 H, m), 1.68-1.77 (3 H, m). LCMS (M+H)=557.55. HPLC purity: >95%.

EXAMPLE 73

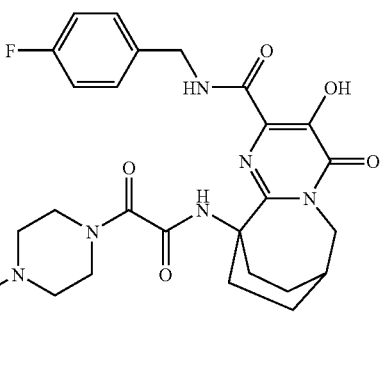

N-(4-Fluorobenzyl)-3-hydroxy-10-(((4-(2-methoxyethyl)-1-piperazinyl)(oxo)acetyl)amino)-4-oxo-4,6,7,8,9,10-hexahydro-7,10-ethanopyrimido[1,2-a]azepine-2-carboxamide. White solid (14 mg, 23% yield). $^1$H NMR (500 MHz, CDCl$_3$) δ: 12.01 (1 H, brs), 8.60 (1 H, s), 8.22 (1 H, brs), 7.32-7.38 (2 H, m), 7.02 (2 H, t, J=8.24 Hz), 4.49-4.66 (3 H, m), 4.07-4.30 (4 H, m), 3.73-3.79 (4 H, m), 3.36 (3 H, s), 3.22-3.27 (3 H, m), 2.48-2.65 (3 H, m), 1.92-2.03 (3 H, m), 1.67-1.78 (2 H, m). LCMS (M+H)=571.58. HPLC purity: >95%.

EXAMPLE 74

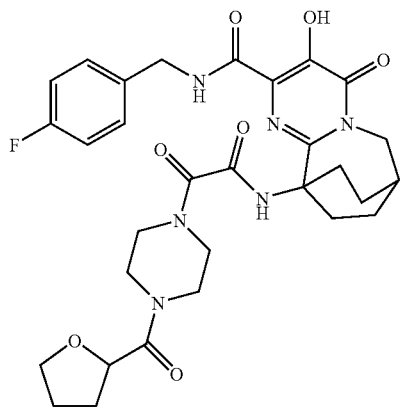

N-(4-Fluorobenzyl)-3-hydroxy-4-oxo-10-((oxo(4-(tetrahydro-2-furanylcarbonyl)-1-piperazinyl)acetyl)amino)-4,6,7,8,9,10-hexahydro-7,10-ethanopyrimido[1,2-a]azepine-2-carboxamide. White solid (6.4 mg, 15% yield). $^1$H NMR (500 MHz, CDCl$_3$) δ: 11.88 (1 H, brs), 8.23-8.52 (2 H, m), 7.35 (2 H, dd, J=8.39, 5.34 Hz), 7.02 (2 H, t, J=8.55 Hz), 4.42-4.66 (3 H, m), 4.05-4.24 (3 H, m), 3.61-4.00 (5 H, m), 3.33-3.60 (3 H, m), 2.74-3.32 (3 H, m), 2.42-2.65 (3 H, m), 2.41-2.65 (3 H, m), 1.80-2.18 (6 H, m), 1.62-1.80 (2 H, m). LCMS (M+H) calcd for C$_{30}$H$_{36}$FN$_6$O$_7$: 611.26; found: 611.73.

EXAMPLE 75

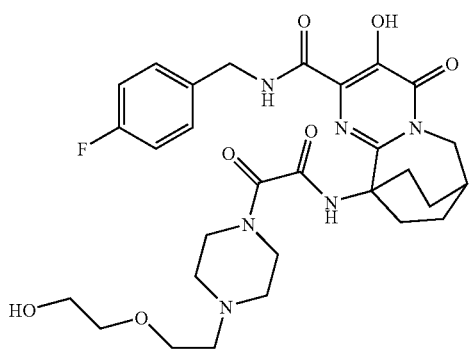

N-(4-Fluorobenzyl)-3-hydroxy-10-(((4-(2-(2-hydroxyethoxy)ethyl)-1-piperazinyl)(oxo)acetyl)amino)-4-oxo-4,6,7,8,9,10-hexahydro-7,10-ethanopyrimido[1,2-a]azepine-2-carboxamide. White solid (11.1 mg, 28% yield). LCMS (M+H) calcd for C$_{29}$H$_{38}$FN$_6$O$_7$: 601.27; found: 601.71.

EXAMPLE 76

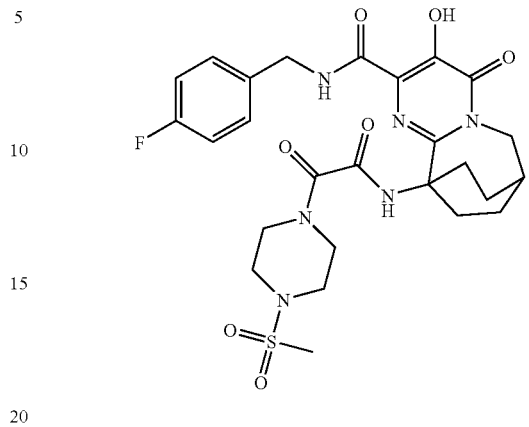

N-(4-Fluorobenzyl)-3-hydroxy-10-(((4-(methylsulfonyl)-1-piperazinyl)(oxo)acetyl)amino)-4-oxo-4,6,7,8,9,10-hexahydro-7,10-ethanopyrimido[1,2-a]azepine-2-carboxamide. White solid (2.0 mg, 6% yield). $^1$H NMR (500 MHz, CDCl$_3$) δ: 11.99 (1 H, brs), 8.45 (1 H, s), 8.37 (1 H, t, J=5.65 Hz), 7.36 (2 H, dd, J=8.55, 5.19 Hz), 6.94-7.09 (2 H, m), 4.56 (2 H, d, J=6.10 Hz), 4.16 (2 H, d, J=3.97 Hz), 4.05-4.13 (2 H, m), 3.55-3.74 (2 H, m), 3.24-3.34 (2H, m), 3.12-3.24 (2 H, m), 2.79 (3 H, s), 2.54-2.65 (2 H, m), 2.51 (1 H, brs), 1.88-2.21 (4 H, m), 1.67-1.78 (2 H, m). LCMS (M+H) calcd for C$_{26}$H$_{32}$FN$_6$O$_7$S: 591.20; found: 591.33.

EXAMPLE 77

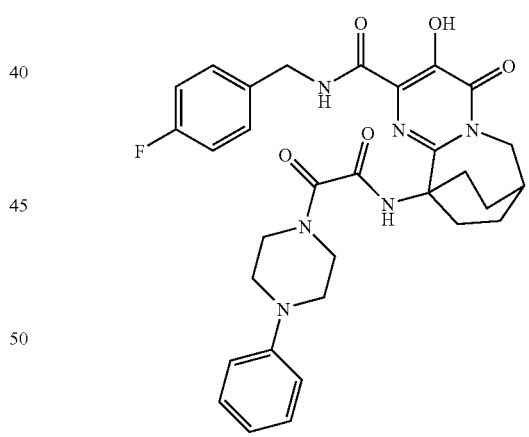

N-(4-Fluorobenzyl)-3-hydroxy-4-oxo-10-((oxo(4-phenyl-1-piperazinyl)acetyl)amino)-4,6,7,8,9,10-hexahydro-7,10-ethanopyrimido[1,2-a]azepine-2-carboxamide. White solid (9.8 mg, 30% yield). $^1$H NMR (500 MHz, CDCl$_3$) δ: 12.00 (1 H, s), 8.52 (1 H, t, J=5.65 Hz), 8.36 (1 H, s), 7.38 (2 H, dd, J=8.55, 5.49 Hz), 7.29 (2 H, t, J=7.93 Hz), 7.02 (2 H, t, J=8.70 Hz), 6.84-6.97 (3 H, m), 4.56 (2 H, d, J=6.10 Hz), 4.17 (2 H, d, J=3.66 Hz), 4.10-4.15 (2 H, m), 3.65-3.72 (2 H, m), 3.19 (4 H, dt, J=14.27, 5.07 Hz), 2.58 (2 H, ddd, J=14.34, 9.31, 5.34 Hz), 2.51 (1 H, brs), 2.02-2.13 (2 H, m), 1.87-2.02 (2 H, m), 1.66-1.77 (2 H, m). LCMS (M+H) calcd for C$_{31}$H$_{34}$FN$_6$O$_5$: 589.25; found: 589.77.

EXAMPLE 78

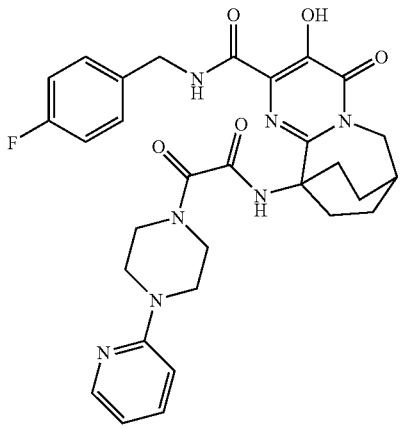

N-(4-Fluorobenzyl)-3-hydroxy-4-oxo-10-((oxo(4-(2-pyridinyl)-1-piperazinyl)acetyl)amino)-4,6,7,8,9,10-hexahydro-7,10-ethanopyrimido[1,2-a]azepine-2-carboxamide. White solid (8.1 mg, 18% yield). $^1$H NMR (500 MHz, CDCl$_3$) δ: 11.93 (1 H, brs), 8.66 (1 H, s), 8.32 (1 H, t, J=5.95 Hz), 8.11-8.26 (1 H, m), 7.86-8.08 (1 H, m), 7.36 (2 H, dd, J=8.55, 5.49 Hz), 7.02 (2 H, t, J=8.70 Hz), 6.89-6.99 (2 H, m), 4.57 (2 H, d, J=6.10 Hz), 4.21-4.33 (2 H, m), 4.16 (2 H, d, J=3.66 Hz), 3.58-3.95 (6 H, m), 2.58-2.78 (2 H, m), 2.51 (1 H, brs), 1.88-2.15 (4 H, m), 1.60-1.78 (2 H, m). LCMS (M+H) calcd for $C_{30}H_{33}FN_7O_5$: 590.25; found: 590.74.

EXAMPLE 79

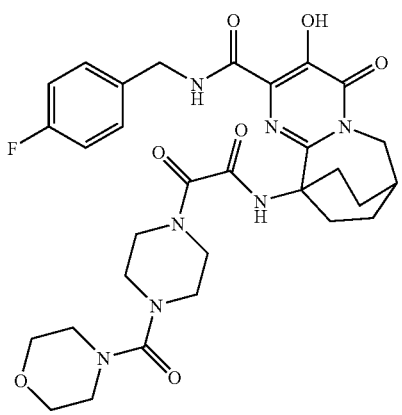

N-(4-Fluorobenzyl)-3-hydroxy-10-(((4-(4-morpholinylcarbonyl)-1-piperazinyl)(oxo)acetyl)amino)-4-oxo-4,6,7,8,9,10-hexahydro-7,10-ethanopyrimido[1,2-a]azepine-2-carboxamide. Pale pink foam (7.3 mg, 21% yield). $^1$H NMR (500 MHz, CDCl$_3$) δ: 12.01 (1 H, brs), 8.45 (1 H, t, J=5.34 Hz), 8.35 (1 H, s), 7.36 (2 H, dd, J=8.39, 5.34 Hz), 7.02 (2 H, t, J=8.55 Hz), 4.55 (2 H, d, J=6.10 Hz), 4.16 (2 H, d, J=3.66 Hz), 3.91-4.01 (2 H, m), 3.60-3.81 (4 H, m), 3.42-3.59 (2 H, m), 3.20-3.39 (8 H, m), 2.41-2.63 (3 H, m), 2.01-2.11 (2 H, m), 1.92-2.01 (2 H, m), 1.64-1.76 (2 H, m). LCMS (M+H) calcd for $C_{30}H_{37}FN_7O_7$: 626.27; found: 626.80.

EXAMPLE 80

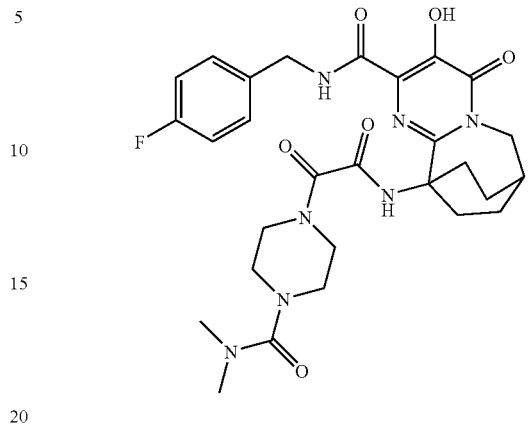

10-(((4-(Dimethylcarbamoyl)-1-piperazinyl)(oxo)acetyl)amino)-N-(4-fluorobenzyl)-3-hydroxy-4-oxo-4,6,7,8,9,10-hexahydro-7,10-ethanopyrimido[1,2-a]azepine-2-carboxamide. White solid (14.4 mg, 44% yield). $^1$H NMR (500 MHz, CDCl$_3$) δ: 12.00 (1 H, s), 8.50 (1 H, t, J=5.95 Hz), 8.30 (1 H, s), 7.36 (2 H, dd, J=8.55, 5.19 Hz), 6.95-7.09 (2 H, m), 4.55 (2 H, d, J=6.10 Hz), 4.16 (2 H, d, J=3.97 Hz), 3.97 (2 H, dd, J=5.95, 4.12 Hz), 3.47-3.58 (2 H, m), 3.25 (4 H, ddd, J=18.77, 5.04, 4.88 Hz), 2.85 (6 H, s), 2.45-2.63 (3 H, m), 2.00-2.12 (2 H, m), 1.86-2.01 (2H, m), 1.63-1.80 (2 H, m). LCMS (M+H) calcd for $C_{28}H_{35}FN_7O_6$: 584.26; found: 584.25.

EXAMPLE 81

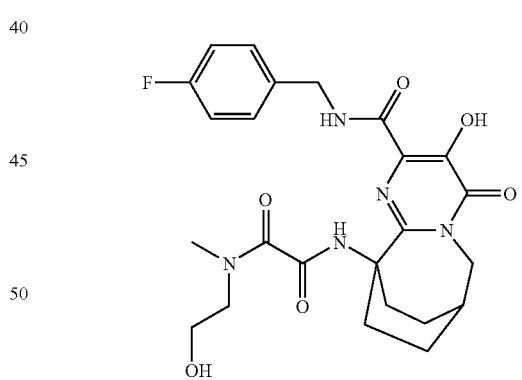

N'-(2-((4-Fluorobenzyl)carbamoyl)-3-hydroxy-4-oxo-6,7,8,9-tetrahydro-7,10-ethanopyrimido[1,2-a]azepin-10 (4H)-yl)-N-(2-hydroxyethyl)-N-methylethanediamide. Thick film (2.5 mg, 6% yield). $^1$H NMR (500 MHz, CDCl$_3$) δ: 13.00 (1 H, brs), 8.54 (1 H, s), 8.40 (1 H, brs), 7.32-7.38 (2 H, m), 6.99-7.05 (2H, m), 4.53-4.60 (2 H, m), 4.17 (2 H, d, J=3.66 Hz), 3.74-3.85 (2 H, m), 3.35 (1.5H, s), 2.94 (1.5 H, s), 2.54-2.66 (4 H, m), 2.50 (1 H, brs), 1.94-2.10 (4 H, m), 1.68-1.76 (2 H, m). LCMS (M+H)=502.44. HPLC purity: >95%.

EXAMPLE 82

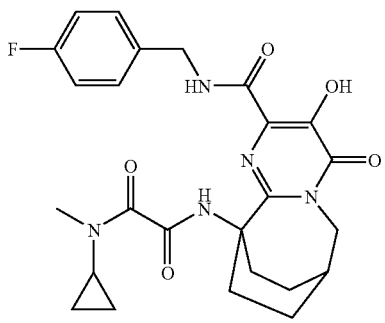

N-Cyclopropyl-N'-(2-((4-fluorobenzyl)carbamoyl)-3-hydroxy-4-oxo-6,7,8,9-tetrahydro-7,10-ethanopyrimido[1,2-a]azepin-10(4H)-yl)-N-methylethanediamide. Off-white solid (1.3 mg, 3% yield). $^1$H NMR (500 MHz, CDCl$_3$) δ: 12.15 (1 H, brs), 9.71 (1 H, brs), 7.67 (1 H, brs), 7.37-7.40 (2 H, m), 7.04-7.07 (2 H, m), 4.60 (2 H, d, J=6.41 Hz), 4.17 (2 H, d, J=3.66 Hz), 2.82-2.90 (2 H, m), 2.52 (1 H, brs), 1.99-2.09 (2 H, m), 1.82-1.89 (2 H, m), 1.73-1.80 (2 H, m). LCMS (M+H)=498.43. HPLC purity: >95%.

From this reaction Examples 83 and 84 were also isolated

EXAMPLE 83

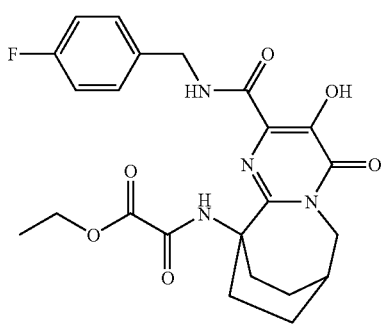

Ethyl((2-((4-fluorobenzyl)carbamoyl)-3-hydroxy-4-oxo-6,7,8,9-tetrahydro-7,10-ethanopyrimido[1,2-a]azepin-10(4H)-yl)amino)(oxo)acetate. White solid (12 mg, 29% yield). $^1$H NMR (500 MHz, CDCl$_3$) δ: 12.00 (1 H, brs), 9.50 (1 H, s), 7.70 (1 H, t, J=5.34 Hz), 7.36-7.41 (2 H, m), 7.02-7.08 (2 H, m), 4.60 (2 H, d, J=6.10 Hz), 4.27 (3 H, q, J=7.02 Hz), 4.17 (2 H, d, J=3.66 Hz), 2.87-2.96 (2 H, m), 2.50 (1H, brs), 1.99-2.08 (2 H, m), 1.77-1.85 (2 H, m), 1.67-1.77 (2 H, m), 1.36 (3 H, t, J=7.17 Hz). LCMS (M+H)=473.43. HPLC purity: >95%.

EXAMPLE 84

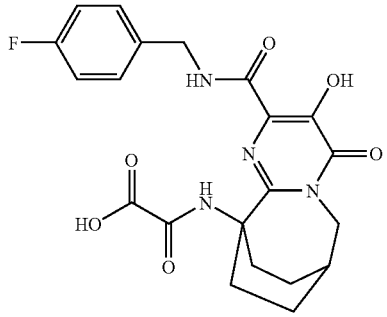

((2-((4-Fluorobenzyl)carbamoyl)-3-hydroxy-4-oxo-6,7,8,9-tetrahydro-7,10-ethanopyrimido[1,2-a]azepin-10(4H)-yl)amino)(oxo)acetic acid. Off-white solid (2.6 mg, 7% yield). $^1$H NMR (500 MHz, CDCl$_3$) δ: 12.05 (1 H, brs), 8.92 (1 H, brs), 7.33-7.38 (2 H, m), 6.98-7.05 (3 H, m), 4.53 (2 H, d, J=6.41 Hz), 4.17 (2 H, d, J=3.97 Hz), 2.98-3.03 (1 H, m), 2.88 (3 H, s), 2.51 (1 H, brs), 2.30-2.38 (2 H, m), 2.20-2.27 (2 H, m), 2.02-2.10 (1 H, m), 1.90-1.98 (2 H, m), 1.71-1.76 (4 H, m) LCMS (M+H)=445.39. HPLC purity: >95%.

EXAMPLE 85

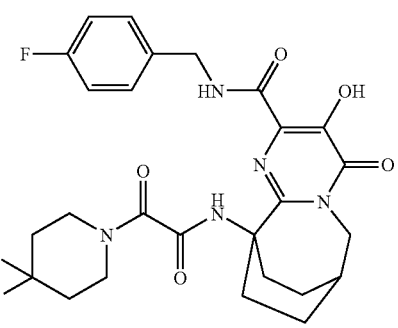

10-(((4,4-Difluoro-1-piperidinyl) (oxo)acetyl)amino)-N-(4-fluorobenzyl)-3-hydroxy-4-oxo-4,6,7,8,9,10-hexahydro-7,10-ethanopyrimido[1,2-a]azepine-2-carboxamide. Off-white solid (4 mg, 8). $^1$H NMR (500 MHz, CDCl$_3$) δ: 12.01 (1 H, brs), 8.43 (1 H, brs), 8.33 (1 H, s), 7.36 (2 H, dd, J=7.78, 5.65 Hz), 7.02 (2 H, t, J=8.55 Hz), 4.55 (2 H, d, J=6.10 Hz), 4.16 (2 H, d, J=3.66 Hz), 4.03 (2 H, t, J=5.49 Hz), 3.64 (2 H, t, J=5.80 Hz), 2.47-2.61 (3 H, m), 2.01-2.11 (4 H, m), 1.91-2.01 (4 H, m), 1.68-1.76 (2 H, m). LCMS (M+H)=548.49. HPLC purity: >95%.

EXAMPLE 86

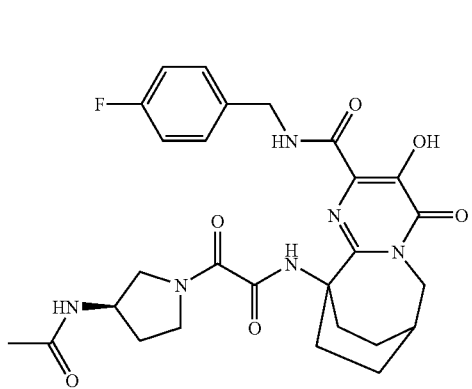

10-((((3R)-3-(Dcetylamino)-1-pyrrolidinyl)(oxo)acetyl) amino)-N-(4-fluorobenzyl)-3-hydroxy-4-oxo-4,6,7,8,9,10-hexahydro-7,10-ethanopyrimido[1,2-a]azepine-2-carboxamide. Off-white solid (17 mg, 0.031 mmol, 28% yield). $^1$H NMR (500 MHz, CDCl$_3$) δ: 12.03 (1 H, brs), 9.46 (0.4 H, s), 9.35 (0.6 H, s), 8.13 (1H, brs), 7.37-7.42 (2 H, m), 7.00-7.06 (2 H, m), 5.73 (1 H, brs), 4.45-4.64 (3 H, m), 4.00-4.24 (4 H, m), 3.85 (0.6 H, dd, J=13.43, 6.10 Hz), 3.71 (0.4 H, dd, J=13.43, 6.18 Hz), 3.49-3.58 (1 H, m), 2.70-2.81 (2 H, m), 2.49 (1 H, brs), 2.11-2.26 (2 H, m), 2.04 & 2.02 (3 H, s), 1.80-2.00 (4 H, m), 1.64-1.75 (2 H, m). LCMS (M+H)= 555.56. HPLC purity: >95%.

EXAMPLE 87

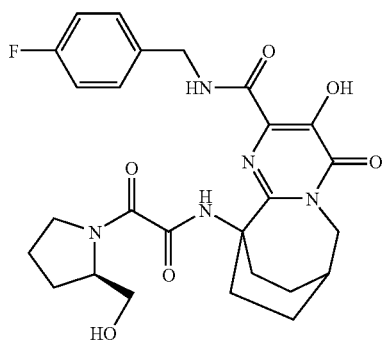

N-(4-Fluorobenzyl)-3-hydroxy-10-((((2R)-2-(hydroxymethyl)-1-pyrrolidinyl)(oxo)acetyl)amino)-4-oxo-4,6,7,8,9,10-hexahydro-7,10-ethanopyrimido[1,2-a]azepine-2-carboxamide. Off-white solid (18 mg, 31% yield). $^1$H NMR (500 MHz, CDCl$_3$) δ: 9.47 (0.5 H, s), 9.25 (0.5 H, s), 8.04-8.17 (1 H, m), 7.32-7.42 (2 H, m), 6.97-7.08 (2 H, m), 4.41-4.69 (3 H, m), 4.09-4.24 (4 H, m), 3.77-4.08 (3 H, m), 3.43-3.70 (2 H, m), 2.68-2.87 (2 H, m), 2.50 (1 H, brs), 1.81-2.11 (4 H, m), 1.67-1.78 (2 H, m). LCMS (M+H)=528.49. HPLC purity: >95%.

EXAMPLE 88

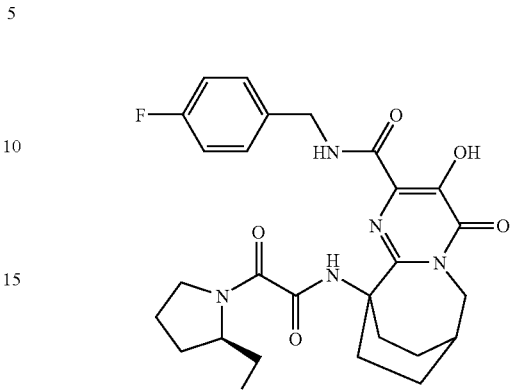

N-(4-Fluorobenzyl)-3-hydroxy-10-((((2R)-2-(methoxymethyl)-1-pyrrolidinyl)(oxo)acetyl)amino)-4-oxo-4,6,7,8,9,10-hexahydro-7,10-ethanopyrimido[1,2-a]azepine-2-carboxamide. Off-white solid (20 mg, 34% yield). $^1$H NMR (500 MHz, CDCl$_3$) δ: 12.03 (1 H, brs), 9.35 (0.6 H, s), 8.93 (0.4 H, s), 8.23-8.37 (1 H, m), 7.34-7.42 (2 H, m), 7.02 (2 H, q, J=8.44 Hz), 4.91-4.98 (1.3 H, m), 4.07-4.26 (1.7 H, m), 4.58 (2 H, dd, J=10.07, 6.41 Hz), 3.97 (2 H, s), 3.89-3.94 (1H, m), 3.35-3.53 (3 H, m), 3.32 (3 H, s), 2.62-2.80 (3 H, m), 2.49 (1 H, brs), 1.85-2.03 (5 H, m), 1.66-1.77 (2 H, m). LCMS (M+H)= 542.69. HPLC purity: >95%.

EXAMPLE 89

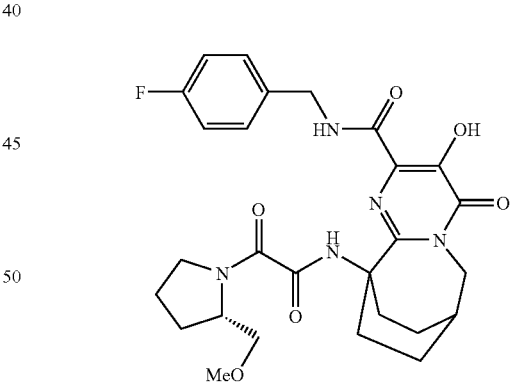

N-(4-Fluorobenzyl)-3-hydroxy-10-((((2S)-2-(methoxymethyl)-1-pyrrolidinyl)(oxo)acetyl)amino)-4-oxo-4,6,7,8,9,10-hexahydro-7,10-ethanopyrimido[1,2-a]azepine-2-carboxamide. Off-white solid (21 mg, 36% yield). $^1$H NMR (500 MHz, CDCl$_3$) δ: 12.03 (1 H, brs), 9.35 (0.6 H, s), 8.93 (0.4 H, s), 8.23-8.37 (1 H, m), 7.34-7.42 (2 H, m), 7.02 (2 H, q, J=8.44 Hz), 4.91-4.98 (1.3 H, m), 4.07-4.26 (1.7 H, m), 4.58 (2 H, dd, J=10.07, 6.41 Hz), 3.97 (2 H, s), 3.89-3.94 (1H, m), 3.35-3.53 (3 H, m), 3.32 (3 H, s), 2.62-2.80 (3 H, m), 2.49 (1 H, brs), 1.85-2.03 (5 H, m), 1.66-1.77 (2 H, m). LCMS (M+H)= 542.69. HPLC purity: >95%.

EXAMPLE 90

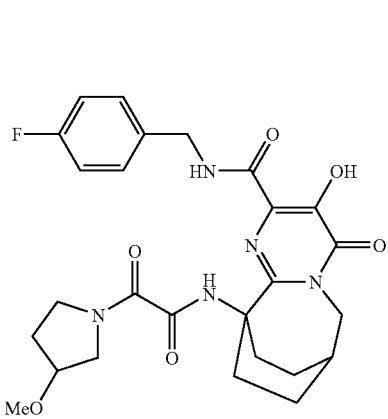

N-(4-Fluorobenzyl)-3-hydroxy-10-(((3-methoxy-1-pyrrolidinyl)(oxo)acetyl)amino)-4-oxo-4,6,7,8,9,10-hexahydro-7,10-ethanopyrimido[1,2-a]azepine-2-carboxamide. Tan solid (12 mg, 21% yield). $^1$H NMR (500 MHz, CDCl$_3$) δ: 12.01 (1 H, brs), 9.37 (1 H, s), 8.18 (1 H, brs), 7.35-7.42 (2 H, m), 6.98-7.06 (2 H, m), 4.52-4.64 (2 H, m), 4.09-4.25 (3 H, m), 3.83-4.04 (2 H, m), 3.40-3.70 (2 H, m), 3.34 (3 H, d, J=6.10 Hz), 2.66-2.82 (3 H, m), 2.49 (1 H, brs), 1.79-2.21 (5 H, m), 1.66-1.76 (2 H, m). LCMS (M+H)=528.66. HPLC purity: >95%.

EXAMPLE 91

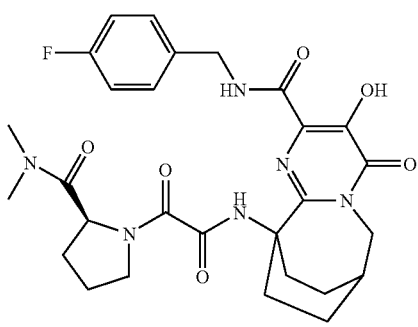

10-((((2S)-2-(Dimethylcarbamoyl)-1-pyrrolidinyl) (oxo)acetyl)amino)-N-(4-fluorobenzyl)-3-hydroxy-4-oxo-4,6,7,8,9,10-hexahydro-7,11-ethanopyrimido[1,2-a]azepine-2-carboxamide. Brown solid (14 mg, 23% yield). $^1$H NMR (500 MHz, CDCl$_3$) δ: 12.24 (1 H, brs), 9.14 (0.4 H, s), 8.78 (0.6 H, s), 8.36 (0.4 H, br.s), 8.24 (0.6 H, brs), 7.30-7.41 (2 H, m), 6.96-7.04 (2 H, m), 4.62-4.70 (2 H, m), 4.45-4.53 (1 H, m), 4.05-4.28 (3 H, m), 3.97 (1 H, s), 3.67-3.75 (1 H, m), 3.48-3.58 (1H, m), 3.11 (1.4 H, s), 3.06 (1.6 H, s), 2.93 (3 H, s), 2.53-2.70 (2 H, m), 2.47 (1 H, brs), 2.27-2.37 (1 H, m), 2.04-2.19 (1 H, m), 1.80-2.04 (5 H, m), 1.62-1.78 (2 H, m). LCMS (M+H)=569.76. HPLC purity: >95%.

EXAMPLE 92

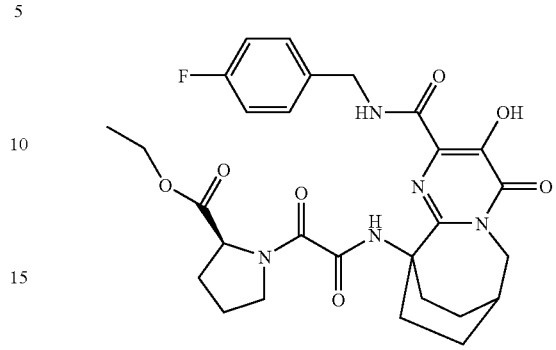

Ethyl 1-(((2-((4-fluorobenzyl)carbamoyl)-3-hydroxy-4-oxo-6,7,8,9-tetrahydro-7,11-ethanopyrimido[1,2-a]azepin-10(4H)-yl)amino) (oxo)acetyl)-L-prolinate. Off-white solid (mixture of isomers) (12 mg, 19% yield). $^1$H NMR (500 MHz, CDCl$_3$) δ: 11.88 (1 H, brs), 9.49 (0.6 H, s), 9.29 (0.4 H, s), 8.06-8.21 (1 H, m), 7.34-7.44 (2 H, m), 6.98-7.08 (2 H, m), 5.15 (1 H, dd, J=8.85, 3.66 Hz) & 4.57 (1 H, d, J=5.80 Hz), 4.61-4.69 (1 H, m), 4.54 (1 H, d, J=5.49 Hz) & 4.39-4.50 (1H, m), 4.12-4.22 (4 H, m), 3.65-3.74 (1 H, m), 3.46-3.57 (1 H, m), 2.64-2.79 (2H, m), 2.26-2.36 (2 H, m), 2.17 (1 H, brs), 1.83-2.02 (6 H, m), 1.65-1.75 (2 H, m), 1.25 (3 H, t, J=7.17 Hz). LCMS (M+H)=570.76. HPLC purity: >95%.

EXAMPLE 93

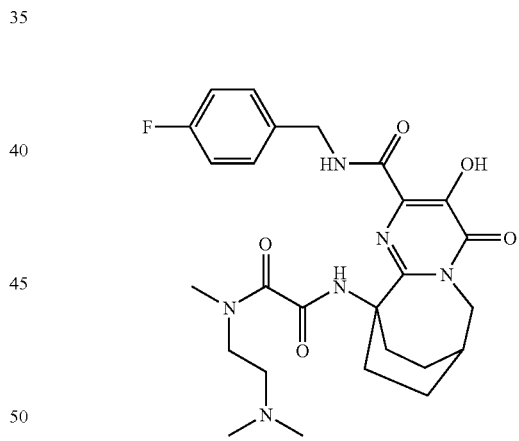

N-(2-(Dimethylamino)ethyl)-N'-(2-((4-fluorobenzyl)carbamoyl)-3-hydroxy-4-oxo-6,7,8,9-tetrahydro-7,10-ethanopyrimido[1,2-a]azepin-10(4H)-yl)-N-methylethanediamide. Off-white solid (20 mg, 48% yield). $^1$H NMR (500 MHz, CDCl$_3$) δ: 11.10 (1 H, brs), 9.14 (0.7 H, brs), 8.95 (0.3 H, s), 8.23 (0.3 H, brs), 8.07 (0.7 H, s), 7.37 (0.5 H, dd, J=8.55, 5.49 Hz), 7.29 (1.5 H, dd, J=8.39, 5.34 Hz), 6.98-7.05 (2 H, m), 4.56 (2 H, d, J=6.41 Hz), 4.17 (1.5 H, d, J=3.66 Hz), 4.15 (0.5 H, d, J=3.97 Hz), 4.04-4.09 (0.5 H, m), 3.55-3.62 (1.5 H, m), 3.33-3.38 (0.5 H, m), 3.22-3.28 (1.5 H, m), 3.11 (2.3 H, s), 2.96 (0.7 H, s), 2.76 (6 H, s), 2.46-2.64 (3 H, m), 2.09-2.18 (1.5 H, m), 1.91-2.01 (2.5 H, m), 1.65-1.77 (2 H, m). LCMS (M+H)=529.68. HPLC purity: >95%.

EXAMPLE 94

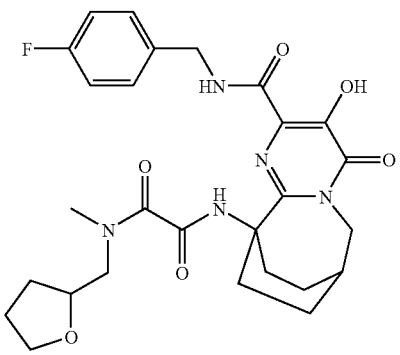

N'-(2-((4-Fluorobenzyl)carbamoyl)-3-hydroxy-4-oxo-6,7,8,9-tetrahydro-7,10-ethanopyrimido[1,2-a]azepin-10(4H)-yl)-N-methyl-N-(tetrahydro-2-furanylmethyl)ethanediamide. White solid (3.5 mg, 9% yield). $^1$H NMR (500 MHz, CDCl$_3$) δ: 12.05 (1 H, brs), 8.55-8.69 (1 H, m), 8.25 (0.7 H, s), 8.02 (0.3 H, s), 7.31-7.39 (2 H, m), 6.96-7.05 (2 H, m), 4.55 (2 H, dd, J=6.10, 2.75 Hz), 4.01-4.29 (3H, m), 3.70-3.89 (3 H, m), 3.33 (1.1 H, s), 2.98 (1.9 H, s), 2.42-2.60 (3 H, m), 1.83-2.27 (8 H, m), 1.62-1.78 (2 H, m), 1.41-1.56 (1 H, m). LCMS (M+H)=542.68. HPLC purity: >95%.

EXAMPLE 95

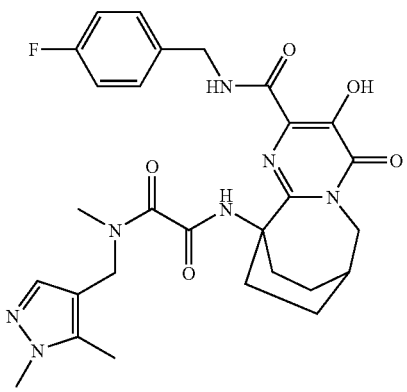

N-((1,5-Dimethyl-1H-pyrazol-4-yl)methyl)-N'-(2-((4-fluorobenzyl)carbamoyl)-3-hydroxy-4-oxo-6,7,8,9-tetrahydro-7,10-ethanopyrimido[1,2-a]azepin-10(4H)-yl)-N-methylethanediamide. Light pink solid (2.6 mg, 7% yield). $^1$H NMR (500 MHz, CDCl$_3$) δ: 12.20 (1 H, brs), 8.55 (0.5 H, brs), 8.45 (1 H, brs), 8.22 (0.5 H, s), 7.62 (0.4 H, s), 7.53 (0.6 H, s), 7.32-7.39 (2 H, m), 6.95-7.02 (2 H, m), 4.76 (1.5 H, s), 4.57 (2.5 H, dd, J=10.22, 6.26 Hz), 4.18 (2H, d, J=3.05 Hz), 3.88 (1.4 H, s), 3.86 (1.6 H, s), 3.19 (1.6 H, s), 2.79 (1.4 H, s), 2.47-2.61 (3 H, m), 2.28 (1.3 H, s), 2.23 (1.7 H, s), 2.03-2.12 (2 H, m), 1.91-2.01 (2 H, m), 1.64-1.77 (2 H, m). LCMS (M+H)=566.63. HPLC purity: >95%.

EXAMPLE 96

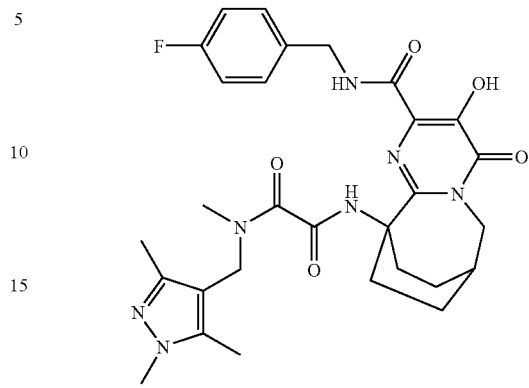

N-((1,3-Dimethyl-1H-pyrazol-4-yl)methyl)-N'-(2-((4-fluorobenzyl)carbamoyl)-3-hydroxy-4-oxo-6,7,8,9-tetrahydro-7,10-ethanopyrimido[1,2-a]azepin-10(4H)-yl)-N-methylethanediamide. Thick film (2.5 mg, 4% yield). $^1$H NMR (500 MHz, CDCl$_3$) δ: 11.55 (1 H, brs), 8.49-8.56 (1 H, m), 8.28 (0.4 H, s), 8.26 (0.6 H, s), 7.48 (0.6 H, s), 7.32-7.39 (2 H, m), 7.19 (0.4 H, s), 6.92-7.02 (2 H, m), 4.62 (1 H, s), 4.52-4.58 (2 H, m), 4.27 (1 H, s), 4.17 (2 H, d, J=3.66 Hz), 3.90 (1.6 H, s), 3.87 (1.4 H, s), 3.20 (1.4 H, s), 2.82 (1.6 H, s), 2.49-2.59 (3 H, m), 2.30 (1.6 H, s), 2.28 (1.4 H, s), 2.04-2.15 (2 H, m), 1.92-2.02 (2 H, m), 1.67-1.77 (2 H, m). LCMS (M+H)=566.65. HPLC purity: >95%.

EXAMPLE 97

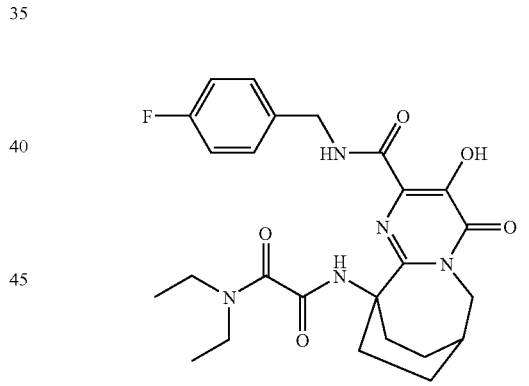

N,N-Diethyl-N'-(2-((4-fluorobenzyl)carbamoyl)-3-hydroxy-4-oxo-6,7,8,9-tetrahydro-7,10-ethanopyrimido[1,2-a]azepin-10(4H)-yl)ethanediamide. To a stirred solution of 10-amino-N-(4-fluorobenzyl)-3-hydroxy-4-oxo-4,6,7,8,9,10-hexahydro-7,10-ethanopyrimido[1,2-a]azepine-2-carboxamide (50 mg, 0.122 mmol) in DMF (3 mL) was added 2-(diethylamino)-2-oxoacetic acid (35.5 mg, 0.245 mmol), diisopropyl-ethylamine (0.128 mL, 0.734 mmol), O-(7-azabenzotriazol-1-yl)-N,N,N',N'-tetramethyluronium hexafluorophosphate (HATU) (93 mg, 0.245 mmol) and 4-(dimethylamino)pyridine (DMAP) (2.99 mg, 0.024 mmol) and the resulting mixture stirred at room temperature for 3 h. After work-up, the crude was then purified by prep HPLC to afford the title compound as a white solid (30 mg, 49% yield). $^1$H NMR (500 MHz, CDCl$_3$) δ: 12.0 (1 H, brs), 8.7 (1 H, brs), 8.2 (1 H, s), 7.4 (2 H, dd, J=8.09, 5.65 Hz), 7.0 (2 H, t, J=8.55 Hz), 4.6 (2 H, d, J=6.41 Hz), 4.2 (2 H, d, J=3.66 Hz), 3.6 (2 H, q, J=6.82 Hz), 3.3 (2 H, q, J=7.02 Hz), 2.5-2.6 (3 H, m), 2.0-2.1 (2 H, m), 1.9-2.0 (2 H, m), 1.7-1.7 (2 H, m), 1.2 (3 H, t, J=7.02 Hz), 1.1 (3 H, t, J=7.02 Hz). LCMS (M+H)=500.45. HPLC purity: >95%.

EXAMPLE 98

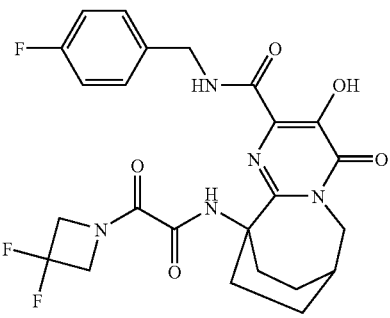

10-(((3,3-Difluoro-1-azetidinyl) (oxo)acetyl)amino)-N-(4-fluorobenzyl)-3-hydroxy-4-oxo-4,6,7,8,9,10-hexahydro-7,10-ethanopyrimido[1,2-a]azepine-2-carboxamide. White solid (25 mg, 39% yield). $^1$H NMR (500 MHz, CDCl$_3$) δ: 12.0 (1 H, brs), 9.7 (1 H, s), 7.9 (1 H, brs), 7.4 (2 H, dd, J=8.09, 5.65 Hz), 7.0 (2 H, t, J=8.55 Hz), 4.9 (2 H, t, J=11.75 Hz), 4.6 (2 H, d, J=6.10 Hz), 4.4 (2 H, t, J=11.60 Hz), 4.2 (2 H, d, J=3.66 Hz), 2.8-2.9 (2 H, m), 2.5 (1 H, brs), 2.0-2.1 (2 H, m), 1.8-1.9 (2 H, m), 1.7-1.8 (2 H, m). LCMS (M+H)=520.34. HPLC purity: >95%.

EXAMPLE 99

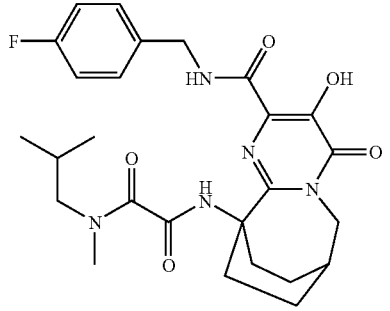

N'-(2-((4-Fluorobenzyl)carbamoyl)-3-hydroxy-4-oxo-6,7,8,9-tetrahydro-7,10-ethanopyrimido[1,2-a]azepin-10(4H)-yl)-N-methyl-N-(2-methylpropyl)ethanediamide. White solid (26 mg, 41% yield). $^1$H NMR (500 MHz, CDCl$_3$) δ: 12.0 (1 H, brs), 8.7 (1 H, brs), 8.1 (0.5 H, s), 8.0 (0.5 H, s), 7.4 (2 H, dd, J=7.78, 5.65 Hz), 7.0 (2 H, t, J=8.55 Hz), 4.5 (2 H, t, J=5.49 Hz), 4.2 (2 H, brs), 3.5 (1 H, d, J=7.63 Hz), 3.2 (1.5 H, s), 2.9 (1.5 H, s), 3.1 (1 H, d, J=7.63 Hz), 2.4-2.6 (3H, m), 2.1-2.1 (2 H, m), 1.9-2.0 (3 H, m), 1.7-1.8 (2 H, m), 0.9 (6 H, t, J=6.56 Hz). LCMS (M+H)=514.48. HPLC purity: >95%.

EXAMPLE 100

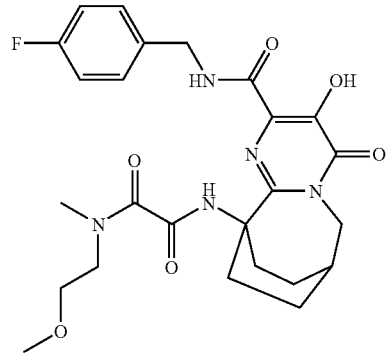

N'-(2-((4-Fluorobenzyl)carbamoyl)-3-hydroxy-4-oxo-6,7,8,9-tetrahydro-7,10-ethanopyrimido[1,2-a]azepin-10(4H)-yl)-N-(2-methoxyethyl)-N-methylethanediamide. Off-white solid (20 mg, 32% yield). $^1$H NMR (500 MHz, CDCl$_3$) δ: 11.95 (1 H, brs), 8.63 (1 H, brs), 8.16 (0.4 H, s), 8.17 (0.6 H, s), 7.34-7.48 (2 H, m), 7.04 (2 H, t, J=8.55 Hz), 4.63 (2 H, t, J=5.95 Hz), 4.26 (2 H, t, J=3.51 Hz), 3.85 (1 H, t, J=5.04 Hz), 3.67 (1 H, t, J=5.19 Hz), 3.51-3.59 (2 H, m), 3.30 (3H, s), 3.35 (1.2 H, s), 3.03 (1.8 H, s), 2.56-2.64 (3 H, m), 2.03-2.11 (2 H, m), 1.94-2.06 (2 H, m), 1.73-1.87 (2 H, m). LCMS (M+H)=516.26. HPLC purity: >95%.

EXAMPLE 101

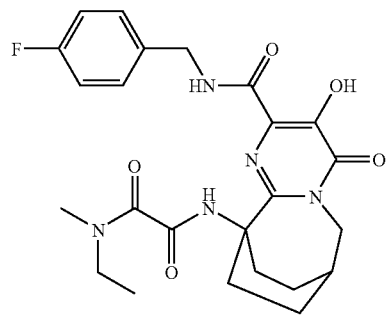

N-Ethyl-N'-(2-((4-fluorobenzyl)carbamoyl)-3-hydroxy-4-oxo-6,7,8,9-tetrahydro-7,10-ethanopyrimido[1,2-a]azepin-10(4H)-yl)-N-methylethanediamide. White solid (25 mg, 42% yield). $^1$H NMR (500 MHz, CDCl$_3$) δ: 11.97 (1 H, brs), 8.57 & 8.62 (1 H, brs), 8.28 (0.4 H, s), 8.05 (0.6 H, s), 7.32-7.37 (2 H, m), 6.96-7.01 (2 H, m), 4.53 (2 H, d, J=6.27 Hz), 4.14 (2 H, d, J=4.02 Hz), 3.62 (1.4 H, q, J=7.19 Hz), 3.32 (1.6 H, q, J=7.19 Hz), 3.23 (1.4 H, s), 2.85 (1.6 H, s), 2.43-2.58 (3H, m), 2.0-2.13 (2 H, m), 1.88-1.99 (2 H, m), 1.63-1.71 (2 H, m), 1.22 (1.3 H, t, J=7.15 Hz), 1.11 (1.7 H, t, J=7.15 Hz). LCMS (M+H)=486.16. HPLC purity: >95%.

EXAMPLE 102

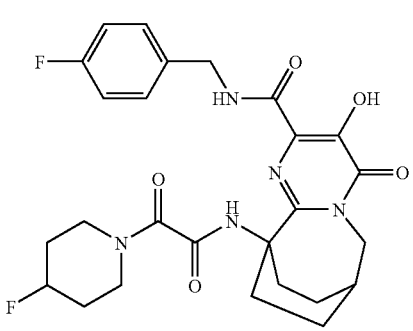

N-(4-Fluorobenzyl)-10-(((4-fluoro-1-piperidinyl)(oxo) acetyl)amino)-3-hydroxy-4-oxo-4,6,7,8,9,10-hexahydro-7, 10-ethanopyrimido[1,2-a]azepine-2-carboxamide. White solid (22 mg, 34% yield). $^1$H NMR (500 MHz, CDCl$_3$) δ: 11.98 (1 H, brs), 8.58 (1 H, brs), 8.06 (1 H, s), 7.32-7.36 (2 H, m), 6.96-7.01 (2 H, m), 4.79-4.96 (1 H, m), 4.52 (2 H, dd, J=6.27, 3.01 Hz), 4.17-4.25 (1 H, m), 4.04-4.15 (2 H, m), 3.68-3.85 (2 H, m), 3.31-3.39 (1 H, m), 2.43-2.57 (3 H, m), 2.11-2.21 (1 H, m), 1.83-2.02 (6 H, m), 1.66-1.81 (3 H, m). LCMS (M+H)=530.15. HPLC purity: >95%.

EXAMPLE 103

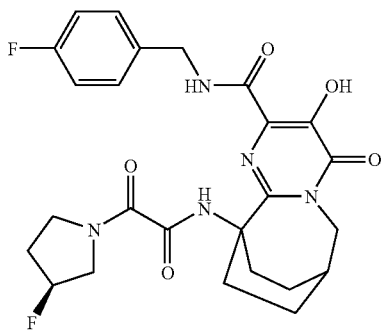

N-(4-Fluorobenzyl)-10-((((3S)-3-fluoro-1-pyrrolidinyl) (oxo)acetyl)amino)-3-hydroxy-4-oxo-4,6,7,8,9,10-hexahydro-7,10-ethanopyrimido[1,2-a]azepine-2-carboxamide. White solid (15 mg, 24% yield). $^1$H NMR (500 MHz, CDCl$_3$) δ: 11.93 (1 H, brs), 9.49 (1 H, br.s.), 8.11 (1 H, brs), 7.35-7.41 (2 H, m), 6.98-7.03 (2H, m), 5.28-5.36 (1 H, m), 4.51-4.64 (2 H, m), 4.30-4.46 (1 H, m), 4.07-4.20 (2H, m), 3.66-4.02 (2 H, m), 3.45-3.61 (1 H, m), 2.70-2.85 (2 H, m), 2.47 (1 H, brs), 2.19-2.41 (1 H, m), 1.80-2.04 (5 H, m), 1.67-1.76 (3 H, m). LCMS (M+H)=516.10. HPLC purity: >95%.

EXAMPLE 104

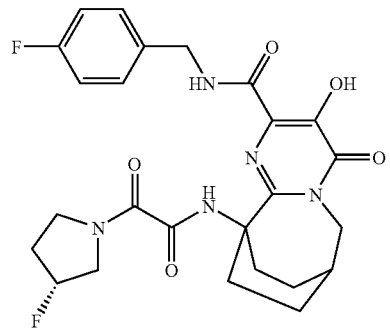

N-(4-Fluorobenzyl)-10-((((3R)-3-fluoro-1-pyrrolidinyl) (oxo)acetyl)amino)-3-hydroxy-4-oxo-4,6,7,8,9,10-hexahydro-7,10-ethanopyrimido[1,2-a]azepine-2-carboxamide. White solid (16 mg, 25% yield). $^1$H NMR (500 MHz, CDCl$_3$) δ: 11.93 (1 H, brs), 9.49 (1 H, br.s.), 8.11 (1 H, brs), 7.35-7.41 (2 H, m), 6.98-7.03 (2H, m), 5.28-5.36 (1 H, m), 4.51-4.64 (2 H, m), 4.30-4.46 (1 H, m), 4.07-4.20 (2H, m), 3.66-4.02 (2 H, m), 3.45-3.61 (1 H, m), 2.70-2.85 (2 H, m), 2.47 (1 H, brs), 2.19-2.41 (1 H, m), 1.80-2.04 (5 H, m), 1.67-1.76 (3 H, m). LCMS (M+H)=516.10. HPLC purity: >95%.

EXAMPLE 105

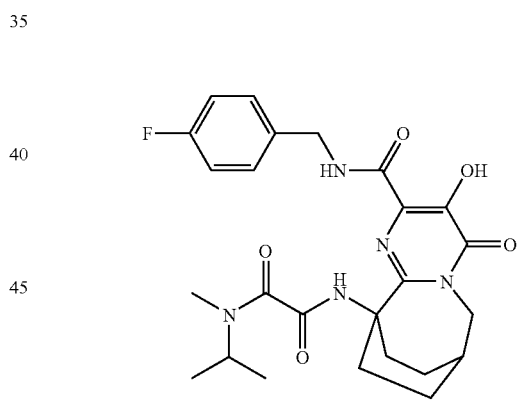

N'-(2-((4-Fluorobenzyl)carbamoyl)-3-hydroxy-4-oxo-6, 7,8,9-tetrahydro-7,10-ethanopyrimido[1,2-a]azepin-10 (4H)-yl)-N-methyl-N-(1-methylethyl)ethanediamide. White solid (25 mg, 39% yield). $^1$H NMR (500 MHz, CDCl$_3$) δ: 11.97 (1 H, brs), 8.95 (0.6 H, brs), 8.76 (0.4 H, brs), 7.95 (0.6 H, brs), 7.42 (0.4 H, s), 7.32-7.39 (2 H, m), 6.96-7.03 (2 H, m), 4.56-4.6 (0.6 H, m), 4.36-4.42 (0.4 H, m), 4.54 (2 H, d, J=6.41 Hz), 4.16 (2 H, d, J=3.66 Hz), 3.05 (1.4 H, s), 2.71 (1.6 H, s), 2.45-2.53 (3 H, m), 2.07-2.24 (2 H, m), 1.90-1.99 (2 H, m), 1.65-1.75 (2 H, m), 1.21 (3 H, d, J=6.71 Hz), 1.12 (3 H, d, J=6.71 Hz). LCMS (M+H)=500.24. HPLC purity: >95%.

Examples 106 through 128 can be synthesized according to Scheme XIII

EXAMPLE 106

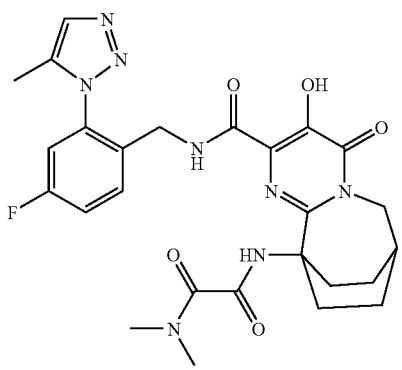

N'-(2-((4-Fluoro-2-(5-methyl-1H-1,2,3-triazol-1-yl)benzyl)carbamoyl)-3-hydroxy-4-oxo-6,7,8,9-tetrahydro-7,10-ethanopyrimido[1,2-a]azepin-10(4H)-yl)-N,N-dimethylethanediamide. A mixture of ethyl 10-(((dimethylamino)(oxo)acetyl)amino)-3-hydroxy-4-oxo-4,6,7,8,9,10-hexahydro-7,10-ethanopyrimido[1,2-a]azepine-2-carboxylat (30 mg, 0.076 mmol), (4-fluoro-2-(5-methyl-1H-1,2,3-triazol-1-yl)phenyl)methanamine, bis-hydrochloride salt (42.7 mg, 0.153 mmol) and triethylamine (0.1 ml, 0.717 mmol) in ethanol (2 mL) was heated at 90° C. for 18 h. The reaction mixture was then cooled, concentrated and purified on preparative reversed phase HPLC to afford the title compound (10 mg, 21% yield) as an off-white solid. $^1$H NMR (500 MHz, CDCl$_3$) δ: 1.66-1.77 (m, 2 H) 1.90-2.01 (m, 2 H) 2.14-2.24 (m, 2 H) 2.27 (s, 3 H) 2.39-2.47 (m, 2 H) 2.50 (br. s., 1 H) 2.89 (s, 3 H) 3.19 (s, 3 H) 4.15 (d, J=3.97 Hz, 2 H) 4.23 (d, J=6.41 Hz, 2 H) 6.99 (dd, J=8.24, 2.44 Hz, 1 H) 7.26-7.33 (m, 2 H) 7.62-7.68 (m, 2 H) 8.86 (t, J=6.10 Hz, 1H) 11.73 (br. s., 1 H). LCMS (M+H)=553.22. HPLC purity: >95%.

EXAMPLE 107

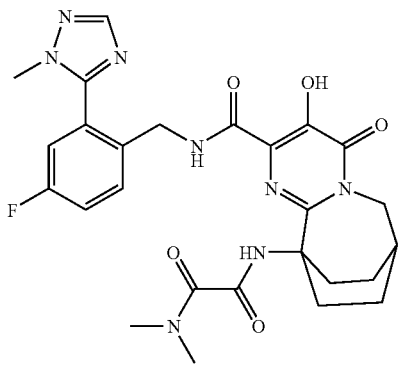

N'-(2-((4-Fluoro-2-(1-methyl-1H-1,2,4-triazol-5-yl)benzyl)carbamoyl)-3-hydroxy-4-oxo-6,7,8,9-tetrahydro-7,10-ethanopyrimido[1,2-a]azepin-10(4H)-yl)-N,N-dimethylethanediamide. Off-white solid (10 mg, 12% yield). $^1$H NMR (500 MHz, CDCl$_3$) δ: 11.90 (1 H, brs), 8.89 (1 H, brs), 8.05 (1 H, s), 8.03 (1 H, s), 7.62 (1H, dd, J=8.55, 5.49 Hz), 7.19-7.24 (1 H, m), 7.02-7.08 (1 H, m), 4.45 (2 H, d, J=6.10 Hz), 4.15 (2 H, d, J=3.97 Hz), 3.85 (3 H, s), 3.24 (3 H, s), 2.88 (3 H, s), 2.46-2.61 (3 H, m), 2.03-2.13 (2 H, m), 1.91-2.01 (2 H, m), 1.65-1.75 (2 H, m). LCMS (M+H)=553.25. HPLC purity: >95%.

EXAMPLE 108

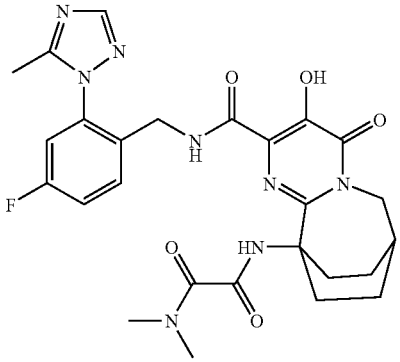

N'-(2-((4-Fluoro-2-(5-methyl-1H-1,2,4-triazol-1-yl)benzyl)carbamoyl)-3-hydroxy-4-oxo-6,7,8,9-tetrahydro-7,10-ethanopyrimido[1,2-a]azepin-10(4H)-yl)-N,N-dimethylethanediamide. White solid (3 mg, 6% yield). $^1$H NMR (500 MHz, CDCl$_3$) δ: 11.77 (1 H, brs), 9.01 (1 H, s), 8.21 (1 H, s), 7.82 (1 H, dd, J=8.85, 5.80 Hz), 7.76 (1 H, s), 7.28-7.35 (1 H, m), 6.99 (1 H, dd, J=7.93, 2.75 Hz), 4.28 (2 H, d, J=5.80 Hz), 4.14 (2 H, d, J=3.97 Hz), 3.12 (3 H, s), 2.90 (3 H, s), 2.53 (3 H, s), 2.51 (1 H, brs), 2.30-2.39 (2 H, m), 2.19-2.29 (2 H, m), 1.90-2.01 (2 H, m), 1.65-1.74 (2 H, m). LCMS (M+H)= 553.24. HPLC purity: >95%.

EXAMPLE 109

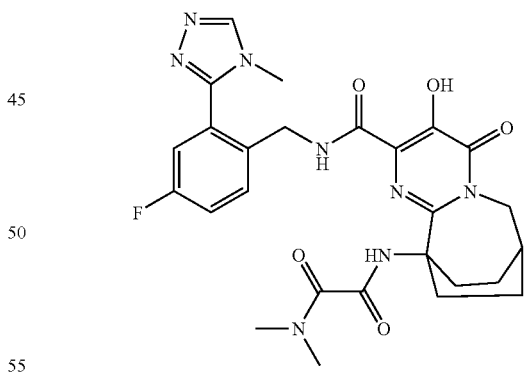

N'-(2-((4-Fluoro-2-(4-methyl-4H-1,2,4-triazol-3-yl)benzyl)carbamoyl)-3-hydroxy-4-oxo-6,7,8,9-tetrahydro-7,10-ethanopyrimido[1,2-a]azepin-10(4H)-yl)-N,N-dimethylethanediamide. White solid (6 mg, 11% yield). $^1$H NMR (500 MHz, CDCl$_3$) δ: 11.67 (1 H, brs), 9.15 (1 H, s), 8.33 (1 H, s), 7.82 (1 H, s), 7.61 (1 H, dd, J=8.70, 5.34 Hz), 7.20-7.24 (1 H, m), 7.02-7.09 (1 H, m), 4.45 (2 H, d, J=6.41 Hz), 4.15 (2 H, d, J=3.66 Hz), 3.65 (3 H, s), 3.15 (3 H, s), 2.86 (3 H, s), 2.39-2.53 (3 H, m), 2.17-2.28 (2 H, m), 1.90-1.99 (2 H, m), 1.65-1.75 (2 H, m). LCMS (M+H)=553.2. HPLC purity: >95%.

EXAMPLE 110

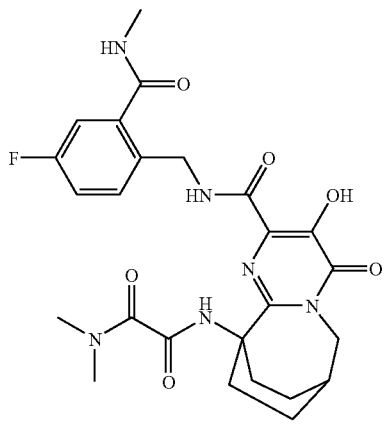

N'-(2-((4-Fluoro-2-(methylcarbamoyl)benzyl)carbamoyl)-3-hydroxy-4-oxo-6,7,8,9-tetrahydro-7,10-ethanopyrimido[1,2-a]azepin-10(4H)-yl)-N,N-dimethylethanediamide. Brown solid (10 mg, 26% yield). $^1$H NMR (500 MHz, CDCl$_3$) δ: 11.89 (1 H, brs), 8.84 (1 H, s), 8.07 (1 H, s), 7.83 (1 H, brs), 7.44 (1 H, dd, J=8.70, 5.34 Hz), 7.28 (1 H, dd, J=8.70, 2.59 Hz), 7.12 (1 H, td, J=8.32, 2.59 Hz), 4.64 (2 H, d, J=5.80 Hz), 4.21 (2 H, d, J=3.66 Hz), 3.32 (3 H, s), 3.07 (3 H, d, J=4.58 Hz), 2.99 (3 H, s), 2.53-2.67 (2 H, m), 2.08-2.15 (3 H, m), 1.92-2.06 (2 H, m), 1.67-1.81 (2 H, m). LCMS (M+H)=529.43. HPLC purity: >95%.

EXAMPLE 111

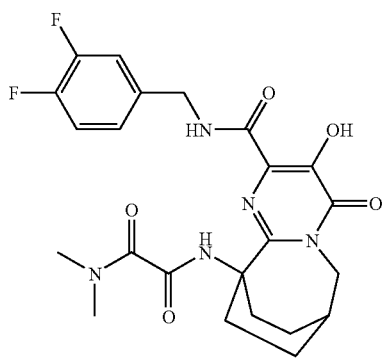

N'-(2-((3,4-Difluorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide. Thick film (2.5 mg, 6% yield). $^1$H NMR (500 MHz, CDCl$_3$) δ: 11.93 (1 H, brs), 8.73 (1 H, brs), 8.12 (1 H, s), 7.27-7.38 (1 H, m), 7.06-7.18 (2 H, m), 4.55 (2 H, d, J=6.10 Hz), 4.22 (2 H, d, J=3.66 Hz), 3.31 (3 H, s), 2.92 (3 H, s), 2.51-2.63 (3 H, m), 2.06-2.16 (2 H, m), 1.92-2.06 (2 H, m), 1.72-1.88 (2 H, m). LCMS (M+H)=490.37. HPLC purity: >95%.

EXAMPLE 112

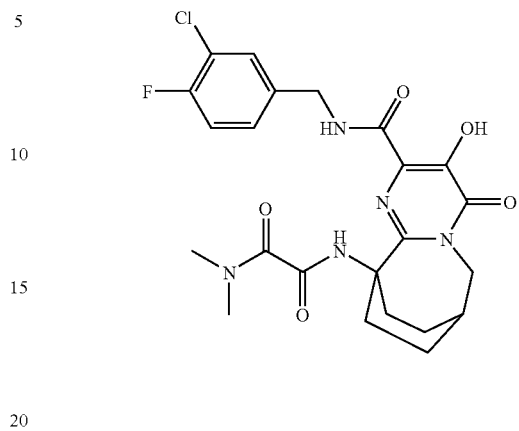

N'-(2-((3-Chloro-4-fluorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide. Off-white solid (7 mg, 17% yield). $^1$H NMR (500 MHz, CDCl$_3$) δ: 11.78 (1 H, brs), 8.73 (1 H, brs), 7.93 (1 H, s), 7.45 (1 H, dd, J=7.02, 2.14 Hz), 7.26-7.36 (1 H, m), 7.14 (1 H, t, J=8.70 Hz), 4.58 (2 H, d, J=6.41 Hz), 4.22 (2H, d, J=3.66 Hz), 3.34 (3 H, s), 2.91 (3 H, s), 2.44-2.58 (3 H, m), 2.13-2.27 (2 H, m), 1.89-2.06 (2 H, m), 1.72-1.87 (2 H, m). LCMS (M+H)=506.27. HPLC purity: >95%.

EXAMPLE 113

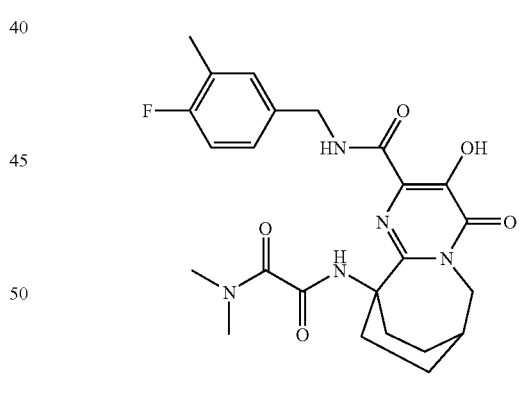

N'-(2-((4-Fluoro-3-methylbenzyl)carbamoyl)-3-hydroxy-4-oxo-6,7,8,9-tetrahydro-7,10-ethanopyrimido[1,2-a]azepin-10(4H)-yl)-N,N-dimethylethanediamide. White solid (13 mg, 33% yield). $^1$H NMR (500 MHz, CDCl$_3$) δ: 12.03 (1 H, brs), 8.64 (1 H, brs), 8.18 (1 H, s), 7.11-7.29 (2 H, m), 6.93 (1H, t, J=8.85 Hz), 4.57 (2 H, d, J=6.41 Hz), 4.25 (2 H, d, J=3.66 Hz), 3.33 (3 H, s), 2.92-3.00 (3 H, m), 2.85 (3 H, s), 2.45-2.57 (3 H, m), 2.34 (3 H, s), 2.07-2.19 (2H, m), 1.88-2.11 (2 H, m), 1.74-1.88 (2 H, m). LCMS (M+H)=486.43. HPLC purity: >95%.

EXAMPLE 114

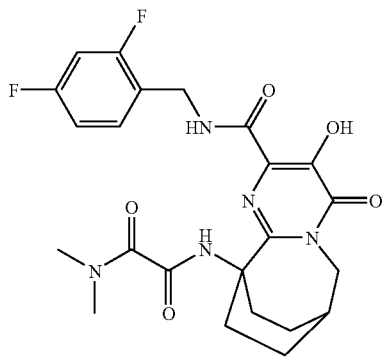

N'-(2-((2,4-Difluorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide. Off-white solid (6 mg, 19% yield). $^1$H NMR (500 MHz, CDCl$_3$) δ: 11.89 (1 H, brs), 8.56 (1 H, brs), 8.11 (1 H, s), 7.34 (1 H, td, J=8.47, 6.56 Hz), 6.78-6.89 (2 H, m), 4.56 (2H, d, J=6.41 Hz), 4.22 (2 H, d, J=3.97 Hz), 3.35 (3 H, s), 2.89 (3 H, s), 2.45-2.62 (3H, m), 2.11-2.28 (2 H, m), 1.89-2.04 (2 H, m), 1.72-1.84 (2 H, m). LCMS (M+H)=490.1. HPLC purity: >95%.

EXAMPLE 115

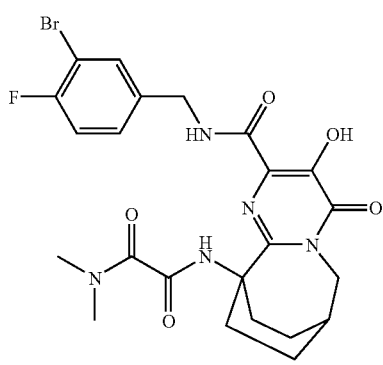

N'-(2-((3-Bromo-4-fluorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide. Off-white solid (5.5 mg, 16% yield). $^1$H NMR (500 MHz, CDCl$_3$) δ: 12.23 (1 H, brs), 8.67 (1 H, brs), 7.89 (1 H, s), 7.56 (1 H, dd, J=6.41, 2.14 Hz), 7.23-7.32 (1 H, m), 7.11 (1 H, t, J=8.39 Hz), 4.56 (2 H, d, J=6.10 Hz), 4.28 (2H, d, J=3.66 Hz), 3.31 (3 H, s), 2.92 (3 H, s), 2.34-2.51 (3 H, m), 2.11-2.23 (2 H, m), 1.89-2.05 (2 H, m), 1.67-1.82 (2 H, m). LCMS (M+H)=552.1. HPLC purity: >95%.

EXAMPLE 116

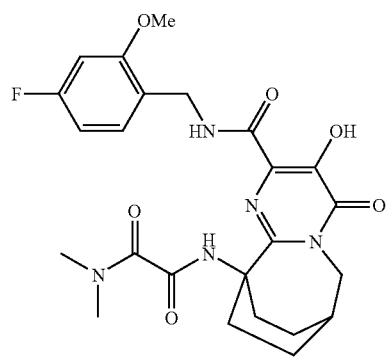

N'-(2-((4-Fluoro-2-methoxybenzyl)carbamoyl)-3-hydroxy-4-oxo-6,7,8,9-tetrahydro-7,10-ethanopyrimido[1,2-a]azepin-10(4H)-yl)-N,N-dimethylethanediamide. Yellow solid (2.7 mg, 11% yield). $^1$H NMR (500 MHz, CDCl$_3$) δ: 12.22 (1 H, brs), 8.62 (1 H, s), 8.28 (1 H, brs), 7.23-7.35 (1 H, m), 6.56-6.68 (2 H, m), 4.62 (2 H, d, J=6.10 Hz), 4.28 (2 H, d, J=3.66 Hz), 3.78 (3 H, s), 3.33 (3 H, s), 2.94 (3 H, s), 2.56-2.72 (2 H, m), 2.54 (1 H, brs), 1.89-2.05 (4 H, m), 1.57-1.83 (2 H, m). LCMS (M+H)=502.2. HPLC purity: >95%.

EXAMPLE 117

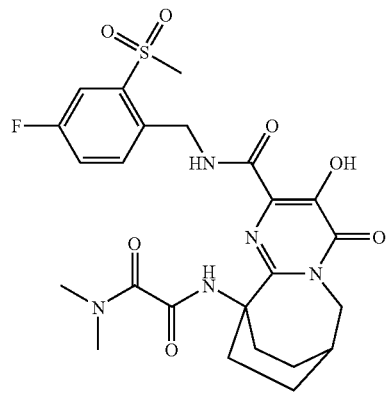

N'-(2-((4-Fluoro-2-(methylsulfonyl)benzyl)carbamoyl)-3-hydroxy-4-oxo-6,7,8,9-tetrahydro-7,10-ethanopyrimido[1,2-a]azepin-10(4H)-yl)-N,N-dimethylethanediamide. Off-white solid (9 mg, 24% yield). $^1$H NMR (500 MHz, CDCl$_3$) δ: 11.89 (1 H, brs), 8.89 (1 H, t, J=6.26 Hz), 7.94 (1 H, s), 7.78 (1 H, dd, J=8.24, 2.75 Hz), 7.66 (1 H, dd, J=8.70, 5.04 Hz), 7.28-7.35 (1 H, m), 4.89 (2 H, d, J=6.71 Hz), 4.25 (2 H, d, J=3.66 Hz), 3.37 (3 H, s), 3.21 (3 H, s), 3.07 (3 H, s), 2.55-2.67 (3 H, m), 2.12-2.26 (2 H, m), 1.89-2.05 (2 H, m), 1.72-1.88 (2 H, m). LCMS (M+H)=550.15. HPLC purity: >95%.

EXAMPLE 118

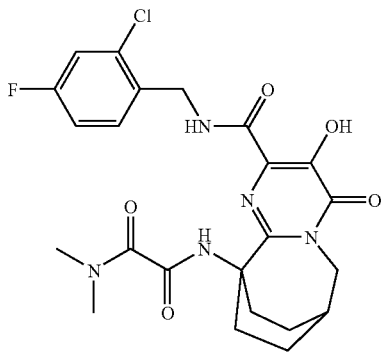

N'-(2-((2-Chloro-4-fluorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide. Off-white solid (4 mg, 16% yield). $^1$H NMR (500 MHz, CDCl$_3$) δ: 11.93 (1 H, brs), 8.54 (1 H, brs), 8.31 (1 H, s), 7.48 (1 H, dd, J=8.55, 6.10 Hz), 7.12-7.19 (1 H, m), 6.89-7.08 (1 H, m), 4.73 (2 H, d, J=6.10 Hz), 4.25 (2 H, d, J=3.36 Hz), 3.33 (3 H, s), 2.92 (3 H, s), 2.45-2.63 (2 H, m), 2.55 (1 H, brs), 2.05-2.15 (2 H, m), 1.93-2.08 (2 H, m), 1.74-1.85 (2 H, m). LCMS (M+H)=506.38. HPLC purity: >95%.

EXAMPLE 119

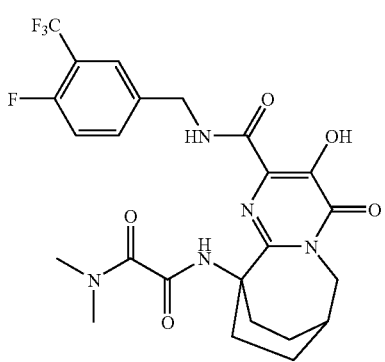

N'-(2-((4-Fluoro-3-(trifluoromethyl)benzyl)carbamoyl)-3-hydroxy-4-oxo-6,7,8,9-tetrahydro-7,10-ethanopyrimido[1,2-a]azepin-10(4H)-yl)-N,N-dimethylethanediamide. Off-white solid (5.5 mg, 20% yield). $^1$H NMR (500 MHz, CDCl$_3$) δ: 11.88 (1 H, brs), 8.89 (1 H, brs), 7.83 (1 H, s), 7.63-7.78 (1 H, m), 7.56-7.68 (1 H, m), 7.12-7.23 (1 H, m), 4.67 (2 H, d, J=6.71 Hz), 4.28 (2 H, d, J=3.66 Hz), 3.33 (3 H, s), 2.94 (3 H, s), 2.44-2.56 (3 H, m), 2.11-2.19 (2 H, m), 1.90-2.08 (2 H, m), 1.67-1.78 (2 H, m). LCMS (M+H)=540.36. HPLC purity: >95%.

EXAMPLE 120

N'-(2-((4-Fluoro-2-methylbenzyl)carbamoyl)-3-hydroxy-4-oxo-6,7,8,9-tetrahydro-7,10-ethanopyrimido[1,2-a]azepin-10(4H)-yl)-N,N-dimethylethanediamide. White solid (7 mg, 23% yield). $^1$H NMR (500 MHz, CDCl$_3$) δ: 12.21 (1 H, brs), 8.32-8.39 (2 H, m), 7.31-7.35 (1 H, m), 6.81-6.91 (2H, m), 4.55 (2 H, d, J=6.10 Hz), 4.16 (2 H, d, J=3.97 Hz), 3.29 (3 H, s), 2.88 (3 H, s), 2.52-2.61 (2 H, m), 2.49 (1 H, brs), 2.39 (3 H, s), 2.01-2.09 (2 H, m), 1.92-2.00 (2H, m), 1.64-1.75 (2 H, m). LCMS (M+H)=486.11. HPLC purity: >95%.

EXAMPLE 121

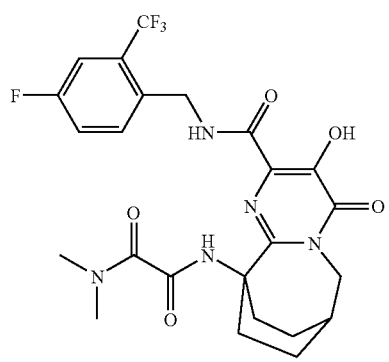

N'-(2-((4-Fluoro-2-(trifluoromethyl)benzyl)carbamoyl)-3-hydroxy-4-oxo-6,7,8,9-tetrahydro-7,10-ethanopyrimido[1,2-a]azepin-10(4H)-yl)-N,N-dimethylethanediamide. White solid (9 mg, 26% yield). $^1$H NMR (500 MHz, CDCl$_3$) δ: 11.87 (1 H, brs), 8.61 (1 H, brs), 8.05 (1 H, s), 7.55 (1 H, dd, J=8.55, 5.49 Hz), 7.37 (1 H, dd, J=8.85, 2.75 Hz), 7.22 (1 H, td, J=8.09, 2.75 Hz), 4.75 (2 H, d, J=6.10 Hz), 4.17 (2 H, d, J=3.97 Hz), 3.26 (3 H, s), 2.86 (3 H, s), 2.47-2.57 (3 H, m), 2.06-2.15 (2 H, m), 1.91-2.01 (2 H, m), 1.68-1.76 (2 H, m). LCMS (M+H)=540.06. HPLC purity: >95%.

EXAMPLE 122

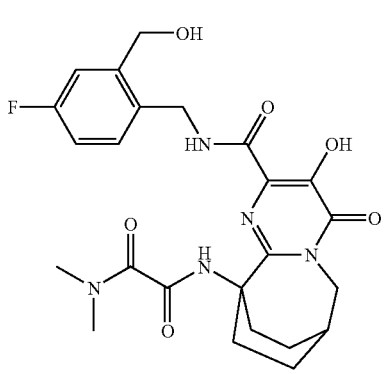

N'-(2-((4-Fluoro-2-(hydroxymethyl)benzyl)carbamoyl)-3-hydroxy-4-oxo-6,7,8,9-tetrahydro-7,10-ethanopyrimido[1,2-a]azepin-10(4H)-yl)-N,N-dimethylethanediamide. Light yellow solid (2 mg, 6% yield). $^1$H NMR (500 MHz, CDCl$_3$) δ: ppm 12.36 (1 H, brs), 8.73 (1 H, brs), 8.70 (1 H, s), 7.43 (1 H, dd, J=8.39, 5.65 Hz), 7.03-7.06 (1 H, m), 6.99 (1 H, td, J=8.39, 2.75 Hz), 4.77 (2 H, s), 4.66 (2H, d, J=6.10 Hz), 4.13 (2 H, d, J=3.97 Hz), 3.32 (3 H, s), 3.00 (3 H, s), 2.80-2.88 (2H, m), 2.46 (1 H, brs), 1.94-2.02 (2 H, m), 1.77-1.85 (2 H, m), 1.64-1.71 (2 H, m). LCMS (M+H)=502.11. HPLC purity: >95%.

EXAMPLE 123

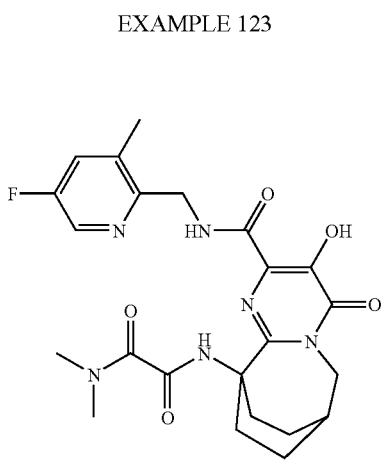

N'-(2-(((3,5-Difluoro-2-pyridinyl)methyl)carbamoyl)-3-hydroxy-4-oxo-6,7,8,9-tetrahydro-7,10-ethanopyrimido[1,2-a]azepin-10(4H)-yl)-N,N-dimethylethanediamide. Yellow film (1.2 mg, 4% yield). $^1$H NMR (500 MHz, CDCl$_3$) δ: 12.14 (1 H, brs), 8.74 (1 H, s), 8.41 (1 H, d, J=2.44 Hz), 8.37 (1 H, s), 7.21-7.24 (1 H, m), 4.76 (2 H, d, J=5.49 Hz), 4.17 (2 H, d, J=3.66 Hz), 3.30 (3 H, s), 2.96 (3 H, s), 2.60-2.67 (2 H, m), 2.50 (1 H, brs), 2.02-2.08 (2 H, m), 1.93-2.00 (2H, m), 1.66-1.76 (2 H, m). LCMS (M+H)=491.39. HPLC purity: >95%.

EXAMPLE 124

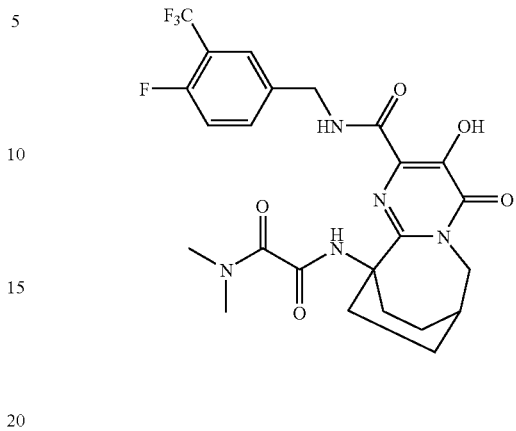

N'-(2-((3-(Difluoromethyl)-4-fluorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide. Off-white solid (4 mg, 12% yield). $^1$H NMR (500 MHz, CDCl$_3$) δ: 11.89 (1 H, brs), 8.83 (1 H, brs), 7.90 (1 H, s), 7.58-7.62 (1 H, m), 7.50-7.55 (1 H, m), 7.09 (1 H, t, J=9.31 Hz), 4.58 (2 H, d, J=6.41 Hz), 4.16 (2 H, d, J=3.97 Hz), 3.26 (3 H, s), 2.92 (3 H, s), 2.44-2.53 (3 H, m), 2.09-2.17 (2 H, m), 1.91-2.00 (2 H, m), 1.67-1.76 (2 H, m). LCMS (M+H)=522.44. HPLC purity: >95%.

EXAMPLE 125

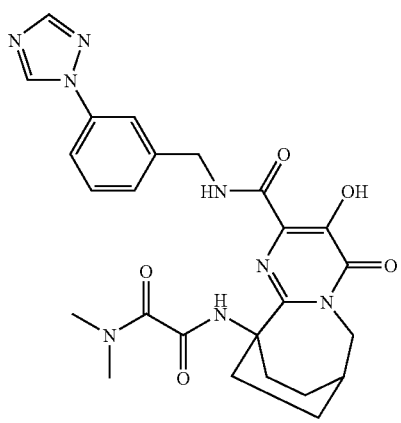

N'-(3-Hydroxy-4-oxo-2-((3-(1H-1,2,4-triazol-1-yl)benzyl)carbamoyl)-6,7,8,9-tetrahydro-7,10-ethanopyrimido[1,2-a]azepin-10(4H)-yl)-N,N-dimethylethanediamide. Thick film (1.5 mg, 5% yield). $^1$H NMR (500 MHz, CDCl$_3$) δ: 12.81 (1 H, brs), 8.97 (1 H, s), 8.92 (1 H, brs), 8.19 (1 H, s), 7.81 (1 H, s), 7.77 (1H, s), 7.67 (1 H, d, J=7.63 Hz), 7.45-7.54 (2 H, m), 4.68 (2 H, d, J=6.71 Hz), 4.17 (2 H, d, J=3.66 Hz), 3.21 (3 H, s), 2.85 (3 H, s), 2.52 (1 H, brs), 2.41-2.47 (2 H, m), 2.15-2.22 (2 H, m), 1.91-2.01 (2 H, m), 1.64-1.76 (2 H, m). LCMS (M+H)=521.59. HPLC purity: >95%.

EXAMPLE 126

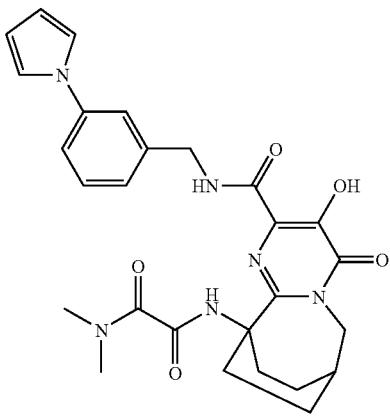

N'-(3-Hydroxy-4-oxo-2-((3-(1H-pyrrol-1-yl)benzyl)carbamoyl)-6,7,8,9-tetrahydro-7,10-ethanopyrimido[1,2-a]azepin-10(4H)-yl)-N,N-dimethylethanediamide. Light yellow solid (16 mg, 51% yield). $^1$H NMR (500 MHz, CDCl$_3$) δ: 11.99 (1 H, brs), 8.77 (1 H, brs), 8.02 (1 H, s), 7.42 (1 H, s), 7.38 (1H, t, J=7.63 Hz), 7.27-7.32 (2 H, m), 7.10 (2 H, s), 6.32 (2 H, brs), 4.63 (2 H, d, J=6.41 Hz), 4.16 (2 H, d, J=3.66 Hz), 3.23 (3 H, s), 2.81 (3 H, s), 2.45-2.54 (3 H, m), 2.08-2.16 (2 H, m), 1.91-2.00 (2 H, m), 1.67-1.76 (2 H, m). LCMS (M+H)= 519.61. HPLC purity: >95%.

EXAMPLE 127

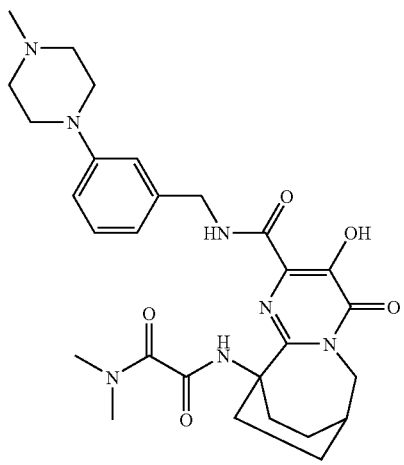

N'-(3-Hydroxy-2-((3-(4-methyl-1-piperazinyl)benzyl)carbamoyl)-4-oxo-6,7,8,9-tetrahydro-7,10-ethanopyrimido[1,2-a]azepin-10(4H)-yl)-N,N-dimethylethanediamide. Light yellow solid (19 mg, 47% yield). $^1$H NMR (500 MHz, CDCl$_3$) δ: 12.08 (1 H, brs), 8.87 (1 H, brs), 7.70 (1 H, s), 7.22-7.27 (1 H, m), 6.99 (1 H, d, J=7.32 Hz), 6.93 (1 H, s), 6.81 (1 H, d, J=7.93 Hz), 4.55 (2 H, d, J=6.41 Hz), 4.16 (2 H, d, J=3.36 Hz), 3.62-3.71 (4 H, m), 3.24-3.33 (2 H, m), 3.22 (3 H, s), 2.96-3.04 (2 H, m), 2.86 (6 H, s), 2.50 (1 H, brs), 2.39-2.47 (2 H, m), 2.13-2.20 (2 H, m), 1.92-1.99 (2 H, m), 1.67-1.76 (2 H, m). LCMS (M+H)=552.80. HPLC purity: >95%.

EXAMPLE 128

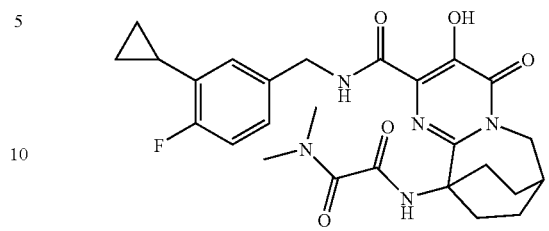

N'-(2-((3-Cyclopropyl-4-fluorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide. A suspension of ethyl 10-(((dimethylamino)(oxo)acetyl)amino)-4-oxo-3-((phenylcarbonyl)oxy)-4,6,7,8,9,10-hexahydro-7,10-ethanopyrimido[1,2-a]azepine-2-carboxylate (0.025 g, 0.050 mmol) and dimethylamine (0.050 mL, 0.101 mmol) (2 M in methanol) in ethanol (1 mL) was stirred at 50° C. for 1 h. Added to the mixture were (3-cyclopropyl-4-fluorophenyl)methanamine hydrochloride salt (0.025 g, 0.126 mmol) and triethylamine (0.070 mL, 0.504 mmol) and the mixture stirred at 90° C. for 5 h. The mixture was cooled to room temperature and concentrated. The brown residue was purified by preparative HPLC: Solvent A=10% ACN/90% H$_2$O/0.1% trifluoroacetic acid; Solvent B=90% ACN/10% H$_2$O/0.1% trifluoroacetic acid; Start % B=0; Final % B=100; Gradient time=20 min; Stop time=23 min; Column=Sunfire 19×100 mm, C18, 5 μm. The resulting purple solid was triturated with hot methanol to give the title compound as a white solid (6.0 mg, 21% yield). $^1$H NMR (500 MHz, CDCl$_3$) δ: 12.03 (1 H, s), 8.56 (1 H, t, J=5.49 Hz), 8.15 (1 H, s), 7.11-7.20 (1 H, m), 6.85-7.01 (2 H, m), 4.49 (2 H, d, J=6.10 Hz), 4.16 (2 H, d, J=3.97 Hz), 3.28 (3 H, s), 2.91 (3 H, s), 2.42-2.65 (3 H, m), 2.01-2.18 (3 H, m), 1.86-2.00 (2 H, m), 1.71 (2 H, ddd, J=13.28, 6.56, 6.41 Hz), 0.90-1.02 (2 H, m), 0.67-0.80 (2 H, m). LCMS (M+H) calcd for C$_{26}$H$_{31}$FN$_5$O$_5$: 512.23; found: 512.24.

Examples 129 through 135 can be synthesized according to Scheme XIV

EXAMPLE 129

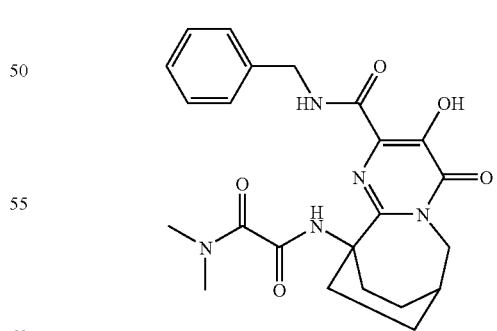

N'-(2-(Benzylcarbamoyl)-3-hydroxy-4-oxo-6,7,8,9-tetrahydro-7,10-ethanopyrimido[1,2-a]azepin-10(4H)-yl)-N,N-dimethylethanediamide. To a mixture of ethyl 10-(((dimethylamino)(oxo)acetyl)amino)-4-oxo-3-((phenylcarbonyl)oxy)-4,6,7,8,9,10-ethanopyrimido[1,2-a]azepine-2-carboxylate (20 mg, 0.040 mmol) in ethanol (2 mL) was added 2M Me$_2$NH (0.040 mL, 0.081 mmol) and the mixture heated at 50° C. for 1 h (mixture became clear after 5-10 min at 50° C. and then precepitate formed). Phenylmethanamine (0.022 mL, 0.201 mmol) followed by triethylamine (0.028 mL, 0.201 mmol) were then added and the mixture heated at 90° C. for 18 h. After work-up the crude product was purified by preparative HPLC to afford the title compound (7 mg, 0.015 mmol, 38% yield) as a white solid. $^1$H NMR (400 MHz, CDCl$_3$) δ: 12.04 (1 H, s), 8.53 (1 H, brs), 8.29 (1 H, s), 7.35-7.39 (2 H, m), 7.28-7.34 (2 H, m), 7.24-7.27 (1 H, m), 4.57 (2 H, d, J=6.27 Hz), 4.14 (2 H, d, J=4.02 Hz), 3.26 (3 H, s), 2.87 (3 H, s), 2.44-2.58 (3 H, m), 2.01-2.10 (2 H, m), 1.86-1.99 (2 H, m), 1.64-1.75 (2 H, m). LCMS (M+H)=454.73. HPLC purity: >95%.

EXAMPLE 130

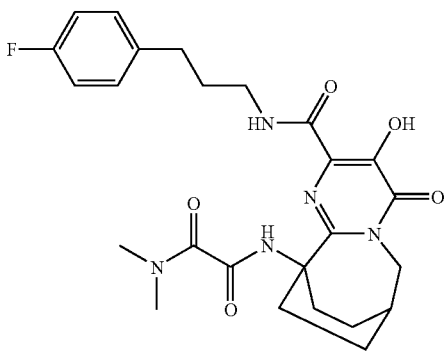

N'-(2-((3-(4-Fluorophenyl)propyl)carbamoyl)-3-hydroxy-4-oxo-6,7,8,9-tetrahydro-7,10-ethanopyrimido[1,2-a]azepin-10(4H)-yl)-N,N-dimethylethanediamide. White solid (19 mg, 47% yield). $^1$H NMR (500 MHz, CDCl$_3$) δ: 12.15 (1 H, brs), 8.54 (1 H, s), 8.08 (1 H, brs), 7.17 (2 H, dd, J=8.24, 5.49 Hz), 6.94 (2 H, t, J=8.70 Hz), 4.17 (2 H, d, J=3.66 Hz), 3.45 (2 H, q, J=6.71 Hz), 3.34 (3 H, s), 2.95 (3 H, s), 2.69 (2 H, t, J=7.63 Hz), 2.57-2.65 (2 H, m), 2.50 (1 H, brs), 1.93-2.09 (6 H, m), 1.68-1.77 (2 H, m). LCMS (M+H)=500.72. HPLC purity: >95%.

EXAMPLE 131

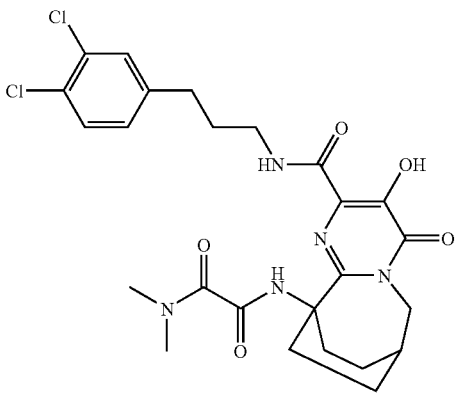

N'-(2-((3-(3,4-Dichlorophenyl)propyl)carbamoyl)-3-hydroxy-4-oxo-6,7,8,9-tetrahydro-7,10-ethanopyrimido[1,2-a]azepin-10(4H)-yl)-N,N-dimethylethanediamide. White solid (21 mg, 47% yield). $^1$H NMR (500 MHz, CDCl$_3$) δ: 12.09 (1 H, s), 8.47 (1 H, s), 8.11 (1 H, brs), 7.29-7.33 (2 H, m), 7.06 (1H, dd, J=8.09, 1.98 Hz), 4.16 (2 H, d, J=3.66 Hz), 3.43-3.49 (2 H, m), 3.34 (3 H, s), 2.97 (3 H, s), 2.66-2.70 (2 H, m), 2.57-2.65 (2 H, m), 2.50 (1 H, brs), 1.93-2.10 (6H, m), 1.68-1.77 (2 H, m). LCMS (M+H)=550.59. HPLC purity: >95%.

EXAMPLE 132

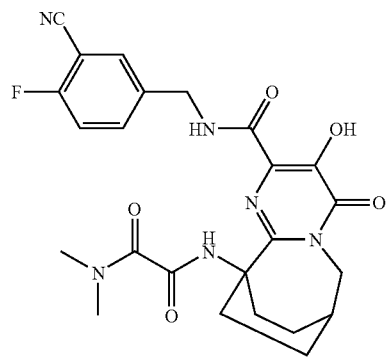

N'-(2-((3-Cyano-4-fluorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide. Crystalline white solid (16 mg, 32% yield). $^1$H NMR (500 MHz, CDCl$_3$) δ: 11.74 (1 H, s), 9.77 (1 H, s), 8.71 (1 H, s), 7.86 (1 H, dd, J=6.27, 2.26 Hz), 7.70-7.76 (1 H, m), 7.49 (1 H, t, J=9.03 Hz), 4.51 (2 H, d, J=6.27 Hz), 4.02 (2 H, d, J=3.76 Hz), 2.94 (3 H, s), 2.85 (3 H, s), 2.40 (1 H, brs), 2.23-2.34 (2 H, m), 1.94-2.08 (2 H, m), 1.73-1.84 (2 H, m), 1.49-1.67 (2 H, m). LCMS (M+H)=497.68. HPLC purity: >95%.

EXAMPLE 133

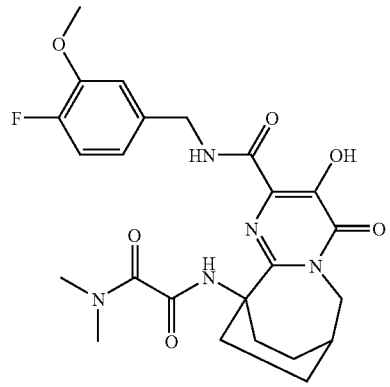

N'-(2-((4-Fluoro-3-methoxybenzyl)carbamoyl)-3-hydroxy-4-oxo-6,7,8,9-tetrahydro-7,10-ethanopyrimido[1,2-a]azepin-10(4H)-yl)-N,N-dimethylethanediamide. White solid (17 mg, 34% yield). $^1$H NMR (500 MHz, CDCl$_3$) δ: 11.97 (1 H, brs), 8.60 (1 H, t, J=5.80 Hz), 8.05 (1 H, s), 6.97-7.04 (2 H, m), 6.88-6.93 (1 H, m), 4.54 (2 H, d, J=6.41 Hz), 4.16 (2 H, d, J=3.66 Hz), 3.88 (3H, s), 3.26 (3 H, s), 2.87 (3 H, s), 2.45-2.55

(3 H, m), 2.07-2.15 (2 H, m), 1.91-2.00 (2 H, m), 1.70-1.75 (2 H, m). LCMS (M+H)=502.60. HPLC purity: >95%.

EXAMPLE 134

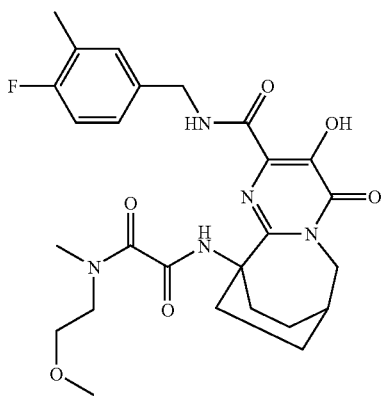

N'-(2-((4-Fluoro-3-methylbenzyl)carbamoyl)-3-hydroxy-4-oxo-6,7,8,9-tetrahydro-7,10-ethanopyrimido[1,2-a]azepin-10(4H)-yl)-N-(2-methoxyethyl)-N-methylethanediamide. White solid (17 mg, 43% yield). $^1$H NMR (500 MHz, CDCl$_3$) δ: 12.09 (1 H, brs), 8.59 (1 H, s), 8.20 & 8.16 (1 H, s), 7.13-7.22 (2 H, m), 6.92-6.97 (1 H, m), 4.51 (2 H, t, J=6.26 Hz), 4.16 (2 H, t, J=3.97 Hz), 3.84 (1 H, t, J=5.19 Hz), 3.56 (1 H, t, J=5.19 Hz), 3.46-3.51 (2 H, m), 3.33 (3 H, s), 3.32 & 2.96 (2 H, s), 2.45-2.58 (3 H, m), 2.25 (3 H, d, J=1.53 Hz), 2.05-2.13 (2 H, m), 1.90-2.00 (2 H, m), 1.67-1.76 (2 H, m). LCMS (M+H)=530.56. HPLC purity: >95%.

EXAMPLE 135

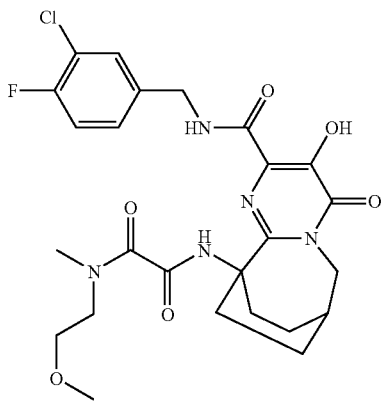

N'-(2-((3-Chloro-4-fluorobenzyl)carbamoyl)-3-hydroxy-4-oxo-6,7,8,9-tetrahydro-7,11-ethanopyrimido[1,2-a]azepin-10(4H)-yl)-N-(2-methoxyethyl)-N-methylethanediamide. White solid (13 mg, 32% yield). $^1$H NMR (500 MHz, CDCl$_3$) δ: 11.89 (1 H, brs), 8.77 (1 H, brs), 7.98 & 7.94 (1 H, s), 7.41-7.48 (1 H, m), 7.26-7.30 (1 H, m), 7.09 (1 H, t, J=8.70 Hz), 4.52 (2 H, t, J=6.87 Hz), 4.16 (2 H, t, J=3.81 Hz), 3.82 (1 H, t, J=5.19 Hz), 3.57 (1 H, t, J=5.19 Hz), 3.47-3.54 (2 H, m), 3.33 (3H, s), 3.31 & 2.98 (2 H, s), 2.39-2.55 (3 H, m), 2.07-2.17 (2 H, m), 1.91-2.01 (2H, m), 1.65-1.75 (2 H, m). LCMS (M+H)=550.13. HPLC purity: >95%.

Examples 136 through 149 can be synthesized according to Scheme XVI

EXAMPLE 136

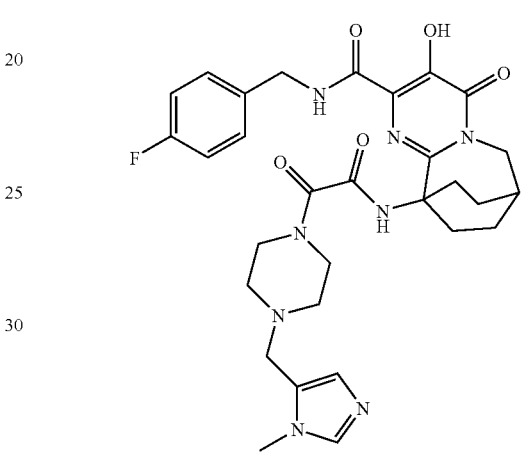

N-(4-Fluorobenzyl)-3-hydroxy-10-(((4-((1-methyl-1H-imidazol-5-yl)methyl)-1-piperazinyl)(oxo)acetyl)amino)-4-oxo-4,6,7,8,9,10-hexahydro-7,10-ethanopyrimido[1,2-a]azepine-2-carboxamide. To a solution of 7,10-ethanopyrimido[1,2-a]azepine-2-carboxamide, 10-[[1,2-dioxo-2-(1-piperazinyl)ethyl]amino]-N-[(4-fluorophenyl)methyl]-4,6,7,8,9,10-hexahydro-3-hydroxy-4-oxo- (0.025 g, 0.040 mmol) in 1,2-dichloroethane (1 mL) and diisopropyl ethylamine (6.97 μL, 0.040 mmol) cooled to 0° C. was added 1-methyl-1H-imidazole-5-carbaldehyde (4.39 mg, 0.040 mmol) and the mixture stirred at 0° C. for 15 min. Acetic acid (2.284 μL, 0.040 mmol) and sodium triacetoxyborohydride (9.30 mg, 0.044 mmol) were added and the mixture stirred at room temperature for 4 h. The solvent was removed under a stream of air and the residue purified by preparative HPLC: Solvent A=10% methanol/90% H$_2$O/0.1% trifluoroacetic acid; Solvent B=90% methanol/10% H$_2$O/0-1% trifluoroacetic acid; Start % B=0; Final % B=100; Gradient time=15 min; Stop time=15 min; Column=Sunfire 19×100 mm, C18, 5 μm to give the title compound as a trifluoroacetic acid salt as a purple solid (14.7 mg, 49% yield). $^1$H NMR (500 MHz, MeOD) δ: 9.67 (1 H, brs), 8.94 (1 H, brs), 8.86 (1 H, brs), 7.60 (1 H, brs), 7.32-7.48 (2 H, m), 7.03 (2 H, t, J=8.39 Hz), 4.56 (2 H, brs), 4.19 (2 H, brs), 3.77-4.08 (4 H, m), 3.50-3.77 (4 H, m), 2.69 (3 H, brs), 2.51 (1 H, brs), 2.39 (2 H, d, J=5.80 Hz), 2.21 (2 H, brs), 1.96 (2 H, d, J=4.88 Hz), 1.74 (2 H, brs). (M+H) calcd for C$_{30}$H$_{36}$FN$_8$O$_5$: 607.27; found: 607.44.

EXAMPLE 137

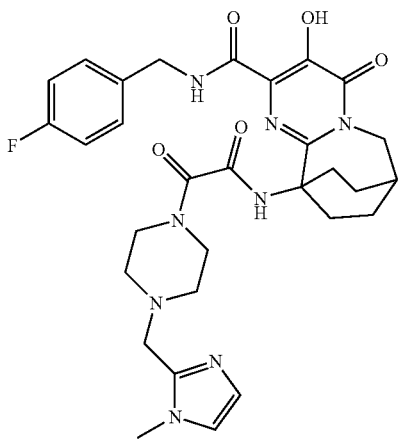

N-(4-Fluorobenzyl)-3-hydroxy-10-(((4-((1-methyl-1H-imidazol-2-yl)methyl)-1-piperazinyl)(oxo)acetyl)amino)-4-oxo-4,6,7,8,9,10-hexahydro-7,10-ethanopyrimido[1,2-a]azepine-2-carboxamide. Purple foam (16.0 mg, 56% yield). $^1$H NMR (500 MHz, MeOD) δ: 7.58 (1 H, s), 7.53 (1 H, brs), 7.41 (2 H, dd, J=8.55, 5.49 Hz), 7.03 (2 H, t, J=8.70 Hz), 4.56 (2 H, s), 4.19 (2 H, d, J=3.66 Hz), 3.85-4.03 (4 H, m), 3.66 (2 H, brs), 3.59 (2 H, brs), 2.54-2.69 (3 H, m), 2.51 (1 H, brs), 2.30-2.46 (2 H, m), 2.20 (2 H, ddd, J=14.42, 9.23, 5.65 Hz), 1.87-2.05 (2 H, m), 1.66-1.81 (2 H, m). LCMS (M+H) calcd for $C_{31}H_{33}FN_7O_6$: 607.27; found: 607.39.

EXAMPLE 138

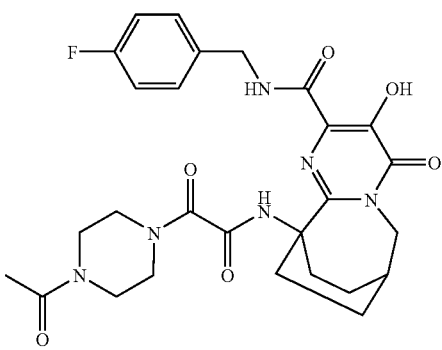

10-(((4-Acetyl-1-piperazinyl)(oxo)acetyl)amino)-N-(4-fluorobenzyl)-3-hydroxy-4-oxo-4,6,7,8,9,10-hexahydro-7,10-ethanopyrimido[1,2-a]azepine-2-carboxamide. To a solution of N-(4-fluorobenzyl)-3-hydroxy-4-oxo-10-((oxo(1-piperazinyl)acetyl)amino)-4,6,7,8,9,10-hexahydro-7,10-ethanopyrimido[1,2-a]azepine-2-carboxamide (25 mg, 0.049 mmol) in $CH_2Cl_2$ (2 mL) was added triethylamine (0.034 mL, 0.244 mmol), followed by acetyl chloride (0.017 mL, 0.244 mmol) and the resulting mixture stirred at room temperature. After 16 h, the reaction mixture was concentrated to give crude product which was dissolved in methanol (2 mL) and treated with 2M dimethylamine in methanol (0.5 mL). The resulting reaction mixture was stirred at 60° C. for 2 h then cooled and purified by preparative HPLC to afford the title compound as a brown solid (13 mg, 46% yield). $^1$H NMR (500 MHz, CDCl$_3$) δ: 12.05 (1 H, brs), 8.53 (1 H, brs), 8.48 (1 78, 5.65 Hz), 7.07 (2H, t, J=8.24 Hz), 4.66 (2 H, d, J=5.80 Hz), 4.24 (2 H, d, J=3.05 Hz), 4.18 (1 H, brs), 3.95-4.03 (1 H, m), 3.75 (2 H, brs), 3.46-3.63 (4 H, m), 2.64-2.73 (2 H, m), 2.51-2.58 (1 H, m), 2.11 (3 H, d, J=9.46 Hz), 1.95-2.14 (4 H, m), 1.76-1.82 (2 H, m). LCMS (M+H)=555.56. HPLC purity: >95%.

EXAMPLE 139

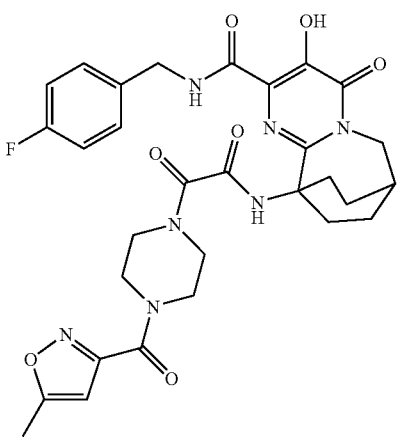

N-(4-Fluorobenzyl)-3-hydroxy-10-(((4-((5-methyl-3-isoxazolyl)carbonyl)-1-piperazinyl)(oxo)acetyl)amino)-4-oxo-4,6,7,8,9,10-hexahydro-7,10-ethanopyrimido[1,2-a]azepine-2-carboxamide. To a suspension N-(4-fluorobenzyl)-3-hydroxy-4-oxo-10-((oxo(1-piperazinyl)acetyl)amino)-4,6,7,8,9,10-hexahydro-7,10-ethanopyrimido[1,2-a]azepine-2-carboxamide (0.024 g, 0.038 mmol) in dichloromethane (1 mL) was added diisopropyl ethylamine (0.027 mL, 0.153 mmol). After stirring for 5 min, 5-methyl-isoxazole-3-carbonyl chloride (0.011 g, 0.077 mmol) was added and the solution stirred at room temperature for 1 h. Dimethylamine (0.192 mL, 0.383 mmol) (2 M in methanol) was added and the solution stirred at room temperature for 1 h then concentrated. The residue was purified by preparative HPLC: Solvent A=10% methanol/90% $H_2O$/0.1% trifluoroacetic acid; Solvent B=90% methanol/10% $H_2O$/0.1% trifluoroacetic acid; Start % B=10; Final % B=100; Gradient time=20 min; Stop time=25 min; Column=XTERRA® 19×50 mm, C18, 5 µm (product elutes at 12.6 min) to give the title compound as a pale lavender solid (12.1 mg, 49% yield). $^1$H NMR (500 MHz, CDCl$_3$) δ: 12.00 (1 H, brs), 8.51 (1 H, d, J=5.80 Hz), 8.40 (1 H, d, J=5.19 Hz), 7.28-7.50 (2 H, m), 6.88-7.12 (2 H, m), 6.33 (1 H, d, J=2.14 Hz), 4.55 (2 H, t, J=6.26 Hz), 4.16 (2 H, brs), 4.02-4.14 (2 H, m), 3.89-4.00 (2 H, m), 3.80 (2 H, dt, J=18.08, 5.00 Hz), 3.50-3.68 (2 H, m), 2.53-2.77 (2 H, m), 2.48 (4 H, d, J=7.93 Hz), 1.87-2.15 (4 H, m), 1.72 (2 H, brs). LCMS (M+H) calcd for $C_{30}H_{33}FN_7O_7$: 622.24; found: 622.78.

EXAMPLE 140

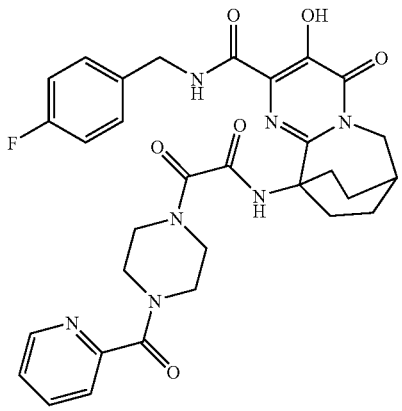

N-(4-Fluorobenzyl)-3-hydroxy-4-oxo-10-((oxo(4-(2-pyridinylcarbonyl)-1-piperazinyl)acetyl)amino)-4,6,7,8,9,10-hexahydro-7,10-ethanopyrimido[1,2-a]azepine-2-carboxamide. Purple foam (14.1 mg, 49% yield). $^1$H NMR (500 MHz, CDCl$_3$) δ: 8.72 (1 H, d, J=12.51 Hz), 8.44 (1 H, t, J=5.80 Hz), 8.26-8.41 (1 H, m), 8.04 (1 H, d, J=6.41 Hz), 7.73 (1 H, d, J=7.93 Hz), 7.60 (1 H, brs), 7.34 (2 H, d, J=18.62 Hz), 6.89-7.12 (2 H, m), 4.54 (2 H, d, J=9.77 Hz), 3.96-4.23 (4 H, m), 3.75-3.94 (2 H, m), 3.39-3.74 (4 H, m), 2.37-2.71 (3 H, m), 1.87-2.16 (4 H, m), 1.72 (2 H, brs). LCMS (M+H) calcd for C$_{31}$H$_{33}$FN$_7$O$_6$: 618.24; found: 618.43.

EXAMPLE 141

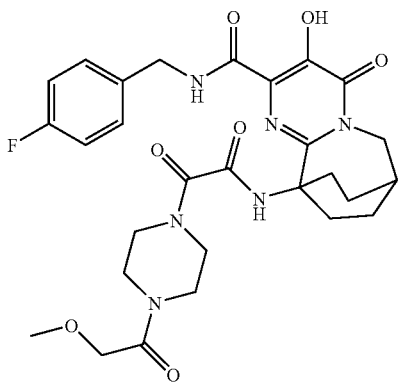

N-(4-Fluorobenzyl)-3-hydroxy-10-(((4-(methoxyacetyl)-1-piperazinyl)(oxo)acetyl)amino)-4-oxo-4,6,7,8,9,10-hexahydro-7,10-ethanopyrimido[1,2-a]azepine-2-carboxamide. White solid (2.7 mg, 11% yield). LCMS (M+H) calcd for C$_{28}$H$_{34}$FN$_6$O$_7$: 585.24; found: 585.75. $^1$H NMR (400 MHz, CDCl$_3$) δ: 11.97 (1 H, brs), 8.42-8.65 (1 H, m), 8.35 (1 H, brs), 7.34 (2 H, dd, J=8.53, 5.27 Hz), 7.00 (2 H, t, J=8.66 Hz), 4.54 (2 H, d, J=6.27 Hz), 4.14 (2 H, d, J=3.76 Hz), 4.10 (2 H, brs), 4.00 (2 H, brs), 3.45-3.72 (6 H, m), 3.40 (3 H, brs), 2.52-2.70 (2 H, m), 2.48 (1 H, brs), 1.86-2.10 (4 H, m), 1.62-1.80 (2 H, m).

EXAMPLE 142

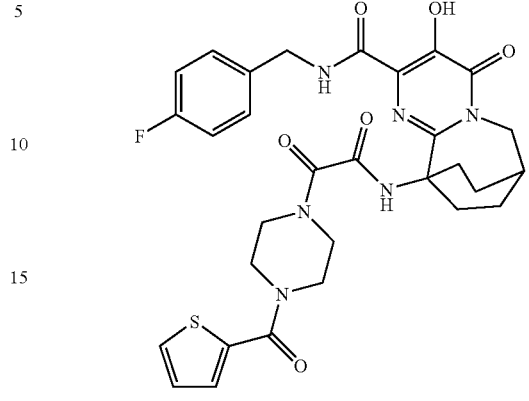

N-(4-Fluorobenzyl)-3-hydroxy-4-oxo-10-((oxo(4-(2-thiophenylcarbonyl)-1-piperazinyl)acetyl)amino)-4,6,7,8,9,10-hexahydro-7,10-ethanopyrimido[1,2-a]azepine-2-carboxamide. White solid (13.1 mg, 51% yield). LCMS (M+H) calcd for C$_{30}$H$_{32}$FN$_6$O$_6$S: 623.20; found: 623.77. $^1$H NMR (400 MHz, CDCl$_3$) δ: 11.97 (1H, s), 8.54 (1 H, s), 8.35 (1 H, t, J=6.02 Hz), 7.48 (1 H, dd, J=5.02, 1.25 Hz), 7.31-7.38 (2 H, m), 7.30 (1 H, dd, J=3.64, 1.13 Hz), 7.06 (1 H, dd, J=5.02, 3.76 Hz), 6.93-7.03 (2 H, m), 4.54 (2 H, d, J=6.27 Hz), 4.14 (2 H, d, J=3.76 Hz), 4.01-4.10 (2 H, m), 3.68-3.86 (4 H, m), 3.57 (2 H, dd, J=6.27, 4.27 Hz), 2.52-2.68 (2H, m), 2.48 (1 H, brs), 1.84-2.15 (4 H, m), 1.63-1.79 (2 H, m).

EXAMPLE 143

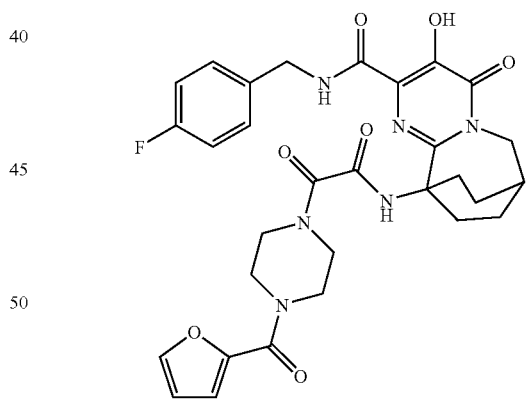

N-(4-Fluorobenzyl)-10-(((4-(2-furanylcarbonyl)-1-piperazinyl)(oxo)acetyl)amino)-3-hydroxy-4-oxo-4,6,7,8,9,10-hexahydro-7,10-ethanopyrimido[1,2-a]azepine-2-carboxamide. White solid (13.9 mg, 52% yield). LCMS (M+H) calcd for C$_{30}$H$_{32}$FN$_6$O$_7$: 607.23; found: 607.76. $^1$H NMR (400 MHz, CDCl$_3$) δ: 11.97 (1 H, s), 8.51 (1 H, s), 8.38 (1 H, t, J=6.15 Hz), 7.48 (1 H, d, J=0.75 Hz), 7.29-7.42 (2 H, m), 7.06 (1 H, dd, J=3.51, 0.75 Hz), 6.95-7.04 (2 H, m), 6.49 (1 H, dd, J=3.39, 1.88 Hz), 4.54 (2 H, d, J=6.27 Hz), 4.14 (2 H, d, J=3.76 Hz), 3.99-4.11 (2 H, m), 3.71-3.93 (4 H, m), 3.59 (2 H, dd, J=6.27, 4.27 Hz), 2.53-2.66 (2 H, m), 2.48 (1 H, d, J=2.26 Hz), 1.86-2.14 (4 H, m), 1.63-1.79 (2 H, m).

EXAMPLE 144

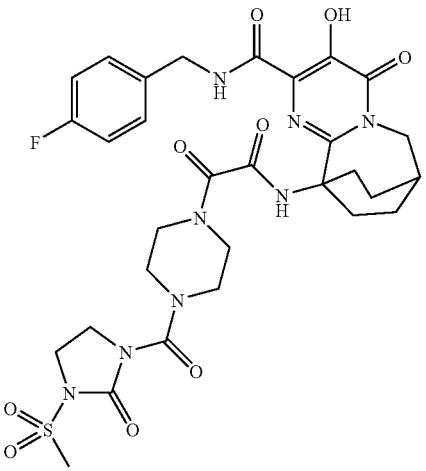

N-(4-Fluorobenzyl)-3-hydroxy-10-(((4-((3-(methylsulfonyl)-2-oxo-1-imidazolidinyl)carbonyl)-1-piperazinyl)(oxo)acetyl)amino)-4-oxo-4,6,7,8,9,10-hexahydro-7,10-ethanopyrimido[1,2-a]azepine-2-carboxamide. Pale purple solid (5.3 mg, 17% yield). LCMS (M+H) calcd for $C_{30}H_{36}FN_8O_9S$: 703.23; found: 703.88. $^1$H NMR (500 MHz, CDCl$_3$) δ: 12.00 (1 H, brs), 8.27-8.53 (2 H, m), 7.36 (2 H, dd, J=8.55, 5.19 Hz), 6.95-7.09 (2 H, m), 4.55 (2 H, d, J=6.10 Hz), 4.16 (2 H, d, J=3.66 Hz), 4.01-4.12 (2 H, m), 3.81-3.99 (4 H, m), 3.59-3.69 (2 H, m), 3.43-3.58 (4 H, m), 3.32 (3 H, s), 2.57 (2 H, ddd, J=14.19, 9.31, 5.49 Hz), 2.50 (1 H, d, J=2.14 Hz), 1.89-2.15 (4 H, m), 1.69 (2 H, brs).

EXAMPLE 145

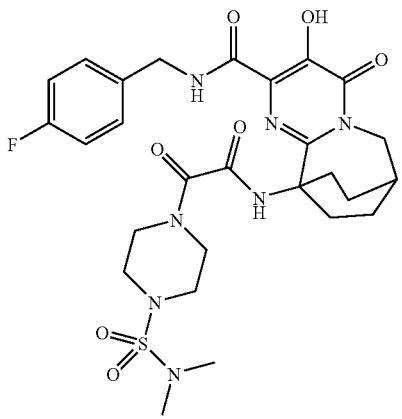

10-(((4-(Dimethylsulfamoyl)-1-piperazinyl)(oxo)acetyl)amino)-N-(4-fluorobenzyl)-3-hydroxy-4-oxo-4,6,7,8,9,10-hexahydro-7,10-ethanopyrimido[1,2-a]azepine-2-carboxamide. To a suspension of N-(4-fluorobenzyl)-3-hydroxy-4-oxo-10-((oxo(1-piperazinyl)acetyl)amino)-4,6,7,8,9,10-hexahydro-7,10-ethanopyrimido[1,2-a]azepine-2-carboxamide (0.025 g, 0.040 mmol) in dichloromethane (1 mL) was added diisopropyl ethylamine (0.028 mL, 0.160 mmol) and the solution was stirred at room temperature for 5 min. Added to this was dimethylsulfamoyl chloride (4.26 µL, 0.040 mmol) and the solution was stirred at room temperature for 16 h. The reaction solution was concentrated and purified by preparative HPLC: Solvent A=10% methanol/90% H$_2$O/0-1% trifluoroacetic acid; Solvent B=90% methanol/10% H$_2$O/0.1% trifluoroacetic acid; Start % B=20; Final % B=100; Gradient time=20 min; Stop time=30 min; Column=XTERRA® 19×50 mm, C18, 5 µm to give the title compound as a white solid (12.2 mg, 45% yield). LCMS (M+H) calcd for $C_{27}H_{35}FN_7O_7S$: 620.23; found: 620.74. $^1$H NMR (500 MHz, CDCl$_3$) δ: 12.00 (1 H, s), 8.45 (1 H, s), 8.39 (1 H, t, J=5.95 Hz), 7.36 (2H, dd, J=8.55, 5.49 Hz), 7.01 (2 H, t, J=8.55 Hz), 4.55 (2 H, d, J=6.10 Hz), 4.16 (2 H, d, J=3.66 Hz), 4.02-4.09 (2 H, m), 3.52-3.61 (2 H, m), 3.26-3.36 (2 H, m), 3.18-3.26 (2 H, m), 2.84 (6 H, s), 2.58 (2 H, ddd, J=14.19, 9.16, 5.65 Hz), 2.50 (1H, brs), 1.86-2.11 (4 H, m), 1.66-1.80 (2 H, m).

EXAMPLE 146

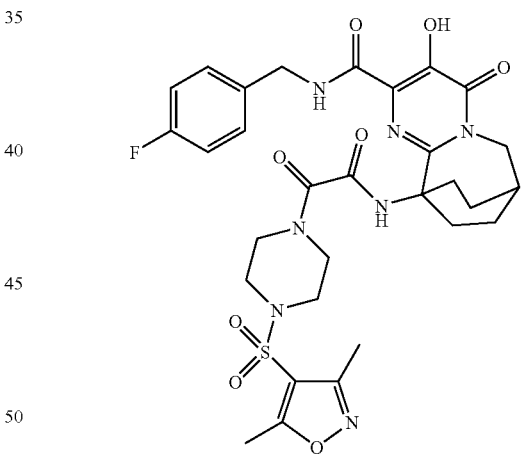

10-(((4-((3,5-Dimethyl-4-isoxazolyl)sulfonyl)-1-piperazinyl)(oxo)acetyl)amino)-N-(4-fluorobenzyl)-3-hydroxy-4-oxo-4,6,7,8,9,10-hexahydro-7,10-ethanopyrimido[1,2-a]azepine-2-carboxamide. Purple solid (4.5 mg, 16% yield). LCMS (M+H) calcd for $C_{31}H_{33}FN_7O_6$: 672.22; found: 672.89. $^1$H NMR (500 MHz, CDCl$_3$) δ: 11.99 (1 H, brs), 8.74 (1 H, brs), 8.22 (1 H, brs), 7.35 (2H, dd, J=8.09, 5.34 Hz), 7.00 (2 H, t, J=8.55 Hz), 4.55 (2 H, d, J=5.19 Hz), 4.03-4.31 (4 H, m), 3.63 (2 H, brs), 3.05-3.24 (4 H, m), 2.54-2.75 (5 H, m), 2.50 (1 H, brs), 2.40 (3 H, s), 1.97 (4 H, brs), 1.67-1.79 (2 H, m).

EXAMPLE 147

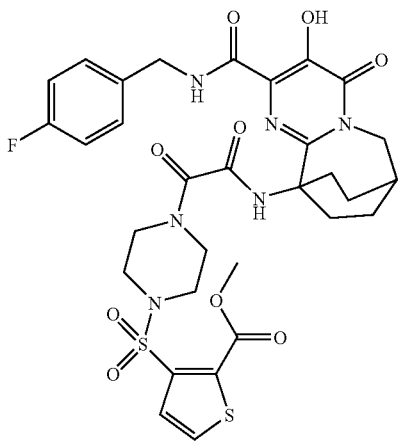

Methyl 3-((4-(((2-((4-fluorobenzyl)carbamoyl)-3-hydroxy-4-oxo-6,7,8,9-tetrahydro-7,10-ethanopyrimido[1,2-a]azepin-10(4H)-yl)amino) (oxo)acetyl)-1-piperazinyl)sulfonyl)-2-thiophenecarboxylate. White solid (6.0 mg, 19% yield). (M+H) calcd for $C_{31}H_{34}FN_6O_9S_2$: 717.18; found: 717.36. $^1$H NMR (500 MHz, CDCl$_3$) δ: 11.98 (1 H, s), 8.28-8.53 (2 H, m), 7.40-7.60 (2 H, m), 7.34 (2 H, dd, J=8.39, 5.34 Hz), 6.99 (2 H, t, J=8.70 Hz), 4.53 (2 H, d, J=6.41 Hz), 4.15 (2 H, d, J=3.66 Hz), 3.99-4.10 (2 H, m), 3.92 (3 H, s), 3.51-3.74 (2 H, m), 3.38 (4 H, dt, J=18.08, 5.00 Hz), 2.39-2.71 (3 H, m), 1.84-2.12 (4 H, m), 1.63-1.79 (2 H, m).

EXAMPLE 148

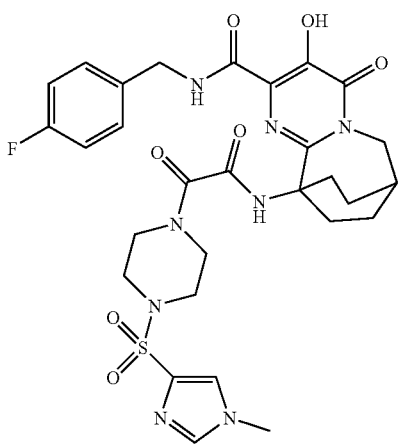

N-(4-Fluorobenzyl)-3-hydroxy-10-(((4-((1-methyl-1H-imidazol-4-yl)sulfonyl)-1-piperazinyl)(oxo)acetyl)amino)-4-oxo-4,6,7,8,9,10-hexahydro-7,10-ethanopyrimido[1,2-a]azepine-2-carboxamide. White solid (5.0 mg, 19% yield). (M+H) calcd for $C_{29}H_{34}FN_8O_7S$: 657.22; found: 657.27. $^1$H NMR (400 MHz, CDCl$_3$) δ: 11.95 (1 H, brs), 8.03-8.67 (2 H, m), 7.44 (2 H, d, J=17.32 Hz), 7.26-7.39 (2 H, m), 6.81-7.10 (2 H, m), 4.24-4.66 (2 H, m), 3.83-4.27 (5 H, m), 3.32-3.86 (6 H, m), 3.24 (2 H, brs), 2.27-2.75 (3 H, m), 1.81-2.16 (4 H, m), 1.69 (2 H, d, J=4.52 Hz).

EXAMPLE 149

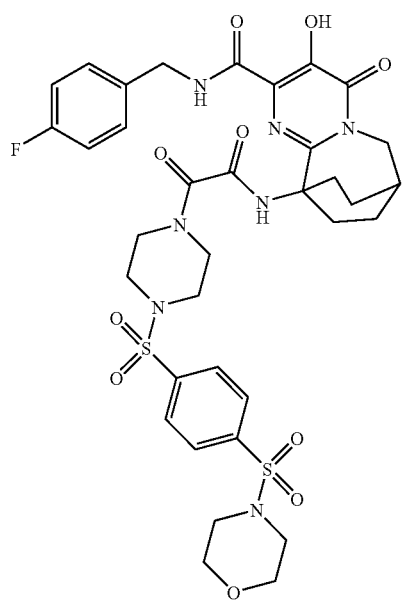

N-(4-Fluorobenzyl)-3-hydroxy-10-(((4-((4-(4-morpholinylsulfonyl)phenyl)sulfonyl)-1-piperazinyl)(oxo)acetyl) amino)-4-oxo-4,6,7,8,9,10-hexahydro-7,10-ethanopyrimido[1,2-a]azepine-2-carboxamide. To a mixture N-(4-fluorobenzyl)-3-hydroxy-4-oxo-10-((oxo(1-piperazinyl) acetyl)amino)-4,6,7,8,9,10-hexahydro-7,10-ethanopyrimido[1,2-a]azepine-2-carboxamide (25 mg, 0.040 mmol) in dichloromethane (1 mL) was added diisopropyl ethylamine (0.028 mL, 0.160 mmol) followed by 4-(morpholinosulfonyl) benzene-1-sulfonyl chloride (13.00 mg, 0.040 mmol) and the resulting solution stirred at room temperature for 24 h. The mixture was treated with sodium ethoxide (0.015 mL, 0.040 mmol) and stirred at room temperature for 1 h. The reaction was diluted with water and dichloromethane. The aqueous phase was acidified with 1N HCl and the product extracted into the organic phase. The organic phase was concentrated and the residue was triturated with methanol. The white solids were collected by filtration to give the title compound (2.2 mg, 7% yield). (M+H) calcd for $C_{35}H_{41}FN_7O_{10}S_2$: 802.23; found: 802.84. $^1$H NMR (400 MHz, CDCl$_3$) δ: 11.94 (1 H, s), 8.70 (1 H, s), 8.17 (1H, t, J=6.02 Hz), 7.91 (4 H, s), 7.31 (2 H, dd, J=8.41, 5.40 Hz), 6.96 (2 H, t, J=8.66 Hz), 4.51 (2 H, d, J=6.02 Hz), 4.04-4.22 (4 H, m), 3.67-3.80 (4 H, m), 3.44-3.65 (2 H, m), 2.88-3.20 (8 H, m), 2.50-2.67 (2 H, m), 2.46 (1 H, brs), 1.79-2.06 (4 H, m), 1.58-1.77 (2 H, m).

Examples 150 through 155 can be synthesized according to Scheme XVII

EXAMPLE 150

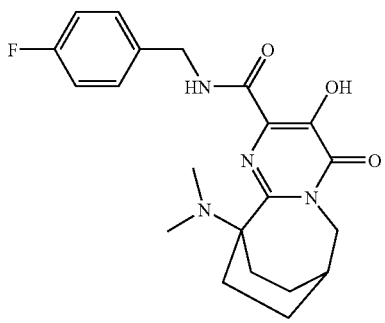

10-(Dimethylamino)-N-(4-fluorobenzyl)-3-hydroxy-4-oxo-4,6,7,8,9,10-hexahydro-7,10-ethanopyrimido[1,2-a]azepine-2-carboxamide. To a solution of 10-amino-N-(4-fluorobenzyl)-3-hydroxy-4-oxo-4,6,7,8,9,10-hexahydro-7,10-ethanopyrimido[1,2-a]azepine-2-carboxamide (50 mg, 0.134 mmol) in 1,2-dichloroethane (2 mL) was added acetic acid (0.038 mL, 0.671 mmol) and aq. formaldehyde (0.022 mL, 0.295 mmol) and the resulting mixture was stirred at room temperature for 3 h. Sodium triacetoxyborohydride (71.1 mg, 0.336 mmol) was then added and the resulting mixture stirred at room temperature overnight. Sat. NaHCO$_3$ was added and the mixture was extracted 3 times with chloroform, dried and filtered. The crude material was then purified by preparative HPLC to afford the title compound as a light yellow solid (7 mg, 13% yield). $^1$H NMR (500 MHz, CDCl$_3$) δ: 12.17 (brs, 1H), 9.78 (brs, 1H), 7.36 (dd, 2H, J=8.55 & 5.49 Hz), 6.96-7.00 (m, 2H), 4.52 (d, 2H, J=6.41 Hz), 4.12 (d, 2H, J=3.36 Hz), 2.83 (s, 6H), 2.59 (brs, 1H), 2.23-2.31 (m, 2H), 2.11-2.18 (m, 2H), 1.98-2.06 (m, 2H), 1.73-1.82 (m, 2H). LCMS (M+H)=401.16. HPLC purity: >95%.

EXAMPLE 151

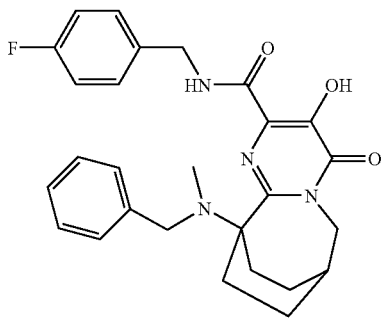

10-(Benzyl(methyl)amino)-N-(4-fluorobenzyl)-3-hydroxy-4-oxo-4,6,7,8,9,10-hexahydro-7,10-ethanopyrimido[1,2-a]azepine-2-carboxamide. To a stirred solution of 10-amino-N-(4-fluorobenzyl)-3-hydroxy-4-oxo-4,6,7,8,9,10-hexahydro-7,10-ethanopyrimido[1,2-a]azepine-2-carboxamide (300 mg, 0.734 mmol) in methanol (7 mL), benzaldehyde (0.295 mL, 2.92 mmol), triethylamine (0.102 mL, 0.734 mmol), AcOH (0.420 mL, 7.34 mmol) and NaCNBH$_3$ (184 mg, 2.94 mmol) was added. The mixture was then stirred at room temperature for 72 h. Aqueous formaldehyde (0.109 mL, 1.468 mmol) was then added to the reaction and the mixture stirred at room temperature for 4 h. The solvent was removed and the crude product purified by preparative HPLC to afford the title compound as the corresponding trifluoroacetic acid salt (280 mg, 65% yield). $^1$H NMR (500 MHz, CDCl$_3$) δ: 11.6 (1 H, brs), 10.1 (1 H, brs), 7.4-7.5 (2 H, m), 7.3 (1 H, t, J=7.63 Hz), 7.3 (2 H, d, J=7.63 Hz), 7.0-7.1 (3 H, m), 4.8 (1 H, dd, J=14.34, 6.71 Hz), 4.4-4.5 (3 H, m), 3.8 (1 H, d, J=15.56 Hz), 3.7 (1 H, d, J=12.82 Hz), 2.8 (3 H, s), 2.6 (1 H, brs), 2.4-2.4 (2 H, m), 2.3-2.4 (1 H, m), 2.2-2.3 (1 H, m), 2.1-2.1 (1 H, m), 2.0-2.0 (2 H, m), 1.5-1.6 (1 H, m). LCMS (M+H)=477.49.

EXAMPLE 152

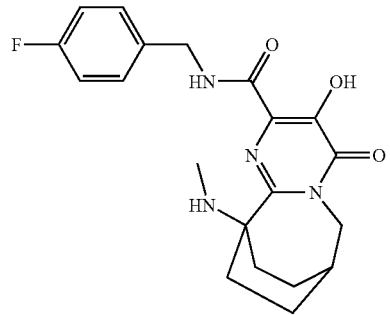

N-(4-Fluorobenzyl)-3-hydroxy-10-(methylamino)-4-oxo-4,6,7,8,9,10-hexahydro-7,10-ethanopyrimido[1,2-a]azepine-2-carboxamide. To a solution of 10-(benzyl(methyl)amino)-N-(4-fluorobenzyl)-3-hydroxy-4-oxo-4,6,7,8,9,10-hexahydro-7,10-ethanopyrimido[1,2-a]azepine-2-carboxamide (255 mg, 0.432 mmol) in methanol (2 mL) was added Pd/C (32.2 mg, 0.030 mmol) and the mixture was stirred under hydrogen atmosphere (balloon) for 1 h. The catalyst was then filtered off, and the filtrate was evaporated under reduced pressure to afford the title compound as a white solid (200 mg, 93% yield). $^1$H NMR (300 MHz, DMSO-d$_6$) δ: 12.3 (1 H, s), 9.5 (1 H, s), 7.3-7.4 (2 H, m), 7.2-7.2 (2 H, m), 4.5 (2 H, d, J=6.22 Hz), 4.0 (2 H, d, J=3.29 Hz), 2.6 (3 H, brs), 2.0-2.1 (4 H, m), 1.7-1.9 (5 H, m). LCMS (M+H)=387.17.

EXAMPLE 153

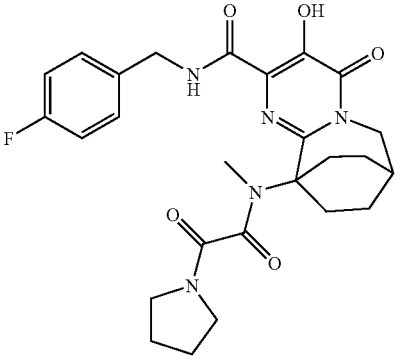

N-(4-Fluorobenzyl)-3-hydroxy-10-(methyl(oxo(1-pyrrolidinyl)acetyl)amino)-4-oxo-4,6,7,8,9,10-hexahydro-7,10-ethanopyrimido[1,2-a]azepine-2-carboxamide. To a stirred solution of N-(4-fluorobenzyl)-3-hydroxy-10-(methylamino)-4-oxo-4,6,7,8,9,10-hexahydro-7,10-ethanopyrimido[1,2-a]azepine-2-carboxamide (50 mg, 0.100 mmol) in (DMF (2 mL) was added 2-oxo-2-(pyrrolidin-1-yl)acetic acid (57.2 mg, 0.400 mmol), diisopropyl-ethylamine (0.105 mL, 0.599 mmol), O-(7-azabenzotriazol-1-yl)-N,N,N',N'-tetramethyluronium hexafluorophosphate (HATU) (152 mg, 0.400 mmol) and 4-(dimethylamino)pyridine (DMAP) (1.221 mg, 9.99 µmol) and the resulting mixture was stirred at room temperature for 3 h. The crude was then purified by preparative HPLC and recrystallized from methanol to afford the title compound as a glassy white crystals (20 mg, 40% yield). $^1$H NMR (500 MHz, CDCl$_3$) δ: 12.1 (1 H, s), 9.6 (1 H, brs), 7.4-7.4 (2 H, m), 7.0-7.0 (2 H, m), 4.8-4.9 (1 H, m), 4.6-4.7 (1 H, m), 4.4-4.5 (1 H, m), 3.6-3.7 (2 H, m), 3.5 (2 H, t, J=6.71 Hz), 3.3-3.4 (2 H, m), 3.0 (3 H, s), 2.5 (1 H, brs), 1.9-2.1 (9 H, m), 1.7-1.8 (2 H, m). LCMS (M+H)=512.24. HPLC purity: >95%.

EXAMPLE 154

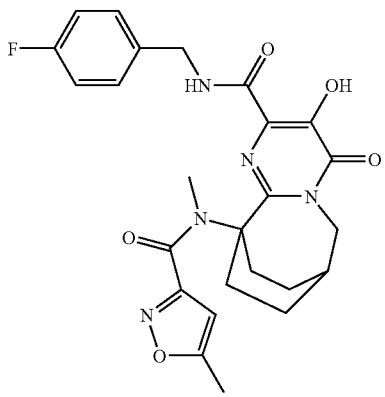

N-(4-Fluorobenzyl)-3-hydroxy-10-(methyl((5-methyl-3-isoxazolyl)carbonyl)amino)-4-oxo-4,6,7,8,9,10-hexahydro-7,10-ethanopyrimido[1,2-a]azepine-2-carboxamide. To a solution of N-(4-fluorobenzyl)-3-hydroxy-10-(methylamino)-4-oxo-4,6,7,8,9,10-hexahydro-7,10-ethanopyrimido[1,2-a]azepine-2-carboxamide (25 mg, 0.061 mmol) in CH$_2$Cl$_2$ (2 mL) was added triethylamine (0.051 mL, 0.365 mmol) followed by 5-methylisoxazole-3-carbonyl chloride (17.69 mg, 0.122 mmol) and the resulting mixture was stirred at room temperature. After 16 at room temperature the reaction mixture was concentrated to give crude product which was dissolved in methanol (2 mL) and treated with 2M dimethylamine in methanol (0.5 mL). The resulting reaction mixture was stirred at 60° C. for 2 h, then cooled and purified by preparative HPLC to afford the title compound (5 mg, 17% yield) as an off-white solid. $^1$H NMR (500 MHz, CDCl$_3$) δ: 11.81 (1 H, brs), 8.70 (1 H, d, J=5.19 Hz), 7.31 (2 H, dd, J=8.55, 5.49 Hz), 6.92-7.01 (2 H, m), 6.09 (1 H, s), 4.75-4.86 (1 H, m), 4.58-4.67 (1 H, m), 4.38-4.47 (1 H, m), 3.67 (1 H, d, J=15.56 Hz), 3.35-3.46 (1 H, m), 3.13 (3 H, s), 2.50 (1 H, brs), 2.41 (3 H, s), 2.07-2.16 (3 H, m), 1.95-2.05 (1 H, m), 1.72-1.86 (2 H, m), 1.37-1.50 (1 H, m). LCMS (M+H)=496.66. HPLC purity: >95%.

EXAMPLE 155

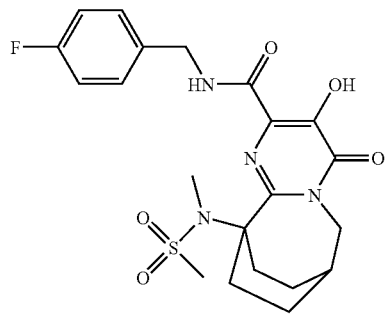

N-(4-Fluorobenzyl)-3-hydroxy-10-(methyl(methylsulfonyl)amino)-4-oxo-4,6,7,8,9,10-hexahydro-7,10-ethanopyrimido[1,2-a]azepine-2-carboxamide. Off-white solid (2.5 mg, 11% yield). $^1$H NMR (500 MHz, CDCl$_3$) δ: 11.94 (1 H, brs), 9.03 (1 H, brs), 7.32 (2 H, dd, J=8.39, 5.34 Hz), 6.96-7.02 (2 H, m), 4.52-4.66 (2H, m), 4.46 (1 H, d, J=6.41 Hz), 4.36-4.43 (1 H, m), 3.69-3.76 (1 H, m), 3.13-3.24 (1 H, m), 2.94 (3 H, s), 2.91 (3 H, s), 2.47 (1 H, brs), 2.04-2.20 (2 H, m), 1.93-2.01 (2 H, m), 1.52-1.63 (2 H, m). LCMS (M+H)= 465.60. HPLC purity: >95%.

Examples 156 through 162 can be prepared according to Scheme XVIII

EXAMPLE 156

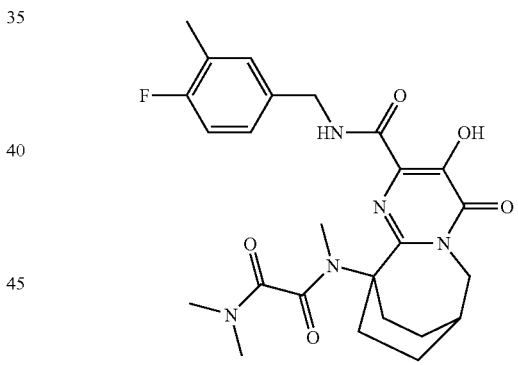

N-(2-((4-Fluoro-3-methylbenzyl)carbamoyl)-3-hydroxy-4-oxo-6,7,8,9-tetrahydro-7,10-ethanopyrimido[1,2-a]azepin-10(4H)-yl)-N,N',N'-trimethylethanediamide. To a mixture of methyl 10-(((dimethylamino)(oxo)acetyl)(methyl)amino)-3-hydroxy-4-oxo-4,6,7,8,9,10-hexahydro-7,10-ethanopyrimido[1,2-a]azepine-2-carboxylate (3 g, 7.65 mmol) in ethanol (80 mL) was added (4-fluoro-3-methylphenyl)methanamine (2.90 mL, 22.94 mmol) and the mixture was heated at 90° C. for 18 h. The reaction mixture was cooled, concentrated, diluted with ethyl acetate and washed twice with 0.2N NaOH (2×100 mL). The organic layer was discarded and the aqueous layer acidified with conc. HCl and extracted with dichloromethane (2×150 mL), dried (Na$_2$SO$_4$), filtered and concentrated. The crude product was recrystallized from methanol to afford the title compound (2.5 g, 66% yield) as a crystalline white solid. $^1$H NMR (500 MHz, CDCl$_3$) δ: 12.13 (1 H, s), 9.56 (1 H, brs), 7.20-7.23 (1 H, m), 7.15-7.20 (1 H, m), 6.88-6.93 (1 H, m), 4.83 (1 H, dd, J=15.56, 7.02 Hz), 4.55-4.62 (1 H, m), 4.39-4.45 (1 H, m), 3.60 (1 H, d, J=15.56 Hz), 3.33-3.47 (2 H, m), 3.01 (3 H, s), 2.99 (3H, s), 2.97 (3 H, s), 2.49 (1 H, brs), 2.23 (3 H, d, J=1.83 Hz), 1.97-2.09 (4 H, m), 1.74-1.84 (2 H, m). LCMS (M+H)= 500.69. HPLC purity: >95%.

EXAMPLE 157

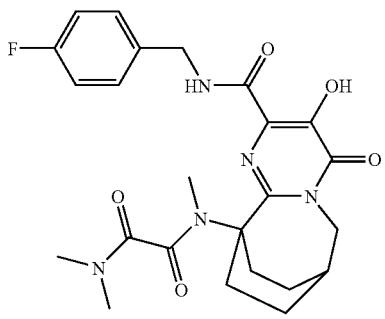

N-(2-((4-Fluorobenzyl)carbamoyl)-3-hydroxy-4-oxo-6,7,8,9-tetrahydro-7,10-ethanopyrimido[1,2-a]azepin-10(4H)-yl)-N,N',N'-trimethylethanediamide. White crystalline solid (27 mg, 40% yield). $^1$H NMR (500 MHz, CDCl$_3$) δ: 12.12 (1 H, s), 9.58 (1 H, brs), 7.37-7.44 (2 H, m), 6.91-7.08 (2 H, m), 4.83-4.95 (1 H, m), 4.56-4.64 (1 H, m), 4.43-4.55 (1 H, m), 3.64 (1 H, d, J=15.26 Hz), 3.44-3.56 (2 H, m), 3.01 (3 H, s), 3.07 (3 H, s), 3.13 (3 H, s), 2.55 (1 H, brs), 2.01-2.18 (4 H, m), 1.72-1.83 (2 H, m). LCMS (M+H)=486.16. HPLC purity: >95%.

EXAMPLE 158

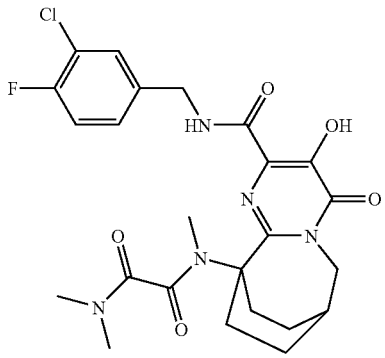

N-(2-((3-Chloro-4-fluorobenzyl)carbamoyl)-3-hydroxy-4-oxo-6,7,8,9-tetrahydro-7,10-ethanopyrimido[1,2-a]azepin-10(4H)-yl)-N,N',N'-trimethylethanediamide. Crystalline white solid (25 mg, 49% yield). $^1$H NMR (500 MHz, CDCl$_3$) δ: 12.00 (1 H, s), 9.63 (1 H, brs), 7.49 (1 H, dd, J=7.02, 2.14 Hz), 7.26-7.31 (1 H, m), 7.02-7.08 (1 H, m), 4.80-4.86 (1 H, m), 4.55-4.62 (1 H, m), 4.41-4.48 (1 H, m), 3.60 (1 H, d, J=14.95 Hz), 3.37-3.49 (2 H, m), 3.02 (3 H, s), 2.99 (3H, s), 2.98 (3 H, s), 2.49 (1 H, brs), 1.93-2.11 (4 H, m), 1.73-1.85 (2 H, m). LCMS (M+H)=520.64. HPLC purity: >95%.

EXAMPLE 159

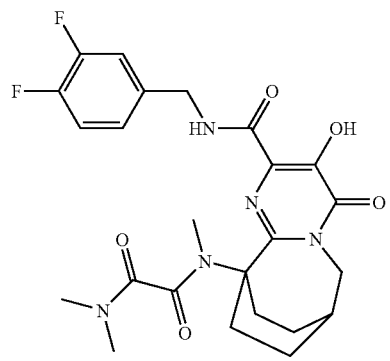

N-(2-((3,4-Difluorobenzyl)carbamoyl)-3-hydroxy-4-oxo-6,7,8,9-tetrahydro-7,10-ethanopyrimido[1,2-a]azepin-10(4H)-yl)-N,N',N'-trimethylethanediamide. Crystalline white solid (18 mg, 37% yield). $^1$H NMR (500 MHz, CDCl$_3$) δ: 12.00 (1H, s), 9.63 (1 H, brs), 7.23-7.28 (1 H, m), 7.02-7.14 (2 H, m), 4.83 (1 H, dd, J=15.26, 7.32 Hz), 4.55-4.63 (1 H, m), 4.41-4.48 (1 H, m), 3.60 (1 H, d, J=15.26 Hz), 3.36-3.47 (1 H, m), 3.02 (3 H, s), 2.99 (3 H, s), 2.98 (3 H, s), 2.49 (1 H, brs), 1.95-2.10 (4 H, m), 1.73-1.86 (2 H, m), 1.43-1.52 (1 H, m). LCMS (M+H)=504.65. HPLC purity: >95%.

EXAMPLE 160

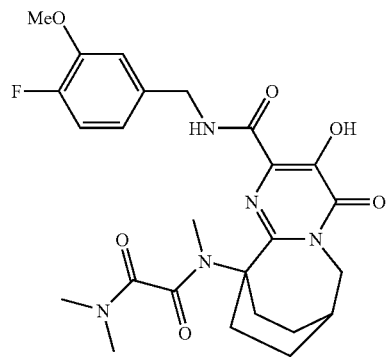

N-(2-((4-Fluoro-3-methoxybenzyl)carbamoyl)-3-hydroxy-4-oxo-6,7,8,9-tetrahydro-7,10-ethanopyrimido[1,2-a]azepin-10(4H)-yl)-N,N',N'-trimethylethanediamide. Crystalline white solid (18 mg, 36% yield). $^1$H NMR (500 MHz, CDCl$_3$) δ: 12.10 (1 H, s), 9.55 (1 H, t, J=6.27 Hz), 7.04 (1 H, dd, J=8.16, 1.88 Hz), 6.93-6.99 (1 H, m), 6.86-6.92 (1 H, m), 4.81 (1 H, dd, J=15.31, 7.53 Hz), 4.53-4.61 (1 H, m), 4.40-4.48 (1 H, m), 3.83 (3 H, s), 3.57 (1 H, d, J=15.31 Hz), 3.31-3.45 (1 H, m), 2.99 (3 H, s), 2.96 (3 H, s), 2.94 (3 H, s), 2.47 (1 H, brs), 1.94-2.08 (4H, m), 1.71-1.82 (2 H, m), 1.40-1.50 (1 H, m). LCMS (M+H)=516.64. HPLC purity: >95%.

EXAMPLE 161

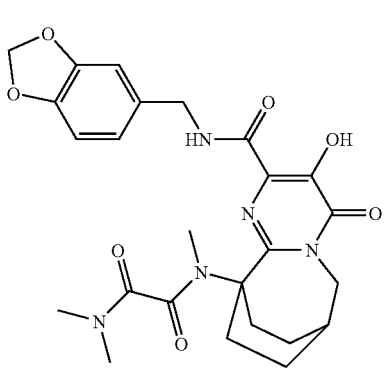

N-(2-((1,3-Benzodioxol-5-ylmethyl)carbamoyl)-3-hydroxy-4-oxo-6,7,8,9-tetrahydro-7,10-ethanopyrimido[1,2-a]azepin-10(4H)-yl)-N,N',N'-trimethylethanediamide. White solid (32 mg, 40% yield). $^1$H NMR (500 MHz, CDCl$_3$) δ: 12.14 (1 H, s), 9.58 (1 H, brs), 6.95 (1 H, d, J=1.53 Hz), 6.88 (1 H, dd, J=7.93, 1.53 Hz), 6.73 (1 H, d, J=7.93 Hz), 5.91 (2 H, s), 4.83 (1 H, dd, J=14.95, 7.32 Hz), 4.54-4.61 (1 H, m), 4.37 (1 H, dd, J=14.34, 5.80 Hz), 3.59 (1 H, d, J=15.26 Hz), 3.35-3.47 (1 H, m), 3.02 (3 H, s), 2.99 (6 H, s), 2.48 (1 H, brs), 1.95-2.09 (4 H, m), 1.72-1.85 (2 H, m), 1.43-1.52 (1 H, m). LCMS (M+H)=512.12. HPLC purity: >95%.

EXAMPLE 162

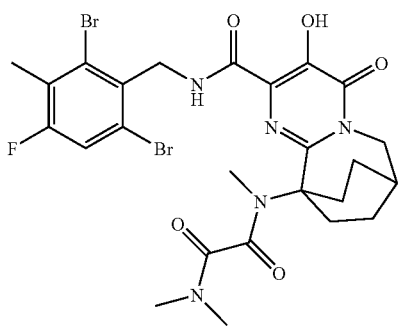

N-(2-((2,6-Dibromo-4-fluoro-3-methylbenzyl)carbamoyl)-3-hydroxy-4-oxo-6,7,8,9-tetrahydro-7,10-ethanopyrimido[1,2-a]azepin-10(4H)-yl)-N,N',N'-trimethylethanediamide. A solution of methyl 10-(((dimethylamino)(oxo)acetyl)(methyl)amino)-3-hydroxy-4-oxo-4,6,7,8,9,10-hexahydro-7,10-ethanopyrimido[1,2-a]azepine-2-carboxylate (0.10 g, 0.246 mmol), (2,6-dibromo-4-fluoro-3-methylphenyl)methanamine (0.225 g, 0.758 mmol) and Et$_3$N (0.279 mL, 2 mmol) in EtOH (5 mL) was heated at reflux for 48 h. Then, cooled and purified by preparative HPLC to afford the title compound (0.0906 g, 0.138 mmol, 56% yield) as a white solid after crystallization from methanol/H$_2$O. $^1$H NMR (500 MHz, CDCl$_3$) δ: 12.18 (1 H, s), 9.08 (1 H, s), 7.32 (1 H, d, J=8.5 Hz), 4.96 (2 H, d, J=8.2 Hz), 4.78-4.90 (1 H, m), 3.57-3.72 (1 H, m), 3.36-3.49 (1 H, m), 2.94 (3 H, s), 2.93 (3 H, s), 2.76 (3 H, s), 2.48-2.54 (1 H, m), 2.34 (3 H, d, J=2.1 Hz), 2.00-2.10 (4 H, m), 1.71-1.87 (2 H, m), 1.45-1.53 (1 H, m). LCMS (M+H) calcd for C$_{25}$H$_{29}$Br$_2$FN$_5$O$_5$: 656.05; found: 656.24.
Examples 163 through 172 can be prepared according to Scheme XIX

EXAMPLE 163

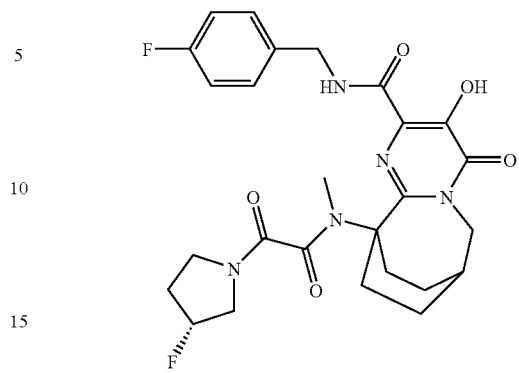

N-(4-Fluorobenzyl)-10-((((3R)-3-fluoro-1-pyrrolidinyl)(oxo)acetyl)(methyl)amino)-3-hydroxy-4-oxo-4,6,7,8,9,10-hexahydro-7,10-ethanopyrimido[1,2-a]azepine-2-carboxamide. To a mixture of ethyl 10-((((3R)-3-fluoro-1-pyrrolidinyl)(oxo)acetyl)(methyl)amino)-4-oxo-3-((phenylcarbonyl)oxy)-4,6,7,8,9,10-hexahydro-7,10-ethanopyrimido[1,2-a]azepine-2-carboxylat (35 mg, 0.063 mmol) in ethanol (2 mL) was added 2M dimethylamine in methanol (0.063 mL, 0.126 mmol) and the resulting mixture was heated at 50° C. for 1 h. (4-Fluorophenyl)methanamine (0.036 mL, 0.316 mmol) followed by triethylamine (0.044 mL, 0.316 mmol) were added and the mixture heated at 90° C. for 18 h. The reaction mixture was then cooled, concentrated and purified by preparative HPLC to afford the title compound (17 mg, 51% yield) as an off-white solid. $^1$H NMR (500 MHz, CDCl$_3$) δ: 11.96 (1 H, brs), 9.45 (1 H, brs), 7.34-7.40 (2H, m), 6.97 (2 H, t, J=8.70 Hz), 5.32-5.39 (0.5 H, m), 5.20-5.29 (0.5 H, m), 4.76-4.86 (1 H, m), 4.56-4.67 (1 H, m), 4.40-4.52 (1 H, m), 3.86-3.93 (0.5 H, m), 3.74-3.82 (0.5 H, m), 3.34-3.71 (6 H, m), 3.03 (1.2 H, s), 3.02 (1.8 H, s), 2.49 (1 H, brs), 2.29-2.41 (1 H, m), 1.99-2.09 (4 H, m), 1.76-1.83 (2 H, m), 1.44-1.51 (1 H, m). LCMS (M+H)=530.61. HPLC purity: >95%.

EXAMPLE 164

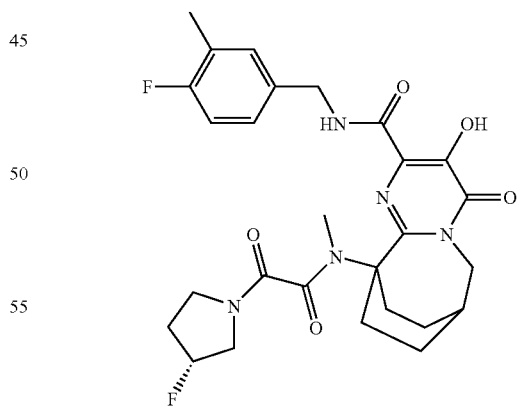

N-(4-Fluoro-3-methylbenzyl)-10-((((3R)-3-fluoro-1-pyrrolidinyl)(oxo)acetyl)(methyl)amino)-3-hydroxy-4-oxo-4,6,7,8,9,10-hexahydro-7,10-ethanopyrimido[1,2-a]azepine-2-carboxamide. Off-white solid (17 mg, 50% yield). $^1$H NMR (500 MHz, CDCl$_3$) δ: 12.17 (1 H, brs), 9.34 (1 H, brs), 7.14-7.23 (2 H, m), 6.91 (1 H, t), 5.32-5.39 (1 H, m), 5.20-5.29 (1 H, m), 4.75-4.86 (1 H, m), 4.54-4.63 (1 H, m), 4.37-4.47 (1 H, m), 3.87-3.93 (1 H, m), 3.75-3.82 (1 H, m), 3.34-

3.71 (6 H, m), 3.03 (1 H, s), 3.02 (1 H, s), 2.49 (1 H, brs), 2.29-2.40 (1 H, m), 2.23 (3 H, d, J=1.83 Hz), 1.96-2.11 (4 H, m), 1.75-1.83 (2 H, m), 1.44-1.51 (1H, m). LCMS (M+H)= 544.67. HPLC purity: >95%.

EXAMPLE 165

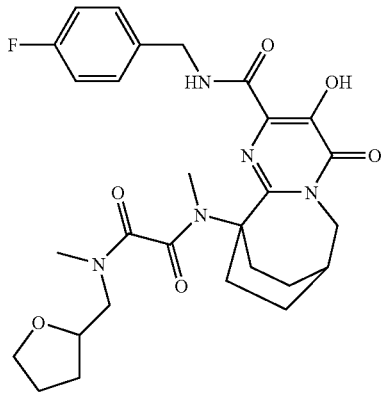

N-(2-((4-Fluorobenzyl)carbamoyl)-3-hydroxy-4-oxo-6,7,8,9-tetrahydro-7,10-ethanopyrimido[1,2-a]azepin-10(4H)-yl)-N,N'-dimethyl-N'-(tetrahydro-2-furanylmethyl)ethanediamide. Off-white solid (7 mg, 18% yield). $^1$H NMR (500 MHz, CDCl$_3$) δ: 12.18 (1 H, brs), 9.66 (0.4 H, brs), 9.58 (0.6 H, brs), 7.32-7.39 (2H, m), 6.93-6.99 (2 H, m), 4.79-4.87 (1 H, m), 4.58-4.66 (1 H, m), 4.40-4.50 (1H, m), 4.05-4.17 (1 H, m), 3.54-3.89 (5 H, m), 3.35-3.47 (2 H, m), 3.20 (0.5 H, d, J=2.75 Hz), 3.17 (0.5 H, d, J=2.75 Hz), 3.10 (1 H, s), 3.06 (1 H, s), 3.03 (2 H, s), 2.99 (1 H, s), 2.98 (1 H, s), 2.49 (1 H, brs), 1.84-2.08 (7 H, m), 1.42-1.58 (2 H, m). LCMS (M+H)= 556.73. HPLC purity: >95%.

EXAMPLE 166

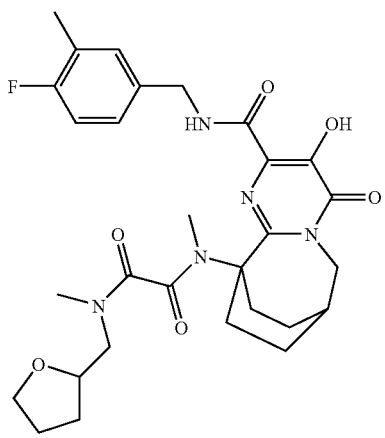

N-(2-((4-Fluoro-3-methylbenzyl)carbamoyl)-3-hydroxy-4-oxo-6,7,8,9-tetrahydro-7,10-ethanopyrimido[1,2-a]azepin-10(4H)-yl)-N,N'-dimethyl-N'-(tetrahydro-2-furanylmethyl)ethanediamide. Off-white solid (12 mg, 31% yield). $^1$H NMR (500 MHz, CDCl$_3$) δ: 12.29 (1 H, brs), 9.64 (0.4 H, brs), 9.56 (0.6 H, brs), 7.13-7.23 (2 H, m), 6.86-6.93 (1 H, m), 4.77-4.87 (1 H, m), 4.53-4.64 (1 H, m), 4.36-4.46 (1 H, m), 4.04-4.17 (1 H, m), 3.56-3.88 (5 H, m), 3.36-3.47 (2 H, m), 3.27-3.34 (0.5 H, m), 3.19 (0.5 H, dd, J=14.50, 2.59 Hz), 3.11 (1 H, s), 3.07 (1 H, s), 3.03 (2 H, s), 3.00 (1 H, s), 2.98 (1 H, s), 2.49 (1 H, brs), 2.23 (3 H, s), 1.86-2.09 (7 H, m), 1.43-1.59 (2 H, m). LCMS (M+H)=570.73. HPLC purity: >95%.

EXAMPLE 167

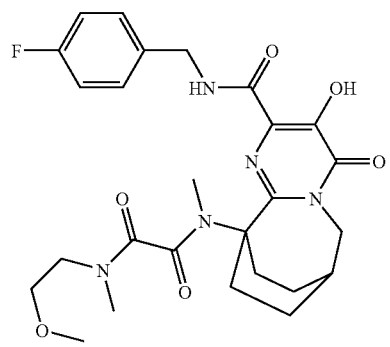

N-(2-((4-Fluorobenzyl)carbamoyl)-3-hydroxy-4-oxo-6,7,8,9-tetrahydro-7,10-ethanopyrimido[1,2-a]azepin-10(4H)-yl)-N'-(2-methoxyethyl)-N,N'-dimethylethanediamide. Off-white solid (9 mg, 31% yield). $^1$H NMR (500 MHz, CDCl$_3$) δ: 11.85 (1 H, brs), 9.53-9.66 (1 H, m), 7.30-7.37 (2 H, m), 6.91-6.98 (2H, m), 4.75-4.86 (1 H, m), 4.55-4.64 (1 H, m), 4.38-4.48 (1 H, m), 3.70-3.81 (0.5 H, m), 3.49-3.66 (2.5 H, m), 3.34-3.45 (1 H, m), 3.33 (1.6 H, s), 3.30 (1.4 H, s), 3.04 (1.6 H, s), 2.97 (3 H, s), 2.94 (1.4 H, s), 2.47 (1 H, brs), 1.94-2.06 (4 H, m), 1.71-1.81 (4 H, m), 1.42-1.47 (1 H, m). LCMS (M+H)=530.64. HPLC purity: >95%.

EXAMPLE 168

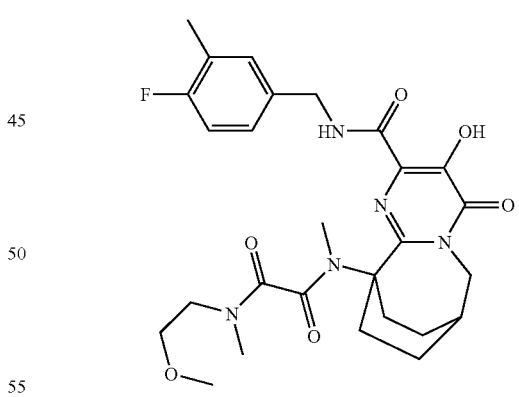

N-(2-((4-Fluoro-3-methylbenzyl)carbamoyl)-3-hydroxy-4-oxo-6,7,8,9-tetrahydro-7,10-ethanopyrimido[1,2-a]azepin-10(4H)-yl)-N'-(2-methoxyethyl)-N,N'-dimethylethanediamide. Off-white solid (14 mg, 48% yield). $^1$H NMR (500 MHz, CDCl$_3$) δ: 11.81 (1 H, brs), 9.50-9.62 (1 H, m), 7.10-7.21 (2 H, m), 6.83-6.92 (1H, m), 4.75-4.85 (1 H, m), 4.51-4.61 (1 H, m), 4.32-4.45 (1 H, m), 3.71-3.82 (0.5 H, m), 3.50-3.67 (2.5 H, m), 3.34-3.45 (1 H, m), 3.33 (1.2 H, s), 3.30 (1.8 H, s), 3.04 (1.6 H, s), 2.98 (3 H, s), 2.95 (1.4 H, s), 2.46 (1 H, brs), 2.21 (3 H, s), 1.94-2.07 (5 H, m), 1.69-1.80 (3 H, m), 1.37-1.51 (1 H, m). LCMS (M+H)=544.67. HPLC purity: >95%.

EXAMPLE 169

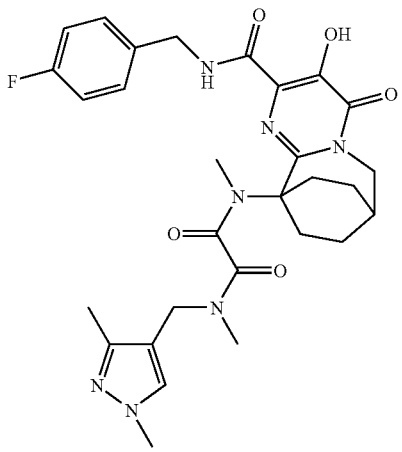

N-((1,3-Dimethyl-1H-pyrazol-4-yl)methyl)-N'-(2-((4-fluorobenzyl)carbamoyl)-3-hydroxy-4-oxo-6,7,8,9-tetrahydro-7,10-ethanopyrimido[1,2-a]azepin-10(4H)-yl)-N,N'-dimethylethanediamide. Off-white solid (16 mg, 42% yield). $^1$H NMR (500 MHz, CDCl$_3$) δ: 12.05 (1 H, brs), 9.49-9.71 (1 H, m), 7.42 (0.5 H, s), 7.31-7.39 (2 H, m), 7.11 (0.5 H, s), 6.89-6.97 (2 H, m), 4.81 (1 H, dd, J=15.43, 7.40 Hz), 4.62 (1 H, dd, J=14.68, 6.90 Hz), 4.28-4.51 (2.5 H, m), 4.04 (0.5 H, d, J=15.31 Hz), 3.77 (1.4 H, s), 3.76 (1.6 H, s), 3.57 (1 H, d, J=14.56 Hz), 3.31-3.47 (1 H, m), 3.02 (1.4 H, s), 2.94 (1.6 H, s), 2.86 (1.6 H, s), 2.80 (1.4 H, s), 2.47 (1 H, brs), 2.22 (1.4 H, s), 2.19 (1.6 H, s), 1.93-2.08 (4 H, m), 1.76-1.81 (2 H, m), 1.41-1.53 (1 H, m). LCMS (M+H)=580.76. HPLC purity: >95%.

EXAMPLE 170

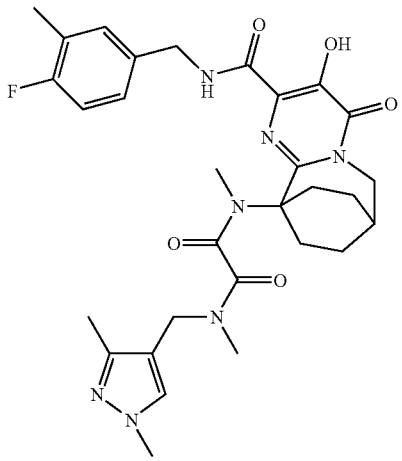

N-((1,3-Dimethyl-1H-pyrazol-4-yl)methyl)-N'-(2-((4-fluoro-3-methylbenzyl)carbamoyl)-3-hydroxy-4-oxo-6,7,8,9-tetrahydro-7,10-ethanopyrimido[1,2-a]azepin-10(4H)-yl)-N,N'-dimethylethanediamide. Off-white solid (17 mg, 43% yield). $^1$H NMR (500 MHz, CDCl$_3$) δ: 11.96 (1 H, brs), 9.49-9.60 (1 H, m), 7.47 (0.4 H, s), 7.13-7.21 (2 H, m), 7.11 (0.6 H, s), 6.83-6.91 (1 H, m), 4.81 (1 H, dd, J=15.43, 7.65 Hz), 4.54-4.62 (1 H, m), 4.26-4.47 (2.5 H, m), 4.02 (0.5 H, d, J=15.31 Hz), 3.80 (1 H, s), 3.78 (2 H, s), 3.57 (1 H, d, J=15.31 Hz), 3.31-3.44 (1 H, m), 3.02 (1 H, s), 2.94 (2 H, s), 2.86 (2 H, s), 2.81 (1 H, s), 2.47 (1H, brs), 2.24 (1 H, s), 2.21 (2 H, s), 2.19 (3 H, d, J=1.76 Hz), 1.95-2.07 (4 H, m), 1.69-1.83 (2 H, m), 1.38-1.55 (1 H, m). LCMS (M+H)=594.80. HPLC purity: >95%.

EXAMPLE 171

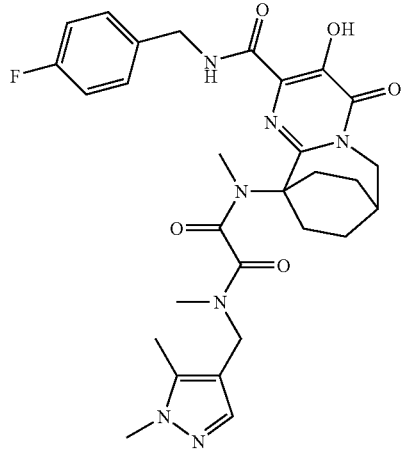

N-((1,5-Dimethyl-1H-pyrazol-4-yl)methyl)-N'-(2-((4-fluorobenzyl)carbamoyl)-3-hydroxy-4-oxo-6,7,8,9-tetrahydro-7,10-ethanopyrimido[1,2-a]azepin-10(4H)-yl)-N,N'-dimethylethanediamide. Off-white solid (8 mg, 24% yield). $^1$H NMR (500 MHz, CDCl$_3$) δ: 12.59 (1 H, brs), 9.56 (1 H, brs), 7.52 (0.3 H, s), 7.49 (0.7 H, s), 7.36 (2 H, dd, J=8.39, 5.34 Hz), 6.93-6.99 (2 H, m), 4.80-4.87 (1 H, m), 4.60-4.69 (1 H, m), 4.33-4.52 (3 H, m), 3.84 (1 H, s), 3.82 (2 H, s), 3.34-3.48 (2 H, m), 3.03 (1 H, s), 2.95 (2 H, s), 2.89 (2 H, s), 2.81 (1H, s), 2.50 (1 H, brs), 2.28 (1 H, s), 2.17 (2 H, s), 1.96-2.10 (4 H, m), 1.71-1.84 (2H, m), 1.44-1.55 (1 H, m). LCMS (M+H)=580.17. HPLC purity: >95%.

EXAMPLE 172

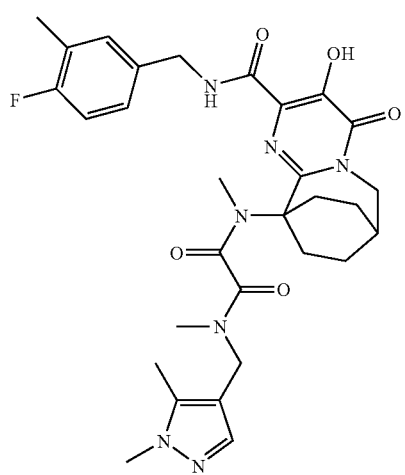

N-((1,5-Dimethyl-1H-pyrazol-4-yl)methyl)-N'-(2-((4-fluoro-3-methylbenzyl)carbamoyl)-3-hydroxy-4-oxo-6,7,8,9-tetrahydro-7,10-ethanopyrimido[1,2-a]azepin-10(4H)-yl)-N,N'-dimethylethanediamide. Off-white solid (8 mg, 23% yield). $^1$H NMR (500 MHz, CDCl$_3$) δ: 11.87 (1 H, brs), 9.50-9.57 (1 H, m), 7.51 (1 H, s), 7.48 (1 H, s), 7.13-7.22 (2 H, m), 6.90 (1 H, t, J=8.85 Hz), 4.79-4.87 (1 H, m), 4.56-4.65 (1 H, m), 4.32-4.48 (3 H, m), 3.83 (1 H, s), 3.81 (2H, s), 3.34-3.47 (2 H, m), 3.03 (1 H, s), 2.96 (2 H, s), 2.89 (2 H, s), 2.82 (1 H, s), 2.49 (1 H, brs), 2.28 (1 H, s), 2.22 (3 H, d, J=1.83 Hz), 2.17 (2 H, s), 1.96-2.10 (4 H, m), 1.71-1.84 (2 H, m), 1.43-1.54 (1 H, m). LCMS (M+H)=594.23. HPLC purity: >95%.

Example 173 can be prepared according to Scheme XX.

EXAMPLE 173

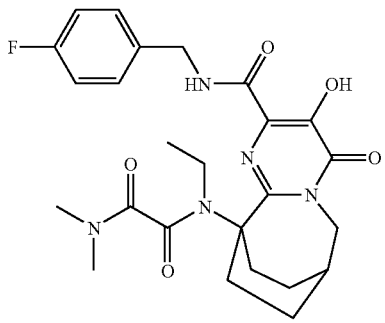

N-Ethyl-N-(2-((4-fluorobenzyl)carbamoyl)-3-hydroxy-4-oxo-6,7,8,9-tetrahydro-7,11-ethanopyrimido[1,2-a]azepin-10(4H)-yl)-N',N'-dimethylethanediamide. To a stirred pre-cooled (0° C.) solution of 2-(dimethylamino)-2-oxoacetic acid (101 mg, 0.866 mmol) in CH$_2$Cl$_2$ (5 mL) was added oxalyl chloride (0.083 mL, 0.953 mmol) and 2 drops of DMF and the resulting solution stirred for 1 h at 0° C., then 2 h at room temp. The mixture was then concentrated and dried under high vacuum to give crude acid chloride which was diluted with CH$_2$Cl$_2$ (3 mL)) and added to a pre-stirred solution of ethyl 10-(ethylamino)-4-oxo-3-((phenylcarbonyl)oxy)-4,6,7,8,9,10-hexahydro-7,10-ethanopyrimido[1,2-a]azepine-2-carboxylate (100 mg, 0.216 mmol) and diisopropyl-ethylamine (0.165 mL, 0.944 mmol) in CH$_2$Cl$_2$ (5 mL). The resulting solution was stirred at room temperature for 16 h. The reaction mixture was poured into sat. NaHCO$_3$ and extracted with dichloromethane (50×3), then dried (Na$_2$SO$_4$) and concentrated to give a yellow oil, which was diluted with ethanol (2 mL) and treated with 2M dimethylamine (0.095 mL, 0.191 mmol). The resulting mixture was heated at 50° C. for 1 h. (4-Fluorophenyl)methanamine (0.054 mL, 0.477 mmol) followed by triethylamine (0.066 mL, 0.477 mmol) was then added and the mixture heated at 90° C. for 18 h. The reaction mixture was cooled, concentrated and purified by preparative HPLC to afford the title compound (5 mg, 11% yield) as an off-white solid. $^1$H NMR (500 MHz, CDCl$_3$) δ: 12.02 (1 H, brs), 9.33 (1 H, s), 7.35-7.38 (2 H, m), 6.95-6.99 (2 H, m), 4.81 (1 H, dd, J=15.26, 7.63 Hz), 4.66 (1 H, dd, J=14.34, 7.02 Hz), 4.42 (1 H, dd, J=14.65, 5.80 Hz), 3.53-3.62 (2 H, m), 3.39-3.47 (1 H, m), 3.26-3.36 (1 H, m), 2.98 (3 H, s), 2.97 (3 H, s), 2.49 (1 H, brs), 1.94-2.17 (4 H, m), 1.77-1.84 (2 H, m), 1.44-1.52 (1 H, m), 1.23 (3 H, t, J=7.02 Hz). LCMS (M+H)=500.08. HPLC purity: >95%.

Examples 174 through 176 can be prepared according to Scheme XXI

EXAMPLE 174

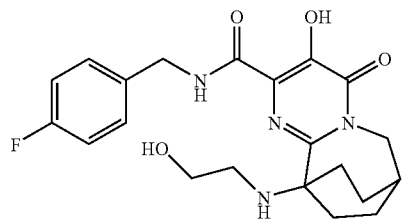

N-(4-Fluorobenzyl)-3-hydroxy-10-((2-hydroxyethyl)amino)-4-oxo-4,6,7,8,9,10-hexahydro-7,11-ethanopyrimido[1,2-a]azepine-2-carboxamide. To a suspension of 10-amino-N-(4-fluorobenzyl)-3-hydroxy-4-oxo-4,6,7,8,9,10-hexahydro-7,10-ethanopyrimido[1,2-a]azepine-2-carboxamide (1.00 g, 2.446 mmol) in methanol (40 mL) was added Et$_3$N (0.341 mL, 2.446 mmol) and the mixture was stirred at room temperature for 30 min. Added to this were glycolaldehyde dimer (0.323 g, 2.69 mmol), acetic acid (0.140 mL, 2.446 mmol) and sodium cyanoborohydride (0.307 g, 4.89 mmol). The suspension dissolved and the resulting solution was stirred at room temperature for 2.5 h then concentrated and purified by preparative HPLC: Solvent A=10% methanol/90% H$_2$O/0-1% trifluoroacetic acid; Solvent B=90% methanol/10% H$_2$O/0-1% trifluoroacetic acid; Start % B=10; Final % B=100; Gradient time=20 min; Stop time=20 min; Column=Sunfire 30×100 mm, C18, 5 µm (product elutes at 12.5 min) to give the title compound as a trifluoroacetic acid salt as a white solid (1.0372 g, 80% yield). LCMS (M+H) calcd for C$_{21}$H$_{26}$FN$_4$O$_4$: 417.19; found: 417.19. $^1$H NMR (500 MHz, MeOD) δ: 7.37-7.51 (2 H, m), 7.01-7.14 (2 H, m), 4.56 (2 H, s), 4.16 (2 H, d, J=3.97 Hz), 3.82-3.92 (2H, m), 3.23-3.30 (2 H, m), 2.58 (1 H, brs), 2.27-2.38 (2 H, m), 2.16-2.26 (2 H, m), 1.95-2.11 (2 H, m), 1.85 (2 H, ddd, J=13.96, 7.32, 7.10 Hz).

EXAMPLE 175

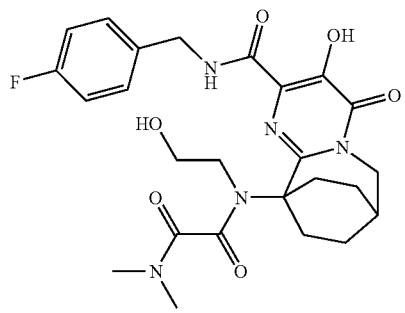

N-(2-((4-Fluorobenzyl)carbamoyl)-3-hydroxy-4-oxo-6,7,8,9-tetrahydro-7,10-ethanopyrimido[1,2-a]azepin-10(4H)-yl)-N-(2-hydroxyethyl)-N',N'-dimethylethanediamide. A solution of N-(4-fluorobenzyl)-3-hydroxy-10-((2-hydroxyethyl)amino)-4-oxo-4,6,7,8,9,10-hexahydro-7,10-ethanopyrimido[1,2-a]azepine-2-carboxamide (0.3358 g, 0.633 mmol) in CH$_2$Cl$_2$ (10 mL) with diisopropyl ethylamine (0.553 mL, 3.17 mmol) was cooled to 0° C. Methyl 2-chloro-2-oxoacetate (0.233 mL, 2.53 mmol) was added and the yellow solution stirred for 5 h, gradually warming to room temperature. The reaction was quenched with water and the organic phase was washed with 1N HCl, dried (Na$_2$SO$_4$), filtered and concentrated to give a yellow foam which was dissolved in hot ethanol (10 mL) and treated with 2M dimethylamine (1.583 mL, 3.17 mmol). The resulting yellow solution was stirred in a sealed tube at 85° C. for 18 h. The solution was concentrated and purified by preparative HPLC to give the title compound as a white solid (0.1692 g, 52% yield). $^1$H NMR (500 MHz, CDCl$_3$) δ: 12.20 (1 H, brs), 9.71 (1 H, brs), 7.34 (2 H, dd, J=8.55, 5.49 Hz), 6.98 (2 H, t, J=8.70 Hz), 4.69 (1 H, dd, J=15.56, 7.63 Hz), 4.50-4.57 (1 H, m), 4.37-4.48 (2 H, m), 3.84-3.91 (1 H, m), 3.75-3.81 (1 H, m), 3.56-3.70 (3 H, m), 3.41-3.51 (1 H, m), 2.97 (3 H, s), 2.96 (3 H, s), 2.49 (1 H, brs), 1.98-2.14 (3 H, m), 1.71-1.91 (3 H, m), 1.38-1.47 (1 H, m). LCMS (M+H)=516.07. HPLC purity: >95%.

EXAMPLE 176

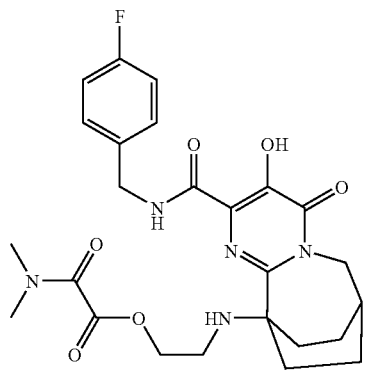

2-((2-((4-Fluorobenzyl)carbamoyl)-3-hydroxy-4-oxo-6,7,8,9-tetrahydro-7,10-ethanopyrimido[1,2-a]azepin-10(4H)-yl)amino)ethyl(dimethylamino)(oxo)acetate. To a stirred solution of N-(4-fluorobenzyl)-3-hydroxy-10-((2-hydroxyethyl)amino)-4-oxo-4,6,7,8,9,10-hexahydro-7,10-ethanopyrimido[1,2-a]azepine-2-carboxamide (90 mg, 0.170 mmol) in DMF (3 mL) was added 2-(dimethylamino)-2-oxoacetic acid (59.6 mg, 0.509 mmol), diisopropyl-ethylamine (0.178 mL, 1.018 mmol), O-(7-azabenzotriazol-1-yl)-N,N,N',N'-tetramethyluronium hexafluorophosphate (HATU) (194 mg, 0.509 mmol) and 4-(dimethylamino)pyridine (DMAP) (4.15 mg, 0.034 mmol) and the resulting mixture was stirred at room temperature for 16 h, purified by preparative HPLC and crystallized from methanol/water to afford the title compound (37 mg, 42% yield) as a crystalline white solid. $^1$H NMR (500 MHz, CDCl$_3$) δ: 12.50 (1 H, brs), 9.46 (1 H, brs), 7.33-7.38 (2 H, m), 6.97-7.01 (2 H, m), 4.55 (2 H, d, J=6.41 Hz), 4.43-4.48 (2 H, m), 4.10 (2 H, d, J=3.97 Hz), 3.28 (2 H, t, J=5.34 Hz), 3.06 (3 H, s), 2.96 (3 H, s), 2.56 (1 H, brs), 2.30-2.37 (2 H, m), 2.15-2.23 (2 H, m), 1.95-2.02 (2 H, m), 1.70-1.79 (2 H, m). LCMS (M+H)=516.32. HPLC purity: >95%.

Example 177 can be synthesized according to Scheme XXII

EXAMPLE 177

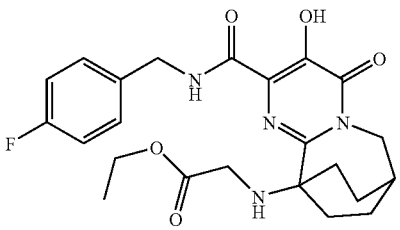

Ethyl N-(2-((4-fluorobenzyl)carbamoyl)-3-hydroxy-4-oxo-6,7,8,9-tetrahydro-7,10-ethanopyrimido[1,2-a]azepin-10(4H)-yl)glycinate. A mixture of 10-amino-N-(4-fluorobenzyl)-3-hydroxy-4-oxo-4,6,7,8,9,10-hexahydro-7,10-ethanopyrimido[1,2-a]azepine-2-carboxamide (0.10 g, 0.245 mmol) and triethylamine (0.251 mL, 1.8 mmol) in 1,2-dichloroethane (10 mL) was stirred at room temperature for 15 min. Added to this was ethyl 2-oxoacetate (0.145 mL, 0.734 mmol) (50% in toluene) and the mixture stirred at 70° C. for 16 h. The mixture was cooled to room temperature. Acetic acid (0.2 mL, 3.49 mmol) followed by sodium cyanoborohydride (0.061 g, 0.978 mmol) were added and mixture stirred at room temperature for 6 h. The mixture was concentrated and the residue was purified by preparative HPLC: Solvent A=10% methanol/90% H$_2$O/0-1% trifluoroacetic acid; Solvent B=90% methanol/10% H$_2$O/0-1% trifluoroacetic acid; Start % B=20; Final % B=100; Gradient time=20 min; Stop time=20 min; Column=Waters-Atlantis 30×100 mm, C18, 5 μm (product eluted at 9.0 min) to give the title compound as a trifluoroacetic acid salt as a white foam (0.0301 g, 22% yield). $^1$H NMR (500 MHz, CDCl$_3$) δ: 12.23 (1 H, brs), 9.07 (1 H, brs), 8.69 (1 H, t, J=6.26 Hz), 7.33 (2 H, dd, J=8.24, 5.49 Hz), 6.98 (2 H, t, J=8.55 Hz), 4.51 (2 H, d, J=6.41 Hz), 3.98-4.07 (4H, m), 3.91 (2 H, s), 2.54 (1 H, brs), 2.36-2.51 (2 H, m), 2.18-2.35 (2 H, m), 1.95-2.08 (2 H, m), 1.64-1.79 (2 H, m), 1.20 (3 H, t, J=7.17 Hz) LCMS (M+H) calcd for C$_{23}$H$_{28}$FN$_4$O$_5$: 459.20; found: 459.04.

Examples 178 through 180 can be prepared according to Scheme XXIII

EXAMPLE 178

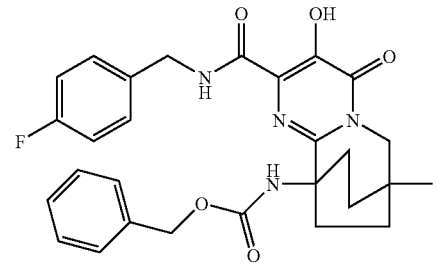

Carbamic acid, [2-[[[(4-fluorophenyl)methyl]amino]carbonyl]-6,7,8,9-tetrahydro-3-hydroxy-7-methyl-4-oxo-7,10-ethanopyrimido[1,2-a]azepin-10(4H)-yl]-, phenylmethyl ester. Yield: 2% (white solid; C-18 prep-HPLC purified). HPLC: retention time=2.73 min. (area percent=100%). LCMS: m/z 520.93 (M+H). $^1$H NMR (500 MHz, CHLOROFORM-d) δ ppm 11.89 (1 H, brs) 7.60 (1 H, brs) 7.33 (3H, brs) 7.18 (3 H, brs) 6.96 (3 H, brs) 4.91 (2 H, s) 4.41 (2 H, d, J=6.10 Hz) 3.92 (2H, brs) 2.44 (2 H, brs) 2.23 (1 H, brs) 1.98-2.08 (2 H, m) 1.72 (2 H, brs) 1.58 (2 H, brs) 1.11 (3 H, s).

EXAMPLE 179

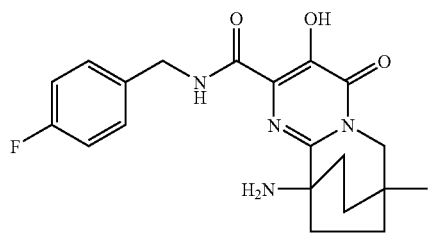

7,10-Ethanopyrimido[1,2-a]azepine-2-carboxamide, 10-amino-N-[(4-fluorophenyl)methyl]-4,6,7,8,9,10-hexahydro-3-hydroxy-7-methyl-4-oxo-. Yield: 77% (white solid). HPLC: retention time=1.43 min (area percent=100%). LCMS: m/z 386.90 (M+H).

EXAMPLE 180

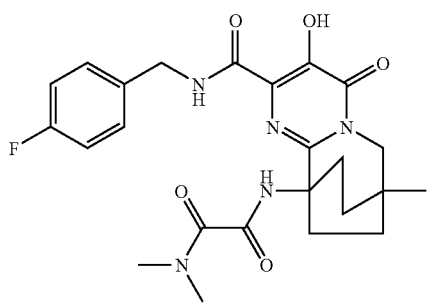

Ethanediamide, N'-[2-[[[(4-fluorophenyl)methyl]amino]carbonyl]-6,7,8,9-tetrahydro-3-hydroxy-7-methyl-4-oxo-7,10-ethanopyrimido[1,2-a]azepin-10(4H)-yl]-N,N-dimethyl-. Yield: 30% (white crystalline solid; purified by preparative HPLC, C-18) HPLC: retention time=8.32 min. LCMS: m/z 485.93 (M+H) $^1$H NMR (500 MHz, CHLOROFORM-d) δ ppm 11.95 (1 H, s) 8.59 (1 H, t, J=5.80 Hz) 8.09 (1 H, s) 7.36 (2 H, dd, J=8.55, 5.49 Hz) 6.93-7.02 (2 H, m) 4.55 (2 H, d, J=6.41 Hz) 3.93 (2H, s) 3.25-3.29 (3 H, m) 2.87-2.93 (3 H, m) 2.52 (2 H, ddd, J=14.50, 9.31, 5.49 Hz) 2.04-2.11 (2 H, m) 1.74-1.79 (2 H, m) 1.58-1.67 (2 H, m) 1.12 (3 H, s).

Examples 181 through 185 can be prepared according to Scheme XXIV

EXAMPLE 181

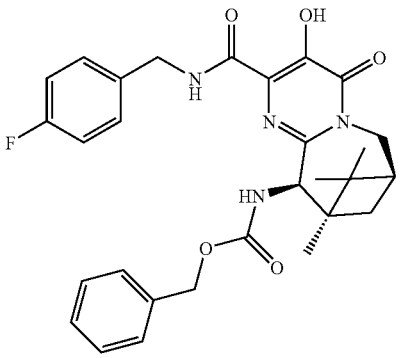

Benzyl((7S,10R,11R)-2-((4-fluorobenzyl)carbamoyl)-3-hydroxy-10,12,12-trimethyl-4-oxo-6,7,8,9,10,11-hexahydro-4H-7,10-methanopyrimido[1,2-a]azocin-11-yl)carbamate. A solution of ethyl (7S,10R)-11-(((benzyloxy)carbonyl)amino)-3-hydroxy-10,12,12-trimethyl-4-oxo-6,7,8,9,10,11-hexahydro-4H-7,10-methanopyrimido[1,2-a]azocine-2-carboxylate (1.4595 g, 3.11 mmol), (4-fluorophenyl)methanamine (1.143 mL, 10.00 mmol) and Et$_3$N (1.394 mL, 10 mmol) in EtOH (25 mL) was heated at reflux for 14 h. the reaction mixture was then cooled, diluted with Et$_2$O (100 mL), washed with 1N aq. HCl (1×25 mL), water (2×25 mL) followed by brine (25 mL), then dried (Na$_2$SO$_4$), filtered and concentrated to give a brown paste. The product was purified by preparative HPLC using a C18-column and 40-90% methanol/water (0.1 trifluoroacetic acid) to afford the title compound (0.367 g, 0.669 mmol, 22% yield) as a light brown solid. $^1$H NMR (500 MHz, CDCl$_3$) δ: 12.21 (0.3 H, brs), 12.08 (0.7 H, s), 8.24 (0.3 H, brs), 7.71 (0.7 H, t, J=6.1 Hz), 7.18-7.38 (8 H, m), 6.92-7.05 (2 H, m), 4.98-5.21 (4 H, m), 4.52-4.58 (1H, m), 4.41-4.47 (1 H, m), 3.67 (0.7 H, d, J=15.6 Hz), 3.56 (0.3 H, d, J=15.6 Hz), 2.08 (0.7 H, t, J=8.1 Hz), 2.01-2.06 (0.3 H, m), 1.73-1.87 (2 H, m), 1.40-1.49 (1H, m), 1.37 (2 H, s), 1.28-1.35 (1 H, m), 1.25 (1 H, s), 1.00 (2 H, s), 0.99 (2 H, s), 0.95 (1 H, s), 0.92 (1 H, s). LCMS (M+H) calcd for C$_{30}$H$_{34}$FN$_4$O$_5$: 549.25; found: 549.28. Purity: >96%.

EXAMPLE 182

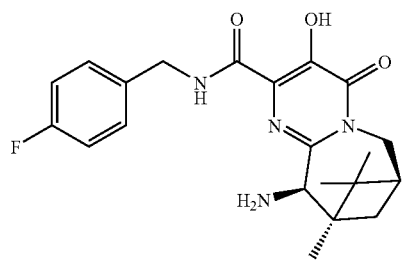

(7S,10R,11R)-11-Amino-N-(4-fluorobenzyl)-3-hydroxy-10,12,12-trimethyl-4-oxo-6,7,8,9,10,11-hexahydro-4H-7,10-methanopyrimido[1,2-a]azocine-2-carboxamide. A stirred solution of benzyl((7S,10R,11R)-2-((4-fluorobenzyl)carbamoyl)-3-hydroxy-10,12,12-trimethyl-4-oxo-6,7,8,9,10,11-hexahydro-4H-7,10-methanopyrimido[1,2-a]azocin-11-yl)carbamate (0.3566 g, 0.650 mmol) and 1N aq. HCl (0.650 mL, 0.650 mmol) in EtOH (25 mL) was sparged with N2. Then, 10% Pd/C (0.1 g, 0.094 mmol) was added and the flask evacuated then replaced with a H$_2$ atmosphere three times. The reaction was and allowed to stir for 3 h under 1 atm H$_2$. The reaction mixture was filtered, concentrated and purified by preparative HPLC on a C18 column using 20-50% methanol/water (trace HCl) to the title compound as the corresponding hydrochloride salt (0.2277 g, 0.505 mmol, 78% yield) as a white solid. $^1$H NMR (500 MHz, CDCl$_3$) δ: 12.43 (1 H, brs), 9.56 (1 H, brs), 8.51 (3 H, brs), 7.20-7.36 (3 H, m), 6.90 (2 H, brs), 4.90-5.01 (1 H, m), 4.65-4.76 (1 H, m), 4.35-4.53 (2 H, m), 3.53-3.64 (1 H, m), 2.04-2.12 (1 H, m), 1.76-1.91 (2 H, m), 1.36-1.46 (1 H, m), 1.20 (3 H, brs), 1.10 (3 H, brs), 0.94 (3 H, brs). LCMS (M+H) calcd for C$_{22}$H$_{28}$FN$_4$O$_3$: 415.21; found: 415.26. Purity: >97%.

EXAMPLE 183

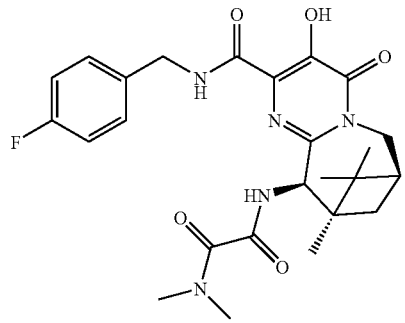

N'-((7S,10R,11R)-2-((4-Fluorobenzyl)carbamoyl)-3-hydroxy-10,12,12-trimethyl-4-oxo-6,7,8,9,10,11-hexahydro- 4H-7,10-methanopyrimido[1,2-a]azocin-11-yl)-N,N-dimethylethanediamide. A solution of benzyl((7S,10R,11R)-2-((4-fluorobenzyl)carbamoyl)-3-hydroxy-10,12,12-trimethyl-4-oxo-6,7,8,9,10,11-hexahydro-4H-7,10-methanopyrimido[1,2-a]azocin-11-yl)carbamate hydrochloride salt (0.0367 g, 0.081 mmol), 2-(dimethylamino)-2-oxoacetic acid (9.53 mg, 0.081 mmol), O-(7-azabenzotriazol-1-yl)-N,N,N',N'-tetramethyluronium hexafluorophosphate (HATU) (0.031 g, 0.081 mmol) and diisopropyl-ethylamine (0.014 mL, 0.081 mmol) in DMF (3 mL) was stirred at room temperature for 24 h. After this the crude reaction mixture was purified by preparative-HPLC using methanol/water (0.1% trifluoroacetic acid) to afford the title compound (0.0301 g, 0.059 mmol, 72% yield) as a purple solid. $^1$H NMR (500 MHz, CDCl$_3$) δ: 12.01 (1H, s), 8.76 (1 H, t, J=6.0 Hz), 8.21 (1 H, d, J=9.8 Hz), 7.36-7.41 (2 H, m), 6.99-7.05 (2 H, m), 5.27 (1 H, d, J=9.8 Hz), 5.18 (1 H, dd, J=15.6, 8.9 Hz), 4.50-4.63 (2 H, m), 3.65 (1 H, d, J=15.6 Hz), 3.34 (3 H, s), 2.95 (3 H, s), 2.14 (1 H, t, J=8.2 Hz), 1.83-1.94 (1 H, m), 1.47-1.52 (1 H, m), 1.41 (1 H, dd, J=9.5, 5.2 Hz), 1.36 (3 H, s), 1.06 (1 H, dd, 9.8, 4.6 Hz), 1.03 (3 H, s), 0.97 (3 H, s). LCMS (M+H) calcd for C$_{26}$H$_{33}$FN$_5$O$_5$: 514.25; found: 514.29.

EXAMPLE 184

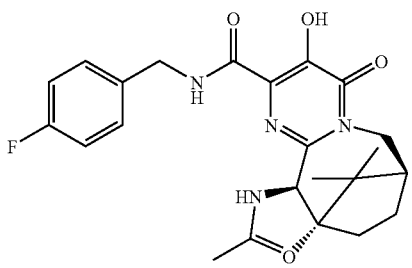

(7S,10R,11R)-11-(Acetylamino)-N-(4-fluorobenzyl)-3-hydroxy-10,12,12-trimethyl-4-oxo-6,7,8,9,10,11-hexahydro-4H-7,10-methanopyrimido[1,2-a]azocine-2-carboxamide. To a stirred solution of benzyl((7S,10R,11R)-2-((4-fluorobenzyl)carbamoyl)-3-hydroxy-10,12,12-trimethyl-4-oxo-6,7,8,9,10,11-hexahydro-4H-7,10-methanopyrimido[1,2-a]azocin-11-yl)carbamate hydrochloride salt (0.025 g, 0.055 mmol) and diisopropyl-ethylamine (0.175 mL, 1 mmol) in CH$_2$Cl$_2$ (3 mL) was added acetyl chloride (0.036 mL, 0.5 mmol). After 4 h, 2M Me$_2$NH/methanol (1 mL) was added and stirring continued at room temperature. After 16 h, the reaction mixture was concentrated and purified by preparative-HPLC using methanol/water (0.1% trifluoroacetic acid) to afford the title compound (0.0188 g, 0.038 mmol, 69% yield) as a white solid. $^1$H NMR (500 MHz, CDCl$_3$) δ: 11.99 (1H, s), 7.56 (1 H, t, J=5.8 Hz), 7.33 (2 H, dd, J=8.5, 5.2 Hz), 7.04-7.09 (2 H, m), 6.42 (1 H, d, J=9.2 Hz), 5.52 (1 H, d, J=9.2 Hz), 5.17 (1 H, dd, J=15.4, 8.7 Hz), 4.54-4.66 (2 H, m, J=14.8, 14.6, 14.6, 6.0 Hz), 3.70 (1 H, d, J=15.3 Hz), 3.48 (3H, s, from CH$_3$OH), 2.09 (1 H, t, J=8.1 Hz), 1.94 (3 H, s), 1.78-1.87 (1 H, m), 1.41-1.49 (1 H, m), 1.38 (3 H, s), 1.30-1.37 (1 H, m), 0.99 (3 H, s), 0.95-0.98 (1 H, m), 0.94 (3 H, s). LCMS (M+H) calcd for C$_{24}$H$_{30}$FN$_4$O$_4$: 457.23; found: 457.27. Purity: >98%.

EXAMPLE 185

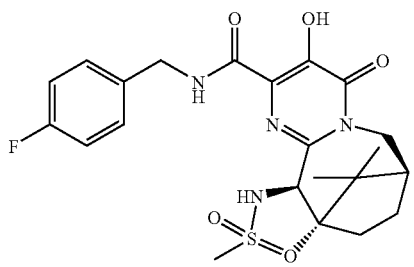

(7S,10R,11R)—N-(4-Fluorobenzyl)-3-hydroxy-10,12,12-trimethyl-11-((methylsulfonyl)amino)-4-oxo-6,7,8,9,10,11-hexahydro-4H-7,10-methanopyrimido[1,2-a]azocine-2-carboxamide. To a stirred solution of benzyl ((7S,10R,11R)-2-((4-fluorobenzyl)carbamoyl)-3-hydroxy-10,12,12-trimethyl-4-oxo-6,7,8,9,10,11-hexahydro-4H-7,10-methanopyrimido[1,2-a]azocin-11-yl)carbamate hydrochloride salt (0.025 g, 0.055 mmol) and diisopropyl-ethylamine (0.175 mL, 1 mmol) in CH$_2$Cl$_2$ (3 mL) was added methanesulfonyl chloride (0.039 mL, 0.5 mmol) at room temperature. After 4 h, 2M Me$_2$NH in methanol (1 mL) was added and stirring continued at room temperature. After 16 h, the reaction mixture was concentrated and purified by preparative-HPLC using methanol/water (0.1% trifluoroacetic acid) to afford the title compound (0.0186 g, 0.038 mmol, 68% yield) as a purple solid after crystallization from methanol/water. $^1$H NMR (500 MHz, CDCl$_3$) δ: 12.39 (1 H, s), 8.60 (1 H, brs), 7.34 (2 H, dd, J=8.5, 5.2 Hz), 7.01 (2 H, t, J=8.7 Hz), 6.07 (1 H, d, J=9.5 Hz), 5.19 (1 H, dd, J=15.6, 8.5 Hz), 4.79 (1 H, d, J=9.8 Hz), 4.52-4.65 (2 H, m), 3.63 (1 H, d, J=15.6 Hz), 2.76 (3 H, s), 2.10 (1 H, t, J=8.1 Hz), 1.80-1.89 (1 H, m), 1.43-1.51 (1 H, m), 1.30-1.35 (1 H, m), 1.29 (3H, s), 1.04 (3 H, s), 1.01 (3 H, s), 0.96-1.01 (1 H, m). LCMS (M+H) calcd for C$_{23}$H$_{30}$FN$_4$O$_5$S: 493.19; found: 493.24. Purity: >98%.

Examples 186 and 187 can be synthesized according to Scheme XXV

EXAMPLE 186

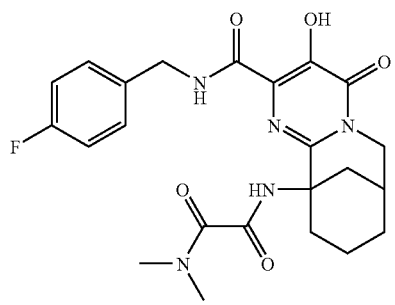

Ethanediamide, N'-[2-[[[(4-fluorophenyl)methyl]amino]carbonyl]-7,8,9,10-tetrahydro-3-hydroxy-4-oxo-7,11-methano-4H-pyrimido[1,2-a]azocin-11(6H)-yl]-N,N-dimethyl-. LCMS: m/z 472.20 (M+H). $^1$H NMR (500 MHz, CHLOROFORM-d) δ ppm 11.89 (1 H, brs) 8.16 (1 H, t, J=5.19 Hz) 7.65 (1 H, s) 7.32 (2 H, dd, J=8.55, 5.19 Hz) 7.02 (2 H, t, J=8.70 Hz) 4.58 (1 H, d, J=7.02 Hz) 4.50 (1 H, d, J=5.80 Hz) 4.08-4.14 (1 H, m) 3.97 (1 H, d, J=6.10 Hz) 3.21 (3 H, s) 2.92 (3 H, s) 2.71-2.81 (1H, m) 2.61 (1 H, brs) 1.95-2.24 (2 H, m) 1.77-1.87 (3 H, m) 1.66-1.73 (2 H, m). $^{13}$C NMR (126 MHz, CHLOROFORM-d) δ ppm 168.20, 163.35, 162.50, 161.86, 161.39, 158.31, 150.35, 146.51, 133.42, 129.77, 129.71, 125.38, 115.73, 115.57, 56.19, 50.52, 42.44, 38.22, 37.92, 36.71, 32.04, 31.33, 27.25, 20.04.

EXAMPLE 187

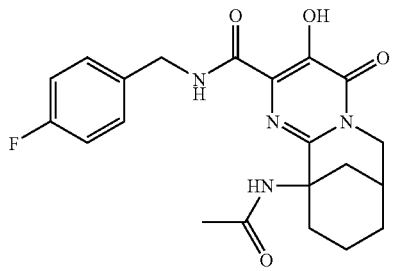

7,11-Methano-4H-pyrimido[1,2-a]azocine-2-carboxamide, 11-(acetylamino)-N-[(4-fluorophenyl)methyl]-6,7,8,9,10,11-hexahydro-3-hydroxy-4-oxo-. glassy-white solid (8% yield). $^1$H NMR (500 MHz, CHLOROFORM-d) δ ppm 10.70 (1 H, brs) 7.71 (1 H, brs) 7.29 (2 H, dd, J=8.09, 5.34 Hz) 7.04 (2 H, t, J=8.55 Hz) 6.07 (1 H, s) 4.62 (1 H, dd, J=14.80, 5.03 Hz) 4.49 (1 H, dd, J=14.80, 5.04 Hz) 4.01-4.10 (1 H, m) 3.94 (1 H, dd, J=15.26, 6.10 Hz) 2.73 (1 H, d, J=12.51 Hz) 2.55 (1 H, brs) 2.08 (1H, d, J=12.51 Hz) 1.93-2.02 (1 H, m) 1.86 (3 H, s) 1.78 (2 H, brs) 1.69 (2 H, brs) 1.67 (1 H, d, J=4.58 Hz) $^{13}$C NMR (126 MHz, CHLOROFORM-d) δ ppm 169.37 168.27, 163.47, 161.51, 158.36, 151.53, 146.33, 133.19, 133.17, 129.55, 129.48, 125.28, 115.99, 115.83, 55.72, 50.75, 42.52, 38.13, 32.55, 31.20, 27.24, 23.96, 20.15. LCMS (M+H)=415.20. HPLC purity: >98%.

Examples 188 through 196 can be synthesized according to Scheme XXVI

EXAMPLE 188

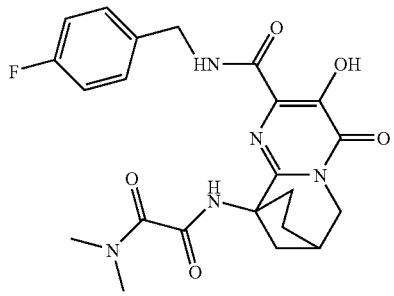

Ethanediamide, N'-[2-[[[(4-fluorophenyl)methyl]amino]carbonyl]-6,7,8,9-tetrahydro-3-hydroxy-4-oxo-7,11-methanopyrimido[1,2-a]azepin-10(4H)-yl]-N,N-dimethyl-. $^1$H NMR (400 MHz, DMSO-D6) δ ppm 1.60 (m, 1 H), 2.00-2.12 (m, 4H), 2.55 (d, J=11.62 Hz, 1 H), 2.75 (br s, 1 H), 2.86 (s, 3 H), 2.91 (s, 3 H), 3.79 (m, 2H), 4.51 (m, 2 H), 7.15-7.21 (m, 2 H), 7.35-7.42 (m, 2 H), 9.09 (s, 1 H), 9.50 (t, J=6.44 Hz, 1 H), 11.84 (s, 1 H).

EXAMPLE 189

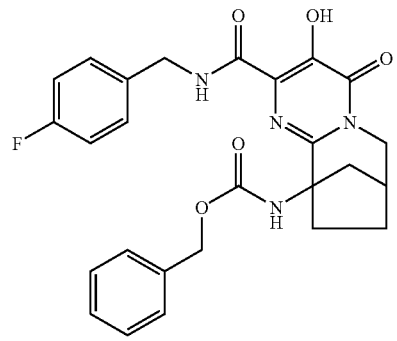

Carbamic acid, [2-[[[(4-fluorophenyl)methyl]amino]carbonyl]-6,7,8,9-tetrahydro-3-hydroxy-4-oxo-7,10-methanopyrimido[1,2-a]azepin-10(4H)-yl]-, phenylmethyl ester. LCMS retention time=1.910 min. on a LCMS fitted with 4.6×30 mm, 5-micron Luna C18 column, mobile phase A=0.5% trifluoroacetic acid in 10:90 acetonitrile/water; mobile phase B=0.5% trifluoroacetic acid in 90:10 acetonitrile/water; gradient =0 to 100% mobile phase B over 2 min. at a flow rate of 4 mL/min.

EXAMPLE 190

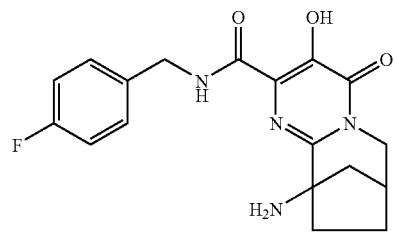

7,10-Methanopyrimido[1,2-a]azepine-2-carboxamide, 10-amino-N-[(4-fluorophenyl)methyl]-4,6,7,8,9,10-hexahydro-3-hydroxy-4-oxo-. LCMS retention time=1.18 min. on a LCMS fitted with 4.6×30 mm, 5-micron Luna C18 column, mobile phase A=0.5% trifluoroacetic acid in 10:90 acetonitrile/water; mobile phase B=0.5% trifluoroacetic acid in 90:10 acetonitrile/water; gradient=0 to 100% mobile phase B over 2 min. at a flow rate of 4 mL/min.

EXAMPLE 191

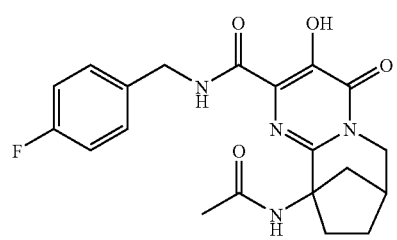

7,10-Methanopyrimido[1,2-a]azepine-2-carboxamide, 10-(acetylamino)-N-[(4-fluorophenyl)methyl]-4,6,7,8,9,10-hexahydro-3-hydroxy-4-oxo-. $^1$H NMR (500 MHz, CDCl$_3$) δ ppm 11.92 (1 H, s), 7.56 (1 H, t, J=5.19 Hz), 7.28-7.36 (2 H, m), 7.02-7.09 (2 H, m), 6.41 (1 H, br s), 4.49-4.65 (2 H, m), 3.93-3.99 (1 H, m), 3.83-3.90 (1 H, m), 2.75-2.83 (1 H, m), 2.56 (1 H, dd, J=1.90, 5.49 Hz), 2.40 (1 H, dt, J=12.74, 5.95 Hz), 2.18-2.30 (2 H, m), 1.91-1.99 (1 H, m), 1.90 (3 H, s), 1.60-1.66 (1 H, m). LCMS=401.19 (M+H). HPLC: >97%.

EXAMPLE 192

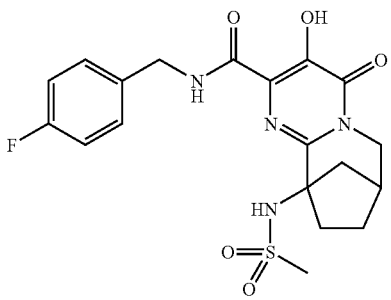

7,10-Methanopyrimido[1,2-a]azepine-2-carboxamide, N-[(4-fluorophenyl)methyl]-4,6,7,8,9,10-hexahydro-3-hydroxy-10-[(methylsulfonyl)amino]-4-oxo-,-. LCMS retention time=1.60 min. on a LCMS fitted with 4.6×30 mm, 5-micron Luna C18 column, mobile phase A=0.5% trifluoroacetic acid in 10:90 acetonitrile/water; mobile phase B=0.5% trifluoroacetic acid in 90:10 acetonitrile/water; gradient =0 to 100% mobile phase B over 2 min. at a flow rate of 4 mL/min.

EXAMPLE 193

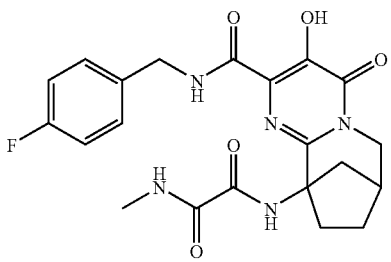

Ethanediamide, N-[2-[[[(4-fluorophenyl)methyl]amino] carbonyl]-6,7,8,9-tetrahydro-3-hydroxy-4-oxo-7,10-methanopyrimido[1,2-a]azepin-10(4H)-yl]-N'-methyl-. $^1$H NMR (500 MHz, CDCl$_3$) δ ppm 12.09 (1 H, s), 8.86 (1 H, s), 7.87 (1 H, t, J=5.65 Hz), 7.32-7.39 (3 H, m), 7.01-7.09 (2 H, m), 4.54-4.64 (2 H, m), 3.97-4.03 (1 H, m), 3.83-3.91 (1 H, m), 2.88 (3 H, d, J=5.19 Hz), 2.80-2.86 (2 H, m), 2.53-2.62 (1 H, m), 2.24-2.35 (1 H, m), 2.03 (1 H, d, J=10.99 Hz), 1.93-2.01 (1H, m), 1.65-1.72 (1 H, m). LCMS 444.17 (M+H). HPLC purity: >97%.

EXAMPLE 194

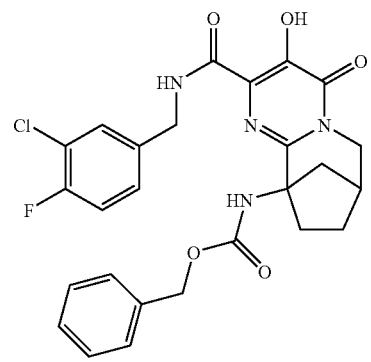

Carbamic acid, [2-[[[(3-chloro-4-fluorophenyl)methyl] amino]carbonyl]-6,7,8,9-tetrahydro-3-hydroxy-4-oxo-7,10-methanopyrimido[1,2-a]azepin-10(4H)-yl]-, phenylmethyl ester. HPLC: retention time=2.90 min (100%) Start % B=0%, Final % B=100%. Gradient Time=4 min, Total Time=5 min. Flow Rate=4 min, Wavelength=254 nm. Solvent A=10% CH$_3$CN-90% H$_2$O-0.1% trifluoroacetic acid. Solvent B=90% CH$_3$CN-10% H$_2$O-0.1% trifluoroacetic acid. Column=YMC ODS-AQ 4.6×50 mm, 3 micron. LC/MS: 527.26 (M+H). Start % B=0%, Final % B=100%. Gradient Time=4 min, Total Time=5 min. Flow Rate=4 min, Wavelength=220 nm. Solvent A=5% CH$_3$CN-95% H$_2$O-10 mM Ammonium Acetate. Solvent B=95% CH$_3$CN-5% H$_2$O-10 mM Ammonium Acetate. Column=XTERRA® 3.0×50 mm, 7 µm. $^1$H NMR (500 MHz, CDCl$_3$) δ ppm 11.94 (1 H, br s), 7.82 (1 H, br), 7.26-7.43 (5 H, m), 6.92-7.16 (3 H, m), 5.96 (1 H, br), 5.00 (2 H, br), 4.50 (1 H, dd, J=15.11, 6.26 Hz), 4.33 (1 H, m), 3.76-4.02 (2 H, m), 2.79 (1 H, br), 2.52 (1 H, br), 2.10-2.41 (2 H, m), 1.98 (1 H, m), 1.61 (1 H, m).

EXAMPLE 195

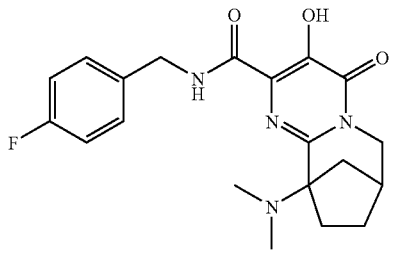

7,10-Methanopyrimido[1,2-a]azepine-2-carboxamide, 10-(dimethylamino)-N-[(4-fluorophenyl)methyl]-4,6,7,8,9,10-hexahydro-3-hydroxy-4-oxo-. HPLC: retention time=1.49 min (98.7%). Column=YMC ODS-AQ 4.6×50 mm, 3 micron. HPLC: retention time=4.62 min (98.6%). Start % B=0%, Final % B=100%. Gradient Time=23 min, Total Time=25 min. Flow Rate=2 min, Wavelength=254 nm. Solvent A=10% CH$_3$CN-90% H$_2$O-0.1% trifluoroacetic acid. Solvent B=90% CH$_3$CN-10% H$_2$O-0.1% trifluoroacetic acid. Column=XTERRA® MS C-18, 4.6×50 mm, 5 micron. LC/MS: 387.29 (M+H). Column=XTERRA® 3.0×50 mm, 7 µm. $^1$H NMR (500 MHz, MeOD) δ ppm 7.42-7.49 (2 H, m), 7.06-7.15 (2 H, m), 4.65-4.71 (1 H, m), 4.52-4.60 (1 H, m), 4.00-4.06 (1 H, m), 3.84-3.91 (1 H, m), 3.06 (3 H, br), 2.99 (4 H, br), 2.50-2.59 (1 H, m), 2.42-2.50 (1 H, m), 2.31-2.43 (1 H, m), 2.25 (1 H, d, J=10.99 Hz), 2.08-2.17 (1 H, m), 1.73-1.86 (1 H, m).

EXAMPLE 196

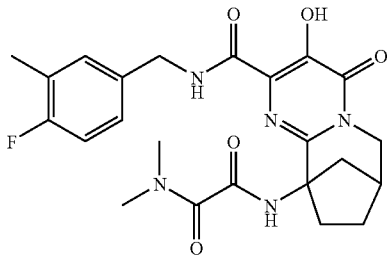

Ethanediamide, N'-[2-[[[(4-fluoro-3-methylphenyl)methyl]amino]carbonyl]-6,7,8,9-tetrahydro-3-hydroxy-4-oxo-7,10-methanopyrimido[1,2-a]azepin-10(4H)-yl]-N,N-dimethyl-. $^1$H NMR (400 MHz, DMSO-D6) δ ppm 9.03 (s, 1 H), 7.23 (d, 1 H), 7.15-7.20 (m, 1 H), 7.08 (t, 1 H), 4.35-4.52 (m, 2 H), 3.71-3.83 (m, 2 H), 2.91 (s, 3 H), 2.84 (s, 3 H), 2.71-2.78 (m, 1 H), 2.20 (s, 3 H), 2.06 (s, 4 H), 1.23-1.29 (m, 2H). LCMS ($^+$ESI, M+H$^+$) m/z 472.2. HPLC purity: 99%.
Examples 197 through 211 can be synthesized according to Scheme XXVIII

EXAMPLE 197

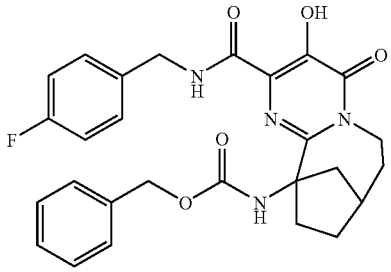

Carbamic acid, [2-[[[(4-fluorophenyl)methyl]amino]carbonyl]-7,8,9,10-tetrahydro-3-hydroxy-4-oxo-8,11-methano-4H-pyrimido[1,2-a]azocin-11(6H)-yl]-, phenylmethyl ester. HPLC: retention time=2.91 min (100%). Column=YMC ODS-AQ 4.6×50 mm, 3 micron.retention time=11.56 min (97.8%). Column=XTERRA® MS C-18, 4.6×50 mm, 5 micron. LC/MS: 507.10 (M+H). Column=Phenomenex 4.6×30 mm, 10.

EXAMPLE 198

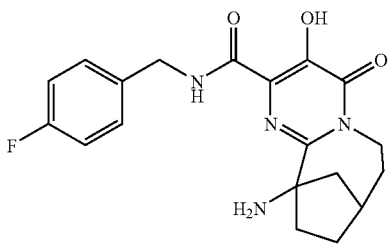

8,11-Methano-4H-pyrimido[1,2-a]azocine-2-carboxamide, 11-amino-N-[(4-fluorophenyl)methyl]-6,7,8,9,10,11-hexahydro-3-hydroxy-4-oxo-. HPLC: retention time=1.51 min (98.9%). Column=YMC ODS-AQ 4.6×50 mm, 3 micron. HPLC: retention time=3.73 min (99.2%). Column=XTERRA® MS C-18, 4.6×50 mm, 5 micron. LC/MS: 373.40 (M+H). Column=Phenomenex 4.6×30 mm, 10μ. $^1$H NMR (500 MHz, MeOD) δ ppm 7.45 (2 H, br), 7.06 (2 H, br), 5.37 (1 H, br), 4.67 (1 H, br), 3.59-3.72 (1 H, m), 3.02 (1 H, br), 2.73 (2 H, br), 2.34 (2 H, br), 2.04-2.18 (1H, m), 1.97 (2 H, br), 1.71 (1 H, br), 1.31 (1 H, br).

EXAMPLE 199

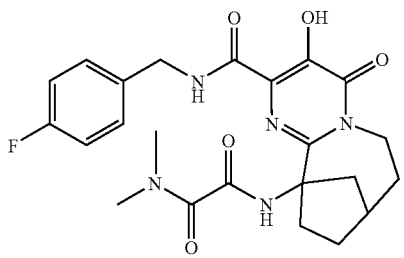

Ethanediamide, N'-[2-[[[(4-fluorophenyl)methyl]amino]carbonyl]-7,8,9,10-tetrahydro-3-hydroxy-4-oxo-8,11-methano-4H-pyrimido[1,2-a]azocin-11(6H)-yl]-N,N-dimethyl-. HPLC: retention time=2.12 min (100%). Column=YMC ODS-AQ 4.6×50 mm, 3 micron. HPLC: retention time=min (100%). Column=XTERRA® MS C-18, 4.6×50 mm, 5 micron. LC/MS: 742.41 (M+H). Column=Phenomenex 4.6×30 mm, 10. $^1$H NMR (500 MHz, CDCl$_3$) δ ppm 12.08 (1 H, s), 8.72 (1 H, t, J=5.80 Hz), 8.27 (1 H, s), 7.36 (2 H, dd, J=8.55, 5.49 Hz), 7.01 (2 H, t, J=8.70 Hz), 5.50 (1 H, dt, J=15.34, 3.78 Hz), 4.49-4.60 (2 H, m), 3.49 (1 H, t, J=14.04 Hz), 3.29 (3 H, s), 2.91 (3 H, s), 2.64 (1 H, q, J=5.90 Hz), 2.53-2.61 (1 H, m), 2.43-2.52 (2H, m), 2.27-2.38 (1 H, m), 1.78-1.92 (3 H, m), 1.60 (1 H, t, J=14.04 Hz). $^{13}$C NMR (126 MHz, CDCl$_3$) δ ppm 168.22, 163.72, 163.29, 161.86, 161.33, 159.54, 152.06, 146.81, 133.74, 133.71, 129.95, 129.89, 123.78, 115.57, 115.40, 66.66, 44.27, 42.49, 40.02, 38.16, 37.19, 36.36, 35.21, 32., 30.24.

EXAMPLE 200

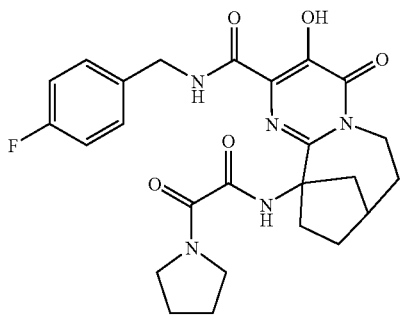

8,11-Methano-4H-pyrimido[1,2-a]azocine-2-carboxamide, 11-[[1,2-dioxo-2-(1-pyrrolidinyl)ethyl]amino]-N-[(4-fluorophenyl)methyl]-6,7,8,9,10,11-hexahydro-3-hydroxy-4-oxo: Off-white crystalline solid (27% yield). $^1$H NMR (500 MHz, CDCl$_3$) δ ppm 11.99 (1 H, s), 9.47 (1 H, s), 8.31 (1 H, t, J=5.80 Hz), 7.39 (2 H, dd, J=8.39, 5.34 Hz), 7.01 (2 H, t, J=8.70 Hz), 5.50 (1 H, ddd, J=15.41, 3.51, 3.36 Hz), 4.51-4.64 (2 H, m), 3.83-3.99 (2 H, m), 3.34-3.56 (3 H, m), 2.61-2.76 (3 H, m), 2.37-2.48 (1 H, m), 2.26-2.37 (1 H, m), 1.78-1.99 (5 H, m), 1.55-1.70 (3 H, m). $^{13}$C NMR (126 MHz, CDCDl3) δ ppm 167.97, 163.37, 161.42, 160.33, 159.82, 159.48, 152.62, 146.87, 133.38, 133.35, 130.05, 129.99, 123.34, 115.67, 115.50, 66.07, 48.55, 47.92, 43.08, 42.63, 40.24, 37.53, 34.18, 32.57, 30.31, 26.85, 23.50. LC/MS (M+H)=498.46. HPLC purity>97%.

EXAMPLE 201

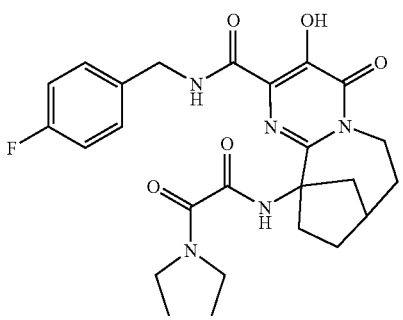

8,11-Methano-4H-pyrimido[1,2-a]azocine-2-carboxamide, 11-[[1,2-dioxo-2-(1-pyrrolidinyl)ethyl]amino]-N-[(4-fluorophenyl)methyl]-6,7,8,9,10,11-hexahydro-3-hydroxy-4-oxo-. White crystalline solid (31% yield). $^1$H NMR (500 MHz, CDCl$_3$) δ ppm 12.08 (1 H, brs), 8.81 (1 H, t, J=5.95 Hz), 8.25 (1 H, s), 7.36 (2 H, dd, J=8.55, 5.49 Hz), 6.96-7.03 (2 H, m), 5.50 (1 H, dt, J=15.56, 3.66 Hz), 4.49-4.59 (2 H, m), 3.62 (2 H, q, J=7.32 Hz), 3.44-3.52 (1 H, m), 3.23-3.37 (2 H, m), 2.64 (1 H, q, J=5.60 Hz), 2.52-2.61 (1 H, m), 2.43-2.52 (2 H, m), 2.26-2.39 (1 H, m), 1.79-1.93 (3 H, m), 1.60 (1 H, t, J=13.73 Hz), 1.25 (3 H, t, J=6.87 Hz), 1.13 (2 H, t, J=7.17 Hz). $^{13}$C NMR (126 MHz, CDCl$_3$) δ ppm 168.25, 163.38, 163.27, 162.03, 161.33, 159.56, 152.08, 146.81, 133.76, 133.73, 129.91, 129.84, 123.82, 115.58, 115.41, 66.62, 44.27, 43.19, 42.50, 41.48, 40.01, 37.18, 35.22, 32.55, 30.25, 14.73, 12.48. LC/MS (M+H)=500.15. HPLC purity>97%.

EXAMPLE 202

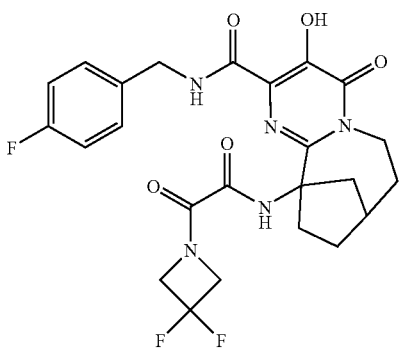

8,1,1-Methano-4H-pyrimido[1,2-a]azocine-2-carboxamide, 1'-[[2-(3,3-difluoro-1-azetidinyl)-1,2-dioxoethyl]amino]-N-[(4-fluorophenyl)methyl]-6,7,8,9,10,11-hexahydro-3-hydroxy-4-oxo-. Off-white crystalline solid (21% yield). $^1$H NMR (500 MHz, CDCl$_3$) δ ppm 12.04 (1 H, s), 9.97 (1 H, s), 7.91 (1 H, t, J=5.65 Hz), 7.39 (2 H, dd, J=8.55, 5.49 Hz), 7.00-7.06 (2 H, m), 5.52 (1 H, dt, J=15.34, 3.62 Hz), 4.92 (2 H, t, J=11.75 Hz), 4.60 (2 H, d, J=6.10 Hz), 4.37 (2 H, td, J=11.75, 3.66 Hz), 3.49 (1 H, t, J=13.89 Hz), 2.84 (1 H, td, J=6.49, 5.34 Hz), 2.64-2.73 (2 H, m), 2.42-2.53 (1 H, m), 2.22 (1 H, ddd, J=15.18, 9.00, 8.77 Hz), 1.79-1.94 (2 H, m), 1.62 (1 H, t, J=14.19 Hz), 1.57 (1 H, brs). $^{13}$C NMR (126 MHz, CDCl$_3$) δ ppm 167.72, 163.47, 161.52, 159.53, 159.32, 156.88, 152.48, 147.16, 133.01, 132.99, 130.14, 130.07, 122.89, 117.77, 115.83, 115.65, 115.60, 65.88, 65.64, 65.48, 65.41, 61.56, 61.32, 61.08, 42.88, 42.29, 40.42, 37.80, 33.58, 32.49, 30.32. LC/MS (M+H)=520.2. HPLC purity>97%.

EXAMPLE 203

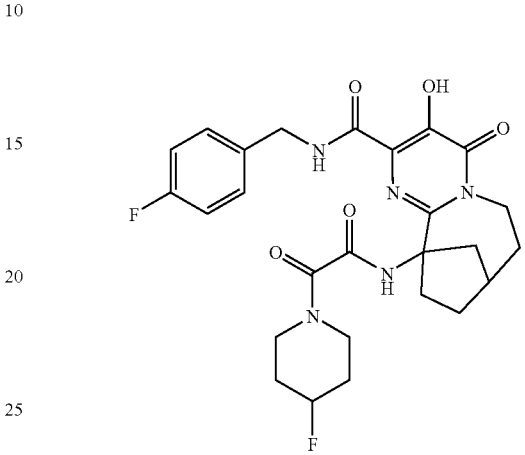

8,1,1-Methano-4H-pyrimido[1,2-a]azocine-2-carboxamide, N-[(4-fluorophenyl)methyl]-11-[[2-(4-fluoro-1-piperidinyl)-1,2-dioxoethyl]amino]-6,7,8,9,10,11-hexahydro-3-hydroxy-4-oxo-. Off-white crystalline solid (23% yield). $^1$H NMR (500 MHz, CDCl$_3$) δ ppm 12.11 (1 H, brs), 8.64-8.84 (1 H, m), 8.33 (1 H, s), 7.35 (2 H, ddd, J=8.62, 5.42, 3.05 Hz), 6.97-7.04 (2 H, m), 5.50 (1 H, dt, J=15.56, 3.66 Hz), 5.29 (1 H, s), 4.82-4.98 (1 H, m), 4.48-4.60 (2 H, m), 4.06-4.18 (1 H, m), 3.77-3.91 (1 H, m), 3.65-3.75 (1 H, m), 3.49 (1 H, td, J=14.19, 6.41 Hz), 3.30-3.44 (1 H, m), 2.61-2.69 (1 H, m), 2.48-2.59 (2 H, m), 2.38-2.48 (1 H, m), 2.25-2.38 (1 H, m), 1.79-1.99 (6 H, m), 1.60-1.67 (1 H, m). $^{13}$C NMR (126 MHz, CDCl$_3$) δ ppm 168.26, 168.18, 163.28, 162.59, 162.33, 162.03, 161.43, 161.33, 159.53, 159.51, 152.01, 151.96, 146.90, 146.86, 133.77, 133.74, 133.62, 133.60, 130.00, 129.97, 129.93, 129.90, 123.82, 123.68, 115.62, 115.58, 115.45, 115.41, 87.71, 86.35, 66.74, 66.67, 53.53, 44.47, 44.05, 42.60, 42.53, 42.09, 40.13, 39.99, 39.03, 38.99, 38.84, 38.81, 37.38, 37.03, 35.27, 35.22, 32.55, 32.52, 32.02, 31.86, 31.83, 31.66, 30.92, 30.81, 30.75, 30.65, 30.33, 30.17. LC/MS (M+H)=530.57. HPLC purity>97%.

EXAMPLE 204

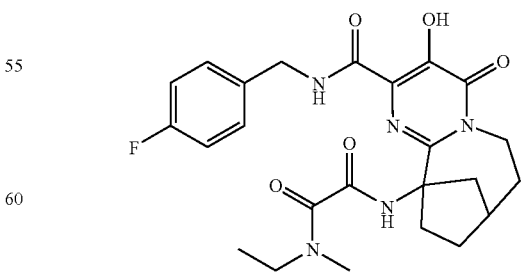

Ethanediamide, N-ethyl-N'-2-[[[(4-fluorophenyl)methyl]amino]carbonyl]-7,8,9,10-tetrahydro-3-hydroxy-4-oxo-8,11-methano-4H-pyrimido[1,2-a]azocin-11(6H)-yl]-N-methyl-. White crystalline solid (11% yield). $^1$H NMR (500

MHz, CDCl₃) δ ppm 12.09 (1 H, s), 8.71-8.84 (1 H, m), 8.09-8.37 (1 H, m), 7.33-7.39 (2 H, m), 6.97-7.04 (2 H, m), 5.50 (1 H, dd, J=15.56, 3.36 Hz), 4.49-4.59 (2 H, m), 3.56-3.71 (1 H, m), 3.48 (1 H, t, J=14.34 Hz), 3.35 (1 H, q, J=7.32 Hz), 2.84-3.27 (3 H, m), 2.60-2.67 (1 H, m), 2.40-2.59 (3 H, m), 2.25-2.38 (1 H, m), 1.77-1.92 (3 H, m), 1.58-1.65 (1 H, m), 1.09-1.27 (3 H, m). ¹³C NMR (126 MHz, CDCl₃) δ ppm 168.25, 168.20, 163.82, 163.30, 163.27, 163.08, 162.04, 161.80, 161.35, 161.32, 159.55, 152.12, 152.00, 146.81, 133.81, 133.67, 130.00 129.93, 129.87, 129.81, 123.84, 123.75, 115.57, 115.41, 66.72, 66.55, 45.59, 44.40, 44.12, 43.93, 42.57, 42.44, 40.06, 40.00, 37.24, 37.15, 35.59, 35.33, 35.07, 33.60, 32.55, 30.27, 30.24, 14.06, 11.74. LC/MS (M+H)=486.25. HPLC purity>97%.

EXAMPLE 205

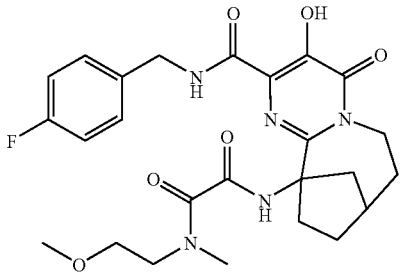

Ethanediamide, N'-[2-[[[(4-fluorophenyl)methyl]amino]carbonyl]-7,8,9,10-tetrahydro-3-hydroxy-4-oxo-8,11-methano-4H-pyrimido[1,2-a]azocin-11(6H)-yl]-N-(2-methoxyethyl)-N-methyl-. White crystalline solid (12% yield). ¹H NMR (500 MHz, CDCl₃) δ ppm 12.09 (1 H, brs), 8.71-8.77 (1 H, m), 8.23-8.33 (1 H, m), 7.32-7.40 (2 H, m), 6.97-7.04 (2 H, m), 5.45-5.54 (1 H, m), 4.50-4.59 (2 H, m), 3.90 (1 H, ddd, J=14.65, 6.87, 4.43 Hz), 3.73-3.79 (1 H, m), 3.55-3.62 (1 H, m), 3.43-3.55 (3 H, m), 3.33 (2 H, s), 3.32-3.33 (1 H, m), 2.95 (2 H, s), 2.59-2.67 (1 H, m), 2.52-2.59 (1 H, m), 2.42-2.51 (2 H, m), 2.26-2.38 (1 H, m), 1.78-1.92 (3 H, m), 1.58-1.65 (1 H, m). ¹³C NMR (126 MHz, CDCl₃) δ ppm 168.22, 168.20, 164.30, 163.72, 163.33, 163.30, 161.75, 161.65, 161.34, 159.55, 152.09, 152.02, 146.85, 146.81, 133.76, 133.73, 129.97, 129.94, 129.91, 129.87, 123.80, 123.74, 115.59, 115.42, 71.39, 70.03, 66.59, 66.57, 59.06, 59.01, 50.27, 48.92, 44.26, 44.14, 42.52, 42.50, 40.06, 40.02, 37.67, 37.24, 37.20, 35.42, 35.21, 35.11, 32.54, 30.28, 30.24. LC/MS (M+H)=516.31. HPLC purity>97%.

EXAMPLE 206

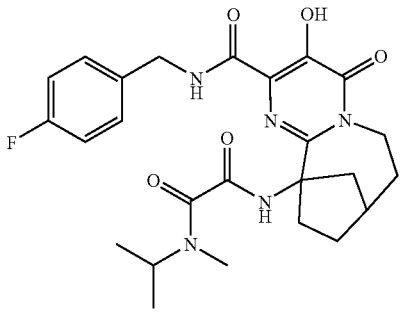

Ethanediamide, N'-[2-[[[(4-fluorophenyl)methyl]amino]carbonyl]-7,8,9,10-tetrahydro-3-hydroxy-4-oxo-8,11-methano-4H-pyrimido[1,2-a]azocin-11(6H)-yl]-N-methyl-N-(1-methylethyl)-. Off-white crystalline solid (9% yield). ¹H NMR (500 MHz, CDCl₃) δ ppm 12.12 (1 H, brs), 8.83-9.07 (1 H, m), 7.62-8.12 (1 H, m), 7.31-7.40 (2 H, m), 6.95-7.03 (2 H, m), 5.45-5.54 (1 H, m), 4.55-4.65 (1 H, m), 4.54 (2 H, d, J=6.41 Hz), 3.42-3.53 (2 H, m), 2.69-3.08 (3 H, m), 2.61-2.68 (1 H, m), 2.40-2.60 (3 H, m), 2.24-2.40 (1 H, m), 1.78-1.94 (2 H, m), 1.58-1.66 (1 H, m), 1.10-1.25 (6 H, m). LC/MS (M+H)=500.5. HPLC purity>97%.

EXAMPLE 207

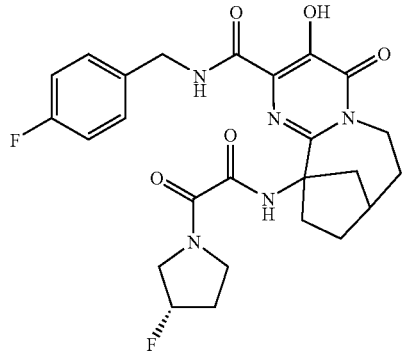

8,11-Methano-4H-pyrimido[1,2-a]azocine-2-carboxamide, N-[(4-fluorophenyl)methyl]-11-[[2-[(3S)-3-fluoro-1-pyrrolidinyl]-1,2-dioxoethyl]amino]-6,7,8,9,10,11-hexahydro-3-hydroxy-4-oxo-. Pale pink crystalline solid (18% yield). ¹H NMR (500 MHz, CDCl₃)) δ ppm 11.97-12.04 (1 H, m), 9.55-9.90 (1 H, m), 8.11-8.23 (1 H, m), 7.37-7.43 (2 H, m), 7.03 (2 H, td, J=8.70, 2.44 Hz), 5.51 (1 H, dt, J=15.56, 3.66 Hz), 5.17-5.38 (1 H, m), 4.52-4.66 (2 H, m), 4.30-4.51 (1 H, m), 3.89-4.03 (1 H, m), 3.72-3.89 (1 H, m), 3.43-3.68 (2 H, m), 2.72-2.85 (1 H, m), 2.63-2.72 (2 H, m), 2.39-2.52 (1 H, m), 2.22-2.39 (2 H, m), 1.93-2.14 (1 H, m), 1.79-1.93 (2 H, m), 1.59-1.67 (2 H, m). LC/MS (M+H)=516.19. HPLC purity>97%.

EXAMPLE 208

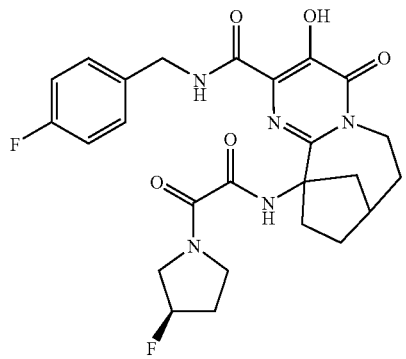

8,11-Methano-4H-pyrimido[1,2-a]azocine-2-carboxamide, N-[(4-fluorophenyl)methyl]-11-[[2-[(3R)-3-fluoro-1-pyrrolidinyl]-1,2-dioxoethyl]amino]-6,7,8,9,10,11-hexahydro-3-hydroxy-4-oxo-. Pale purple crystalline solid (13% yield). ¹H NMR (500 MHz, CDCl₃) δ ppm 12.01 (1 H, brs), 9.55-9.89 (1 H, m), 8.11-8.24 (1 H, m), 7.37-7.43 (2 H, m), 6.97-7.06 (2 H, m), 5.52 (1 H, ddd, J=15.41, 3.51, 3.36 Hz), 5.17-5.38 (1 H, m), 4.52-4.66 (2 H, m), 4.31-4.51 (1 H, m), 3.89-4.04 (1 H, m), 3.73-3.89 (1 H, m), 3.41-3.69 (2 H, m), 2.62-2.87 (3 H, m), 2.39-2.52 (1 H, m), 2.22-2.40 (2 H, m), 1.93-2.14 (1 H, m), 1.78-1.93 (2 H, m), 1.58-1.67 (2 H, m). LC/MS (M+H)=516.53. HPLC purity>97%.

EXAMPLE 209

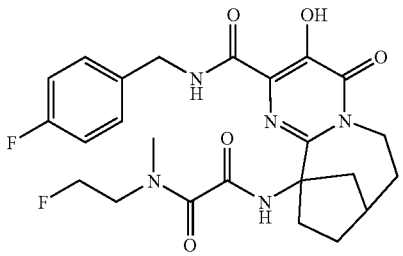

Ethanediamide, N-(2-fluoroethyl)-N'-[2-[[[(4-fluorophenyl)methyl]amino]carbonyl-7,8,9,10-tetrahydro-3-hydroxy-4-oxo-8,11-methano-4H-pyrimido[1,2-a]azocin-1](6H)-yl]-N-methyl. Pale purple crystalline solid (31% yield). $^1$H NMR (500 MHz, CDCl$_3$) δ ppm 12.06 (1 H, brs), 8.41-8.75 (2 H, m), 7.29-7.43 (2 H, m), 6.95-7.07 (2 H, m), 5.49 (1 H, brs), 4.43-4.74 (3 H, m), 3.88-4.16 (1 H, m), 3.87-4.16 (1 H, m), 3.42-3.77 (1 H, m), 3.35-3.41 (1 H, m), 2.96-3.04 (2 H, m), 2.27-2.71 (4 H, m), 1.71-1.96 (2 H, m), 1.58 (4 H, brs). LC/MS (M+H)=504.18. HPLC purity>97%.

EXAMPLE 210

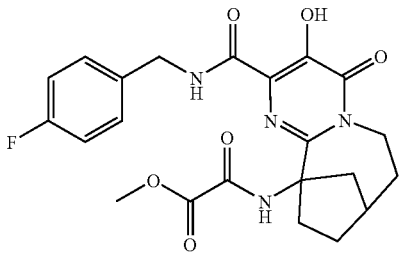

Acetic acid, [[2-[[[(4-fluorophenyl)methyl]amino]carbonyl]-7,8,9,10-tetrahydro-3-hydroxy-4-oxo-8,1'-methano-4H-pyrimido[1,2-a]azocin-11(6H)-yl]amino]oxo-, methyl ester. Pale purple solid (58% yield). $^1$H NMR (500 MHz, CDCl$_3$) δ ppm 12.07 (1 H, s), 9.66 (1 H, s), 7.69 (1 H, t, J=5.80 Hz), 7.37-7.41 (2 H, m), 7.02-7.08 (2 H, m), 5.53 (1 H, dt, J=15.49, 3.85 Hz), 4.61 (2 H, d, J=6.10 Hz), 3.83 (3 H, s), 3.47-3.55 (1 H, m), 2.90 (1 H, ddd, J=12.89, 6.79, 1.68 Hz), 2.66-2.75 (2 H, m), 2.48-2.59 (1 H, m), 2.22 (1 H, ddd, J=15.11, 9.00, 8.85 Hz), 1.86-1.95 (1 H, m), 1.77-1.85 (1 H, m), 1.49-1.56 (2 H, m). LC/MS (M+H)=458.88. HPLC purity>87%.

EXAMPLE 211

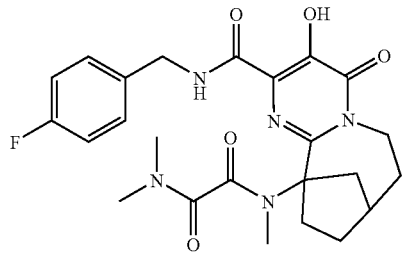

Ethanediamide, N-[2-[[[(4-fluorophenyl)methyl]amino]carbonyl]-7,8,9,10-tetrahydro-3-hydroxy-4-oxo-8,11-methano-4H-pyrimido[1,2-a]azocin-11(6H)-yl]-N,N',N'-trimethyl-. White crystalline solid (4% yield). $^1$H NMR (500 MHz, CDCl$_3$) δ ppm 12.35-12.54 (1 H, m), 9.72-9.91 (1 H, m), 7.33-7.41 (2 H, m), 6.91-7.00 (2 H, m), 5.46 (1 H, dt, J=15.03, 3.78 Hz), 4.44-4.64 (2 H, m), 3.46 (1 H, t, J=13.58 Hz), 3.01-3.06 (3 H, m), 2.98-3.01 (3 H, m), 2.94-2.98 (3 H, m), 2.59-2.67 (1 H, m), 2.42-2.53 (1 H, m), 2.29 (1 H, dd, J=11.60, 6.71 Hz), 2.08-2.20 (1 H, m), 1.78-1.90 (3 H, m), 1.57-1.63 (2 H, m). LC/MS (M+H)=486.48. HPLC purity>97%.

Examples 212 through 216 can be synthesized according to Scheme XXIX

EXAMPLE 212

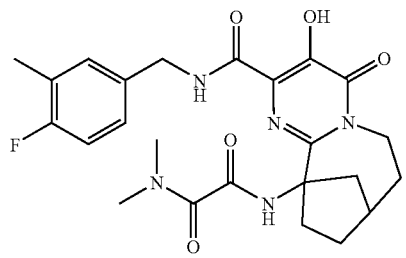

Ethanediamide, N'-[2-[[[(4-fluoro-3-methylphenyl)methyl]amino]carbonyl]-7,8,9,10-tetrahydro-3-hydroxy-4-oxo-8,11-methano-4H-pyrimido[1,2-a]azocin-11(6H)-yl]-N,N-dimethyl-. White crystalline solid (46% yield). $^1$H NMR (500 MHz, CDCl$_3$) δ ppm 12.11 (1 H, s), 8.71 (1 H, t, J=5.95 Hz), 8.26 (1 H, s), 7.13-7.21 (2 H, m), 6.94 (1 H, t, J=8.85 Hz), 5.50 (1 H, dt, J=15.26, 3.66 Hz), 4.50 (2 H, d, J=6.10 Hz), 3.48 (1 H, t, J=13.89 Hz), 3.28 (3 H, s), 2.91 (3 H, s), 2.64 (1 H, q, J=5.29 Hz), 2.50-2.60 (1 H, m), 2.42-2.50 (2 H, m), 2.27-2.39 (1 H, m), 2.25 (3 H, s), 1.78-1.93 (3 H, m), 1.57 (1 H, brs). $^{13}$C NMR (126 MHz, CDCl$_3$) δ ppm 168.16, 163.66, 161.81, 161.78, 159.86, 159.57, 152.03, 146.81, 133.39, 133.36, 131.34, 131.30, 127.11, 127.05, 125.07, 124.94, 123.82, 115.18, 115.00, 66.65, 44.23, 42.50, 40.04, 38.19, 37.20, 36.40, 35.17, 32.53, 30.26, 14.66, 14.64. LC/MS (M+H)=486.28. HPLC purity>97%.

EXAMPLE 213

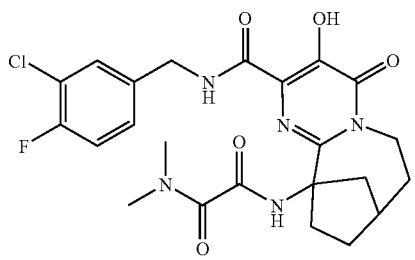

Ethanediamide, N'-[2-[[[(3-chloro-4-fluorophenyl)methyl]amino]carbonyl]-7,8,9,10-tetrahydro-3-hydroxy-4-oxo-8,11-methano-4H-pyrimido[1,2-a]azocin-11(6H)-yl]-N,N-dimethyl-. Off-white crystalline solid (62% yield). $^1$H NMR (500 MHz, CDCl$_3$) δ ppm 11.97 (1 H, s), 8.86 (1 H, t, J=5.95 Hz), 8.09 (1 H, s), 7.44 (1 H, dd, J=7.02, 2.14 Hz), 7.26-7.29 (1 H, m), 7.09 (1 H, t, J=8.70 Hz), 5.50 (1 H, dt, J=15.56, 3.81 Hz), 4.45-4.56 (2 H, m), 3.44-3.54 (1 H, m), 3.28 (3 H, s), 2.94 (3 H, s), 2.64 (1 H, q, J=5.59 Hz), 2.48-2.60 (2 H, m), 2.40-2.47 (1H, m), 2.26-2.37 (1H, m), 1.81-1.94 (3 H, m), 1.59-1.66 (1 H, m). $^{13}$C NMR (126 MHz, CDCl$_3$) δ ppm 168.28, 163.88, 161.88, 159.46, 158.62, 156.64, 152.13, 146.85, 135.14, 135.11, 130.52, 128.15, 128.09, 123.68, 121.13, 120.99, 116.77, 116.60, 66.71, 44.32, 42.09, 40.03, 38.14, 37.19, 36.34, 35.23, 32.55, 30.23. LC/MS (M+H)=506.19. HPLC purity>97%.

EXAMPLE 214

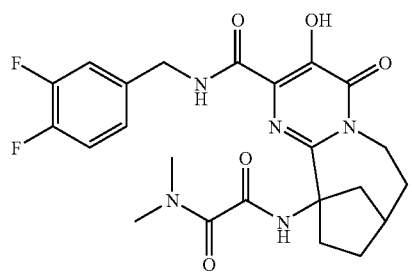

Ethanediamide, N'-[2-[[[(3,4-difluorophenyl)methyl]amino]carbonyl]-7,8,9,10-tetrahydro-3-hydroxy-4-oxo-8,11-methano-4H-pyrimido[1,2-a]azocin-11(6H)-yl]-N,N-dimethyl. Pale yellow crystalline solid (61% yield). $^1$H NMR (500 MHz, CDCl$_3$) δ ppm 11.98 (1 H, s), 8.82 (1 H, t, J=5.34 Hz), 8.15 (1 H, s), 7.21-7.29 (1 H, m), 7.05-7.16 (2 H, m), 5.45-5.55 (1 H, m), 4.46-4.57 (2 H, m), 3.49 (1H, t, J=14.34 Hz), 3.29 (3 H, s), 2.95 (3 H, s), 2.61-2.69 (1 H, m), 2.42-2.61 (3 H, m), 2.26-2.39 (1 H, m), 1.79-1.94 (3 H, m), 1.60-1.67 (1 H, m). $^{13}$C NMR (126 MHz, CDCl$_3$) δ ppm 168.28, 163.88, 161.92, 159.50, 152.11, 151.44, 151.34, 150.93, 150.83, 149.46, 149.36, 148.96, 148.86, 146.84, 135.02, 134.98, 134.95, 124.33, 124.30, 124.28, 124.25, 123.69, 117.43, 117.40, 117.29, 117.26, 66.69, 44.32, 42.23, 40.04, 38.18, 37.17, 36.31, 35.24, 32.52, 30.24. LC/MS (M+H)=490.26. HPLC purity>95%.

EXAMPLE 215

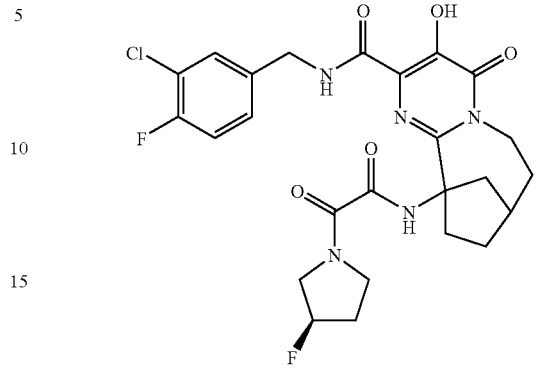

8,11-Methano-4H-pyrimido[1,2-a]azocine-2-carboxamide, N-[(3-chloro-4-fluorophenyl)methyl]-11-[[2-[(3R)-3-fluoro-1-pyrrolidinyl]-1,2-dioxoethyl]amino]-6,7,8,9,10,11-hexahydro-3-hydroxy-4-oxo-. Off-white crystalline solid (54% yield). $^1$H NMR (500 MHz, CDCl$_3$) δ ppm 11.84-11.90 (1 H, m), 9.49-9.90 (1 H, m), 8.17-8.31 (1 H, m), 7.46-7.54 (1 H, m), 7.27-7.33 (1 H, m), 7.08-7.14 (1 H, m), 5.51 (1 H, dt, J=15.49, 3.70 Hz), 5.18-5.39 (1 H, m), 4.48-4.65 (2 H, m), 4.30-4.48 (1H, m), 3.56-4.05 (3 H, m), 3.46-3.55 (1 H, m), 2.64-2.86 (3 H, m), 2.39-2.52 (1H, m), 2.23-2.40 (2 H, m), 1.79-1.94 (3 H, m), 1.60-1.67 (2 H, m). LC/MS (M+H)=550.23. HPLC purity>95%.

EXAMPLE 216

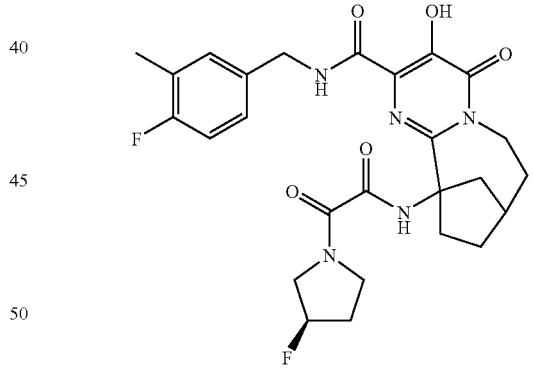

8,11-Methano-4H-pyrimido[1,2-a]azocine-2-carboxamide, N-[(4-fluoro-3-methylphenyl)methyl]-11-[[2-[(3R)-3-fluoro-1-pyrrolidinyl]-1,2-dioxoethyl]amino]-6,7,8,9,10,11-hexahydro-3-hydroxy-4-oxo-. White crystalline solid (44% yield). $^1$H NMR (500 MHz, CDCl$_3$) δ ppm 12.02-12.07 (1 H, m), 9.54-9.89 (1 H, m), 8.09-8.22 (1 H, m), 7.18-7.24 (2 H, m), 6.91-6.99 (1 H, m), 5.51 (1 H, dt, J=15.49, 3.70 Hz), 5.17-5.38 (1 H, m), 4.48-4.62 (2 H, m), 4.31-4.48 (1 H, m), 3.54-4.03 (3 H, m), 3.46-3.54 (1 H, m), 2.63-2.85 (3 H, m), 2.39-2.50 (1 H, m), 2.27-2.36 (1 H, m), 2.26 (3 H, s), 1.79-1.92 (3 H, m), 1.60-1.66 (2 H, m). LC/MS (M+H)=486.15. HPLC purity>97%.

Examples 217 and 218 can be synthesized according to Scheme XXX

EXAMPLE 217

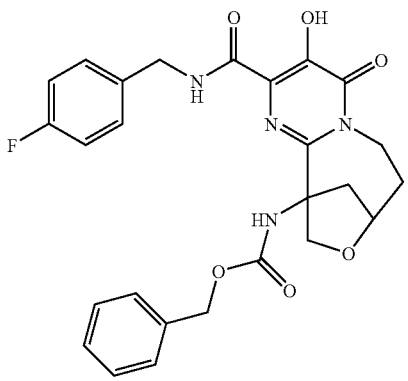

Benzyl (2-((4-fluorobenzyl)carbamoyl)-3-hydroxy-4-oxo-7,8-dihydro-4 H,6H-8,11-methanopyrimido[2,1-d][1,5]oxazocin-11(10H)-yl)carbamate. A mixture of ethyl 11-(((benzyloxy)carbonyl)amino)-3-hydroxy-4-oxo-7,8,10,11-tetrahydro-4 H,6H-8,11-methanopyrimido[2,1-d][1,5]oxazocine-2-carboxylate (0.070 g, 0.163 mmol), (4-fluorophenyl)methanamine (0.125 g, 1 mmol) and Et$_3$N (0.418 mL, 3 mmol) in EtOH (5 mL) was heated at reflux for 7 h. The reaction was cooled, concentrated and the residue purified by preparative-HPLC to afford title compound (0.0405 g, 0.080 mmol, 49%) as an off-white solid. $^1$H NMR (500 MHz, CDCl$_3$) δ: 11.99 (0.6 H, brs), 11.92 (0.4 H, brs), 7.82 (0.4 H, t, J=5.8 Hz), 7.58 (0.6 H, t, J=5.8 Hz), 7.32-7.39 (3 H, m), 7.17-7.28 (2 H, m), 7.09 (1 H, dd, J=8.1, 5.6 Hz), 7.01-7.06 (1 H, m), 6.91-6.99 (2 H, m), 5.60 (0.6 H, s), 5.41-5.51 (1 H, m), 5.10 (0.4 H, s), 5.02 (0.6 H, d, J=12.5 Hz), 4.89 (1 H, d, J$_{AB}$=12.4 Hz.), 4.79 (0.6 H, d, J=10.7 Hz), 4.69-4.75 (2 H, m), 4.60 (0.4 H, d, J=10.4 Hz), 4.37-4.49 (2.8 H, m), 4.12 (0.6 H, dd, J=18.8, 6.0 Hz), 3.70 (0.6 H, t, J=13.7 Hz), 3.63 (0.4 H, t, J=13.7 Hz), 2.47-2.60 (1 H, m), 2.13-2.21 (1 H, m.), 1.97-2.05 (1 H, m). LCMS (M+H) calcd for C$_{26}$H$_{26}$FN$_4$O$_6$: 509.18; found: 509.14.

EXAMPLE 218

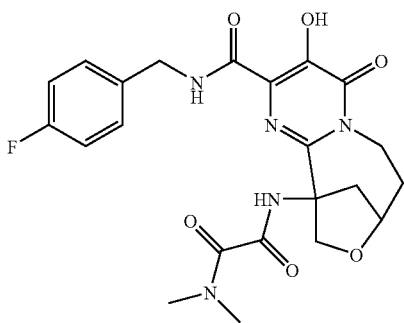

N'-(2-((4-Fluorobenzyl)carbamoyl)-3-hydroxy-4-oxo-7,8-dihydro-4 H,6H-8,11-methanopyrimido[2,1-d][1,5]oxazocin-11(10H)-yl)-N,N-dimethylethanediamide. A solution of benzyl (2-((4-fluorobenzyl)carbamoyl)-3-hydroxy-4-oxo-7,8-dihydro-4 H,6H-8,11-methanopyrimido[2,1-d][1,5]oxazocin-11(10H)-yl)carbamate (0.039 g, 0.077 mmol) and 1N aq. HCl (0.5 mL, 0.500 mmol) in THF (10 mL) was sparged for 5 min by with N$_2$. The flask was evacuated and replaced with 1 atm H$_2$ after which the reaction was stirred for 5 h. The mixture was filtered and concentrated to give amine hydrochloride salt (33 mg) as a white solid which was used in the next step without purification. To a stirred mixture of this compound in DMF (3 mL) was added, 2-(dimethylamino)-2-oxoacetic acid (0.027 g, 0.230 mmol), diisopropyl-ethylamine (0.134 mL, 0.767 mmol) and 4-(dimethylamino)pyridine (DMAP) (3 mg, 0.025 mmol) and O-(7-azabenzotriazol-1-yl)-N,N,N',N'-tetramethyluronium hexafluorophosphate (HATU) (0.087 g, 0.230 mmol) at room temperature. After 18 h, the reaction mixture was purified by preparative-HPLC to afford the title compound (0.0214 g, 0.045 mmol, 59% yield) as a crystalline off-white solid after crystallization from methanol/H$_2$O. $^1$H NMR (500 MHz, CDCl$_3$) δ: 12.23 (1 H, s), 9.06 (1 H, t, J=6.0 Hz), 7.43 (1 H, s), 7.33 (2 H, dd, J=8.4, 5.3 Hz), 6.97-7.03 (2 H, t, J=8.7 Hz), 5.48 (1 H, td, J=15.6, 3.7 Hz), 4.88 (1 H, d, J=10.7 Hz), 4.72 (1 H, t, J=6.7 Hz), 4.51 (2 H, qd, J=14.7, 6.4 Hz), 4.42 (1 H, d, J=10.7 Hz), 3.69 (1 H, td, J=13.3, 1.2 Hz), 3.17 (3 H, s), 2.89 (3 H, s), 2.59 (1 H, dd, J=11.9, 7.6 Hz), 2.15-2.22 (1 H, m), 2.09 (1 H, d, J=12.2 Hz), 1.60 (1 H, td, J=13.9, 3.4 Hz). LCMS (M+H) calcd for C$_{22}$H$_{25}$FN$_5$O$_6$: 474.18; found: 474.10.

Examples 219 through 222 can be syntehsized according to Scheme XXXI

EXAMPLE 219

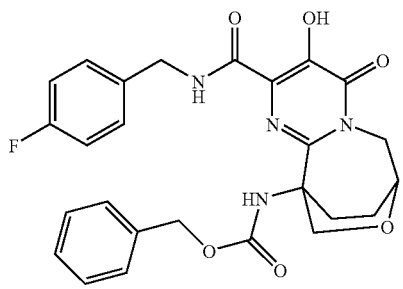

Benzyl (2-((4-fluorobenzyl)carbamoyl)-3-hydroxy-4-oxo-6,7,8,9-tetrahydro-7,10-(epoxymethano)pyrimido[1,2-a]azepin-10(4H)-yl)carbamate. A mixture of ethyl 10-(((benzyloxy)carbonyl)amino)-3-hydroxy-4-oxo-4,6,7,8,9,10-hexahydro-7,10-(epoxymethano)pyrimido[1,2-a]azepine-2-carboxylate (150 mg, 0.349 mmol) and 4-fluorobenzylamine (0.200 mL, 1.75 mmol) in EtOH (3 mL) was heated at 90° C. for 20 h. The reaction mixture was cooled, concentrated and purified by preparative reversed phase HPLC using a C-18 column (10% to 70% methanol/water) to afford the title compound (110 mg, 62% yield) as a yellow solid. $^1$H NMR (500 MHz, CDCl$_3$) δ: 7.29-7.38 (m, 4H), 7.11-7.18 (m, 2H), 6.96-7.04 (m, 4H), 5.48 (s, 1H), 4.93-4.98 (m, 1H), 4.81 (d, 1H, J=11.6 Hz), 4.55-4.65 (m, 2H), 4.45-4.52 (m, 2H), 4.27-4.32 (m, 1H), 3.86 (s, 2H), 2.44-2.48 (m, 1H), 2.28-2.33 (m, 1H), 1.77-1.82 (m, 1H), 1.46-1.52 (m, 1H). LCMS (M+H)= 509.32.

EXAMPLE 220

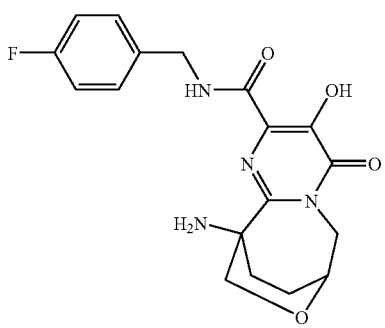

10-Amino-N-(4-fluorobenzyl)-3-hydroxy-4-oxo-4,6,7,8,9,10-hexahydro-7,10-(epoxymethano)pyrimido[1,2-a]azepine-2-carboxamide. To a mixture of benzyl (2-((4-fluorobenzyl)carbamoyl)-3-hydroxy-4-oxo-6,7,8,9-tetrahydro-7,10-(epoxymethano)pyrimido[1,2-a]azepin-10(4H)-yl) carbamate (110 mg, 0.216 mmol) in methanol (3 mL) was added 10% Pd/C (115 mg, 0.108 mmol) and the mixture stirred under 1 atm H$_2$ for 18 h. The mixture was then filtered through a pad of CELITE® and the pad washed with ethyl acetate. The filtrate was concentrated to afford the title compound (70 mg, 86% yield) as a light yellow solid. $^1$H NMR (500 MHz, CDCl$_3$) δ: 7.84 (brs, 1H), 7.29 (dd, 2H, J=8.09 & 5.34 Hz), 7.02 (t, 2H, J=8.55 Hz), 4.56 (d, 2H, J=6.1 Hz), 4.43-4.50 (m, 2H), 4.04-4.11 (m, 2H), 3.87 (d, 1H, J=10.99 Hz), 2.28-2.32 (m, 2H), 1.98-2.09 (m, 3H), 1.55-1.61 (m, 1H). LCMS (M+H)=375.2.

EXAMPLE 221

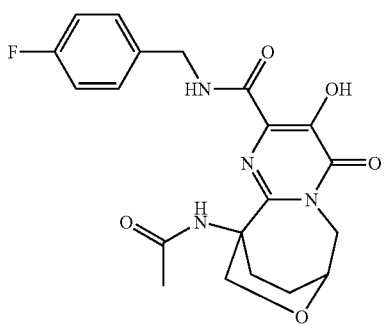

10-(Acetylamino)-N-(4-fluorobenzyl)-3-hydroxy-4-oxo-4,6,7,8,9,10-hexahydro-7,10-(epoxymethano)pyrimido[1,2-a]azepine-2-carboxamide. To a solution of 10-amino-N-(4-fluorobenzyl)-3-hydroxy-4-oxo-4,6,7,8,9,10-hexahydro-7,10-(epoxymethano)pyrimido[1,2-a]azepine-2-carboxamide (30 mg, 0.080 mmol) in CH$_2$Cl$_2$ (2 mL) was added Et$_3$N (0.056 mL, 0.401 mmol) followed by acetyl chloride (0.05 mL, 0.401 mmol) and the resulting mixture stirred at room temperature for 16 h. The reaction mixture was concentrated and the resulting residue dissolved in methanol (2 mL) and treated with 2M dimethylamine in methanol (0.5 mL). The resulting reaction mixture was stirred at 60° C. for 2 h, cooled and purified by preparative HPLC to afford the title compound as a white solid (9 mg, 27% yield). $^1$H NMR (500 MHz, CDCl$_3$) δ: 11.92 (s, 1H), 7.39 (brs, 1H), 7.29-7.33 (m, 2H), 7.05-7.09 (m, 2H), 6.13 (s, 1H), 4.59-4.65 (m, 2H), 4.48-4.55 (m, 3H), 4.30 (d, 1H, J=11.9 Hz), 4.10 (d, 1H, J=16.17 Hz), 2.52-2.58 (m, 1H), 2.30-2.36 (m, 1H), 1.82 (s, 3H), 1.75-1.82 (m, 1H), 1.50-1.55 (m, 1H). LCMS (M+H)=417.25. HPLC purity>95%.

EXAMPLE 222

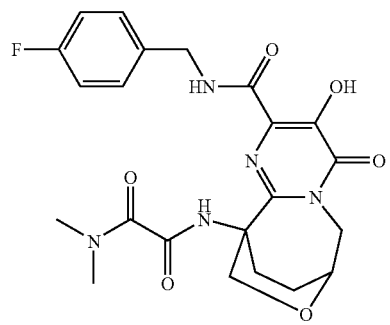

N'-(2-((4-Fluorobenzyl)carbamoyl)-3-hydroxy-4-oxo-6,7,8,9-tetrahydro-7,10-(epoxymethano)pyrimido[1,2-a]azepin-10(4H)-yl)-N,N-dimethylethanediamide. To a stirred solution of 10-amino-N-(4-fluorobenzyl)-3-hydroxy-4-oxo-4,6,7,8,9,10-hexahydro-7,10-(epoxymethano)pyrimido[1,2-a]azepine-2-carboxamide (70 mg, 0.187 mmol) and 2-(dimethylamino)-2-oxoacetic acid (32.8 mg, 0.280 mmol) in DMF (3 mL) was added diisopropyl-ethylamine (0.175 mL, 1.002 mmol), 4-(dimethylamino)pyridine (DMAP) (4.57 mg, 0.037 mmol) and O-(7-azabenzotriazol-1-yl)-N,N,N',N'-tetramethyluronium hexafluorophosphate (HATU) (107 mg, 0.280 mmol) and the resulting mixture stirred at room temperature for 3 h. After work-up the crude was purified by preparative HPLC to afford the title compound as an off-white solid (35 mg, 40% yield). $^1$H NMR (500 MHz, CDCl$_3$) δ: 12.11 (s, 1H), 8.73 (brs, 1H), 7.47 (s, 1H), 7.34 (dd, 2H, J=8.39 & 5.34 Hz), 6.98-7.03 (m, 2H), 4.62-4.70 (m, 2H), 4.53 (d, 2H, J=6.71 Hz), 4.49-4.52 (m, 1H), 4.29 (d, 1H, J=11.6 Hz), 4.08 (d, 1H, J=16.79 Hz), 3.21 (s, 3H), 2.89 (s, 3H), 2.46-2.53 (m, 1H), 2.33-2.38 (m, 1H), 1.86-1.92 (m, 1H), 1.53-1.58 (m, 1H). LCMS (M+H)=474.24. HPLC purity>95%.

Examples 223 and 224 can be synthesized according to Scheme XXXII

EXAMPLE 223

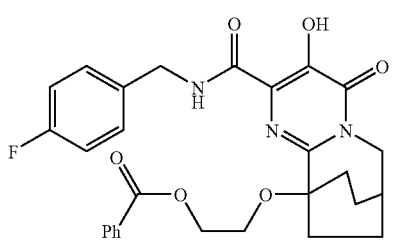

7,10-Ethanopyrimido[1,2-a]azepine-2-carboxamide, 10-[2-(benzoyloxy)ethoxy]-N-[(4-fluorophenyl)methyl]-4,6,7,8,9,10-hexahydro-3-hydroxy-4-oxo-. A mixture of 5-benzyloxy-1-(2-benzoyloxy-ethoxy)-6-oxo-3,7-diazatricyclo

[7.2.2.0²,⁷]trideca-2,4-diene-4-carboxylic acid ethyl ester (33 mg, 0.060 mmol) and (4-fluorophenyl)methanamine (60.4 mg, 0.483 mmol) in DMF (1 mL) was stirred at 100° C. for 2 h under $N_2$. The mixture was concentrated in vacuo and the residue was dissolved in $CH_2Cl_2$ (10 mL), washed with 1N-HCl followed by brine, then dried ($Na_2SO_4$) and concentrated to provide 54 mg of an amber oil which was purified by C-18 reverse phase silica gel, eluting with 34-38-42-50% $CH_3CN/H_2O$ (0.1% trifluoroacetic acid) to obtain the title compound (16 mg, 0.031 mmol, 51% yield) after crystallization from 95% EtOH as a light-pink crystalline powder: HPLC: retention time=2.97 min (area percent=100%); LCMS: m/z 522 (M+H); $^1$H NMR (500 MHz, $CDCl_3$) δ ppm 1.60-1.72 (2H, m), 1.84-1.96 (2H, m), 2.05 (4H, t, J=7.5 Hz), 2.45 (1H, brs), 3.81 (2H, t, J=5.8 Hz), 4.08 (2H, d, J=3.7 Hz), 4.38 (2H, t, J=5.8 Hz), 4.49 (2H, d, J=6.4 Hz), 6.97 (2H, t, J=8.7 Hz), 7.26 (2H, dd, J=8.6, 5.5 Hz), 7.43 (1H, t, J=7.8 Hz), 7.57 (1H, t, J=7.5 Hz), 7.98 (2H, d, J=7.3 Hz), 8.24 (H, t, J=5.8 Hz), 11.99 (1 H, s); $^{13}$C NMR (126 MHz, $CDCl_3$) δ ppm 23.3, 27.7, 30.9, 42.5, 53.8, 60.7, 64.0, 77.3, 115.7, 124.9, 128.6, 129.6, 129.7, 130.1, 133.3, 133.5, 146.6, 153.0, 160.0, 162.4, 166.7, 168.6. Anal. calcd for $C_{28}N_{28}FN_3O_6$: C64.48, H5.41, N8.05; found: C64.45, H5.44, N7.92.

EXAMPLE 224

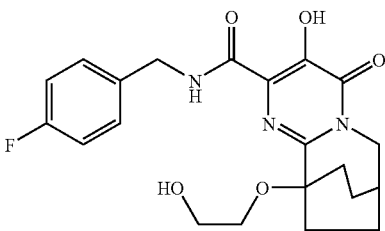

7,10-Ethanopyrimido[1,2-a]azepine-2-carboxamide, N-[(4-fluorophenyl)methyl]-4,6,7,8,9,10-hexahydro-3-hydroxy-10-(2-hydroxyethoxy)-4-oxo-. To a solution of 7,10-ethanopyrimido[1,2-a]azepine-2-carboxamide, 10-[2-(benzoyloxy)ethoxy]-N-[(4-fluorophenyl)methyl]-4,6,7,8,9,10-hexahydro-3-hydroxy-4-oxo- (8 mg, 0.015 mmol) in a mixture of methanol (0.5 mL) and THF (0.500 mL) was added 0.5 M sodium methoxide (0.092 mL, 0.046 mmol) in methanol at room temp. and the mixture left under $N_2$ for 15 min. The mixture diluted with ethyl acetate (10 mL) and washed with 1N HCl (2×5 mL) followed by brine, then dried ($Na_2SO_4$), and concentrated to provide a light-pink solid which was triturated with 95% EtOH to yield the title compound (4 mg, 0.01 mmol, Y 63% yield) as a light-pink crystalline powder: HPLC: retention time=2.01 min (area percent=100%); LCMS: m/z 418 (M+H); $^1$H NMR (500 MHz, $CDCl_3$) δ ppm 1.66-1.71 (2H, m), 1.89-1.96 (2H, m), 2.04 (4H, t, J=7.8 Hz), 2.45 (1H, br.s), 2.83 (1H, br), 3.69 (4H, s), 4.09 (2H, d, J=4.0 Hz), 4.50 (2H, d, J=6.1 Hz), 7.00 (2H, t, J=8.7 Hz), 7.33 (2H, dd, J=8.4, 5.3 Hz), 9.35 (H, t, J=5.2 Hz), 12.28 (1H, s); $^{13}$C NMR (126 MHz, $CDCl_3$) δ ppm 23.3, 27.7, 30.9, 42.4, 53.8, 61.8, 62.9, 76.5, 115.5, 125.2, 129.9, 134.0, 146.8, 152.1, 160.1, 162.3, 168.8.

Examples 225 through 228 can be synthesized according to Scheme XXXIII

EXAMPLE 225

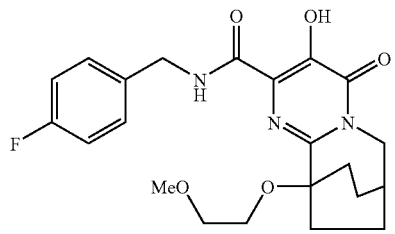

7,10-Ethanopyrimido[1,2-a]azepine-2-carboxamide, N-[(4-fluorophenyl)methyl]-4,6,7,8,9,10-hexahydro-3-hydroxy-10-(2-methoxyethoxy)-4-oxo-. A solution of 5-benzyloxy-1-(2-methoxy-ethoxy)-6-oxo-3,7-diazatricyclo[7.2.2.0²,⁷]trideca-2,4-diene-4-carboxylic acid methyl ester (8 mg, 0.019 mmol) in trifluoroacetic acid (1 mL, 13 mmol) was kept at room temperature for 3 h. The trifluoroacetic acid was removed in vacuo to obtain a light-pink film: HPLC: retention time=1.35 min (area percent=100%); LCMS: m/z 339 (M+H). $^1$H NMR (500 MHz, $CDCl_3$) δ ppm 1.74 (2H, br.s), 1.97 (2H, br.s), 2.15 (4H, br.s), 2.50 (1H, br.s), 3.46 (3H, s), 3.69 (2H, br.s), 3.73 (2H, br.s), 4.01 (3H, s), 4.17 (2H, br.s). A mixture of this compound and (4-fluorophenyl)methanamine (11 mg, 0.089 mmol) in DMF (1 mL) was heated in an oil bath at 100° C. under $N_2$ for 5 h. The mixture was concentrated and the residue purified by C-18 reverse phase column (30% $CH_3CN/H_2O$ (0.1% trifluoroacetic acid)) to obtain the title compound (2.8 mg, 6.4 μmol, 36% yield) as a film: HPLC: retention time=2.41 min (area percent=100%); LCMS: m/z 432 (M+H); $^1$H NMR (500 MHz, $CDCl_3$) δ ppm 1.62-1.76 (2H, m), 1.86-1.97 (2H, m), 1.98-2.15 (4H, m), 2.45 (1H, d, J=1.2 Hz), 3.25 (3H, s), 3.52 (2H, t, J=3.5 Hz), 3.75 (2H, d, J=3.5 Hz), 4.10 (2H, d, J=3.4 Hz), 4.57 (2H, d, J=6.4 Hz), 7.01 (2H, t, J=8.4 Hz), 7.28 (2H, dd, J=7.6, 5.5 Hz), 9.00 (1H, t, J=5.2 Hz); $^{13}$C NMR (126 MHz, $CDCl_3$) δ ppm 23.3, 27.7, 30.8, 42.4, 53.9, 59.9, 62.6, 72.9, 76.4, 115.6, 125.2, 129.0, 133.8, 146.5, 152.3, 160.3, 162.2, 169.1.

EXAMPLE 226

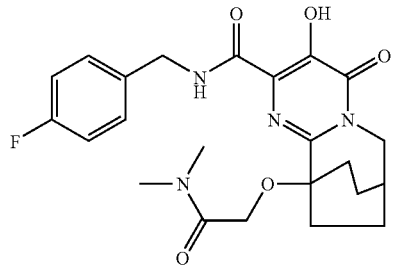

7,10-Ethanopyrimido[1,2-a]azepine-2-carboxamide, 10-[2-(dimethylamino)-2-oxoethoxy]-N-[(4-fluorophenyl)methyl]-4,6,7,8,9,10-hexahydro-3-hydroxy-4-oxo-. A solution of 5-benzyloxy-1-dimethylcarbamoylmethoxy-6-oxo-3,7-diazatricyclo[7.2.2.0²,⁷]trideca-2,4-diene-4-carboxylic acid ethyl ester (36 mg, 0.057 mmol) in trifluoroacetic acid (1 mL, 12.98 mmol) was left at room temperature overnight. The mixture was concentrated in vacuo to provide an amber film: HPLC: retention time=1.39 min; LCMS: m/z 380 (M+H); $^1$H NMR (400 MHz, CDCl$_3$) δ ppm 1.44 (3H, t, J=7.2 Hz), 1.68-1.80 (2H, m), 1.99 (2H, m), 2.15-2.33 (4H, m), 2.53 (1H, br.s), 3.00 (3H, s), 3.01 (3H, s), 4.23 (2H, d, J=3.1 Hz), 4.48-4.56 (4H, m). A solution of this film (40 mg, 0.057 mmol) and (4-fluorophenyl)methanamine (93 mg, 0.740 mmol) in DMF (1 mL) was heated at 100° C. (oil bath temp.) for 2 h under N$_2$. The mixture was concentrated to remove DMF and the residue purified by C-18 reverse phase column (22% CH$_3$CN/H$_2$O (0.1% trifluoroacetic acid)) to yield the title compound (11 mg, 0.024 mmol, 42% yield) after crystallization from 95% EtOH as an off-white crystal): HPLC: retention time=2.05 min (area percent=100%); LCMS: m/z 459 (M+H); $^1$H NMR (500 MHz, CDCl$_3$) δ ppm 1.60-1.78 (2H, m), 1.87-1.98 (2H, m), 1.98-2.09 (2H, m), 2.09-2.19 (2H, m), 2.43 (1H, br.s), 2.87 (3H, s), 3.04 (3H, s), 4.09 (2H, d, J=3.7 Hz), 4.28 (2H, s), 4.56 (2H, d, J=6.4 Hz), 6.98 (2H, t, J=6.6 Hz), 7.41 (2H, dd, J=8.7, 5.3 Hz), 9.55 (1H, t, J=5.8 Hz), 12.33 (1H, br); $^{13}$C NMR (126 MHz, CDCl$_3$) δ ppm 23.3, 27.6, 30.7, 35.4, 37.1, 42.2, 53.8, 63.8, 77.5, 115.2, 125.5, 130.1, 134.4, 146.8, 151.7, 160.1, 162.2, 168.8, 169.5. Anal. Calcd for C$_{23}$H$_{27}$FN$_4$O$_5$: C, 60.25; H, 5.93; N, 12.22; found C, 60.08; H, 5.80; N, 12.13.
Examples 227 through 233 can be synthesized according to Scheme XXXIV

EXAMPLE 227

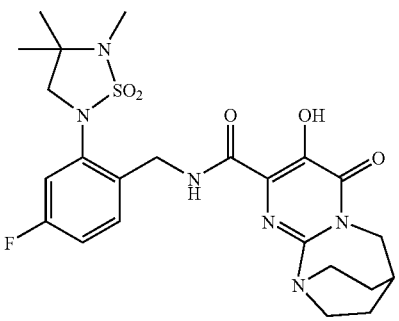

N-(4-Fluoro-2-(4,4,5-trimethyl-1,1-dioxido-1,2,5-thiadiazolidin-2-yl)benzyl)-3-hydroxy-4-oxo-6,7,8,9-tetrahydro-4H-7,10-ethanopyrimido[1,2-a][1,3]diazepine-2-carboxamide. A solution of 3-(benzyloxy)-N-(4-fluoro-2-(4,4,5-trimethyl-1,1-dioxido-1,2,5-thiadiazolidin-2-yl)benzyl)-4-oxo-6,7,8,9-tetrahydro-4H-7,10-ethanopyrimido[1,2-a][1,3]diazepine-2-carboxamide (0.054 g, 0.088 mmol) in CH$_2$Cl$_2$ (5 mL) and trifluoroacetic acid (0.7 mL, 9.09 mmol) was stirred at room temperature for 18 h. The solution was concentrated to give a yellow oil that was purified by preparative HPLC (Solvent A=10% methanol/90% H$_2$O/0.1% trifluoroacetic acid; Solvent B=90% methanol/10% H$_2$O/0-1% trifluoroacetic acid; Start % B=20; Final % B=100; Gradient time=20 min; Stop time=25 min; Column=Sunfire 19×100 mm, C18, 5 μm) to give the title compound (as a trifluoroacetic acid salt) as a pale yellow solid (0.0075 g, 13% yield). LCMS (M+H) calcd for C$_{23}$H$_{30}$FN$_6$O$_5$S: 521.19; found: 521.25. $^1$H NMR (500 MHz, CDCl$_3$) δ: 8.64 (1H, t, J=5.6 Hz), 7.60 (1H, dd, J=8.2, 6.4 Hz), 7.22 (1H, dd, J=9.2, 2.4 Hz), 7.11 (1H, td, J=8.1, 2.2 Hz), 4.64 (2H, d, J=5.8 Hz), 4.00-3.94 (2H, m), 3.79-3.76 (2H, m), 3.72 (2H, s), 3.58 (2H, s), 3.03 (1H, brs), 2.73 (3H, s), 2.32-2.28 (2H, m), 1.91-1.87 (2H, m), 1.46 (6H, s).

EXAMPLE 238

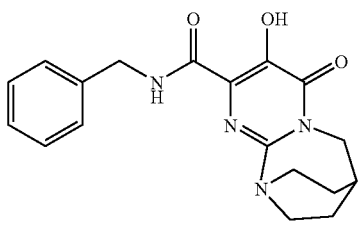

N-Benzyl-3-hydroxy-4-oxo-6,7,8,9-tetrahydro-4H-7,10-ethanopyrimido[1,2-a][1,3]diazepine-2-carboxamide. Pale yellow solid (3.3 mg, 14% yield). LCMS (M+H) calcd for C$_{18}$H$_{21}$N$_4$O$_3$: 341.16; found: 341.20. $^1$H NMR (500 MHz, CD$_3$OD) δ: 7.39-7.33 (5H, m), 7.29-7.27 (1H, m), 4.62 (2H, s), 4.00-3.94 (4H, m), 3.88 (2H, s), 3.10-3.08 (1H, m), 2.38-2.34 (2H, m), 2.02-1.97 (2H, m).

EXAMPLE 229

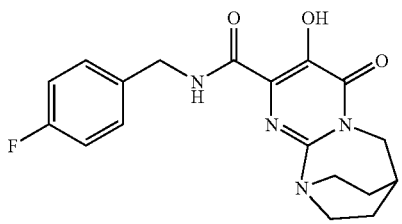

N-(4-Fluorobenzyl)-3-hydroxy-4-oxo-6,7,8,9-tetrahydro-4H-7,10-ethanopyrimido[1,2-a][1,3]diazepine-2-carboxamide. Pale yellow solid (2.1 mg, 9% yield). LCMS (M+H) calcd for C$_{18}$H$_{20}$FN$_4$O$_3$: 359.15; found: 359.20. $^1$H NMR (500 MHz, CD$_3$OD) δ: 7.42-7.39 (2H, m), 7.09-7.04 (3H, m), 4.59 (2H, s), 3.99-3.91 (4H, m), 3.86 (2H, s), 3.09-3.07 (1H, m), 2.38-2.33 (2H, m), 2.02-1.97 (2H, m).

EXAMPLE 230

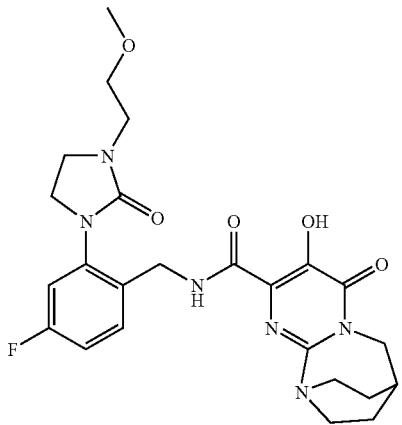

N-(4-Fluoro-2-(3-(2-methoxyethyl)-2-oxo-1-imidazolidinyl)benzyl)-3-hydroxy-4-oxo-6,7,8,9-tetrahydro-4H-7,10-ethanopyrimido[1,2-a][1,3]diazepine-2-carboxamide. Amber solid (2.1 mg, 6% yield). LCMS (M+H) calcd for C$_{24}$H$_{30}$FN$_6$O$_5$: 501.22; found: 501.33. $^1$H NMR (500 MHz, CD$_3$OD) δ: 7.54-7.51 (1H, m), 7.39 (1H, s), 4.56 (2H, s), 3.98-3.84 (8 H, m), 3.69 (2H, t, J=7.8 Hz), 3.58 (2H, t, J=5.3 Hz), 3.47-3.44 (2H, m), 3.38 (3H, s), 3.06-3.04 (1H, m), 2.36-2.29 (2H, m), 2.00-1.94 (2H, m).

EXAMPLE 231

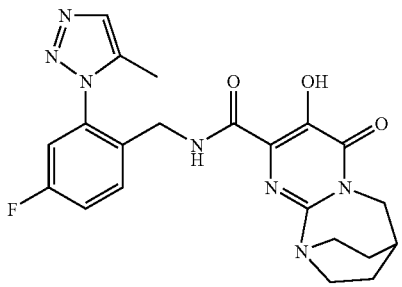

N-(4-Fluoro-2-(5-methyl-1H-1,2,3-triazol-1-yl)benzyl)-3-hydroxy-4-oxo-6,7,8,9-tetrahydro-4H-7,10-ethanopyrimido[1,2-a][1,3]diazepine-2-carboxamide. White solid (1.4 mg, 23% yield). LCMS (M+H) calcd for C$_{21}$H$_{23}$FN$_7$O$_3$: 440.18; found: 440.23. $^1$H NMR (500 MHz, CD$_3$OD) δ: 9.02 (1H, brs), 7.75 (1H, s), 7.74 (1H, t, J=7.2 Hz), 7.43 (1H, td, J=8.4, 2.6 Hz), 7.35 (1H, dd, J=8.5, 2.9 Hz), 4.33 (2H, s), 4.02 (4H, t, J=7.9 Hz), 3.14 (1H, t, J=4.3 Hz), 2.44-2.37 (2H, m), 2.33 (3H, s), 2.07-2.02 (2H, m).

EXAMPLE 232

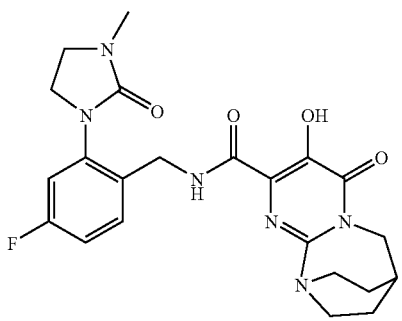

N-(4-Fluoro-2-(3-methyl-2-oxo-1-imidazolidinyl)benzyl)-3-hydroxy-4-oxo-6,7,8,9-tetrahydro-4H-7,10-ethanopyrimido[1,2-a][1,3]diazepine-2-carboxamide. Pale orange solid (2.0 mg, 40% yield). LCMS (M+H) calcd for C$_{22}$H$_{26}$FN$_6$O$_4$: 457.20; found: 457.24. $^1$H NMR (500 MHz, CD$_3$OD) δ: 9.30 (1H, brs), 7.52 (1H, dd, J=8.5, 6.4 Hz), 7.17 (1H, dd, J=9.8, 2.7 Hz), 7.09 (1H, td, J=8.3, 2.5 Hz), 4.58 (2H, s), 4.02-3.98 (4H, m), 3.92 (2H, s), 3.87 (2H, dd, J=8.8, 7.0 Hz), 3.61 (2H, t, J=7.9 Hz), 3.10 (1H, t, J=4.0 Hz), 2.87 (3H, s), 2.38-2.33 (2H, m), 2.04-1.98 (2H, m).

EXAMPLE 233

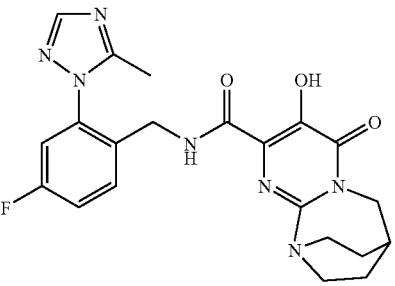

N-(4-Fluoro-2-(5-methyl-1H-1,2,4-triazol-1-yl)benzyl)-3-hydroxy-4-oxo-6,7,8,9-tetrahydro-4H-7,10-ethanopyrimido[1,2-a][1,3]diazepine-2-carboxamide. Pale orange solid (5.2 mg, 13% yield) LCMS (M+H) calcd for C$_{21}$H$_{23}$FN$_7$O$_3$: 440.18; found: 440.10. $^1$H NMR (500 MHz, CD$_3$OD) δ: 8.14 (1H, s), 7.70 (1H, dd, J=8.5, 5.8 Hz), 7.42-7.36 (2H, m), 4.41 (2H, s), 4.02 (4H, t, J=7.8 Hz), 3.93 (2H, m), 3.15 (1H, t, J=4.3 Hz), 2.44 (3H, s), 2.42-2.37 (2H, m), 2.08-2.03 (2H, m).

EXAMPLE 234

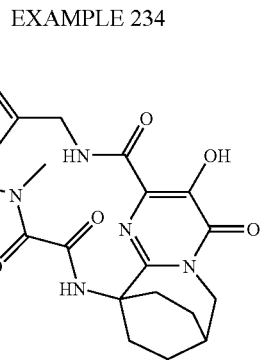

Ethanediamide, N,N-dimethyl-N'-[6,7,8,9-tetrahydro-3-hydroxy-2-[[[(1H-indol-3-ylmethyl)amino]carbonyl]-4-oxo-7,10-ethanopyrimido[1,2-a]azepin-10(4H)-yl]-. $^1$H NMR (500 MHz, DMSO-d$_6$) δ ppm 11.97 (1 H, s), 9.58 (1 H, t, J=6.10 Hz), 8.75 (1 H, s), 6.18 (1 H, d, J=3.05 Hz), 5.99 (1 H, d, J=2.14 Hz), 4.43 (2 H, d, J=6.10 Hz), 4.04 (2 H, d, J=3.66 Hz), 3.26-3.47 (3 H, m), 2.94 (3 H, s), 2.88 (3 H, s), 2.42 (1 H, brs), 2.25-2.34 (2 H, m), 2.04 (2 H, ddd, J=14.34, 9.16, 5.80 Hz), 1.73-1.86 (2 H, m), 1.55-1.66 (2 H, m). LCMS (M+H)+= 458.2.

EXAMPLE 235

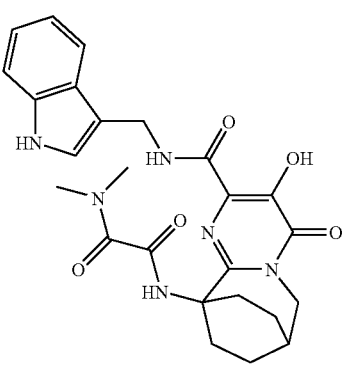

Ethanediamide, N,N-dimethyl-N'-[6,7,8,9-tetrahydro-3-hydroxy-2-[[[(1H-indol-3-ylmethyl)amino]carbonyl]-4-oxo- 7,10-ethanopyrimido[1,2-a]azepin-10(4H)-yl]-. ¹H NMR (500 MHz, DMSO-d₆) δ ppm 12.32 (1 H, s), 10.96 (1 H, brs), 9.61 (1H, t, J=6.26 Hz), 8.70 (1 H, s), 7.70 (1 H, d, J=7.93 Hz), 7.30-7.39 (2 H, m), 7.07 (1H, t, J=7.17 Hz), 6.98 (1 H, t, J=7.17 Hz), 4.65 (2 H, d, J=6.10 Hz), 3.99-4.07 (2 H, m), 2.88-2.94 (6 H, m), 2.39 (1 H, brs), 2.20-2.30 (2 H, m), 2.00 (2 H, ddd, J=14.27, 9.08, 5.65 Hz), 1.71-1.81 (2 H, m), 1.55-1.65 (2 H, m). LCMS (M+H)+=493.3.

EXAMPLE 236

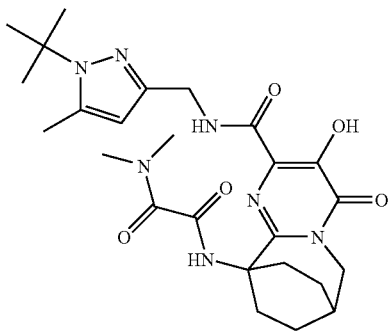

Ethanediamide, N'-[2-[[[[1-(1,1-dimethylethyl)-5-methyl-1H-pyrazol-3-yl]methyl]amino]carbonyl]-6,7,8,9-tetrahydro-3-hydroxy-4-oxo-7,10-ethanopyrimido[1,2-a]azepin-10(4H)-yl]-N,N-dimethyl-. ¹H NMR (500 MHz, DMSO-d₆) δ ppm 12.15 (1 H, brs), 9.51 (1 H, t, J=6.41 Hz), 8.74 (1 H, s), 5.98 (1 H, s), 4.36 (2 H, d, J=6.41 Hz), 4.04 (2 H, d, J=3.97 Hz), 2.94 (3 H, s), 2.87 (3 H, s), 2.42 (1 H, brs), 2.34-2.39 (3 H, m), 2.23-2.31 (2 H, m), 2.07 (2 H, ddd, J=14.19, 9.00, 5.49 Hz), 1.75-1.84 (2 H, m), 1.59-1.65 (2 H, m), 1.51-1.55 (9 H, m). LCMS (M+H)+=514.3.

EXAMPLE 237

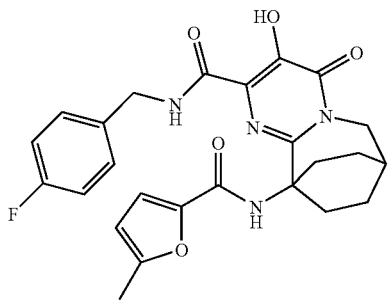

7,10-Ethanopyrimido[1,2-a]azepine-2-carboxamide, N-[(4-fluorophenyl)methyl]-4,6,7,8,9,10-hexahydro-3-hydroxy-10-[[(5-methyl-2-furanyl)carbonyl]amino]-4-oxo-. ¹H NMR (500 MHz, DMSO-d₆) δ ppm 11.84 (1 H, brs), 8.86 (1 H, t, J=6.26 Hz), 8.37 (1 H, s), 7.24-7.30 (2 H, m), 7.11-7.19 (2 H, m), 6.93 (1 H, d, J=3.36 Hz), 6.20 (1 H, d, J=2.44 Hz), 4.44 (2 H, d, J=6.41 Hz), 4.04 (2 H, d, J=3.66 Hz), 2.52-2.60 (2 H, m), 2.43 (1 H, brs), 2.17 (3 H, s), 2.03-2.11 (2H, m), 1.79-1.89 (2 H, m), 1.61-1.71 (2 H, m). LCMS (M+H)+=481.36.

EXAMPLE 238

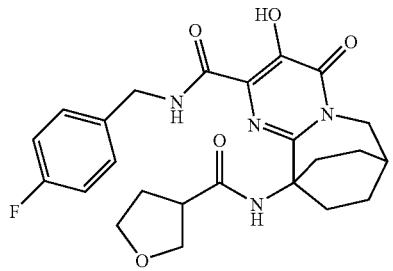

7,10-Ethanopyrimido[1,2-a]azepine-2-carboxamide, N-[(4-fluorophenyl)methyl]-4,6,7,8,9,10-hexahydro-3-hydroxy-4-oxo-10-[[(tetrahydro-3-furanyl)carbonyl]amino]-. ¹H NMR (500 MHz, DMSO-d₆) δ ppm 11.98 (1 H, brs), 8.92 (1 H, t, J=6.41 Hz), 8.04 (1 H, s), 7.33-7.43 (2 H, m), 7.15-7.21 (2 H, m), 4.44-4.60 (2 H, m), 4.01 (2 H, d, J=3.66 Hz), 3.68-3.75 (1 H, m), 3.60-3.67 (1 H, m), 3.52-3.59 (1 H, m), 2.98-3.10 (1 H, m), 2.39 (1 H, brs), 2.30-2.38 (2 H, m), 1.94-2.06 (2 H, m), 1.83-1.92 (2 H, m), 1.72-1.79 (2 H, m), 1.54-1.65 (2 H, m). LCMS (M+H)+=471.2.

EXAMPLE 239

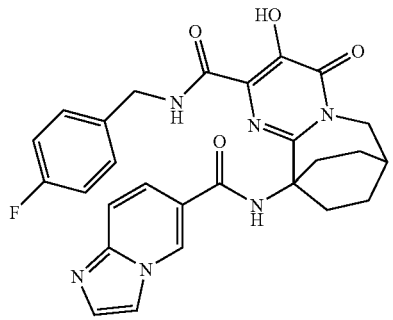

7,10-Ethanopyrimido[1,2-a]azepine-2-carboxamide, N-[(4-fluorophenyl)methyl]-4,6,7,8,9,10-hexahydro-3-hydroxy-10-[(imidazo[1,2-a]pyridin-6-ylcarbonyl)amino]-4-oxo-. ¹H NMR (500 MHz, DMSO-d₆) δ ppm 11.82 (1 H, brs), 9.41 (1 H, s), 8.79 (1 H, s), 8.66 (1 H, t, J=6.26 Hz), 8.26 (1 H, d, J=1.83 Hz), 8.20 (1H, s), 8.09 (1 H, d, J=9.46 Hz), 7.84 (1 H, d, J=9.46 Hz), 7.05 (2 H, dd, J=8.70, 5.65 Hz), 6.86-6.91 (2 H, m), 4.36 (2 H, d, J=6.41 Hz), 4.08 (2 H, d, J=3.66 Hz), 2.45-2.48 (1 H, m), 2.32-2.39 (2 H, m), 2.24-2.31 (2 H, m), 1.83-1.91 (2 H, m), 1.65-1.73 (2 H, m). LCMS (M+H)+=517.37.

EXAMPLE 240

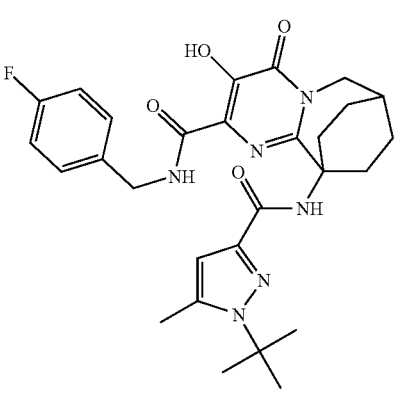

7,10-Ethanopyrimido[1,2-a]azepine-2-carboxamide, 10-[[[1-(1,1-dimethylethyl)-5-methyl-1H-pyrazol-3-yl]carbonyl]amino]-N-[(4-fluorophenyl)m. $^1$H NMR (500 MHz, DMSO-d$_6$) δ ppm 11.82 (1 H, brs), 8.78 (1 H, t, J=6.41 Hz), 8.56 (1H, s), 7.27 (2 H, dd, J=8.70, 5.65 Hz), 7.10-7.17 (2 H, m), 6.41 (1 H, s), 4.44 (2 H, d, J=6.41 Hz), 4.04 (2 H, d, J=3.66 Hz), 2.75 (2 H, ddd, J=14.04, 9.00, 5.65 Hz), 2.42-2.45 (1 H, m), 2.41 (3 H, s), 1.92-2.02 (2 H, m), 1.81-1.91 (2 H, m), 1.62-1.71 (2 H, m), 1.48-1.53 (9 H, m). LCMS (M+H)+= 537.3.

EXAMPLE 241

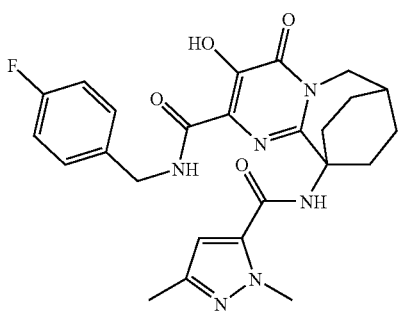

7,10-Ethanopyrimido[1,2-a]azepine-2-carboxamide, 10-[[[(1,3-dimethyl-1H-pyrazol-5-yl)carbonyl]amino]-N-[(4-fluorophenyl)methyl]-4,6,7,8,9,10-hexahydro-3-hydroxy-4-oxo-. $^1$H NMR (500 MHz, DMSO-d$_6$) δ ppm 8.64 (1 H, t, J=6.41 Hz), 8.32 (1 H, s), 7.16-7.21 (2 H, m), 7.09-7.15 (2 H, m), 6.57 (1 H, s), 4.40 (2 H, d, J=6.41 Hz), 4.05 (2 H, d, J=3.66 Hz), 3.83 (3 H, s), 2.44 (1 H, brs), 2.36 (2 H, ddd, J=14.19, 9.00, 5.80 Hz), 2.15-2.23 (2 H, m), 2.07 (3 H, s), 1.78-1.88 (2 H, m), 1.60-1.69 (2H, m). LCMS (M+H)+=495.3.

EXAMPLE 242

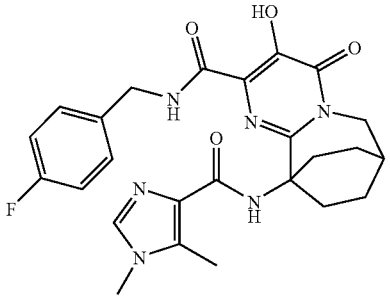

7,10-Ethanopyrimido[1,2-a]azepine-2-carboxamide, 10-[[[(1,5-dimethyl-1H-imidazol-4-yl)carbonyl]amino]-N-[(4-fluorophenyl)methyl]-4,6,7,8,9,10-hexahydro-3-hydroxy-4-oxo-. $^1$H NMR (500 MHz, DMSO-d$_6$) δ ppm 11.75 (1 H, brs), 9.23 (1 H, brs), 8.80 (1 H, t, J=6.10 Hz), 7.79 (1 H, brs), 7.37 (2 H, dd, J=8.70, 5.65 Hz), 7.19 (2 H, t, J=8.85 Hz), 4.55 (2 H, d, J=6.41 Hz), 4.04 (2 H, d, J=3.66 Hz), 3.55 (3 H, s), 2.69-2.80 (2 H, m), 2.43 (1 H, brs), 2.38 (3 H, s), 1.81-1.96 (4 H, m), 1.64-1.74 (2H, m). LCMS (M+H)+=495.3.

EXAMPLE 243

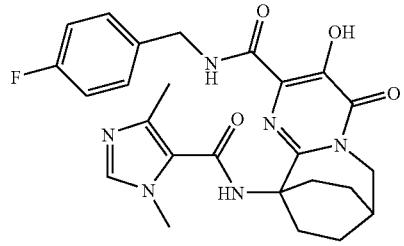

7,10-Ethanopyrimido[1,2-a]azepine-2-carboxamide, 10-[[[(1,4-dimethyl-1H-imidazol-5-yl)carbonyl]amino]-N-[(4-fluorophenyl)methyl]-4,6,7,8,9,10-hexahydro-3-hydroxy-4-oxo-. $^1$H NMR (500 MHz, CHLOROFORM-d) δ ppm 8.64 (1 H, brs), 8.31 (1 H, brs), 7.99 (1 H, brs), 7.23-7.31 (2 H, m), 6.98 (2 H, t, J=8.24 Hz), 4.50 (2H, d, J=6.10 Hz), 4.18 (2 H, d, J=3.36 Hz), 3.75 (3 H, s), 2.77-2.88 (2 H, m), 2.53 (1 H, brs), 2.41 (3 H, s), 1.97-2.09 (4 H, m), 1.69-1.79 (2 H, m). LCMS (M+H)+=495.3.

EXAMPLE 244

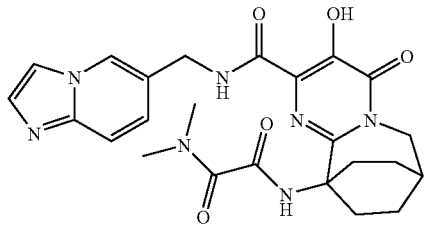

Ethanediamide, N,N-dimethyl-N'-[6,7,8,9-tetrahydro-3-hydroxy-2-[[(imidazo[1,2-a]pyridin-6-ylmethyl)amino]carbonyl]-4-oxo-7,10-ethanopyrimido[1,2-a]azepin-10(4H)-yl]-. $^1$H NMR (500 MHz, DMSO-d$_6$) δ ppm 11.70 (1 H, brs), 9.85 (1 H, t, J=6.26 Hz), 8.89 (1 H, s), 8.75 (1 H, s), 8.37 (1 H, d, J=1.53 Hz), 8.18 (1 H, d, J=1.83 Hz), 7.96-8.00 (1 H, m), 7.91-7.94 (1 H, m), 4.65 (2 H, d, J=6.41 Hz), 4.05 (3 H, d, J=3.97 Hz), 2.95 (3 H, s), 2.82 (3 H, s), 2.43 (1 H, brs), 2.25-2.34 (2 H, m), 2.00-2.09 (2 H, m), 1.75-1.85 (2 H, m), 1.57-1.67 (2 H, m). LCMS (M+H)+=494.3.

EXAMPLE 245

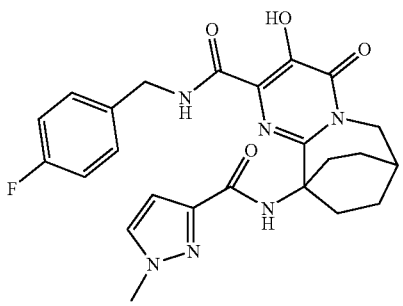

7,10-Ethanopyrimido[1,2-a]azepine-2-carboxamide, N-[(4-fluorophenyl)methyl]-4,6,7,8,9,10-hexahydro-3-hydroxy-10-[[(1-methyl-1H-pyrazol-3-yl)carbonyl]amino]-4-oxo-. $^1$H NMR (500 MHz, DMSO-d$_6$) δ ppm 11.77 (1 H, brs), 8.69 (1 H, s), 8.47 (1 H, t, J=6.56 Hz), 7.73 (1 H, d, J=2.14 Hz), 7.28 (2 H, dd, J=8.55, 5.49 Hz), 7.10-7.21 (2 H, m), 6.56 (1 H, d, J=2.14 Hz), 4.53 (2 H, d, J=6.71 Hz), 4.06 (2 H, d, J=3.66 Hz), 3.67 (3 H, s), 2.66 (2 H, ddd, J=14.19, 9.16, 5.65 Hz), 2.41-2.47 (1 H, m), 1.98-2.08 (2 H, m), 1.79-1.92 (2 H, m), 1.62-1.74 (2 H, m). LCMS (M+H)+=481.28.

EXAMPLE 246

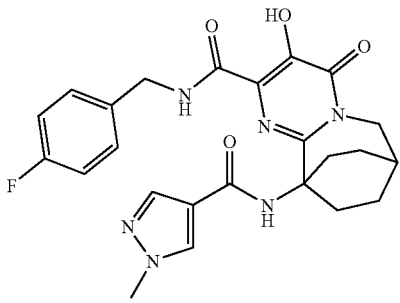

7,10-Ethanopyrimido[1,2-a]azepine-2-carboxamide, N-[(4-fluorophenyl)methyl]-4,6,7,8,9,10-hexahydro-3-hydroxy-10-[[(1-methyl-1H-pyrazol-4-yl)carbonyl]amino]-4-oxo-. $^1$H NMR (500 MHz, DMSO-$d_6$) δ ppm 11.62 (1 H, brs), 8.56 (1 H, t, J=6.26 Hz), 8.08 (1 H, s), 7.96 (1 H, s), 7.80 (1 H, s), 7.09-7.19 (4H, m), 4.36 (2 H, d, J=6.41 Hz), 4.04 (2 H, d, J=3.66 Hz), 3.79 (3 H, s), 2.43 (1 H, brs), 2.33 (2 H, ddd, J=14.34, 9.00, 5.95 Hz), 2.20 (2 H, ddd, J=13.96, 7.32, 7.10 Hz), 1.77-1.86 (2 H, m), 1.59-1.68 (2 H, m). LCMS (M+H)+=481.28.

EXAMPLE 247

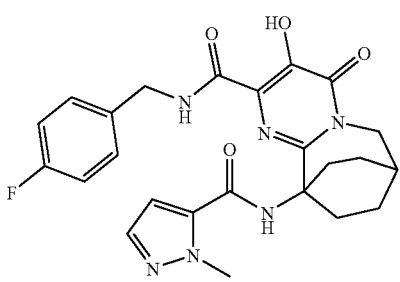

7,10-Ethanopyrimido[1,2-a]azepine-2-carboxamide, N-[(4-fluorophenyl)methyl]-4,6,7,8,9,10-hexahydro-3-hydroxy-10-[[(1-methyl-1H-pyrazol-5-yl)carbonyl]amino]-4-oxo-. $^1$H NMR (500 MHz, DMSO-$d_6$) δ ppm 11.72 (1 H, brs), 8.66 (1 H, t, J=6.26 Hz), 8.41 (1 H, s), 7.39-7.43 (1 H, m), 7.17-7.23 (2 H, m), 7.10-7.17 (2 H, m), 6.76 (1 H, d, J=2.14 Hz), 4.38 (2 H, d, J=6.41 Hz), 4.05 (2H, d, J=3.66 Hz), 3.90 (3 H, s), 2.36-2.48 (3 H, m), 2.14-2.22 (2 H, m), 1.84 (2 H, td, J=14.19, 5.80 Hz), 1.59-1.71 (2 H, m). LCMS (M+H)+=481.28.

EXAMPLE 248

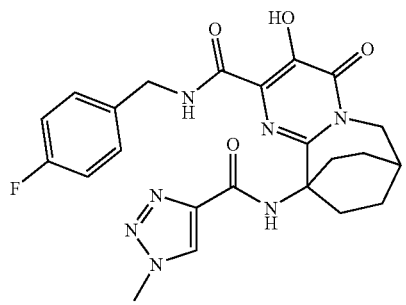

7,10-Ethanopyrimido[1,2-a]azepine-2-carboxamide, N-[(4-fluorophenyl)methyl]-4,6,7,8,9,10-hexahydro-3-hydroxy-10-[[(1-methyl-1H-1,2,3-triazol-4-yl)carbonyl]amino]-4-oxo-. $^1$H NMR (500 MHz, DMSO-$d_6$) δ ppm 11.65 (1H, brs), 9.20 (1 H, s), 8.71 (1 H, t, J=6.56 Hz), 8.51 (1 H, s), 7.34-7.42 (2 H, m), 7.12-7.19 (2 H, m), 4.48 (2 H, d, J=6.41 Hz), 4.10 (3 H, s), 4.05 (2 H, d, J=3.66 Hz), 2.60-2.68 (2 H, m), 2.42-2.47 (1 H, m), 2.03-2.12 (2 H, m), 1.82-1.93 (2 H, m), 1.69 (2 H, dd, J=7.32, 6.10 Hz). LCMS (M+H)+=482.27.

EXAMPLE 249

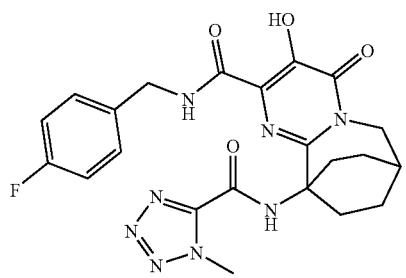

7,10-Ethanopyrimido[1,2-a]azepine-2-carboxamide, N-[(4-fluorophenyl)methyl]-4,6,7,8,9,10-hexahydro-3-hydroxy-10-[[(1-methyl-1H-tetrazol-5-yl)carbonyl]amino]-4-oxo-. $^1$H NMR (500 MHz, CHLOROFORM-d) δ ppm 12.12 (1 H, brs), 10.12 (1 H, s), 8.26-8.33 (1 H, m), 7.50-7.55 (2 H, m), 7.00-7.06 (2 H, m), 4.68 (2 H, d, J=6.41 Hz), 4.38 (3 H, s), 4.18 (2 H, d, J=3.97 Hz), 2.95-3.04 (2H, m), 2.50-2.56 (1 H, m), 2.03-2.12 (2 H, m), 1.87-1.97 (2 H, m), 1.74-1.84 (2H, m). LCMS (M+H)+=483.3.

EXAMPLE 250

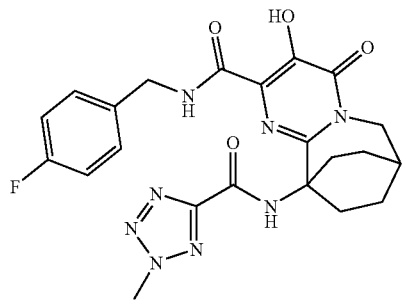

7,10-Ethanopyrimido[1,2-a]azepine-2-carboxamide, N-[(4-fluorophenyl)methyl]-4,6,7,8,9,10-hexahydro-3-hydroxy-10-[[(2-methyl-2H-tetrazol-5-yl)carbonyl]amino]-4-oxo-. ¹H NMR (500 MHz, DMSO-d₆) δ ppm 11.83 (1 H, s), 9.26 (1 H, s), 8.87 (1 H, t, J=6.26 Hz), 7.32-7.38 (2 H, m), 7.13-7.20 (2 H, m), 4.47 (2 H, d, J=6.41 Hz), 4.38 (3 H, s), 4.06 (2 H, d, J=3.66 Hz), 2.59 (2 H, td, J=9.38, 4.73 Hz), 2.54-2.55 (1 H, m), 2.08-2.17 (2 H, m), 1.83-1.92 (2 H, m), 1.65-1.74 (2 H, m). LCMS (M+H)+=483.3.

EXAMPLE 251

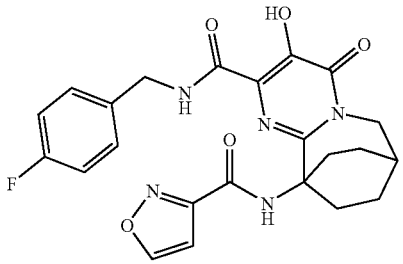

7,10-Ethanopyrimido[1,2-a]azepine-2-carboxamide, N-[(4-fluorophenyl)methyl]-4,6,7,8,9,10-hexahydro-10-[(3-isoxazolylcarbonyl)amino]-3-methoxy-4-oxo-. ¹H NMR (500 MHz, DMSO-d₆) δ ppm 11.75 (1 H, s), 9.08 (1 H, d, J=1.53 Hz), 8.96 (1 H, s), 8.80 (1 H, t, J=6.41 Hz), 7.29-7.34 (2 H, m), 7.13-7.19 (2 H, m), 6.83 (1 H, d, J=1.83 Hz), 4.45 (2 H, d, J=6.71 Hz), 4.05 (2 H, d, J=3.66 Hz), 2.40-2.48 (3 H, m), 2.14-2.22 (2 H, m), 1.84 (2 H, td, J=14.11, 5.34 Hz), 1.63-1.71 (2 H, m). LCMS (M+H)+=486.29.

EXAMPLE 252

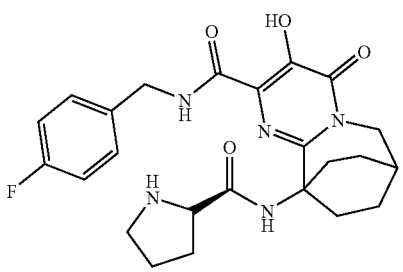

7,10-Ethanopyrimido[1,2-a]azepine-2-carboxamide, N-[(4-fluorophenyl)methyl]-4,6,7,8,9,10-hexahydro-3-hydroxy-4-oxo-10-[[(2R)-2-pyrrolidinylcarbonyl]amino]-. ¹H NMR (500 MHz, DMSO-d₆) δ ppm 11.95 (1 H, s), 9.16 (1 H, d, J=5.49 Hz), 9.02 (1 H, t, J=6.26 Hz), 8.53 (1 H, s), 7.36-7.43 (2 H, m), 7.15-7.22 (2 H, m), 4.63 (1 H, dd, J=14.80, 6.87 Hz), 4.43 (1 H, dd, J=14.95, 5.49 Hz), 4.26-4.34 (1 H, m), 3.98-4.10 (2 H, m), 3.14-3.23 (2 H, m), 2.41-2.45 (1 H, m), 2.29-2.40 (2 H, m), 2.07-2.16 (2 H, m), 1.99-2.07 (1 H, m), 1.72-1.86 (5 H, m), 1.58-1.69 (2 H, m). LCMS (M+H)+=470.3.

EXAMPLE 253

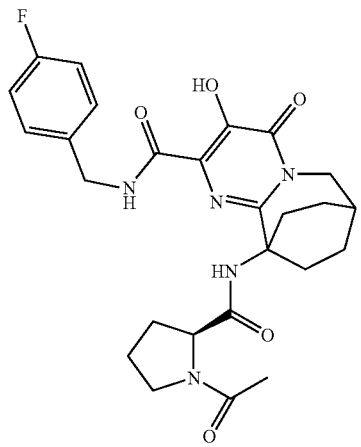

7,10-Ethanopyrimido[1,2-a]azepine-2-carboxamide, 10-[[[(2R)-1-acetyl-2-pyrrolidinyl]carbonyl]amino]-N-[(4-fluorophenyl)methyl]-4,6,7,8,9,10-hexahydro-3-hydroxy-4-oxo-. ¹H NMR (500 MHz, CHLOROFORM-d) δ ppm 10.10 (1 H, brs), 9.24 (1 H, s), 7.33-7.39 (2 H, m), 6.97-7.04 (2 H, m), 4.65-4.72 (2 H, m), 4.55 (1H, dd, J=14.65, 6.10 Hz), 4.23 (1 H, dd, J=15.26, 3.05 Hz), 4.08 (1 H, dd, J=15.26, 1.83 Hz), 3.48-3.54 (1 H, m), 3.39 (1 H, td, J=10.07, 7.02 Hz), 2.92-3.01 (2 H, m), 2.53 (1 H, dd, J=12.51, 6.41 Hz), 2.44 (1 H, brs), 2.07-2.19 (1 H, m), 1.91-2.06 (3H, m), 1.88 (3 H, s), 1.66-1.80 (3 H, m), 1.56-1.66 (2 H, m). LCMS (M+H)+= 512.55.

EXAMPLE 254

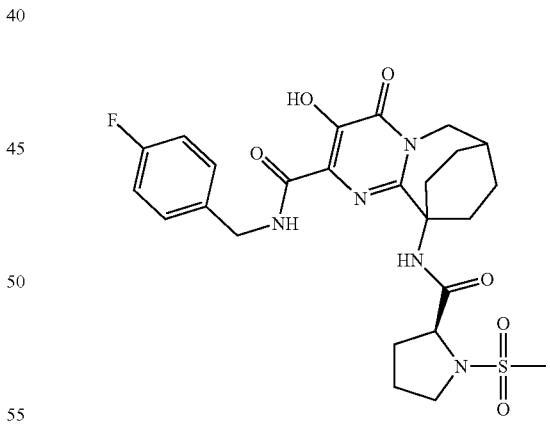

7,10-Ethanopyrimido[1,2-a]azepine-2-carboxamide, N-[(4-fluorophenyl)methyl]-4,6,7,8,9,10-hexahydro-3-hydroxy-10-[[[(2R)-1-(methylsulfonyl)-2-pyrrolidinyl]carbonyl]amino]-4-oxo-. ¹H NMR (500 MHz, CHLOROFORM-d) δ ppm 8.65 (1 H, s), 8.37 (1 H, t, J=6.41 Hz), 7.37 (2 H, dd, J=8.55, 5.19 Hz), 6.98-7.03 (2 H, m), 4.61 (2 H, d, J=6.41 Hz), 4.25 (1 H, dd, J=15.26, 3.05 Hz), 4.13 (1 H, dd, J=8.70, 3.20 Hz), 4.08 (1 H, dd, J=15.41, 1.98 Hz), 3.38 (1 H, ddd, J=10.61, 6.94, 4.12 Hz), 3.22 (1 H, td, J=9.46, 7.02 Hz), 2.96 (1 H, ddd, J=14.04, 9.61, 6.87 Hz), 2.80-2.87 (1 H, m), 2.79

EXAMPLE 255

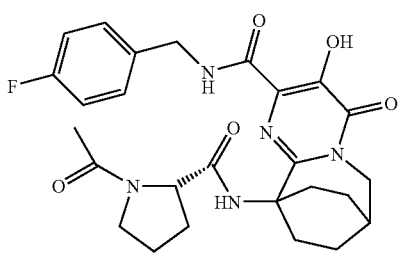

7,10-Ethanopyrimido[1,2-a]azepine-2-carboxamide, 10-[[[(2S)-1-acetyl-2-pyrrolidinyl]carbonyl]amino]-N-[(4-fluorophenyl)methyl]-4,6,7,8,9,10-hexahydro-3-hydroxy-4-oxo-. $^1$H NMR (500 MHz, CHLOROFORM-d) δ ppm 10.10 (1 H, brs), 9.24 (1 H, s), 7.33-7.39 (2 H, m), 6.97-7.04 (2 H, m), 4.65-4.72 (2 H, m), 4.55 (1H, dd, J=14.65, 6.10 Hz), 4.23 (1 H, dd, J=15.26, 3.05 Hz), 4.08 (1 H, dd, J=15.26, 1.83 Hz), 3.48-3.54 (1 H, m), 3.39 (1 H, td, J=10.07, 7.02 Hz), 2.92-3.01 (2 H, m), 2.53 (1 H, dd, J=12.51, 6.41 Hz), 2.44 (1 H, brs), 2.07-2.19 (1 H, m), 1.91-2.06 (3H, m), 1.88 (3 H, s), 1.66-1.80 (3 H, m), 1.56-1.66 (2 H, m). LCMS (M+H)+=512.55.

EXAMPLE 256

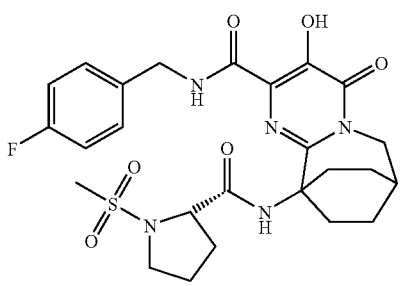

7,10-Ethanopyrimido[1,2-a]azepine-2-carboxamide, N-[(4-fluorophenyl)methyl]-4,6,7,8,9,10-hexahydro-3-hydroxy-10-[[[(2S)-1-(methylsulfonyl)-2-pyrrolidinyl]carbonyl]amino]-4-oxo-. $^1$H NMR (500 MHz, CHLOROFORM-d) δ ppm 8.65 (1 H, s), 8.37 (1 H, t, J=6.41 Hz), 7.37 (2 H, dd, J=8.55, 5.19 Hz), 6.98-7.03 (2 H, m), 4.61 (2 H, d, J=6.41 Hz), 4.25 (1 H, dd, J=15.26, 3.05 Hz), 4.13 (1 H, dd, J=8.70, 3.20 Hz), 4.08 (1 H, dd, J=15.41, 1.98 Hz), 3.38 (1 H, ddd, J=10.61, 6.94, 4.12 Hz), 3.22 (1 H, td, J=9.46, 7.02 Hz), 2.96 (1 H, dd, J=14.04, 9.61, 6.87 Hz), 2.80-2.87 (1 H, m), 2.79 (3 H, s), 2.47 (1 H, brs), 2.35-2.41 (1 H, m), 1.75-2.10 (7 H, m), 1.68-1.75 (1 H, m), 1.58-1.66 (1 H, m). LCMS (M+H)+=548.60.

EXAMPLE 257

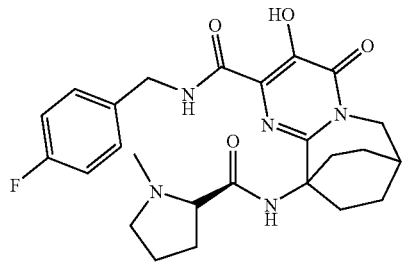

7,10-Ethanopyrimido[1,2-a]azepine-2-carboxamide, N-[(4-fluorophenyl)methyl]-4,6,7,8,9,10-hexahydro-3-hydroxy-10-[[[(2R)-1-methyl-2-pyrrolidinyl]carbonyl]amino]-4-oxo-. $^1$H NMR (500 MHz, DMSO-d$_6$) δ ppm 11.86 (1 H, brs), 9.49 (1 H, brs), 8.92 (1 H, t, J=6.26 Hz), 8.76 (1 H, s), 7.38 (2 H, dd, J=8.55, 5.49 Hz), 7.19 (2 H, t, J=8.85 Hz), 4.53-4.60 (1 H, m), 4.45 (1 H, dd, J=14.80, 5.95 Hz), 4.13 (1 H, q, J=8.14 Hz), 3.98-4.09 (2 H, m), 3.50 (1 H, d, J=3.36 Hz), 3.05-3.13 (1 H, m), 2.67 (3 H, s), 2.43 (1 H, brs), 2.28-2.38 (1 H, m), 2.10-2.26 (4 H, m), 1.89-1.99 (1 H, m), 1.70-1.85 (4 H, m), 1.58-1.67 (2 H, m). LCMS (M+H)+=484.32.

EXAMPLE 258

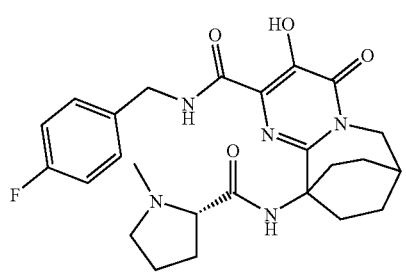

7,10-Ethanopyrimido[1,2-a]azepine-2-carboxamide, N-[(4-fluorophenyl)methyl]-4,6,7,8,9,10-hexahydro-3-hydroxy-10-[[[(2S)-1-methyl-2-pyrrolidinyl]carbonyl]amino]-4-oxo-. $^1$H NMR (500 MHz, DMSO-d$_6$) δ ppm 11.86 (1 H, brs), 9.49 (1 H, brs), 8.92 (1 H, t, J=6.26 Hz), 8.76 (1 H, s), 7.38 (2 H, dd, J=8.55, 5.49 Hz), 7.19 (2 H, t, J=8.85 Hz), 4.53-4.60 (1 H, m), 4.45 (1 H, dd, J=14.80, 5.95 Hz), 4.13 (1 H, q, J=8.14 Hz), 3.98-4.09 (2 H, m), 3.50 (1 H, d, J=3.36 Hz), 3.05-3.13 (1 H, m), 2.67 (3 H, s), 2.43 (1 H, brs), 2.28-2.38 (1 H, m), 2.10-2.26 (4 H, m), 1.89-1.99 (1 H, m), 1.70-1.85 (4 H, m), 1.58-1.67 (2 H, m). LCMS (M+H)+=484.32.

EXAMPLE 259

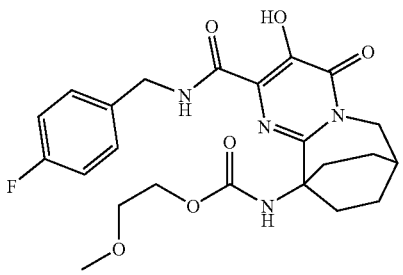

Carbamic acid, [2-[[[(4-fluorophenyl)methyl]amino-0] carbonyl]-6,7,8,9-tetrahydro-3-hydroxy-4-oxo-7,10-ethanopyrimido[1,2-a]azepin-10(4H)-yl]-, 2-methoxyethyl ester. $^1$H NMR (500 MHz, CHLOROFORM-d) δ ppm 7.76 (1 H, brs), 7.31 (2 H, d, J=17.70 Hz), 7.04 (2 H, t, J=8.55 Hz), 4.58 (2 H, d, J=5.80 Hz), 4.15 (2H, d, J=3.66 Hz), 3.98-4.02 (2 H, m), 3.45 (2 H, brs), 3.34 (3 H, brs), 2.48 (1 H, brs), 2.01-2.09 (2 H, m), 1.86-1.97 (4 H, m), 1.64-1.72 (2 H, m). LCMS (M+H)+=475.33.

EXAMPLE 260

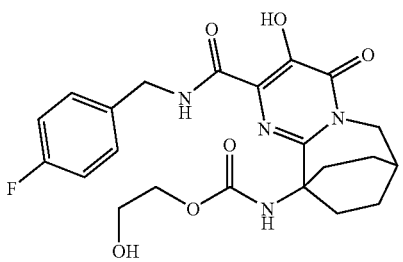

Carbamic acid, [2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-, 2-hydroxyethyl ester. $^1$H NMR (500 MHz, CHLOROFORM-d) δ ppm 7.72 (1 H, brs), 7.29-7.35 (2 H, m), 7.05 (2 H, t, J=8.55 Hz), 4.58 (2 H, d, J=5.19 Hz), 4.16 (2 H, d, J=3.66 Hz), 3.98-4.02 (2 H, m), 3.67 (2 H, brs), 2.49 (1 H, brs), 2.03-2.09 (4 H, m), 1.88-1.97 (2 H, m), 1.64-1.73 (2 H, m). LCMS (M+H)+=461.29.

EXAMPLE 261

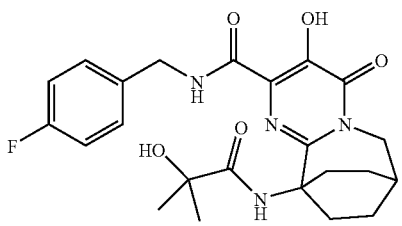

7,10-Ethanopyrimido[1,2-a]azepine-2-carboxamide, N-[(4-fluorophenyl)methyl]-4,6,7,8,9,10-hexahydro-3-hydroxy-10-[(2-hydroxy-2-methyl-1-oxopropyl)amino]-4-oxo-. $^1$H NMR (500 MHz, DMSO-d$_6$) δ ppm 11.80 (1 H, brs), 8.73 (1 H, s), 8.61 (1 H, t, J=6.41 Hz), 7.39 (2 H, dd, J=8.55, 5.49 Hz), 7.14-7.21 (2H, m), 5.70 (1 H, brs), 4.51 (2 H, d, J=6.41 Hz), 4.02 (2 H, d, J=3.66 Hz), 2.56-2.65 (2 H, m), 2.41 (1 H, brs), 1.77-1.91 (4 H, m), 1.61-1.71 (2 H, m), 1.21-1.26 (6 H, m). LCMS (M+H)+=459.5.

EXAMPLE 262

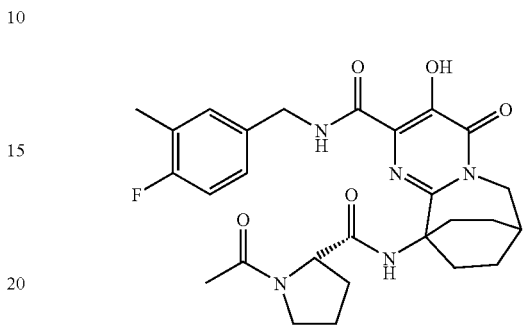

7,10-Ethanopyrimido[1,2-a]azepine-2-carboxamide, 10-[[[(2S)-1-acetyl-2-pyrrolidinyl]carbonyl]amino]-N-[(4-fluoro-3-methylphenyl)methyl]-4,6,7,8,9,10-hexahydro-3-hydroxy-4-oxo-. $^1$H NMR (500 MHz, DMSO-d$_6$) δ ppm 12.50 (1 H, brs), 9.89 (1 H, t, J=6.41 Hz), 8.68 (1 H, s), 7.25 (1 H, d, J=7.32 Hz), 7.17-7.22 (1H, m), 7.07-7.12 (1 H, m), 4.49-4.55 (3 H, m), 3.96-4.07 (2 H, m), 3.48-3.54 (1H, m), 3.41-3.47 (1 H, m), 2.40-2.48 (2 H, m), 2.38 (1 H, brs), 2.21 (3 H, s), 2.07-2.13 (1 H, m), 1.92 (3 H, s), 1.85-1.90 (3 H, m), 1.73-1.82 (3 H, m), 1.55-1.64 (2H, m). LCMS (M+H)+= 526.2.

EXAMPLE 263

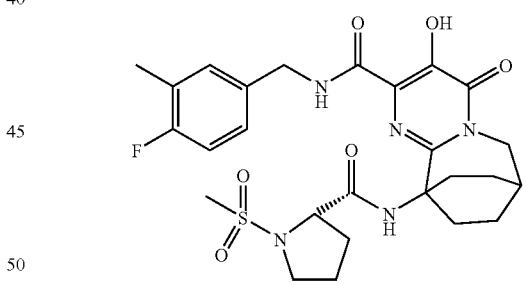

7,10-Ethanopyrimido[1,2-a]azepine-2-carboxamide, N-[(4-fluoro-3-methylphenyl)methyl]-4,6,7,8,9,10-hexahydro-3-hydroxy-10-[[[(2S)-1-(methylsulfonyl)-2-pyrrolidinyl]carbonyl]amino]-4-oxo-. $^1$H NMR (500 MHz, DMSO-d$_6$) δ ppm 12.34 (1 H, brs), 8.62 (1 H, t, J=6.41 Hz), 8.43 (1 H, s), 7.25 (1 H, d, J=7.63 Hz), 7.16-7.21 (1 H, m), 7.09 (1 H, t, J=9.00 Hz), 4.49-4.55 (1 H, m), 4.43-4.48 (1 H, m), 4.29 (1 H, t, J=5.95 Hz), 4.09 (1 H, dd, J=15.26, 3.66 Hz), 3.95 (1 H, dd, J=15.11, 2.59 Hz), 3.32-3.42 (1 H, m), 3.26-3.32 (1 H, m), 3.02 (3 H, s), 2.57-2.65 (1 H, m), 2.36-2.42 (1 H, m), 2.21 (3 H, s), 2.00-2.06 (2 H, m), 1.88-1.97 (2 H, m), 1.70-1.86 (5 H, m), 1.56-1.68 (2 H, m). LCMS (M+H)+=562.2.

EXAMPLE 264

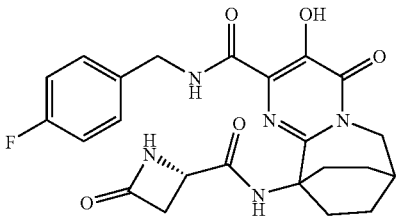

7,10-Ethanopyrimido[1,2-a]azepine-2-carboxamide, N-[(4-fluorophenyl)methyl]-4,6,7,8,9,10-hexahydro-3-hydroxy-4-oxo-10-[[[(2S)-4-oxo-2-azetidinyl]carbonyl]amino]-. $^1$H NMR (500 MHz, DMSO-d$_6$) δ ppm 12.04 (1 H, brs), 8.96-9.05 (1 H, m), 8.28 (1 H, s), 8.19 (1 H, s), 7.37-7.43 (2 H, m), 7.14-7.21 (2H, m), 4.51-4.55 (2 H, m), 4.10 (1 H, dd, J=5.49, 2.44 Hz), 4.00-4.04 (2 H, m), 3.02-3.08 (1 H, m), 2.83 (1 H, dd, J=17.55, 6.26 Hz), 2.63-2.72 (1 H, m), 2.35-2.43 (2 H, m), 1.97 (2 H, dd, J=13.58, 5.34 Hz), 1.75-1.84 (2 H, m), 1.58-1.68 (2H, m). LCMS (M+H)+=470.1.

EXAMPLE 265

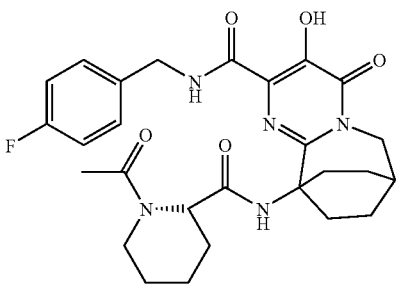

7,10-Ethanopyrimido[1,2-a]azepine-2-carboxamide, 10-[[[(2S)-1-acetyl-2-piperidinyl]carbonyl]amino]-N-[(4-fluorophenyl)methyl]-4,6,7,8,9,10-hexahydro-3-hydroxy-4-oxo-. $^1$H NMR (500 MHz, DMSO-d$_6$) δ ppm 12.44 (1 H, brs), 9.47 (1 H, t, J=6.41 Hz), 8.27 (1 H, s), 7.37-7.43 (2 H, m), 7.14-7.20 (2 H, m), 5.09 (1 H, d, J=4.58 Hz), 4.61-4.67 (1 H, m), 4.52-4.59 (1 H, m), 4.05-4.11 (1 H, m), 3.94-3.99 (1 H, m), 3.75-3.72 (1 h, m), 3.05 (1 H, td, J=12.97, 2.75 Hz), 2.57-2.65 (1 H, m), 2.45-2.48 (1 H, m), 2.36-2.41 (1 H, m), 1.97-2.02 (1 H, m), 1.96 (3 H, s), 1.88-1.94 (1 H, m), 1.73-1.86 (3 H, m), 1.58-1.66 (3 H, m), 1.53-1.58 (2 H, m), 1.38-1.47 (2 H, m). LCMS (M+H)+=526.4.

EXAMPLE 266

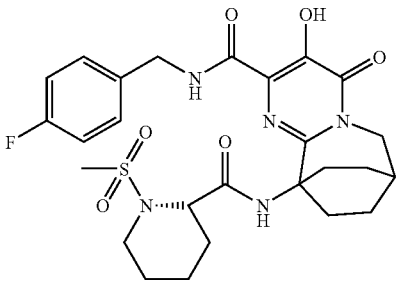

7,10-Ethanopyrimido[1,2-a]azepine-2-carboxamide, N-[(4-fluorophenyl)methyl]-4,6,7,8,9,10-hexahydro-3-hydroxy-10-[[[(2S)-1-(methylsulfonyl)-2-piperidinyl]carbonyl]amino]-4-oxo-. $^1$H NMR (500 MHz, DMSO-d$_6$) δ ppm 12.24 (1 H, brs), 8.79 (1 H, t, J=6.41 Hz), 8.30 (1 H, s), 7.36-7.41 (2 H, m), 7.15-7.20 (2 H, m), 4.68 (1 H, dd, J=14.80, 7.48 Hz), 4.62 (1 H, d, J=4.58 Hz), 4.40 (1 H, dd, J=14.80, 5.34 Hz), 4.13 (1 H, dd, J=15.11, 3.81 Hz), 3.93 (1 H, dd, J=15.11, 2.59 Hz), 3.54-3.59 (1 H, m), 3.22 (1 H, td, J=12.82, 2.75 Hz), 2.95 (3 H, s), 2.54-2.57 (1 H, m), 2.38-2.48 (2 H, m), 1.99-2.14 (2 H, m), 1.74-1.83 (3 H, m), 1.53-1.69 (5 H, m), 1.37-1.47 (1 H, m), 1.23-1.33 (1 H, m). LCMS (M+H)+=562.5.

EXAMPLE 267

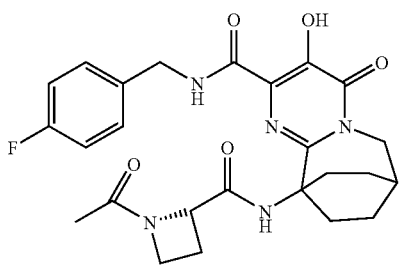

7,10-Ethanopyrimido[1,2-a]azepine-2-carboxamide, 10-[[[(2S)-1-acetyl-2-azetidinyl]carbonyl]amino]-N-[(4-fluorophenyl)methyl]-4,6,7,8,9,10-hexahydro-3-hydroxy-4-oxo-. $^1$H NMR (500 MHz, DMSO-d$_6$) δ ppm 12.66 (1 H, brs), 10.04 (1 H, t, J=6.26 Hz), 8.99 (1 H, s), 7.38 (2 H, dd, J=8.70, 5.65 Hz), 7.14-7.21 (2 H, m), 4.80 (1 H, dd, J=9.31, 6.26 Hz), 4.56-4.63 (1 H, m), 4.50-4.56 (1 H, m), 4.03-4.10 (2 H, m), 3.96-4.02 (2 H, m), 2.72-2.80 (1 H, m), 2.66-2.72 (1 H, m), 2.36-2.43 (2 H, m), 2.24-2.33 (1 H, m), 1.75-1.85 (4 H, m), 1.74 (3 H, s), 1.58-1.67 (2H, m). LCMS (M+H)+=498.4.

EXAMPLE 268

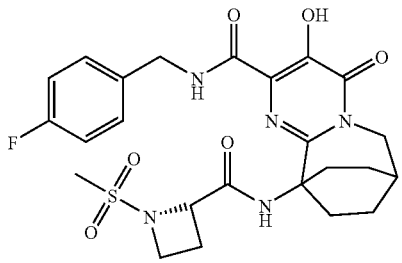

7,10-Ethanopyrimido[1,2-a]azepine-2-carboxamide, N-[(4-fluorophenyl)methyl]-4,6,7,8,9,10-hexahydro-3-hydroxy-10-[[[(2S)-1-(methylsulfonyl)-2-azetidinyl]carbonyl]amino]-4-oxo-. $^1$H NMR (500 MHz, DMSO-d$_6$) δ ppm 12.35 (1 H, brs), 8.78 (1 H, t, J=6.41 Hz), 8.51 (1 H, s), 7.38 (2 H, dd, J=8.55, 5.80 Hz), 7.16 (2 H, t, J=8.85 Hz), 4.81 (1 H, dd, J=9.77, 7.63 Hz), 4.57 (1H, dd, J=14.65, 7.02 Hz), 4.44 (1 H, dd, J=14.80, 5.95 Hz), 4.12 (1 H, dd, J=14.95, 3.66 Hz), 3.97-4.02 (1 H, m), 3.91-3.97 (1 H, m), 3.67 (1 H, td, J=8.62, 4.73 Hz), 3.21 (3 H, s), 2.75 (1 H, ddd, J=13.20, 9.23, 6.87 Hz), 2.63 (1 H, ddd, J=13.73, 9.31, 4.12 Hz), 2.38-2.48 (2 H, m), 2.19-2.28 (1 H, m), 1.93-2.02 (1 H, m), 1.76-1.85 (2 H, m), 1.65-1.75 (2 H, m), 1.57-1.64 (1 H, m). LCMS (M+H)+=534.5.

EXAMPLE 269

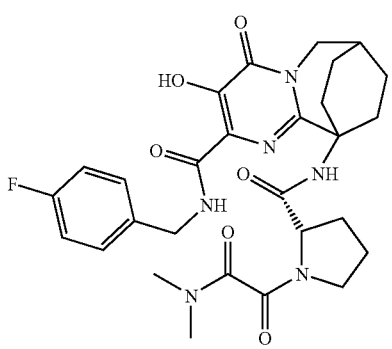

7,10-Ethanopyrimido[1,2-a]azepine-2-carboxamide, 10-[[[(2S)-1-[2-(dimethylamino)-1,2-dioxoethyl]-2-pyrrolidinyl]carbonyl]amino]-N-[(4-fluorophenyl)methyl]-4,6,7,8,9,10-hexahydro-3-hydroxy-4-oxo-. $^1$H NMR (500 MHz, DMSO-$d_6$) δ ppm 12.29 (1 H, brs), 9.31 (1 H, t, J=6.41 Hz), 8.44 (1 H, s), 7.33 (2 H, dd, J=8.55, 5.49 Hz), 7.15 (2 H, t, J=8.85 Hz), 4.54-4.63 (2 H, m), 4.37 (1 H, dd, J=14.65, 6.10 Hz), 4.17 (1 H, dd, J=15.11, 4.12 Hz), 3.86-3.92 (1 H, m), 3.33-3.42 (2 H, m), 2.84 (3 H, s), 2.79-2.82 (3 H, m), 2.36-2.41 (1 H, m), 2.13-2.33 (3 H, m), 1.99-2.07 (1 H, m), 1.92-1.99 (1 H, m), 1.82-1.93 (3 H, m), 1.70-1.82 (2 H, m), 1.53-1.66 (2 H, m). LCMS (M+H)+=569.2.

EXAMPLE 270

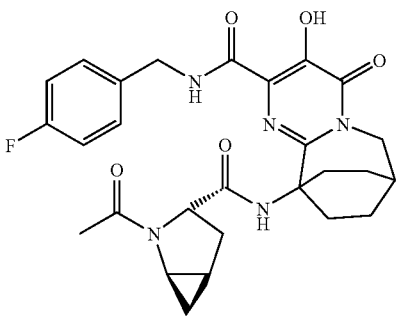

7,10-Ethanopyrimido[1,2-a]azepine-2-carboxamide, 10-[[[(1R,3S,5R)-2-acetyl-2-azabicyclo[3.1.0]hex-3-yl]carbonyl]amino]-N-[(4-fluorophenyl)methyl]-4,6,7,8,9,10-hexahydro-3-hydroxy-4-oxo-. $^1$H NMR (500 MHz, DMSO-$d_6$) δ ppm 9.86 (1 H, brs), 8.60 (1 H, brs), 7.38 (2 H, dd, J=8.55, 5.49 Hz), 7.17 (2 H, t, J=8.85 Hz), 4.56 (2 H, d, J=6.41 Hz), 4.46-4.49 (1 H, m), 4.02 (2 H, t, J=3.51 Hz), 3.37-3.41 (1 H, m), 3.17 (1 H, d, J=5.19 Hz), 2.47 (2 H, brs), 2.37-2.40 (1 H, m), 2.05 (3H, s), 1.83-1.93 (3 H, m), 1.71-1.83 (3 H, m), 1.56-1.65 (2 H, m), 0.92-0.98 (1H, m), 0.54 (1 H, td, J=4.81, 2.29 Hz). LCMS (M+H)+=524.2.

EXAMPLE 271

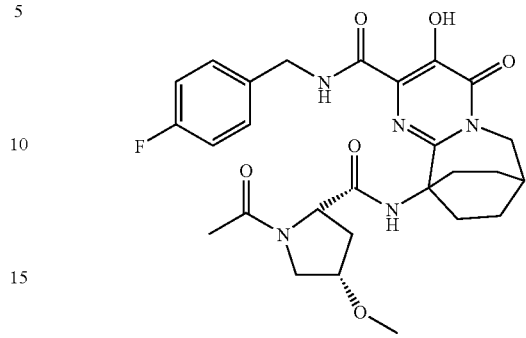

7,10-Ethanopyrimido[1,2-a]azepine-2-carboxamide, 10-[[[(2S,4S)-1-acetyl-4-methoxy-2-pyrrolidinyl]carbonyl]amino]-N-[(4-fluorophenyl)methyl]-4,6,7,8,9,10-hexahydro-3-hydroxy-4-oxo-. $^1$H NMR (500 MHz, DMSO-$d_6$) δ ppm 12.40 (1 H, brs), 9.71 (1 H, t, J=6.41 Hz), 8.26 (1 H, s), 7.39 (2 H, dd, J=8.55, 5.49 Hz), 7.14-7.21 (2 H, m), 4.63 (1 H, dd, J=14.80, 6.87 Hz), 4.52 (1 H, dd, J=14.95, 6.10 Hz), 4.37 (1 H, dd, J=9.46, 2.14 Hz), 4.02-4.05 (1 H, m), 3.98-4.00 (1 H, m), 3.94-3.97 (1 H, m), 3.67 (1 H, dd, J=11.14, 4.73 Hz), 3.42 (1 H, d, J=10.99 Hz), 3.17 (3 H, s), 2.35-2.42 (3 H, m), 1.96-2.03 (1 H, m), 1.71-1.90 (5 H, m), 1.55-1.62 (2 H, m). LCMS (M+H)+=542.1.

EXAMPLE 272

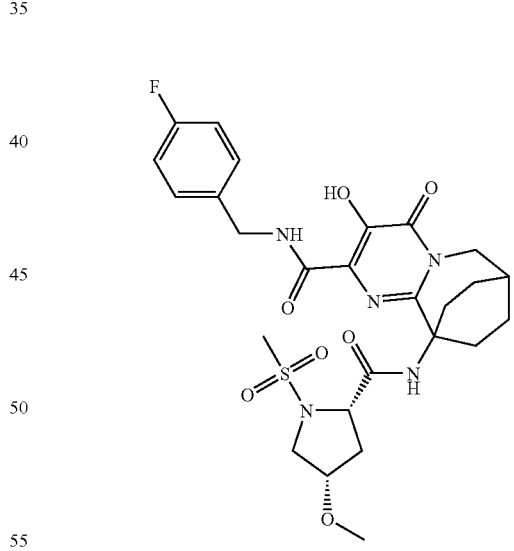

7,10-Ethanopyrimido[1,2-a]azepine-2-carboxamide, N-[(4-fluorophenyl)methyl]-4,6,7,8,9,10-hexahydro-3-hydroxy-10-[[[(2S,4S)-4-methoxy-1-(methylsulfonyl)-2-pyrrolidinyl]carbonyl]amino]-4-oxo-. $^1$H NMR (500 MHz, DMSO-$d_6$) δ ppm 12.34 (1 H, s), 8.63 (1 H, t, J=6.56 Hz), 8.48 (1 H, s), 7.39 (2 H, dd, J=8.39, 5.65 Hz), 7.16 (2 H, t, J=8.85 Hz), 4.49-4.61 (2 H, m), 4.26 (1 H, d, J=9.16 Hz), 4.02-4.08 (1 H, m), 3.97-4.02 (1 H, m), 3.95 (1 H, brs), 3.47 (1 H, dd, J=10.99, 3.97 Hz), 3.24 (1 H, d, J=10.68 Hz), 3.08 (3 H, s), 3.06 (3 H, s), 2.74-2.83 (1 H, m), 2.60-2.67 (1 H, m), 2.43-

2.48 (1 H, m), 2.37 (1 H, brs), 2.09 (1 H, ddd, J=13.81, 9.99, 3.97 Hz), 1.70-1.83 (4 H, m), 1.57-1.68 (2 H, m). LCMS (M+H)+=578.1.

EXAMPLE 273

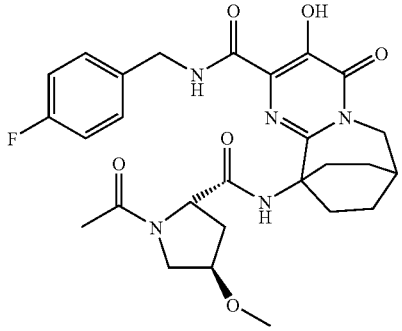

7,10-Ethanopyrimido[1,2-a]azepine-2-carboxamide, 10-[[[(2S,4R)-1-acetyl-4-methoxy-2-pyrrolidinyl]carbonyl]amino]-N-[(4-fluorophenyl)methyl]-4,6,7,8,9,10-hexahydro-3-hydroxy-4-oxo-. $^1$H NMR (500 MHz, DMSO-d$_6$) δ ppm 12.43 (1 H, brs), 9.77 (1 H, t, J=6.26 Hz), 8.61 (1 H, s), 7.35-7.41 (2 H, m), 7.16 (2 H, t, J=8.70 Hz), 4.50-4.64 (3 H, m), 4.05-4.11 (H, m), 3.96-4.02 (2 H, m), 3.56-3.61 (1 H, m), 3.50-3.54 (1 H, m), 3.25 (3 H, s), 2.29-2.41 (3 H, m), 2.17-2.25 (1 H, m), 1.92-2.04 (2 H, m), 1.71-1.81 (3 H, m), 1.55-1.64 (2 H, m). LCMS (M+H)+=542.1.

EXAMPLE 274

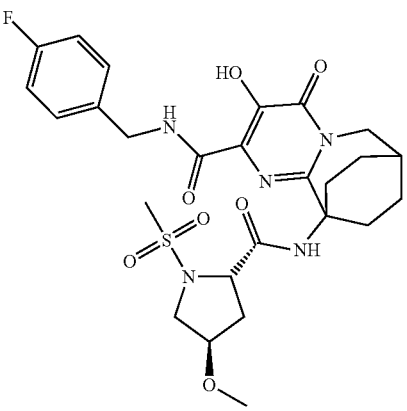

7,10-Ethanopyrimido[1,2-a]azepine-2-carboxamide, N-[(4-fluorophenyl)methyl]-4,6,7,8,9,10-hexahydro-3-hydroxy-10-[[[(2S,4R)-4-methoxy-1-(methylsulfonyl)-2-pyrrolidinyl]carbonyl]amino]-4-oxo-. $^1$H NMR (500 MHz, DMSO-d$_6$) δ ppm 12.34 (1 H, s), 8.63 (1 H, t, J=6.56 Hz), 8.48 (1 H, s), 7.39 (2 H, dd, J=8.39, 5.65 Hz), 7.16 (2 H, t, J=8.85 Hz), 4.49-4.61 (2 H, m), 4.26 (1 H, d, J=9.16 Hz), 4.02-4.08 (1 H, m), 3.97-4.02 (1 H, m), 3.95 (1 H, brs), 3.47 (1 H, dd, J=10.99, 3.97 Hz), 3.24 (1 H, d, J=10.68 Hz), 3.08 (3 H, s), 3.06 (3 H, s), 2.74-2.83 (1 H, m), 2.60-2.67 (1 H, m), 2.43-

EXAMPLE 275

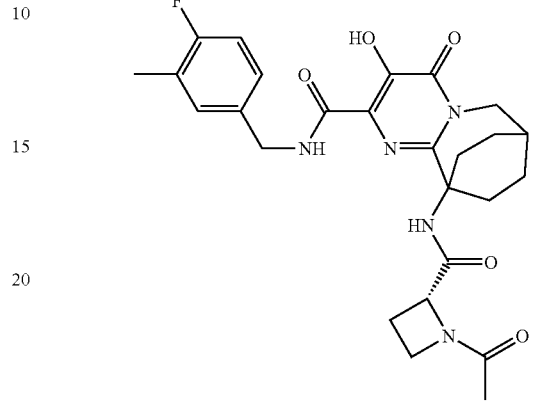

7,10-Ethanopyrimido[1,2-a]azepine-2-carboxamide, 10-[[[(2S)-1-acetyl-2-azetidinyl]carbonyl]amino]-N-[(4-fluoro-3-methylphenyl)methyl]-4,6,7,8,9,10-hexahydro-3-hydroxy-4-oxo-. $^1$H NMR (500 MHz, DMSO-d$_6$) δ ppm 12.68 (1 H, brs), 10.01 (1 H, t, J=6.26 Hz), 8.98 (1 H, s), 7.24 (1 H, d, J=7.32 Hz), 7.18 (1 H, d, J=5.19 Hz), 7.09 (1 H, t, J=9.16 Hz), 4.80 (1 H, dd, J=8.85, 6.71 Hz), 4.46-4.57 (2H, m), 4.03-4.10 (2 H, m), 3.95-4.02 (2 H, m), 2.71-2.80 (1 H, m), 2.62-2.71 (1H, m), 2.52-2.57 (1 H, m), 2.35-2.42 (2 H, m), 2.24-2.33 (1 H, m), 2.22 (3 H, s), 1.75-1.84 (3 H, m), 1.74 (3 H, s), 1.58-1.66 (2 H, m). LCMS (M+H)+=512.1.

EXAMPLE 276

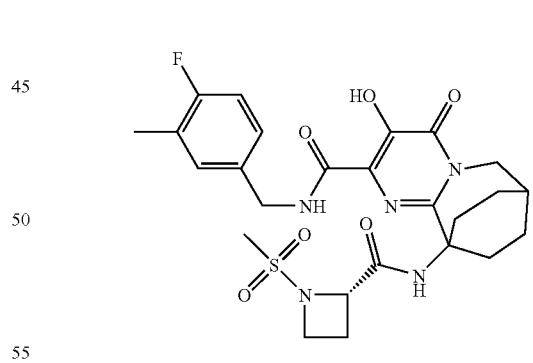

7,10-Ethanopyrimido[1,2-a]azepine-2-carboxamide, N-[(4-fluoro-3-methylphenyl)methyl]-4,6,7,8,9,10-hexahydro-3-hydroxy-10-[[[(2S)-1-(methylsulfonyl)-2-azetidinyl]carbonyl]amino]-4-oxo-. $^1$H NMR (500 MHz, DMSO-d$_6$) δ ppm 12.37 (1 H, brs), 8.76 (1 H, t, J=6.41 Hz), 8.50 (1 H, s), 7.24 (1 H, d, J=7.93 Hz), 7.16-7.20 (1 H, m), 7.08 (1 H, t, J=9.00 Hz), 4.78-4.83 (1 H, m), 4.53 (1 H, dd, J=14.65, 7.02 Hz), 4.40 (1 H, dd, J=14.50, 5.95 Hz), 4.12 (1 H, dd, J=15.11, 4.12 Hz), 3.90-4.02 (2 H, m), 3.64-3.70 (1 H, m), 3.21 (3 H, s), 2.70-2.78 (1 H, m), 2.58-2.66 (1 H, m), 2.53-2.58 (1 H, m), 2.38-2.48 (2 H, m), 2.23-2.28 (1 H, m), 2.21 (3 H, s), 1.93-

2.02 (1 H, m), 1.76-1.86 (2 H, m), 1.65-1.76 (1H, m), 1.57-1.64 (1 H, m). LCMS (M+H)+=548.1.

EXAMPLE 277

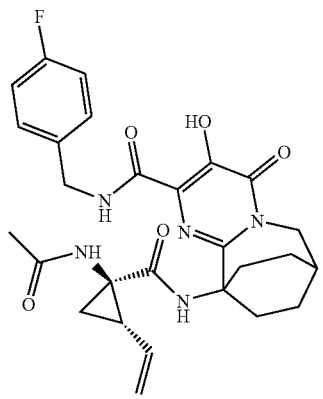

7,10-Ethanopyrimido[1,2-a]azepine-2-carboxamide, 10-[[[(1R,2S)-1-(acetylamino)-2-ethenylcyclopropyl]carbonyl]amino]-N-[(4-fluorophenyl)methyl]-4,6,7,8,9,10-hexahydro-3-hydroxy-4-oxo-. $^1$H NMR (500 MHz, DMSO-d$_6$) δ ppm 12.60 (1 H, brs), 9.98 (1 H, t, J=6.10 Hz), 8.95 (1 H, s), 8.67 (1 H, s), 7.41 (2 H, dd, J=8.24, 5.80 Hz), 7.13-7.21 (2 H, m), 5.39-5.50 (1 H, m), 5.13 (1 H, d, J=17.09 Hz), 4.98 (1 H, d, J=10.68 Hz), 4.55-4.59 (2 H, m), 4.17 (1 H, dd, J=15.11, 4.73 Hz), 3.85 (1 H, d, J=14.65 Hz), 2.61-2.71 (1 H, m), 2.47 (1 H, m), 2.37 (1 H, brs), 1.89-2.04 (2 H, m), 1.71-1.82 (4 H, m), 1.60-1.69 (2 H, m), 1.51-1.60 (2 H, m), 1.48 (1 H, dd, J=7.02, 5.49 Hz), 1.09 (1 H, dd, J=9.46, 5.19 Hz). LCMS (M+H)+=524.1.

EXAMPLE 278

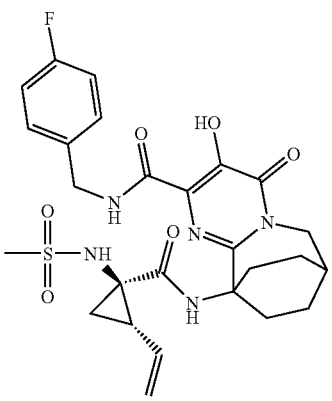

7,10-Ethanopyrimido[1,2-a]azepine-2-carboxamide, 10-[[[(1R,2S)-2-ethenyl-1-[(methylsulfonyl)amino]cyclopropyl]carbonyl]amino]-N-[(4-fluorophenyl)methyl]-4,6,7,8,9,10-hexahydro-3-hydroxy-4-oxo-. $^1$H NMR (500 MHz, DMSO-d$_6$) δ ppm 12.45 (1 H, brs), 8.78-8.83 (1 H, m), 8.65 (1 H, s), 8.51 (1 H, s), 7.41 (2 H, dd, J=8.09, 5.95 Hz), 7.16 (2 H, t, J=8.70 Hz), 5.58-5.68 (1 H, m), 5.24 (1 H, d, J=17.70 Hz), 5.03 (1 H, d, J=10.68 Hz), 4.48-4.51 (2 H, m), 4.08-4.14 (1 H, m), 3.95 (1 H, brs), 3.00 (3 H, s), 2.78 (1 H, brs), 2.57-2.65 (1 H, m), 2.35-2.42 (1 H, m), 2.14-2.23 (1 H, m), 1.75-1.85 (3 H, m), 1.65-1.75 (3 H, m), 1.61 (2 H, dd, J=9.61, 5.04 Hz). LCMS (M+H)+=524.1.

EXAMPLE 279

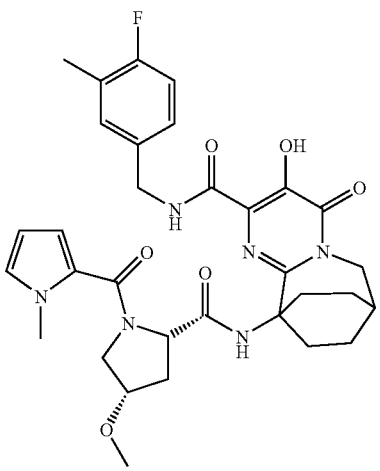

7,10-Ethanopyrimido[1,2-a]azepine-2-carboxamide, N-[(4-fluoro-3-methylphenyl)methyl]-4,6,7,8,9,10-hexahydro-3-hydroxy-10-[[[(2S,4S)-4-methoxy-1-[(1-methyl-1H-pyrrol-2-yl)carbonyl]-2-pyrrolidinyl]carbonyl]amino]-4-oxo-. $^1$H NMR (500 MHz, DMSO-d$_6$) δ ppm 12.20 (1 H, brs), 9.29 (1 H, brs), 7.87 (1 H, s), 7.09-7.20 (2 H, m), 7.02-7.09 (1 H, m), 6.87 (1 H, brs), 6.56 (1 H, brs), 6.04 (1 H, brs), 4.86 (1 H, brs), 4.56 (1 H, brs), 4.27 (1 H, d, J=6.41 Hz), 4.04-4.10 (2 H, m), 3.95 (1 H, brs), 3.76 (1 H, brs), 3.64 (1 H, brs), 3.60 (3 H, s), 3.27 (3 H, brs), 2.39 (1H, brs), 2.21-2.29 (2 H, m), 2.19 (3 H, brs), 2.13 (1 H, brs), 1.99 (2 H, brs), 1.87-1.94 (1 H, m), 1.76 (2 H, brs), 1.59 (2 H, brs). LCMS (M+H)+=621.1.

EXAMPLE 280

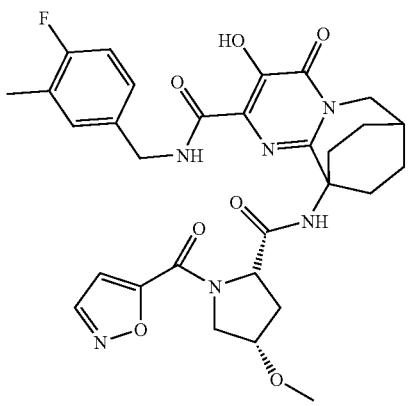

7,10-Ethanopyrimido[1,2-a]azepine-2-carboxamide, N-[(4-fluoro-3-methylphenyl)methyl]-4,6,7,8,9,10-hexahydro-3-hydroxy-10-[[[(2S,4S)-1-(5-isoxazolylcarbonyl)-4-methoxy-2-pyrrolidinyl]carbonyl]amino]-4-oxo-. $^1$H NMR (500 MHz, DMSO-d$_6$) δ ppm 12.28 (1 H, brs), 9.21 (1 H, t, J=6.26 Hz), 8.77 (1 H, d, J=1.53 Hz), 8.26 (1 H, s), 7.12-7.22 (2 H, m), 7.03-7.09 (2 H, m), 4.94 (1 H, d, J=7.02 Hz), 4.66 (1 H, dd, J=14.50, 7.17 Hz), 4.40 (1 H, dd, J=14.50, 5.34 Hz), 4.24 (1 H, dd, J=15.11, 4.43 Hz), 4.06-4.13 (1 H, m), 3.84 (2 H, d, J=11.60 Hz), 3.72-3.80 (1 H, m), 3.33 (3 H, s), 2.30-2.43 (2 H, m), 2.15-2.26 (5 H, m), 2.06 (2 H, q, J=6.61 Hz), 1.87-1.95 (1 H, m), 1.70-1.82 (2 H, m), 1.60-1.68 (1 H, m), 1.55 (1H, brs). LCMS (M+H)+=609.2.

EXAMPLE 281

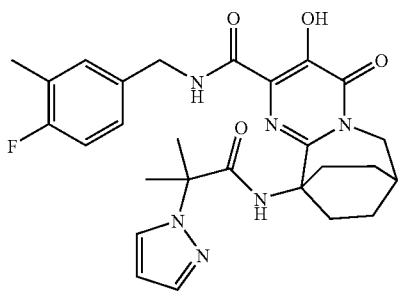

7,10-Ethanopyrimido[1,2-a]azepine-2-carboxamide, N-[(4-fluoro-3-methylphenyl)methyl]-4,6,7,8,9,10-hexahydro-3-hydroxy-10-[[2-methyl-1-oxo-2-(1H-pyrazol-1-yl)propyl]amino]-4-oxo-. $^1$H NMR (500 MHz, DMSO-d$_6$) δ ppm 12.08 (1H, brs), 9.49 (1 H, brs), 7.97 (1 H, s), 7.48 (1 H, s), 7.22 (1 H, d, J=7.32 Hz), 7.16 (2H, brs), 7.08 (1 H, t, J=9.00 Hz), 6.34 (1 H, s), 4.60 (2 H, d, J=6.10 Hz), 3.99 (2 H, d, J=3.36 Hz), 3.31 (3 H, s), 2.37 (1 H, brs), 2.20-2.29 (2 H, m), 2.18 (3 H, s), 1.68-1.82 (4 H, m), 1.64 (6 H, s), 1.53-1.61 (2 H, m). LCMS (M+H)+=523.2.

EXAMPLE 282

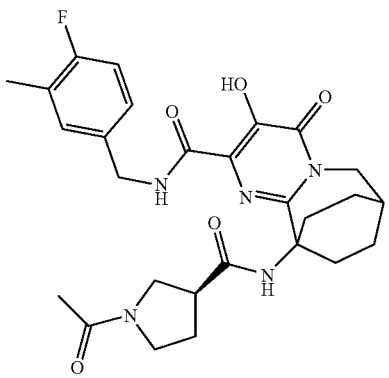

7,10-Ethanopyrimido[1,2-a]azepine-2-carboxamide, 10-[[[(3S)-1-acetyl-3-pyrrolidinyl]carbonyl]amino]-N-[(4-fluoro-3-methylphenyl)methyl]-4,6,7,8,9,10-hexahydro-3-hydroxy-4-oxo-. $^1$H NMR (500 MHz, DMSO-d$_6$) δ ppm 11.93 (1 H, brs), 8.82-8.93 (1 H, m), 8.03 (1 H, s), 7.26 (1 H, d, J=5.80 Hz), 7.16-7.23 (1 H, m), 7.07-7.15 (1 H, m), 4.50-4.60 (1 H, m), 4.41-4.49 (1 H, m), 3.99-4.04 (2 H, m), 3.41-3.54 (2 H, m), 3.25-3.39 (2 H, m), 3.20 (1 H, dd, J=11.29, 7.63 Hz), 3.08-3.15 (1 H, m), 2.98-3.05 (1 H, m), 2.38-2.43 (1 H, m), 2.24-2.33 (2 H, m), 2.22 (3 H, brs), 1.97-2.11 (2 H, m), 1.90-1.93 (3 H, m), 1.73-1.80 (2 H, m), 1.55-1.64 (2 H, m). LCMS (M+H)+=526.1.

EXAMPLE 283

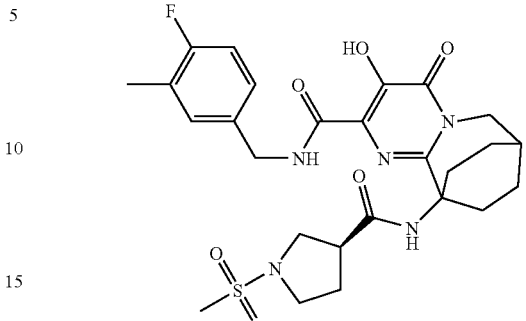

7,10-Ethanopyrimido[1,2-a]azepine-2-carboxamide, N-[(4-fluoro-3-methylphenyl)methyl]-4,6,7,8,9,10-hexahydro-3-hydroxy-10-[[[(3S)-1-(methylsulfonyl)-3-pyrrolidinyl]carbonyl]amino]-4-oxo-. $^1$H NMR (500 MHz, DMSO-d$_6$) δ ppm 11.93 (1 H, brs), 8.90 (1 H, t, J=6.41 Hz), 8.04 (1 H, s), 7.24 (1 H, d, J=7.32 Hz), 7.16-7.21 (1 H, m), 7.09-7.14 (1 H, m), 4.56 (1 H, dd, J=14.95, 6.71 Hz), 4.41 (1 H, dd, J=14.65, 5.80 Hz), 3.95-4.08 (2 H, m), 3.38-3.45 (1 H, m), 3.10-3.27 (4 H, m), 2.86 (3 H, s), 2.36-2.43 (1 H, m), 2.25-2.33 (2 H, m), 2.23 (3 H, s), 1.97-2.10 (2 H, m), 1.84-1.95 (2 H, m), 1.72-1.82 (2 H, m), 1.55-1.65 (2 H, m). LCMS (M+H)+=562.2.

EXAMPLE 284

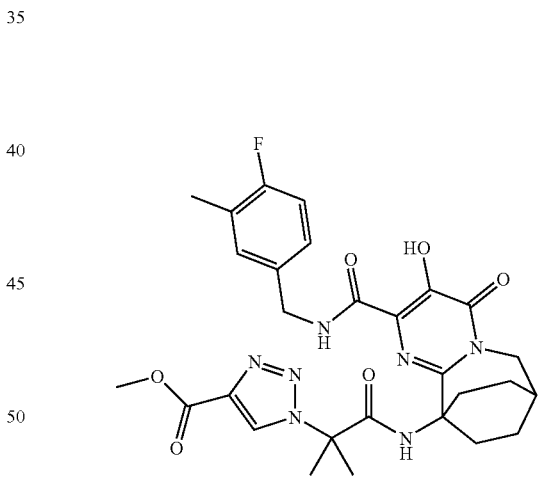

1H-1,2,3-Triazole-4-carboxylic acid, 1-[2-[[2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]amino]-1,1-dimethyl-2-oxoethyl]-, methyl ester. $^1$H NMR (500 MHz, DMSO-d$_6$) δ ppm 11.93-12.06 (1 H, m), 9.03 (1 H, t, J=6.56 Hz), 8.93 (1 H, s), 7.91 (1 H, s), 7.29 (1 H, d, J=7.63 Hz), 7.21 (1 H, brs), 7.07 (1 H, t, J=9.16 Hz), 4.61 (2 H, d, J=6.41 Hz), 4.00 (2 H, d, J=3.05 Hz), 3.87 (3H, s), 2.39 (1 H, brs), 2.19 (3 H, s), 2.08-2.16 (2 H, m), 2.04 (2 H, ddd, J=13.96, 7.32, 7.10 Hz), 1.68-1.81 (8 H, m), 1.53-1.62 (2 H, m). LCMS (M+H)+=582.2.

EXAMPLE 285

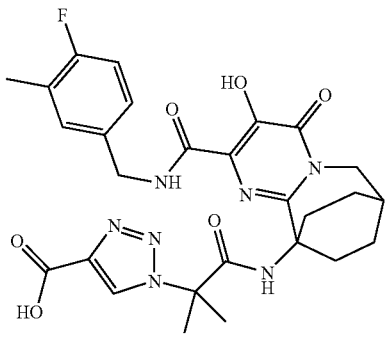

1H-1,2,3-Triazole-4-carboxylic acid, 1-[2-[[2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]amino]-1,1-dimethyl-2-oxoethyl]-. $^1$H NMR (500 MHz, DMSO-$d_6$) δ ppm 12.04 (1 H, brs), 9.07 (1 H, t, J=6.41 Hz), 8.82 (1 H, s), 7.94 (1 H, s), 7.31 (1 H, d, J=7.32 Hz), 7.22 (1 H, t, J=5.65 Hz), 7.06 (1 H, t, J=9.16 Hz), 4.62 (2 H, d, J=6.41 Hz), 4.00 (2 H, d, J=3.66 Hz), 2.38 (1 H, brs), 2.19 (3 H, s), 2.10-2.17 (2 H, m), 1.98-2.08 (2 H, m), 1.70-1.81 (8 H, m), 1.53-1.62 (2 H, m). LCMS (M+H)+= 568.0.

EXAMPLE 286

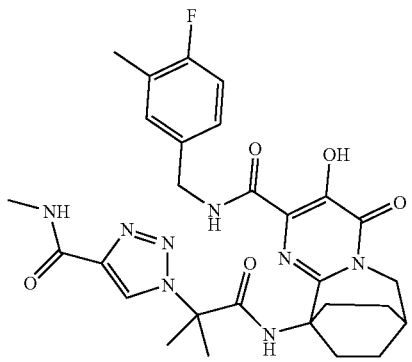

7,10-Ethanopyrimido[1,2-a]azepine-2-carboxamide, N-[(4-fluoro-3-methylphenyl)methyl]-4,6,7,8,9,10-hexahydro-3-hydroxy-10-[[2-methyl-2-[4-[(methylamino)carbonyl]-1H-1,2,3-triazol-1-yl]-1-oxopropyl]amino]-4-oxo-. $^1$H NMR (500 MHz, DMSO-$d_6$) δ ppm 11.99 (1 H, brs), 9.03 (1 H, t, J=6.41 Hz), 8.93 (1H, s), 7.91 (1 H, s), 7.29 (1 H, d, J=7.32 Hz), 7.20 (1 H, d, J=5.80 Hz), 7.07 (1 H, t, J=9.16 Hz), 4.61 (2 H, d, J=6.41 Hz), 4.00 (2 H, d, J=3.36 Hz), 3.87 (3 H, s), 2.38 (1H, brs), 2.19 (3 H, s), 2.09-2.16 (2 H, m), 2.00-2.09 (2 H, m), 1.70-1.81 (8 H, m), 1.54-1.62 (2 H, m). LCMS (M+H)+=581.1.

EXAMPLE 287

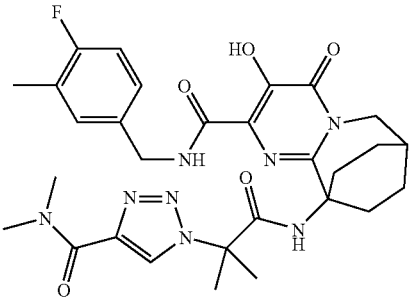

7,10-Ethanopyrimido[1,2-a]azepine-2-carboxamide, 10-[[2-[4-[(dimethylamino)carbonyl]-1H-1,2,3-triazol-1-yl]-2-methyl-1-oxopropyl]amino]-N-[(4-fluoro-3-methylphenyl)methyl]-4,6,7,8,9,10-hexahydro-3-hydroxy-4-oxo-. $^1$H NMR (500 MHz, DMSO-$d_6$) δ ppm 12.03 (1 H, brs), 9.13 (1 H, t, J=6.41 Hz), 8.65 (1H, s), 7.96 (1 H, s), 7.24 (1 H, d, J=7.63 Hz), 7.15-7.21 (1 H, m), 7.06 (1 H, t, J=9.00 Hz), 4.61 (2 H, d, J=6.41 Hz), 4.00 (2 H, d, J=3.66 Hz), 3.30 (3 H, s), 3.00 (3H, s), 2.39 (1 H, brs), 2.13-2.21 (5 H, m), 1.98-2.06 (2 H, m), 1.71-1.80 (8 H, m), 1.55-1.63 (2 H, m). LCMS (M+H)+=595.2.

EXAMPLE 288

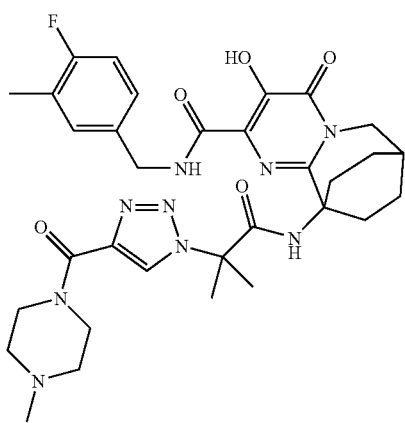

7,10-Ethanopyrimido[1,2-a]azepine-2-carboxamide, N-[(4-fluoro-3-methylphenyl)methyl]-4,6,7,8,9,10-hexahydro-3-hydroxy-10-[[2-methyl-2-[4-[(4-methyl-1-piperazinyl)carbonyl]-1H-1,2,3-triazol-1-yl]-1-oxopropyl]amino]-4-oxo-. $^1$H NMR (500 MHz, DMSO-$d_6$) δ ppm 11.92 (1 H, brs), 9.82 (1 H, brs), 9.00 (1 H, t, J=6.41 Hz), 8.76 (1 H, s), 8.01 (1 H, s), 7.23 (1 H, d, J=7.63 Hz), 7.15-7.21 (1 H, m), 7.09 (1 H, t, J=9.00 Hz), 4.59 (2 H, d, J=6.41 Hz), 4.01 (2 H, d, J=3.66 Hz), 3.52 (3 H, brs), 3.11 (3 H, brs), 2.85 (3 H, s), 2.38-2.42 (1 H, m), 2.14-2.23 (5 H, m), 1.99-2.06 (2 H, m), 1.72-1.81 (8 H, m), 1.55-1.64 (2 H, m). LCMS (M+H)+= 650.2.

EXAMPLE 289

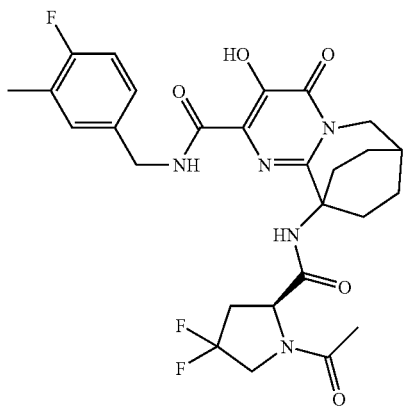

7,10-Ethanopyrimido[1,2-a]azepine-2-carboxamide, 10-[[[(2S)-1-acetyl-4,4-difluoro-2-pyrrolidinyl]carbonyl]amino]-N-[(4-fluoro-3-methylphenyl)methyl]-4,6,7,8,9,10-hexahydro-3-hydroxy-4-oxo-. $^1$H NMR (500 MHz, DMSO-d$_6$) δ ppm 12.40 (1 H, brs), 9.59 (1 H, t, J=6.41 Hz), 8.54 (1 H, s), 7.24 (1 H, d, J=7.32 Hz), 7.17-7.21 (1 H, m), 7.06-7.13 (1 H, m), 4.76 (1 H, dd, J=9.16, 4.27 Hz), 4.47-4.60 (2 H, m), 4.04-4.16 (2 H, m), 3.89-4.02 (2 H, m), 2.57-2.67 (2 H, m), 2.30-2.43 (3 H, m), 2.21 (3 H, s), 1.89-2.01 (5 H, m), 1.72-1.83 (2 H, m), 1.56-1.64 (2H, m). LCMS (M+H)+=562.0.

EXAMPLE 290

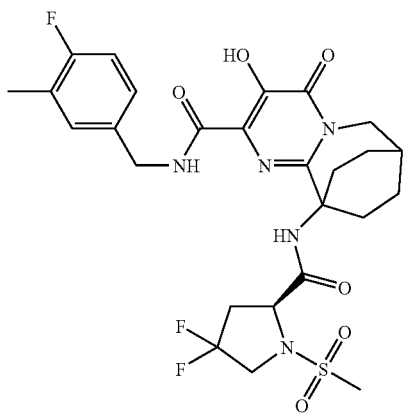

7,10-Ethanopyrimido[1,2-a]azepine-2-carboxamide, 10-[[[(2S)-4,4-difluoro-1-(methylsulfonyl)-2-pyrrolidinyl]carbonyl]amino]-N-[(4-fluoro-3-methylphenyl)methyl]-4,6,7,8,9,10-hexahydro-3-hydroxy-4-oxo-. $^1$H NMR (500 MHz, DMSO-d$_6$) δ ppm 12.29 (1 H, s), 8.64 (1 H, t, J=6.71 Hz), 8.48 (1 H, s), 7.24 (1H, d, J=7.63 Hz), 7.17-7.21 (1 H, m), 7.06-7.11 (1 H, m), 4.67 (1 H, dd, J=9.31, 4.73 Hz), 4.51-4.57 (1 H, m), 4.40-4.46 (1 H, m), 4.06-4.12 (1 H, m), 3.90-3.99 (2 H, m), 3.65-3.75 (1 H, m), 3.14 (3 H, s), 2.56-2.65 (2 H, m), 2.45-2.48 (2 H, m), 2.38-2.42 (1 H, m), 2.21 (3 H, s), 1.90-1.99 (1 H, m), 1.75-1.90 (3 H, m), 1.57-1.68 (2 H, m). LCMS (M+H)+=598.1.

EXAMPLE 291

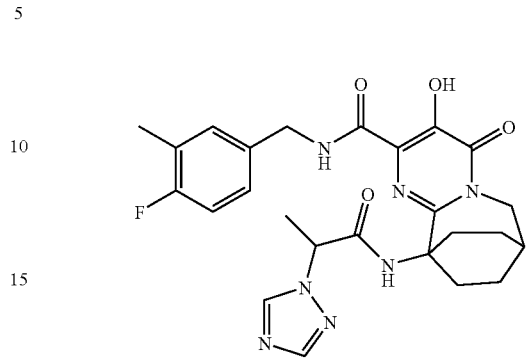

7,10-Ethanopyrimido[1,2-a]azepine-2-carboxamide, N-[(4-fluoro-3-methylphenyl)methyl]-4,6,7,8,9,10-hexahydro-3-hydroxy-4-oxo-10-[[1-oxo-2-(1H-1,2,4-triazol-1-yl)propyl]amino]-. $^1$H NMR (500 MHz, DMSO-d$_6$) δ ppm 12.08 (1 H, brs), 9.03 (1 H, t, J=6.41 Hz), 8.61 (1 H, s), 8.35 (1 H, s), 7.94 (1 H, s), 7.26 (1 H, d, J=7.63 Hz), 7.20 (1 H, td, J=5.42, 2.59 Hz), 7.08-7.14 (1 H, m), 5.33 (1 H, q, J=7.12 Hz), 4.62 (1 H, dd, J=14.95, 7.02 Hz), 4.50 (1 H, dd, J=14.95, 6.10 Hz), 4.10 (1 H, dd, J=15.26, 3.97 Hz), 3.93 (1 H, dd, J=14.95, 2.75 Hz), 2.39 (1 H, brs), 2.23-2.32 (2 H, m), 2.21 (3 H, s), 2.07-2.16 (1 H, m), 1.87-1.96 (1 H, m), 1.71-1.82 (2H, m), 1.54-1.66 (5 H, m). LCMS (M+H)+=510.1.

EXAMPLE 292

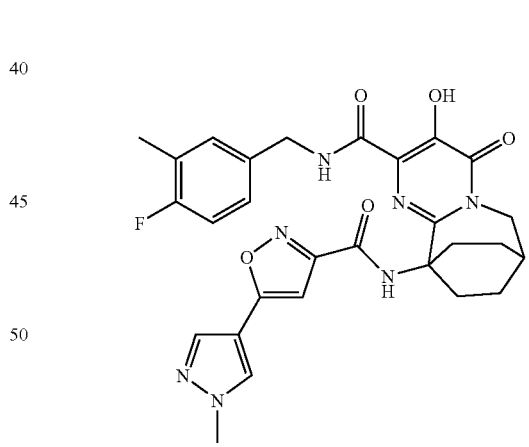

7,10-Ethanopyrimido[1,2-a]azepine-2-carboxamide, N-[(4-fluoro-3-methylphenyl)methyl]-4,6,7,8,9,10-hexahydro-3-hydroxy-10-[[[5-(1-methyl-1H-pyrazol-4-yl)-3-isoxazolyl]carbonyl]amino]-4-oxo-. $^1$H NMR (500 MHz, DMSO-d$_6$) δ ppm 11.77 (1 H, brs), 8.92 (1 H, s), 8.74 (1 H, t, J=6.41 Hz), 8.33 (1 H, s), 7.96 (1H, s), 7.14 (1 H, d, J=7.32 Hz), 7.06-7.11 (1 H, m), 6.99 (1 H, t, J=9.00 Hz), 6.89 (1H, s), 4.42 (2 H, d, J=6.41 Hz), 4.05 (2 H, d, J=3.66 Hz), 3.93 (3 H, s), 2.39-2.48 (3H, m), 2.16-2.24 (2 H, m), 2.14 (3 H, s), 1.80-1.89 (2 H, m), 1.62-1.72 (2 H, m). LCMS (M+H)+= 562.1.

Example 293

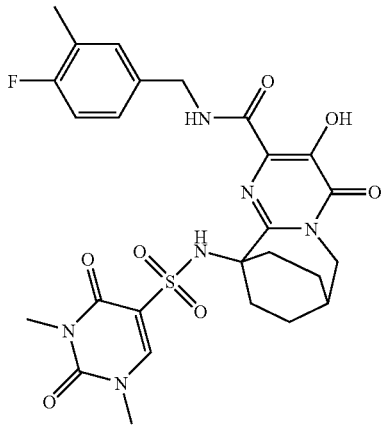

7,10-Ethanopyrimido[1,2-a]azepine-2-carboxamide, N-[(4-fluoro-3-methylphenyl)methyl]-4,6,7,8,9,10-hexahydro-3-hydroxy-4-oxo-10-[[(1,2,3,4-tetrahydro-1,3-dimethyl-2,4-dioxo-5-pyrimidinyl)sulfonyl]amino]-. $^1$H NMR (500 MHz, DMSO-$d_6$) δ ppm 11.85 (1 H, brs), 9.25 (1 H, t, J=6.56 Hz), 8.40 (1 H, s), 8.02 (1 H, s), 7.28 (1 H, d, J=7.32 Hz), 7.17-7.22 (1 H, m), 7.07-7.15 (1 H, m), 4.50 (2 H, d, J=6.41 Hz), 3.96 (2 H, d, J=3.66 Hz), 3.41 (3 H, s), 2.96 (3 H, s), 2.39 (1 H, brs), 2.31 (2 H, ddd, J=14.11, 8.93, 5.65 Hz), 2.22 (3 H, s), 2.07 (2 H, ddd, J=13.66, 7.17, 6.94 Hz), 1.69-1.80 (2 H, m), 1.52-1.62 (2 H, m). LCMS (M+H)+=589.0.

Example 294

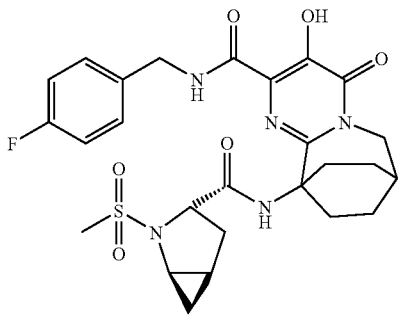

7,10-Ethanopyrimido[1,2-a]azepine-2-carboxamide, N-[(4-fluorophenyl)methyl]-4,6,7,8,9,10-hexahydro-3-hydroxy-10-[[[(1R,3S,5R)-2-(methylsulfonyl)-2-azabicyclo[3.1.0]hex-3-yl]carbonyl]amino]-4-oxo-. $^1$H NMR (500 MHz, DMSO-$d_6$) δ ppm 12.23 (1 H, brs), 8.53 (1 H, t, J=6.56 Hz), 8.33 (1 H, s), 7.39 (2 H, dd, J=8.55, 5.49 Hz), 7.14-7.21 (2 H, m), 4.56-4.65 (1 H, m), 4.46-4.56 (1 H, m), 4.15 (1 H, dd, J=15.26, 4.27 Hz), 3.89-3.95 (2 H, m), 3.07 (3 H, s), 2.99 (1H, td, J=5.95, 2.44 Hz), 2.57-2.66 (1 H, m), 2.43-2.48 (1 H, m), 2.38-2.42 (1 H, m), 2.31-2.37 (1 H, m), 2.06 (1 H, dt, J=13.20, 6.68 Hz), 1.92-2.01 (1 H, m), 1.72-1.83 (3 H, m), 1.63-1.70 (1 H, m), 1.54-1.63 (2 H, m), 0.79 (1 H, ddd, J=7.71, 2.98, 2.75 Hz), 0.63 (1 H, dt, J=8.55, 5.80 Hz). LCMS (M+H)+=560.2.

Example 295

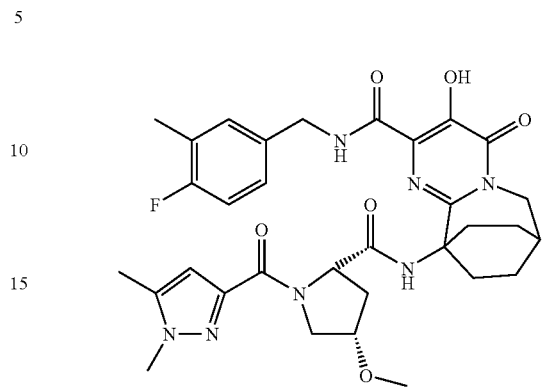

7,10-Ethanopyrimido[1,2-a]azepine-2-carboxamide, 10-[[[(2S,4S)-1-[(1,5-dimethyl-1H-pyrazol-3-yl)carbonyl]-4-methoxy-2-pyrrolidinyl]carbonyl]amino]-N-[(4-fluoro-3-methylphenyl)methyl]-4,6,7,8,9,10-hexahydro-3-hydroxy-4-oxo-. $^1$H NMR (500 MHz, DMSO-$d_6$) δ ppm 12.30 (1 H, brs), 9.29 (1 H, t, J=6.26 Hz), 8.08-8.17 (1 H, m), 7.04-7.19 (3 H, m), 6.24 (1 H, s), 4.83-4.94 (1 H, m), 4.64 (1 H, dd, J=14.65, 7.32 Hz), 4.48 (1 H, dd, J=14.65, 5.49 Hz), 4.26 (1 H, dd, J=14.95, 4.58 Hz), 4.01-4.11 (2 H, m), 3.94 (2 H, dd, J=7.48, 4.12 Hz), 3.75 (3 H, s), 3.31 (3 H, s), 2.34-2.41 (2 H, m), 2.16-2.24 (6 H, m), 2.09-2.16 (2 H, m), 1.99-2.06 (1 H, m), 1.90-1.97 (1 H, m), 1.68-1.86 (3 H, m), 1.48-1.67 (2 H, m). LCMS (M+H)+=636.1.

Example 296

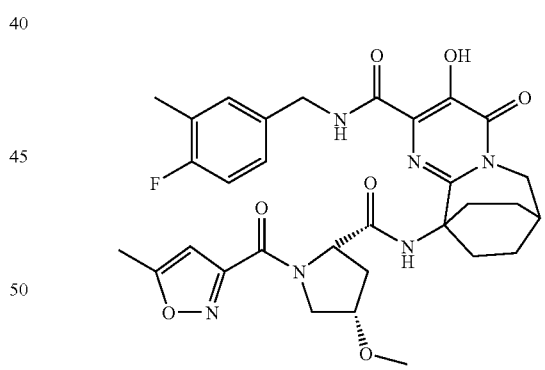

7,10-Ethanopyrimido[1,2-a]azepine-2-carboxamide, N-[(4-fluoro-3-methylphenyl)methyl]-4,6,7,8,9,10-hexahydro-3-hydroxy-10-[[[(2S,4S)-4-methoxy-1-[(5-methyl-3-isoxazolyl)carbonyl]-2-pyrrolidinyl]carbonyl]amino]-4-oxo-. $^1$H NMR (500 MHz, DMSO-$d_6$) δ ppm 12.28 (1 H, brs), 9.20 (1 H, t, J=6.26 Hz), 8.24 (1 H, s), 7.03-7.18 (3 H, m), 6.33 (1 H, s), 4.93 (1 H, d, J=7.02 Hz), 4.61 (1 H, dd, J=14.65, 7.02 Hz), 4.37 (1 H, dd, J=14.95, 5.80 Hz), 4.26 (1 H, dd, J=15.26, 5.19 Hz), 4.04-4.11 (1 H, m), 3.99-4.04 (1 H, m), 3.74-3.81 (1 H, m), 3.65-3.73 (1 H, m), 3.31 (3H, s), 2.31-2.44 (5 H, m), 2.15-2.23 (4 H, m), 2.02 (2 H, q, J=8.04 Hz), 1.91 (1 H, brs), 1.70-1.84 (3 H, m), 1.61-1.69 (1 H, m), 1.49-1.60 (1 H, m). LCMS (M+H)+=623.2.

Example 297

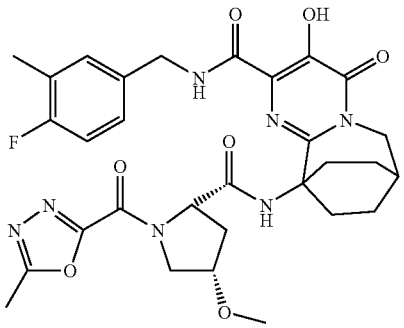

7,10-Ethanopyrimido[1,2-a]azepine-2-carboxamide, N-[(4-fluoro-3-methylphenyl)methyl]-4,6,7,8,9,10-hexahydro-3-hydroxy-10-[[[(2S,4S)-4-methoxy-1-[(5-methyl-1,3,4-oxadiazol-2-yl)carbonyl]-2-pyrrolidinyl]carbonyl]amino]-4-oxo-. HPLC(A): Solvent(A): 0.1% trifluoroacetic acid/95% water/5% Acetonitrile: Solvent(B): 0.1% trifluoroacetic acid/95% Acetonitrile/5% water: Column: Sunfire C18 3.5 μm, 4.5×150 mm: Gradient time: 15 min: Stop time: 18 min: Start B %=10% Final B %=100%: Flow rate: 2 ml/min: UV Det: 220/254 nm. HPLC(B): Solvent(A): 10 mM amm. Bicarb (pH=9.5) 95% water/5% Methanol: Solvent(B): 10 mM amm. Bicarb (pH=9.5) 5% water/95% Methanol: Column: Xbridge Phenyl 3.5 μm, 4.5×150 mm: Gradient time: 15 min: Stop time: 18 min: Start B %=10% Final B %=100%: Flow rate: 2 ml/min: UV Det: 220/254 nm. LCMS (M+H)+= 624.0. HPLC(A): $R_t$=6.22 min, HPLC(B): $R_t$=6.99.

Example 298

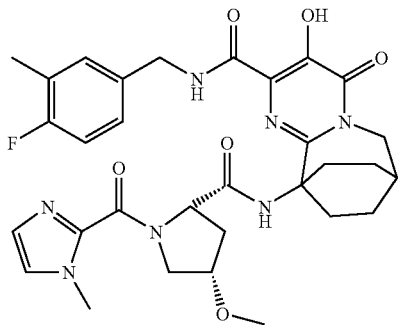

7,10-Ethanopyrimido[1,2-a]azepine-2-carboxamide, N-[(4-fluoro-3-methylphenyl)methyl]-4,6,7,8,9,10-hexahydro-3-hydroxy-10-[[[(2S,4S)-4-methoxy-1-[(1-methyl-1H-imidazol-2-yl)carbonyl]-2-pyrrolidinyl]carbonyl]amino]-4-oxo-. $^1$H NMR (500 MHz, DMSO-$d_6$) δ ppm 12.29 (1 H, brs), 9.24 (1 H, t, J=6.10 Hz), 8.14 (1H, s), 7.46 (1 H, s), 7.24 (1 H, brs), 7.01-7.18 (3 H, m), 4.93 (1 H, d, J=6.71 Hz), 4.57 (1 H, dd, J=14.65, 6.71 Hz), 4.34 (1 H, dd, J=15.26, 5.80 Hz), 4.13-4.20 (1 H, m), 4.07 (1 H, q, J=6.21 Hz), 4.01 (1 H, d, J=11.29 Hz), 3.91-3.98 (1 H, m), 3.79-3.87 (1 H, m), 3.71-3.76 (3 H, m), 3.27 (3 H, s), 2.37-2.42 (1 H, m), 2.27-2.36 (2H, m), 2.18 (3 H, s), 1.90-2.00 (2 H, m), 1.74-1.89 (2 H, m), 1.51-1.71 (4 H, m). LCMS (M+H)+=622.0.

Example 299

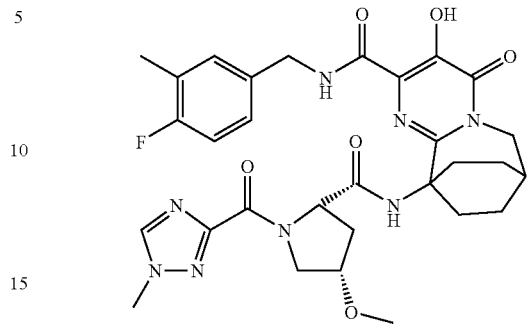

7,10-Ethanopyrimido[1,2-a]azepine-2-carboxamide, N-[(4-fluoro-3-methylphenyl)methyl]-4,6,7,8,9,10-hexahydro-3-hydroxy-10-[[[(2S,4S)-4-methoxy-1-[(1-methyl-1H-1,2,4-triazol-3-yl)carbonyl]-2-pyrrolidinyl]carbonyl]amino]-4-oxo-. $^1$H NMR (500 MHz, DMSO-$d_6$) δ ppm 12.42 (1 H, brs), 9.22 (1 H, t, J=6.41 Hz), 8.61 (1 H, s), 8.31 (1 H, s), 7.17-7.22 (2 H, m), 7.01-7.08 (1 H, m), 4.91 (1 H, d, J=7.32 Hz), 4.67-4.71 (2 H, m), 4.34 (1 H, dd, J=15.11, 5.65 Hz), 4.08 (1 H, q, J=7.63 Hz), 3.93-4.00 (1 H, m), 3.89-3.93 (3 H, m), 3.79-3.87 (2 H, m), 3.35 (3H, s), 2.39 (1 H, brs), 2.16-2.24 (4 H, m), 2.03-2.11 (4 H, m), 1.62-1.92 (4 H, m), 1.44-1.54 (1 H, m). LCMS (M+H)+=623.0.

Example 300

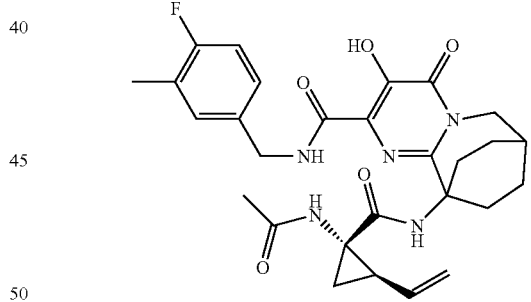

7,10-Ethanopyrimido[1,2-a]azepine-2-carboxamide, 10-[[[(1S,2R)-1-(acetylamino)-2-ethenylcyclopropyl]carbonyl]amino]-N-[(4-fluoro-3-methylphenyl)methyl]-4,6,7,8,9,10-hexahydro-3-hydroxy-4-oxo-. $^1$H NMR (500 MHz, DMSO-$d_6$) δ ppm 12.62 (1 H, brs), 9.96 (1 H, t, J=6.10 Hz), 8.95 (1 H, s), 8.68 (1 H, brs), 7.28 (1 H, d, J=7.63 Hz), 7.21 (1 H, t, J=5.80 Hz), 7.08 (1 H, t, J=9.16 Hz), 5.40-5.50 (1 H, m), 5.13 (1 H, d, J=17.40 Hz), 4.98 (1 H, d, J=11.29 Hz), 4.47-4.59 (2 H, m), 4.17 (1 H, dd, J=15.11, 4.73 Hz), 3.85 (1 H, d, J=14.95 Hz), 2.62-2.71 (1 H, m), 2.37 (1 H, brs), 2.21 (3 H, s), 1.89-2.01 (2 H, m), 1.72-1.80 (4 H, m), 1.46-1.69 (4 H, m), 1.16-1.20 (1 H, m), 1.06-1.14 (2 H, m). LCMS (M+H)+= 538.2.

Example 301

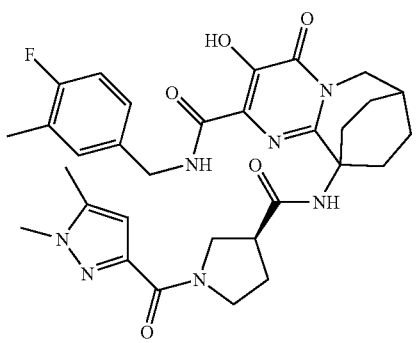

7,10-Ethanopyrimido[1,2-a]azepine-2-carboxamide, 10-[[[(3S)-1-[(1,5-dimethyl-1H-pyrazol-3-yl)carbonyl]-3-pyrrolidinyl]carbonyl]amino]-N-[(4-fluoro-3-methylphenyl)methyl]-4,6,7,8,9,10-hexahydro-3-hydroxy-4-oxo-. $^1$H NMR (500 MHz, DMSO-d$_6$) δ ppm 11.95 (1 H, brs), 8.83-8.96 (1 H, m), 8.06 (1 H, d, J=9.77 Hz), 7.01-7.29 (3 H, m), 6.40 (1 H, d, J=2.44 Hz), 4.48-4.64 (1 H, m), 4.30-4.48 (1 H, m), 3.98-4.04 (2 H, m), 3.90 (1 H, ddd, J=11.37, 7.71, 4.12 Hz), 3.73-3.79 (3H, m), 3.60-3.68 (1 H, m), 3.52 (1 H, ddd, J=11.83, 8.01, 3.97 Hz), 3.28-3.45 (1 H, m), 3.01-3.18 (1 H, m), 2.40 (1 H, brs), 2.24-2.35 (5 H, m), 2.20 (3 H, d, J=5.19 Hz), 1.82-2.14 (4 H, m), 1.73-1.82 (2 H, m), 1.54-1.65 (2 H, m). LCMS (M+H)+=606.2.

Example 302

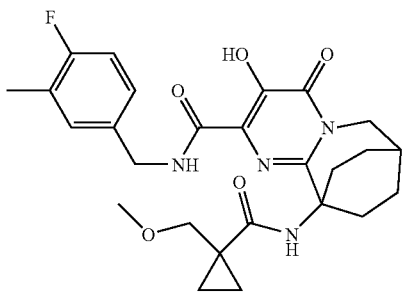

7,10-Ethanopyrimido[1,2-a]azepine-2-carboxamide, N-[(4-fluoro-3-methylphenyl)methyl]-4,6,7,8,9,10-hexahydro-3-hydroxy-10-[[[1-(methoxymethyl)cyclopropyl]carbonyl]amino]-4-oxo-. $^1$H NMR (500 MHz, DMSO-d$_6$) δ ppm 12.13 (1 H, s), 8.92 (1 H, t, J=6.26 Hz), 8.69 (1 H, s), 7.23 (1 H, d, J=7.02 Hz), 7.14-7.19 (1 H, m), 7.11 (1 H, t, J=9.00 Hz), 4.48 (2 H, d, J=6.10 Hz), 4.02 (2H, d, J=3.66 Hz), 3.53 (2 H, s), 3.18 (3 H, s), 2.63-2.73 (2 H, m), 2.39 (1 H, brs), 2.22 (3 H, s), 1.74-1.85 (4 H, m), 1.58-1.68 (2 H, m), 0.94-0.99 (2 H, m), 0.59-0.64 (2 H, m). LCMS (M+H)+=499.2.

Example 303

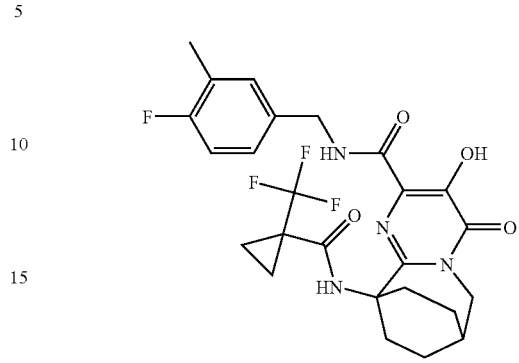

7,10-Ethanopyrimido[1,2-a]azepine-2-carboxamide, N-[(4-fluoro-3-methylphenyl)methyl]-4,6,7,8,9,10-hexahydro-3-hydroxy-4-oxo-10-[[[1-(trifluoromethyl)cyclopropyl]carbonyl]amino]-. $^1$H NMR (500 MHz, DMSO-d$_6$) δ ppm 9.26 (1 H, t, J=6.41 Hz), 7.22 (1 H, d, J=7.32 Hz), 7.14-7.18 (1 H, m), 7.10 (1H, t, J=9.16 Hz), 4.43 (2 H, d, J=6.10 Hz), 4.05 (2 H, d, J=3.05 Hz), 2.48 (1 H, brs), 2.16-2.26 (5 H, m), 2.02-2.11 (2 H, m), 1.82-1.92 (2 H, m), 1.73-1.82 (4 H, m), 1.63-1.68 (2 H, m). LCMS (M+H)+=523.1.

Example 304

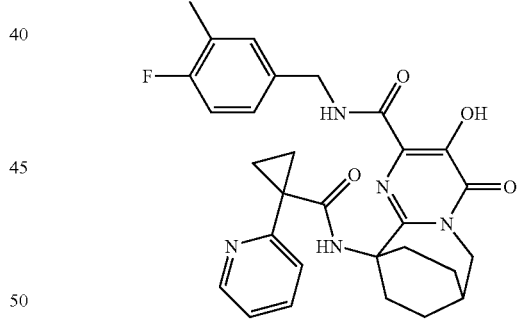

7,10-Ethanopyrimido[1,2-a]azepine-2-carboxamide, N-[(4-fluoro-3-methylphenyl)methyl]-4,6,7,8,9,10-hexahydro-3-hydroxy-4-oxo-10-[[[1-(2-pyridinyl)cyclopropyl]carbonyl]amino]-. $^1$H NMR (500 MHz, DMSO-d$_6$) δ ppm 11.85 (1 H, brs), 9.35 (1 H, t, J=5.80 Hz), 8.45 (1 H, d, J=4.58 Hz), 7.89 (1 H, t, J=7.63 Hz), 7.48 (1 H, d, J=7.93 Hz), 7.34-7.43 (2 H, m), 7.12 (1 H, d, J=7.32 Hz), 7.01-7.09 (2 H, m), 4.47 (2 H, d, J=6.41 Hz), 3.99-4.04 (2 H, m), 2.39 (1 H, brs), 2.17 (3 H, s), 2.08-2.14 (2 H, m), 2.01 (2 H, ddd, J=14.50, 7.17, 7.02 Hz), 1.67-1.78 (2 H, m), 1.52-1.61 (2 H, m), 1.28-1.33 (2 H, m), 1.01-1.07 (2 H, m). LCMS (M+H)+=532.16.

Example 305

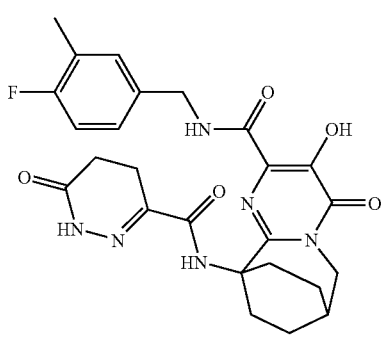

7,10-Ethanopyrimido[1,2-a]azepine-2-carboxamide, N-[(4-fluoro-3-methylphenyl)methyl]-4,6,7,8,9,10-hexahydro-3-hydroxy-4-oxo-10-[[(1,4,5,6-tetrahydro-6-oxo-3-pyridazinyl)carbonyl]amino]-. $^1$H NMR (500 MHz, DMSO-d$_6$) δ ppm 11.79 (1 H, brs), 11.04 (1 H, s), 8.47 (1 H, s), 8.43 (1 H, t, J=6.26 Hz), 7.19 (1H, d, J=7.02 Hz), 7.04-7.15 (2 H, m), 4.53 (2 H, d, J=6.10 Hz), 4.03 (2 H, d, J=3.05 Hz), 2.57 (2 H, t, J=8.24 Hz), 2.40-2.47 (3 H, m), 2.27 (2 H, t, J=8.39 Hz), 2.20 (3H, s), 2.00-2.10 (2 H, m), 1.77-1.87 (2 H, m), 1.61-1.70 (2 H, m). LCMS (M+H)+=511.18.

Example 306

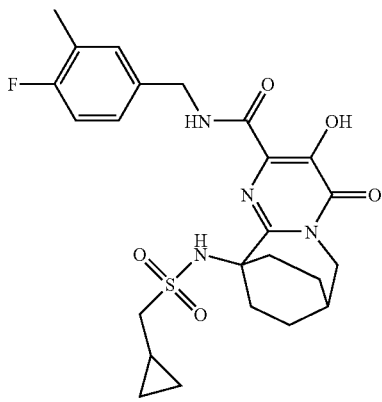

7,10-Ethanopyrimido[1,2-a]azepine-2-carboxamide, 10-[[[(cyclopropylmethyl)sulfonyl]amino]-N-[(4-fluoro-3-methylphenyl)methyl]-4,6,7,8,9,10-hexahydro-3-hydroxy-4-oxo-. $^1$H NMR (500 MHz, DMF) δ ppm 9.56 (1H, t, J=6.26 Hz), 8.98 (2 H, brs), 7.68 (1 H, d, J=7.63 Hz), 7.58-7.63 (1 H, m), 7.53 (1 H, t, J=9.16 Hz), 4.87 (2 H, d, J=6.10 Hz), 4.48 (2 H, d, J=3.66 Hz), 4.08 (2 H, d, J=7.32 Hz), 2.89 (1 H, brs), 2.60-2.68 (5 H, m), 2.43-2.51 (2 H, m), 2.26-2.35 (2H, m), 2.19-2.26 (2 H, m), 1.62-1.71 (1 H, m), 1.05-1.11 (2 H, m), 0.90 (2 H, q, J=4.88 Hz). LCMS (M+H)+=505.1.

Example 307

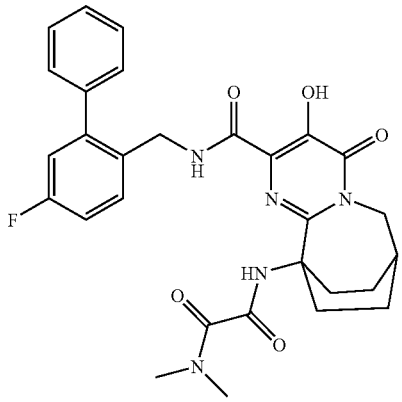

Ethanediamide, N'-[2-[[[(5-fluoro/[1,1'-biphenyl]-2-yl)methyl]amino]carbonyl]-6,7,8,9-tetrahydro-3-hydroxy-4-oxo-7,10-ethanopyrimido[1,2-a]azepin-10(4H)-yl]-N,N-dimethyl-. $^1$H NMR (400 MHz, CDCl$_3$) δ ppm 12.01 (s, 1 H), 8.30 (s, 2 H), 7.31-7.46 (m, 6 H), 7.03 (td, J=8.47, 2.64 Hz, 1 H), 6.97 (dd, J=9.54, 2.76 Hz, 1 H), 4.50 (d, J=6.02 Hz, 2 H), 4.15 (d, J=3.76 Hz, 2 H), 3.27 (s, 3 H), 2.79 (s, 3 H), 2.46-2.62 (m, 3 H), 1.90-2.11 (m, 4H), 1.64-1.76 (m, 2 H). LCMS (+ESI, M+H+) m/z 548.2. HPLC purity: 98%.

Example 308

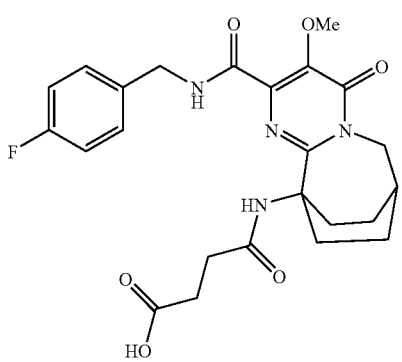

Butanoic acid, 4-[[2-[[[(4-fluorophenyl)methyl]amino]carbonyl]-6,7,8,9-tetrahydro-3-methoxy-4-oxo-7,10-ethanopyrimido[1,2-a]azepin-10(4H)-yl]amino]-4-oxo-. $^1$H NMR (500 MHz, CDCl$_3$) δ ppm 8.37 (t, 1 H), 8.29 (s, 1 H), 7.30 (dd, J=8.70, 5.34 Hz, 2 H), 7.01 (t, 2 H), 4.58 (d, J=5.80 Hz, 2 H), 4.06 (d, J=3.66 Hz, 2H), 3.96 (s, 3 H), 2.86-2.97 (m, 2 H), 2.58-2.64 (m, 2 H), 2.51-2.58 (m, 2 H), 2.42 (s, 1 H), 1.91-2.00 (m, 2 H), 1.76-1.86 (m, 2 H), 1.59-1.68 (m, 2 H). LCMS (+ESI, M+H+) m/z 487.3. HPLC purity: 96%.

Example 309

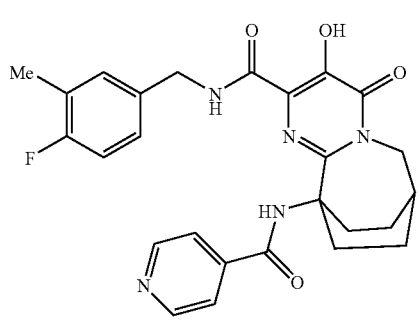

7,10-Ethanopyrimido[1,2-a]azepine-2-carboxamide, N-[(4-fluoro-3-methylphenyl)methyl]-4,6,7,8,9,10-hexahydro-3-hydroxy-4-oxo-10-[(4-pyridinylcarbonyl)amino]-. $^1$H NMR (500 MHz, DMSO-D6) δ ppm 8.83 (s, 1 H), 8.71 (d, J=5.49 Hz, 2 H), 8.66 (t, J=6.26 Hz, 1 H), 7.85 (d, J=4.88 Hz, 2 H), 7.02 (dd, J=18.92, 9.16 Hz, 2 H), 6.93-6.98 (m, 1 H), 4.33 (d, J=6.10 Hz, 2 H), 4.02-4.07 (m, 2 H), 2.42-2.46 (m, 1 H), 2.33-2.42 (m, 2 H), 2.18-2.25 (m, 2 H), 2.16 (s, 3H), 1.79-1.89 (m, 2 H), 1.66 (d, J=5.49 Hz, 2 H). LCMS ($^+$ESI, M+H$^+$) m/z 492.1. HPLC purity: 91%.

Example 310

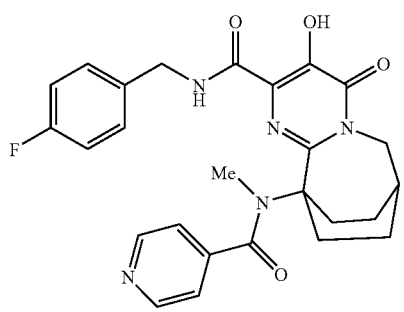

7,10-Ethanopyrimido[1,2-a]azepine-2-carboxamide, N-[(4-fluorophenyl)methyl]-4,6,7,8,9,10-hexahydro-3-hydroxy-10-[methyl(4-pyridinylcarbonyl)amino]-4-oxo-. $^1$H NMR (500 MHz, DMSO-d$_6$) δ ppm (major rotamer) 8.49 (d, J=5.19 Hz, 2 H), 7.36 (dd, J=8.24, 5.80 Hz, 2 H), 7.30 (br. s., 2 H), 7.16 (t, J=8.70 Hz, 2 H), 4.01-4.09 (m, 4 H), 2.96-3.01 (m, 3 H), 2.39-2.46 (m, 1H), 1.23-2.19 (m, 8H). LCMS ($^+$ESI, M+H$^+$) m/z 492.2. HPLC purity: 95%.

Example 311

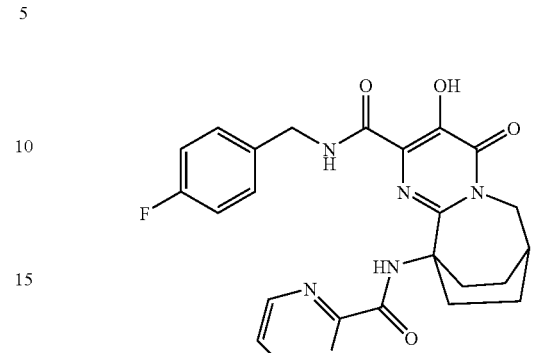

7,10-Ethanopyrimido[1,2-a]azepine-2-carboxamide, N-[(4-fluorophenyl)methyl]-4,6,7,8,9,10-hexahydro-3-hydroxy-4-oxo-10-[(2-pyrimidinylcarbonyl)amino]-. $^1$H NMR (500 MHz, DMSO-d$_6$) δ ppm 11.88 (br. s., 1H), 9.62 (br. s., 1 H), 8.87 (br. s., 1 H), 8.74 (d, J=2.75 Hz, 2 H), 7.61 (br. s., 1 H), 7.35 (br. s., 2 H), 7.12-7.23 (m, 2 H), 4.58 (d, J=4.58 Hz, 2 H), 4.07 (br. s., 2 H), 2.64 (br. s., 2 H), 2.42-2.47 (m, 1 H), 2.07 (br. s., 2 H), 1.88 (br. s., 2 H), 1.70 (br. s., 2 H). LCMS ($^+$ESI, M+H$^+$) m/z 479.1. HPLC purity: 96%.

Example 312

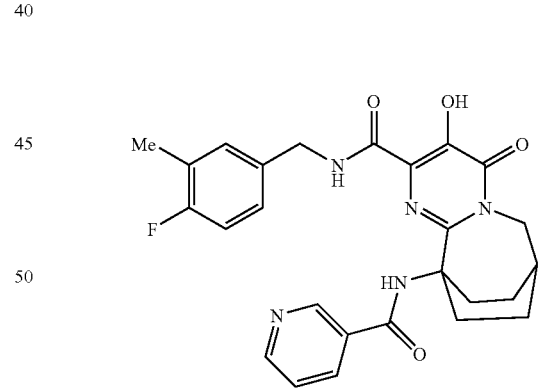

7,10-Ethanopyrimido[1,2-a]azepine-2-carboxamide, N-[(4-fluoro-3-methylphenyl)methyl]-4,6,7,8,9,10-hexahydro-3-hydroxy-4-oxo-10-[(3-pyridinylcarbonyl)amino]-. $^1$H NMR (500 MHz, CHLOROFORM-d) δ ppm 9.00 (d, J=1.83 Hz, 1 H), 8.70 (dd, J=4.88, 1.53 Hz, 1 H), 8.10 (d, J=8.24 Hz, 1 H), 7.75 (s, 1H), 7.32 (dd, J=8.09, 5.04 Hz, 1 H), 7.02-7.07 (m, 1 H), 6.96-7.01 (m, 1 H), 6.89 (t, J=8.85 Hz, 1 H), 4.46 (d, J=6.10 Hz, 2 H), 4.21 (d, J=3.66 Hz, 2 H), 3.49 (s, 1 H), 2.80-2.90 (m, 2 H), 2.53 (br. s., 1 H), 2.22 (d, J=1.83 Hz, 3 H), 1.99-2.12 (m, 4 H), 1.71-1.87 (m, 2 H). LCMS (+ESI, M+H+) m/z 492.1. HPLC purity: 97%.

Example 313

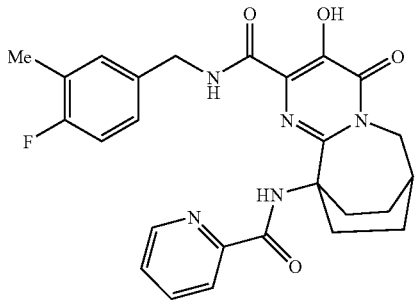

7,10-Ethanopyrimido[1,2-a]azepine-2-carboxamide, N-[(4-fluoro-3-methylphenyl)methyl]-4,6,7,8,9,10-hexahydro-3-hydroxy-4-oxo-10-[(2-pyridinylcarbonyl)amino]-. $^1$H NMR (500 MHz, CHLOROFORM-d) δ ppm 12.03 (br. s., 1 H), 10.14 (s, 1 H), 8.12 (d, J=7.63 Hz, 1 H), 8.08 (t, J=5.95 Hz, 1 H), 7.80 (td, J=7.71, 1.68 Hz, 1 H), 7.74 (d, J=4.88 Hz, 1 H), 7.23-7.29 (m, 1 H), 7.17 (d, J=7.32 Hz, 1 H), 7.10-7.15 (m, 1 H), 6.97 (t, J=8.85 Hz, 1 H), 4.62 (d, J=6.10 Hz, 2H), 4.21 (d, J=3.97 Hz, 2 H), 3.05-3.13 (m, 2 H), 2.47-2.58 (m, 1 H), 2.23 (d, J=1.83 Hz, 3 H), 2.03-2.12 (m, 2 H), 1.88-1.97 (m, 2 H), 1.70-1.81 (m, 2 H). LCMS (+ESI, M+H+) m/z 492.1. HPLC purity: 92%.

Example 314

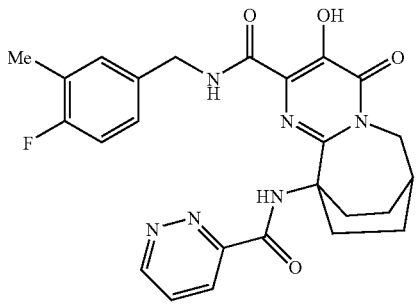

7,10-Ethanopyrimido[1,2-a]azepine-2-carboxamide, N-[(4-fluoro-3-methylphenyl)methyl]-4,6,7,8,9,10-hexahydro-3-hydroxy-4-oxo-10-[(3-pyridazinylcarbonyl)amino]-. $^1$H NMR (500 MHz, CHLOROFORM-d) δ ppm 12.03 (br. s., 1 H), 10.84 (s, 1 H), 9.30 (dd, J=5.04, 1.68 Hz, 1 H), 8.49 (t, J=6.56 Hz, 1 H), 8.30 (dd, J=8.55, 1.83 Hz, 1 H), 7.69 (dd, J=8.55, 4.88 Hz, 1 H), 7.33 (dd, J=7.17, 1.68 Hz, 1 H), 7.26-7.30 (m, 1 H), 6.85-6.94 (m, 1 H), 4.67 (d, J=6.71 Hz, 2 H), 4.20 (d, J=3.66 Hz, 2 H), 3.08 (ddd, J=14.42, 9.54, 5.34 Hz, 2 H), 2.53 (br. s., 1 H), 2.22 (d, J=1.83 Hz, 3 H), 2.05-2.16 (m, 2 H), 1.91-2.00 (m, 2 H), 1.73-1.84 (m, 2H). LCMS (+ESI, M+H+) m/z 493.0. HPLC purity: 95%.

Example 315

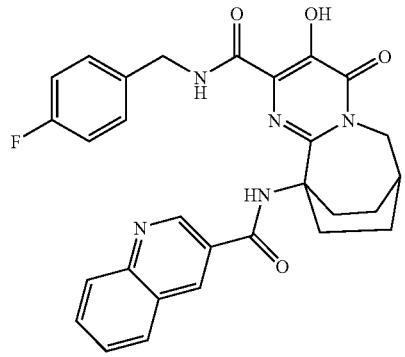

7,10-Ethanopyrimido[1,2-a]azepine-2-carboxamide, N-[(4-fluorophenyl)methyl]-4,6,7,8,9,10-hexahydro-3-hydroxy-4-oxo-10-[(3-quinolinylcarbonyl)amino]-. $^1$H NMR (500 MHz, CHLOROFORM-d) δ ppm 9.62 (br. s., 1 H), 9.11 (s, 1 H), 8.39 (d, J=8.85 Hz, 1 H), 8.09-8.16 (m, 2 H), 8.04 (d, J=7.93 Hz, 1 H), 7.91 (t, J=7.63 Hz, 1 H), 7.50 (br. s., 1 H), 6.95 (dd, J=8.24, 5.49 Hz, 2 H), 6.58 (t, J=8.55 Hz, 2 H), 4.41 (d, J=6.10 Hz, 2 H), 4.23 (d, J=3.66 Hz, 2 H), 2.62-2.72 (m, 2 H), 2.56 (br. s., 1 H), 2.28 (br. s., 2 H), 1.98-2.08 (m, 2 H), 1.75 (br. s., 2 H). LCMS (+ESI, M+H+) m/z 528.0. HPLC purity: 91%.

Example 316

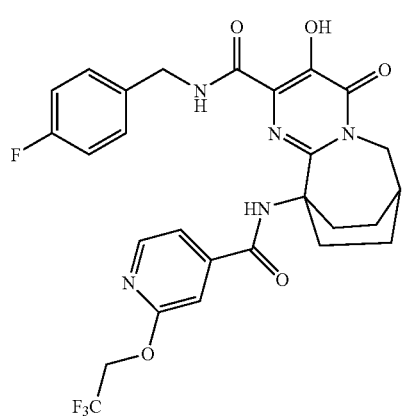

7,10-Ethanopyrimido[1,2-a]azepine-2-carboxamide, N-[(4-fluorophenyl)methyl]-4,6,7,8,9,10-hexahydro-3-hydroxy-4-oxo-10-[[[2-(2,2,2-trifluoroethoxy)-4-pyridinyl]carbonyl]amino]-. $^1$H NMR (500 MHz, DMSO-d$_6$) δ ppm 11.78 (br. s., 1 H), 8.74 (t, J=6.26 Hz, 1 H), 8.58 (d, J=2.14 Hz, 1 H), 8.55 (s, 1H), 8.10 (dd, J=8.55, 2.44 Hz, 1 H), 7.14-7.20 (m, 2 H), 7.04-7.11 (m, 2 H), 6.94 (d, J=8.55 Hz, 1 H), 5.05 (q, J=9.05 Hz, 2 H), 4.38 (d, J=6.10 Hz, 2 H), 4.05 (d, J=3.66 Hz, 2 H), 2.45 (br. s., 1 H), 2.36-2.44 (m, 2 H), 2.15-2.24 (m, 2 H), 1.84 (td, J=13.89, 5.49 Hz, 2 H), 1.61-1.69 (m, 2 H). LCMS (⁺ESI, M+H⁺) m/z 575.9. HPLC purity: 91%.

Example 317

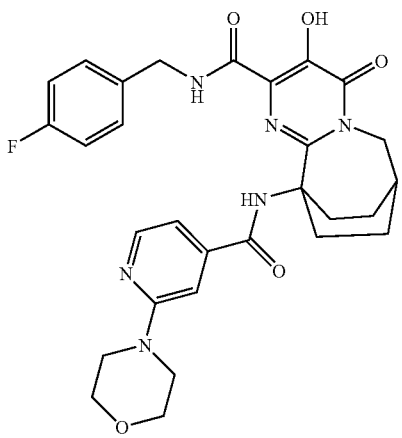

7,10-Ethanopyrimido[1,2-a]azepine-2-carboxamide, N-[(4-fluorophenyl)methyl]-4,6,7,8,9,10-hexahydro-3-hydroxy-10-[[[2-(4-morpholinyl)-4-pyridinyl]carbonyl]amino]-4-oxo-. ¹H NMR (500 MHz, MeOD) δ ppm 7.94 (br. s., 1 H), 7.48 (br. s., 1 H), 7.20 (br. s., 2 H), 7.10 (br. s., 1 H), 6.96-7.04 (m, 2 H), 4.49 (br. s., 2 H), 4.17-4.23 (m, 2 H), 3.85 (br. s., 4 H), 3.65 (br. s., 4 H), 2.55 (br. s., 1H), 2.36-2.47 (m, 4 H), 2.02 (d, J=5.49 Hz, 2 H), 1.78 (d, J=5.49 Hz, 2 H). LCMS (⁺ESI, M+H⁺) m/z 563.0. HPLC purity: 93%.

Example 318

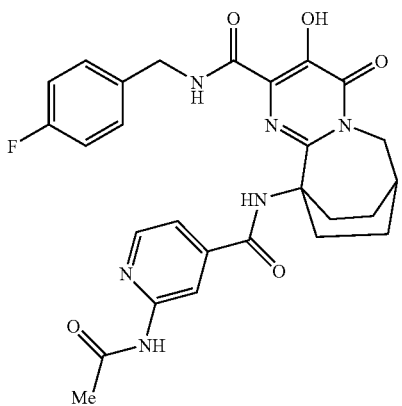

7,10-Ethanopyrimido[1,2-a]azepine-2-carboxamide, 10-[[[2-(acetylamino)-4-pyridinyl]carbonyl]amino]-N-[(4-fluorophenyl)methyl]-4,6,7,8,9,10-hexahydro-3-hydroxy-4-oxo-. ¹H NMR (500 MHz, MeOD) δ ppm 8.45 (br. s., 1 H), 8.38 (br. s., 1H), 7.48 (br. s., 1 H), 7.24 (br. s., 2 H), 6.98 (br. s., 2 H), 4.53 (br. s., 2 H), 4.16 (br. s., 2 H), 2.74 (br. s., 2 H), 2.49 (br. s., 1 H), 2.20 (s, 3 H), 2.08-2.16 (m, 2 H), 2.03 (br. s., 2 H), 1.70-1.80 (m, 2 H). LCMS (⁺ESI, M+H⁺) m/z 535.1. HPLC purity: 97%.

Example 319

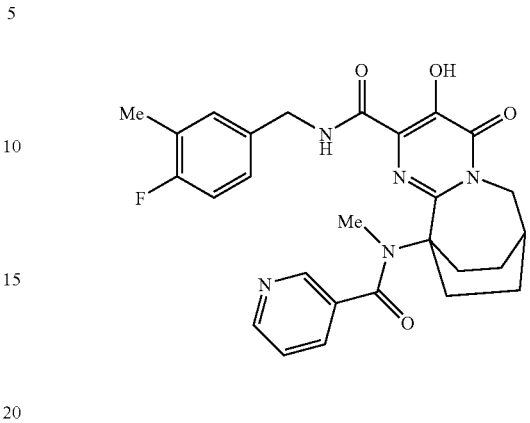

7,10-Ethanopyrimido[1,2-a]azepine-2-carboxamide, N-[(4-fluoro-3-methylphenyl)methyl]-4,6,7,8,9,10-hexahydro-3-hydroxy-10-[methyl(3-pyridinylcarbonyl)amino]-4-oxo-. ¹H NMR (400 MHz, DMSO-d6) (spectrum complicated by rotamers) δ ppm 11.91 (s, 1 H), 8.58-8.64 (m, 2 H), 8.49-8.57 (m, 1 H), 7.72 (d, J=7.28 Hz, 1 H), 7.31 (dd, J=7.53, 5.02 Hz, 1 H), 7.10-7.18 (m, 2 H), 7.04 (t, J=8.91 Hz, 1 H), 4.28-4.67 (m, 3 H), 3.76 (br. s., 1 H), 3.09 (s, 3 H), 2.44-2.49 (m, 1 H), 2.16 (s, 3 H), 2.10-2.24 (m, 2 H), 1.93 (br. s., 2 H), 1.76 (br. s., 2 H), 1.35-1.53 (m, 2 H). LCMS (⁺ESI, M+H⁺) m/z 506.1. HPLC purity: 91%.

Example 320

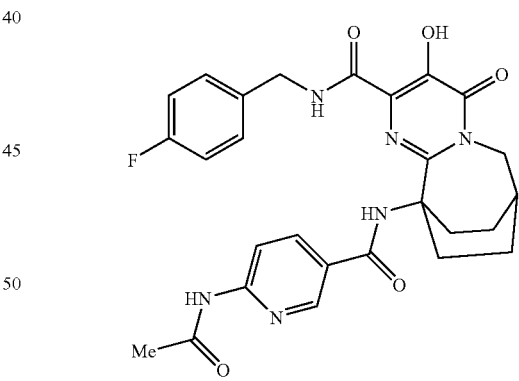

7,10-Ethanopyrimido[1,2-a]azepine-2-carboxamide, 10-[[[6-(acetylamino)-3-pyridinyl]carbonyl]amino]-N-[(4-fluorophenyl)methyl]-4,6,7,8,9,10-hexahydro-3-hydroxy-4-oxo-. ¹H NMR (500 MHz, CHLOROFORM-d) δ ppm 11.19 (br. s., 1 H), 8.51 (d, J=2.14 Hz, 1 H), 8.46 (d, J=8.85 Hz, 1 H), 8.14 (dd, J=9.00, 2.29 Hz, 1 H), 7.53 (s, 1 H), 7.15-7.21 (m, 3 H), 6.94-7.02 (m, 2 H), 4.52 (d, J=5.80 Hz, 2 H), 4.21 (d, J=3.66 Hz, 2 H), 2.71-2.81 (m, 2 H), 2.54 (br. s., 1 H), 2.36 (s, 3 H), 1.95-2.13 (m, 4 H), 1.74 (br. s., 2 H). LCMS (⁺ESI, M+H⁺) m/z 535.0. HPLC purity: 81%.

Example 321

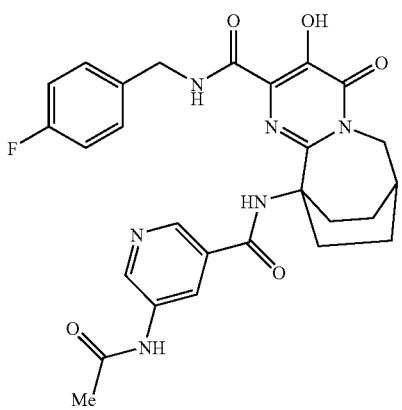

7,10-Ethanopyrimido[1,2-a]azepine-2-carboxamide, 10-[[[5-(acetylamino)-3-pyridinyl]carbonyl]amino]-N-[(4-fluorophenyl)methyl]-4,6,7,8,9,10-hexahydro-3-hydroxy-4-oxo-. $^1$H NMR (500 MHz, CHLOROFORM-d) δ ppm 9.93 (s, 1 H), 9.44 (d, J=1.53 Hz, 1 H), 9.22 (s, 1 H), 8.80 (d, J=1.22 Hz, 1 H), 8.52 (s, 1 H), 7.89 (t, J=6.10 Hz, 1 H), 7.12 (dd, J=8.70, 5.34 Hz, 2 H), 6.85-6.92 (m, 2 H), 4.51 (d, J=6.10 Hz, 2 H), 4.22 (d, J=3.66 Hz, 2 H), 2.70 (ddd, J=14.19, 9.00, 5.80 Hz, 2 H), 2.56 (br. s., 1 H), 2.26 (s, 3 H), 2.19-2.26 (m, 2 H), 1.99-2.09 (m, 2 H), 1.69-1.80 (m, 2 H). LCMS ($^+$ESI, M+H$^+$) m/z 535.0. HPLC purity: 98%.

Example 322

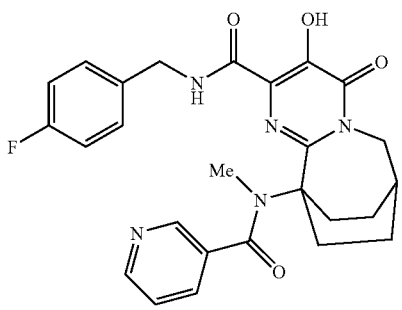

7,10-Ethanopyrimido[1,2-a]azepine-2-carboxamide, N-[(4-fluorophenyl)methyl]-4,6,7,8,9,10-hexahydro-3-hydroxy-10-[methyl(3-pyridinylcarbonyl)amino]-4-oxo. LCMS ($^+$ESI, M+H$^+$) m/z 492.0. HPLC purity: 97%.

Example 323

7,10-Ethanopyrimido[1,2-a]azepine-2-carboxamide, N-[(4-fluorophenyl)methyl]-4,6,7,8,9,10-hexahydro-3-hydroxy-4-oxo-10-[[[6-(trifluoromethyl)-3-pyridinyl]carbonyl]amino]-. $^1$H NMR (500 MHz, DMSO-d$_6$) δ ppm 11.53-11.83 (m, 1 H), 9.11 (br. s., 2 H), 8.36 (br. s., 1 H), 7.89 (d, J=7.02 Hz, 1 H), 7.19 (br. s., 2 H), 7.06 (br. s., 2 H), 4.41 (d, J=3.05 Hz, 2 H), 4.04 (br. s., 2 H), 2.44 (br. s., 1 H), 2.12 (br. s., 2 H), 1.80-1.94 (m, 4 H), 1.67 (br. s., 2 H). $^{19}$F NMR (471 MHz, DMSO-d$_6$) δ ppm-67.12 (br. s., 3F), −116.29 (br. s., 1F). LCMS ($^+$ESI, M+H$^+$) m/z 545.9. HPLC purity: 93%.

Example 324

7,10-Ethanopyrimido[1,2-a]azepine-2-carboxamide, N-[(4-fluorophenyl)methyl]-4,6,7,8,9,10-hexahydro-3-hydroxy-4-oxo-10-[[(2-pyridinylamino)carbonyl]amino]-. $^1$H NMR (400 MHz, DMF) δ ppm 12.32 (br. s., 1H), 9.27 (br. s., 1 H), 9.04 (br. s., 1 H), 8.52 (br. s., 1 H), 8.33 (d, J=4.27 Hz, 1 H), 7.76-7.90 (m, 2 H), 7.40-7.50 (m, 2 H), 7.24 (t, J=8.66 Hz, 2 H), 7.08 (t, J=5.90 Hz, 1 H), 4.60 (d, J=6.27 Hz, 2 H), 4.29 (d, J=3.26 Hz, 2 H), 2.76-2.87 (m, 2 H), 2.63 (br. s., 1 H), 2.19-2.33 (m, 2 H), 2.00-2.14 (m, 2 H), 1.90 (br. s., 2 H). LCMS ($^+$ESI, M+H$^+$) m/z 493.2. HPLC purity: 98%.

Example 325

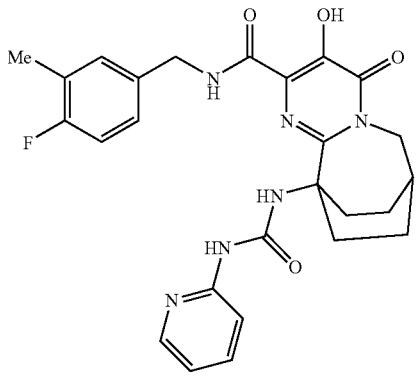

7,10-Ethanopyrimido[1,2-a]azepine-2-carboxamide, N-[(4-fluoro-3-methylphenyl)methyl]-4,6,7,8,9,10-hexahydro-3-hydroxy-4-oxo-10-[[(2-pyridinylamino)carbonyl]amino]-. ¹H NMR (500 MHz, DMSO-d₆) d ppm 11.92 (br. s., 1 H), 9.39 (s, 1 H), 8.92 (br. s., 1 H), 8.14 (d, J=4.27 Hz, 1 H), 7.63-7.68 (m, 1 H), 7.52-7.59 (m, 1 H), 7.09 (d, J=7.02 Hz, 1 H), 6.96-7.06 (m, 2 H), 6.86-6.94 (m, 1 H), 4.38 (d, J=6.41 Hz, 2 H), 4.05 (d, J=3.36 Hz, 2 H), 2.55-2.65 (m, 2 H), 2.42 (br. s., 1 H), 2.17 (s, 3 H), 1.94-2.03 (m, 2 H), 1.82 (td, J=13.89, 5.49 Hz, 2 H), 1.65 (d, J=5.80 Hz, 2 H). LCMS (⁺ESI, M+H⁺) m/z 507.1. HPLC purity: 99%.

Example 326

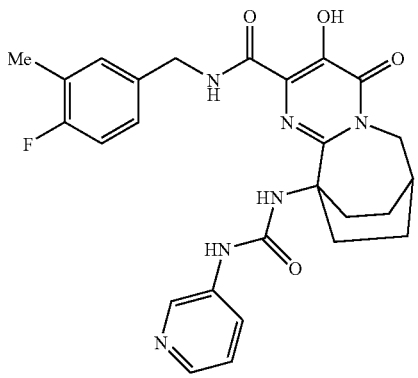

7,10-Ethanopyrimido[1,2-a]azepine-2-carboxamide, N-[(4-fluoro-3-methylphenyl)methyl]-4,6,7,8,9,10-hexahydro-3-hydroxy-4-oxo-10-[[(3-pyridinylamino)carbonyl]amino]-. ¹H NMR (500 MHz, DMSO-d₆) δ ppm 12.16 (br. s., 1 H), 10.15 (br. s., 1 H), 9.17-9.24 (m, 1 H), 9.02 (br. s., 1 H), 8.43 (d, J=4.88 Hz, 1 H), 8.18 (d, J=8.24 Hz, 1 H), 7.82 (dd, J=8.24, 5.49 Hz, 1 H), 7.35 (s, 1 H), 7.15 (d, J=7.32 Hz, 1 H), 7.03-7.11 (m, 1 H), 6.92 (t, J=9.00 Hz, 1 H), 4.45 (d, J=5.80 Hz, 2 H), 4.05 (br. s., 2 H), 2.46-2.53 (m, 2 H), 2.43 (br. s., 1 H), 2.14 (s, 3 H), 1.97-2.07 (m, 2 H), 1.82 (d, J=5.19 Hz, 2 H), 1.65 (br. s., 2 H). LCMS (⁺ESI, M+H⁺) m/z 507.0. HPLC purity: 94%.

Example 327

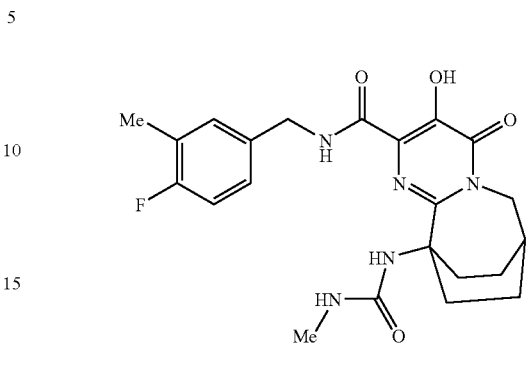

7,10-Ethanopyrimido[1,2-a]azepine-2-carboxamide, N-[(4-fluoro-3-methylphenyl)methyl]-4,6,7,8,9,10-hexahydro-3-hydroxy-10-[[(methylamino)carbonyl]amino]-4-oxo-. ¹H NMR (500 MHz, CHLOROFORM-d) δ ppm 11.97 (br. s., 1 H), 8.03-8.12 (m, 1 H), 7.10 (d, J=7.32 Hz, 1 H), 7.05 (td, J=5.26, 2.29 Hz, 1 H), 6.91 (t, J=8.85 Hz, 1 H), 4.46 (d, J=6.10 Hz, 2 H), 4.07 (d, J=3.36 Hz, 2 H), 2.46 (s, 3 H), 2.44 (br. s., 1 H), 2.34 (ddd, J=14.11, 8.93, 5.65 Hz, 2 H), 2.22 (d, J=1.53 Hz, 3 H), 2.05-2.15 (m, 2 H), 1.82-1.94 (m, 2 H), 1.54-1.67 (m, 2 H). LCMS (⁺ESI, M+H⁺) m/z 444.1. HPLC purity: 98%.

Example 328

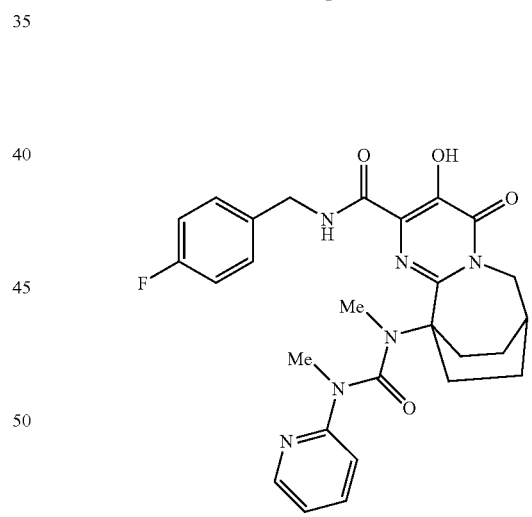

7,10-Ethanopyrimido[1,2-a]azepine-2-carboxamide, N-[(4-fluorophenyl)methyl]-4,6,7,8,9,10-hexahydro-3-hydroxy-10-[methyl[(methyl-2-pyridinylamino)carbonyl]amino]-4-oxo-. ¹H NMR (500 MHz, CHLOROFORM-d) d ppm 8.31 (d, J=4.27 Hz, 1 H), 7.98 (t, J=5.95 Hz, 1 H), 7.73 (t, J=7.93 Hz, 1 H), 7.19 (d, J=8.55 Hz, 1 H), 7.15 (dd, J=8.39, 5.34 Hz, 2 H), 7.09 (t, J=6.10 Hz, 1 H), 6.94 (t, J=8.70 Hz, 2 H), 4.46 (br. s., 2 H), 3.49 (s, 3 H), 3.24 (s, 2 H), 2.91 (s, 3 H), 2.50 (br. s., 1 H), 1.43-2.04 (m, 8H). LCMS (⁺ESI, M+H⁺) m/z 521.2. HPLC purity: 93%.

Example 329

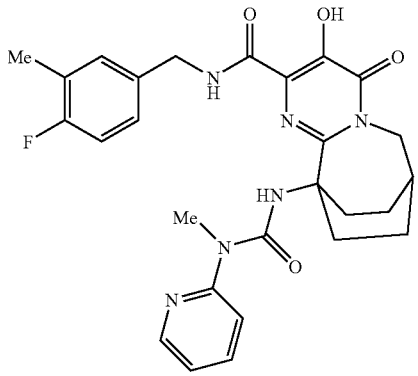

7,10-Ethanopyrimido[1,2-a]azepine-2-carboxamide, N-[(4-fluoro-3-methylphenyl)methyl]-4,6,7,8,9,10-hexahydro-3-hydroxy-10-[[(methyl-2-pyridinylamino)carbonyl]amino]-4-oxo-. $^1$H NMR (500 MHz, CHLOROFORM-d) δ ppm 11.71 (s, 1 H), 9.80 (s, 1 H), 8.09-8.17 (m, 2 H), 7.66-7.72 (m, 1 H), 6.94 (dd, J=7.32, 4.88 Hz, 1 H), 6.84 (d, J=8.55 Hz, 1 H), 6.81 (d, J=6.41 Hz, 1 H), 6.70-6.78 (m, 2 H), 4.24 (d, J=6.41 Hz, 2 H), 4.18 (d, J=3.97 Hz, 2 H), 3.07 (s, 3 H), 2.48 (d, J=2.44 Hz, 1 H), 2.21-2.36 (m, 4 H), 2.16 (d, J=1.83 Hz, 3 H), 1.84-1.94 (m, 2 H), 1.61-1.72 (m, 2 H). LCMS ($^+$ESI, M+H$^+$) m/z 521.0. HPLC purity: 96%.

Example 330

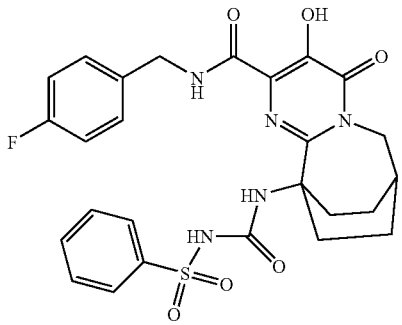

7,10-Ethanopyrimido[1,2-a]azepine-2-carboxamide, N-[(4-fluorophenyl)methyl]-4,6,7,8,9,10-hexahydro-3-hydroxy-4-oxo-10-[[[(phenylsulfonyl)amino]carbonyl]amino]- $^1$H NMR (500 MHz, CHLOROFORM-d) δ ppm 12.56 (br. s., 1 H), 9.06 (s, 1 H), 8.76 (t, J=6.10 Hz, 1 H), 7.67-7.70 (m, 2 H), 7.63 (t, J=7.48 Hz, 1 H), 7.45 (t, J=7.93 Hz, 2 H), 7.18-7.25 (m, 3 H), 6.75-6.82 (m, 2 H), 4.53 (d, J=6.41 Hz, 2 H), 4.16 (d, J=3.97 Hz, 2 H), 2.80-2.90 (m, 2 H), 2.45 (d, J=1.83 Hz, 1 H), 1.89-1.99 (m, 2 H), 1.59-1.72 (m, 4 H). LCMS (+ESI, M+H$^+$) m/z 556.2. HPLC purity: 90%.

Example 331

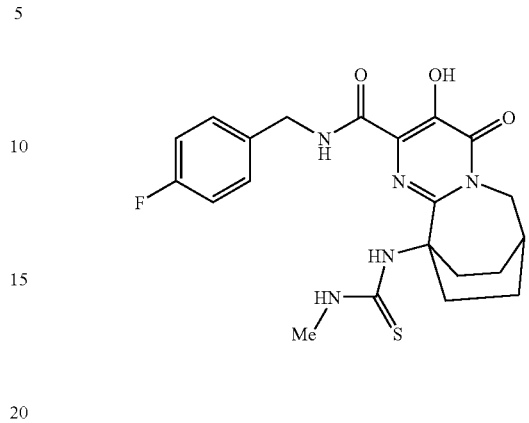

7,10-Ethanopyrimido[1,2-a]azepine-2-carboxamide, N-[(4-fluorophenyl)methyl]-4,6,7,8,9,10-hexahydro-3-hydroxy-10-[[(methylamino)thioxomethyl]amino]-4-oxo-. $^1$H NMR (500 MHz, DMSO-d$_6$) δ ppm 11.98 (br. s., 1 H), 8.97 (br. s., 1 H), 7.82 (br. s., 1 H), 7.39 (dd, J=8.24, 5.80 Hz, 3 H), 7.15-7.20 (m, 2 H), 4.51 (d, J=6.41 Hz, 2 H), 4.00 (d, J=3.66 Hz, 2 H), 2.72-2.88 (m, 5 H), 2.41 (br. s., 1 H), 2.05 (d, J=4.88 Hz, 2 H), 1.79 (td, J=14.04, 5.80 Hz, 2 H), 1.57-1.65 (m, 2 H). LCMS ($^+$ESI, M+H$^+$) m/z 446.1. HPLC purity: 92%.

Example 332

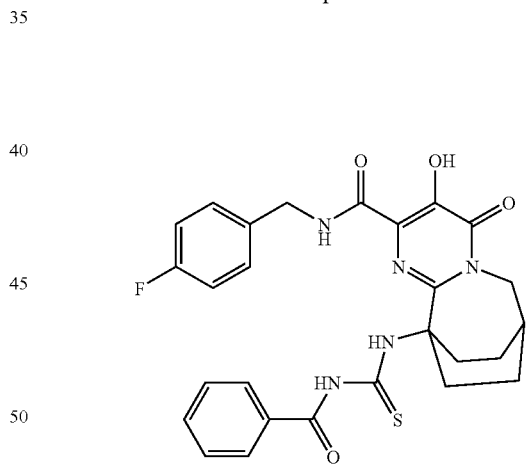

7,10-Ethanopyrimido[1,2-a]azepine-2-carboxamide, 10-[[(benzoylamino)thioxomethyl]amino]-N-[(4-fluorophenyl)methyl]-4,6,7,8,9,10-hexahydro-3-hydroxy-4-oxo- $^1$H NMR (500 MHz, CHLOROFORM-d) δ ppm 12.51 (s, 1 H), 12.48 (s, 1 H), 9.45 (t, J=6.26 Hz, 1 H), 8.86 (s, 1 H), 7.63 (t, J=7.48 Hz, 1 H), 7.57 (d, J=7.32 Hz, 2 H), 7.46 (t, J=7.93 Hz, 2 H), 7.33 (dd, J=8.55, 5.19 Hz, 2 H), 6.90-6.98 (m, 2 H), 4.70 (d, J=6.41 Hz, 2 H), 4.22 (d, J=3.66 Hz, 2 H), 3.81-3.92 (m, 2 H), 2.53 (br. s., 1 H), 1.99-2.12 (m, 2 H), 1.69-1.83 (m, 4 H). LCMS (+ESI, M+H$^+$) m/z 536.2. HPLC purity: 90%.

Example 333

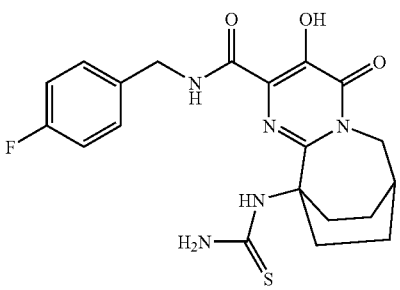

7,10-Ethanopyrimido[1,2-a]azepine-2-carboxamide, 10-[(aminothioxomethyl)amino]-N-[(4-fluorophenyl)methyl]-4,6,7,8,9,10-hexahydro-3-hydroxy-4-oxo-. $^1$H NMR (500 MHz, DMSO-d$_6$) δ ppm 9.10 (br. s., 1 H), 7.98 (br. s., 1 H), 7.41 (dd, J=8.39, 5.65 Hz, 2 H), 7.15-7.23 (m, 2 H), 4.52 (d, J=6.41 Hz, 2 H), 3.99 (br. s., 2 H), 3.37-3.55 (m, 4 H), 2.38-2.43 (m, 1 H), 1.71-1.84 (m, 2 H), 1.60 (d, J=1.53 Hz, 2 H). LCMS ($^+$ESI, M+H$^+$) m/z 432.1. HPLC purity: 94%.

Example 334

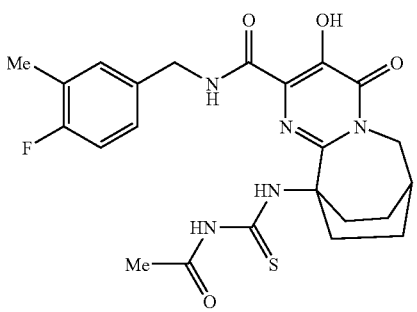

7,10-Ethanopyrimido[1,2-a]azepine-2-carboxamide, N-[(4-fluorophenyl)methyl]-4,6,7,8,9,10-hexahydro-3-hydroxy-10-(1H-imidazol-2-ylamino)-4-oxo-. $^1$H NMR (400 MHz, DMF) δ ppm 11.40-11.91 (m, 2 H), 9.81 (br. s., 1 H), 7.55 (t, J=6.27 Hz, 2 H), 7.32 (t, J=8.41 Hz, 2 H), 6.71 (s, 2 H), 6.45 (br. s., 1 H), 4.69 (d, J=6.02 Hz, 2 H), 4.24 (d, J=3.51 Hz, 2 H), 2.56-2.75 (m, 3 H), 2.20-2.34 (m, 2 H), 2.04 (dd, J=13.80, 8.78 Hz, 2 H), 1.85 (d, J=6.78 Hz, 2 H). LCMS ($^+$ESI, M+H$^+$) m/z 439.1. HPLC purity: 98%.

Example 335

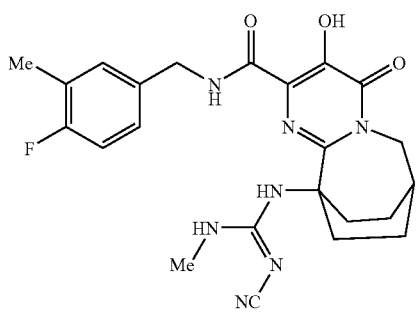

7,10-Ethanopyrimido[1,2-a]azepine-2-carboxamide, 10-[[(1Z)-(cyanoamino)(methylamino)methylene]amino]-N-[(4-fluoro-3-methylphenyl)methyl]-4,6,7,8,9,10-hexahydro-3-hydroxy-4-oxo-. $^1$H NMR (500 MHz, DMSO-d$_6$) δ ppm 11.95 (br. s., 1 H), 8.95 (t, J=6.26 Hz, 1 H), 7.34 (br. s., 1 H), 7.21-7.25 (m, 1 H), 7.14-7.20 (m, 1 H), 7.08-7.14 (m, 1 H), 6.86 (br. s., 1 H), 4.44 (d, J=6.41 Hz, 2 H), 4.00 (d, J=3.66 Hz, 2 H), 2.68 (d, J=4.58 Hz, 3 H), 2.49-2.53 (m, 2 H), 2.42 (br. s., 1 H), 2.22 (d, J=1.53 Hz, 3 H), 1.94-2.03 (m, 2 H), 1.84 (d, J=5.19 Hz, 2 H), 1.62 (d, J=6.71 Hz, 2 H). LCMS ($^+$ESI, M+H$^+$) m/z 468.0. HPLC purity: 85%.

The compounds in Table 5 were synthesized using methods similar to those described previously. After synthesis the compounds were analyzed reverse phase LCMS on an HPLC system coupled to Waters LCT mass spectrometer. LC Conditions; 50×4.6 mm, 5 micron Supelco Ascentis C18 column; mobile phase A=10 mM NH$_4$OAc in 5:95 acetonitril/water mobile phase B=10 mM NH$_4$OAc in 95:95 acetonitril/water; 2 mL/min flow rate; gradient=0 to 100% mobile phase B over 8 min.

TABLE 5

| Example | Structure | Observed MS | HPLC retention time |
|---|---|---|---|
| 336 | N'-(3-Hydroxy-2-((2-(1-methyl-2-pyrrolidinyl)ethyl)carbamoyl)-4-oxo-6,7,8,9-tetrahydro-7,10-ethanopyrimido[1,2-a]azepin-10(4H)-yl)-N,N-dimethylethanediamide | 475.2 | 1.255 |

TABLE 5-continued

| Example | Structure | Observed MS | HPLC retention time |
|---|---|---|---|
| 337 | N'-(3-Hydroxy-4-oxo-2-((3-(2-oxo-1-pyrrolidinyl)propyl)carbamoyl)-6,7,8,9-tetrahydro-7,10-ethanopyrimido[1,2-a]azepin-10(4H)-yl)-N,N-dimethylethanediamide | 489.2 | 1.686 |
| 338 | N'-(3-Hydroxy-4-oxo-2-((tetrahydro-2-furanylmethyl)carbamoyl)-6,7,8,9-tetrahydro-7,10-ethanopyrimido[1,2-a]azepin-10(4H)-yl)-N,N-dimethylethanediamide | 448.2 | 1.914 |
| 339 | N'-(3-Hydroxy-2-((1-methyl-3-phenylpropyl)carbamoyl)-4-oxo-6,7,8,9-tetrahydro-7,10-ethanopyrimido[1,2-a]azepin-10(4H)-yl)-N,N-dimethylethanediamide | 496.3 | 3.786 |

TABLE 5-continued

| Example | Structure | Observed MS | HPLC retention time |
|---|---|---|---|
| 340 | N'-(2-((2,2-Diphenylethyl)carbamoyl)-3-hydroxy-4-oxo-6,7,8,9-tetrahydro-7,10-ethanopyrimido[1,2-a]azepin-10(4H)-yl)-N,N-dimethylethanediamide | 544.3 | 3.914 |
| 341 | N'-(3-Hydroxy-2-((2-methylpropyl)carbamoyl)-4-oxo-6,7,8,9-tetrahydro-7,10-ethanopyrimido[1,2-a]azepin-10(4H)-yl)-N,N-dimethylethanediamide | 420.3 | 2.592 |
| 342 | N'-(3-Hydroxy-4-oxo-2-((2-(phenylamino)ethyl)carbamoyl)-6,7,8,9-tetrahydro-7,10-ethanopyrimido[1,2-a]azepin-10(4H)-yl)-N,N-dimethylethanediamide | 483.2 | 1.947 |

TABLE 5-continued

| Example | Structure | Observed MS | HPLC retention time |
|---------|-----------|-------------|---------------------|
| 343 | N'-(3-Hydroxy-4-oxo-2-((2-phenylethyl)carbamoyl)-6,7,8,9-tetrahydro-7,10-ethanopyrimido[1,2-a]azepin-10(4H)-yl)-N,N-dimethylethanediamide | 468.2 | 3.032 |
| 344 | N'-(2-((2-(2-Chlorophenyl)ethyl)carbamoyl)-3-hydroxy-4-oxo-6,7,8,9-tetrahydro-7,10-ethanopyrimido[1,2-a]azepin-10(4H)-yl)-N,N-dimethylethanediamide | 502.2 | 3.391 |
| 345 | N'-(2-((2-(4-Chlorophenyl)ethyl)carbamoyl)-3-hydroxy-4-oxo-6,7,8,9-tetrahydro-7,10-ethanopyrimido[1,2-a]azepin-10(4H)-yl)-N,N-dimethylethanediamide | 502.2 | 3.464 |

TABLE 5-continued

| Example | Structure | Observed MS | HPLC retention time |
|---------|-----------|-------------|---------------------|
| 346 | 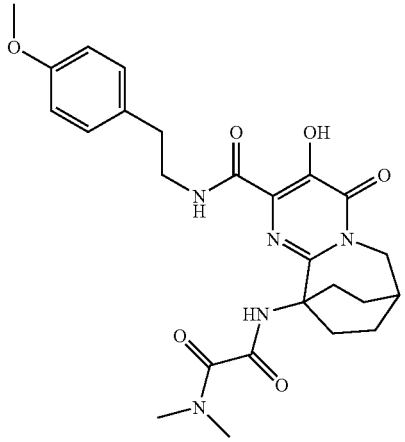 N'-(3-Hydroxy-2-((2-(4-methoxyphenyl)ethyl)carbamoyl)-4-oxo-6,7,8,9-tetrahydro-7,10-ethanopyrimido[1,2-a]azepin-10(4H)-yl)-N,N-dimethylethanediamide | 498.3 | 2.983 |
| 347 | 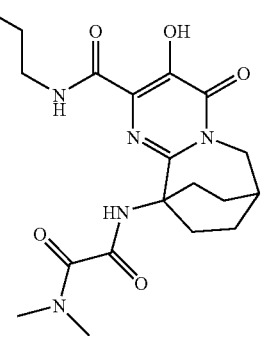 N'-(3-Hydroxy-2-((2-(4-hydroxyphenyl)ethyl)carbamoyl)-4-oxo-6,7,8,9-tetrahydro-7,10-ethanopyrimido[1,2-a]azepin-10(4H)-yl)-N,N-dimethylethanediamide | 484.2 | 2.195 |
| 348 | 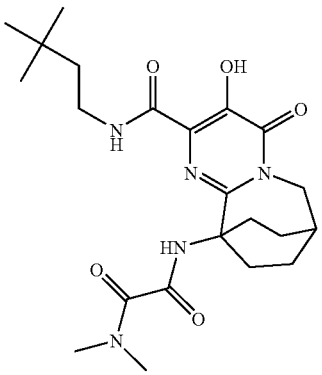 N'-(2-((3,3-Dimethylbutyl)carbamoyl)-3-hydroxy-4-oxo-6,7,8,9-tetrahydro-7,10-ethanopyrimido[1,2-a]azepin-10(4H)-yl)-N,N-dimethylethanediamide | 448.3 | 3.434 |

TABLE 5-continued

| Example | Structure | Observed MS | HPLC retention time |
|---|---|---|---|
| 349 | N'-(3-Hydroxy-4-oxo-2-((3-phenylpropyl)carbamoyl)-6,7,8,9-tetrahydro-7,10-ethanopyrimido[1,2-a]azepin-10(4H)-yl)-N,N-dimethylethanediamide | 482.2 | 3.387 |
| 350 | N'-(3-Hydroxy-2-((3-(1H-imidazol-1-yl)propyl)carbamoyl)-4-oxo-6,7,8,9-tetrahydro-7,10-ethanopyrimido[1,2-a]azepin-10(4H)-yl)-N,N-dimethylethanediamide | 472.2 | 1.219 |
| 351 | N'-(3-Hydroxy-4-oxo-2-((2-(4-sulfamoylphenyl)ethyl)carbamoyl)-6,7,8,9-tetrahydro-7,10-ethanopyrimido[1,2-a]azepin-10(4H)-yl)-N,N-dimethylethanediamide | 547.3 | 1.95 |

TABLE 5-continued

| Example | Structure | Observed MS | HPLC retention time |
|---|---|---|---|
| 352 | 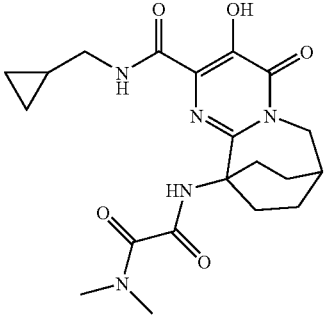<br>N'-(2-((Cyclopropylmethyl)carbamoyl)-3-hydroxy-4-oxo-6,7,8,9-tetrahydro-7,10-ethanopyrimido[1,2-a]azepin-10(4H)-yl)-N,N-dimethylethanediamide | 418.2 | 2.356 |
| 353 | 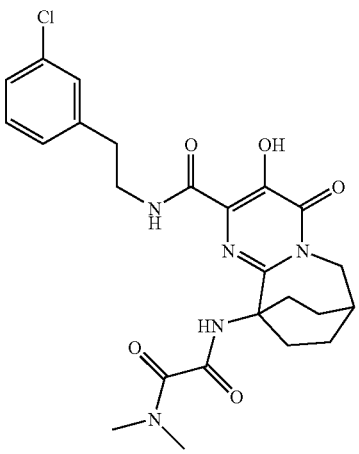<br>N'-(2-((2-(3-Chlorophenyl)ethyl)carbamoyl)-3-hydroxy-4-oxo-6,7,8,9-tetrahydro-7,10-ethanopyrimido[1,2-a]azepin-10(4H)-yl)-N,N-dimethylethanediamide | 502.2 | 3.433 |
| 354 | 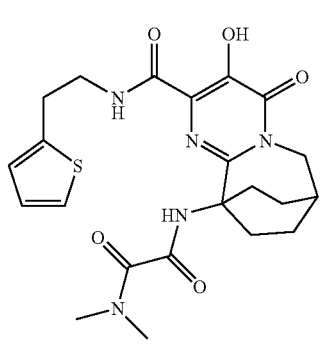<br>N'-(3-Hydroxy-4-oxo-2-((2-(2-thiophenyl)ethyl)carbamoyl)-6,7,8,9-tetrahydro-7,10-ethanopyrimido[1,2-a]azepin-10(4H)-yl)-N,N-dimethylethanediamide | 474.2 | 2.859 |

TABLE 5-continued

| Example | Structure | Observed MS | HPLC retention time |
|---|---|---|---|
| 355 | N'-(3-Hydroxy-4-oxo-2-((2-phenoxyethyl)carbamoyl)-6,7,8,9-tetrahydro-7,10-ethanopyrimido[1,2-a]azepin-10(4H)-yl)-N,N-dimethylethanediamide | 484.2 | 2.98 |
| 356 | N'-(2-((1-Benzyl-3-pyrrolidinyl)carbamoyl)-3-hydroxy-4-oxo-6,7,8,9-tetrahydro-7,10-ethanopyrimido[1,2-a]azepin-10(4H)-yl)-N,N-dimethylethanediamide | 523.3 | 1.868 |
| 357 | N'-(3-Hydroxy-4-oxo-2-((((1S,2R)-2-phenylcyclopropyl)carbamoyl)-6,7,8,9-tetrahydro-7,10-ethanopyrimido[1,2-a]azepin-10(4H)-yl)-N,N-dimethylethanediamide | 480.2 | 3.366 |

TABLE 5-continued

| Example | Structure | Observed MS | HPLC retention time |
|---|---|---|---|
| 358 | 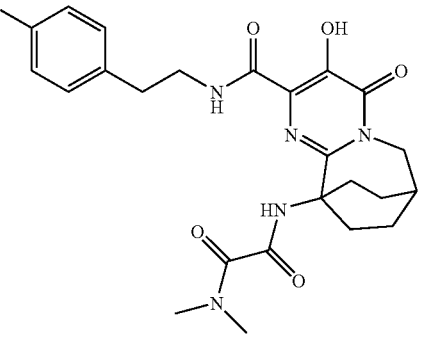 Ethanediamide, N'-[2-[[[2-(4-fluorophenyl)ethyl]amino]carbonyl]-6,7,8,9-tetrahydro-3-hydroxy-4-oxo-7,10-ethanopyrimido[1,2-a]azepin-10(4H)-yl]-N,N-dimethyl- | 486.2 | 3.108 |
| 359 | 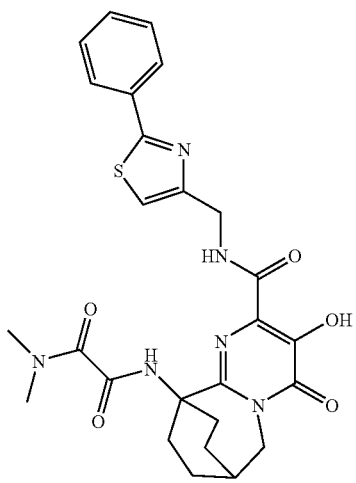 Ethanediamide, N,N-dimethyl-N'-[6,7,8,9-tetrahydro-3-hydroxy-4-oxo-2-[[[(2-phenyl-4-thiazolyl)methyl]amino]carbonyl]-7,10-ethanopyrimido[1,2-a]azepin-10(4H)-yl]- | 537.2 | 3.263 |
| 360 | 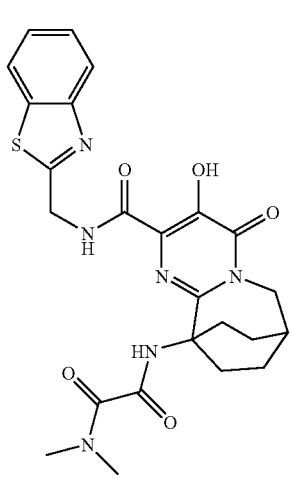 Ethanediamide, N'-[2-[[(2-benzothiazolylmethyl)amino]carbonyl]-6,7,8,9-tetrahydro-3-hydroxy-4-oxo-7,10-ethanopyrimido[1,2-a]azepin-10(4H)-yl]-N,N-dimethyl- | 511.2 | 2.715 |

The compounds in Table 2 were synthesized using methods similar to those described previously. After synthesis the compounds were analyzed reverse phase LCMS on a Waters ZQ HPLC system coupled to a ESCi mass spectrometer. LC Conditions; 50×4.66 mm, 2.7 micron Supelco Ascentis C18 columns; mobile phase A=0.1% trifluoroacetic acid in water, mobile phase B=acetonitrile; 2 mL/min flow rate; gradient =0 to 95% mobile phase B over 7 min.

TABLE 2

| Example | Structure | Observed MS | HPLC retention time |
|---|---|---|---|
| 361 | 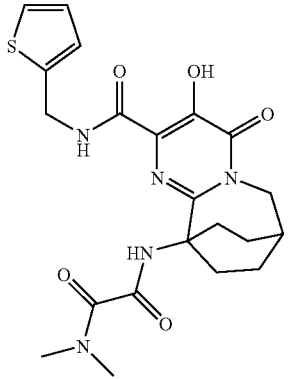 N'-(3-Hydroxy-4-oxo-2-((2-thiophenylmethyl)carbamoyl)-6,7,8,9-tetrahydro-7,10-ethanopyrimido[1,2-a]azepin-10(4H)-yl)-N,N-dimethylethanediamide | 458.5 | 3.21 |
| 362 | 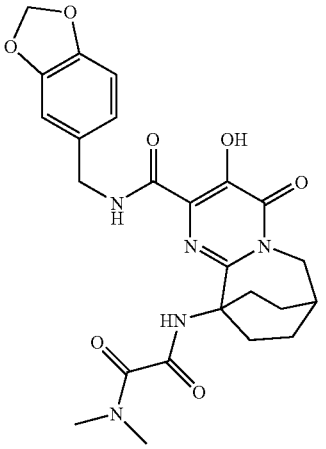 N'-(2-(((1,3-Benzodioxol-5-ylmethyl)carbamoyl)-3-hydroxy-4-oxo-6,7,8,9-tetrahydro-7,10-ethanopyrimido[1,2-a]azepin-10(4H)-yl)-N,N-dimethylethanediamide | 496.6 | 3.51 |
| 363 | 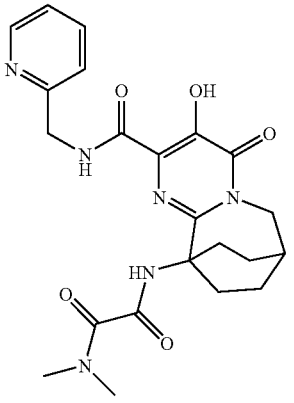 N'-(3-Hydroxy-4-oxo-2-((2-pyridinylmethyl)carbamoyl)-6,7,8,9-tetrahydro-7,10-ethanopyrimido[1,2-a]azepin-10(4H)-yl)-N,N-dimethylethanediamide | 453.6 | 2.42 |

TABLE 2-continued

| Example | Structure | Observed MS | HPLC retention time |
|---|---|---|---|
| 364 | N′-(3-Hydroxy-4-oxo-2-((3-pyridinylmethyl)carbamoyl)-6,7,8,9-tetrahydro-7,10-ethanopyrimido[1,2-a]azepin-10(4H)-yl)-N,N-dimethylethanediamide | 453.5 | 2.26 |
| 365 | N′-(3-Hydroxy-4-oxo-2-((4-pyridinylmethyl)carbamoyl)-6,7,8,9-tetrahydro-7,10-ethanopyrimido[1,2-a]azepin-10(4H)-yl)-N,N-dimethylethanediamide | 453.6 | 2.21 |
| 366 | Ethanediamide, N,N-dimethyl-N′-[6,7,8,9-tetrahydro-3-hydroxy-4-oxo-2-[[(1-phenylethyl)amino]carbonyl]-7,10-ethanopyrimido[1,2-a]azepin-10(4H)-yl]- | 466.5 | 3.79 |

TABLE 2-continued

| Example | Structure | Observed MS | HPLC retention time |
|---|---|---|---|
| 367 | 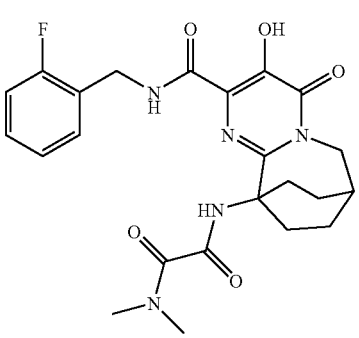 Ethanediamide, N'-[2,[[[(2-fluorophenyl)methyl]amino]carbonyl]-6,7,8,9-tetrahydro-3-hydroxy-4-oxo-7,10-ethanopyrimido[1,2-a]azepin-10(4H)-yl]-N,N-dimethyl- | 470.7 | 3.46 |
| 368 | 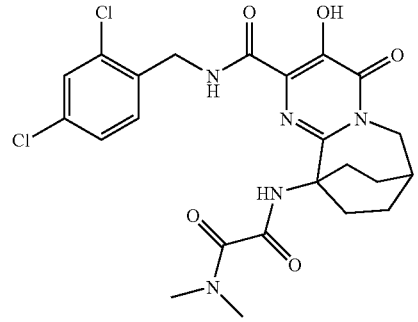 N'-(2-((2,4-Dichlorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide | 520.5 | 4.42 |
| 369 | 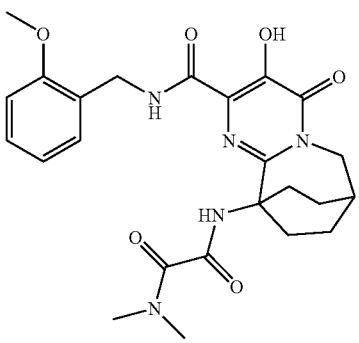 N'-(3-Hydroxy-2-((2-methoxybenzyl)carbamoyl)-4-oxo-6,7,8,9-tetrahydro-7,10-ethanopyrimido[1,2-a]azepin-10(4H)-yl)-N,N-dimethylethanediamide | 482.6 | 3.48 |

TABLE 2-continued

| Example | Structure | Observed MS | HPLC retention time |
|---|---|---|---|
| 370 | 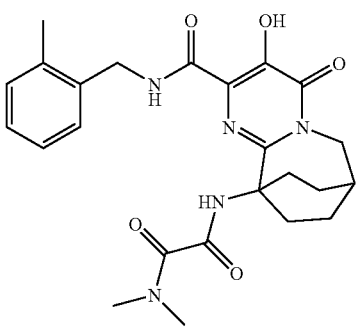 N'-(3-Hydroxy-2-((2-methylbenzyl)carbamoyl)-4-oxo-6,7,8,9-tetrahydro-7,10-ethanopyrimido[1,2-a]azepin-10(4H)-yl)-N,N-dimethylethanediamide | 466.7 | 3.74 |
| 371 | 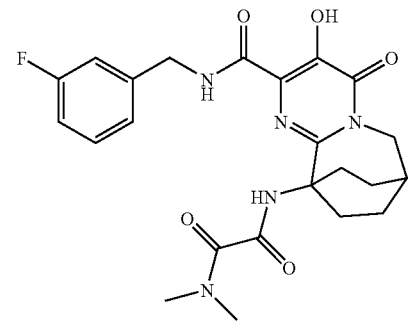 N'-(2-((3-Fluorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide | 470.6 | 3.54 |
| 372 | 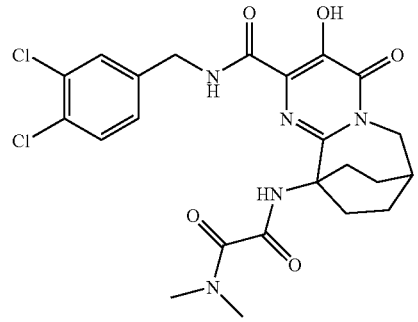 N'-(2-((3,4-Dichlorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide | 522.3 | 4.46 |

TABLE 2-continued

| Example | Structure | Observed MS | HPLC retention time |
|---|---|---|---|
| 373 | 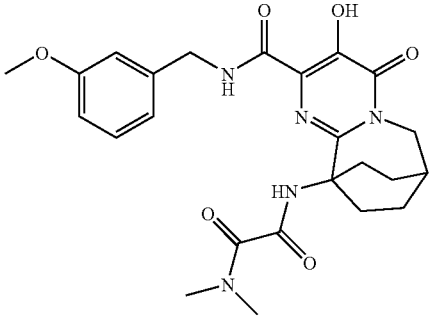<br>N'-(3-Hydroxy-2-((3-methoxybenzyl)carbamoyl)-4-oxo-6,7,8,9-tetrahydro-7,10-ethanopyrimido[1,2-a]azepin-10(4H)-yl)-N,N-dimethylethanediamide | 482.6 | 3.42 |
| 374 | 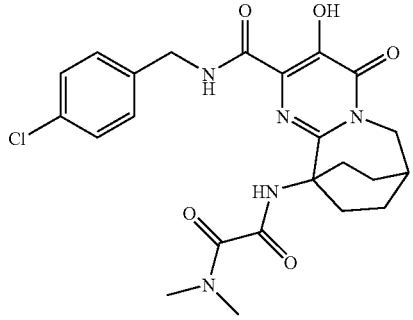<br>N'-(2-((4-Chlorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide | 486.6 | 3.88 |
| 375 | 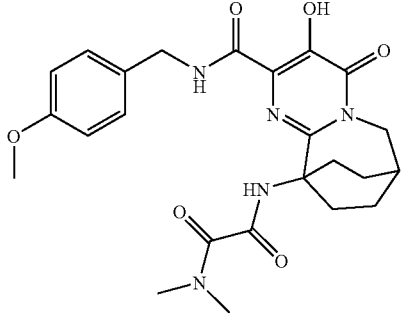<br>N'-(3-Hydroxy-2-((4-methoxybenzyl)carbamoyl)-4-oxo-6,7,8,9-tetrahydro-7,10-ethanopyrimido[1,2-a]azepin-10(4H)-yl)-N,N-dimethylethanediamide | 482.7 | 3.4 |

TABLE 2-continued

| Example | Structure | Observed MS | HPLC retention time |
|---|---|---|---|
| 376 | N'-(3-Hydroxy-2-((4-methoxybenzyl)carbamoyl)-4-oxo-6,7,8,9-tetrahydro-7,10-ethanopyrimido[1,2-a]azepin-10(4H)-yl)-N,N-dimethylethanediamide | 466.6 | 3.77 |
| 377 | N'-(3-Hydroxy-4-oxo-2-((2-(trifluoromethyl)benzyl)carbamoyl)-6,7,8,9-tetrahydro-7,10-ethanopyrimido[1,2-a]azepin-10(4H)-yl)-N,N-dimethylethanediamide | 520.6 | 4.01 |
| 378 | N'-(2-((4-(Dimethylamino)benzyl)carbamoyl)-3-hydroxy-4-oxo-6,7,8,9-tetrahydro-7,10-ethanopyrimido[1,2-a]azepin-10(4H)-yl)-N,N-dimethylethanediamide | 495.7 | 3.58 |

TABLE 2-continued

| Example | Structure | Observed MS | HPLC retention time |
|---|---|---|---|
| 379 | N'-(3-Hydroxy-4-oxo-2-((4-sulfamoylbenzyl)carbamoyl)-6,7,8,9-tetrahydro-7,10-ethanopyrimido[1,2-a]azepin-10(4H)-yl)-N,N-dimethylethanediamide | 531.6 | 2.4 |
| 380 | N'-(2-((3-Chlorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide | 486.6 | 3.97 |
| 381 | N'-(2-((2,3-Dimethoxybenzyl)carbamoyl)-3-hydroxy-4-oxo-6,7,8,9-tetrahydro-7,10-ethanopyrimido[1,2-a]azepin-10(4H)-yl)-N,N-dimethylethanediamide | 512.7 | 3.3 |

TABLE 2-continued

| Example | Structure | Observed MS | HPLC retention time |
|---|---|---|---|
| 382 | N'-(2-((2,4-Dimethoxybenzyl)carbamoyl)-3-hydroxy-4-oxo-6,7,8,9-tetrahydro-7,10-ethanopyrimido[1,2-a]azepin-10(4H)-yl)-N,N-dimethylethanediamide | 512.7 | 3.61 |
| 383 | N'-(2-((3,5-Dichlorobenzyl)carbamoyl)-3-hydroxy-4-oxo-6,7,8,9-tetrahydro-7,10-ethanopyrimido[1,2-a]azepin-10(4H)-yl)-N,N-dimethylethanediamide | 520.6 | 4.43 |
| 384 | N'-(3-Hydroxy-4-oxo-2-((3-(trifluoromethoxy)benzyl)carbamoyl)-6,7,8,9-tetrahydro-7,10-ethanopyrimido[1,2-a]azepin-10(4H)-yl)-N,N-dimethylethanediamide | 536.6 | 4.28 |

TABLE 2-continued

| Example | Structure | Observed MS | HPLC retention time |
|---------|-----------|-------------|---------------------|
| 385 | N'-(2-((4-Aminobenzyl)carbamoyl)-3-hydroxy-4-oxo-6,7,8,9-tetrahydro-7,10-ethanopyrimido[1,2-a]azepin-10(4H)-yl)-N,N-dimethylethanediamide | 467.6 | 2.49 |
| 386 | N'-(3-Hydroxy-4-oxo-2-((2-(trifluoromethoxy)benzyl)carbamoyl)-6,7,8,9-tetrahydro-7,10-ethanopyrimido[1,2-a]azepin-10(4H)-yl)-N,N-dimethylethanediamide | 536.7 | 4.17 |
| 387 | N'-(2-((2-Biphenylylmethyl)carbamoyl)-3-hydroxy-4-oxo-6,7,8,9-tetrahydro-7,10-ethanopyrimido[1,2-a]azepin-10(4H)-yl)-N,N-dimethylethanediamide | 528.6 | 4.55 |

TABLE 2-continued

| Example | Structure | Observed MS | HPLC retention time |
|---|---|---|---|
| 388 | N'-(2-((3-Biphenylylmethyl)carbamoyl)-3-hydroxy-4-oxo-6,7,8,9-tetrahydro-7,10-ethanopyrimido[1,2-a]azepin-10(4H)-yl)-N,N-dimethylethanediamide | 530.5 | 4.59 |
| 389 | N'-(3-Hydroxy-2-(((5-methyl-2-pyrazinyl)methyl)carbamoyl)-4-oxo-6,7,8,9-tetrahydro-7,10-ethanopyrimido[1,2-a]azepin-10(4H)-yl)-N,N-dimethylethanediamide | 468.7 | 2.15 |
| 390 | N'-(3-Hydroxy-2-((4-hydroxybenzyl)carbamoyl)-4-oxo-6,7,8,9-tetrahydro-7,10-ethanopyrimido[1,2-a]azepin-10(4H)-yl)-N,N-dimethylethanediamide | 468.6 | 2.59 |

The compounds in Table 3 were synthesized using methods similar to those described previously. After synthesis the compounds were analyzed reverse phase LCMS on a Shimadzu HPLC system coupled to a mass spectrometer. LC Conditions; 50×4.6 mm, 5 micron SunfireC18 column; mobile phase A 10 mM NH₄OAc in 5:95 acetonitrile/water, mobile phase B=10 mM NH₄OAc in 95:5 acetonitrile/water; 4 mL/min flow rate; gradient =0 to 100% mobile phase B over 4 min.

TABLE 3

| Example | Structure | Observed MS ion | HPLC retention time |
|---|---|---|---|
| 391 | 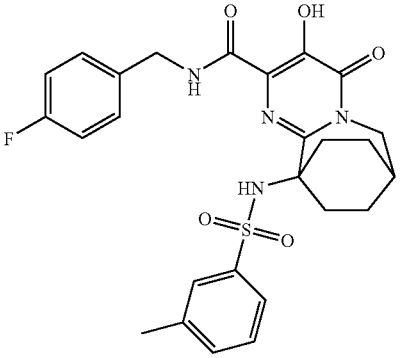 N-(4-Fluorobenzyl)-3-hydroxy-10-(((3-methylphenyl)sulfonyl)amino)-4-oxo-4,6,7,8,9,10-hexahydro-7,10-ethanopyrimido[1,2-a]azepine-2-carboxamide | 525.7 | 4.96 |
| 392 | 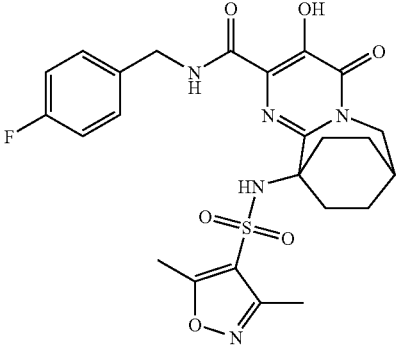 10-(((3,5-Dimethyl-4-isoxazolyl)sulfonyl)amino)-N-(4-fluorobenzyl)-3-hydroxy-4-oxo-4,6,7,8,9,10-hexahydro-7,10-ethanopyrimido[1,2-a]azepine-2-carboxamide | 530.5 | 3.98 |
| 393 | 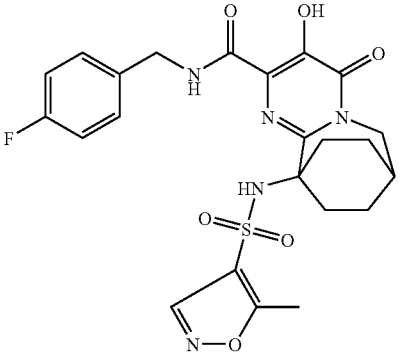 N-(4-Fluorobenzyl)-3-hydroxy-10-(((5-methyl-4-isoxazolyl)sulfonyl)amino)-4-oxo-4,6,7,8,9,10-hexahydro-7,10-ethanopyrimido[1,2-a]azepine-2-carboxamide | 518.3 | 3.22 |

TABLE 3-continued

| Example | Structure | Observed MS ion | HPLC retention time |
|---|---|---|---|
| 394 | 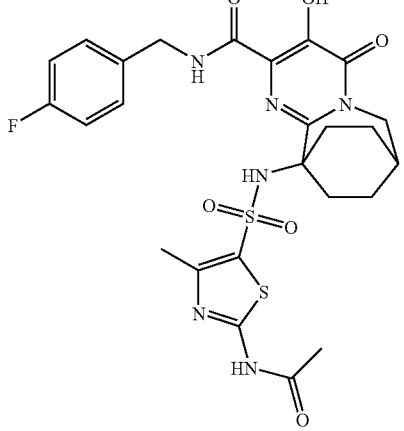 10-(((2-(Acetylamino)-4-methyl-1,3-thiazol-5-yl)sulfonyl)amino)-N-(4-fluorobenzyl)-3-hydroxy-4-oxo-4,6,7,8,9,10-hexahydro-7,10-ethanopyrimido[1,2-a]azepine-2-carboxamide | 591.7 | 3.12 |
| 395 | 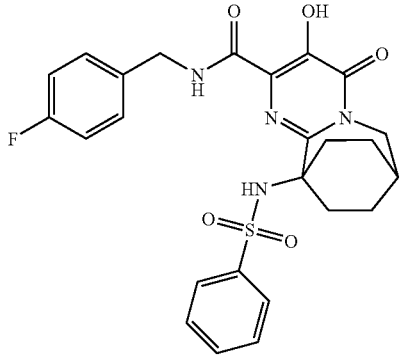 N-(4-Fluorobenzyl)-3-hydroxy-4-oxo-10-((phenylsulfonyl)amino)-4,6,7,8,9,10-hexahydro-7,10-ethanopyrimido[1,2-a]azepine-2-carboxamide | 513.6 | 4.61 |
| 396 | 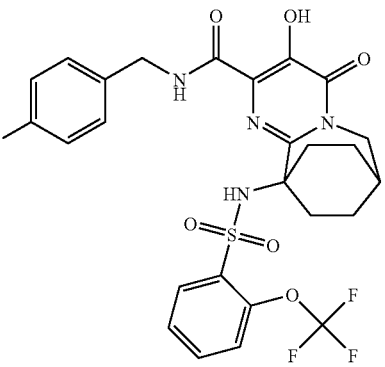 N-(4-Fluorobenzyl)-3-hydroxy-4-oxo-10-(((2-(trifluoromethoxy)phenyl)sulfonyl)amino)-4,6,7,8,9,10-hexahydro-7,10-ethanopyrimido[1,2-a]azepine-2-carboxamide | 597.4 | 4.54 |

The compounds in Table 4 were synthesized using methods similar to those described previously. After synthesis the compounds were analyzed reverse phase LCMS on a Shimadzu HPLC system coupled to a mass spectrometer. LC Conditions; 50×4.6 mm, 5 micron Phenomonex Luna C18 column; mobile phase A 10 mM NH$_4$OAc in 5:95 acetonitrile/water, mobile phase B=10 mM NH$_4$Oac in 95:5 acetonitrile/water; 4 mL/min flow rate; gradient =0 to 100% mobile phase B over 4 min.

TABLE 4

| Example | Structure | Observed MS | HPLC retention time |
|---|---|---|---|
| 397 | 1-Pyrrolidinecarboxylic acid, 2-[[[2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]amino]carbonyl]-, ethyl ester | 542.26 | 6.62 |
| 398 | 1-Pyrrolidinecarboxylic acid, 2-[[[2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]amino]carbonyl]-, propyl ester | 556.29 | 6.95 |
| 399 | 7,10-Ethanopyrimido[1,2-a]azepine-2-carboxamide, N-[(4-fluorophenyl)methyl]-4,6,7,8,9,10-hexahydro-3-hydroxy-10-[[[1-(2-methyl-1-oxopropyl)-2-pyrrolidinyl]carbonyl]amino]-4-oxo- | 540.3 | 6.69 |
| 400 | 7,10-Ethanopyrimido[1,2-a]azepine-2-carboxamide, 10-[[[1-(cyclobutylcarbonyl)-2-pyrrolidinyl]carbonyl]amino]-N-[(4-fluorophenyl)methyl]-4,6,7,8,9,10-hexahydro-3-hydroxy-4-oxo- | 552.3 | 6.83 |

TABLE 4-continued

| Example | Structure | Observed MS | HPLC retention time |
|---|---|---|---|
| 401 | 1,2-Pyrrolidinedicarboxamide, N~2~-[2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N~1~-methyl- | 527.25 | 5.97 |
| 402 | 7,10-Ethanopyrimido[1,2-a]azepine-2-carboxamide, N-[(4-fluorophenyl)methyl]-4,6,7,8,9,10-hexahydro-3-hydroxy-10-[[[1-[(1-methylethyl)sulfonyl]-2-pyrrolidinyl]carbonyl]amino]-4-oxo- | 576.25 | 6.42 |
| 403 | 7,10-Ethanopyrimido[1,2-a]azepine-2-carboxamide, 10-[[[1-(ethylsulfonyl)-2-pyrrolidinyl]carbonyl]amino]-N-[(4-fluorophenyl)methyl]-4,6,7,8,9,10-hexahydro-3-hydryox-4-oxo- | 562.27 | 6.14 |
| 404 | 7,10-Ethanopyrimido[1,2-a]azepine-2-carboxamide, N-[(4-fluorophenyl)methyl]-4,6,7,8,9,10-hexahydro-3-hydryox-4-oxo-10-[[[1-(propylsulfonyl)-2-pyrrolidinyl]carbonyl]amino]- | 576.28 | 6.49 |

TABLE 4-continued

| Example | Structure | Observed MS | HPLC retention time |
|---|---|---|---|
| 405 | 1-Pyrrolidinecarboxylic acid, 2-[[[2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]amino]carbonyl]-, 1-methylethyl ester | 556.3 | 6.92 |
| 406 | 1-Pyrrolidinecarboxylic acid, 2-[[[2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]amino]carbonyl]-, methyl ester | 528.27 | 6.21 |
| 407 | 7,10-Ethanopyrimido[1,2-a]azepine-2-carboxamide, 10-[[[1-(cyclopropylcarbonyl)-2-pyrrolidinyl]carbonyl]amino]-N-[(4-fluorophenyl)methyl]-4,6,7,8,9,10-hexahydro-3-hydroxy-4-oxo- | 538.26 | 6.5 |
| 408 | 7,10-Ethanopyrimido[1,2-a]azepine-2-carboxamide, 10-[[[1-(cyclopentylsulfonyl)-2-pyrrolidinyl]carbonyl]amino]-N-[(4-fluorophenyl)methyl]-4,6,7,8,9,10-hexahydro-3-hydroxy-4-oxo- | 602.31 | 6.82 |

TABLE 4-continued

| Example | Structure | Observed MS | HPLC retention time |
|---|---|---|---|
| 409 | 7,10-Ethanopyrimido[1,2-a]azepine-2-carboxamide, N-[(4-fluorophenyl)methyl]-4,6,7,8,9,10-hexahydro-3-hydroxy-4-oxo-10-[[[1-(1H-1,2,4-triazol-3-ylsulfonyl)-2-pyrrolidinyl]carbonyl]amino]- | 601.23 | 5.82 |
| 410 | 7,10-Ethanopyrimido[1,2-a]azepine-2-carboxamide, N-[(4-fluorophenyl)methyl]-10-[[[1-(2-furanylsulfonyl)-2-pyrrolidinyl]carbonyl]amino]-4,6,7,8,9,10-hexahydro-3-hydroxy-4-oxo- | 600.24 | 6.54 |

Isolation of Single Diastereomers

Scheme XXXV

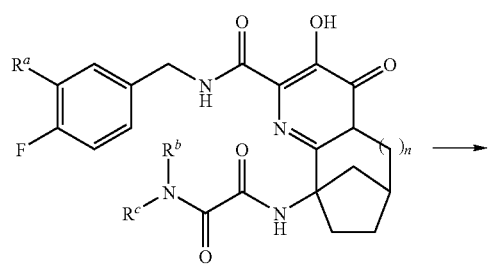

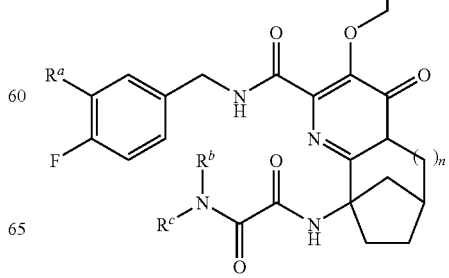

1. SCF column separation
2. deprotection

-continued

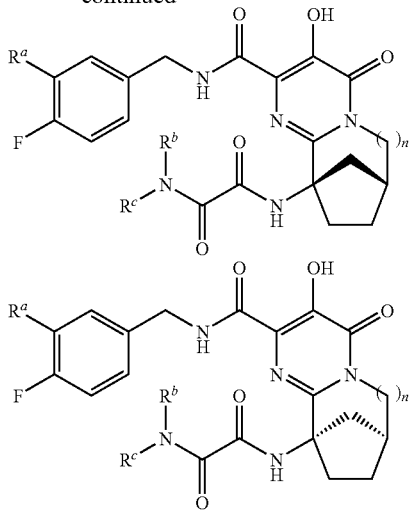

The isolation of the single diastereomers of certain compounds of this invention is illustrated in Scheme XXXV.

Method A

Separation N'-[2-[[[(4-fluorophenyl)methyl]amino]carbonyl]-6,7,8,9-tetrahydro-3-hydroxy-4-oxo-7,10-methanopyrimido[1,2-a]azepin-10(4H)-yl]-N,N-dimethyl into its individual enantiomers,

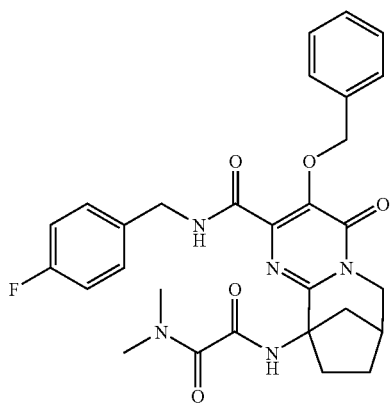

Ethanediamide, N'-[2-[[[(4-fluorophenyl)methyl]amino]carbonyl]-6,7,8,9-tetrahydro-4-oxo-3-(phenylmethoxy)-7,11-methanopyrimido[1,2-a]azepin-10(4H)-yl]-N,N-dimethyl-. A solution of ethanediamide, N'-[2-[[[(4-fluorophenyl)methyl]amino]carbonyl]-6,7,8,9-tetrahydro-3-hydroxy-4-oxo-7,10-methanopyrimido[1,2-a]azepin-10 (4H)-yl]-N,N-dimethyl (0.160 g, 0.350 mmol) in dry DMF (5 mL) was treated with benzyl bromide (0.050 mL, 0.420 mmol) and potassium carbonate (0.276 g, 2 mmol) and stirred with heating (60° C. oil bath) overnight. The solvent was removed under reduced pressure and the residue was dissolved in EtOAc (20 mL) and washed with 1.0 N HCl (2×20 mL). The organic layer was dried (MgSO$_4$), filtered, and concentrated under reduced pressure to give the crude product as a light brown oil, which partially solidified upon standing. The solid was triturated with Et$_2$O several times then loaded onto a Biotage 25+M samplet and purified with Biotage flash chromatography system, eluting with a solvent gradient of 40% to 100% hexanes in EtOAc. The individual diastereomers of this compound were separated by chiral SFC chromatography (5 micron 30×250 mm Chiralcel OD-H column eluting with 70% CO$_2$ 30% MeOH and 0.1% diethylamine at 35° C. and 150 Bar). Two separately eluting compounds were isolated, a faster eluting compound (isomer A) and a slower eluting compound (isomer B).

Example 411

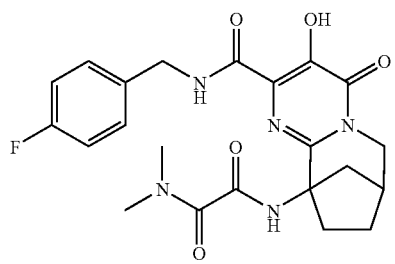

Ethanediamide, N'-[2-[[[(4-fluorophenyl)methyl]amino]carbonyl]-6,7,8,9-tetrahydro-3-hydroxy-4-oxo-7,11-methanopyrimido[1,2-a]azepin-10(4H)-yl]-N,N-dimethyl-.

Removal of the benzyl group (H$_2$, Pd/C) from the faster eluting isomer (isomer A) provided the title compound white crystalline solid (54% yield). $^1$H NMR (500 MHz, MeOD) δ ppm 1.65-1.74 (m, 1 H) 1.90-1.99 (m, 1 H) 2.02-2.12 (m, 1 H) 2.21-2.32 (m, 1 H) 2.62 (td, J=12.51, 5.49 Hz, 1 H) 2.75-2.82 (m, 1 H) 2.91-2.98 (m, 1 H) 2.99-3.03 (m, 3 H) 3.11 (s, 3 H) 3.78-3.95 (m, 2 H) 4.59 (s, 1 H) 4.89 (br. s., 4 H) 7.04 (t, J=8.70 Hz, 2 H) 7.39 (dd, J=8.55, 5.49 Hz, 2 H). LC/MS (M+H)=458.16. HPLC purity>97%.

Example 412

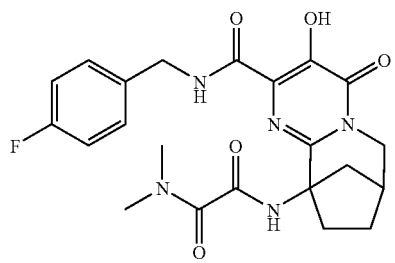

Ethanediamide, N'-[2-[[[(4-fluorophenyl)methyl]amino]carbonyl]-6,7,8,9-tetrahydro-3-hydroxy-4-oxo-7,11-methanopyrimido[1,2-a]azepin-10(4H)-yl]-N,N-dimethyl-.

Removal of the benzyl group (H$_2$, Pd/C) from the slower eluting isomer (isomer B) provided the title compound as an off-white crystalline solid (52% yield). LC/MS (M+H)= 458.08. HPLC purity>97%.

Method B

Separation of Ethanediamide, N'-[2-[[[(4-fluorophenyl)methyl]amino]carbonyl]-7,8,9,10-tetrahydro-3-hydroxy-4-oxo-8,11-methano-4H-pyrimido[1,2-a]azocin-11(6H)-yl]-N,N-dimethyl. into its individual enantiomers

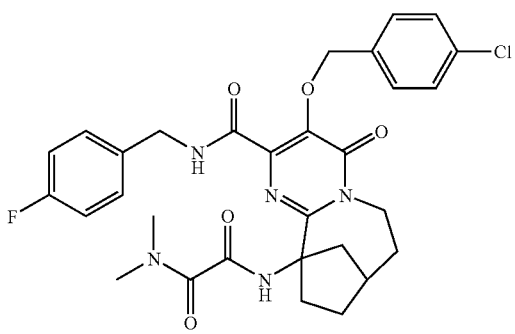

Ethanediamide, N'-[3-[(4-chlorophenyl)methoxy]-2-[[[(4-fluorophenyl)methyl]amino]carbonyl-7,8,9,10-tetrahydro-4-oxo-8,11-methano-4H-pyrimido[1,2-a]azocin-1](6H)-yl]-N,N-dimethyl-. A solution of ethanediamide, N'-[2-[[[(4-fluorophenyl)methyl]amino]carbonyl]-7,8,9,10-tetrahydro-3-hydroxy-4-oxo-8,11-methano-4H-pyrimido[1,2-a]azocin-11(6H)-yl]-N,N-dimethyl (0.367 g, 0.779 mmol) in dry DMF (10 mL) was treated with cesium carbonate (0.512 g, 1.571 mmol) and 4-chlorobenzyl bromide (0.218 g, 1.040 mmol), and the reaction stirred with heating (60° C. oil bath) for 1 hr. Additional 4-chlorobenzyl bromide (0.219 g, 1.040 mmol) and cesium carbonate (0.501 g, 1.55 mmol) were added and the reaction was stirred for and 45 min, then cooled and concentrated under reduced pressure. The crude residue, was dissolved in $CH_2Cl_2$, and washed with 1.0N HCl, then dried ($MgSO_4$), filtered, and concentrated under reduced pressure to give a yellow oil. The oil crystallized upon standing for two days at room temperature. Trituration with ether (2 times), followed by crystallization from 95% EtOH—$H_2O$ yielded the title compound (0.242 g, 0.406 mmol, 52.1% yield), as a white crystalline solid. $^1$H NMR (500 MHz, $CDCl_3$) δ ppm 8.87 (1 H, s), 8.22 (1 H, t, J=5.95 Hz), 7.50 (2 H, d, J=8.55 Hz), 7.27-7.35 (4 H, m), 6.98 (2 H, t, J=8.70 Hz), 5.44 (1 H, dt, J=15.49, 3.70 Hz), 5.21 (2 H, s), 4.48-4.59 (2 H, m), 3.48-3.56 (1 H, m), 3.31 (3 H, s), 2.89 (3 H, s), 2.57-2.70 (3 H, m), 2.36-2.48 (2 H, m), 1.80-1.93 (2 H, m), 1.76 (1 H, m), 1.61 (1H, m). The individual diastereomers of this compound were separated on by chiral SFC chromatography (5 micron 30×250 mm Chiralpak AS-H column eluting with 85% $CO_2$ 15% MeOH and 0.1% diethylamine at 35° C. and 150 Bar). Two separately eluting compounds were isolated., the faster eluting compound (isomer A, Intermediate 159) and a slower eluting compound (isomer B, Intermediate 160).

Intermediate 159

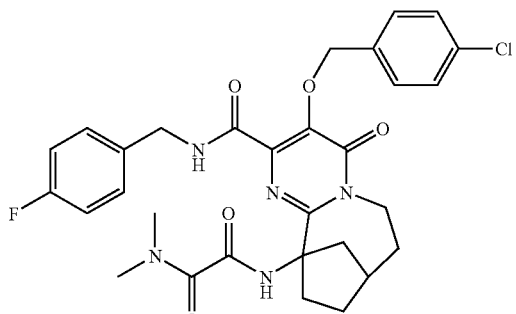

Isomer A. Earlier eluting peak. 0.08 g (34% yield) was isolated as a glassy solid.

Intermediate 159

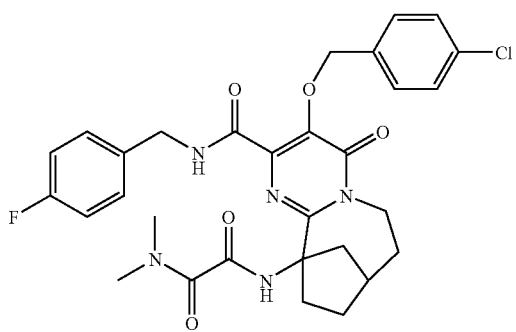

Isomer B. The later eluting peak. 0.08 g (34% yield) was isolated as a crystalline solid from 95% EtOH. This material was analyzed by chiral SFC chromatography, retention time=12.97 min; Chiralpak AS-H column, 4.6×250 mm, 5 microns solvent: 85% $CO_2$, 15% MeOH with 0.1% diethylamine, Temp: 35° C., Pressure: 150 bar, flow rate at 2.0 ml/min, UV at 210 nm.

EXAMPLE 413

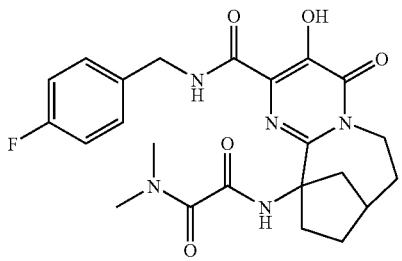

Ethanediamide, N'-[2-[[[(4-fluorophenyl)methyl]amino]carbonyl]-7,8,9,10-tetrahydro-3-hydroxy-4-oxo-8,11-methano-4H-pyrimido[1,2-a]azocin-11(6H)-yl]-N,N-dimethyl-. Hydrogenolysis ($H_2$, Pd/C) of Intermediate 158 provided the title compound as a single diastereomer. Off-white crystalline solid (86% yield). $^1$H NMR (500 MHz, $CDCl_3$) δ ppm 12.08 (1 H, s), 8.71 (1 H, t, J=6.10 Hz), 8.27 (1 H, s), 7.36 (2 H, dd, J=8.55, 5.49 Hz), 6.98-7.04 (2 H, m), 5.50 (1 H, dt, J=15.56, 3.81 Hz), 4.49-4.59 (2 H, m), 3.49 (1 H, t, J=13.58 Hz), 3.29 (3 H, s), 2.91 (3 H, s), 2.64 (1 H, q, J=5.70 Hz), 2.52-2.61 (1 H, m), 2.43-2.52 (2 H, m), 2.27-2.38 (1 H, m), 1.78-1.93 (3 H, m), 1.57-1.65 (1 H, m). $^{13}$C NMR (126 MHz, CDCl$_3$) δ ppm 168.20, 163.58, 163.33, 161.55, 161.38, 159.49, 152.11, 146.86, 133.72, 133.69, 129.96, 129.89, 123.72, 115.57, 115.40, 66.61, 44.13, 42.52, 40.05, 38.17, 37.26, 36.51, 35.09, 32.57, 30.25. LC/MS (M+H)=472.12. HPLC purity>97%.

EXAMPLE 414

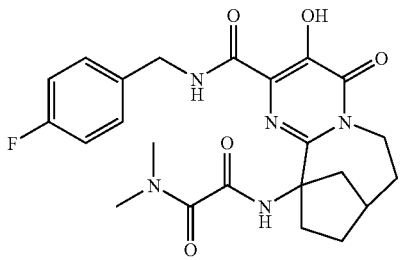

Ethanediamide, N'-[2-[[[(4-fluorophenyl)methyl]amino]carbonyl]-7,8,9,10-tetrahydro-3-hydroxy-4-oxo-8,11-methano-4H-pyrimido[1,2-a]azocin-11(6H)-yl]-N,N-dimethyl-1 Hydrogenolysis (H$_2$, Pd/C) of Intermediate 159 provided the title compound as a single diastereomer White crystalline solid (96% yield). $^1$H NMR (500 MHz, CDCl$_3$) δ ppm 12.08 (1 H, s), 8.70 (1 H, t, J=5.95 Hz), 8.29 (1 H, s), 7.33-7.39 (2 H, m), 6.97-7.04 (2 H, m), 5.50 (1 H, dt, J=15.56, 3.81 Hz), 4.49-4.60 (2H, m), 3.44-3.53 (1 H, m), 3.29 (3 H, s), 2.91 (3 H, s), 2.64 (1 H, q, J=5.49 Hz), 2.53-2.61 (1 H, m), 2.42-2.52 (2 H, m), 2.33 (1 H, td, J=12.97, 7.02 Hz), 1.77-1.93 (3 H, m), 1.57-1.66 (1 H, m). $^{13}$C NMR (126 MHz, CDCl$_3$) δ ppm 168.20, 163.58, 163.33, 161.55, 161.38, 159.49, 152.11, 146.86, 133.72, 133.69, 129.96, 129.89, 123.72, 115.56, 115.40, 66.61, 44.13, 42.52, 40.05, 38.16, 37.26, 36.51, 35.09, 32.57, 30.25. LCMS (M+H)=472.35.

Method C

Separation of Ethanediamide, N'-[(8S,11R)-2-[[[(4-fluoro-3-methylphenyl)methyl]amino]carbonyl]-7,8,9,10-tetrahydro-3-hydroxy-4-oxo-8,11-methano-4H-pyrimido[1,2-a]azocin-11(6H)-yl]-N,N-dimethyl-into its individual enantiomers Intermediate 160

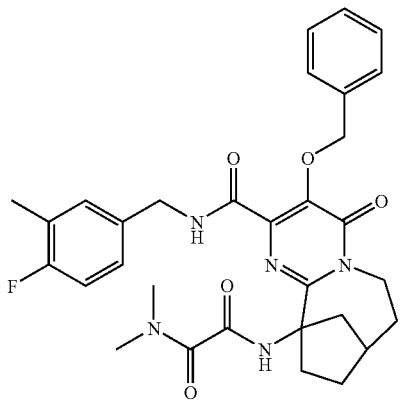

Isomer A was isolated as the faster eluting compound from a racemic mixture of ethanediamide, N'-[2-[[[(4-fluoro-3-methylphenyl)methyl]amino]carbonyl]-7,8,9,10-tetrahydro-4-oxo-3-(phenylmethoxy)-8,11-methano-4H-pyrimido[1,2-a]azocin-11(6H)-yl]-N,N-dimethyl- by chiral SCF chromatography. LCMS (M+H)=576.42 min. OLD=+16.60 (5.02 mg/mL in CHCl$_3$). Chiral SCG analysis; Chiralcel OD-H column, 4.6×250 mm, 5 microns; solvent: 75% CO$_2$, 25% MeOH with 0.1% diethylamine; Temp: 35° C., Pressure: 150 bar; Flow rate at 1.0 ml/min, UV at 300 nm.

Intermediate 170

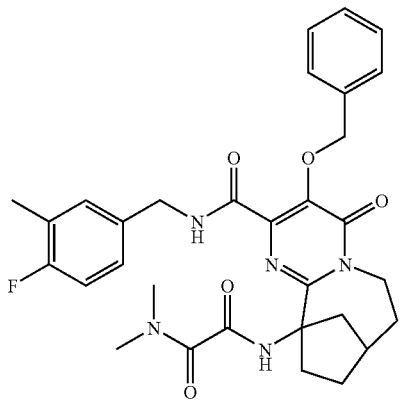

Isomer B was isolated from a as the slower moving compound from a racemic mixture of ethanediamide, N'-[2-[[[(4-fluoro-3-methylphenyl)methyl]amino]carbonyl]-7,8,9,10-tetrahydro-4-oxo-3-(phenylmethoxy)-8,11-methano-4H-pyrimido[1,2-a]azocin-11(6H)-yl]-N,N-dimethyl- by chiral SCF chromatography. LCMS (M+H)=576.21 min. α$_D$=−16.60 (5.02 mg/mL in CHCl$_3$). Chiral SCG analysis; Chiralcel OD-H column, 4.6×250 mm, 5 microns; solvent: 75% CO$_2$, 25% MeOH with 0.1% diethylamine; Temp: 35° C., Pressure: 150 bar; Flow rate at 1.0 ml/min, UV at 300 nm.

Example 415

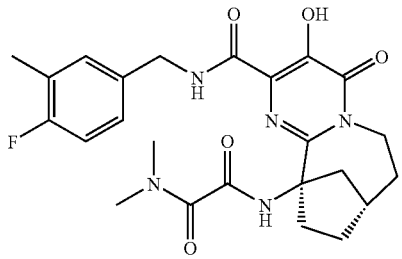

Ethanediamide, N'-[(8S,11R)-2-[[[(4-fluoro-3-methylphenyl)methyl]amino]carbonyl]-7,8,9,10-tetrahydro-3-hydroxy-4-oxo-8,11-methano-4H-pyrimido[1,2-a]azocin-1](6H)-yl]-N,N-dimethyl-. A solution of Intermediate 160 (35 mg, 0.061 mmol) in ethyl acetate (2 mL) and methanol (2 mL) was treated with 10% palladium on carbon (65 mg) and stirred under hydrogen for 16 hrs. The reaction was filtered and the filtrate concentrated. The residue was dissolved in 95% EtOH (2 mL) and the solution was allowed to stand for 16 hrs. Solids were collected by vacuum filtration to afford the title compound as an off-white crystalline solid (24 mg, 0.049 mmol, 81% yield). $^1$H NMR (500 MHz, CDCl$_3$) δ ppm 12.14 (1 H, s), 8.72 (1 H, t, J=6.10 Hz), 8.32 (1 H, s), 7.17-

7.25 (2 H, m), 6.92-7.01 (1 H, m), 5.54 (1 H, ddd, J=15.41, 3.81, 3.66 Hz), 4.54 (2 H, d, J=6.41 Hz), 3.52 (1 H, t, J=13.73 Hz), 3.32 (3 H, s), 2.94 (3 H, s), 2.67 (1 H, q, J=5.49 Hz), 2.56-2.64 (1 H, m), 2.46-2.55 (2 H, m), 2.30-2.42 (1 H, m), 2.28 (3H, d, J=1.83 Hz), 1.81-1.96 (3 H, m), 1.60-1.68 (1 H, m). $^{13}$C NMR (126 MHz, CDCl$_3$) δ ppm 168.15, 163.62, 161.82, 161.70, 159.88, 159.56, 152.04, 146.83, 133.38, 133.35, 131.35, 131.31, 127.13, 127.06, 125.07, 124.94, 123.79 115.19, 115.00, 109.69, 66.63, 44.20, 42.51, 40.04, 38.19, 37.22, 36.44, 35.14, 32.55, 30.27, 14.66, 14.63. LCMS (M+H)=486.15. HPLC purity: >97%.

Example 416

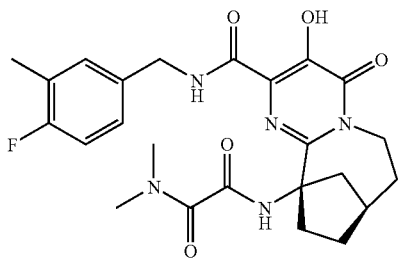

Ethanediamide, N'-[(8R,11S)-2-[[[(4-fluoro-3-methylphenyl)methyl]amino]carbonyl]-7,8,9,10-tetrahydro-3-hydroxy-4-oxo-8,11-methano-4H-pyrimido[1,2-a]azocin-11(6H)-yl]-N,N-dimethyl-. White crystalline solid (71% yield). $^1$H NMR (500 MHz, CDCl$_3$) δ ppm 12.11 (1 H, brs), 8.70 (1 H, t, J=6.10 Hz), 8.27 (1 H, s), 7.12-7.21 (2 H, m), 6.90-6.98 (1 H, m), 5.50 (1 H, dt, J=15.49, 3.70 Hz), 4.50 (2 H, d, J=6.41 Hz), 3.48 (1 H, t, J=13.58 Hz), 3.29 (3 H, s), 2.91 (3 H, s), 2.64 (1 H, q, J=5.49 Hz), 2.52-2.61 (1 H, m), 2.43-2.53 (2 H, m), 2.27-2.39 (1 H, m), 2.25 (3 H, d, J=1.83 Hz), 1.78-1.93 (3 H, m), 1.57-1.65 (1 H, m). $^{13}$C NMR (126 MHz, CDCl$_3$) δ ppm 168.15, 163.65, 161.81, 161.75, 159.87, 159.56, 152.03, 146.82, 133.39, 133.36, 131.35, 131.31, 127.12, 127.06, 125.07, 124.94, 123.81, 115.19, 115.00, 66.64, 44.22, 42.50, 40.03, 38.19, 37.21, 36.42, 35.16, 32.54, 30.26, 14.67, 14.64. LC/MS (M+H)=486.12. HPLC purity>97%.

Method D

Separation of 8,11-methano-4H-pyrimido[1,2-a]azocine-2-carboxamide, N-[(4-fluorophenyl)methyl]-11-[[2-[(3R)-3-fluoro-1-pyrrolidinyl]-1,2-dioxoethyl]amino]-6,7,8,9,10, 11-hexahydro-3-hydroxy-4-oxo- into its individual diastereomers.

A solution of 8,11-methano-4H-pyrimido[1,2-a]azocine-2-carboxamide, N-[(4-fluorophenyl)methyl]-11-[[2-[(3R)-3-fluoro-1-pyrrolidinyl]-1,2-dioxoethyl]amino]-6,7,8,9,10, 11-hexahydro-3-hydroxy-4-oxo- (0.196 g, 0.38 mmol) in dry DMF (5 mL) was treated with 4-chlorobenzyl bromide (0.094 g, 0.46 mmol) and potassium carbonate (0.079 g, 0.57 mmol), and the reaction was heated (60° C.) for 90 min. Solvent was removed under reduced pressure, and the residue, dissolved in CH$_2$Cl$_2$, was washed with 1.0 N HCl. The organic layer was dried (Na$_2$SO$_4$), filtered, and concentrated under reduced pressure to give an oily solid which was triturated with ether (2x). The residue was subjected to chiral SCF chromatography (Chiralcel OD-H column, 4.6×250 mm, 5 microns, solvents: 75% CO$_2$, 25% methanol with 0.1% diethylamine, Temp: 35° C., Pressure: 150 bar, Flow rate at 2.0 ml/min UV at 300 nm) for separation to the component diastereomers.

Intermediate 171

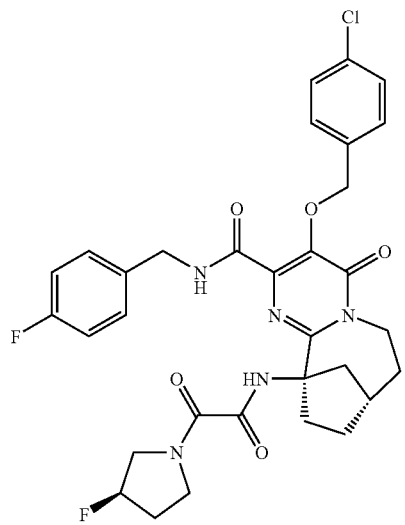

8,11-Methano-4H-pyrimido[1,2-a]azocine-2-carboxamide, 3-[(4-chlorophenyl)methoxy]-N-[(4-fluorophenyl)methyl]-11-[[2-[(3R)-3-fluoro-1-pyrrolidinyl]-1,2-dioxoethyl]amino]-6,7,8,9,10,11-hexahydro-4-oxo-, (8S,11R)— First eluting compound isolated from the chiral SCF chromatographic purification, was recrystallized from EtOH and water, resulting in the title compound (0.047 g, 0.073 mmol, 38% yield) as a crystalline white solid. $^1$H NMR (500 MHz, CDCl$_3$) δ ppm 9.71-9.90 (1 H, m), 7.48 (2 H, dd, J=8.24, 2.75 Hz), 7.32-7.39 (2 H, m), 7.29 (2 H, d, J=8.55 Hz), 6.96-7.02 (2 H, m), 5.46 (1 H, dt, J=15.26, 3.66 Hz), 5.16-5.37 (3H, m), 4.38-4.63 (3 H, m), 3.74-4.02 (2 H, m), 3.42-3.63 (2 H, m), 2.78-2.87 (1H, m), 2.65-2.74 (2 H, m), 2.49 (1 H, brs), 2.21-2.39 (2 H, m), 1.80-2.01 (3 H, m), 1.60-1.68 (2 H, m). LC/MS (M+H)=640.09. HPLC purity>98%.

Intermediate 172

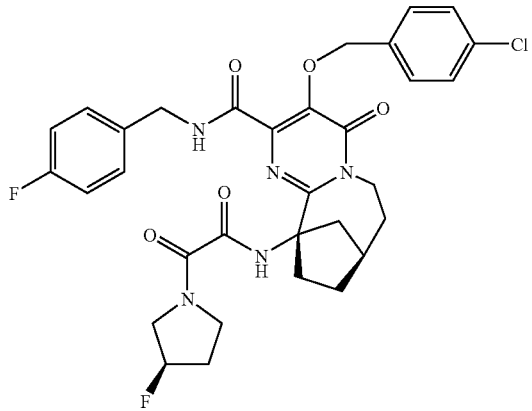

8,11-Methano-4H-pyrimido[1,2-a]azocine-2-carboxamide, 3-[(4-chlorophenyl)methoxy]-N-[(4-fluorophenyl)methyl]-11-[[2-[(3R)-3-fluoro-1-pyrrolidinyl]-1,2-dioxoethyl]amino]-6,7,8,9,10,11-hexahydro-4-oxo-, (8R,11S)— Second eluting compound isolated from the chiral SCF chromatographic purification. White crystalline solid (37% yield). $^1$H NMR (500 MHz, CDCl$_3$) δ ppm 1.57-1.61 (m, 3 H), 1.62-1.70 (m, 2 H), 1.78-2.12 (m, 3 H), 2.20-2.41 (m, 2 H), 2.41-2.55 (m, 1 H), 2.64-2.78 (m, 2 H), 2.81 (dd, J=13.12, 6.71 Hz, 1 H), 3.46-3.69 (m, 2 H), 3.78-4.02 (m, 1 H), 4.29-

4.42 (m, 1 H), 4.47-4.66 (m, 2 H), 5.17-5.36 (m, 3 H), 5.42-5.51 (m, 1 H), 6.99 (t, J=8.70 Hz, 2 H), 7.29 (d, J=8.24 Hz, 2 H), 7.32-7.39 (m, 2 H), 7.49 (dd, J=7.17, 5.04 Hz, 2 H), 7.92-8.05 (m, 1 H), 9.55-9.82 (m, 1 H). LC/MS (M+H)= 640.11. HPLC purity>97%.

Example 417

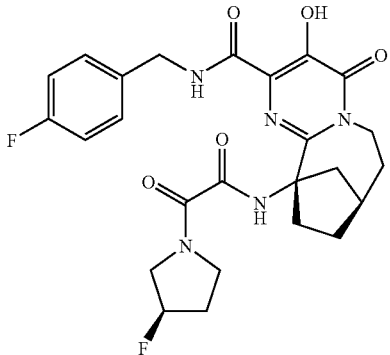

8,1,1-Methano-4H-pyrimido[1,2-a]azocine-2-carboxamide, N-[(4-fluorophenyl)methyl]-11-[[2-[(3R)-3-fluoro-1-pyrrolidinyl]-1,2-dioxoethyl]amino]-6,7,8,9,10,11-hexahydro-3-hydroxy-4-oxo-, (8R,11S)—. The 4-chloro-benzyl group of 8,11-methano-4H-pyrimido[1,2-a]azocine-2-carboxamide, 3-[(4-chlorophenyl)methoxy]-N-[(4-fluorophenyl)methyl]-11-[[2-[(3R)-3-fluoro-1-pyrrolidinyl]-1,2-dioxoethyl]amino]-6,7,8,9,10,11-hexahydro-4-oxo-, (8S,11R)— was removed under hydrogenolytic conditions (H$_2$, Pd/C) to yield the title compound as a white crystalline solid. $^1$H NMR (500 MHz, CDCl$_3$) δ ppm 11.98-12.03 (1 H, m), 9.54-9.71 (1 H, m), 8.14-8.23 (1 H, m), 7.39 (2 H, dd, J=8.24, 5.49 Hz), 7.02 (2 H, t, J=8.70 Hz), 5.51 (1 H, ddd, J=15.41, 3.66, 3.51 Hz), 5.17-5.38 (1 H, m), 4.52-4.66 (2 H, m), 4.30-4.41 (1 H, m), 3.89-4.03 (1 H, m), 3.45-3.87 (3 H, m), 2.63-2.78 (3 H, m), 1.79-2.50 (6 H, m), 1.60-1.66 (2 H, m). $^{13}$C NMR (126 MHz, CDCl$_3$) δ ppm 167.91, 167.87, 160.43, 160.40, 159.45, 159.12, 158.75, 152.59, 152.57, 146.96, 146.94, 133.30, 130.11, 130.06, 130.00, 123.26, 123.20, 115.76, 115.71, 115.58, 115.54, 94.04, 92.63, 90.93, 89.53, 66.00, 65.91, 55.20, 55.02, 54.55, 54.35, 46.23, 45.62, 43.07, 42.91, 42.75, 42.67, 40.33, 40.27, 37.61, 37.47, 33.92, 33.88, 33.61, 33.45, 32.55, 30.37, 30.35, 30.23, 30.05. LC/MS (M+H)=515.91. HPLC purity>97%.

Example 418

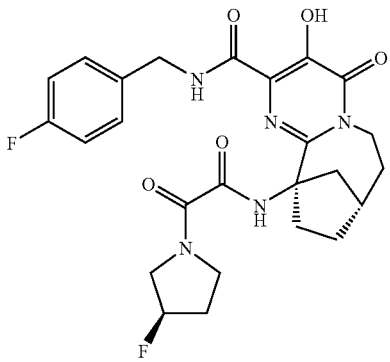

8,1,1-Methano-4H-pyrimido[1,2-a]azocine-2-carboxamide, N-[(4-fluorophenyl)methyl]-11-[[2-[(3R)-3-fluoro-1-pyrrolidinyl]-1,2-dioxoethyl]amino]-6,7,8,9,10,11-hexahydro-3-hydroxy-4-oxo-, (8S,11R)—. A solution of 8,11-methano-4H-pyrimido[1,2-a]azocine-2-carboxamide, 3-[(4-chlorophenyl)methoxy]-N-[(4-fluorophenyl)methyl]-11-[[2-[(3R)-3-fluoro-1-pyrrolidinyl]-1,2-dioxoethyl]amino]-6,7,8,9,10,11-hexahydro-4-oxo-, (8R,11S)— (0.045 g, 0.070 mmol) in methanol (5 mL) was treated with palladium on carbon (10 mg, 9.40 μmol), and hydrogen, with stirring for 16 hrs. The reaction was filtered, then concentrated under reduced pressure. The film residue recrystallized from EtOH and water over several days. The crystals were isolated and vacuum dried, resulting in the title compound (10.1 mg, 0.0196 mmol, 28% yield) as a purple crystalline solid (28% yield). The crystal structure of 8,11-methano-4H-pyrimido[1,2-a]azocine-2-carboxamide, N-[(4-fluorophenyl)methyl]-11-[[2-[(3R)-3-fluoro-1-pyrrolidinyl]-1,2-dioxoethyl]amino]-6,7,8,9,10,11-hexahydro-3-hydroxy-4-oxo-, (8S,11R)— was determined by crystallography to elucidate the absolute configuration of the two chiral centers at the bicyclic ring. Crystal system: monoclinic; space group: C2; a=18.1035(3) Å (α=90), b=27.1111(4) Å (β=98.947(1)°), c=10.0563(5) Å (γ=90°); V=4875.6(3) Å$^3$; no. of molecules/cell: Z=8, calculated crystal density: d$_x$=1.405 g cm$^{-3}$; absorption coefficient: μ=0.110 mm$^{-1}$; θ range for lattice parameters (°): 2.53 to 27.30. The prismatic crystal from which the X-ray data was collected is chiral, and there are two molecules per asymmetric unit. Based on the known R configuration of C(1), the absolute configuration at C(7) and C(11) are established to be R$^x$ and S, respectively. Intramolecular H-bonding was observed between the hydroxyl 0(4) and the amide oxygen 0(5) [O4 . . . O5=2.590/2.570 Å, H . . . O5=1.889/1.862 Å, O4-H . . . O5=143/144°]. $^1$H NMR (500 MHz, CDCl$_3$) δ ppm 11.98-12.05 (1 H, m), 9.66-9.90 (1 H, m), 8.10-8.23 (1 H, m), 7.36-7.44 (2 H, m), 6.99-7.06 (2 H, m), 5.47-5.56 (1 H, m), 5.16-5.40 (1 H, m), 4.52-4.65 (2 H, m), 4.39-4.51 (1 H, m), 3.71-4.04 (2 H, m), 3.39-3.61 (2 H, m), 2.80 (1 H, td, J=12.89, 6.56 Hz), 2.62-2.73 (2H, m), 2.40-2.51 (1 H, m), 2.21-2.39 (2 H, m), 1.95-2.14 (1 H, m), 1.79-1.93 (3H, m), 1.63 (1 H, brs). $^{13}$C NMR (126 MHz, CDCl$_3$) δ ppm 167.87, 167.83, 163.43, 163.40, 161.27, 160.45, 160.17, 159.46, 158.73, 158.43, 152.61, 146.98, 146.95, 133.26, 133.24, 133.18, 133.15, 130.16, 130.12, 130.10, 130.06, 123.20, 123.14, 115.76, 115.73, 115.58, 115.56, 94.11, 92.71, 90.95, 89.55, 65.91, 65.82, 55.22, 55.03, 54.53, 54.34, 46.08, 45.78, 42.79, 42.74, 42.66, 42.48, 40.38, 40.32, 37.80, 37.64, 34.05, 34.00, 33.58, 33.41, 32.55, 30.33, 30.29, 30.23, 30.05. HPLC purity>97%.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of Formula I

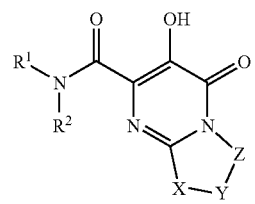

I wherein:

R$^1$ is (Ar$^1$)alkyl, alkyl, (cycloalkyl)alkyl, diphenylalkyl, phenoxyalkyl, (PhNH)alkyl, (methylpyrrolidinyl)alkyl, (imidazolyl)alkyl (valerolactamyl)alkyl, (tetrahydrofuranyl)alkyl, ((fluoro)(methyl)pyridinyl)methyl, phenylcyclopropyl, or benzylpyrrolidinyl;

$R^2$ is hydrogen, alkyl, hydroxy or alkoxy;

$R^3$ is hydrogen, halo, hydroxy, alkoxy, cyano, alkyl, cycloalkyl, haloalkyl, hydroxyalkyl, alkoxyalkyl, alkoxy, haloalkoxy, $N(R^8)(R^9)$, $N(R^6)COR^7$, $N(R^6)SO_2R^7$, $N(R^6)CO_2R^7$, $N(R^6)SO_2N(R^8)(R^9)$, $CO_2R^6$, $CON(R^8)(R^9)$, $SOR^7$, $SO_2R^7$, $SO_2N(R^8)(R^9)$, $PO(OR^6)_2$, $R^{12}$, or $Ar^2$;

$R^4$ is hydrogen, halo, hydroxy, cyano, alkyl, alkoxy, haloalkyl, haloalkoxy, or $N(R^6)(R^6)$;

$R^5$ is hydrogen, halo, hydroxy, cyano, alkyl, alkoxy, haloalkyl, haloalkoxy, or $N(R^6)(R^6)$;

$R^6$ is hydrogen, alkyl, haloalkyl, or cycloalkyl;

$R^7$ is alkyl, haloalkyl, or cycloalkyl;

$R^8$ is hydrogen, alkyl, haloalkyl, hydroxyalkyl, alkoxyalkyl or dialkylaminoalkyl;

$R^9$ is hydrogen, alkyl, haloalkyl, hydroxyalkyl, alkoxyalkyl or dialkylaminoalkyl; or $N(R^8)(R^9)$ taken together is azetidinyl, pyrrolidinyl, $(R^{10})$-piperidinyl, $N$—$(R^{11})$-piperazinyl, morpholinyl, thiomorpholinyl, or dioxothiazinyl;

$R^{10}$ is hydrogen, alkyl, hydroxy, or hydroxyalkyl;

$R^{11}$ is hydrogen, alkyl, cyclolkyl, hydroxyalkyl, alkoxyalkyl, hydroxyalkoxyalkyl, phenyl, pyridinyl, (methylimidazolyl)methyl, $COR^6$, $CO_2R^6$, (hydroxyalkyl)CO, (alkoxyalkyl)CO, (tetrahydrofuranyl)CO, (methylisoxazolyl)CO, (thienyl)CO, (furanyl)CO, (pyridinyl)CO, $CON(R^8)(R^9)$, $SO_2R^7$, $SO_2N(R^8)(R^9)$, (dimethylisoxazolyl)$SO_2$, ((carboethoxy)thienyl)$SO_2$, (methylimidazolyl)$SO_2$,

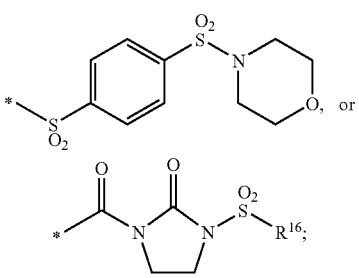, or $R^{12}$ is azetidinonyl, pyrrolidinonyl, valerolactamyl, caprolactamyl, maleimido, oxazolidinonyl, imidazolidinonyl, triazolonyl, $N$—$(R^6)$-dioxothiazolidinyl or dioxothiazinyl, and is substituted with 0-2 substituents selected from the group consisting of alkyl, hydroxyalkyl, haloalkyl, alkoxyalkyl, and aminoalkyl;

$R^{13}$ is hydrogen, alkyl, alkylcarbonyl, alkoxycarbonyl, benzyloxycarbonyl, or alkylsulfonyl;

$R^{14}$ is $N(R^{15})(R^{15})$, $N(R^{15})$(benzyloxycarbonyl), $N(R^{15})$(alkyloxycarbonyl), $N(R^{15})$((hydroxyalkyl)oxycarbonyl), $N(R^{15})$((alkyloxy)alkyloxycarbonyl), $N(R^{15})CO(R^{16})$, $N(R^{15})((CO(N(R^{15})_2)alkyl)$, $N(R^{15})((CO_2CO(N(R^{15})_2)alkyl)$, $N(R^{15})CO((N(R^{15})_2)alkyl)$, $N(R^{15})CO((CON(R^{15})(R^{15})alkyl)$, $N(R^{15})COCO_2(R^{15})$, $N(R^{15})CO((CO_2(R^{15})alkyl)$, $N(R^{15})COCON(R^{15})(R^{15})$, $N(R^{15})COCO((N(R^{15})(R^{15}))alkyl)$, $N(R^{15})CO(N(R^{15})_2)$, $N(R^{15})SO_2R^{16}$, $N(R^{15})SO_2(N(R^{15})_2)$, or $N(R^{15})COAr^3$;

or $R^{14}$ is hydroxy, alkoxy, (hydroxy)alkoxy, (alkoxy)alkoxy, $(R^{16}CO_2)$alkoxy, or $(PhCO_2)$alkoxy;

or $R^{14}$ is $N(R^{15})COCON(R^{15})$(alkoxyalkyl), $N(R^{15})COCON(R^{15})$(hydroxyalkyl), $N(R^{15})COCON(R^{15})$((tetrahydrofuranyl)methyl), $N(R^{15})COCON(R^{15})$((N,N-dimethylpyrazolyl)methyl), or $N(R^{15})CO((Ar^4)alkyl)$;

or $R^{14}$ is

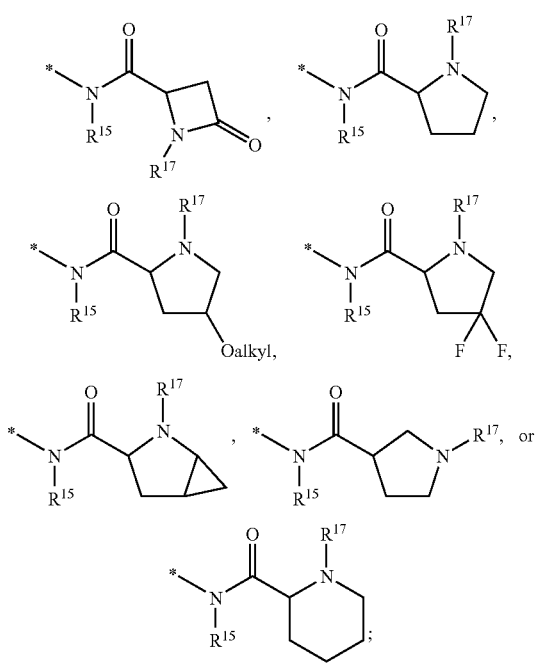

or $R^{14}$ is

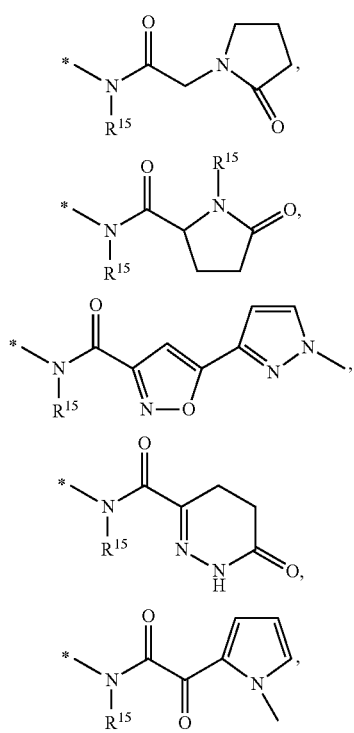

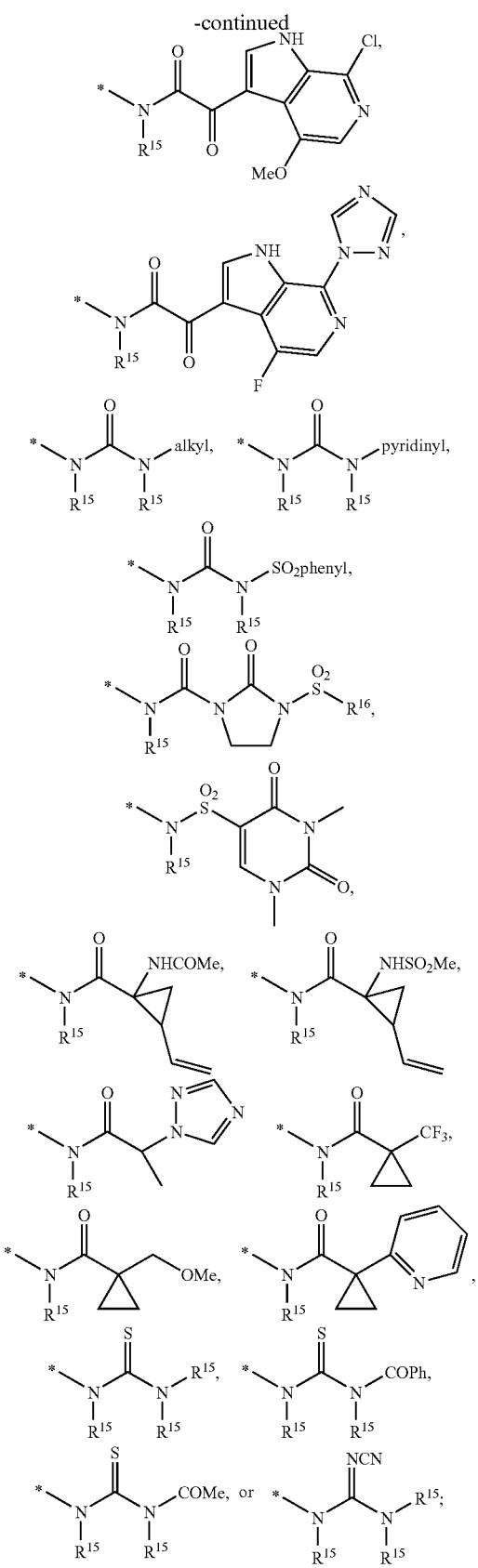

R[15] is hydrogen, alkyl, hydroxyalkyl, alkoxyalkyl, haloalkyl, or cycloalkyl;

or N(R[15])(R[15]) taken together is azetidinyl, pyrrolidinyl, (R[10])-piperidinyl, N—(R[11])-piperazinyl, morpholinyl, or thiomorpholinyl, and is substituted with 0-2 substituents selected from halo, hydroxy, alkoxy, alkyl, hydroxyalkyl, alkoxyalkyl, hydroxyalkyloxyalkyl, acetamido, CO₂R[6], and CON(R[8])(R[9]);

R[16] is alkyl, haloalkyl, cycloalkyl, (cycloalkyl)alkyl, hydroxyalkyl, alkoxyalkyl, tetrahydropyranyl, or Ar[3];

R[17] is hydrogen, alkyl, alkylCO, cycloalkylCO, alkyloxyCO, CON(R[15])(R[15]), COCON(R[15])(R[15]), COAr₃, alkylSO₂, cycloalkylSO₂, furanylSO₂, triazolylSO₂, or N-methylpyrrolylSO₂;

Ar[1] is

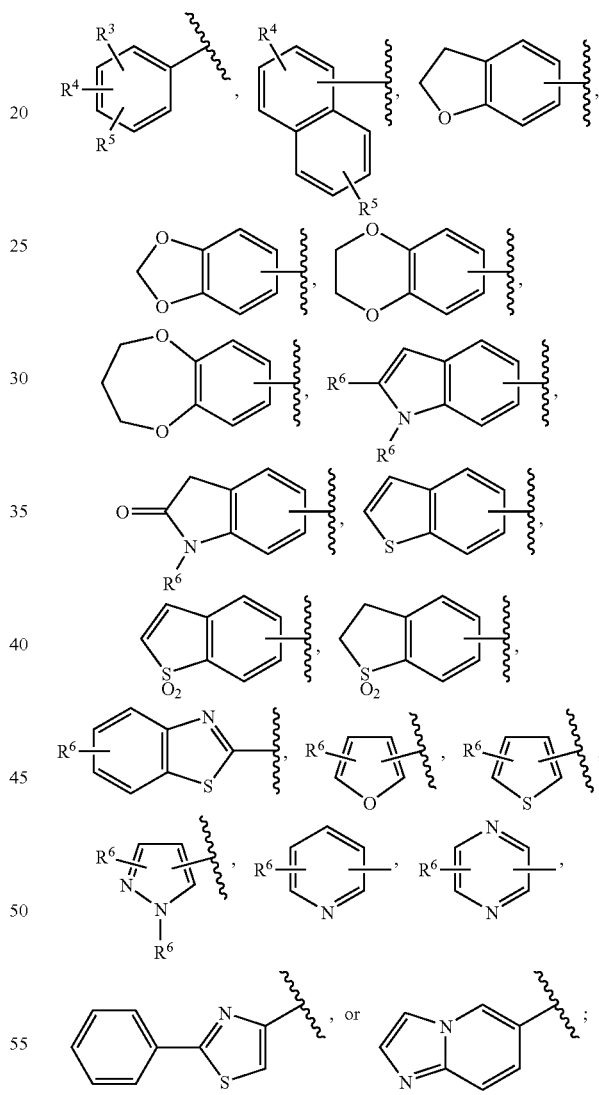

Ar[2] is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, or hydroxypyridinyl, and is substituted with 0-3 substituents selected from the group consisting of oxo, halo, cyano, benzyl, alkyl, alkoxy, N(R[8])(R[9]), CO₂R[6], and CON(R[8])(R[9]);

Ar[3] is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyridinyl, pyrimidinyl, pyrazinyl, imidazopyridinyl, quinolinyl, isoquinolinyl, or phenyl, and is substituted with 0-3 substituents selected from the group consisting of oxo, halo, alkoxy, haloalkoxy, cyano, benzyl, alkyl, haloalkyl, $N(R^8)(R^9)$, and $N(R^{15})CO(R^{16})$;

$Ar^4$ is pyrazolyl or triazolyl, and is substituted with 0-1 substituents selected from $CO_2R^6$ and $CON(R^8)(R^9)$; and X—Y—Z is

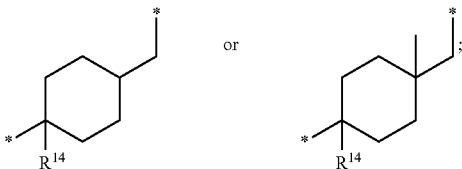

or a pharmaceutically acceptable salt thereof.

2. A compound of claim 1 where $R^1$ is $(Ar^1)$alkyl;

$R^2$ is hydrogen, alkyl, hydroxy or alkoxy;

$R^3$ is hydrogen, halo, hydroxy, cyano, alkyl, haloalkyl, alkoxy, haloalkoxy, $N(R^8)(R^9)$, $N(R^6)COR^7$, $N(R^6)SO_2R^7$, $N(R^6)CO_2R^7$, $N(R^6)SO_2N(R^8)(R^9)$, $CO_2R^6$, $CON(R^8)(R^9)$, $SOR^7$, $SO_2R^7$, $SO_2N(R^8)(R^9)$, $PO(OR^6)_2$, $R^{12}$, or $Ar^2$;

$R^4$ is hydrogen, halo, hydroxy, cyano, alkyl, alkoxy, haloalkyl, haloalkoxy, or $N(R^6)(R^6)$;

$R^5$ is hydrogen, halo, hydroxy, cyano, alkyl, alkoxy, haloalkyl, haloalkoxy, or $N(R^6)(R^6)$;

$R^6$ is hydrogen, alkyl, haloalkyl, or cycloalkyl;

$R^7$ is alkyl, haloalkyl, or cycloalkyl;

$R^8$ is hydrogen, alkyl, haloalkyl, hydroxyalkyl, alkoxyalkyl or dialkylaminoalkyl;

$R^9$ is hydrogen, alkyl, haloalkyl, hydroxyalkyl, alkoxyalkyl or dialkylaminoalkyl; or $N(R^8)(R^9)$ taken together is azetidinyl, pyrrolidinyl, $(R^{10})$-piperidinyl, N—$(R^{11})$-piperazinyl, morpholinyl, thiomorpholinyl, or dioxothiazinyl;

$R^{10}$ is hydrogen, alkyl, hydroxy, or hydroxyalkyl;

$R^{11}$ is hydrogen, alkyl, cyclolkyl, $COR^6$, or $CO_2R^6$;

$R^{12}$ is azetidinonyl, pyrrolidinonyl, valerolactamyl, caprolactamyl, maleimido, oxazolidinonyl, imidazolidinonyl, triazolonyl, N—$(R^6)$-dioxothiazolidinyl or dioxothiazinyl, and is substituted with 0-2 substituents selected from the group consisting of alkyl, hydroxyalkyl, haloalkyl, alkoxyalkyl, and aminoalkyl;

$R^{13}$ is hydrogen, alkyl, alkylcarbonyl, alkoxycarbonyl, benzyloxycarbonyl, or alkylsulfonyl;

$R^{14}$ is $N(R^{15})(R^{15})$, $N(R^{15})$(benzyloxycarbonyl), $N(R^{15})$(alkyloxycarbonyl), $N(R^{15})CO(R^{16})$, $N(R^{15})CO(alkyl(N(R^{15})_2))$, $N(R^{15})COCO_2(R^{15})$, $N(R^{15})COCON(R^{15})(R^{15})$, $N(R^{15})CO(N(R^{15})_2)$, $N(R^{15})SO_2R^{16}$, $N(R^{15})SO_2(N(R^{15})_2)$, or $N(R^{15})COAr^3$;

or $R^{14}$ is hydroxy, alkoxy, (hydroxy)alkoxy, (alkoxy)alkoxy, $(R^{16}CO_2)$alkoxy, or $(PhCO_2)$alkoxy;

or $R^{14}$ is

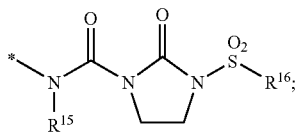

$R^{15}$ is hydrogen, alkyl, haloalkyl, or cycloalkyl;

or $N(R^{15})(R^{15})$ taken together is azetidinyl, pyrrolidinyl, $(R^{10})$-piperidinyl, N—$(R^{11})$-piperazinyl, morpholinyl, or thiomorpholinyl;

$R^{16}$ is alkyl, haloalkyl, or cycloalkyl;

$Ar^1$ is

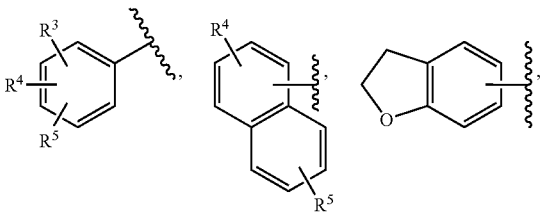

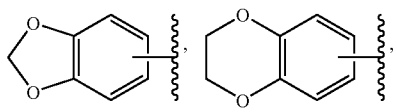

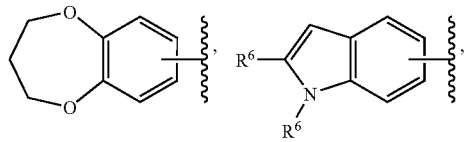

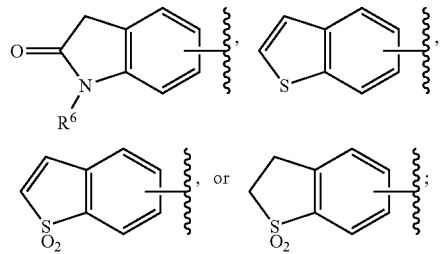

$Ar^2$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, or hydroxypyridinyl, and is substituted with 0-3 substituents selected from the group consisting of oxo, halo, cyano, benzyl, alkyl, alkoxy, $N(R^8)(R^9)$, $CO_2R^6$, and $CON(R^8)(R^9)$;

$Ar^3$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, or pyridinyl, and is substituted with 0-3 substituents selected from the group consisting of oxo, halo, alkoxy, cyano, benzyl, and alkyl; and X—Y—Z is

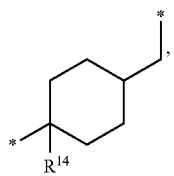

or a pharmaceutically acceptable salt thereof.

3. A compound of claim 1 where $R^1$ is

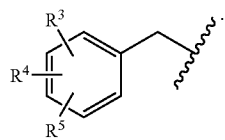

4. A compound of claim 1 where $R^1$ is

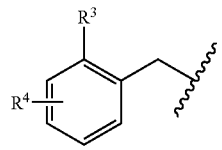

and $R^3$ is other than hydrogen or halo.

5. A compound of claim 1 where $R^3$ is $CON(R^8)(R^9)$, $SO_2N(R^8)(R^9)$, azetidinonyl, pyrrolidinonyl, valerolactamyl, caprolactamyl, oxazolidinonyl, imidazolidinonyl, dioxothiazinyl, N—$(R^6)$-dioxothiazolidinyl, or triazolyl where triazolyl is substituted with 0-2 alkyl or oxo substituents.

6. A compound of claim 1 where $R^3$ is halo, $CON(R^8)(R^9)$, oxazolidinonyl, or triazolyl where triazolyl is substituted with 0-2 alkyl or oxo substituents.

7. A compound of claim 1 where $Ar^3$ is oxadiazolyl, pyrazolyl, or isoxazolyl.

8. A compound of claim 1 where $R^{14}N(R^{15})(R^{15})$, $N(R^{15})$(benzyloxycarbonyl), $N(R^{15})$(alkyloxycarbonyl), $N(R^{15})$((hydroxyalkyl)oxycarbonyl), $N(R^{15})$((alkyloxy)alkyloxycarbonyl), $N(R^{15})CO(R^{16})$, $N(R^{15})((CO(N(R^{15})_2)alkyl)$, $N(R^{15})((CO_2CO(N(R^{15})_2)alkyl)$, $N(R^{15})CO((N(R^{15})_2)alkyl)$, $N(R^{15})CO((CON(R^{15})(R^{15})alkyl)$, $N(R^{15})COCO_2(R^{15})$, $N(R^{15})CO((CO_2(R^{15})alkyl)$, $N(R^{15})COCON(R^{15})(R^{15})$, $N(R^{15})COCO((N(R^{15})(R^{15}))alkyl)$, $N(R^{15})CO(N(R^{15})_2)$, $N(R^{15})SO_2R^{16}$, $N(R^{15})SO_2(N(R^{15})_2)$, or $N(R^{15})COAr^3$;

or $R^{14}$ is hydroxy, alkoxy, (hydroxy)alkoxy, (alkoxy)alkoxy, $(R^{16}CO_2)$alkoxy, or $(PhCO_2)$alkoxy;

or $R^{14}$ is $N(R^{15})COCON(R^{15})$(alkoxyalkyl), $N(R^{15})CO$-$CON(R^{15})$(hydroxyalkyl), $N(R^{15})COCON(R^{15})$((tetrahydrofuranyl)methyl), $N(R^{15})COCON(R^{15})$((N,N-dimethylpyrazolyl)methyl), or $N(R^{15})CO((Ar^4)alkyl)$;

or $R^{14}$ is

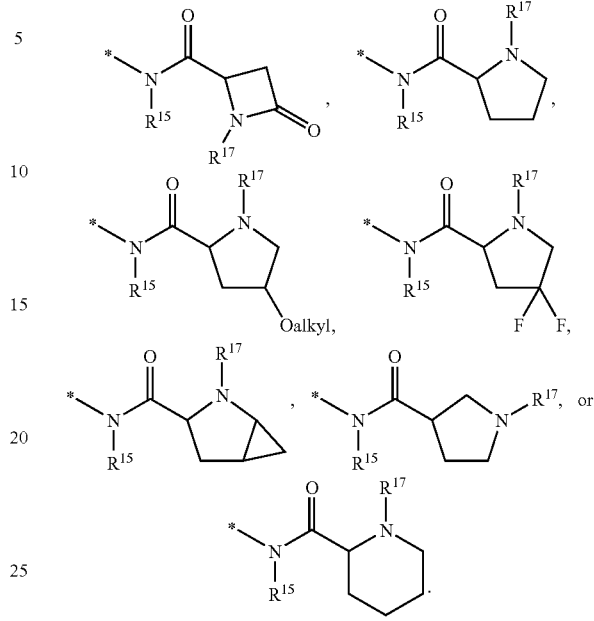

9. A compound of claim 1 where $R^1$ is $(Ar^1)$alkyl, alkyl, (cycloalkyl)alkyl, diphenylalkyl, phenoxyalkyl, (PhNH)alkyl, (methylpyrrolidinyl)alkyl, (imidazolyl)alkyl (valerolactamyl)alkyl, (tetrahydrofuranyl)alkyl, ((fluoro)(methyl)pyridinyl)methyl, phenylcyclopropyl, or benzylpyrrolidinyl;

$R^2$ is hydrogen;

$R^3$ is hydrogen, halo, hydroxy, alkoxy, cyano, alkyl, cycloalkyl, haloalkyl, hydroxyalkyl, alkoxyalkyl, alkoxy, haloalkoxy, $N(R^8)(R^9)$, $N(R^6)COR^7$, $N(R^6)SO_2R^7$, $N(R^6)CO_2R^7$, $N(R^6)SO_2N(R^8)(R^9)$, $CO_2R^6$, $CON(R^8)(R^9)$, $SO_2R^7$, $SO_2N(R^8)(R^9)$, or $Ar^2$;

$R^4$ is hydrogen, halo, or alkyl;

$R^5$ is hydrogen, halo, or alkyl;

$R^6$ is hydrogen, alkyl, haloalkyl, or cycloalkyl;

$R^7$ is alkyl, haloalkyl, or cycloalkyl;

$R^8$ is hydrogen or alkyl;

$R^9$ is hydrogen or alkyl; or $N(R^8)(R^9)$ taken together is azetidinyl, pyrrolidinyl, $(R^{10})$-piperidinyl, N—$(R^{11})$-piperazinyl, morpholinyl, thiomorpholinyl, or dioxothiazinyl;

$R^{10}$ is hydrogen, alkyl, hydroxy, or hydroxyalkyl;

$R^{11}$ is hydrogen, alkyl, cyclolkyl, hydroxyalkyl, alkoxyalkyl, hydroxyalkoxyalkyl, phenyl, pyridinyl, (methylimidazolyl)methyl, $COR^6$, $CO_2R^6$, (hydroxyalkyl)CO, (alkoxyalkyl)CO, (tetrahydrofuranyl)CO, (methylisoxazolyl)CO, (thienyl)CO, (furanyl)CO, (pyridinyl)CO, $CON(R^8)(R^9)$, $SO_2R^7$, $SO_2N(R^8)(R^9)$, (dimethylisoxazolyl)$SO_2$, ((carboethoxy)thienyl)$SO_2$, (methylimidazolyl)$SO_2$,

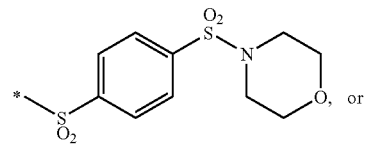

, or

R¹³ is hydrogen, alkyl, alkylcarbonyl, alkoxycarbonyl, benzyloxycarbonyl, or alkylsulfonyl;

R¹⁴ is N(R¹⁵)(R¹⁵), N(R¹⁵)(benzyloxycarbonyl), N(R¹⁵)(alkyloxycarbonyl), N(R¹⁵)((hydroxyalkyl)oxycarbonyl), N(R¹⁵)((alkyloxy)alkyloxycarbonyl), N(R¹⁵)CO(R¹⁶), N(R¹⁵)((CO(N(R¹⁵)₂)alkyl), N(R¹⁵)((CO₂CO(N(R¹⁵)₂)alkyl), N(R¹⁵)CO((N(R¹⁵)₂)alkyl), N(R¹⁵)CO((CON(R¹⁵)(R¹⁵)alkyl), N(R¹⁵)COCO₂(R¹⁵), N(R¹⁵)CO((CO₂(R¹⁵)alkyl), N(R¹⁵)COCON(R¹⁵)(R¹⁵), N(R¹⁵)COCO((N(R¹⁵)(R¹⁵))alkyl), N(R¹⁵)CO(N(R¹⁵)₂), N(R¹⁵)SO₂R¹⁶, N(R¹⁵)SO₂(N(R¹⁵)₂), or N(R¹⁵)COAr³;

or R¹⁴ is hydroxy, alkoxy, (hydroxy)alkoxy, (alkoxy)alkoxy, (R¹⁶CO₂)alkoxy, or (PhCO₂)alkoxy;

or R¹⁴ is N(R¹⁵)COCON(R¹⁵)(alkoxyalkyl), N(R¹⁵)COCON(R¹⁵)(hydroxyalkyl), N(R¹⁵)COCON(R¹⁵)((tetrahydrofuranyl)methyl), N(R¹⁵)COCON(R¹⁵)((N,N-dimethylpyrazolyl)methyl), or N(R¹⁵)CO((Ar⁴)alkyl);

or R¹⁴ is

407

-continued

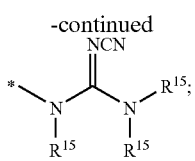

$R^{15}$ is hydrogen, alkyl, hydroxyalkyl, alkoxyalkyl, haloalkyl, or cycloalkyl;
or $N(R^{15})(R^{15})$ taken together is azetidinyl, pyrrolidinyl, $(R^{10})$-piperidinyl, $N$—$(R^{11})$-piperazinyl, morpholinyl, or thiomorpholinyl, and is substituted with 0-2 substituents selected from halo, hydroxy, alkoxy, alkyl, hydroxyalkyl, alkoxyalkyl, hydroxyalkyloxyalkyl, acetamido, $CO_2R^6$, and $CON(R^8)(R^9)$;
$R^{16}$ is alkyl, haloalkyl, cycloalkyl, (cycloalkyl)alkyl, hydroxyalkyl, alkoxyalkyl, tetrahydropyranyl, or $Ar^3$;
$R^{17}$ is hydrogen, alkyl, alkylCO, cycloalkylCO, alkyloxyCO, $CON(R^{15})(R^{15})$, $COCON(R^{15})(R^{15})$, $COAr_3$, alkylSO$_2$, cycloalkylSO$_2$, furanylSO$_2$, triazolylSO$_2$, or N-methylpyrrolylSO$_2$;
$Ar^1$ is

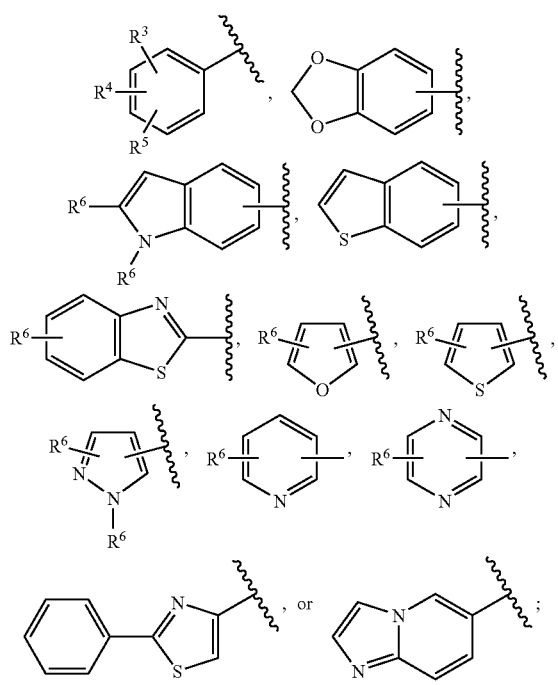

$Ar^2$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, or hydroxypyridinyl, and is substituted with 0-3 substituents selected from the group consisting of oxo, halo, cyano, benzyl, alkyl, alkoxy, $N(R^8)(R^9)$, $CO_2R^6$, and $CON(R^8)(R^9)$;
$Ar^3$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyridinyl, pyrimidinyl, pyrazinyl, imidazopyridinyl, quinolinyl, isoquinolinyl, or phenyl, and is substituted with 0-3 substituents selected from the group consisting of oxo, halo, alkoxy, haloalkoxy, cyano, benzyl, alkyl, haloalkyl, $N(R^8)(R^9)$, and $N(R^{15})CO(R^{16})$;

408

$Ar^4$ is pyrazolyl or triazolyl, and is substituted with 0-1 substituents selected from $CO_2R^6$ and $CON(R^8)(R^9)$; and
X—Y—Z is

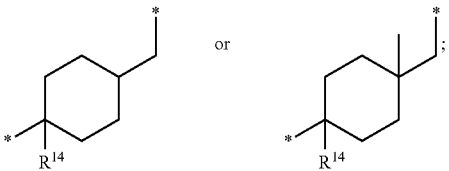

or a pharmaceutically acceptable salt thereof.

10. A compound of claim 9 where $R^1$ is $(Ar^1)$alkyl and $R^2$ is hydrogen.

11. A compound of claim 10 where
$R^{14}$ is $N(R^{15})(R^{15})$, $N(R^{15})$(benzyloxycarbonyl), $N(R^{15})$(alkyloxycarbonyl), $N(R^{15})$((hydroxyalkyl)oxycarbonyl), $N(R^{15})$((alkyloxy)alkyloxycarbonyl), $N(R^{15})CO(R^{16})$, $N(R^{15})$((CO($N(R^{15})_2$)alkyl), $N(R^{15})$((CO$_2$CO($N(R^{15})_2$)alkyl), $N(R^{15})CO((N(R^{15})_2)$alkyl), $N(R^{15})CO((CON(R^{15})(R^{15})$alkyl), $N(R^{15})COCO_2(R^{15})$, $N(R^{15})CO((CO_2(R^{15}))$alkyl), $N(R^{15})COCON(R^{15})(R^{15})$, $N(R^{15})COCO((N(R^{15})(R^{15}))$alkyl), $N(R^{15})CO(N(R^{15})_2)$, $N(R^{15})SO_2R^{16}$, $N(R^{15})SO_2(N(R^{15})_2)$, or $N(R^{15})COAr^3$.

12. A compound of claim 11 where X—Y—Z is

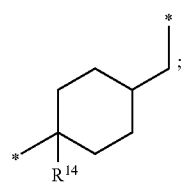

or a pharmaceutically acceptable salt thereof.

13. A compound of claim 1 selected from the group consisting of
ethanediamide, N-[2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-;
ethanediamide, N-[2-[[[(3-chloro-4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-;
ethanediamide, N-[2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N',N'-trimethyl-;
ethanediamide, N'-[2-[[[(4-fluoro-3-methylphenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-;
ethanediamide, N'-[2-[[[(3-cyclopropyl-4-fluorophenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-; and
ethanediamide, N'-[2-[[[(4-fluorophenyl)methyl]amino]carbonyl]-6,7,8,9-tetrahydro-3-hydroxy-4-oxo-7,10-ethanopyrimido[1,2-a]azepin-10(4H)-yl]-N,N-dimethyl-;

or a pharmaceutically acceptable salt thereof.

14. A pharmaceutical composition useful for treating HIV infection comprising a therapeutic amount of a compound of claim 1 and a pharmaceutically acceptable carrier.

15. A pharmaceutical composition of claim 14 further comprising a therapeutically effective amount at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

16. A method for treating HIV infection comprising administering a therapeutically effective amount of a compound of claim 1, or a pharmaceutically acceptable salt thereof, to a patient in need thereof.

17. The method of claim 16 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *

UNITED STATES PATENT AND TRADEMARK OFFICE
CERTIFICATE OF CORRECTION

PATENT NO. : 8,129,398 B2  
APPLICATION NO. : 12/406268  
DATED : March 6, 2012  
INVENTOR(S) : Francis Beaulieu et al.

It is certified that error appears in the above-identified patent and that said Letters Patent is hereby corrected as shown below:

In the Claims:

Claim 1:

Column 397, line 26, change "cyclolkyl," to -- cycloalkyl, --.

Column 397, line 59, change "$N(R^{15})((CO(N(R^{15})_2)alkyl),$" to -- $N(R^{15})((CON(R^{15})_2)alkyl),$ --.

Column 397, lines 59 and 60, change "$N(R^{15})((CO_2CO(N(R^{15})_2)alkyl),$" to -- $N(R^{15})((CO_2CON(R^{15})_2)alkyl),$ --.

Column 397, lines 60 and 61, change "$N(R^{15})CO((CON(R^{15})(R^{15})alkyl),$" to -- $N(R^{15})CO(CON(R^{15})(R^{15})alkyl),$ --.

Column 399, lines 45 to 49, after " 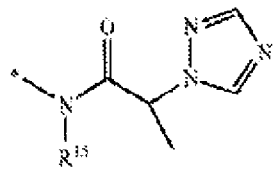 " insert -- , --.

Claim 2:

Column 401, line 50, change "cyclolkyl," to -- cycloalkyl, --.

Column 403, lines 5 to 11, change " 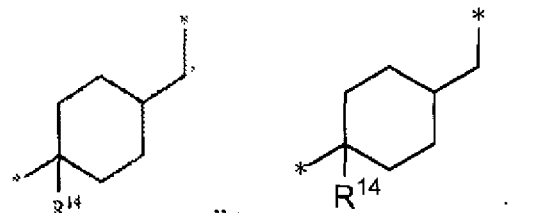 " to -- ; --.

Signed and Sealed this  
Twenty-ninth Day of April, 2014

Michelle K. Lee  
*Deputy Director of the United States Patent and Trademark Office*

CERTIFICATE OF CORRECTION (continued)
U.S. Pat. No. 8,129,398 B2

<u>In the Claims:</u>

Claim 8:

Column 403, line 54, change "N($R^{15}$)((CO(N($R^{15}$)$_2$)alkyl)," to -- N($R^{15}$)((CON($R^{15}$)$_2$)alkyl), --.

Column 403, line 55, change "N($R^{15}$)((CO$_2$CO(N($R^{15}$)$_2$)alkyl)," to -- N($R^{15}$)((CO$_2$CON($R^{15}$)$_2$)alkyl), --.

Column 403, line 56, change "N($R^{15}$)CO((CON($R^{15}$)($R^{15}$)alkyl)," to -- N($R^{15}$)CO(CON($R^{15}$)($R^{15}$)alkyl), --.

Column 403, line 57, change "N($R^{15}$)CO((CO$_2$($R^{15}$)alkyl)," to -- N($R^{15}$)CO(CO$_2$($R^{15}$)alkyl), --.

Claim 9:

Column 404, line 52, change "cyclolkyl," to -- cycloalkyl, --.

Column 405, line 14, change "N($R^{15}$)((CO(N($R^{15}$)$_2$)alkyl)," to -- N($R^{15}$)((CON($R^{15}$)$_2$)alkyl), --.

Column 405, lines 14 and 15, change "N($R^{15}$)((CO$_2$CO(N($R^{15}$)$_2$)alkyl)," to -- N($R^{15}$)((CO$_2$CON($R^{15}$)$_2$)alkyl), --.

Column 405, lines 15 and 16, change "N($R^{15}$)CO((CON($R^{15}$)($R^{15}$)alkyl)," to -- N($R^{15}$)CO(CON($R^{15}$)($R^{15}$)alkyl), --.

Column 405, lines 16 and 17, change "N($R^{15}$)CO((CO$_2$($R^{15}$)alkyl)," to -- N($R^{15}$)CO(CO$_2$($R^{15}$)alkyl), --.

Claim 11:

Column 408, line 22, change "N($R^{15}$)((CO(N($R^{15}$)$_2$)alkyl)," to -- N($R^{15}$)((CON($R^{15}$)$_2$)alkyl), --.

Column 408, lines 22 and 23, change "N($R^{15}$)((CO$_2$CO(N($R^{15}$)$_2$)alkyl)," to -- N($R^{15}$)((CO$_2$CON($R^{15}$)$_2$)alkyl), --.

Column 408, lines 23 and 24, change "N($R^{15}$)CO((CON($R^{15}$)($R^{15}$)alkyl)," to -- N($R^{15}$)CO(CON($R^{15}$)($R^{15}$)alkyl), --.

Column 408, lines 24 and 25, change "N($R^{15}$)CO((CO$_2$($R^{15}$)alkyl)," to -- N($R^{15}$)CO(CO$_2$($R^{15}$)alkyl), --.

Claim 15:

Column 409, line 5, change "amount" to -- amount of --.